US012441699B2

(12) United States Patent
Kim et al.

(10) Patent No.: US 12,441,699 B2
(45) Date of Patent: *Oct. 14, 2025

(54) ORGANIC ELECTROLUMINESCENCE DEVICE AND AMINE COMPOUND FOR ORGANIC ELECTROLUMINESCENCE DEVICE

(71) Applicant: Samsung Display Co., Ltd., Yongin-si (KR)

(72) Inventors: Dongjun Kim, Suwon-si (KR); Minji Kim, Hwaseong-si (KR); Eunjae Jeong, Hwaseong-si (KR); Sohee Jo, Seoul (KR); Sanghyun Han, Hwaseong-si (KR)

(73) Assignee: Samsung Display Co., Ltd., Yongin-si (KR)

( * ) Notice: Subject to any disclaimer, the term of this patent is extended or adjusted under 35 U.S.C. 154(b) by 0 days.

This patent is subject to a terminal disclaimer.

(21) Appl. No.: 18/496,738

(22) Filed: Oct. 27, 2023

(65) Prior Publication Data

US 2024/0090323 A1 Mar. 14, 2024

Related U.S. Application Data

(63) Continuation of application No. 17/080,732, filed on Oct. 26, 2020, now Pat. No. 11,856,844.

(30) Foreign Application Priority Data

Nov. 21, 2019 (KR) ........................ 10-2019-0150292

(51) Int. Cl.

| | |
|---|---|
| ***C07D 307/91*** | (2006.01) |
| ***C07D 209/86*** | (2006.01) |
| ***C07D 333/76*** | (2006.01) |
| ***H10K 85/60*** | (2023.01) |
| *H10K 50/15* | (2023.01) |
| *H10K 50/17* | (2023.01) |

(52) U.S. Cl.

CPC ......... *C07D 307/91* (2013.01); *C07D 209/86* (2013.01); *C07D 333/76* (2013.01); *H10K 85/633* (2023.02); *H10K 85/636* (2023.02); *H10K 50/15* (2023.02); *H10K 50/17* (2023.02); *H10K 85/6572* (2023.02); *H10K 85/6574* (2023.02); *H10K 85/6576* (2023.02)

(58) Field of Classification Search

None

See application file for complete search history.

(56) References Cited

U.S. PATENT DOCUMENTS

| | | | | |
|---|---|---|---|---|
| 2011/0147717 | A1 | 6/2011 | LeCloux et al. | |
| 2014/0197378 | A1* | 7/2014 | Lecloux ............... | H10K 85/633 257/40 |
| 2016/0293843 | A1 | 10/2016 | Itoi | |
| 2017/0194569 | A1* | 7/2017 | Kim ..................... | C09K 11/025 |
| 2018/0114906 | A1 | 4/2018 | Itoi et al. | |
| 2018/0226585 | A1* | 8/2018 | Park ..................... | C07D 405/04 |
| 2020/0287140 | A1* | 9/2020 | Chae .................... | C07D 409/14 |
| 2020/0308129 | A1* | 10/2020 | Montenegro ........ | H10K 85/615 |
| 2020/0365815 | A1* | 11/2020 | Oh ....................... | H10K 85/615 |
| 2021/0147358 | A1* | 5/2021 | Kim ..................... | C07D 407/12 |
| 2022/0109116 | A1* | 4/2022 | Montenegro ........ | C07D 307/91 |
| 2022/0238811 | A1* | 7/2022 | Park ..................... | C07D 209/86 |
| 2023/0025656 | A1 | 1/2023 | Liu et al. | |

FOREIGN PATENT DOCUMENTS

| | | | | |
|---|---|---|---|---|
| KR | 10-1108519 B1 | 1/2012 | | |
| KR | 10-2016-0052136 A | 5/2016 | | |
| KR | 10-2016-0118123 A | 10/2016 | | |
| KR | 10-1994448 B1 | 6/2019 | | |
| WO | WO-2019128849 A1 * | 7/2019 | ........... | C07D 307/91 |
| WO | WO 2020/073605 A1 | 4/2020 | | |

OTHER PUBLICATIONS

Machine translation of WO-2019128849-A1, translation generated Dec. 2023, 24 pages. (Year: 2023).*

* cited by examiner

*Primary Examiner* — Robert S Loewe

(74) *Attorney, Agent, or Firm* — Womble Bond Dickinson (US) LLP

(57) ABSTRACT

An organic electroluminescence device of an embodiment of the present disclosure includes a first electrode, a second electrode facing the first electrode, and a plurality of organic layers disposed between the first electrode and the second electrode, wherein at least one organic layer of the plurality of organic layers includes an amine compound containing a fluorene group; an aryl group having 6 to 60 ring-forming carbon atoms, which is substituted to the fluorene group; a heteroaryl group having 2 to 60 ring-forming carbon atoms, which is substituted to the fluorene group; and at least one amine group, which is substituted to the fluorene group; wherein all the carbons of the aryl group are substituted with deuterium, and the organic electroluminescence device exhibits high efficiency and a long service life.

19 Claims, 2 Drawing Sheets

ORGANIC ELECTROLUMINESCENCE DEVICE AND AMINE COMPOUND FOR ORGANIC ELECTROLUMINESCENCE DEVICE

CROSS-REFERENCE TO RELATED APPLICATION

This application is a continuation of U.S. patent application Ser. No. 17/080,732, filed on Oct. 26, 2020, which claims priority to and the benefit of Korean Patent Application No. 10-2019-0150292, filed in the Korean Intellectual Property Office on Nov. 21, 2019, the entire content of which are hereby incorporated herein by reference.

BACKGROUND

One or more aspects of embodiments of the present disclosure relate to an organic electroluminescence device and an amine compound used therein.

Organic electroluminescence displays are being actively developed as image display devices. An organic electroluminescence display is a so-called self-luminescent displays in which holes and electrons respectively injected from a first electrode and a second electrode recombine in an emission layer, and a luminescent material including an organic compound in the emission layer emits light to implement display.

In the application of an organic electroluminescence device to a display device, there is a demand for an organic electroluminescence device having a low driving voltage, high luminous efficiency, and/or a long service life (life span), and materials capable of stably attaining such characteristics in an organic electroluminescence device are demanded.

Amine compounds are being developed as hole transport region materials, and an amine compound providing high efficiency and/or a long service life to an organic electroluminescence device is demanded.

SUMMARY

One or more aspects of embodiments of the present disclosure are directed toward an organic electroluminescence device having an increased or improved luminous efficiency and/or service life (life span).

One or more aspects of embodiments of the present disclosure are directed toward an amine compound that can provide increased or improved luminous efficiency and/or device service life (life span) when applied to a luminescence device.

One or more example embodiments of the present disclosure provide an organic electroluminescence device including a first electrode, a second electrode facing the first electrode, and a plurality of organic layers disposed between the first electrode and the second electrode, wherein at least one organic layer of the plurality of organic layers includes an amine compound containing a fluorene group; an aryl group having 6 to 60 ring-forming carbon atoms, which is substituted to the fluorene group; a heteroaryl group having 2 to 60 ring-forming carbon atoms, which is substituted to the fluorene group; and at least one amine group, which is substituted to the fluorene group; wherein all the carbons of the aryl group are substituted with deuterium (e.g., the aryl group is a deuterated aryl group).

In an embodiment, the heteroaryl group may be a substituted or unsubstituted dibenzofuranyl group, a substituted or unsubstituted dibenzothiophene group, or a substituted or unsubstituted carbazole group.

In embodiment, the organic layers may include a hole transport region, an emission layer, and an electron transport region, and the hole transport region may include the amine compound.

In an embodiment, the hole transport region may include a hole transport layer and a hole injection layer, and the hole transport layer or the hole injection layer may include the amine compound.

In an embodiment, the amine compound may be represented by Formula 1:

Formula 1

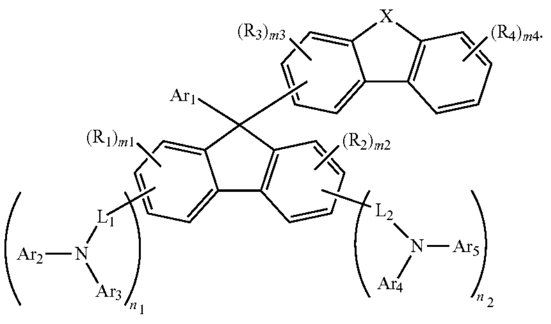

In Formula 1, X may be O, S, or $NAr_6$; $L_1$ and $L_2$ may each independently be a direct linkage, a substituted or unsubstituted arylene group having 6 to 60 ring-forming carbon atoms, or a substituted or unsubstituted heteroarylene group having 2 to 60 ring-forming carbon atoms; $R_1$ to $R_4$ may each independently be a hydrogen atom, a deuterium atom, a halogen atom, a substituted or unsubstituted alkyl group having 1 to 20 carbon atoms, a substituted or unsubstituted aryl group having 6 to 60 ring-forming carbon atoms, or a substituted or unsubstituted heteroaryl group having 2 to 60 ring-forming carbon atoms, and/or may be bonded to an adjacent group to form a ring; $m_1$, $m_2$, and $m_4$ may each independently be an integer of 0 to 4; $m_3$ may be an integer of 0 to 3; $Ar_1$ may be a phenyl group substituted with deuterium, a naphthyl group substituted with deuterium, or a biphenyl group substituted with deuterium; Are to $Ar_6$ may each independently be a substituted or unsubstituted aryl group having 6 to 60 ring-forming carbon atoms, or a substituted or unsubstituted heteroaryl group having 3 to 60 ring-forming carbon atoms; $n_1$ and $n_2$ may each independently be 0 or 1, and at least one of $n_1$ and $n_2$ may be 1.

In an embodiment, $Ar_1$ may be represented by at least one of Formula $t_1$ to Formula $t_5$:

Formula $t_1$

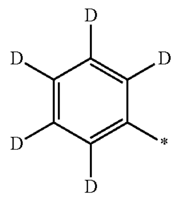

-continued

Formula $t_2$

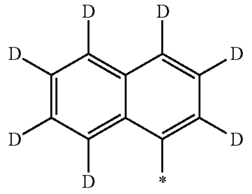

Formula $t_3$

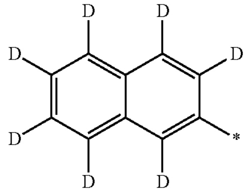

Formula $t_4$

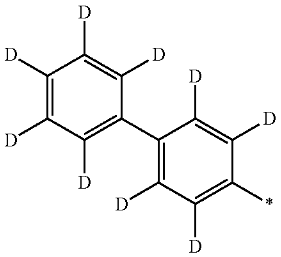

Formula $t_5$

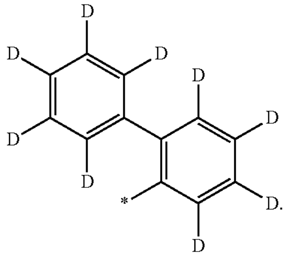

In an embodiment, the amine compound represented by Formula 1 may represented by at least one of Formula 1-1 to Formula 1-3:

Formula 1-1

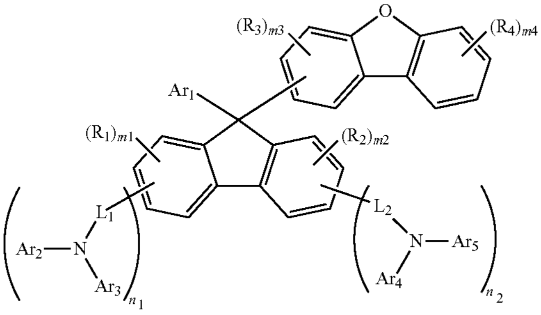

-continued

Formula 1-2

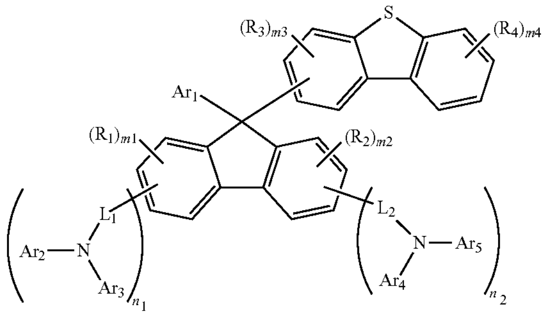

Formula 1-3

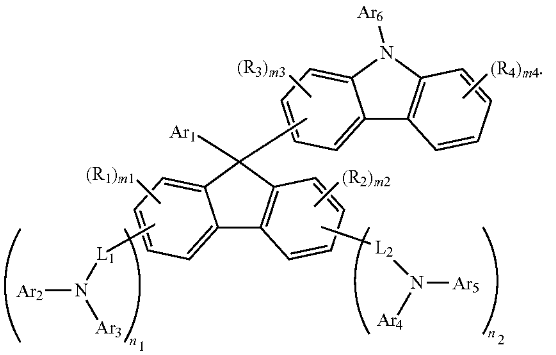

In Formula 1-1 to Formula 1-3, $L_1$, $L_2$, $R_1$ to $R_4$, $m_1$ to $m_4$, $Ar_1$ to $Ar_6$, $n_1$ and $n_2$ may each independently be the same as defined in Formula 1.

In an embodiment, the amine compound represented by Formula 1 may be represented by at least one of Formula 2-1 to Formula 2-5:

Formula 2-1

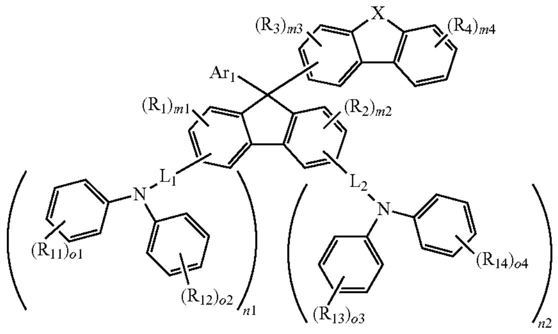

-continued

Formula 2-2

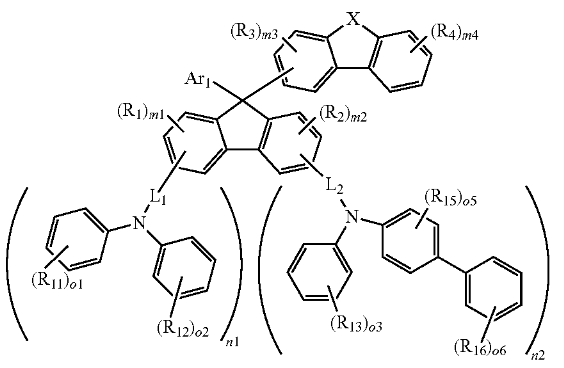

Formula 2-3

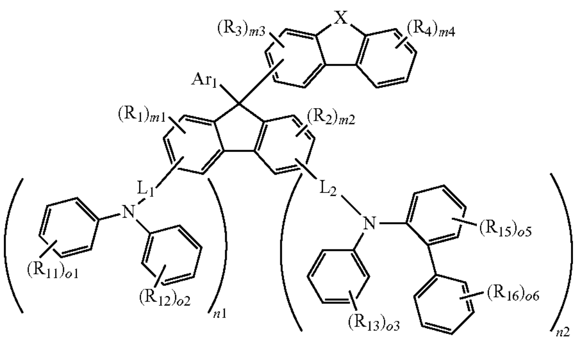

Formula 2-4

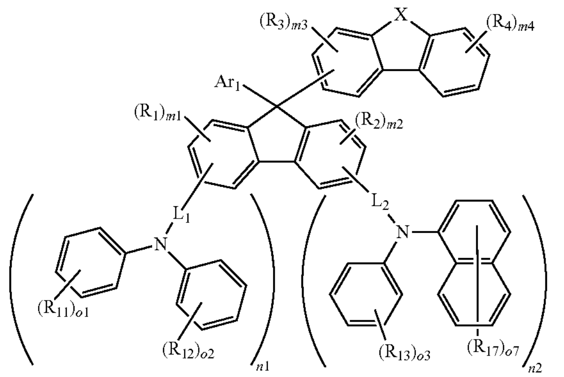

Formula 2-5

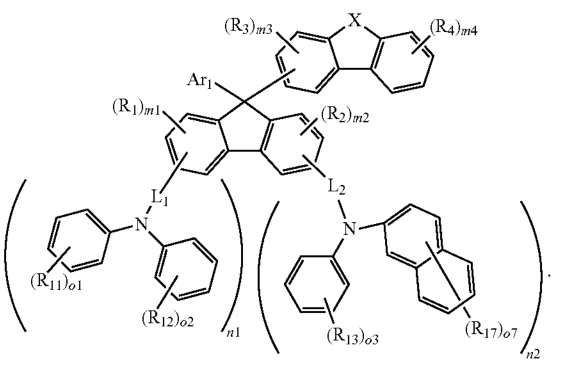

In Formula 2-1 to Formula 2-5, Ru to Rig may each independently be a hydrogen atom, a deuterium atom, a halogen atom, a substituted or unsubstituted alkyl group having 1 to 20 carbon atoms, a substituted or unsubstituted aryl group having 6 to 60 ring-forming carbon atoms, or a substituted or unsubstituted heteroaryl group having 2 to 60 ring-forming carbon atoms, and/or may be bonded to an adjacent group to form a ring; $o_1$ to $o_4$ and $o_6$ may be each independently an integer of 0 to 5; $o_5$ may be an integer of 0 to 4; 07 may be an integer of 0 to 7; and X, $R_1$ to $R_4$, $L_1$, $L_2$, $n_1$, $n_2$, $m_1$ to $m_4$, and $Ar_1$ may each independently be the same as defined in Formula 1.

In an embodiment, the amine compound represented by Formula 1 may be represented by Formula 3-1:

Formula 3-1

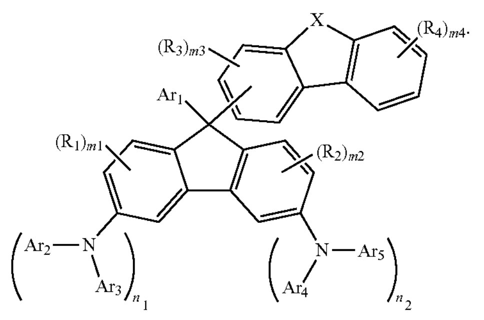

In Formula 3-1, X, $Ar_1$ to $Ar_5$, $R_1$ to $R_4$, $n_1$, $n_2$, and $m_1$ to $m_4$ may each independently be the same as defined in Formula 1.

In an embodiment, X may be $NAr_6$, and $Ar_6$ may be a substituted or unsubstituted phenyl group.

In an embodiment, the amine compound represented by Formula 1 may be represented by at least one of Formula 4-1 or Formula 4-2:

Formula 4-1

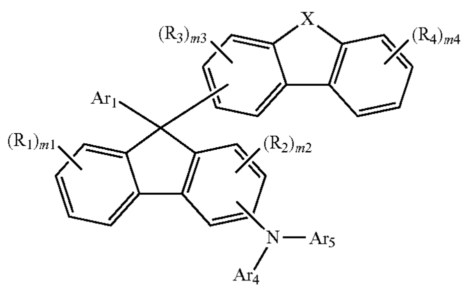

Formula 4-2

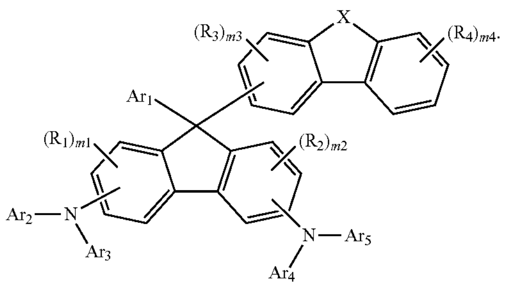

In Formula 4-1 and Formula 4-2, X, $Ar_1$ to $Ar_5$, $R_1$ to $R_4$, $m_1$ to $m_4$ may each independently be the same as defined in Formula 1.

In an embodiment, the amine compound represented by the Formula 1 may include at least one of the compounds represented by Compound Group 1:

-continued
Compound Group 1
1
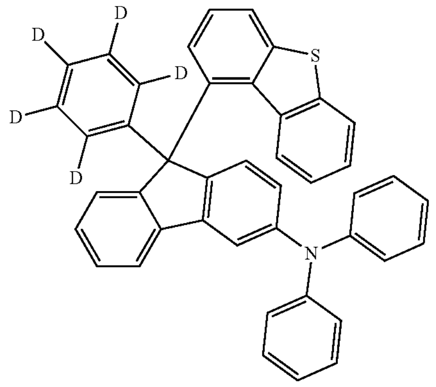
4
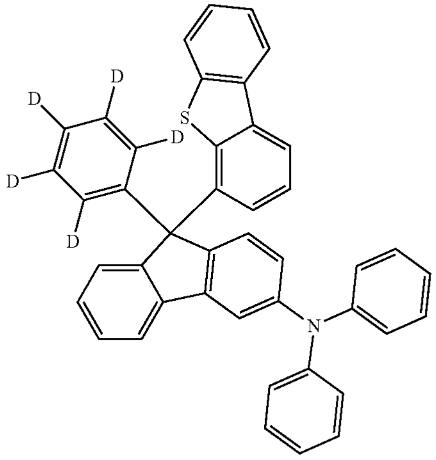
2
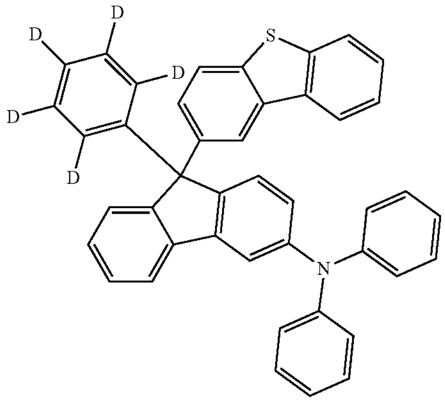
5
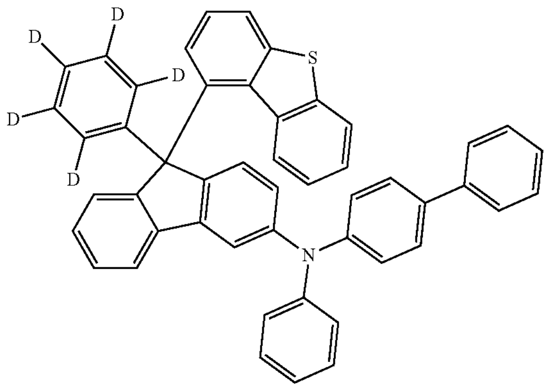
3
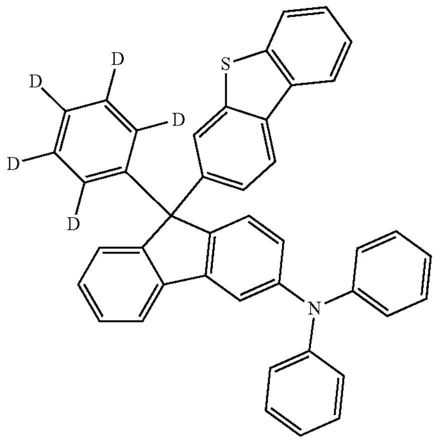
6
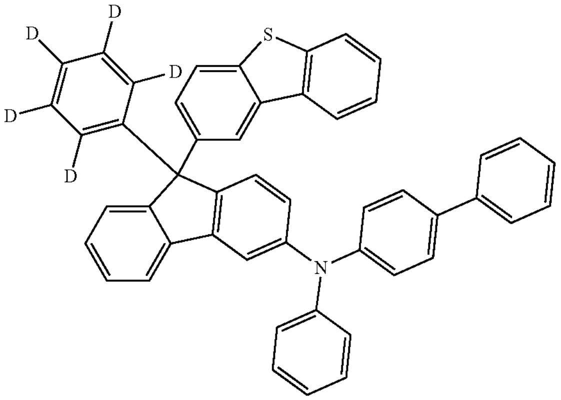

-continued
7
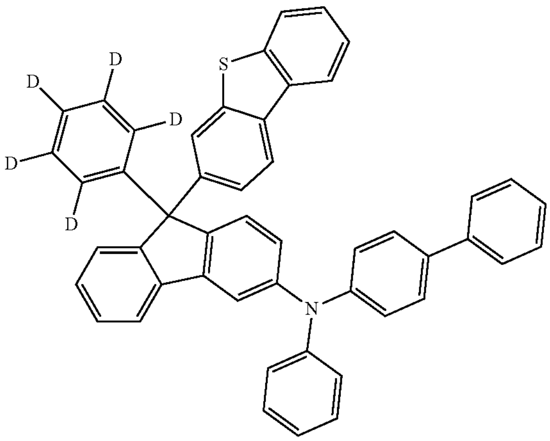
8
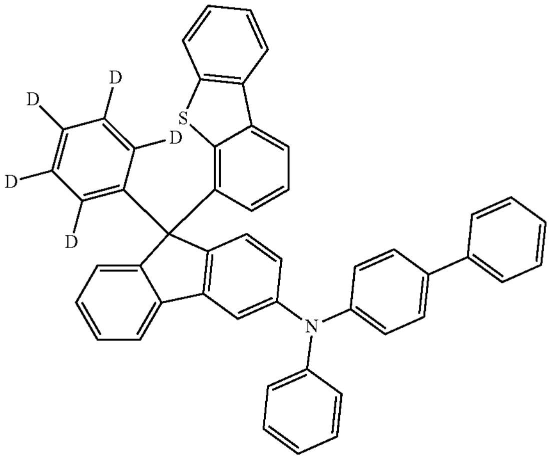
9
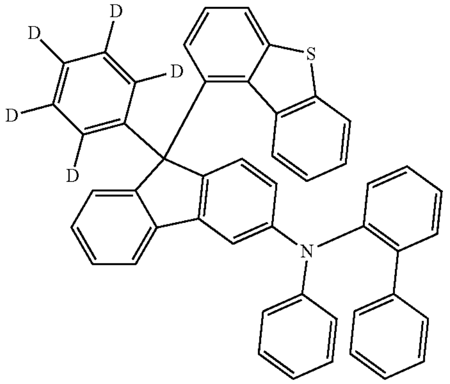
-continued
10
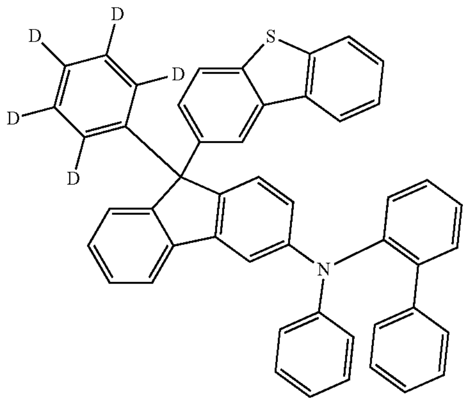
11
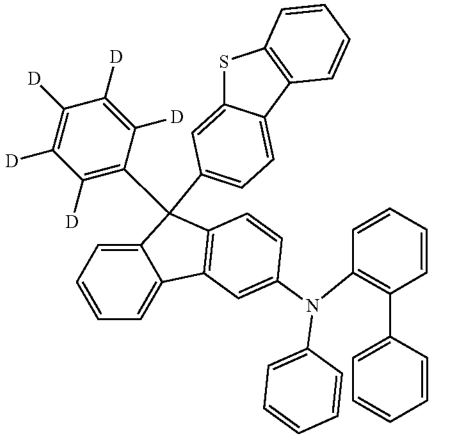
12
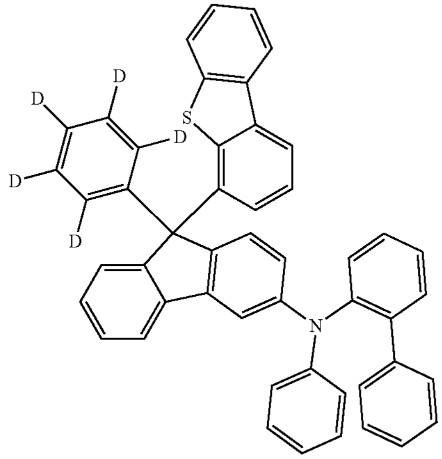

-continued
13
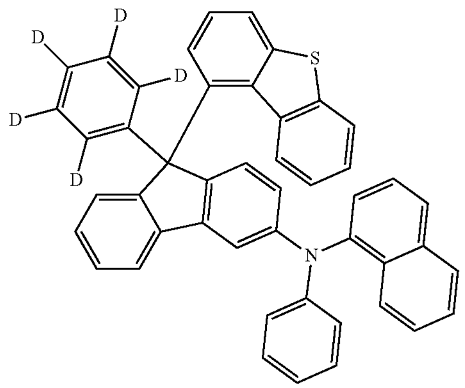
14
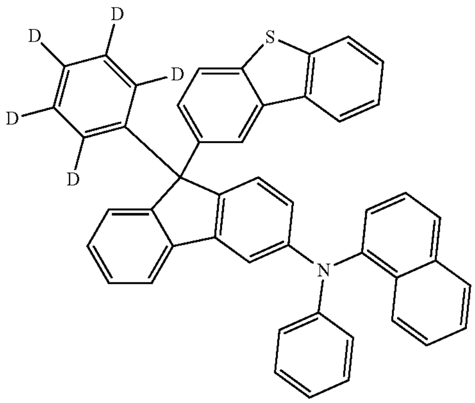
15
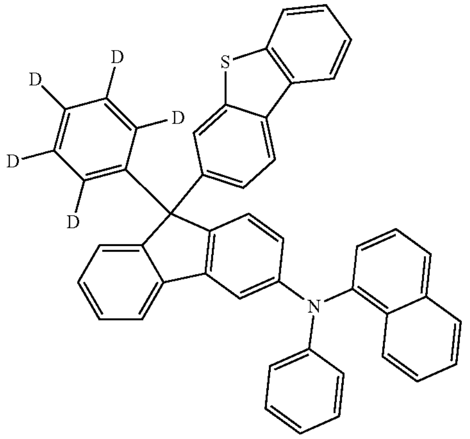
-continued
16
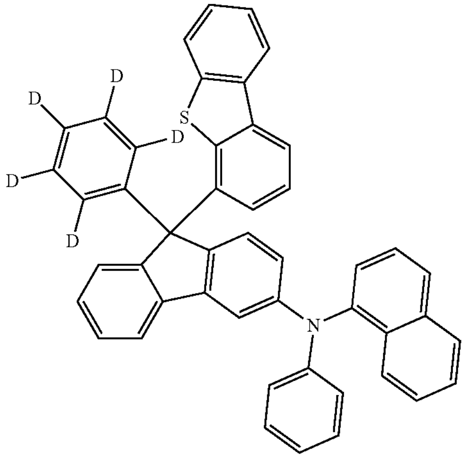
17
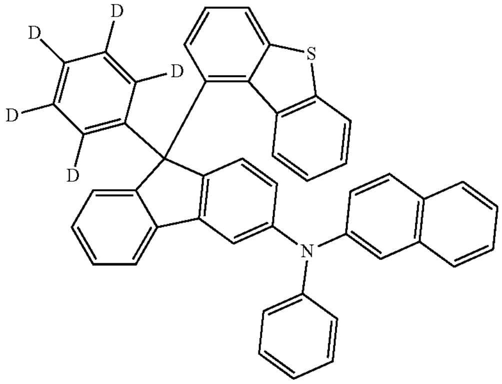
18
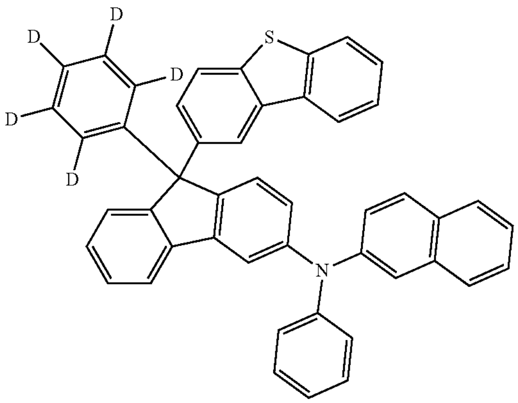

-continued
19
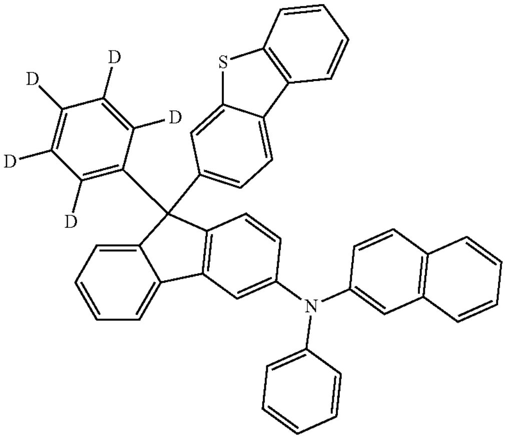
20
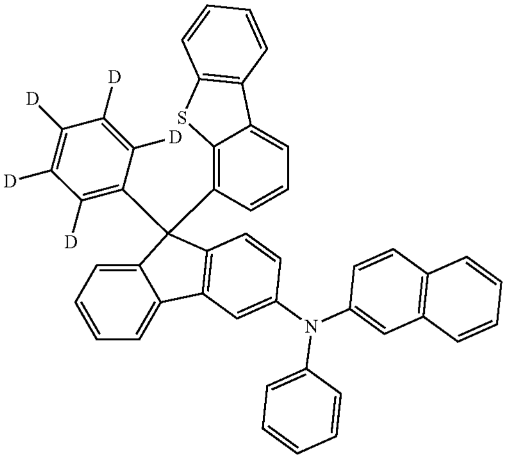
21
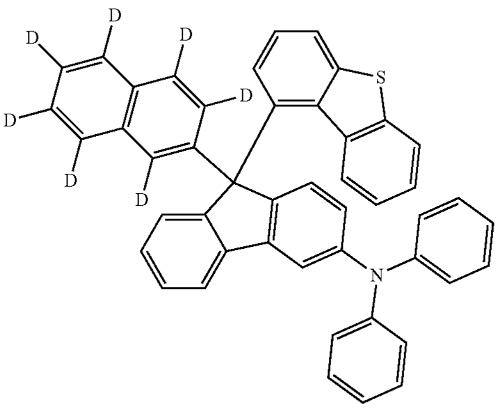
-continued
22
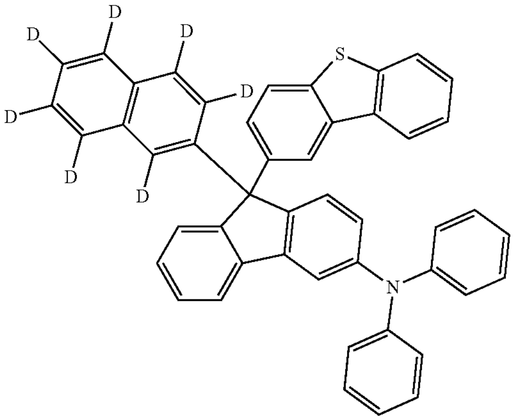
23
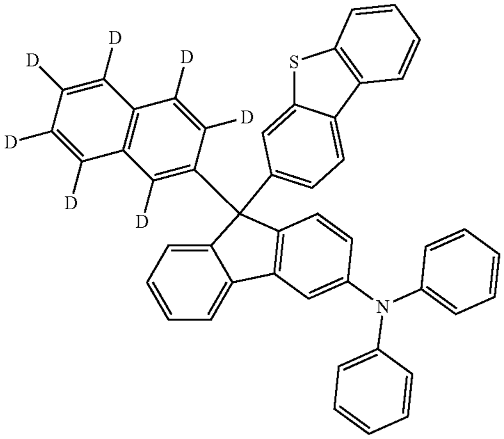
24
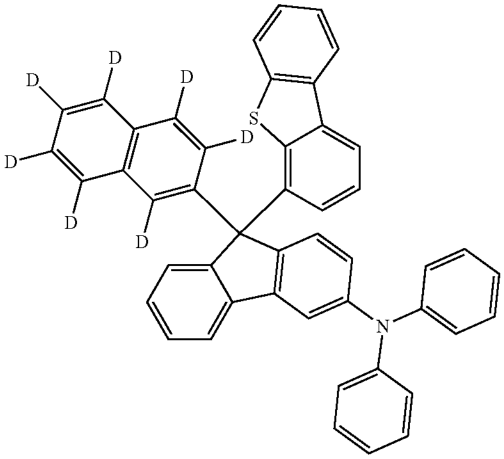

-continued
25
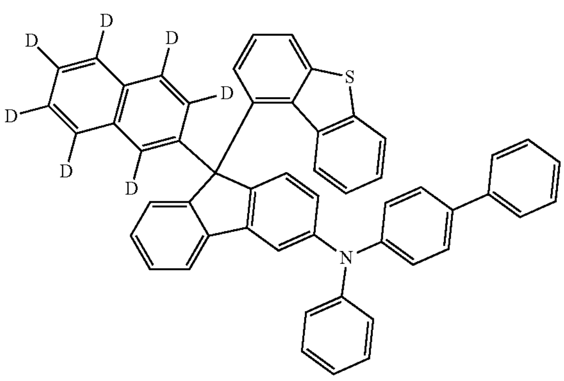
26
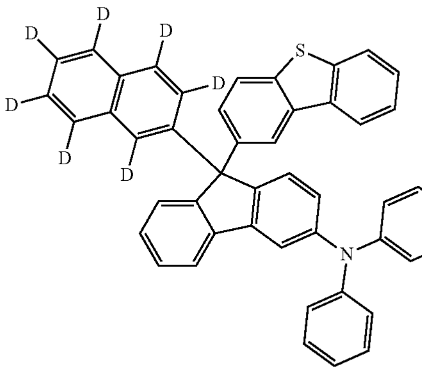
27
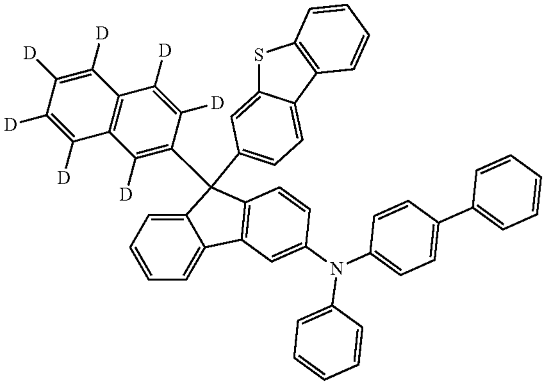
28
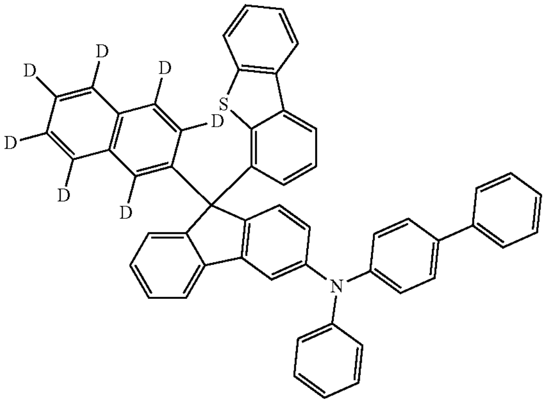
-continued
29
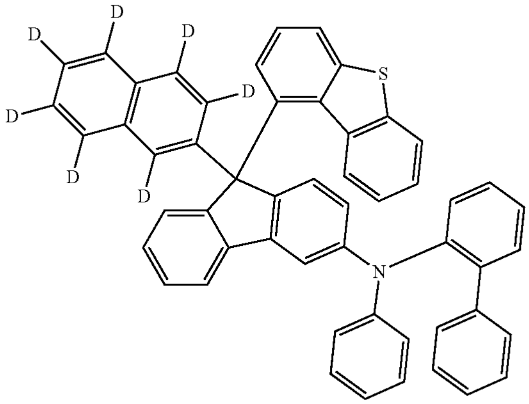
30
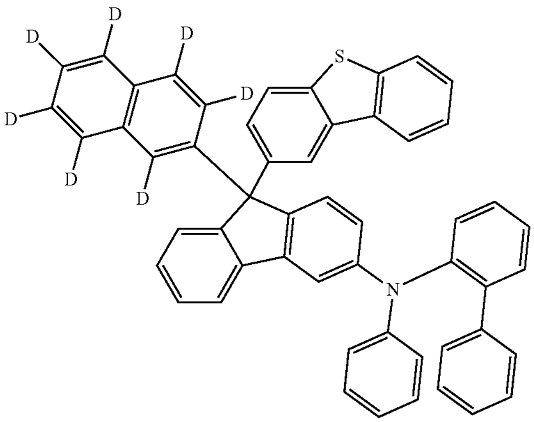
31
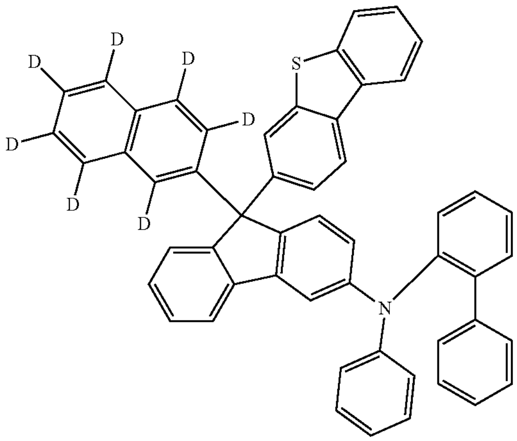

-continued
32
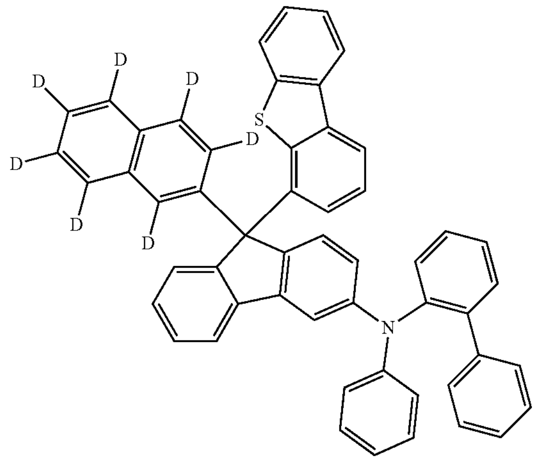
33
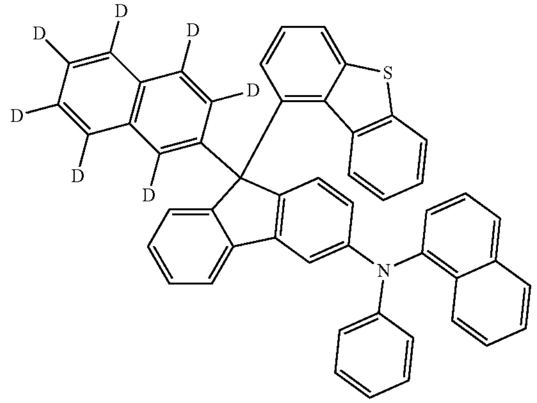
34
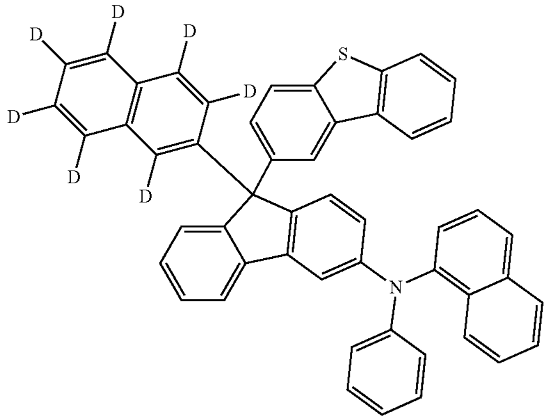
-continued
35
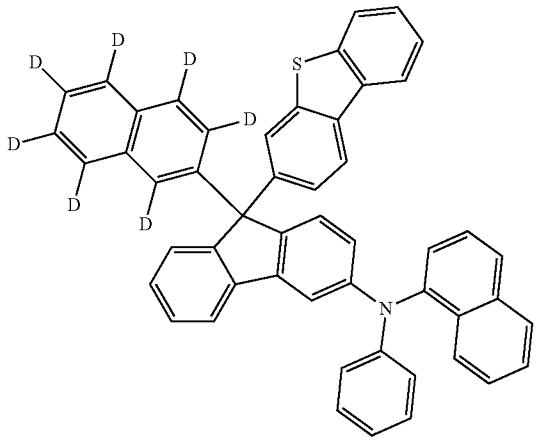
36
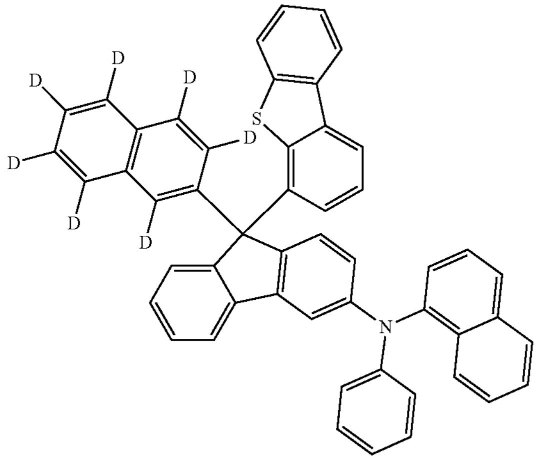
37
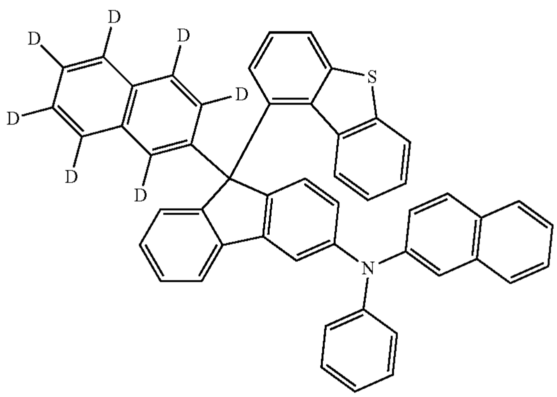

-continued
38
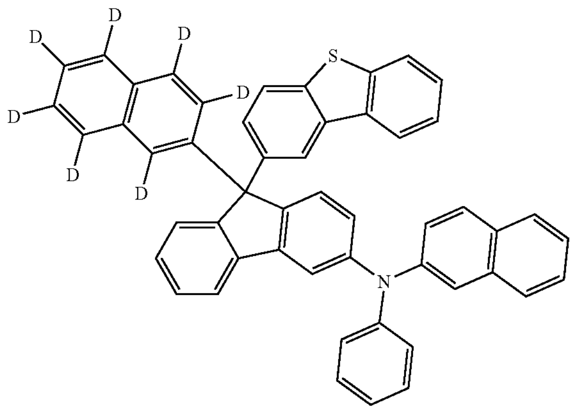
39
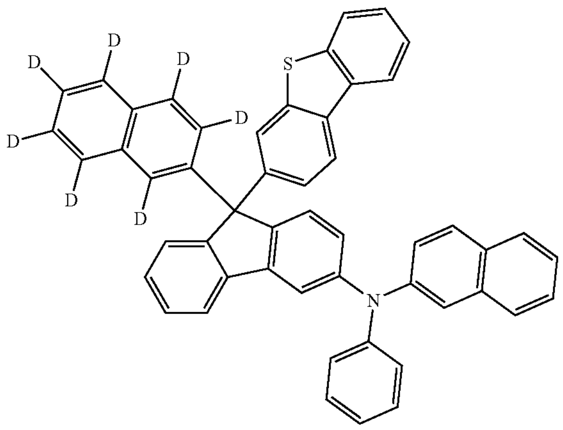
40
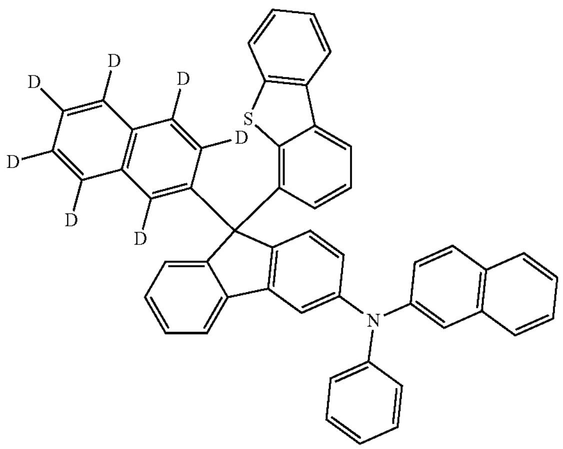
-continued
41
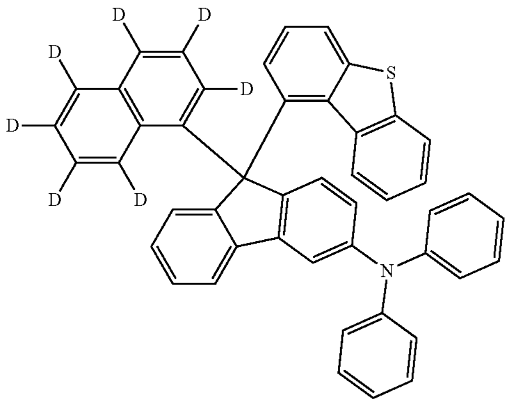
42
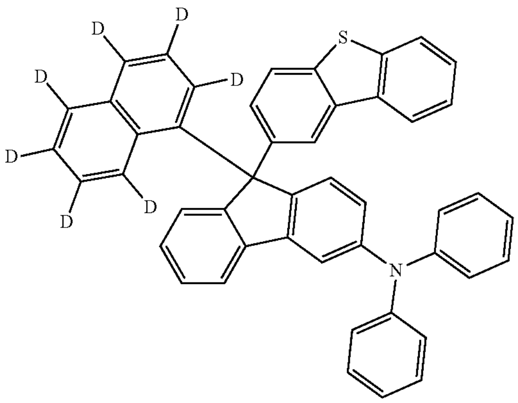
43
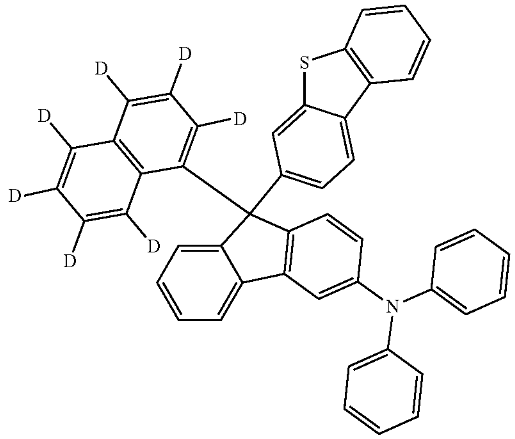

-continued
44
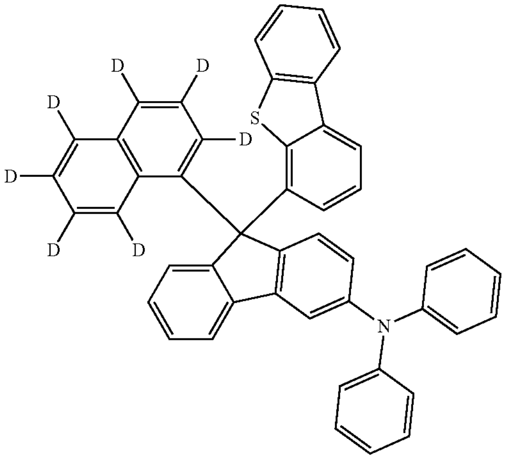
45
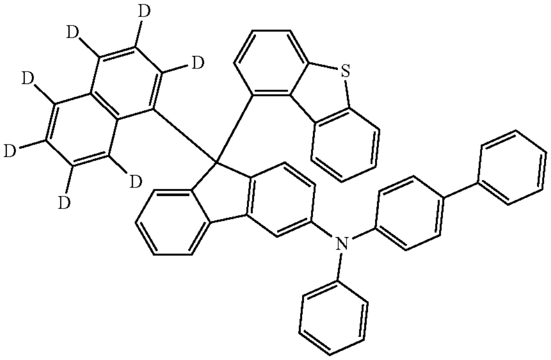
46
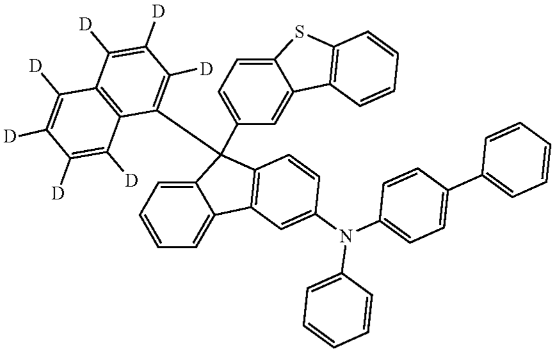
47
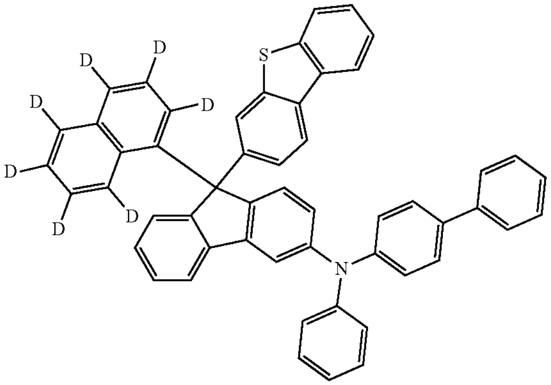
-continued
48
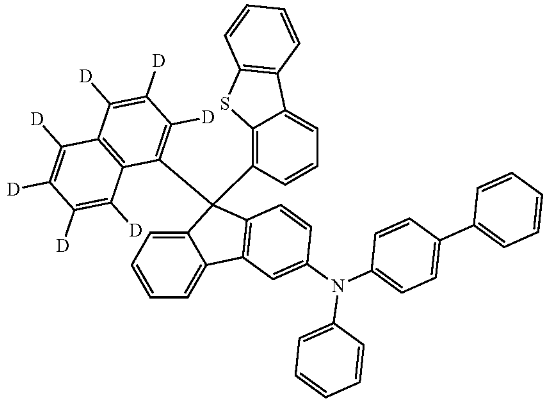
49
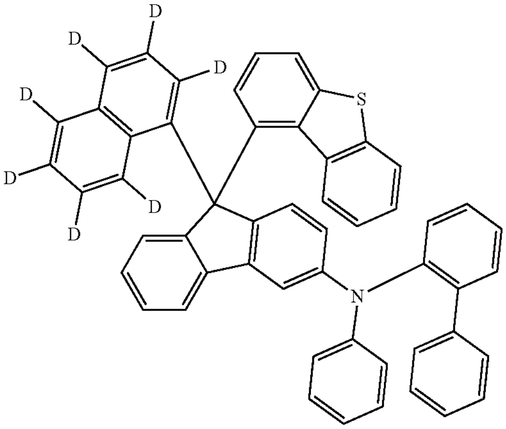
50
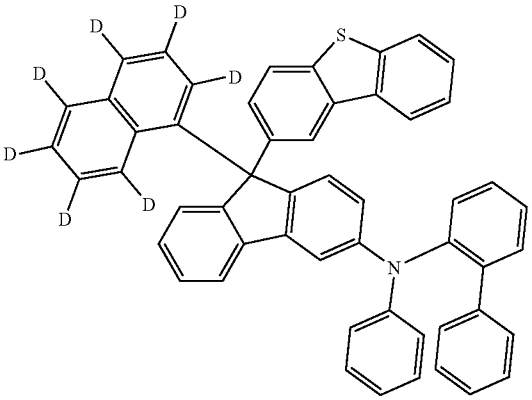

-continued
51
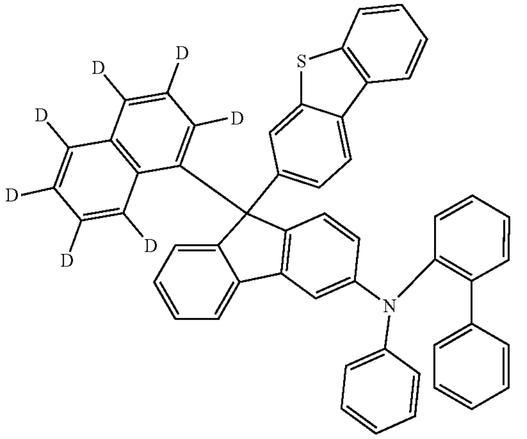
52
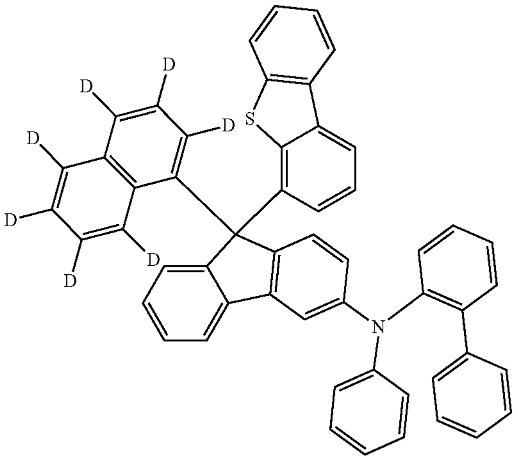
53
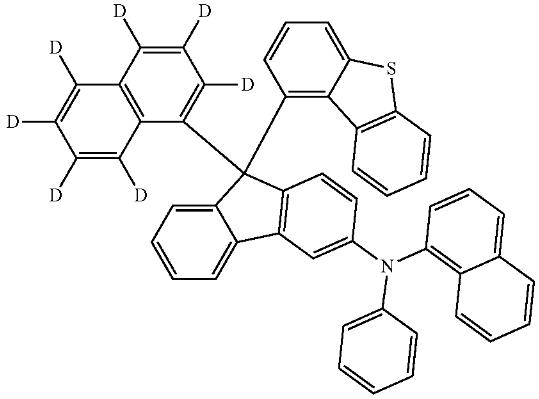
-continued
54
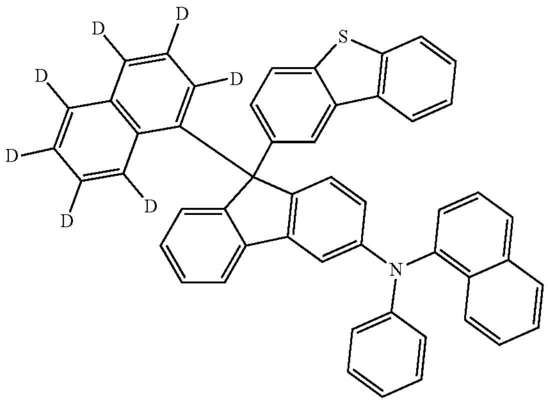
55
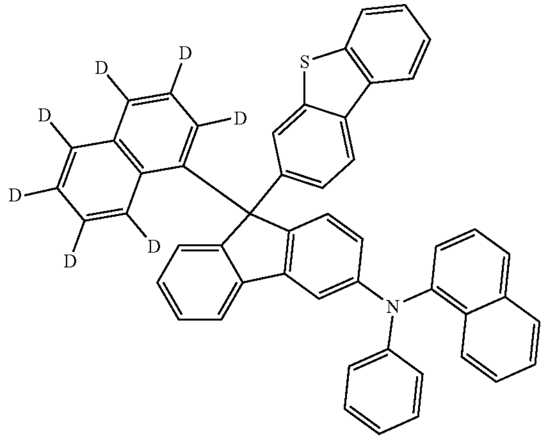
56
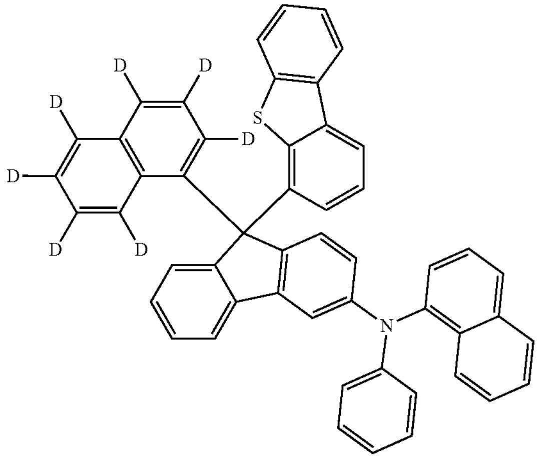

-continued
57
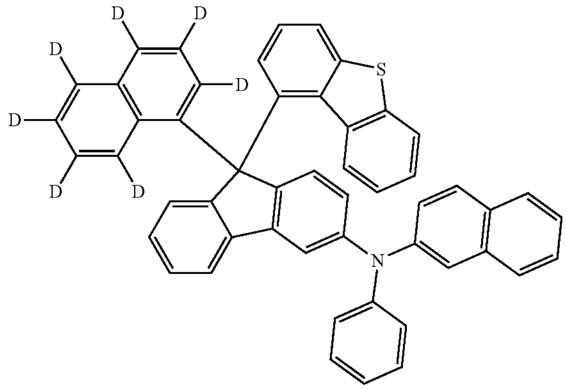
58
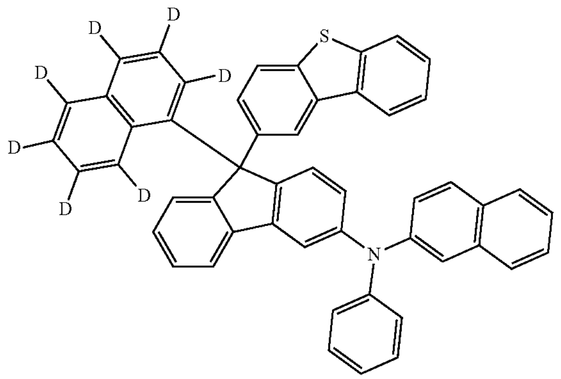
59
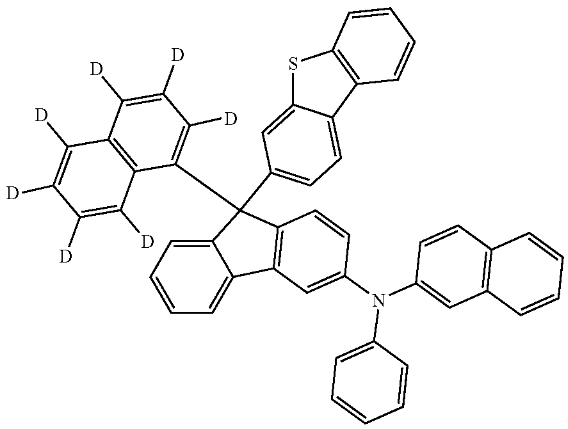
-continued
60
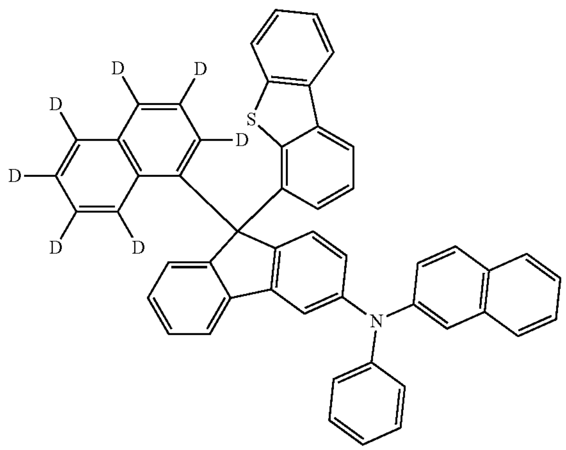
61
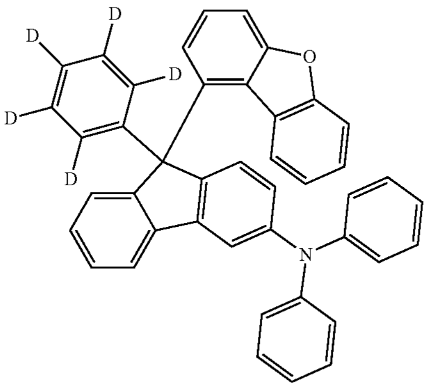
62
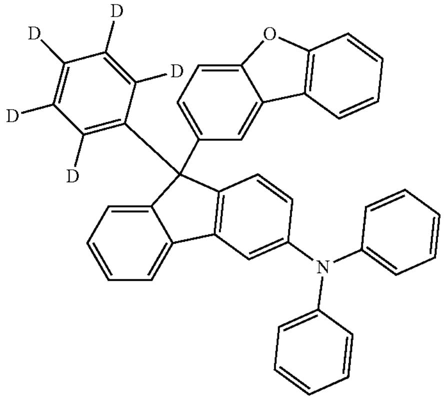

-continued
63
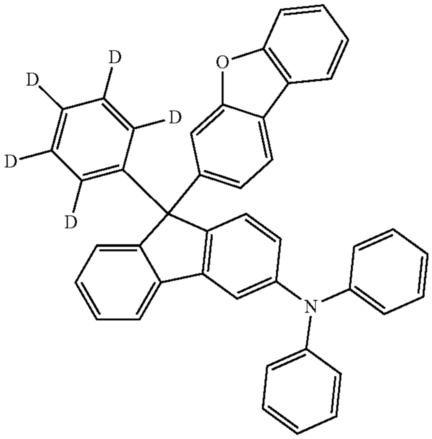
64
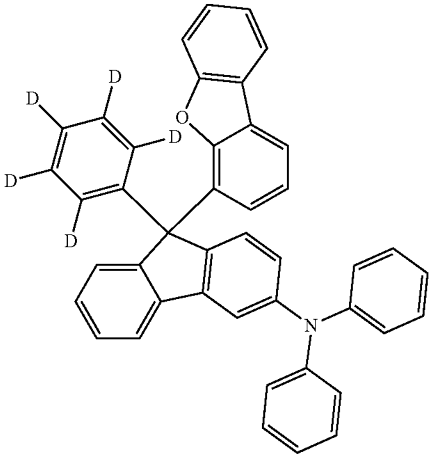
65
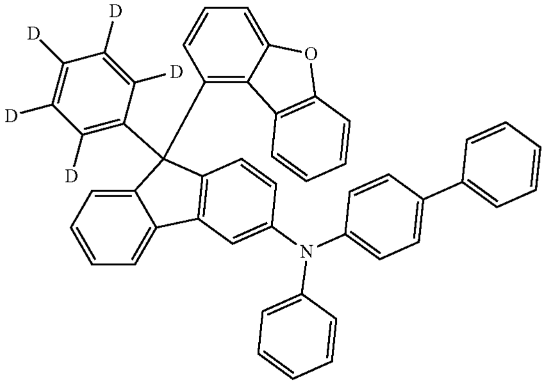
-continued
66
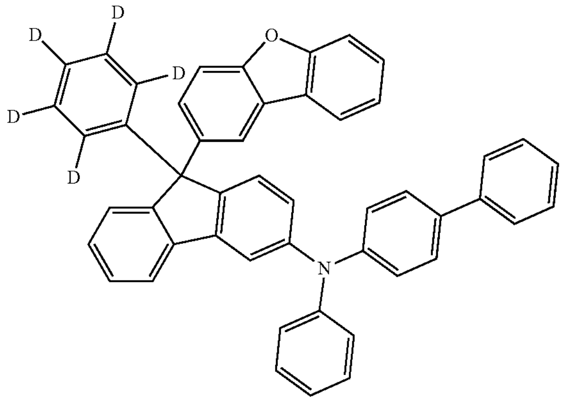
67
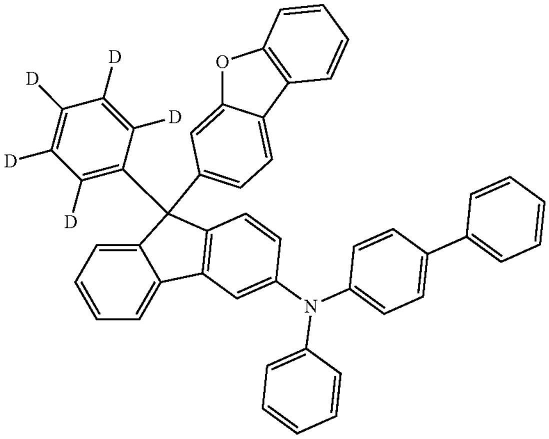
68
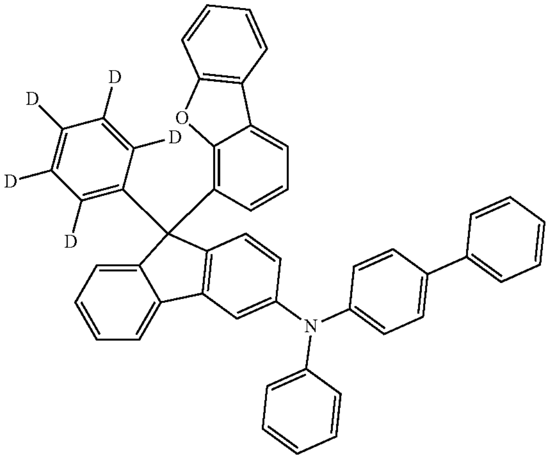

-continued
69
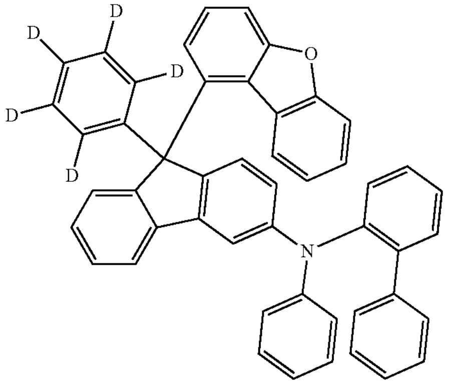
70
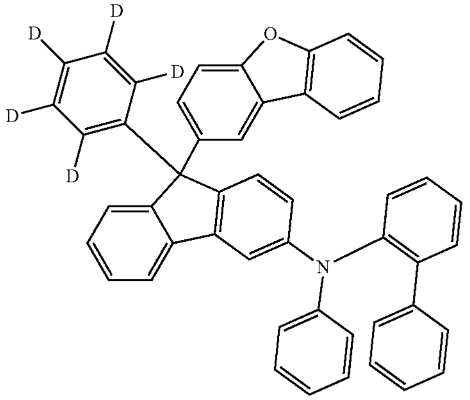
71
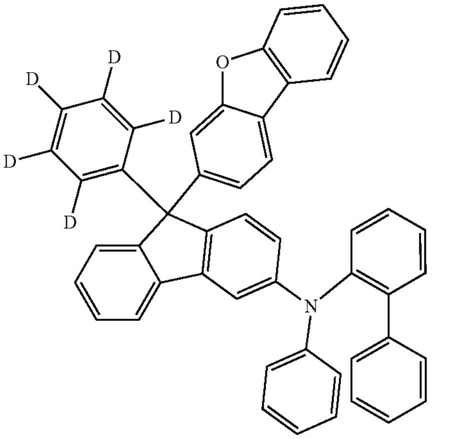
-continued
72
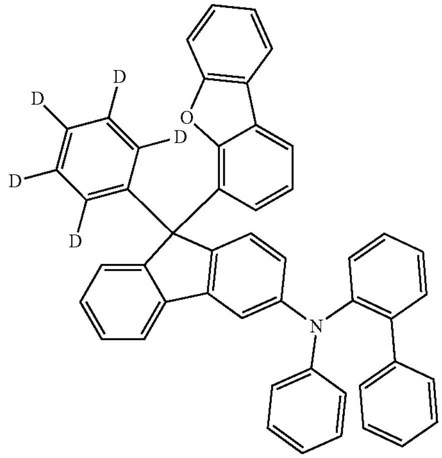
73
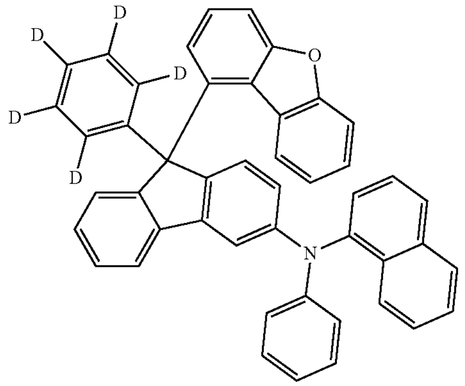
74
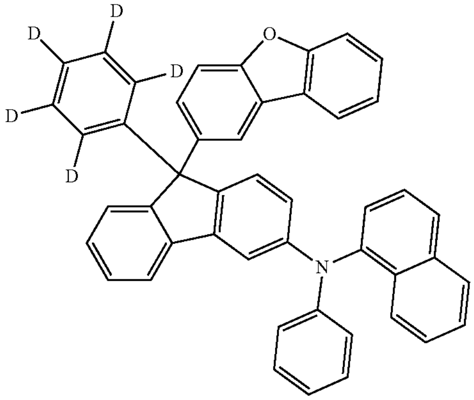

-continued
75
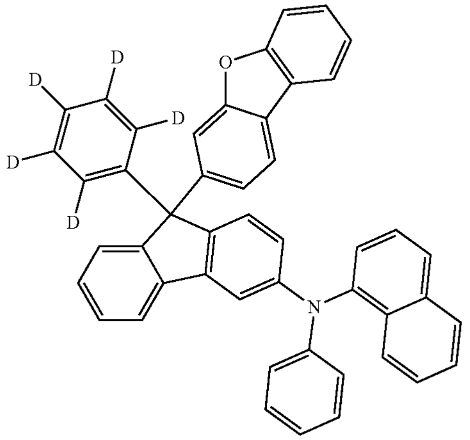
76
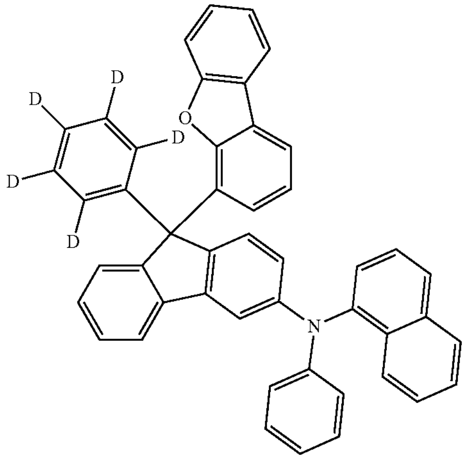
77
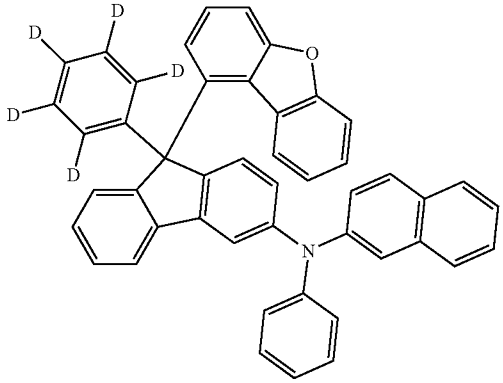
-continued
78
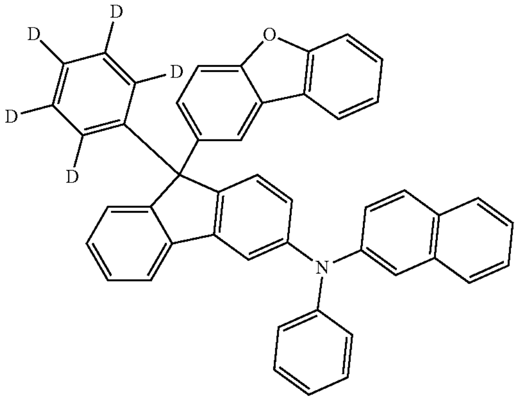
79
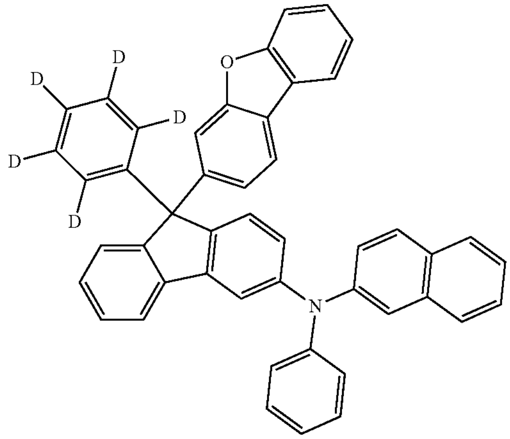
80
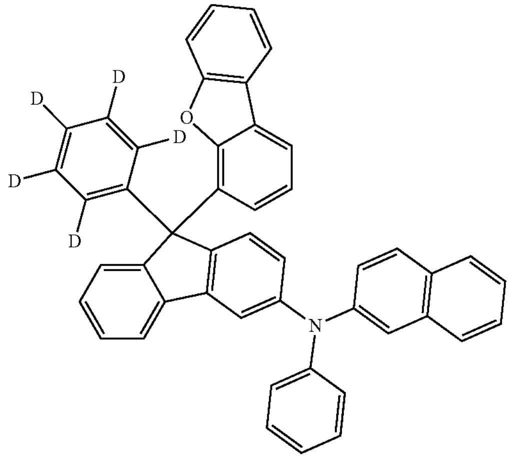

-continued
81
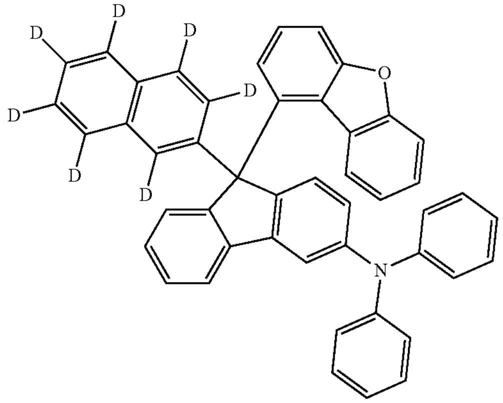
82
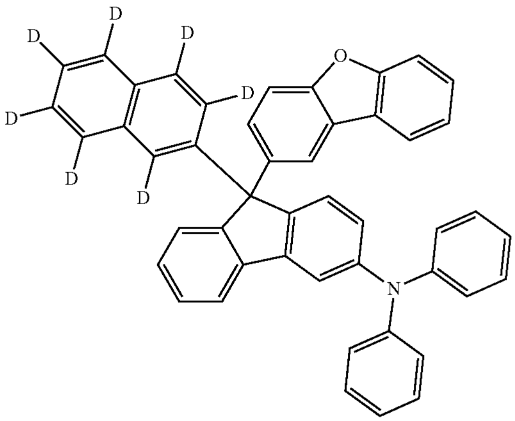
83
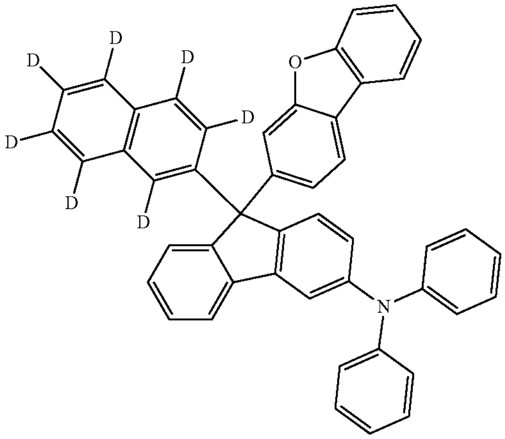
-continued
84
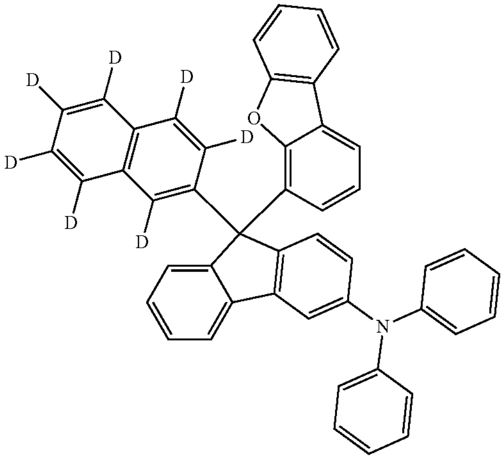
85
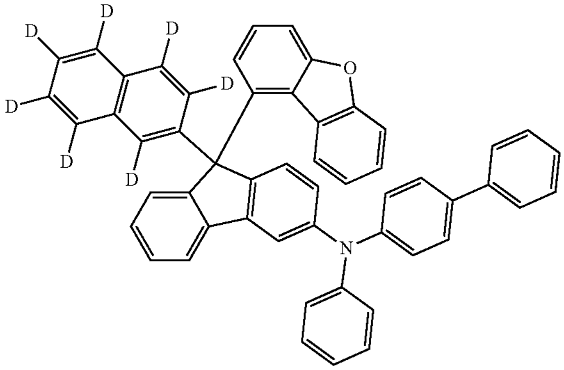
86
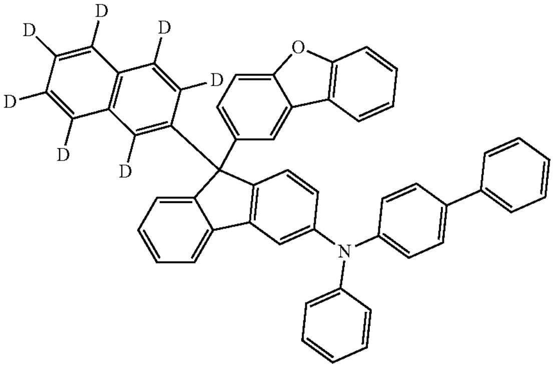
87
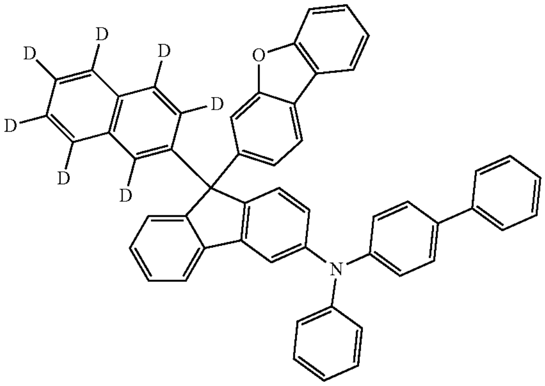

-continued
88
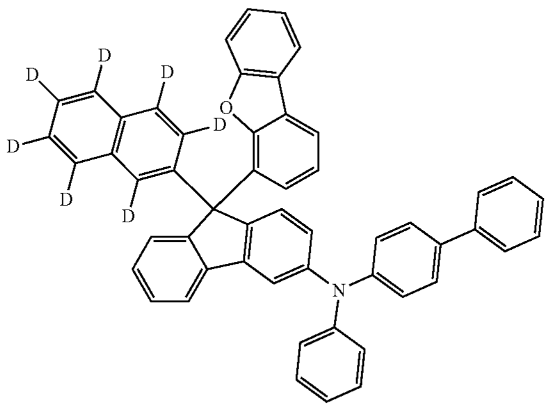
89
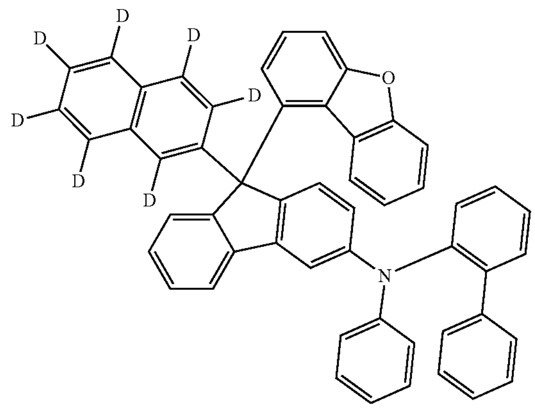
90
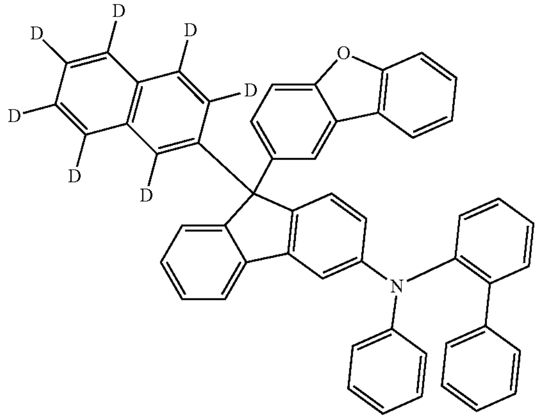
-continued
91
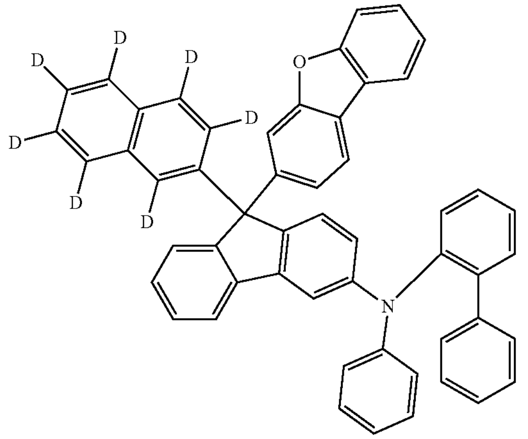
92
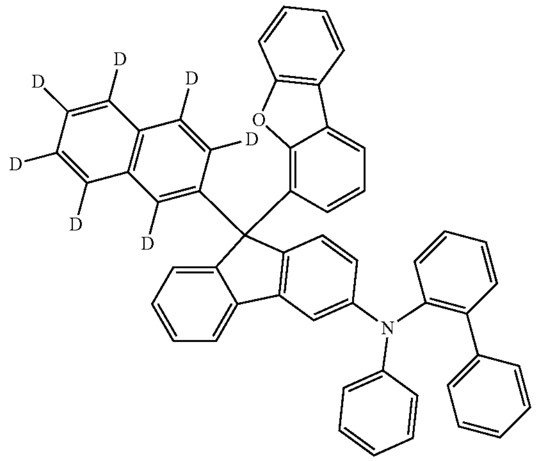
93
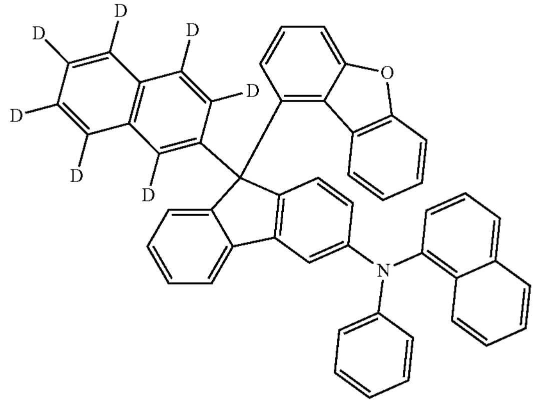

-continued
94
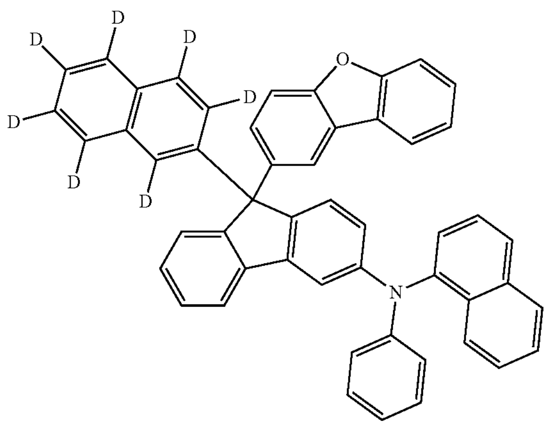
95
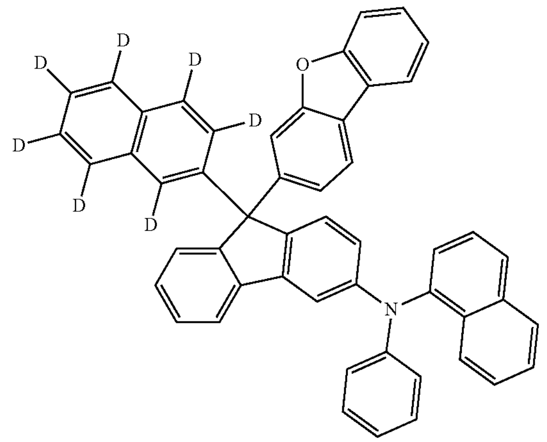
96
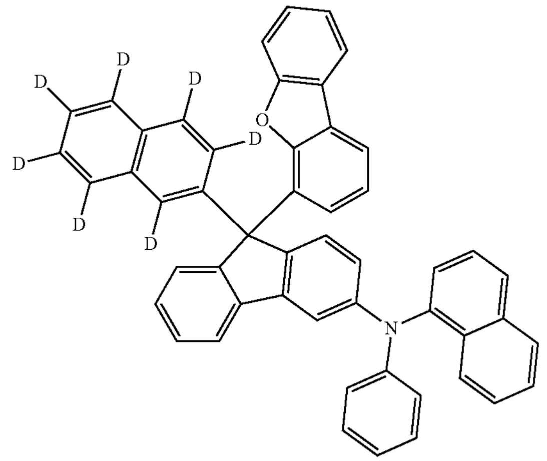
-continued
97
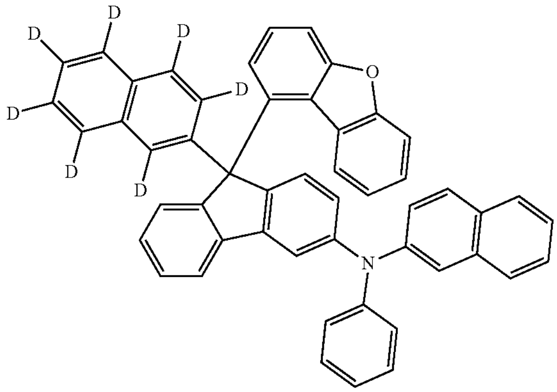
98
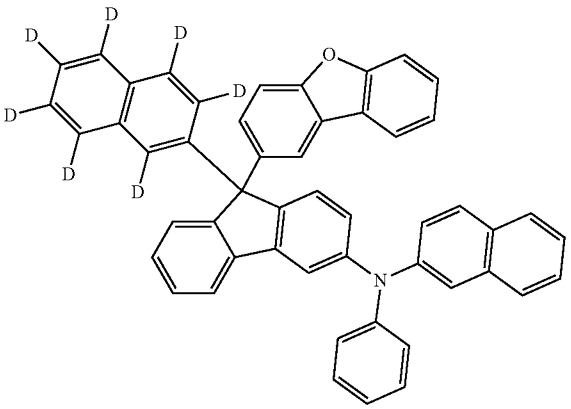
99
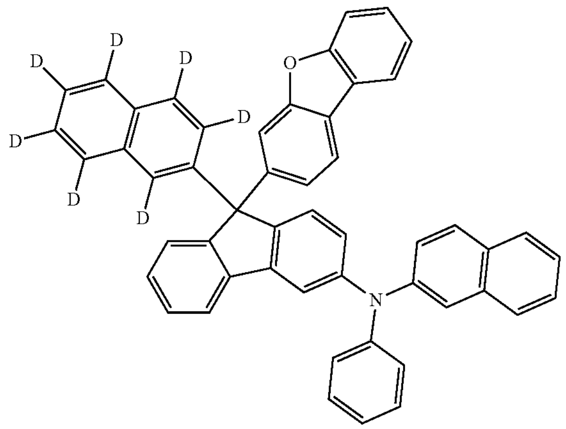

-continued
100
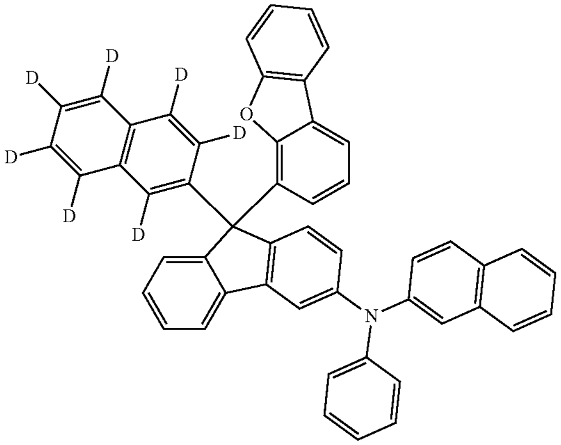
101
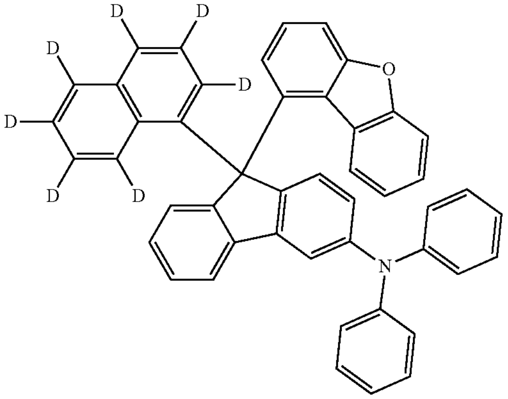
102
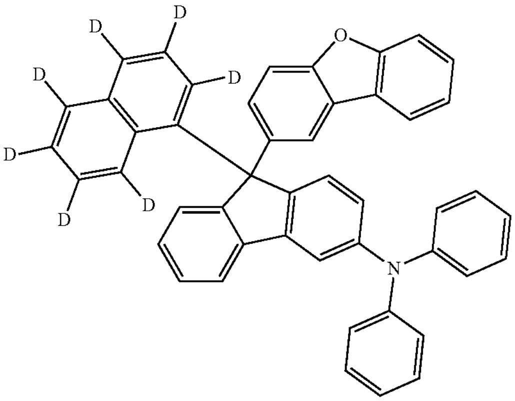
-continued
103
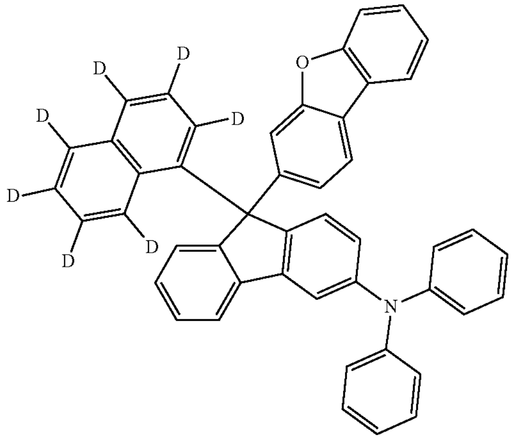
104
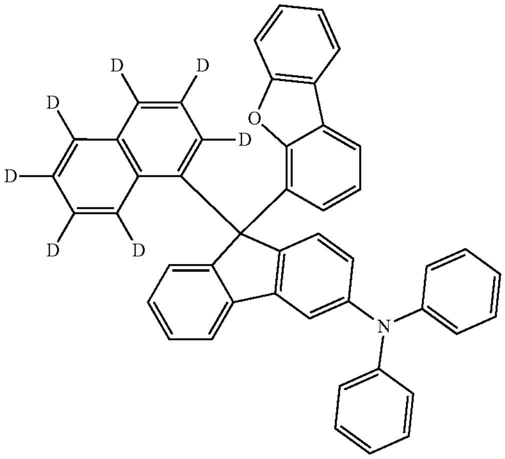
105
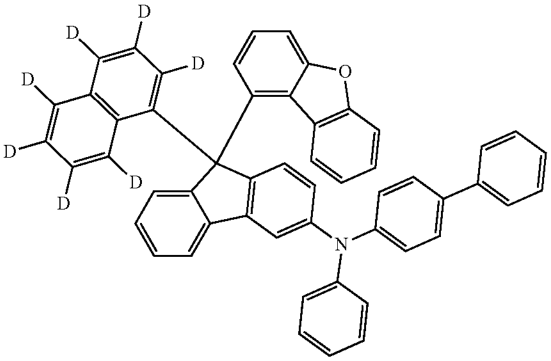
106
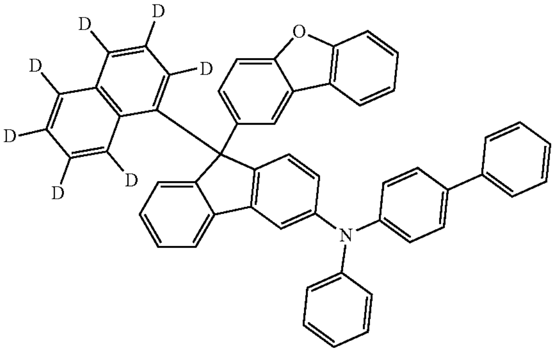

-continued
107
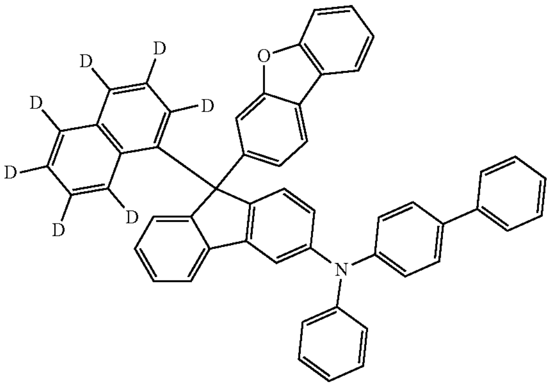
108
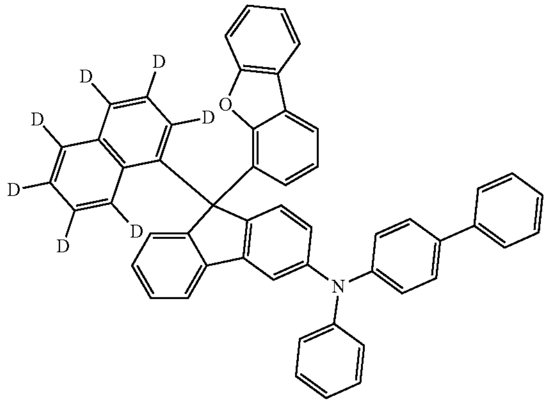
109
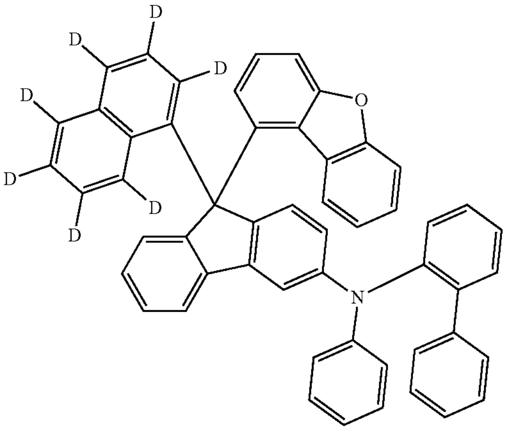
-continued
110
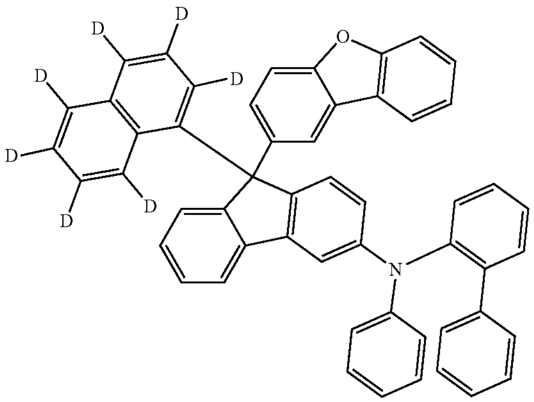
111
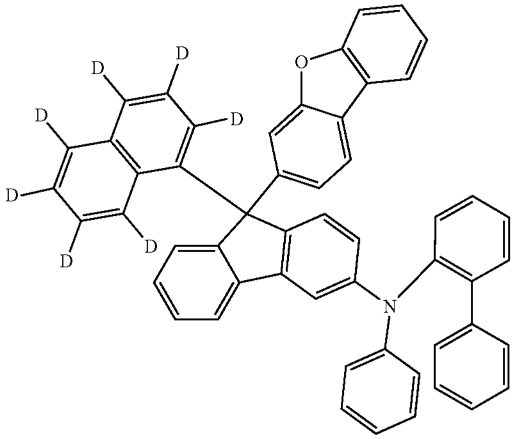
112
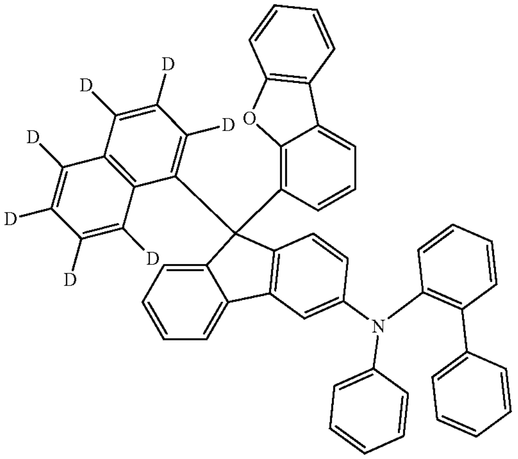

-continued
113
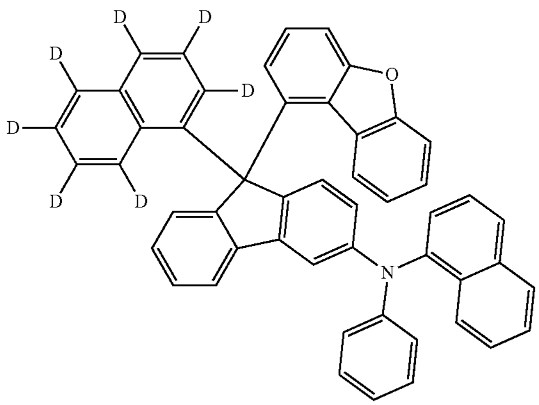
114
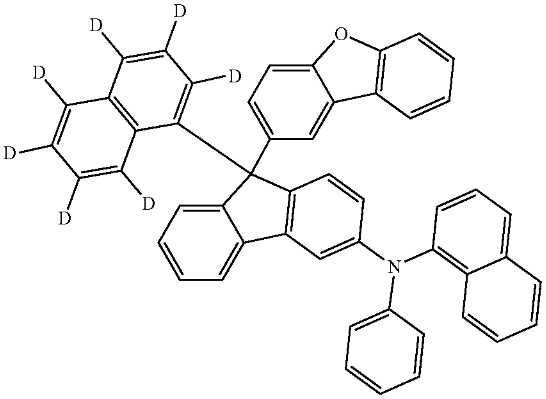
115
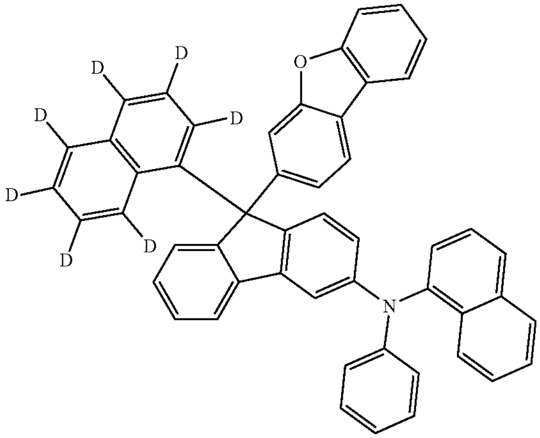
-continued
116
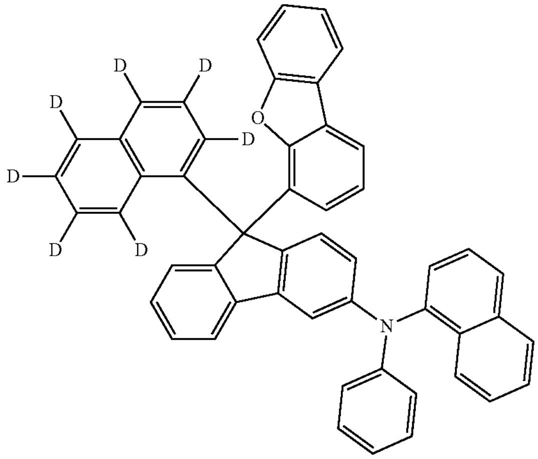
117
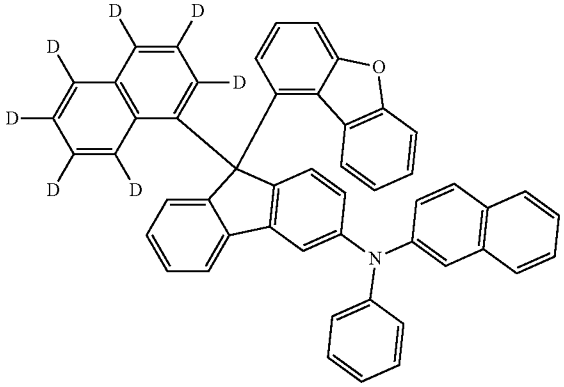
118
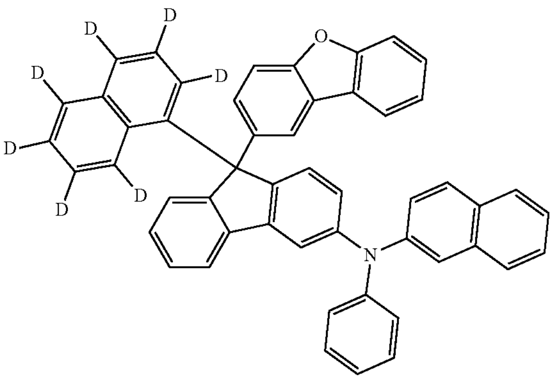

-continued
119
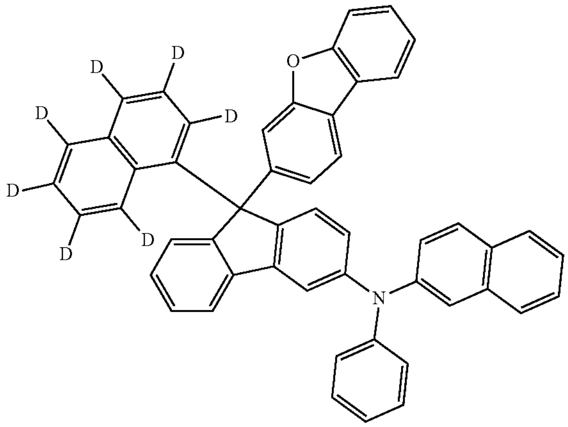
120
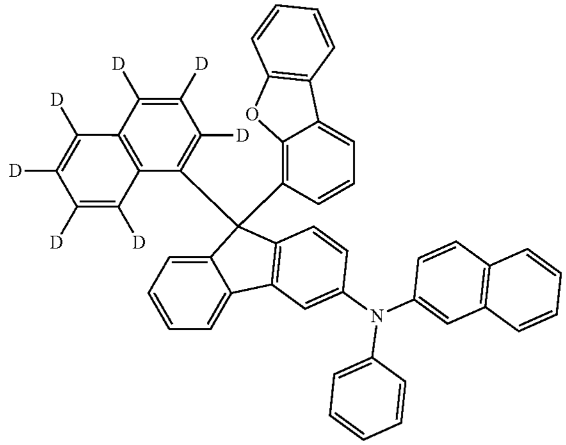
121
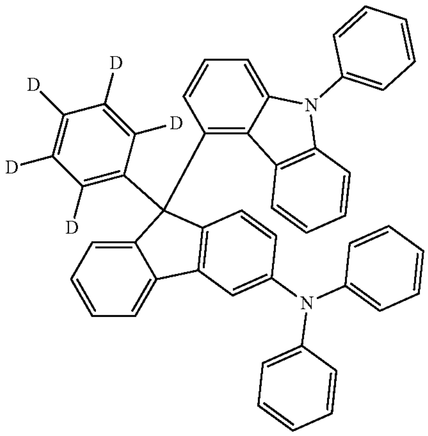
-continued
122
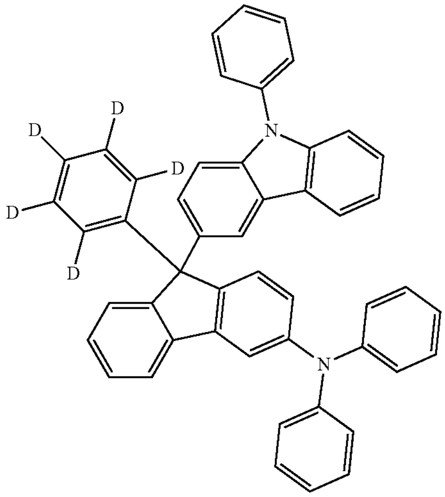
123
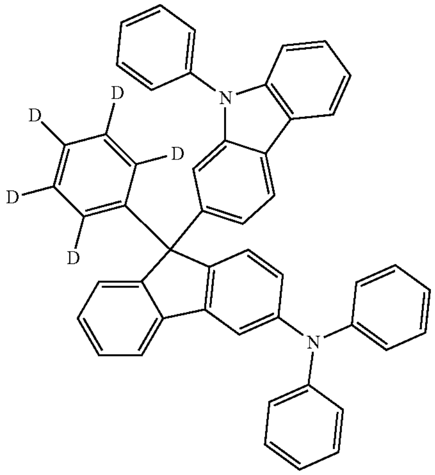
124
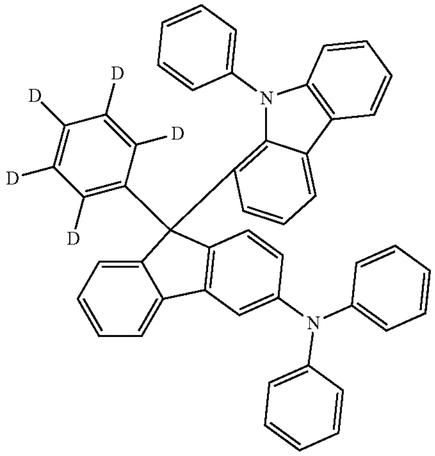

-continued
125
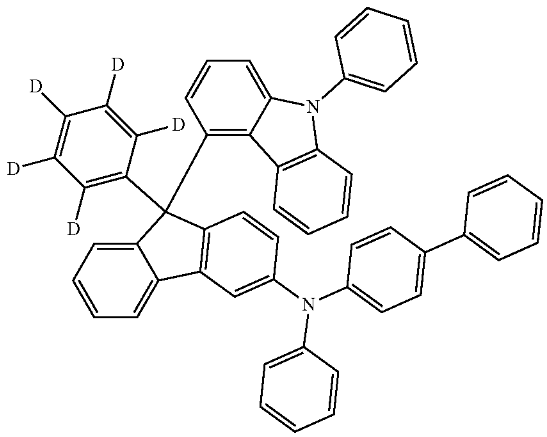
126
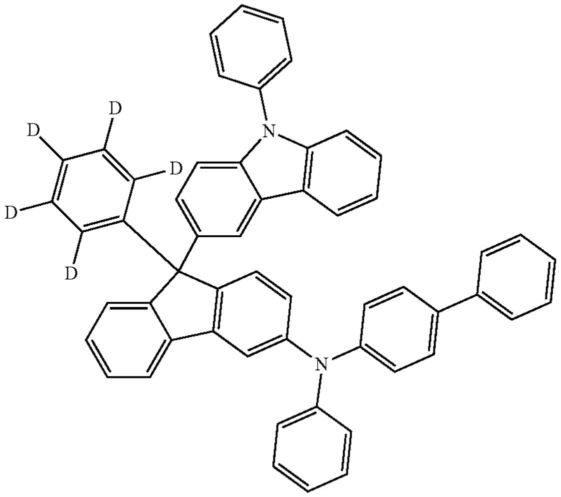
127
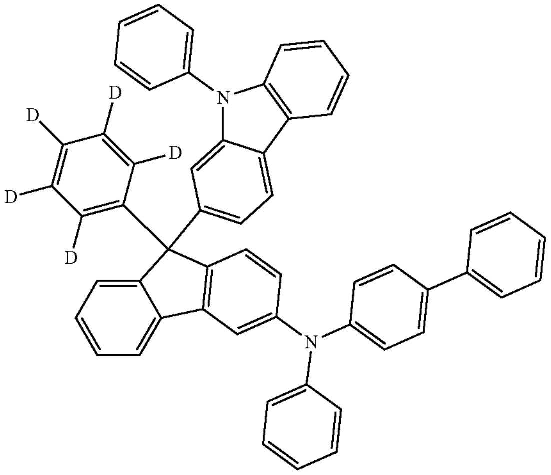
-continued
128
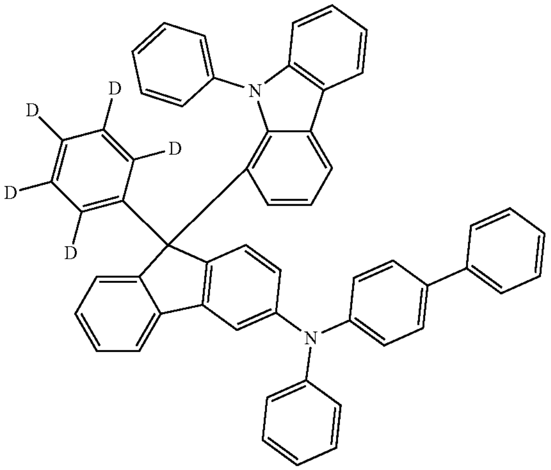
129
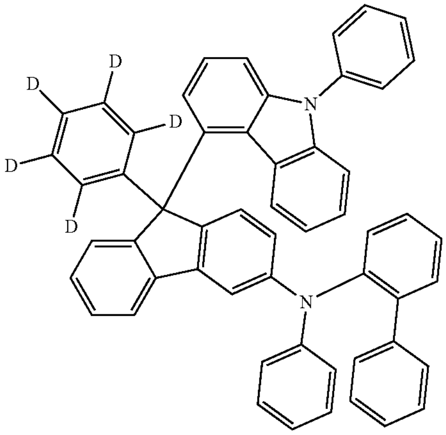
130
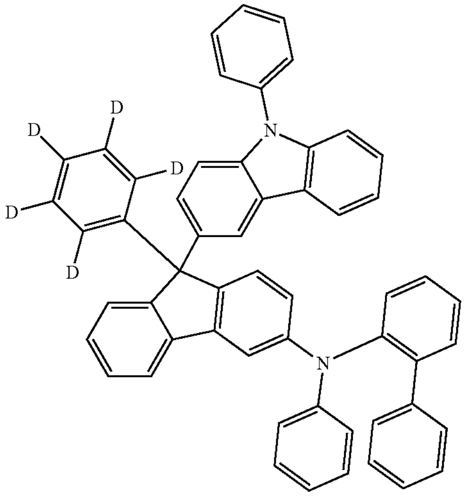

-continued
131
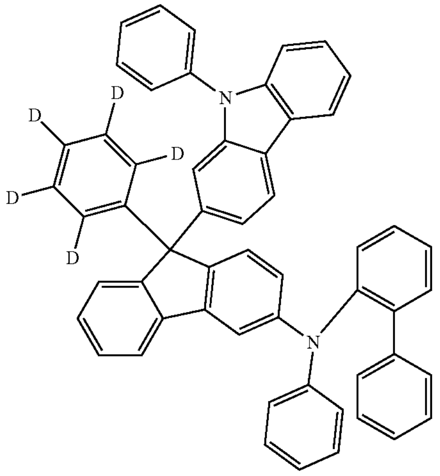
132
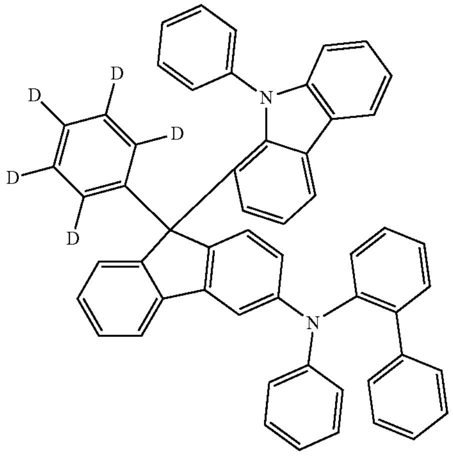
133
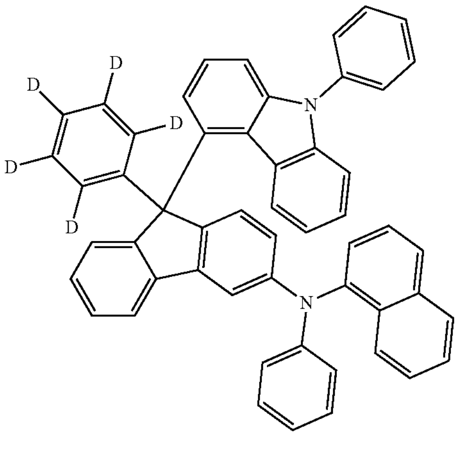
-continued
134
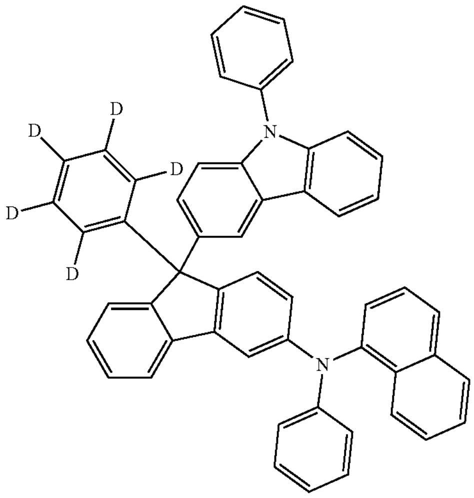
135
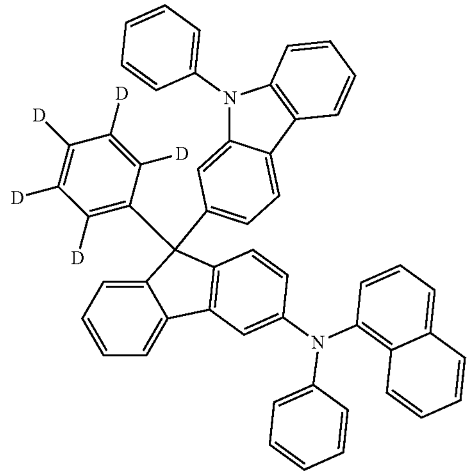
136
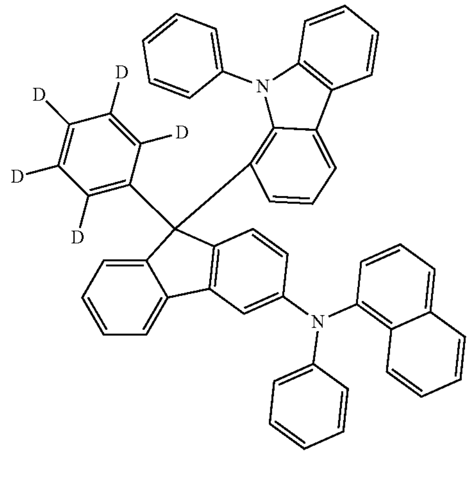

-continued
137
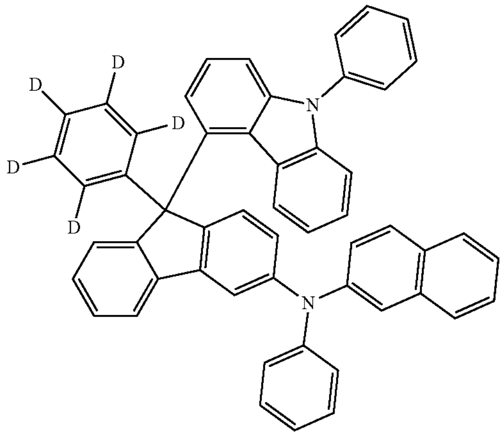
138
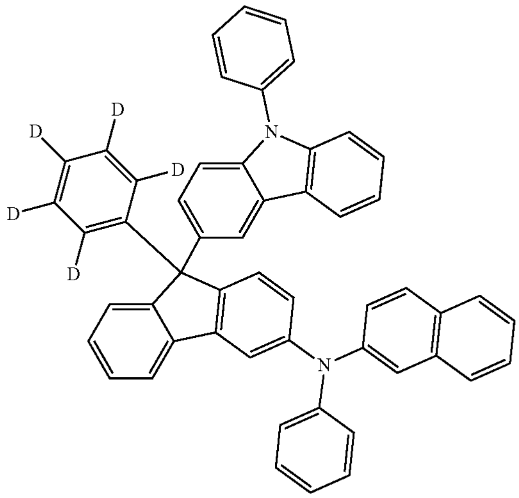
139
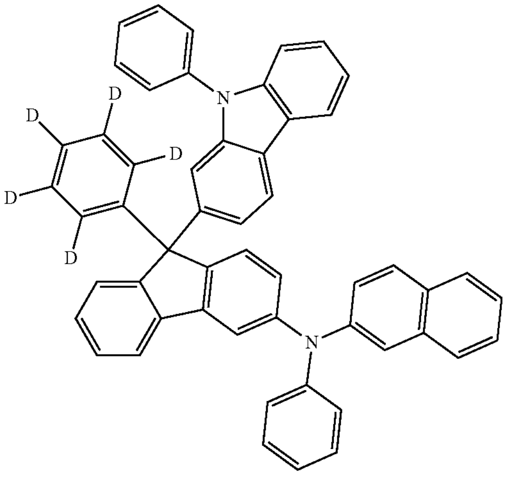
-continued
140
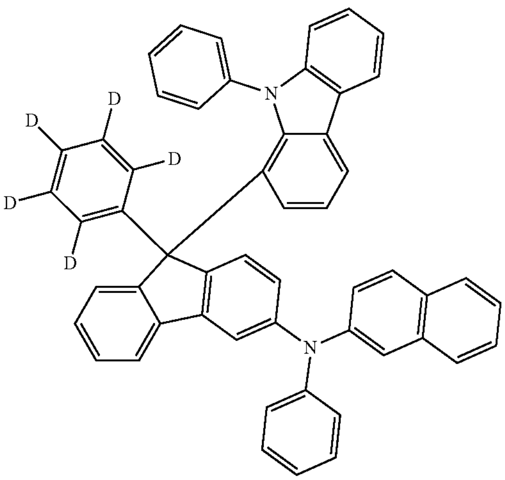
141
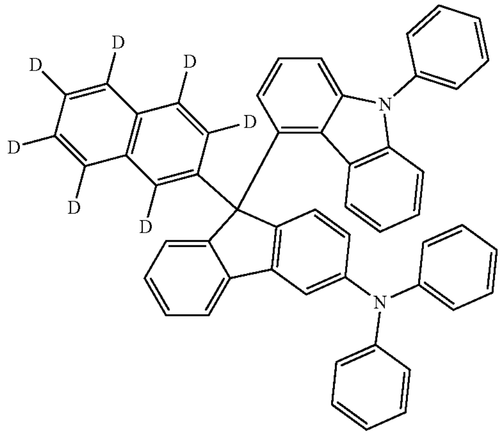
142
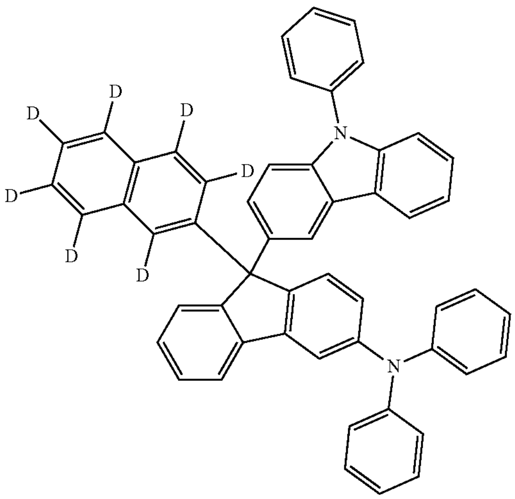

-continued
143
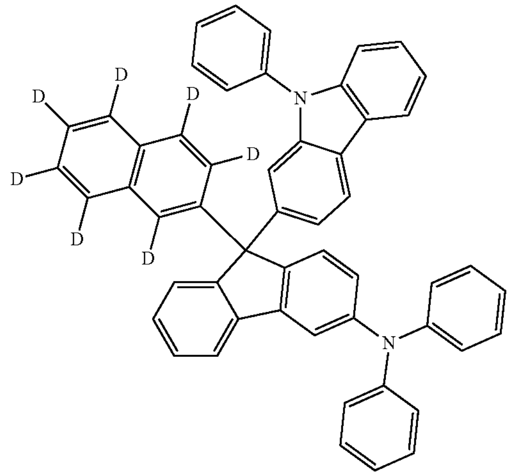
144
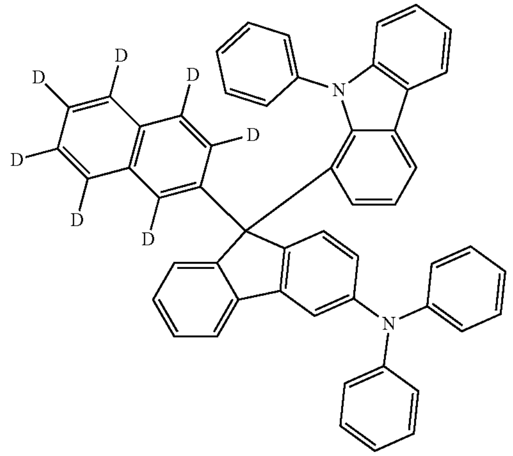
145
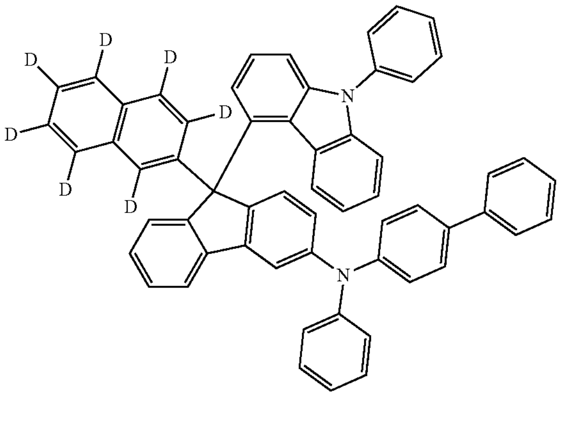
-continued
146
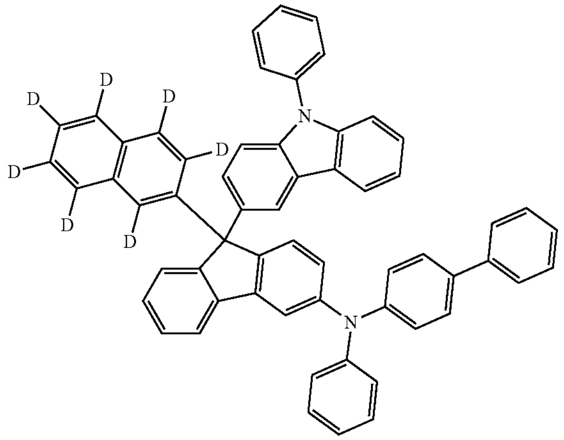
147
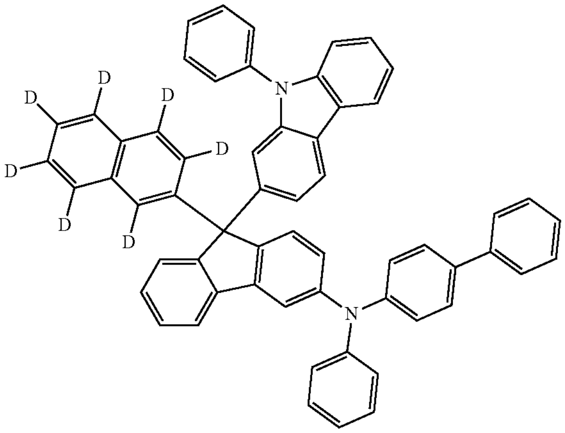
148
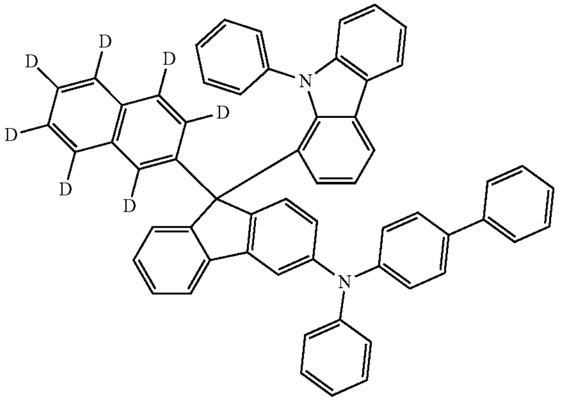

-continued
149
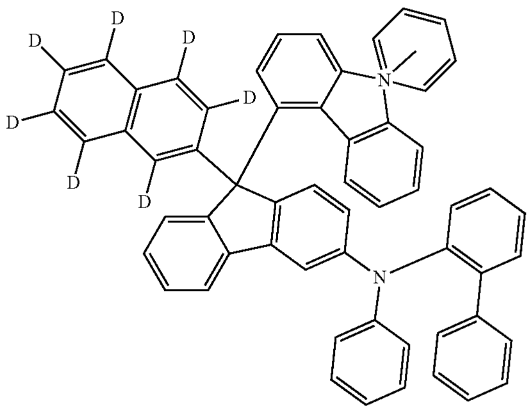
150
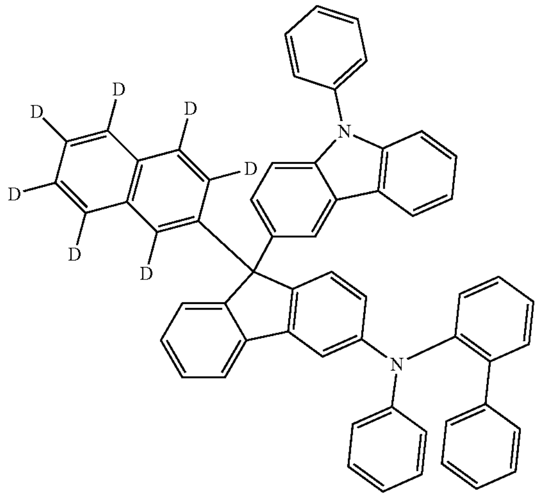
151
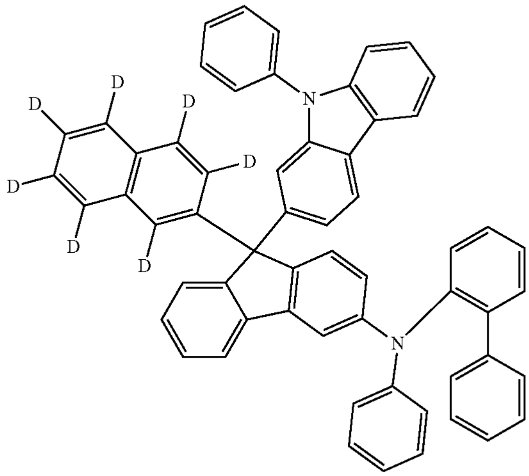
-continued
152
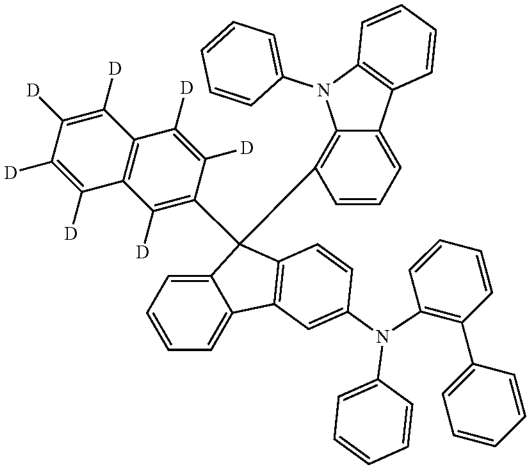
153
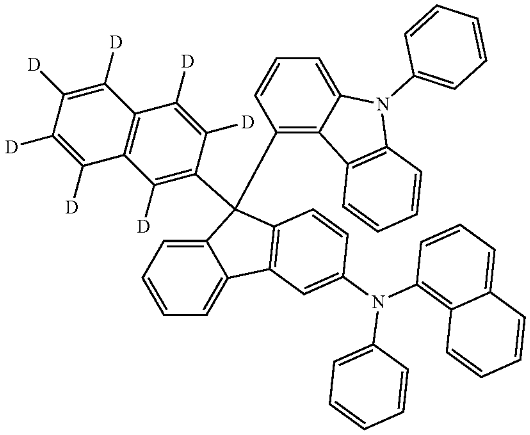
154
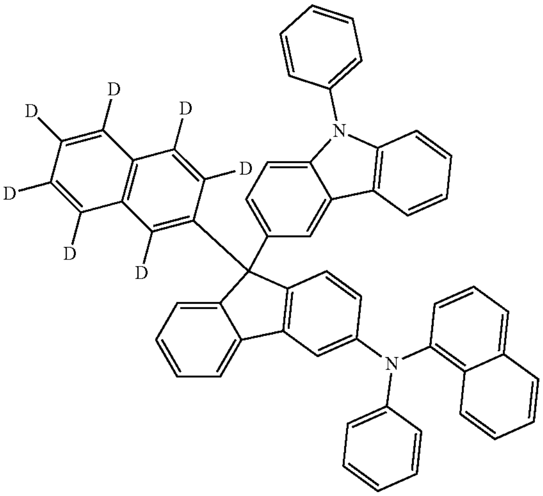

155
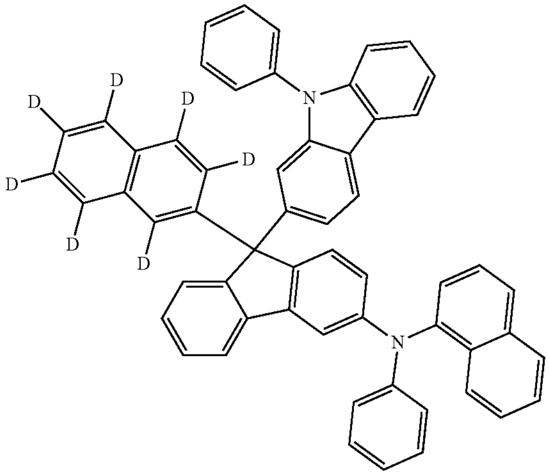
156
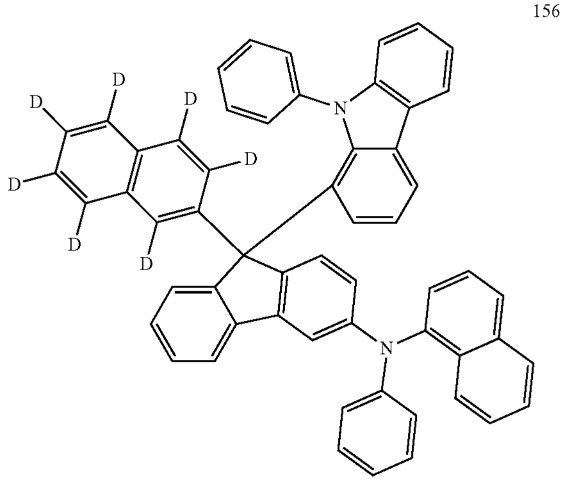
157
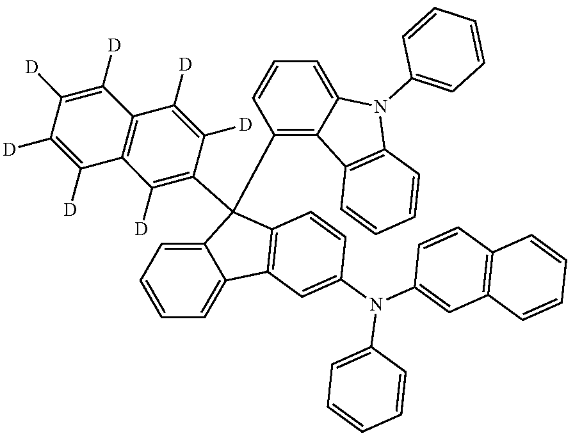
158
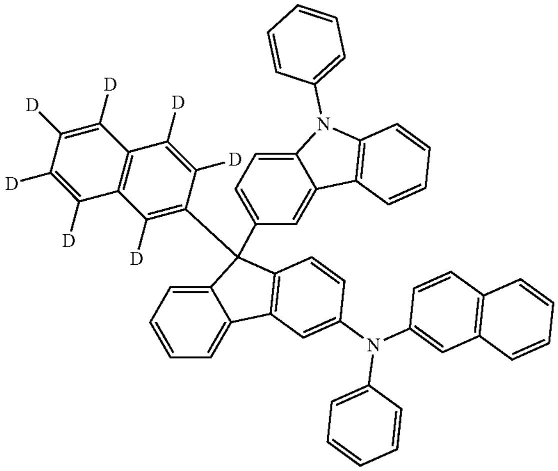
159
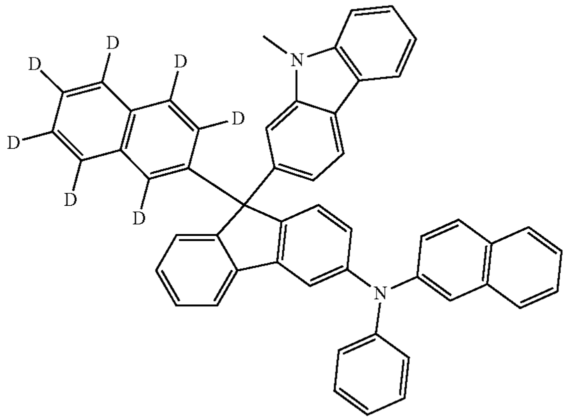
160
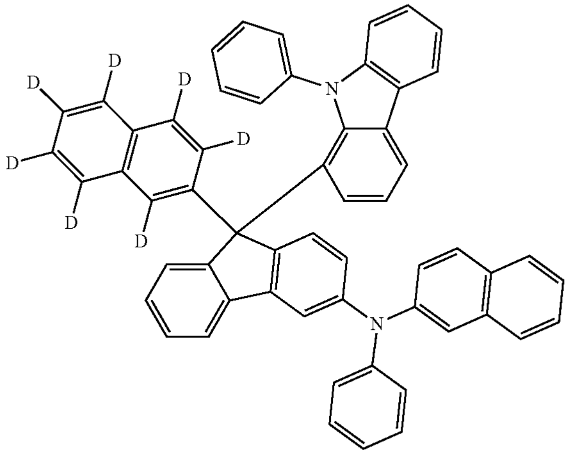

-continued
161
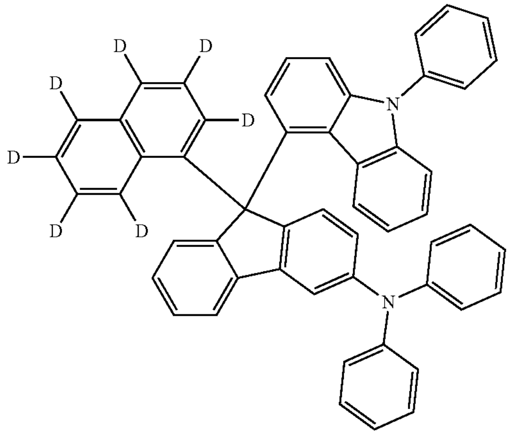
162
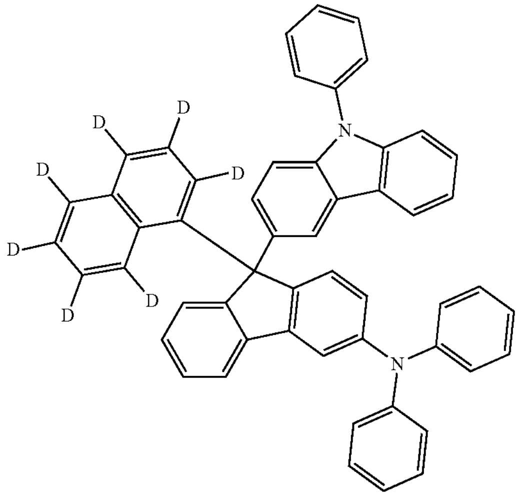
163
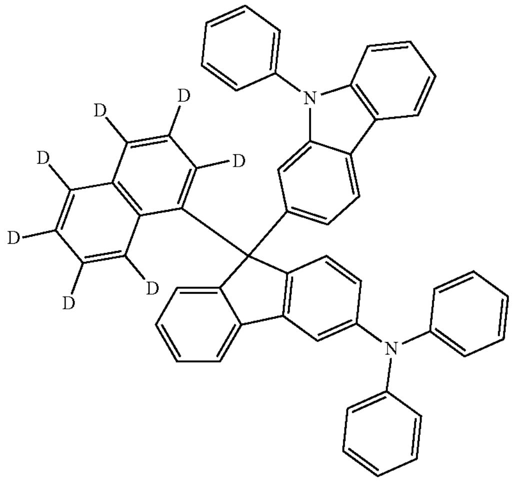
-continued
164
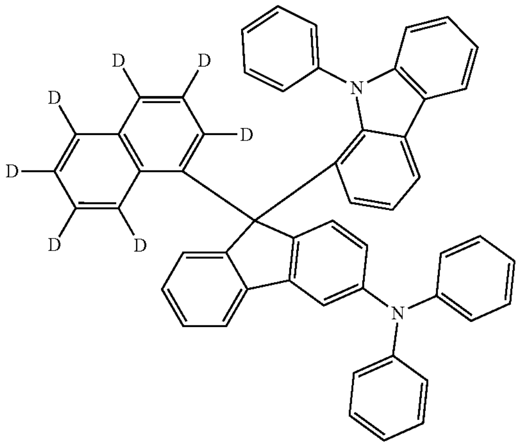
165
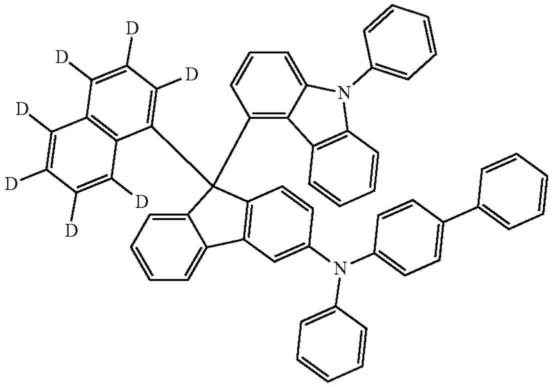
166
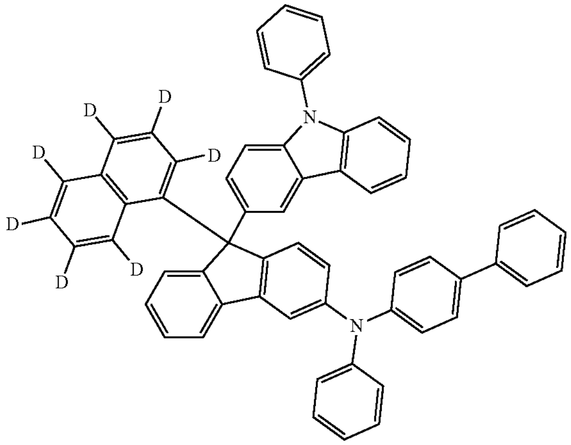

167
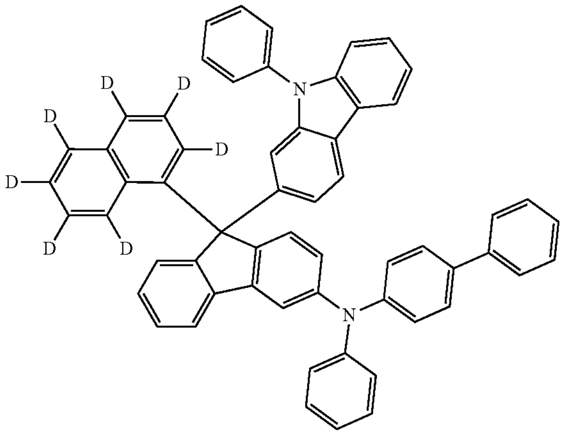
168
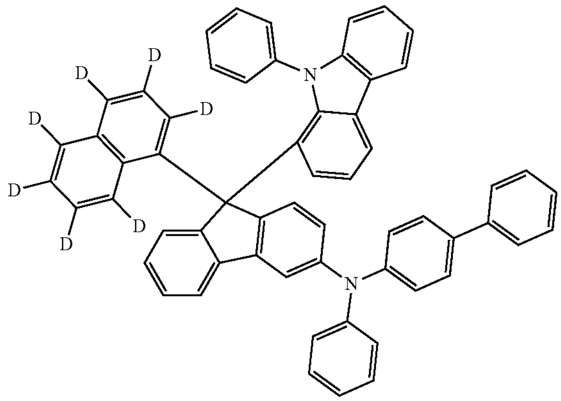
169
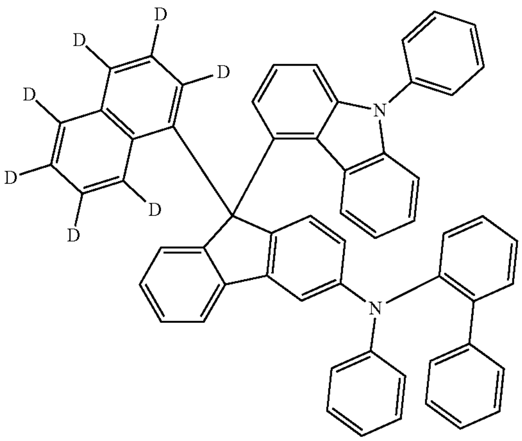
170
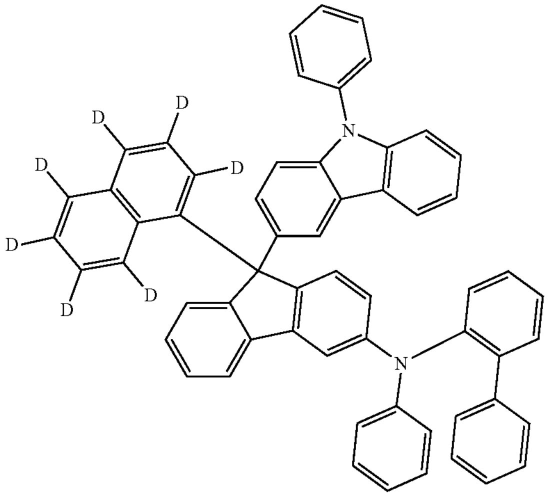
171
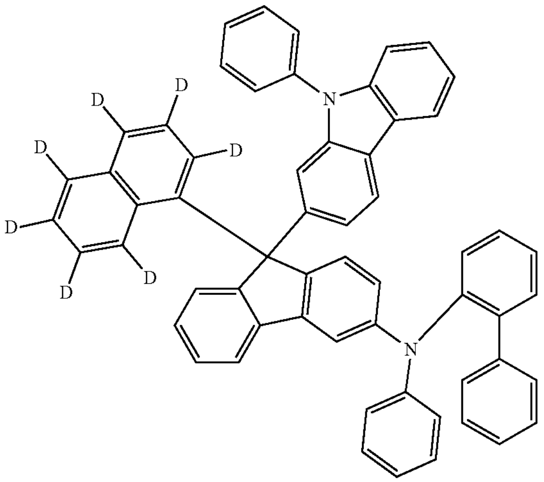
172
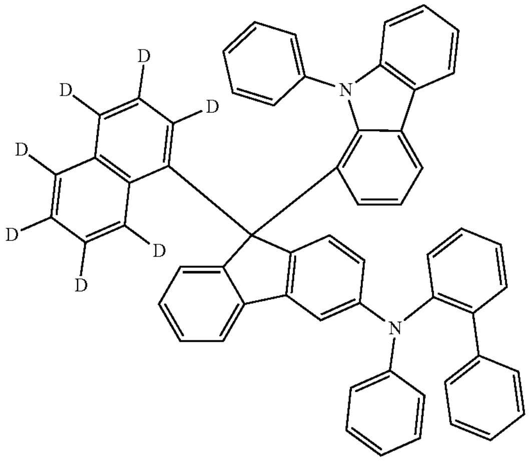

-continued
173
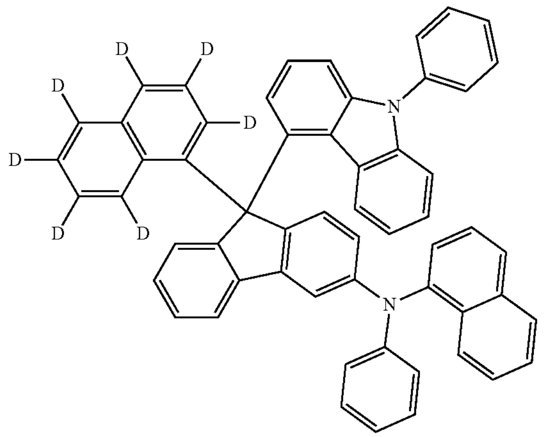
174
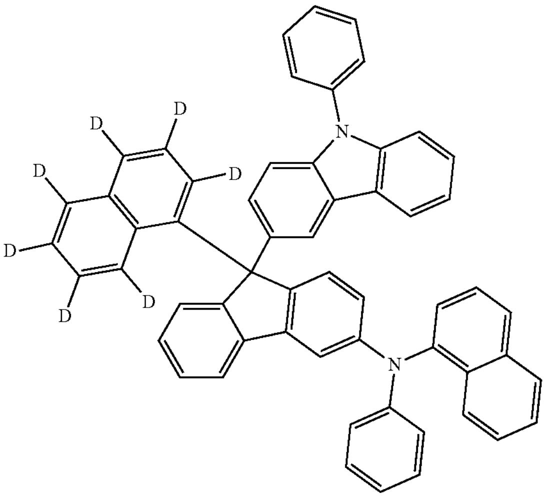
173
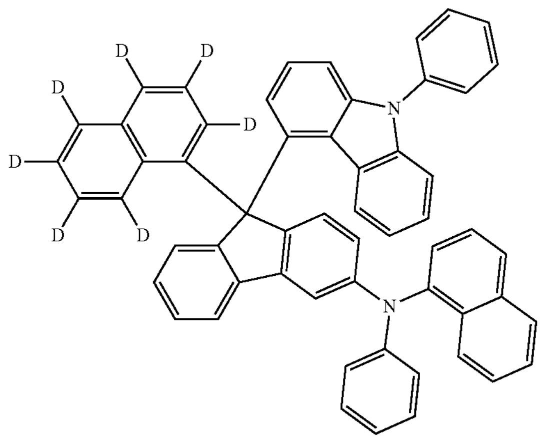
-continued
174
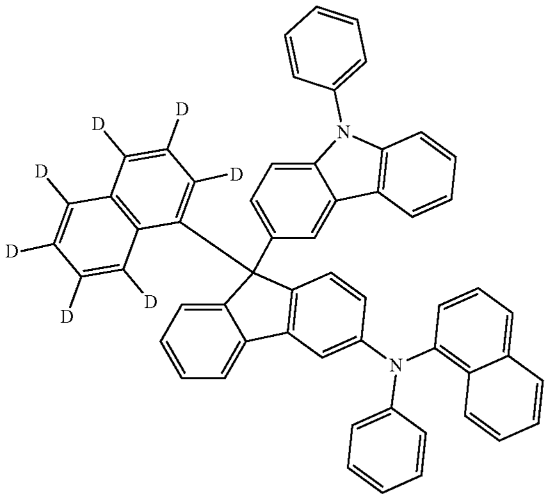
177
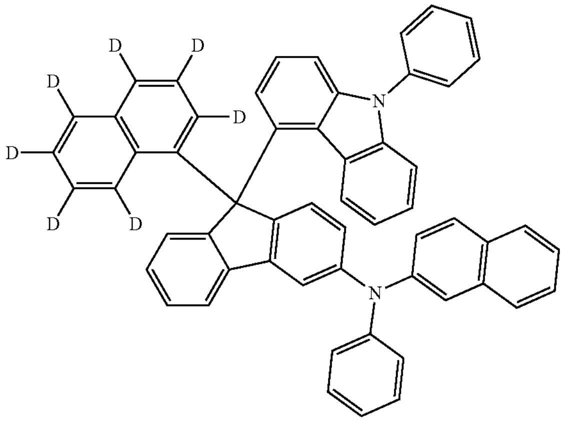
178
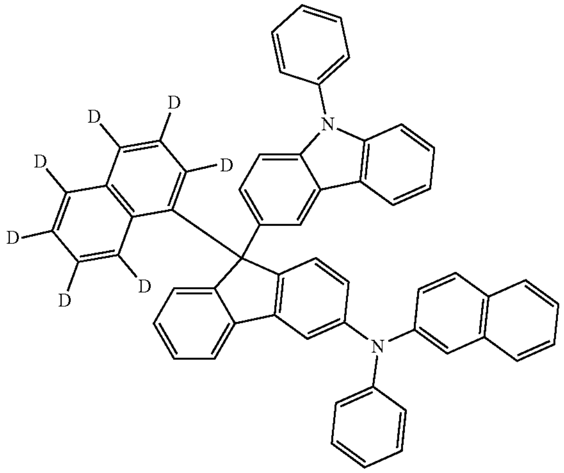

179
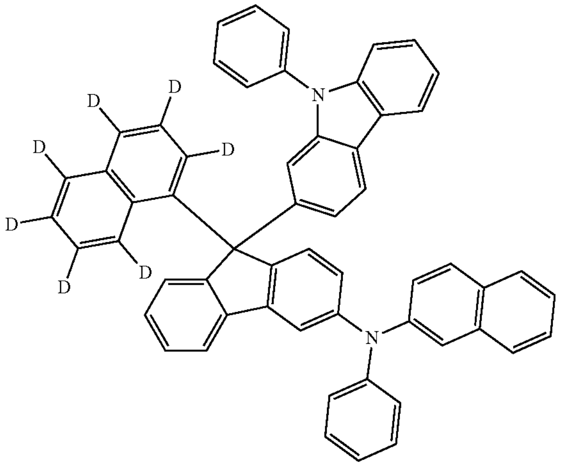
180
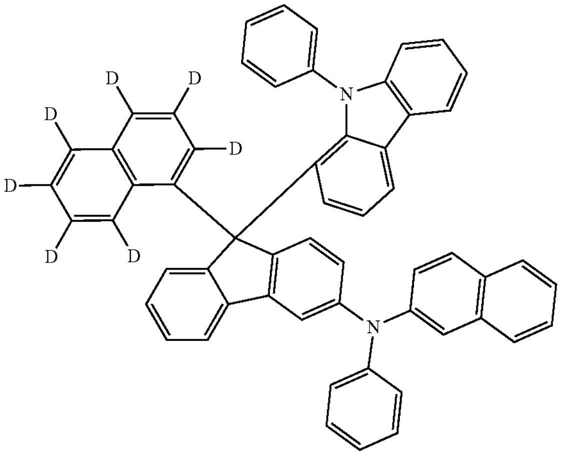
181
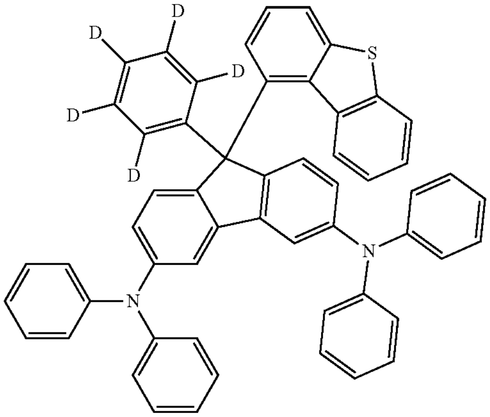
182
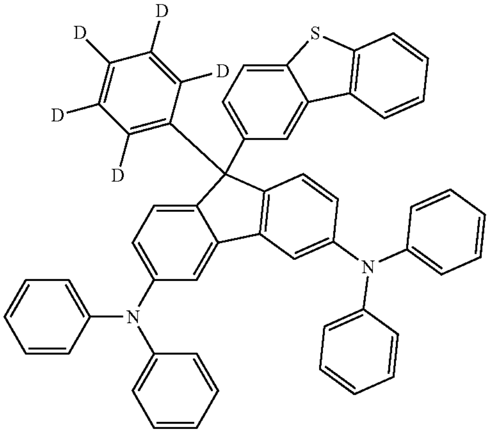
183
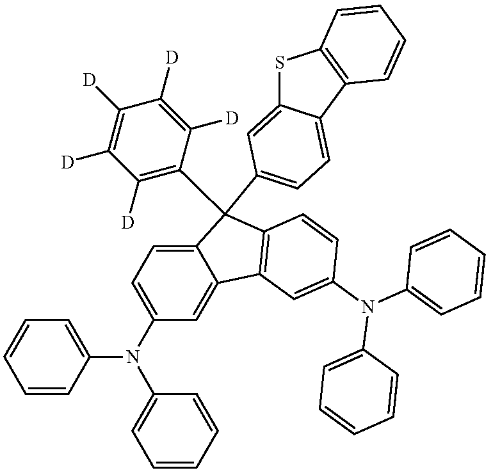
184
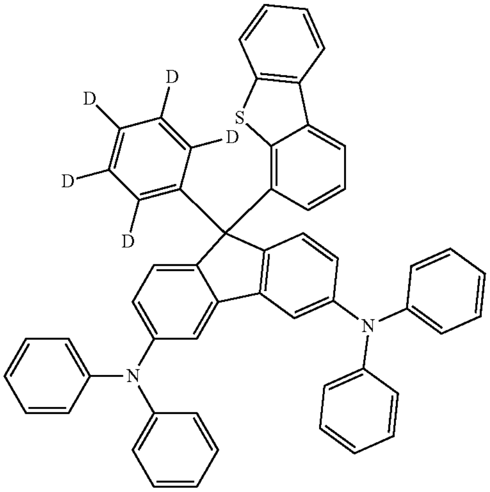

185
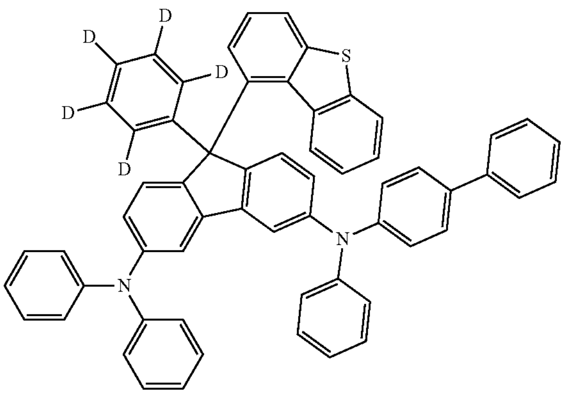
186
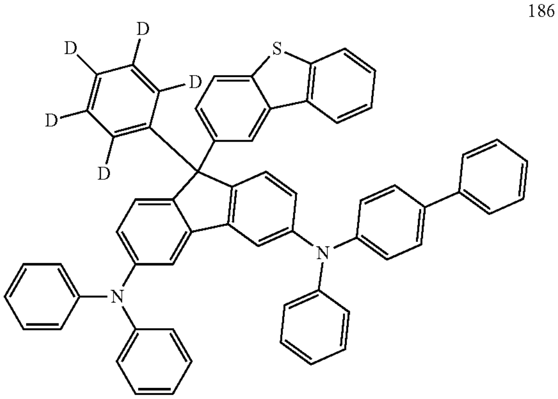
187
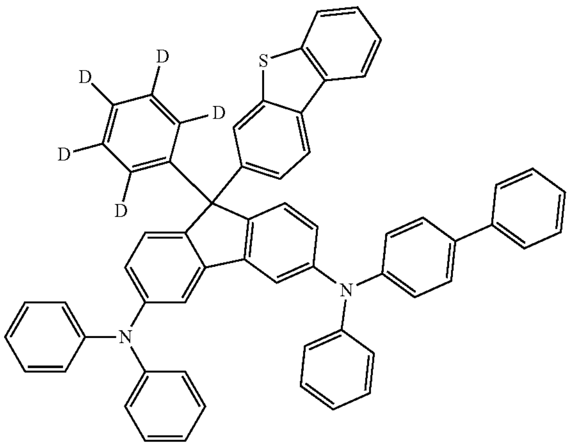
188
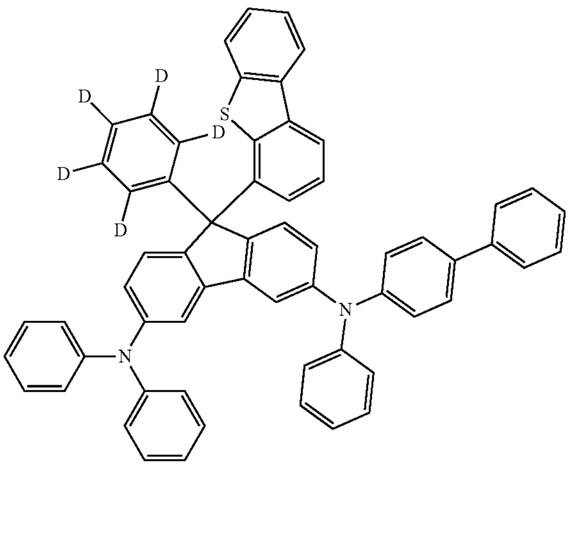
189
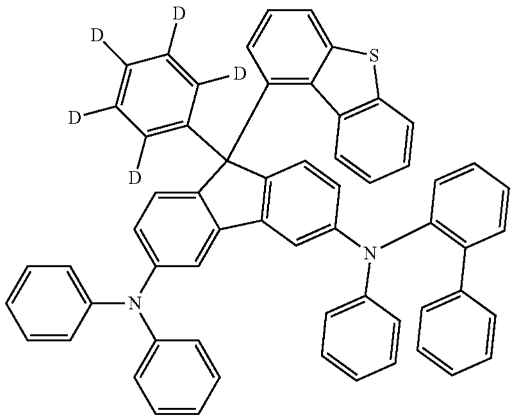
190
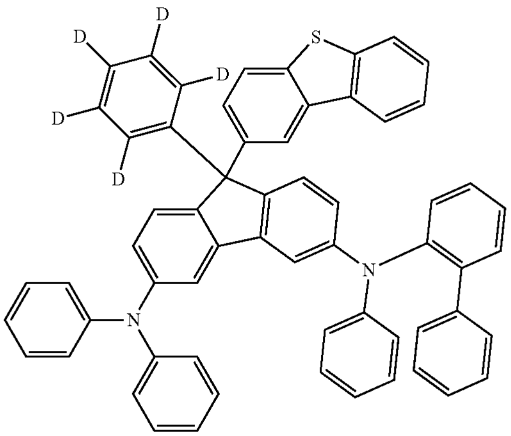

-continued
191
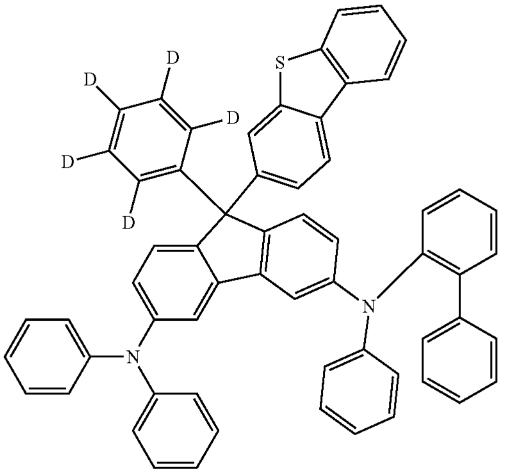
192
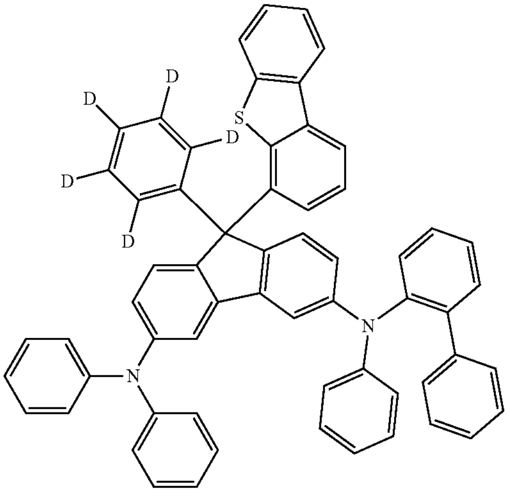
193
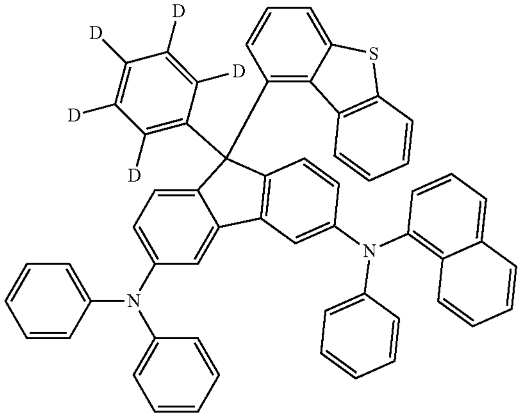
-continued
194
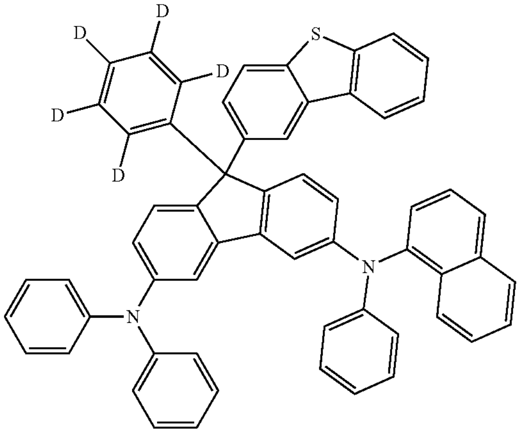
195
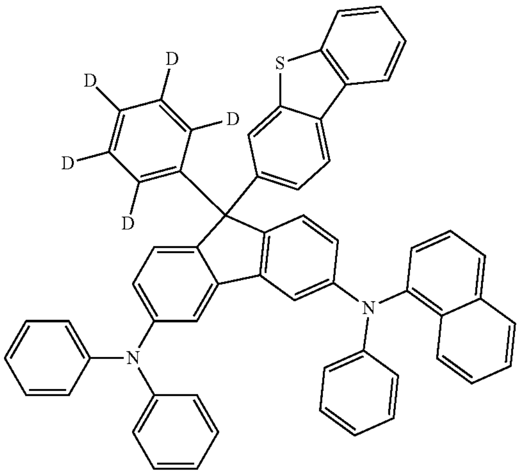
196
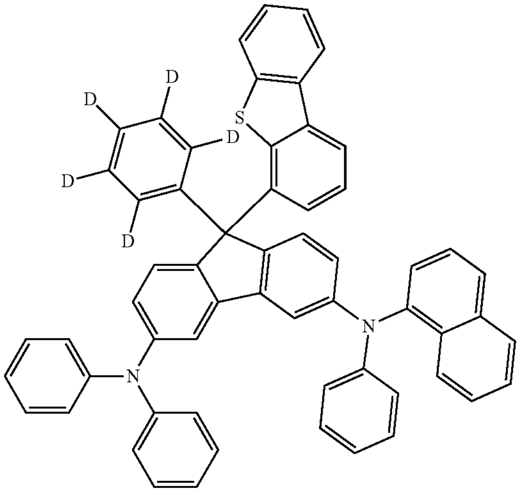

-continued
197
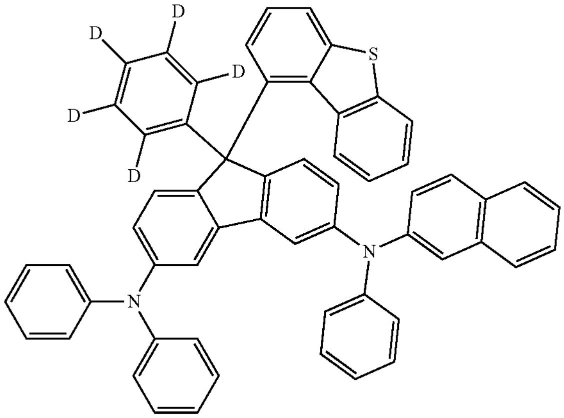
198
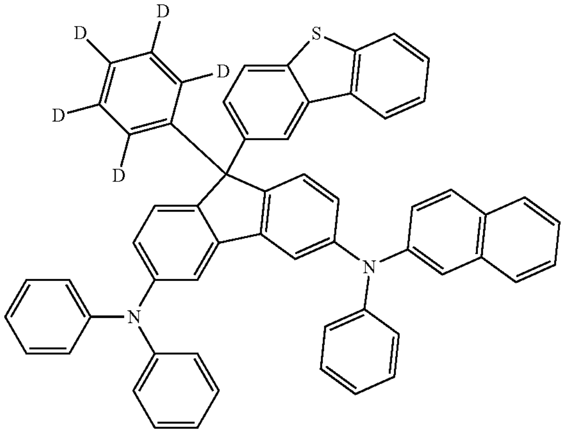
199
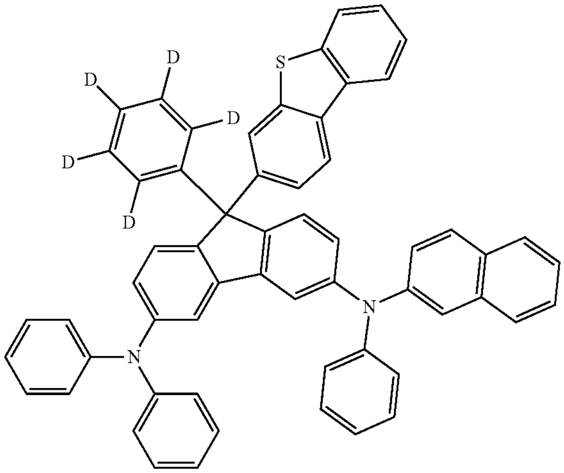
-continued
200
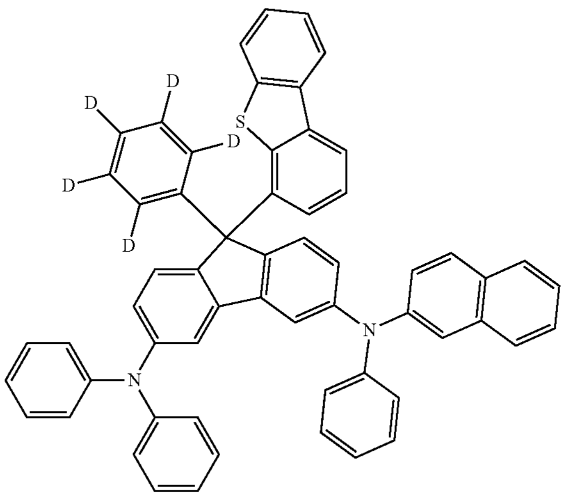
201
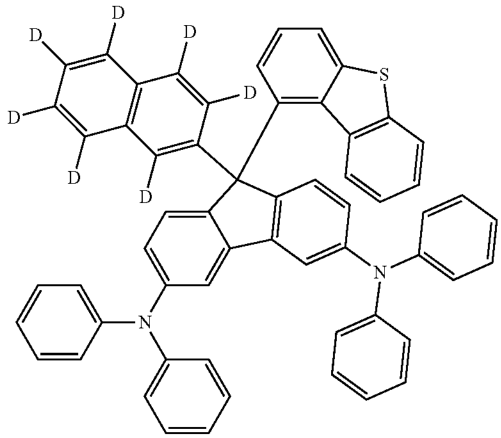
202
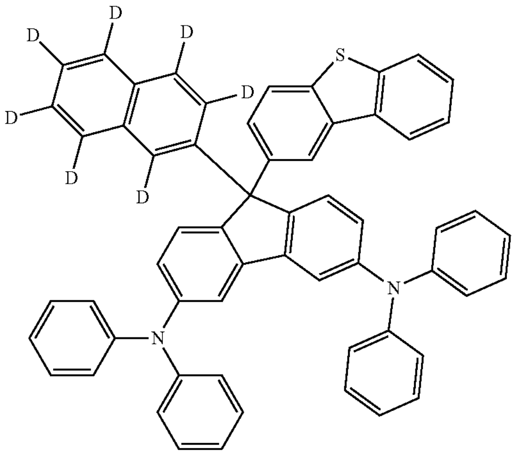

-continued
203
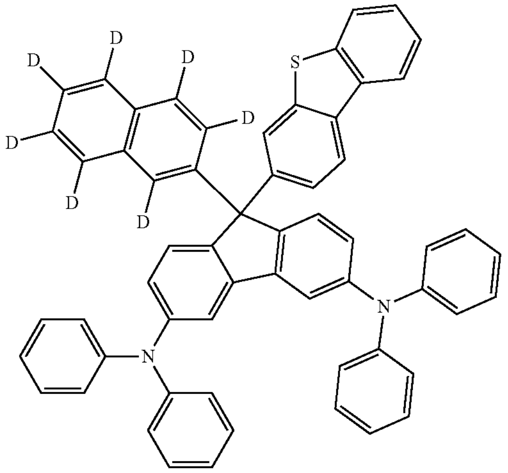
204
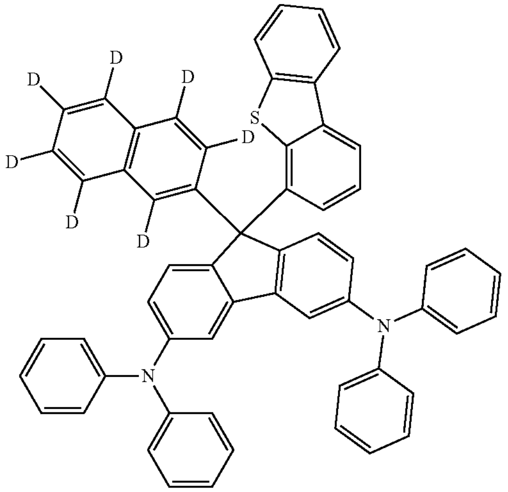
205
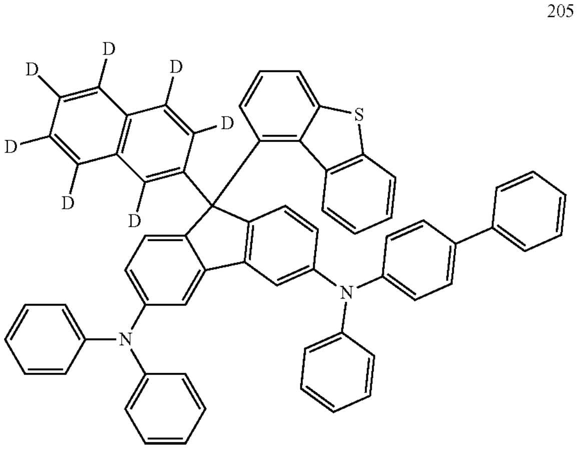
-continued
206
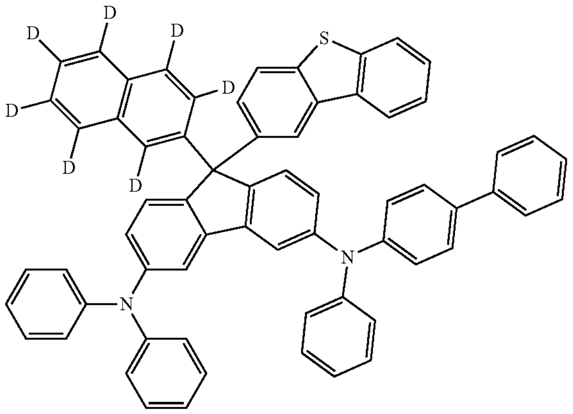
207
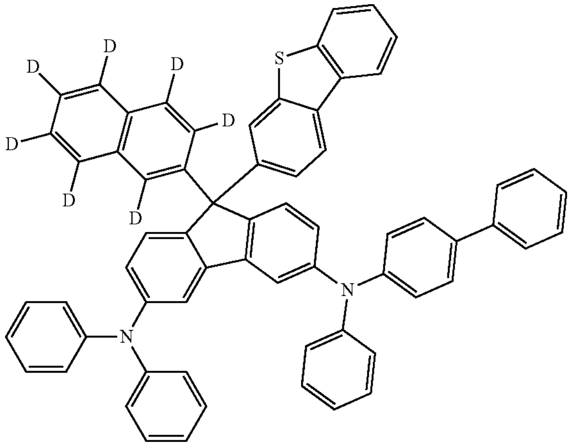
208
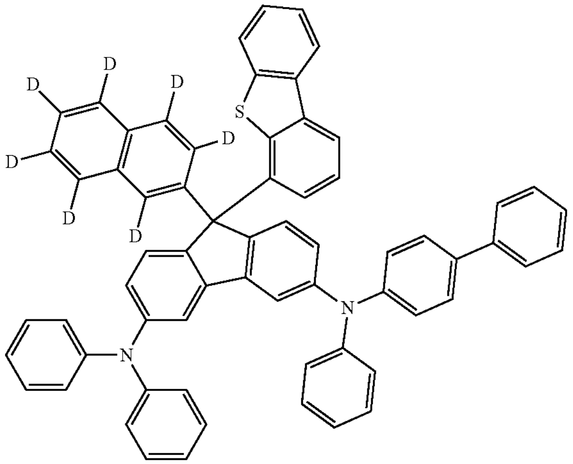

-continued
209
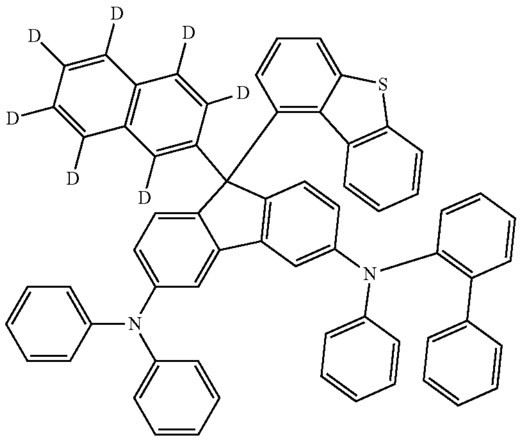
210
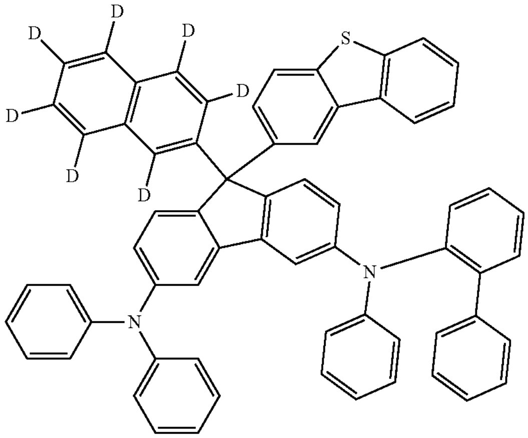
211
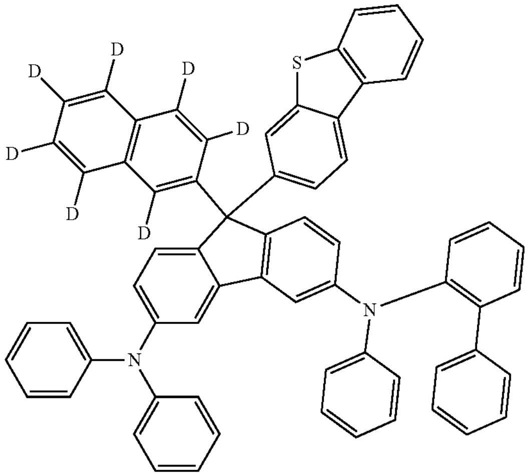
-continued
212
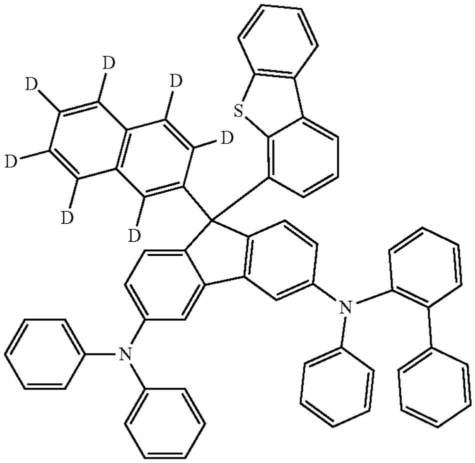
213
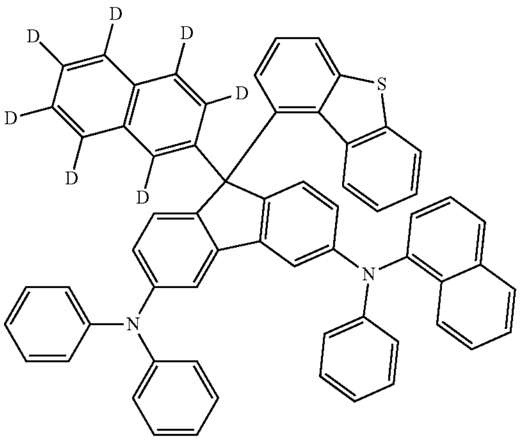
214
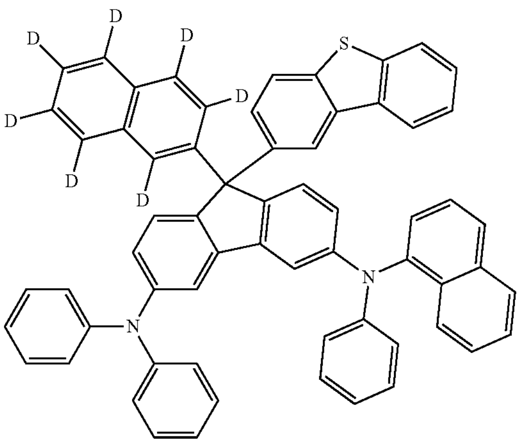

-continued
215
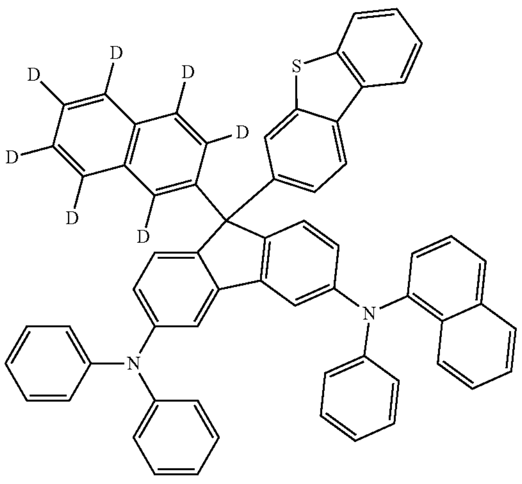
216
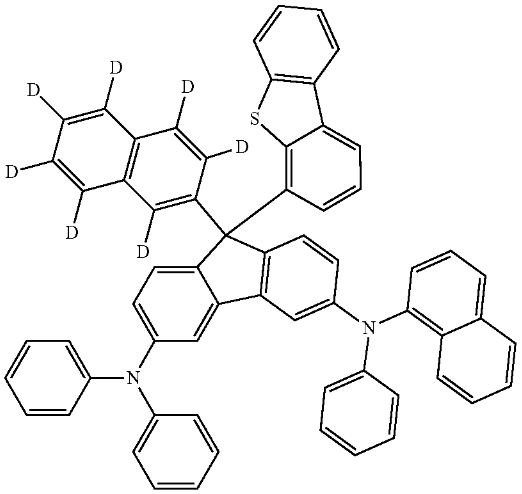
217
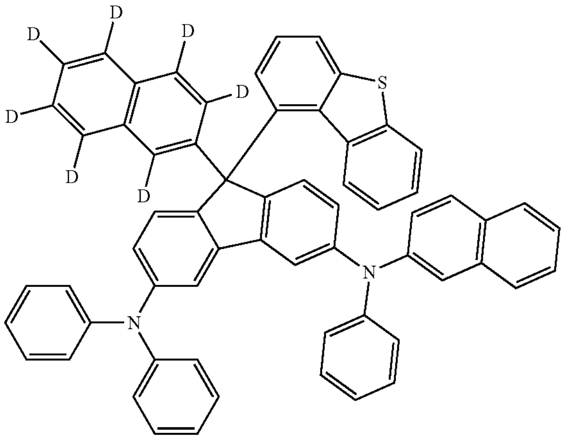
-continued
218
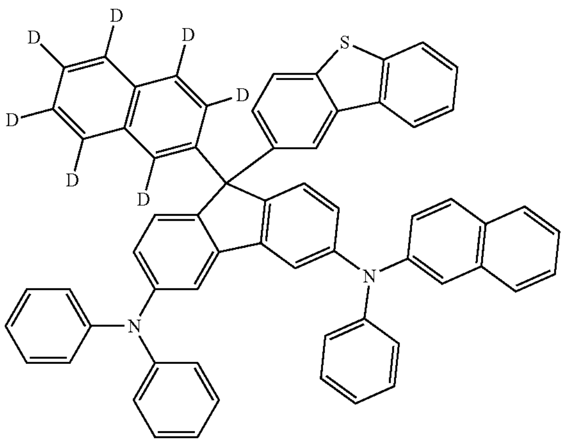
219
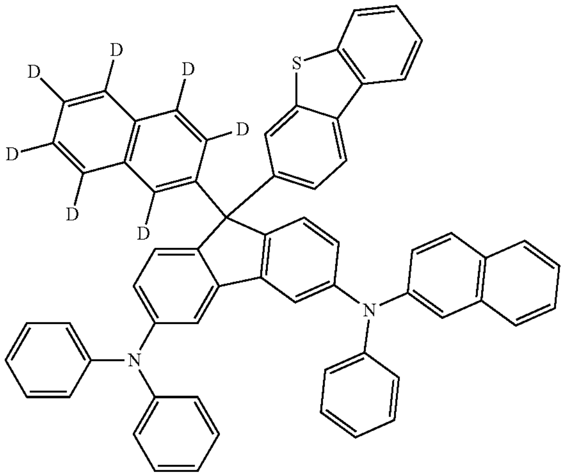
220
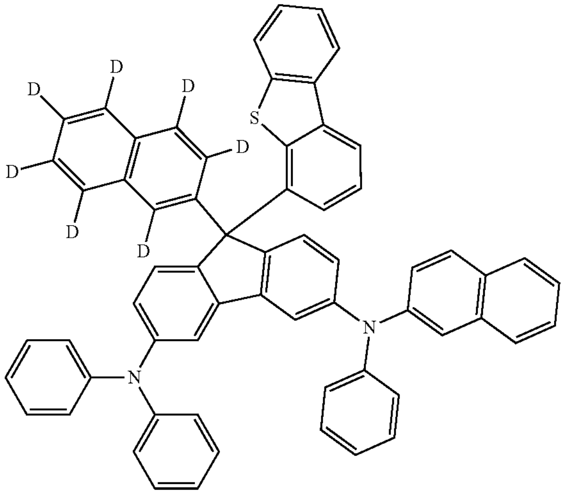

-continued
221
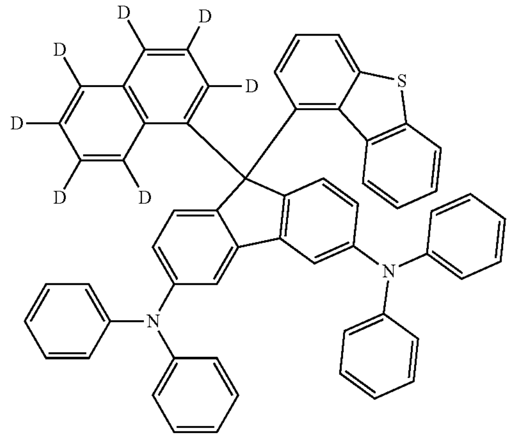
222
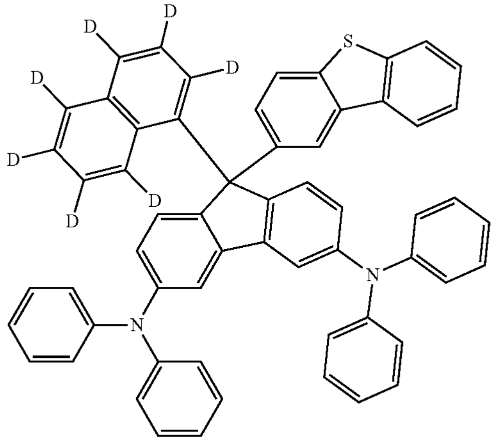
223
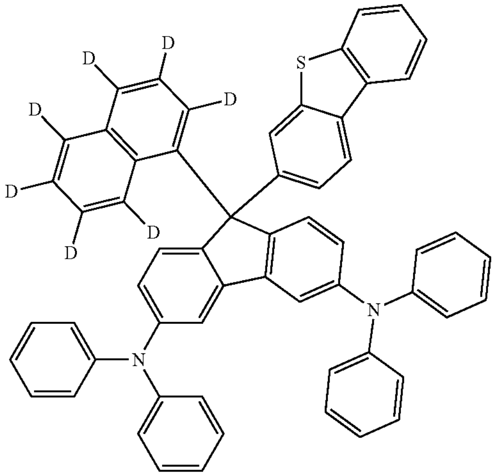
-continued
224
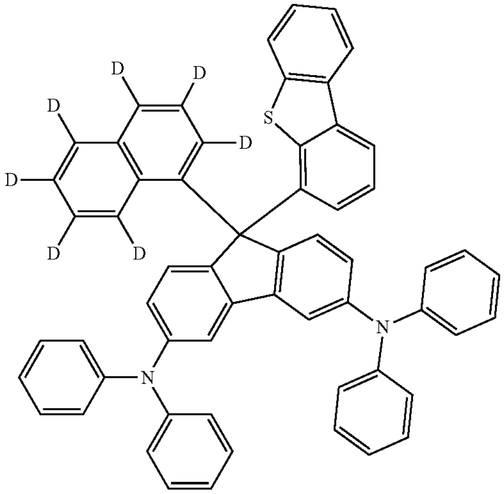
225
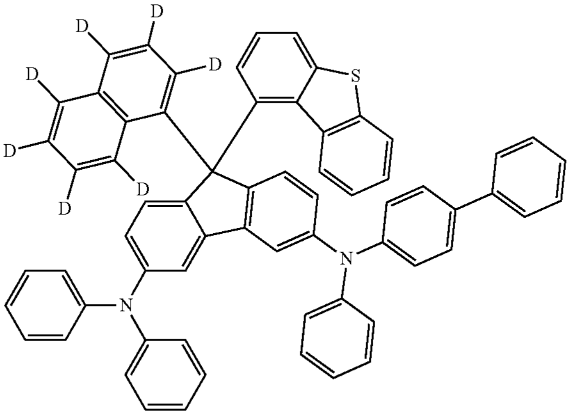
226
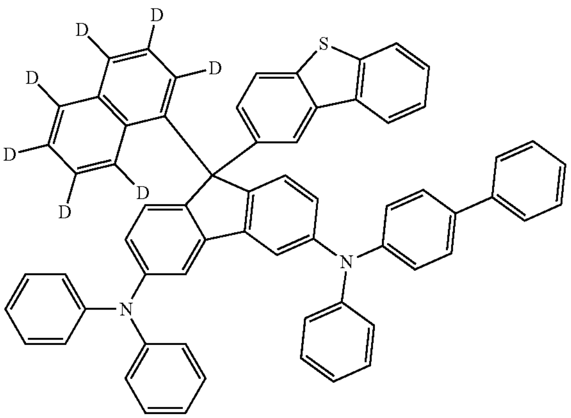

-continued
227
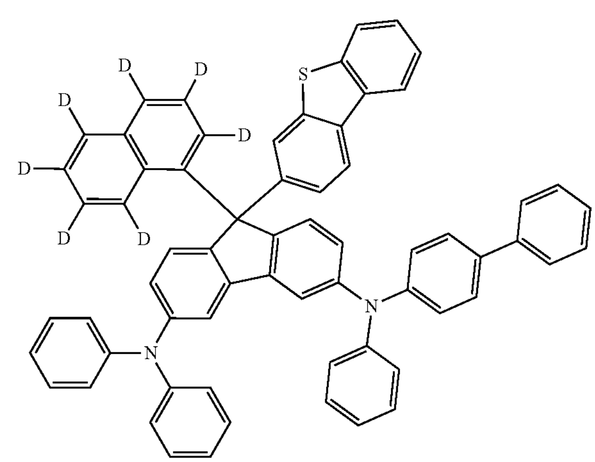
228
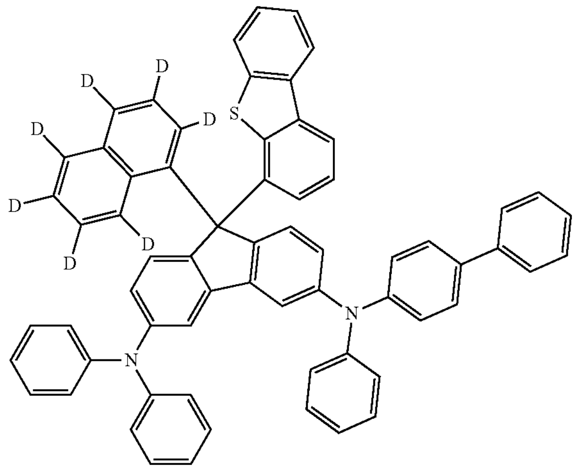
229
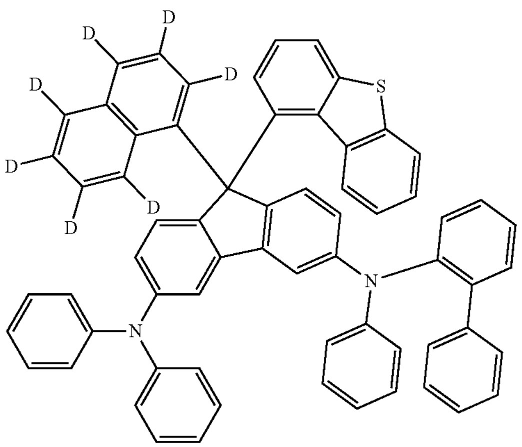
-continued
230
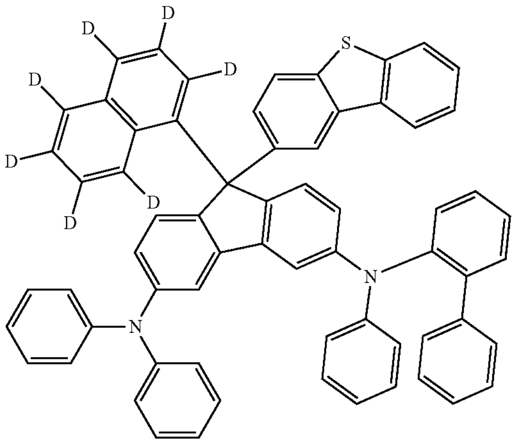
231
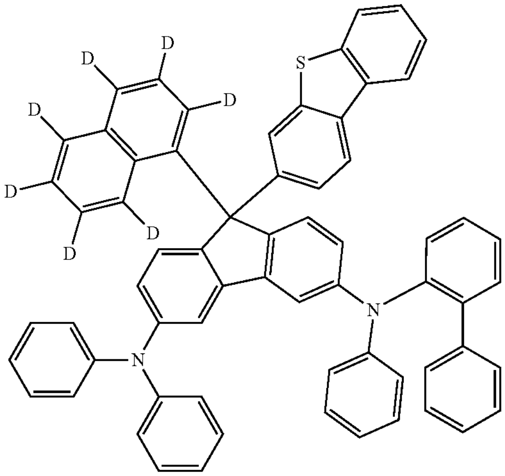
232
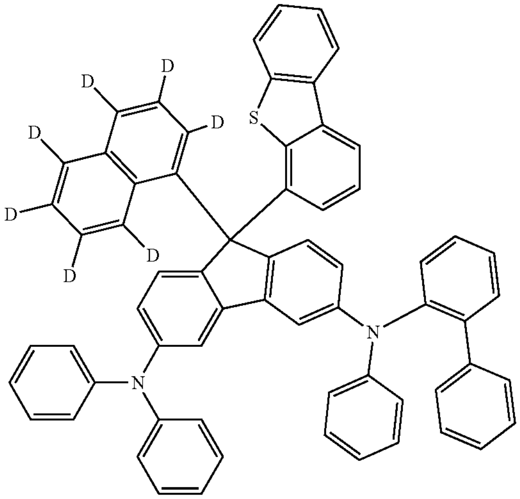

-continued
233
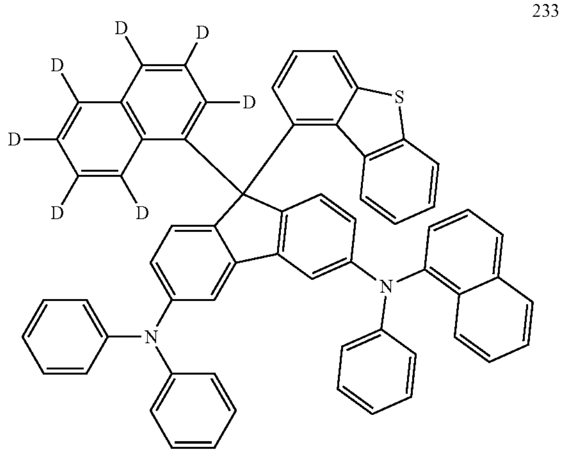
234
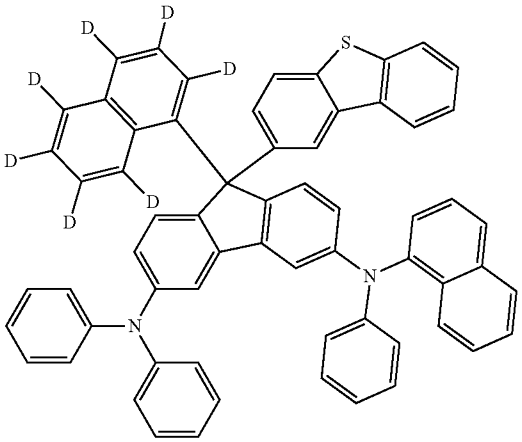
235
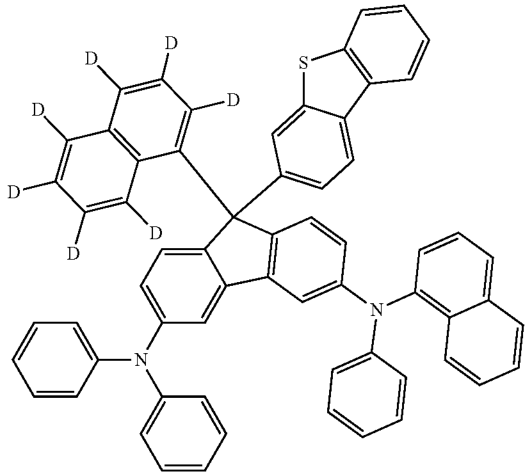
-continued
236
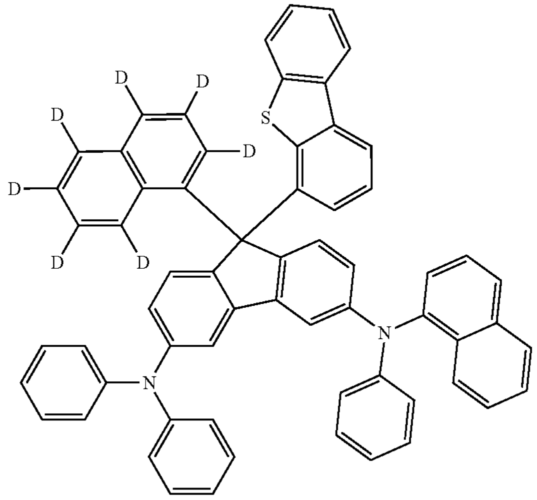
237
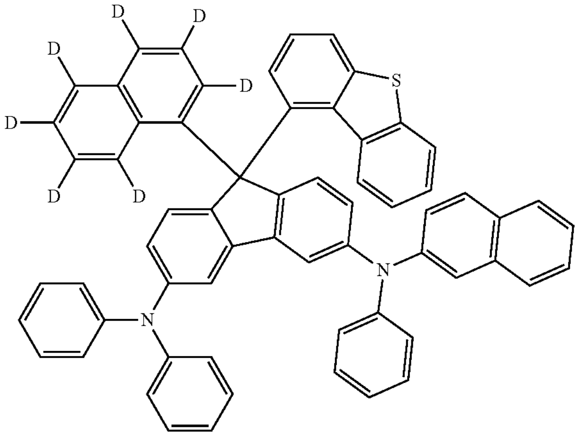
238
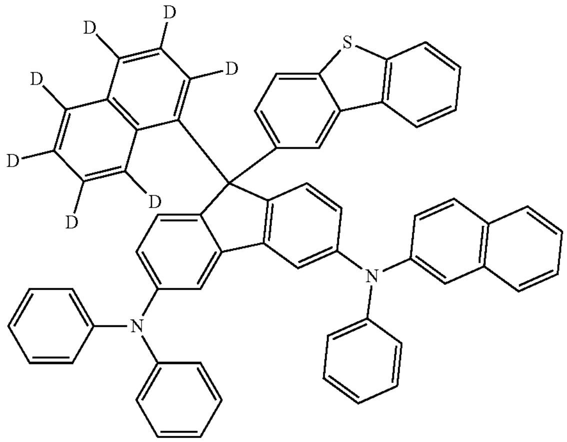

239
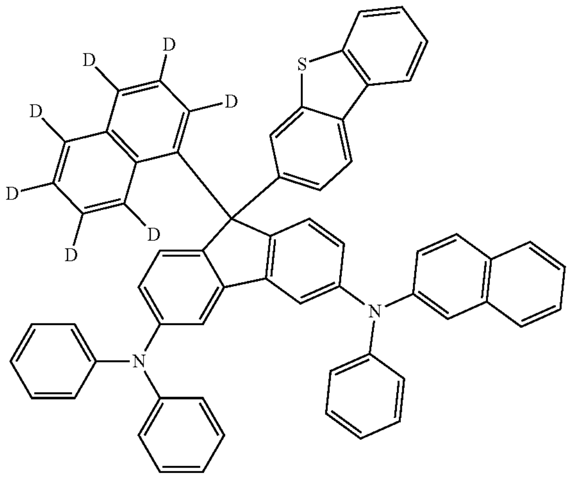
240
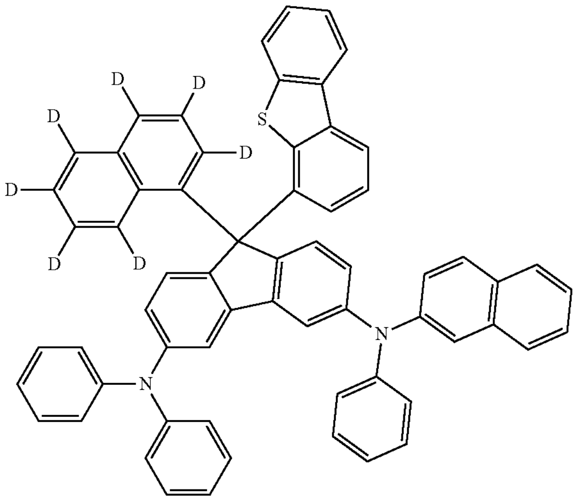
241
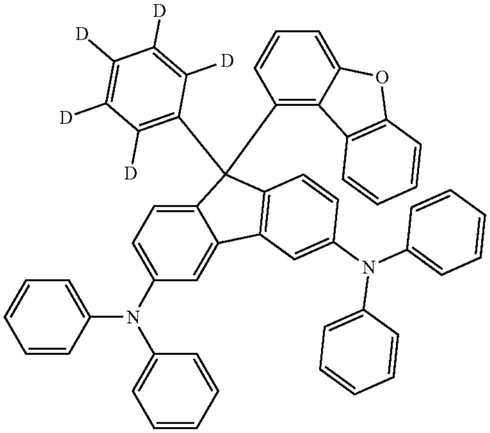
242
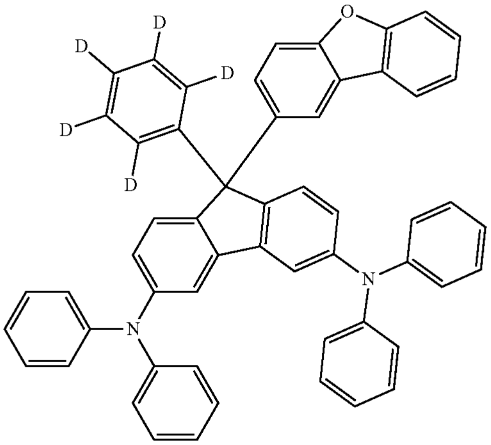
243
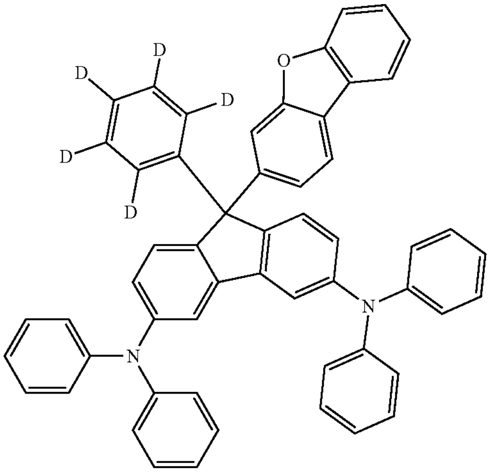
244
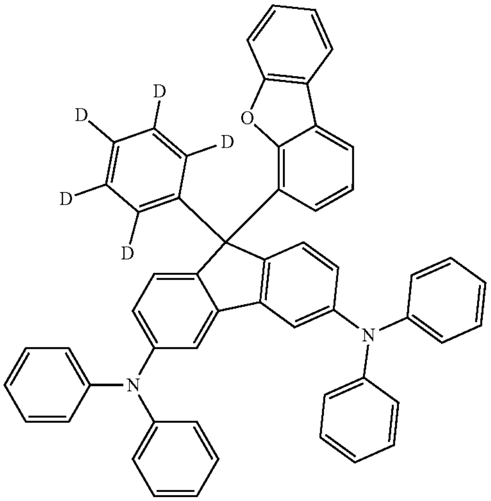

-continued
245
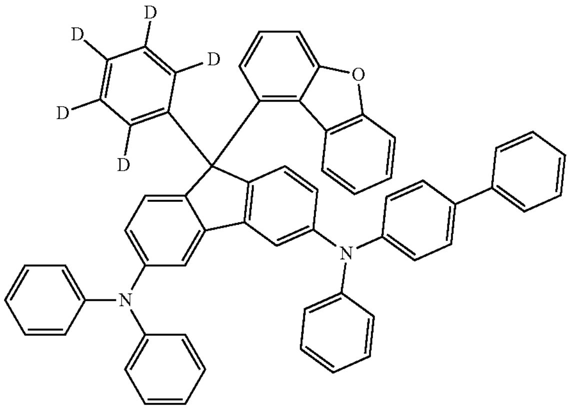
246
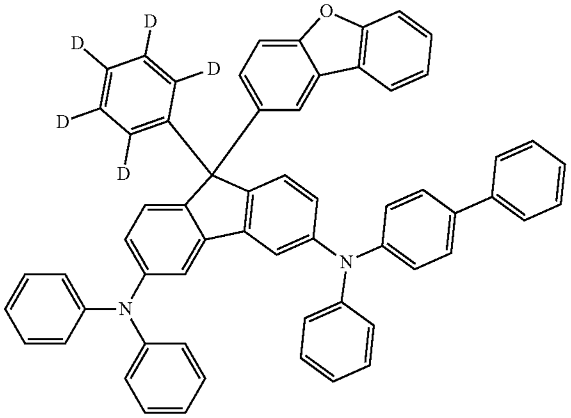
247
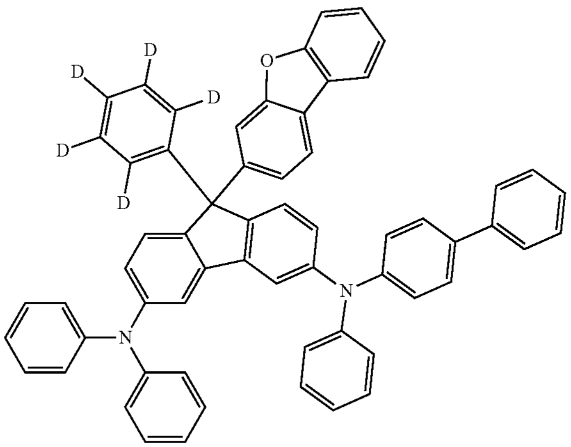
-continued
248
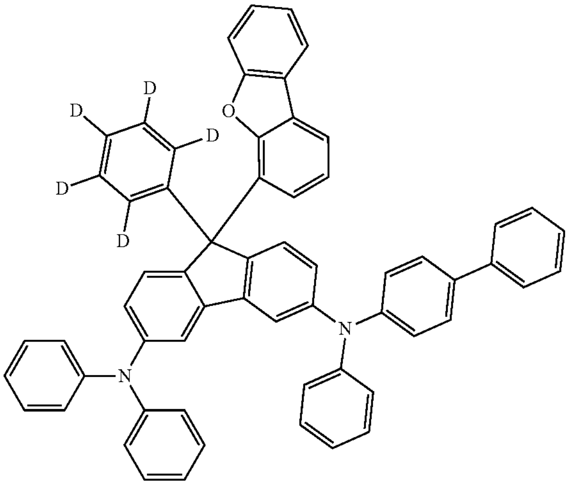
249
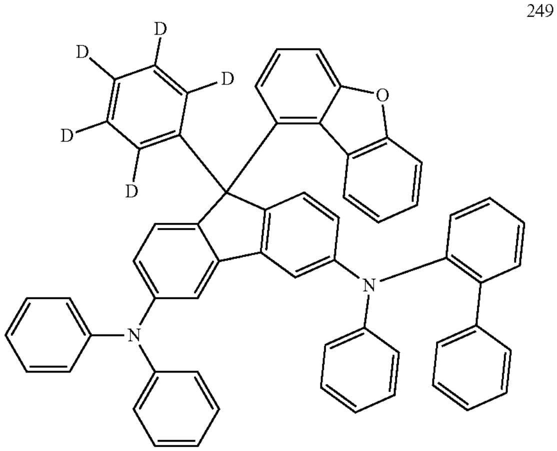
250
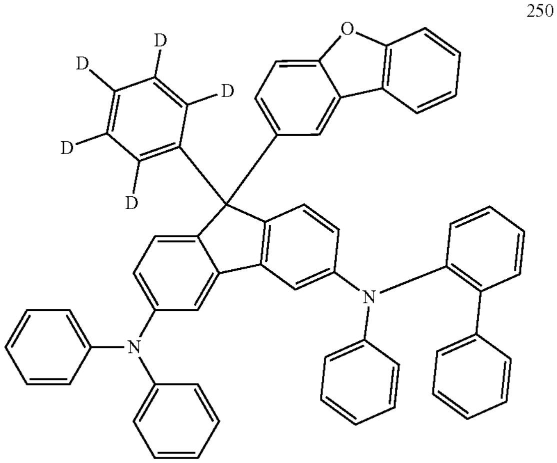

-continued
251
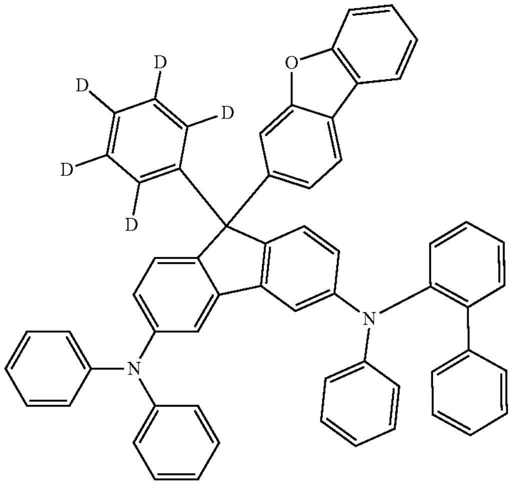
252
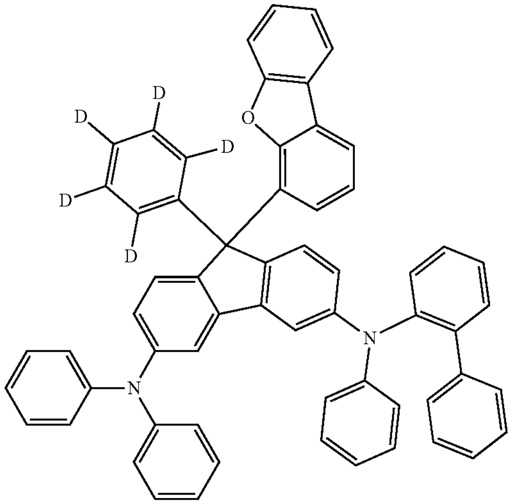
253
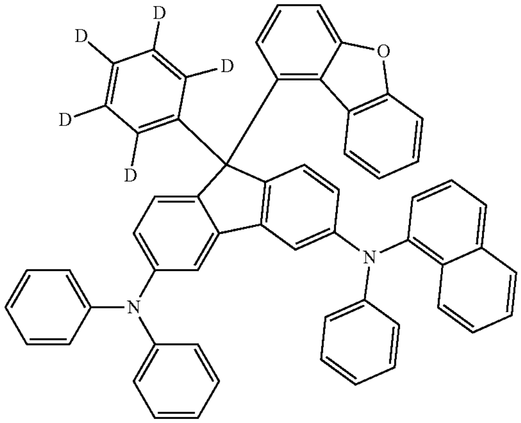
-continued
254
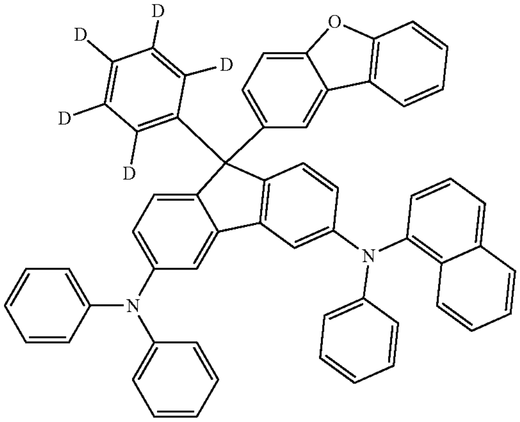
255
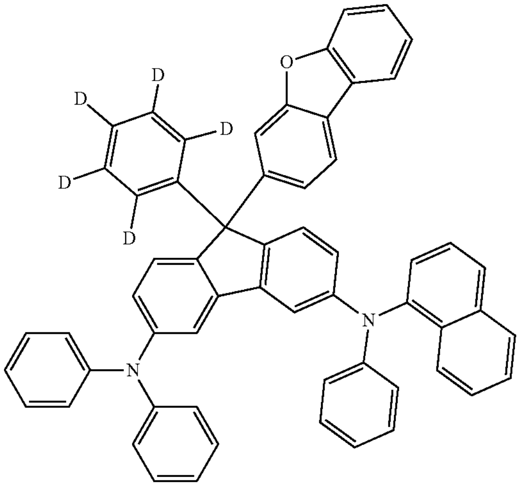
256
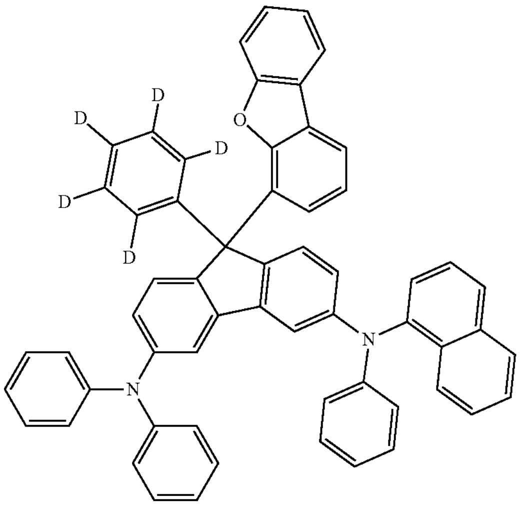

-continued
257
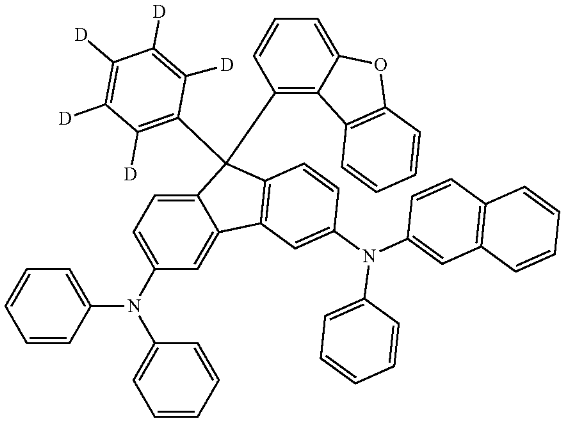
258
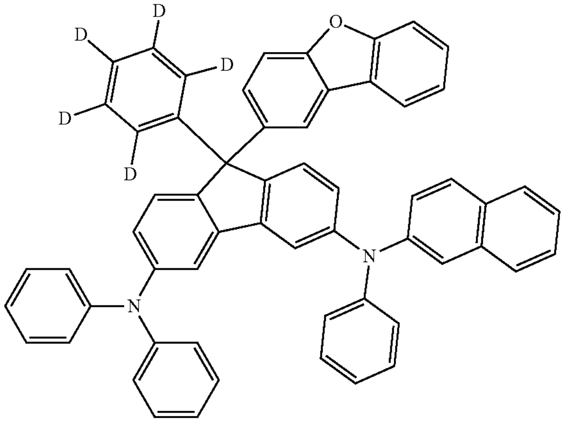
259
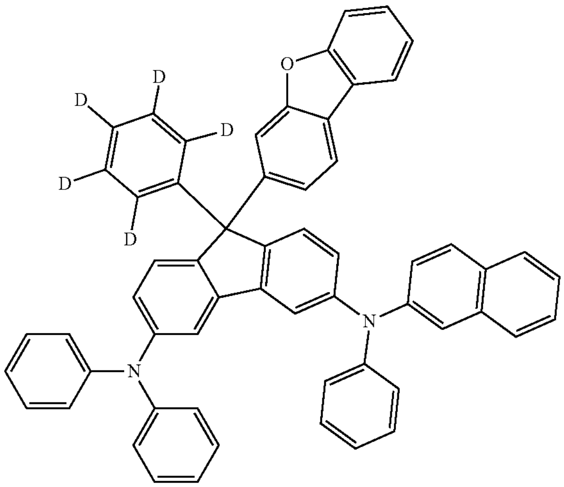
-continued
260
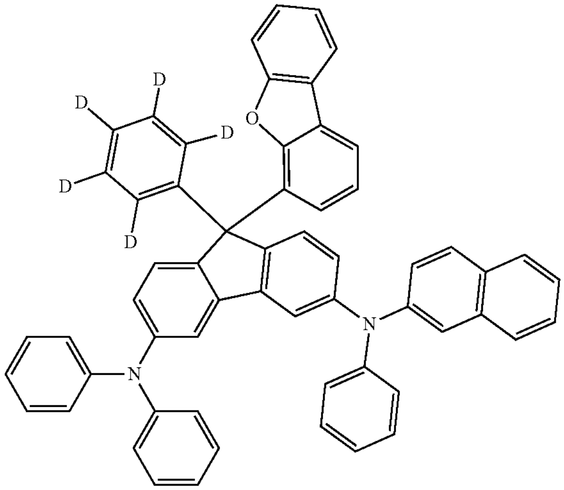
261
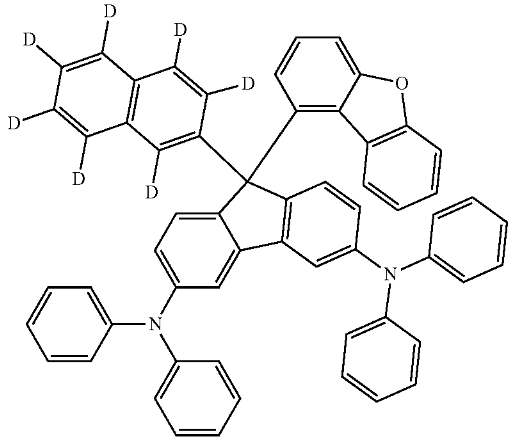
262
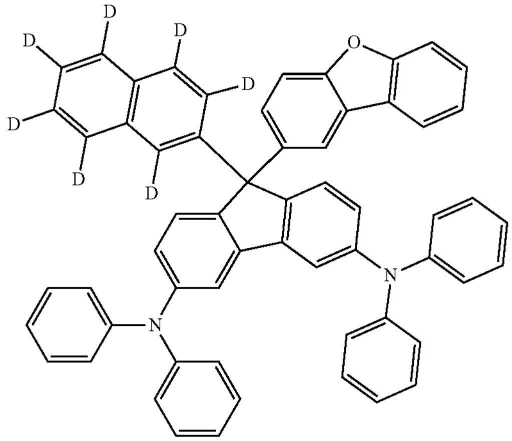

-continued
263
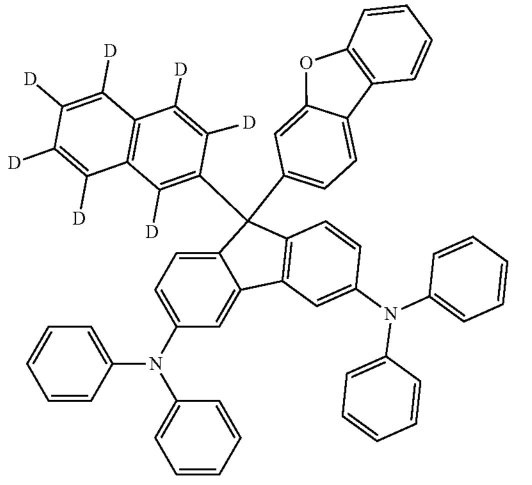
264
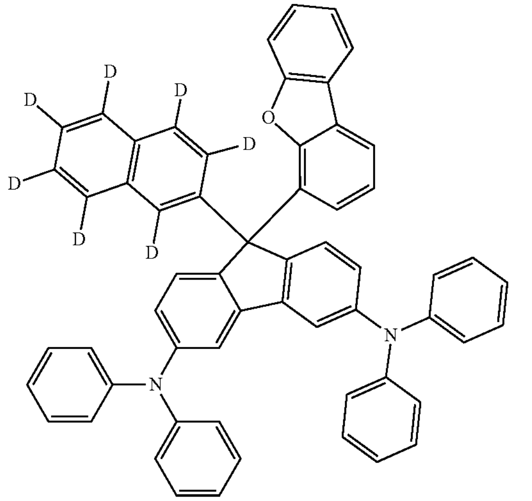
265
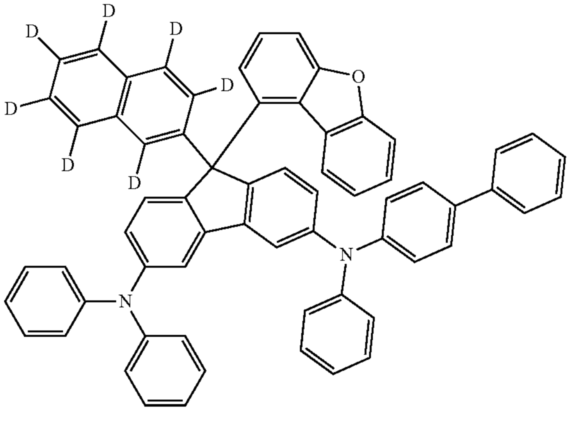
-continued
266
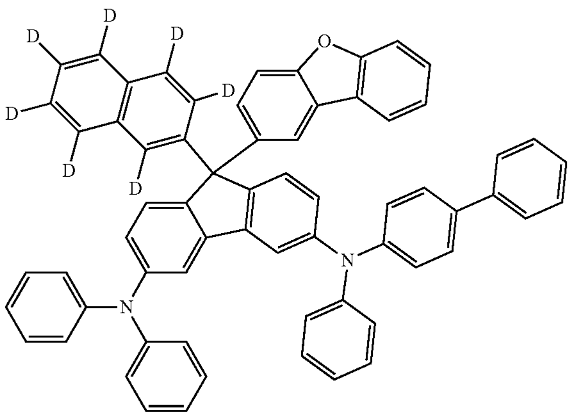
267
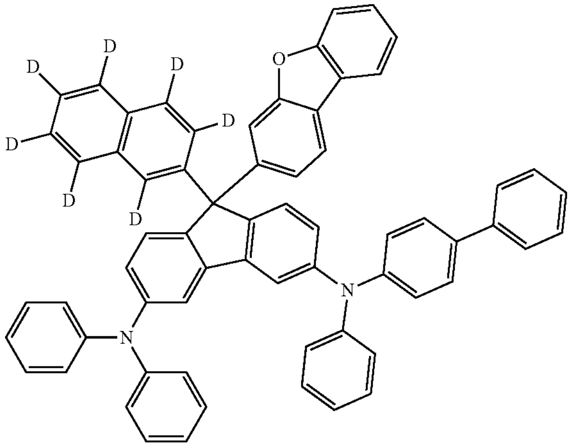
268
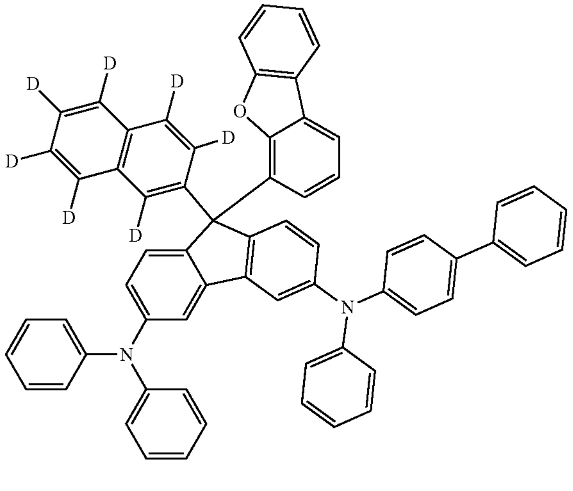

-continued
269
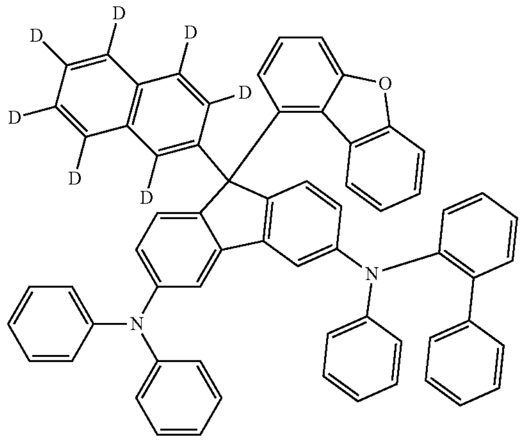
270
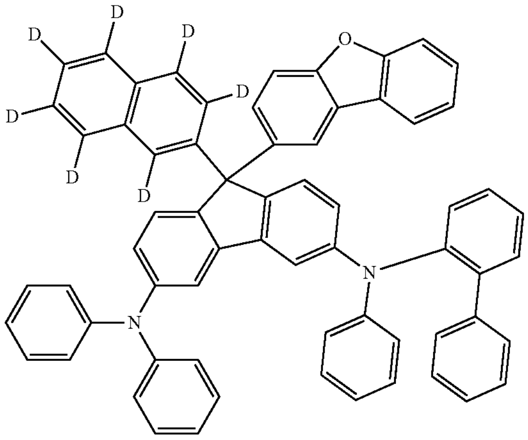
271
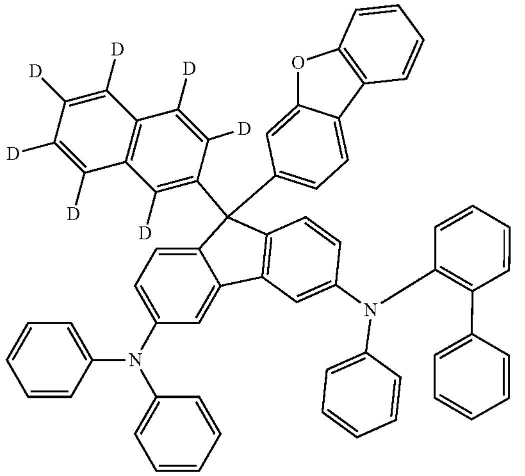
-continued
272
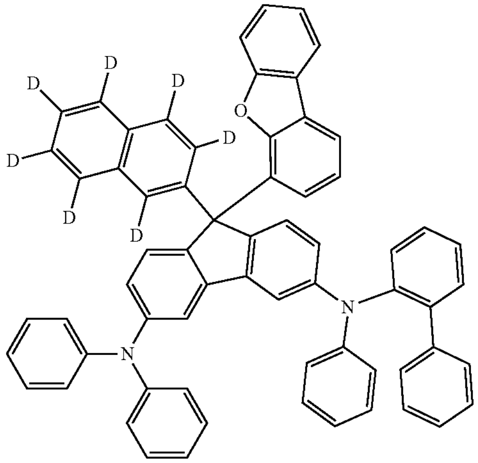
273
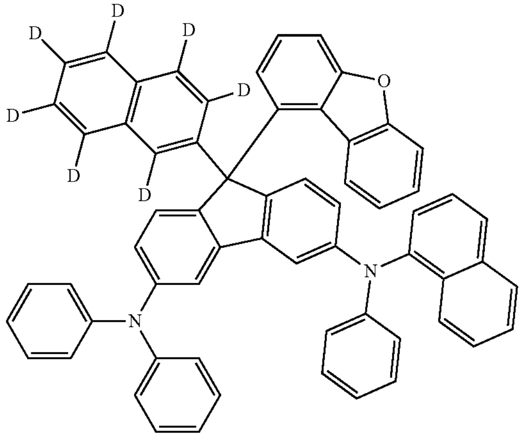
274
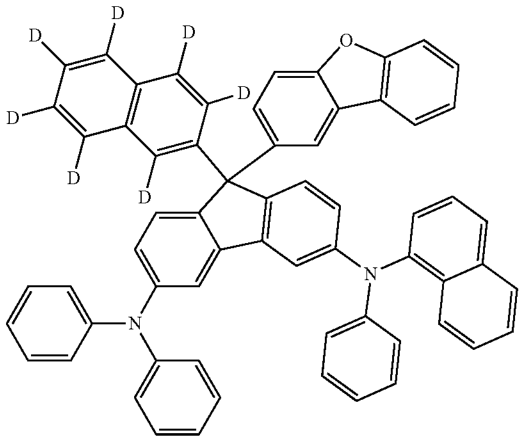

-continued
275
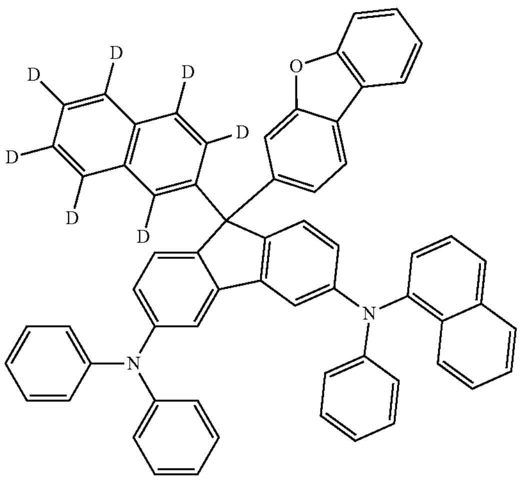
276
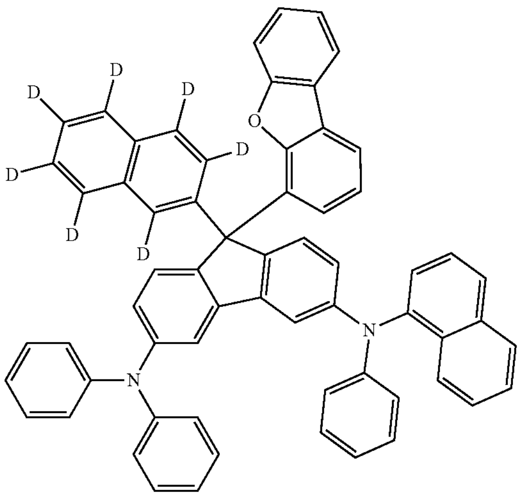
277
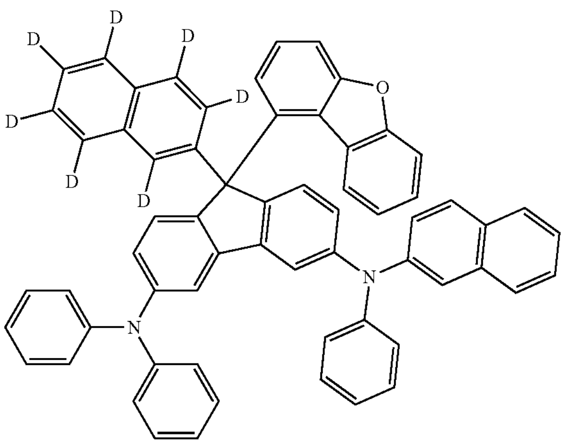
-continued
278
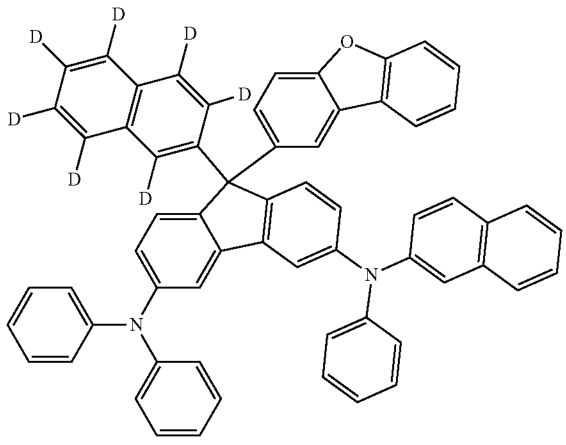
279
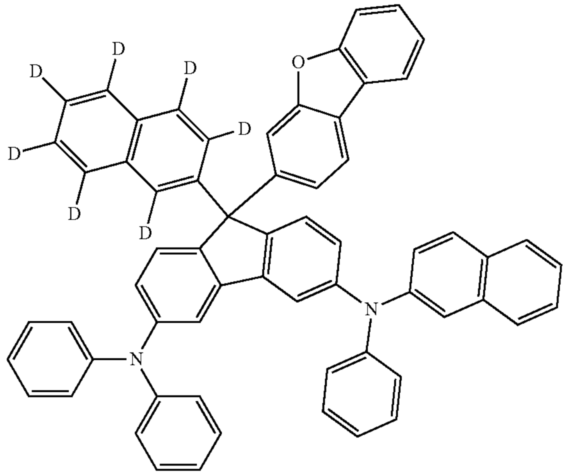
280
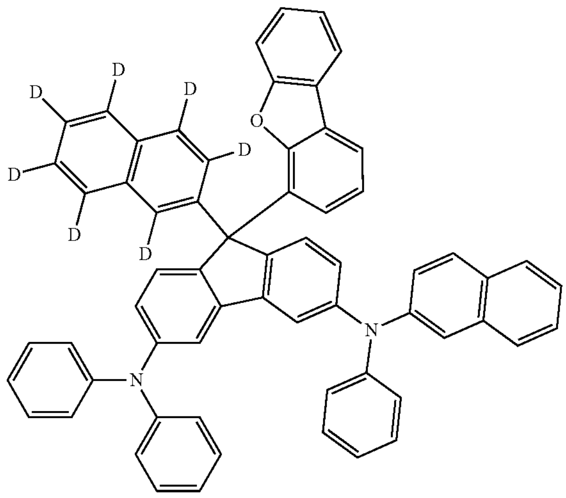

-continued
281
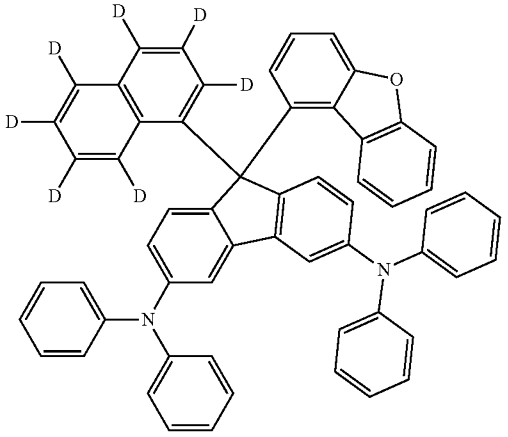
282
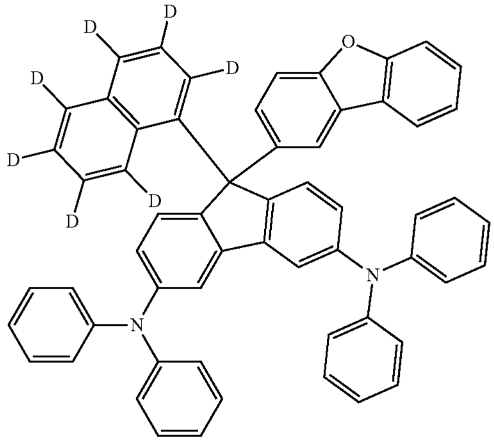
283
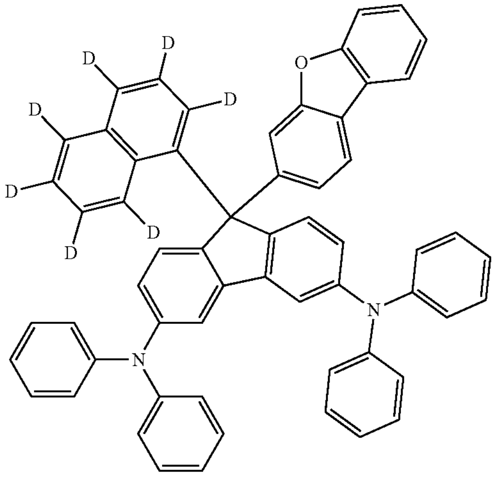
-continued
284
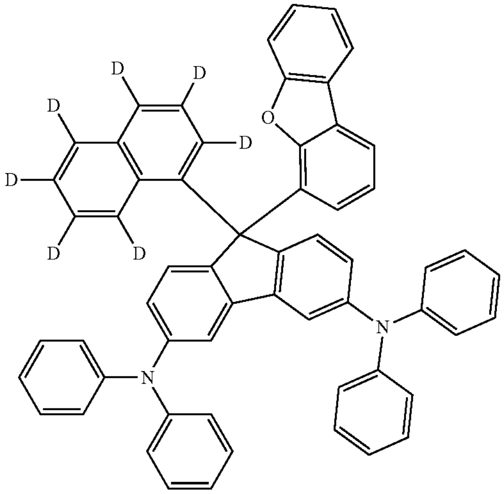
285
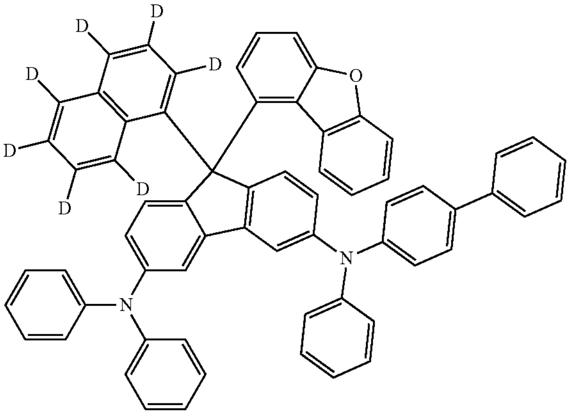
286
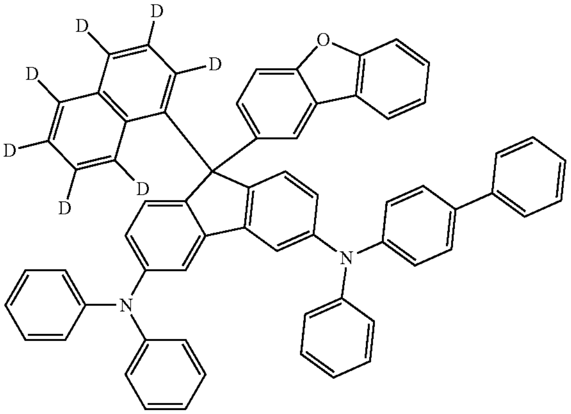

-continued
287
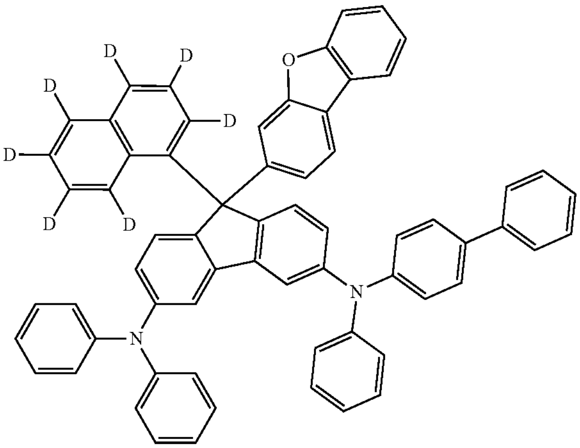
288
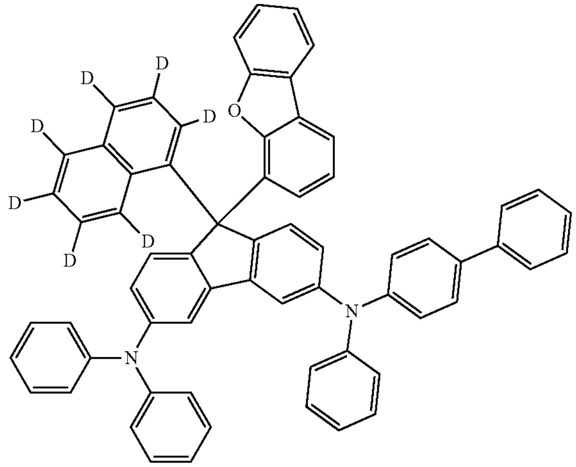
289
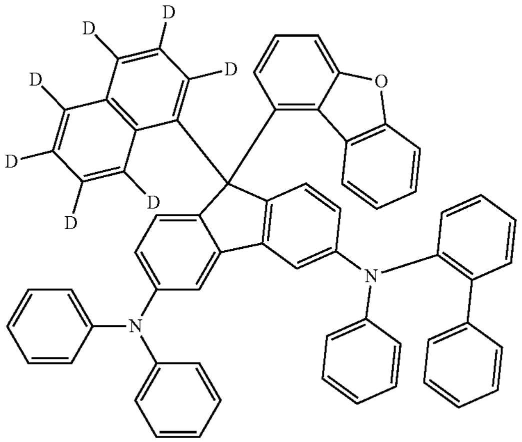
-continued
290
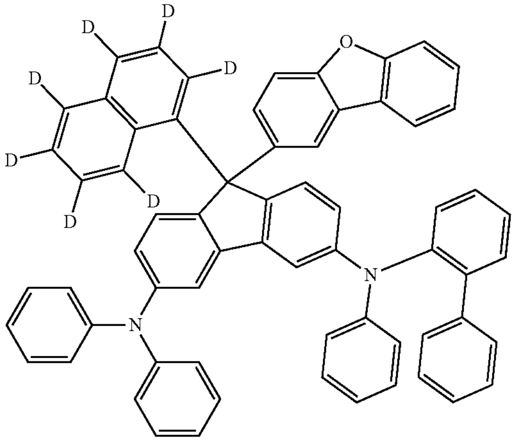
291
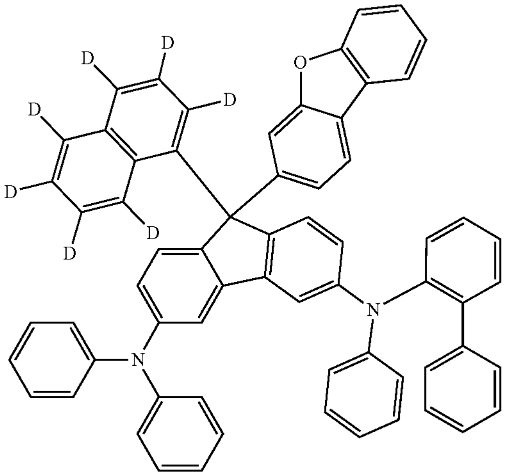
292
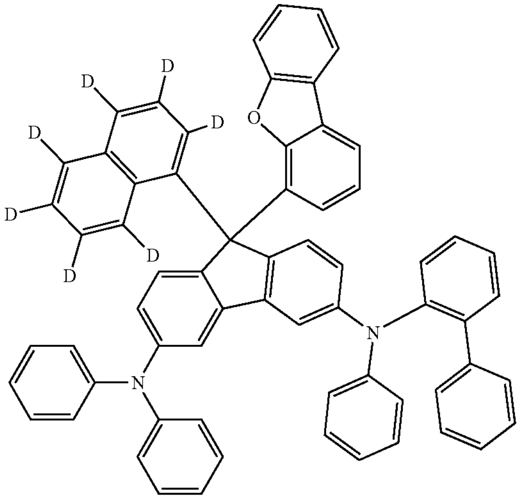

-continued
293
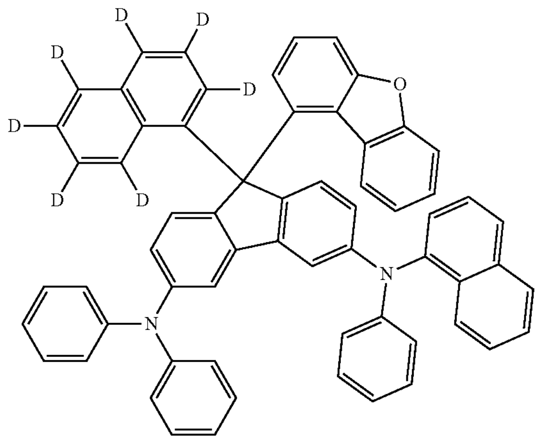
294
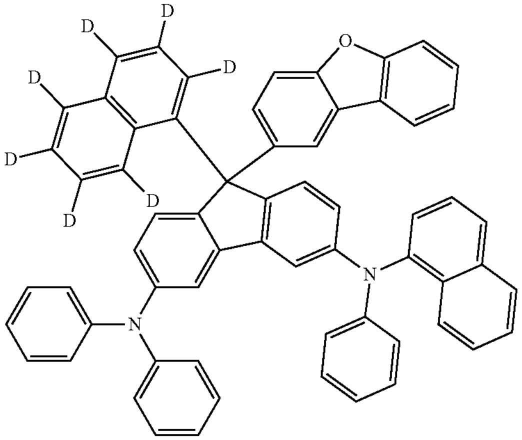
295
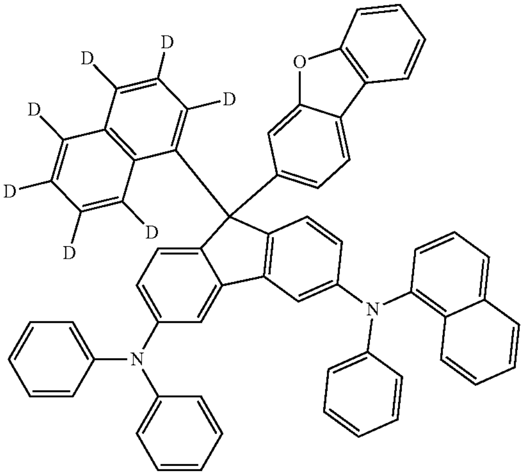
-continued
296
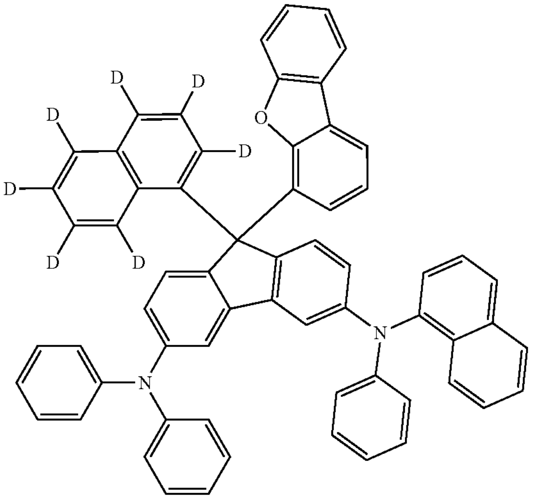
297
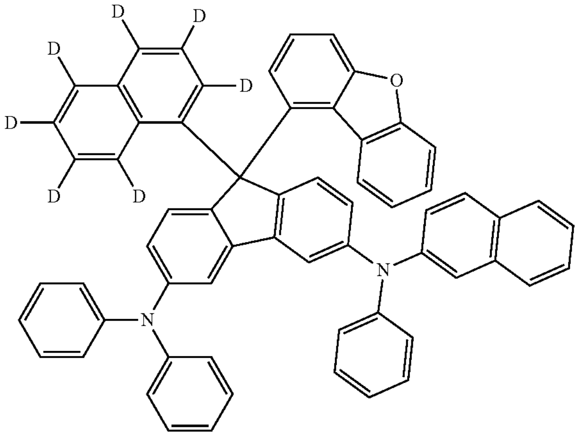
298
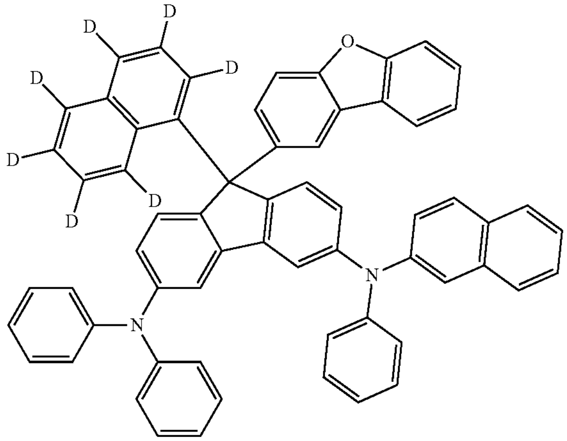

-continued
299
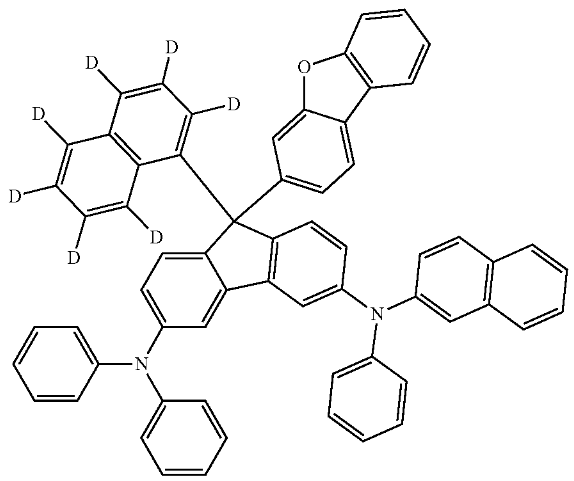
300
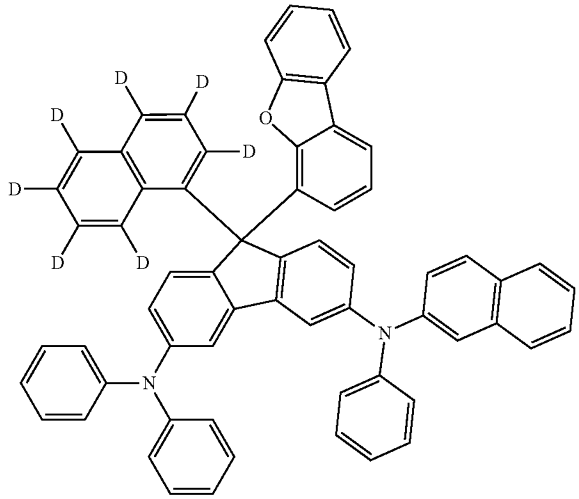
301
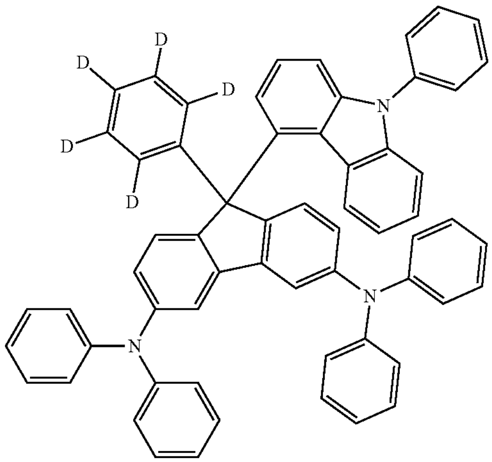
-continued
302
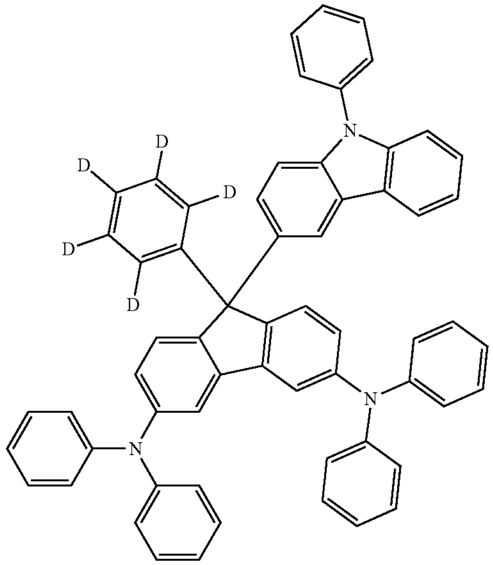
303
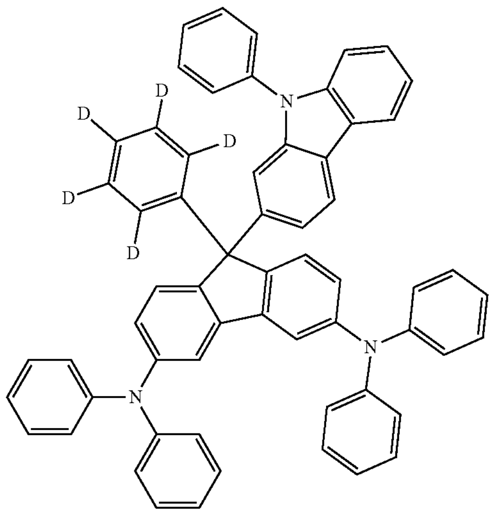
304
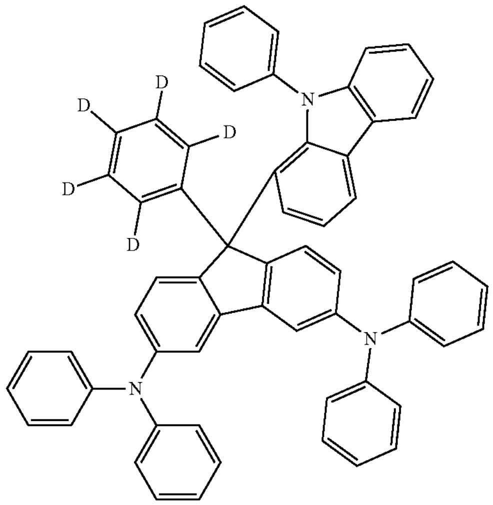

-continued
305
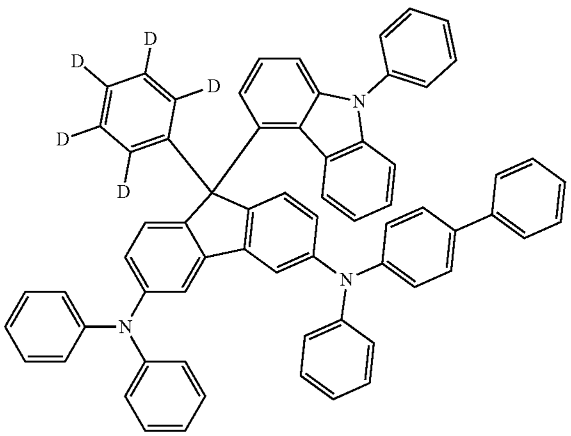
306
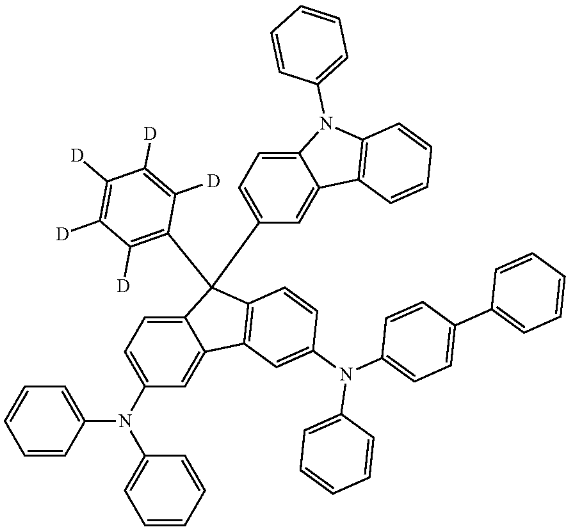
307
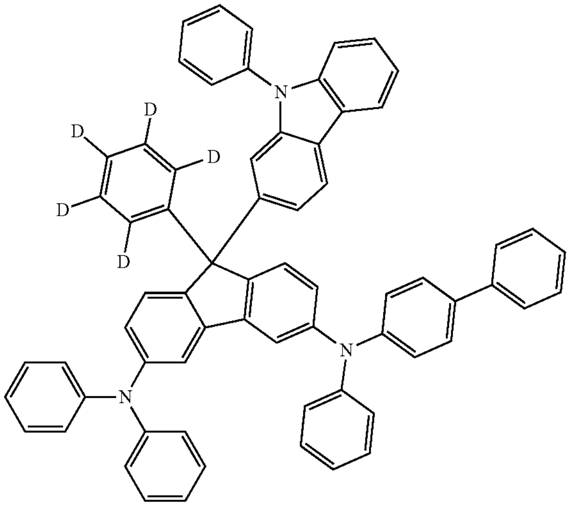
-continued
308
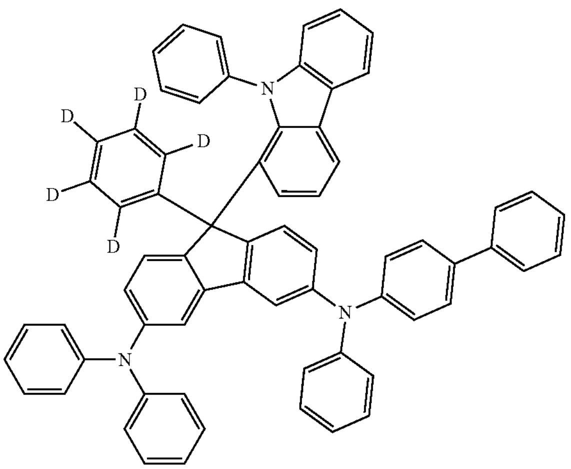
309
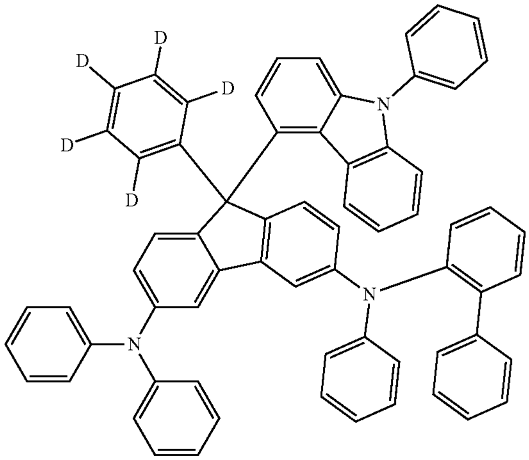
310
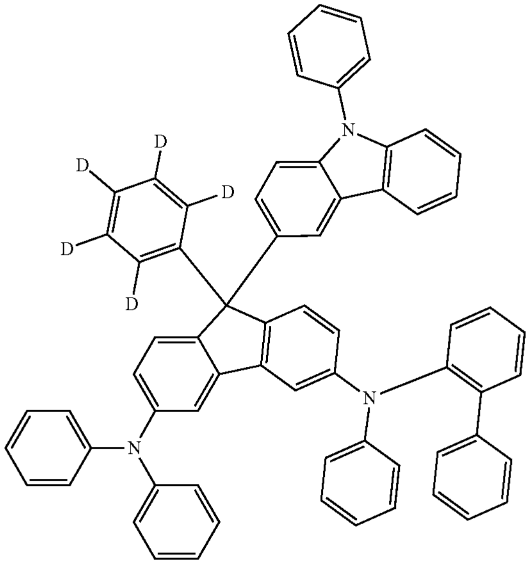

-continued
311
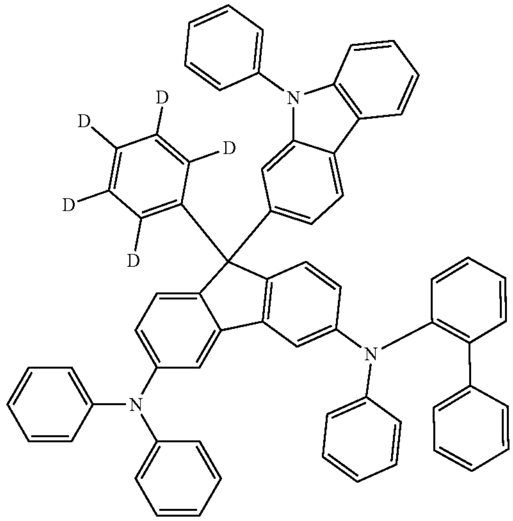
312
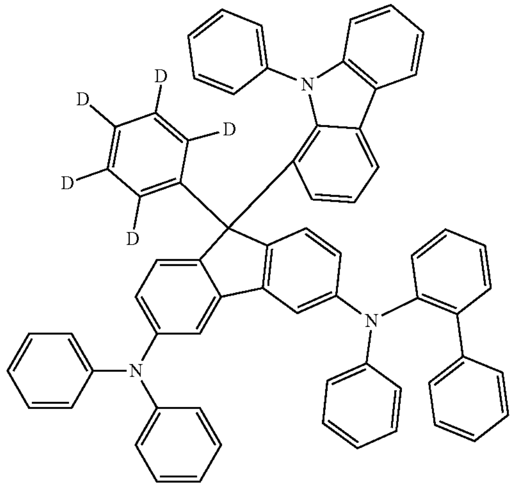
313
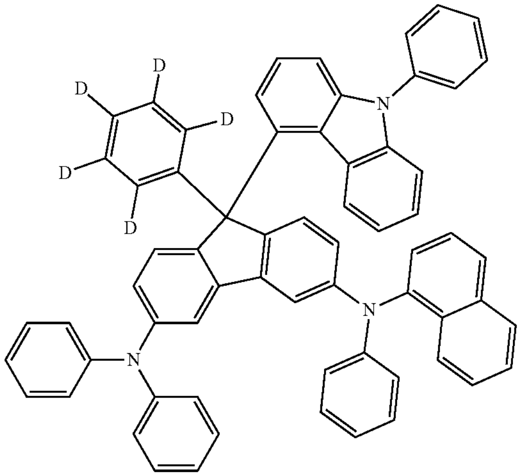
-continued
314
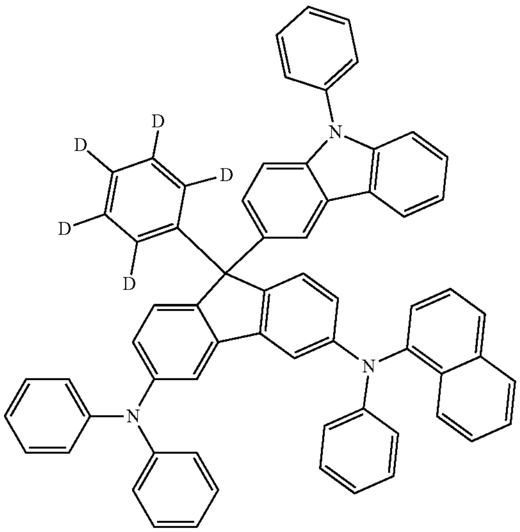
315
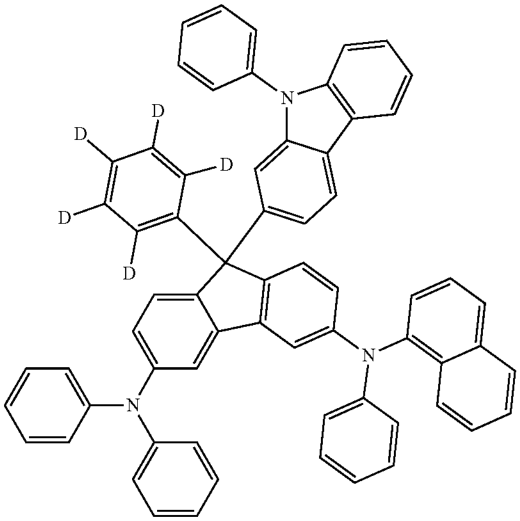
316
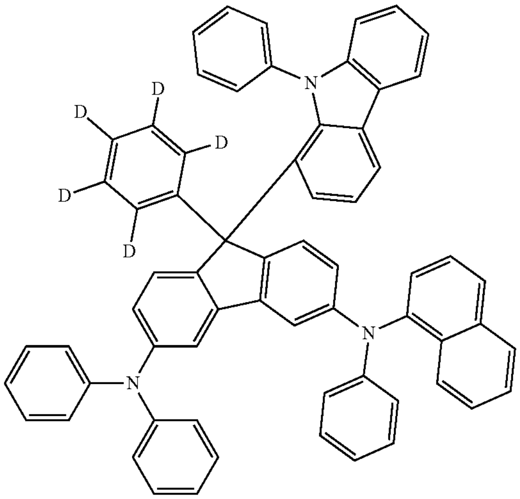

-continued
317
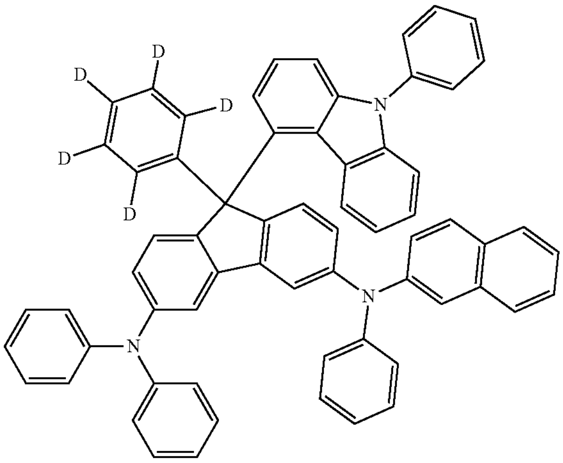
318
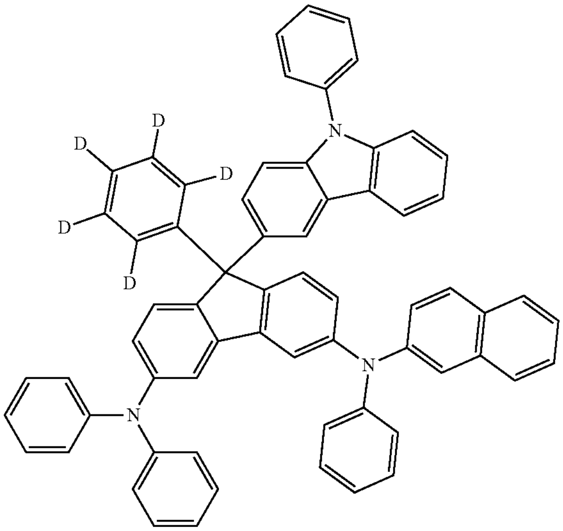
319
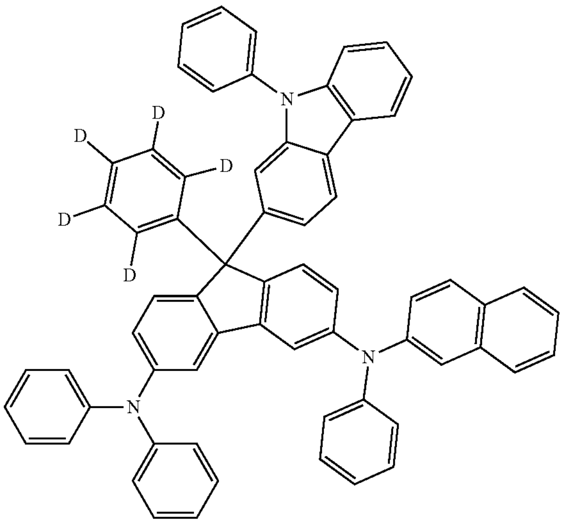
-continued
320
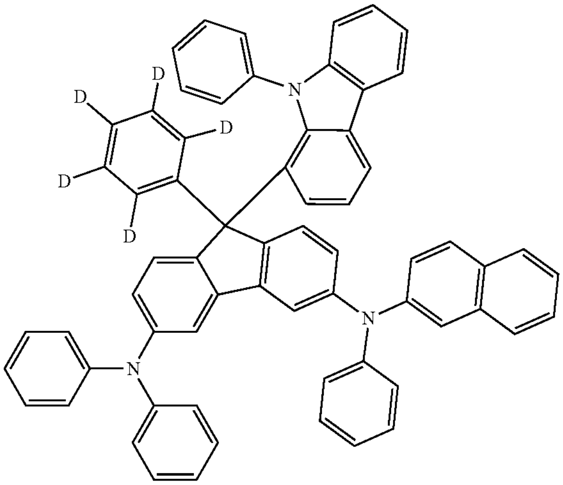
321
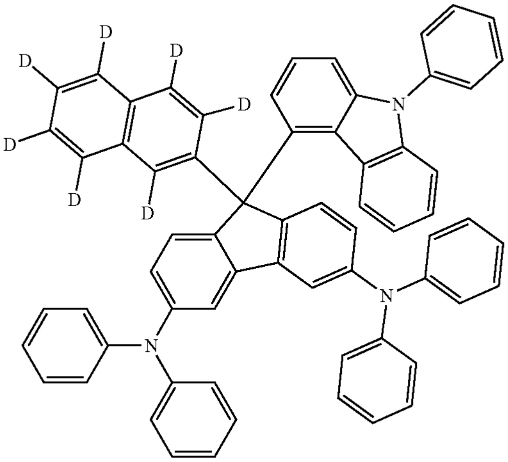
322
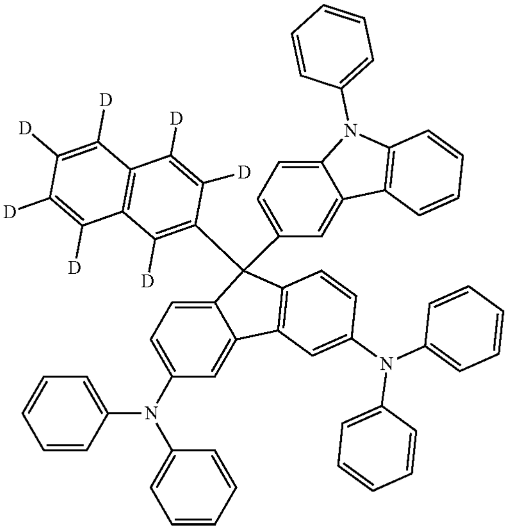

-continued
323
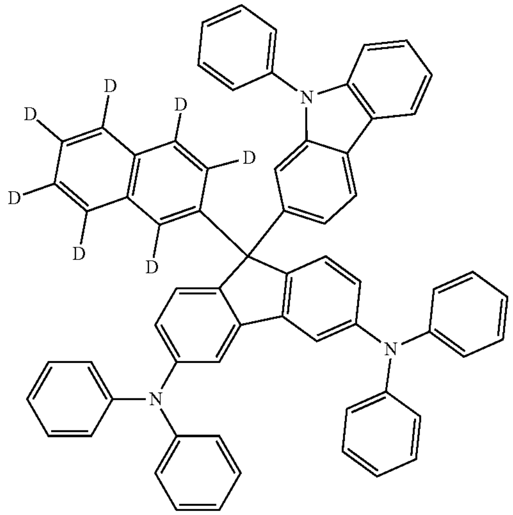
324
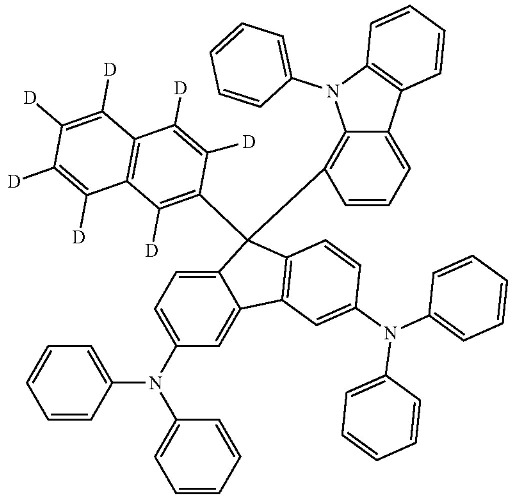
325
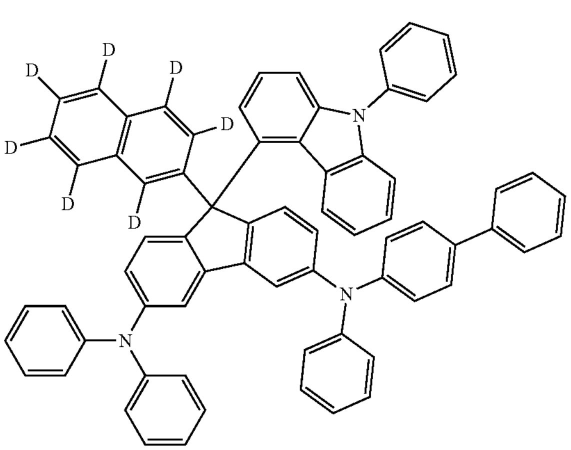
-continued
326
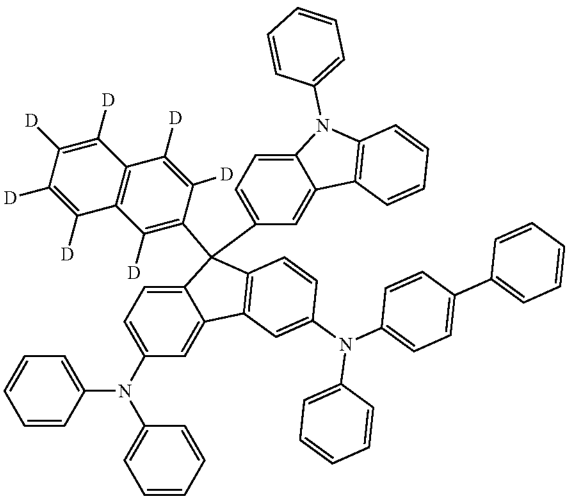
327
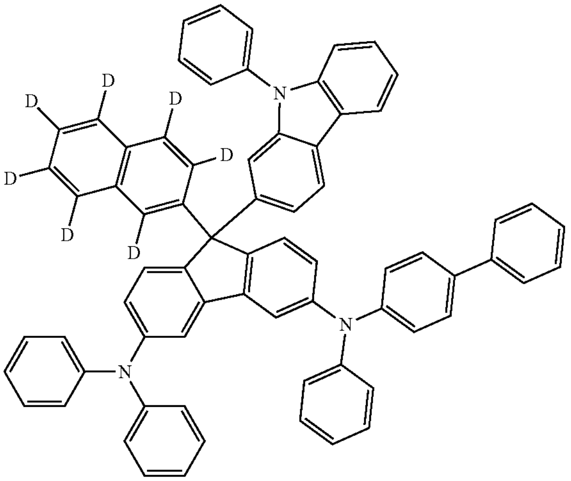
328
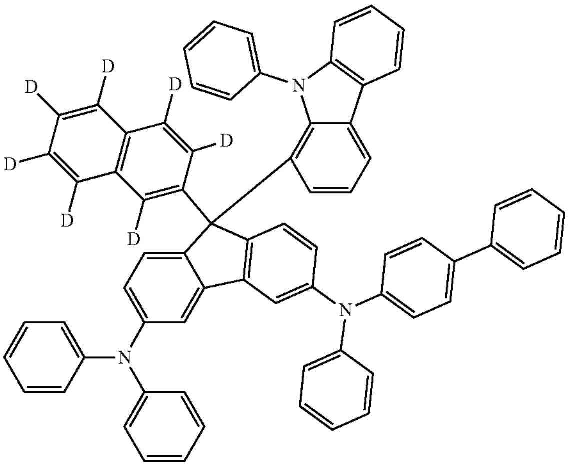

-continued
329
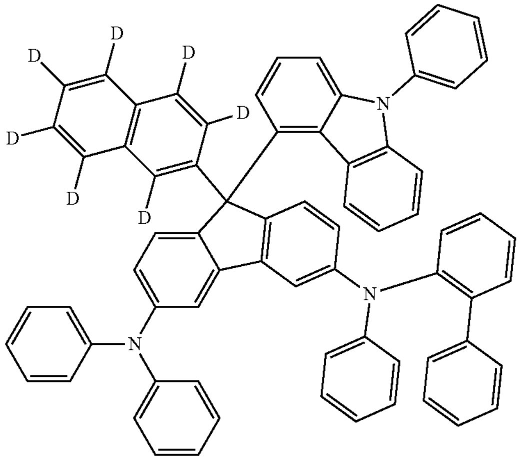
330
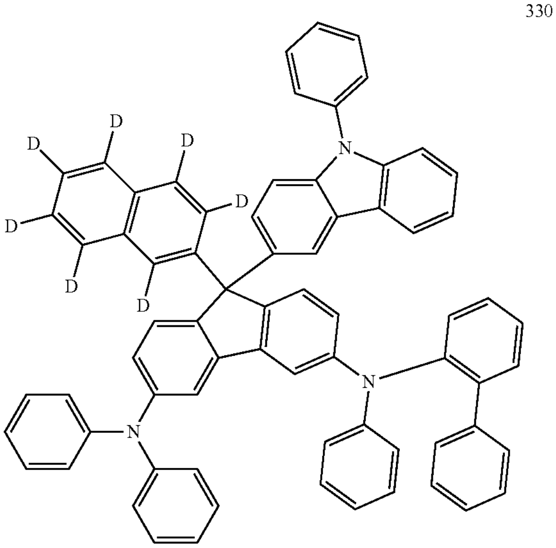
331
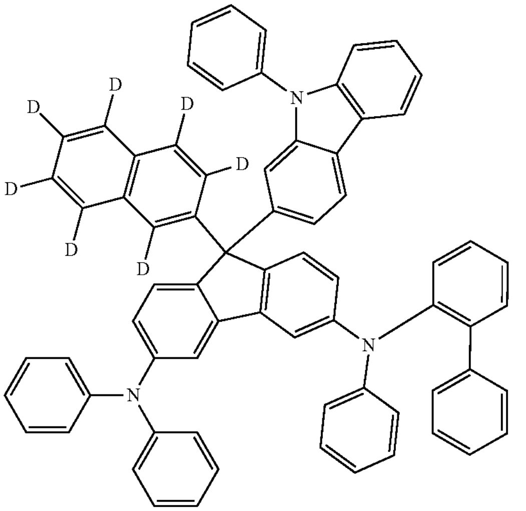
-continued
332
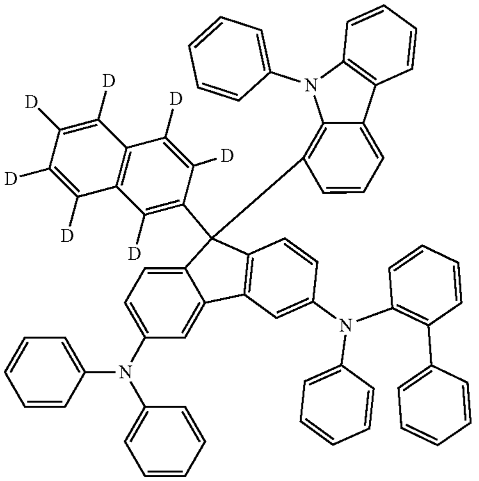
333
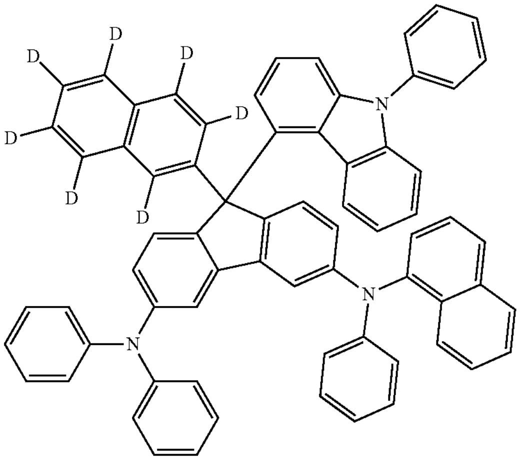
334
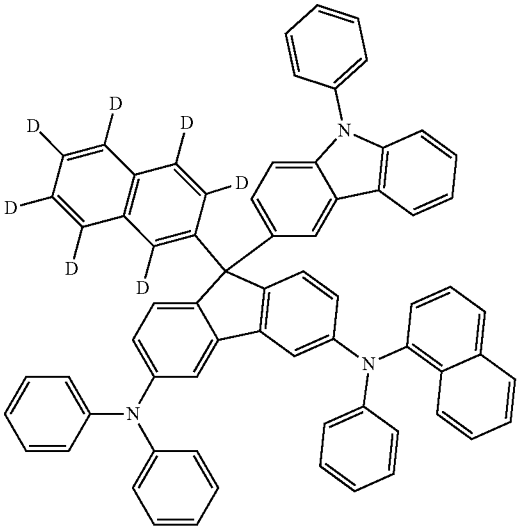

-continued
335
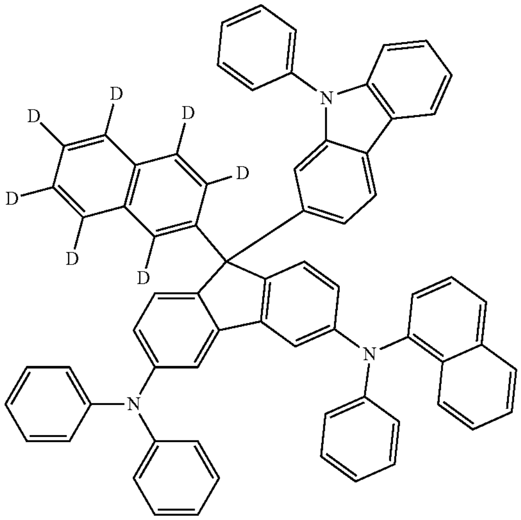
336
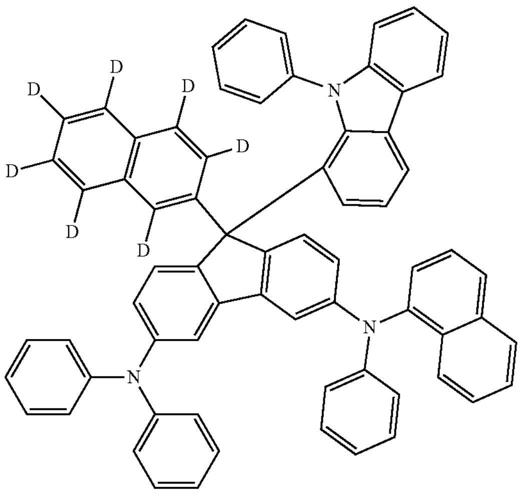
339
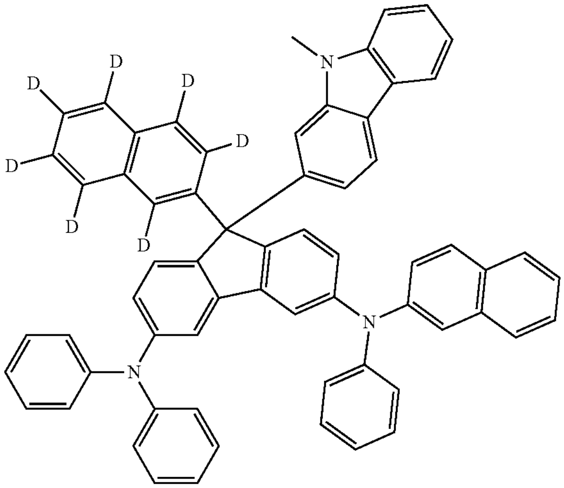
-continued
340
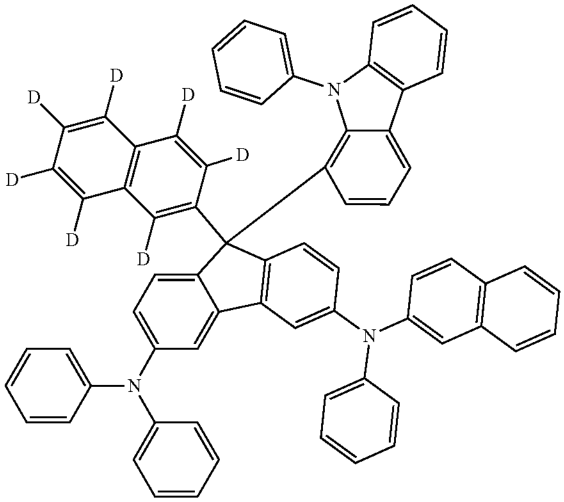
341
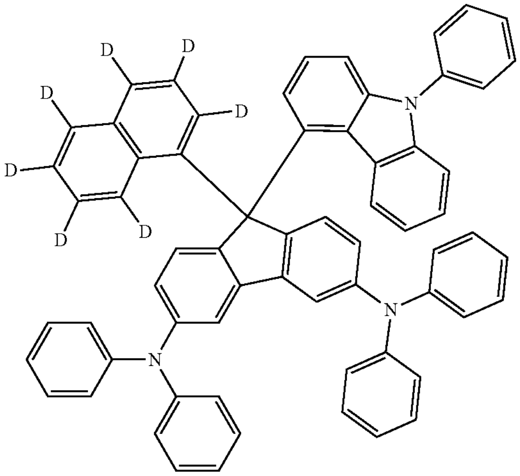
342
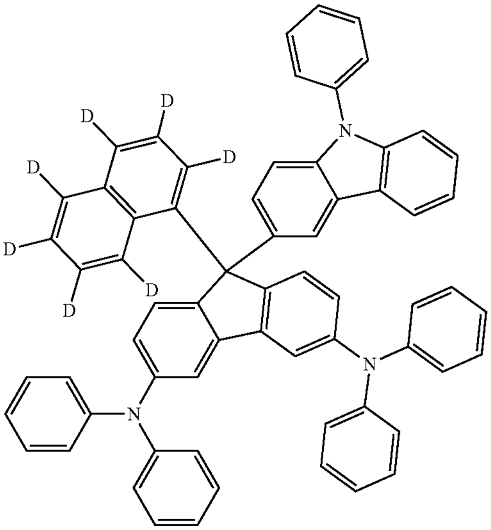

-continued
343
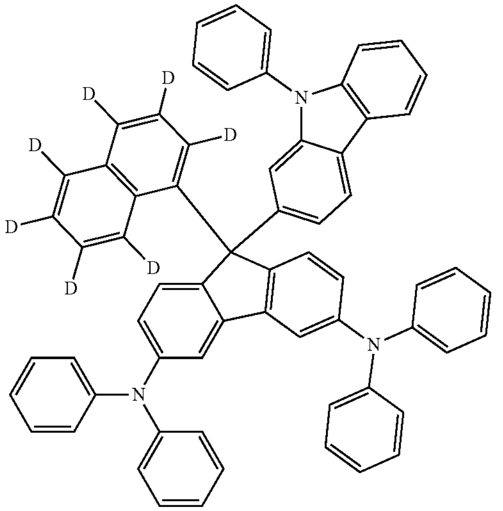
344
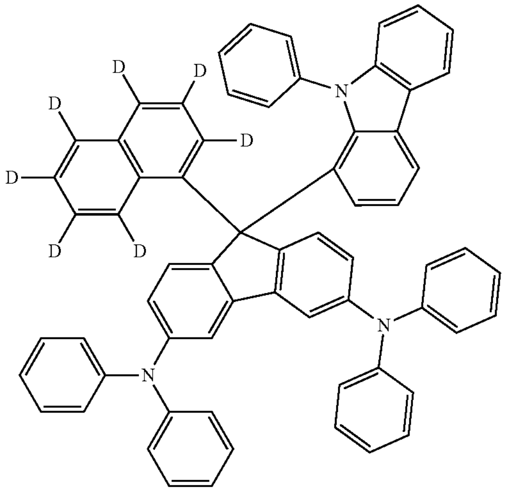
345
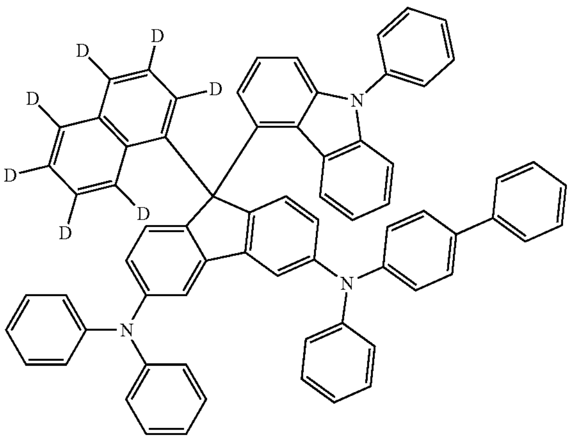
-continued
346
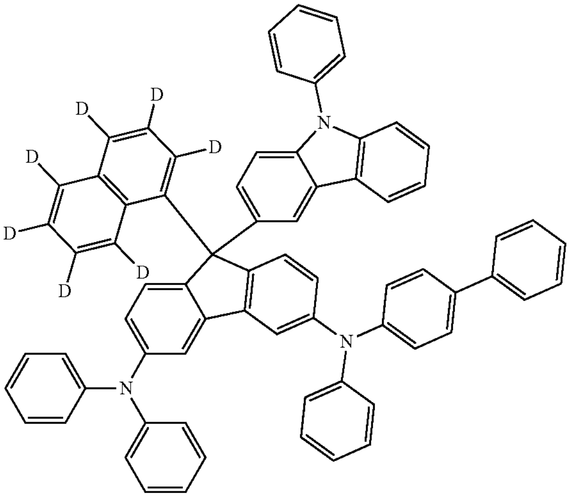
347
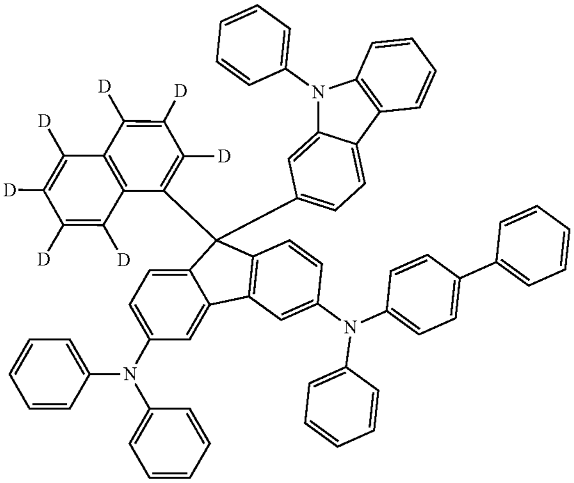
348
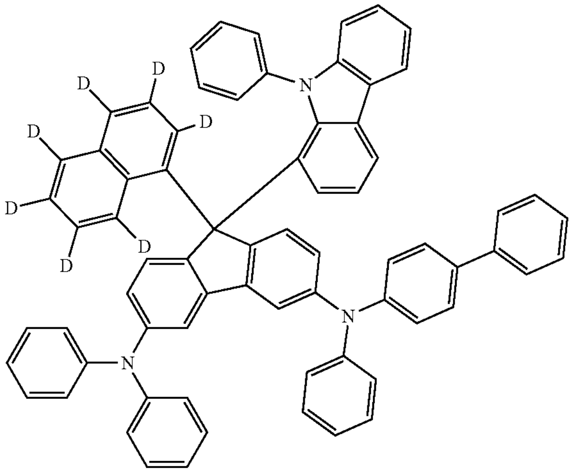

-continued
349
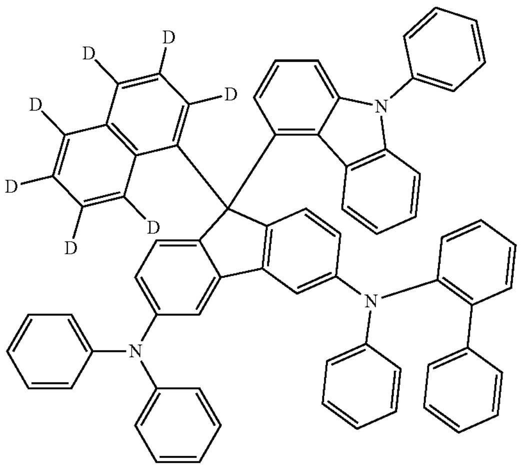
350
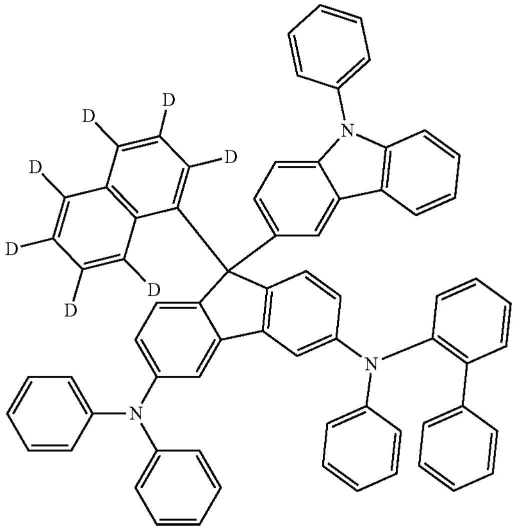
351
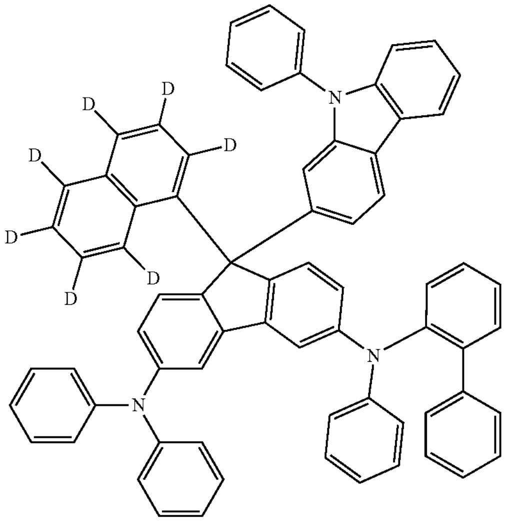
-continued
352
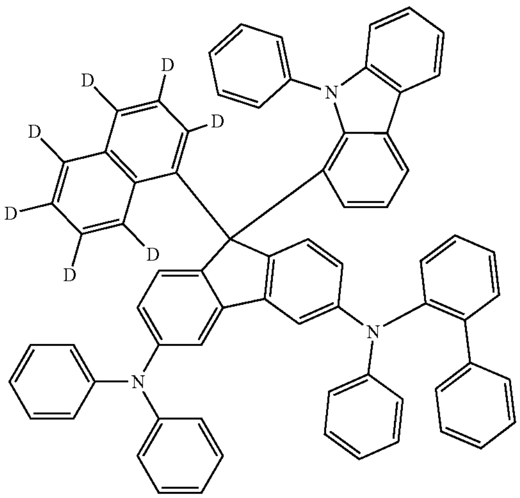
353
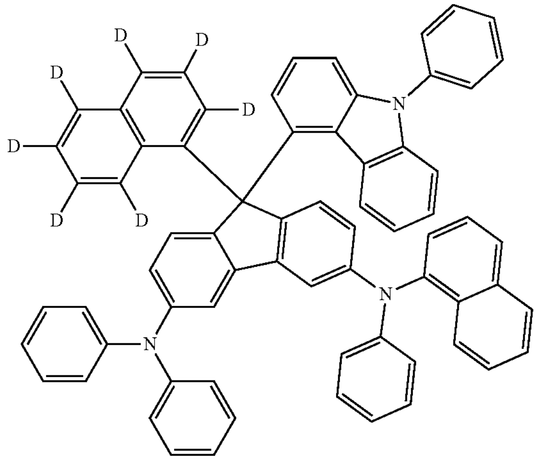
354
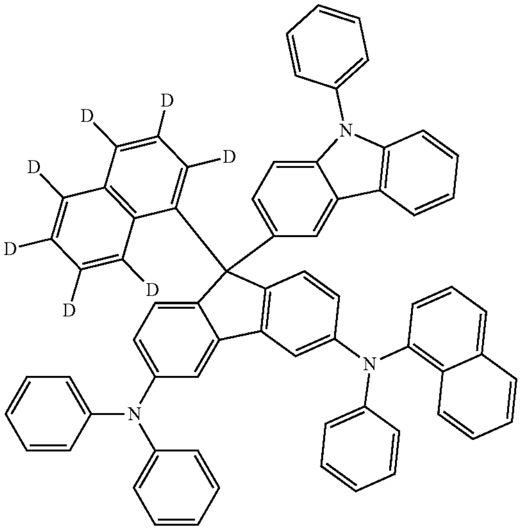

-continued
355
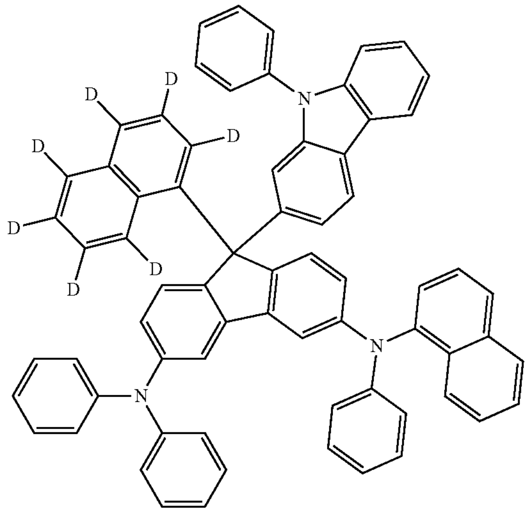
356
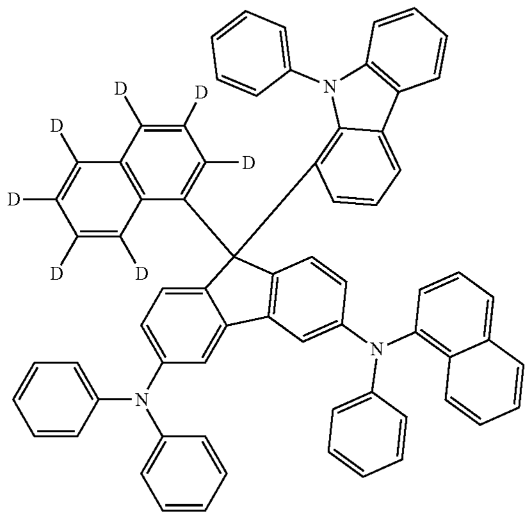
357
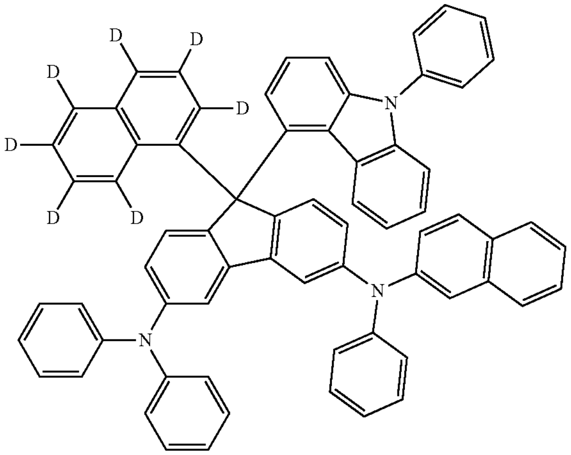
-continued
358
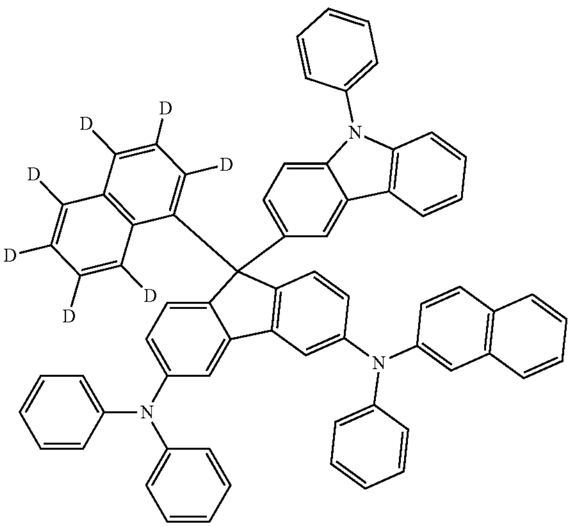
359
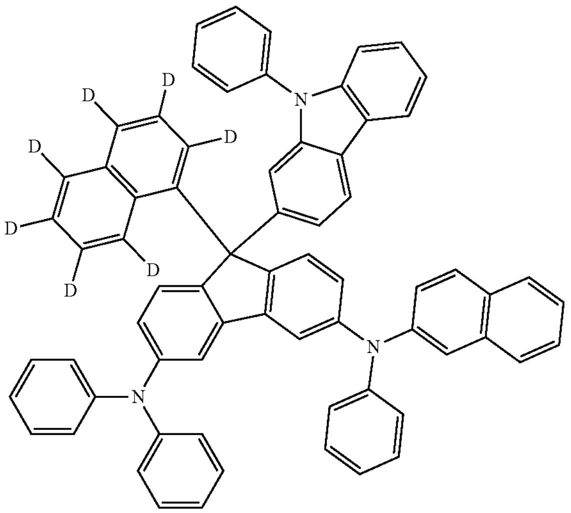
360
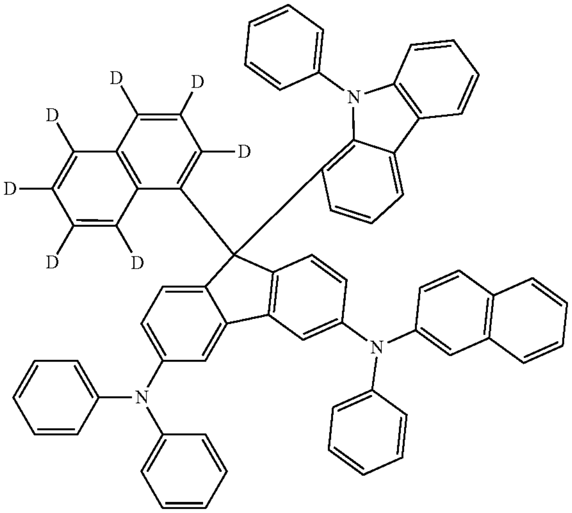

-continued

175

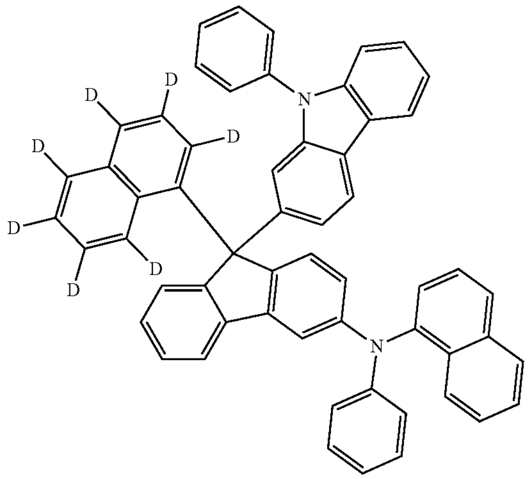

176

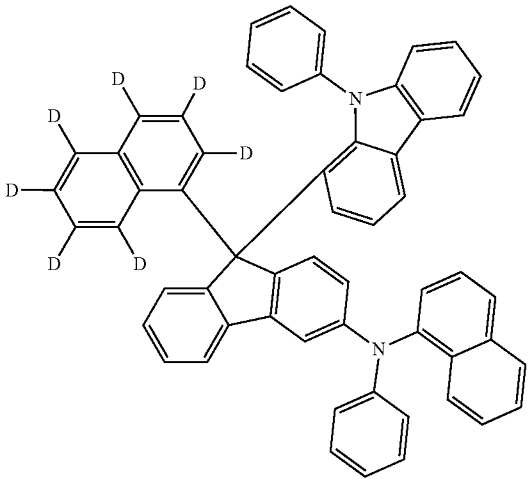

337

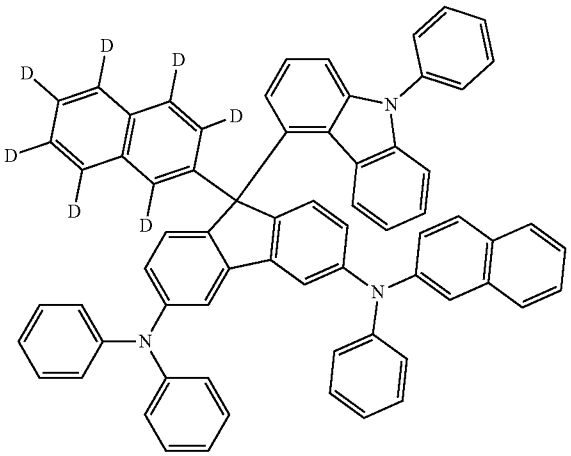

-continued

338

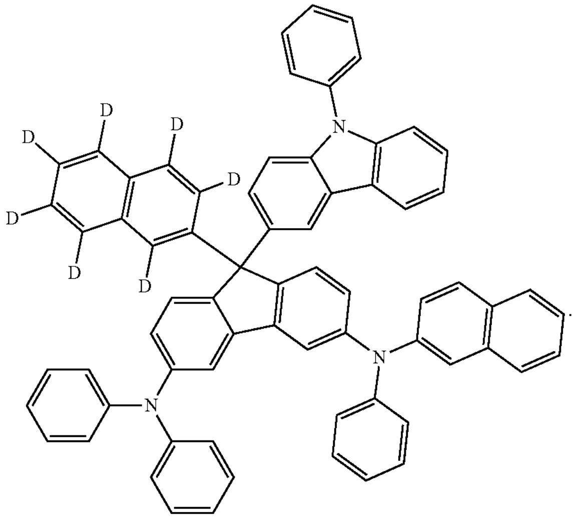

BRIEF DESCRIPTION OF THE DRAWINGS

The accompanying drawings are included to provide further understanding of the present disclosure, and are incorporated in and constitute a part of this specification. The drawings illustrate example embodiments of the present disclosure and, together with the description, serve to explain principles of the present disclosure. In the drawings.

DETAILED DESCRIPTION

Figure 1:
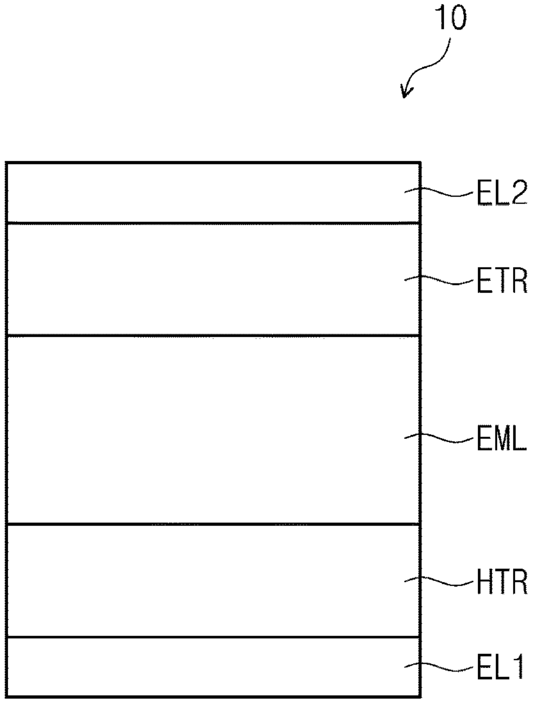
FIG. 1 is a schematic cross-sectional view illustrating an organic electroluminescence device according to an embodiment of the present disclosure.

The present disclosure may have various modifications and may be embodied in different forms, and example embodiments will be explained in detail with reference to the accompanying drawings. The present disclosure may, however, be embodied in different forms, and should not be construed as being limited to the embodiments set forth herein. Rather, any and all modifications, equivalents, and/or substituents that are in the spirit and technical scope of the present disclosure are included in the present disclosure.

In the accompanying drawings, like reference numbers refer to like elements, and duplicative descriptions thereof may not be provided. The dimensions of each structure may be exaggerated for clarity. It will be understood that, although the terms "first," "second," etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present disclosure. The terms of a singular form may include plural forms unless the context clearly indicates otherwise.

As used herein, the singular forms "a," "an," and "the" are intended to include the plural forms as well, unless the context clearly indicates otherwise.

In the present application, it will be understood that the meaning of "includes," "including," "comprises," "comprising," and/or "have" specifies the presence of a feature, a fixed number, a step, a process, an element, a component, or a combination thereof disclosed in the specification, but does not exclude the possibility of presence or addition of one or more other features, fixed numbers, steps, processes, elements, components, or combinations thereof.

In the present application, when a layer, a film, a region, or a plate is referred to as being "above" or "in a upper portion of" another layer, film, region, or plate, it can be not only directly on the layer, film, region, or plate, but intervening layers, films, regions, or plates may also be present. When a layer, a film, a region, or a plate is referred to as being "under" or "in a lower portion of" another layer, film, region, or plate, it can be not only directly under the layer, film, region, or plate, but intervening layers, films, regions, or plates may also be present. In addition, it will be understood that when a layer, a film, a region, or a plate is referred to as being 'on' another layer, film, region, or plate, it can be not only disposed on the layer, film, region, or plate, but also disposed under the layer, film, region, or plate.

As used herein, expressions such as "at least one of," "one of," and "selected from," when preceding a list of elements, modify the entire list of elements and do not modify the individual elements of the list.

As used herein, the term "and/or" includes any and all combinations of one or more of the associated listed items. Further, the use of "may" when describing embodiments of the present disclosure refers to "one or more embodiments of the present disclosure".

In an embodiment of the description, the term "substituted or unsubstituted" may refer to a state of being unsubstituted, or being substituted or with at least one substituent selected from the group consisting of a deuterium atom, a halogen atom, a cyano group, a nitro group, an amino group, a silyl group, an oxy group, a thio group, a sulfinyl group, a sulfonyl group, a carbonyl group, a boron group, a phosphine oxide group, a phosphine sulfide group, an alkyl group, an alkenyl group, an alkoxy group, a hydrocarbon ring group, an aryl group, and a heterocyclic group. Each of these example substituents may be further substituted or unsubstituted. For example, a biphenyl group may be interpreted as a named aryl group, and/or as a phenyl group substituted with a phenyl group.

In the description, the phrase "bonded to an adjacent group to form a ring" refers to a state of being bonded to an adjacent group to form a substituted or unsubstituted hydrocarbon ring, or a substituted or unsubstituted heterocycle. The hydrocarbon ring may be an aliphatic hydrocarbon ring or an aromatic hydrocarbon ring. The heterocycle may be an aliphatic heterocycle or an aromatic heterocycle. The hydrocarbon ring and the heterocycle may each independently be monocyclic or polycyclic. In addition, the rings formed by being bonded to each other may be connected to another ring to form a spiro structure.

In the description, the term "an adjacent group" may refer to a substituent on the same atom or point, a substituent on an atom that is directly connected to the base atom or point, or a substituent sterically positioned (e.g., within intramolecular bonding distance) to the corresponding substituent. For example, two methyl groups in 1,2-dimethylbenzene may be interpreted as "adjacent groups" to each other and two ethyl groups in 1,1-diethylcyclopentane may be interpreted as "adjacent groups" to each other.

In the description, non-limiting examples of the halogen atom include a fluorine atom, a chlorine atom, a bromine atom, and an iodine atom.

In the description, the term "alkyl group" may refer to a linear, branched or cyclic alkyl group. The number of carbons in the alkyl group may be 1 to 50, 1 to 30, 1 to 20, 1 to 10, or 1 to 6. Non-limiting examples of the alkyl group include a methyl group, ethyl group, n-propyl group, isopropyl group, n-butyl group, s-butyl group, t-butyl group, i-butyl group, 2-ethylbutyl group, 3,3-dimethylbutyl group, n-pentyl group, i-pentyl group, neopentyl group, t-pentyl group, cyclopentyl group, 1-methylpentyl group, 3-methylpentyl group, 2-ethylpentyl group, 4-methyl-2-pentyl group, n-hexyl group, 1-methylhexyl group, 2-ethylhexyl group, 2-butylhexyl group, cyclohexyl group, 4-methylcyclohexyl group, 4-t-butylcyclohexyl group, n-heptyl group, 1-methylheptyl group, 2,2-dimethylheptyl group, 2-ethylheptyl group, 2-butylheptyl group, n-octyl group, t-octyl group, 2-ethyloctyl group, 2-butyloctyl group, 2-hexyloctyl group, 3,7-dimethyloctyl group, cyclooctyl group, n-nonyl group, n-decyl group, adamantyl group, 2-ethyldecyl group, 2-butyldecyl group, 2-hexyldecyl group, 2-octyldecyl group, n-undecyl group, n-dodecyl group, 2-ethyldodecyl group, 2-butyldodecyl group, 2-hexyldocecyl group, 2-octyldodecyl group, n-tridecyl group, n-tetradecyl group, n-pentadecyl group, n-hexadecyl group, 2-ethylhexadecyl group, 2-butylhexadecyl group, 2-hexylhexadecyl group, 2-octylhexadecyl group, n-heptadecyl group, n-octadecyl group, n-nonadecyl group, n-eicosyl group, 2-ethyleicosyl group, 2-butyleicosyl group, 2-hexyleicosyl group, 2-octyleicosyl group, n-henicosyl group, n-docosyl group, n-tricosyl group, n-tetracosyl group, n-pentacosyl group, n-hexacosyl group, n-heptacosyl group, n-octacosyl group, n-nonacosyl group, n-triacontyl group, etc.

In the description, the term "hydrocarbon ring" may refer to any functional group or substituent derived from an aliphatic hydrocarbon ring. The hydrocarbon ring group may be a saturated hydrocarbon ring group having 5 to 20 ring-forming carbon atoms.

In the description, the term "aryl group" may refer to any functional group or substituent derived from an aromatic hydrocarbon ring. The aryl group may be a monocyclic aryl group or a polycyclic aryl group. The number of ring-forming carbon atoms in the aryl group may be 6 to 60, 6 to 30, 6 to 20, or 6 to 15. Non-limiting examples of the aryl group include phenyl, naphthyl, fluorene, anthracenyl, phenanthryl, biphenyl, terphenyl, quaterphenyl, quinquephenyl, sexiphenyl, triphenylenyl, pyrenyl, benzofluoranthenyl, chrysenyl, etc.

In the description, the fluorene group may be substituted, and two substituents (e.g., at the 9H position) may be connected to each other to form a spiro structure. Non-limiting examples of the substituted fluorene group are as follows. However, embodiments of the present disclosure are not limited thereto.

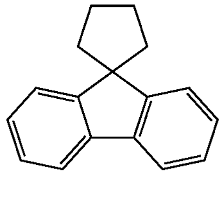

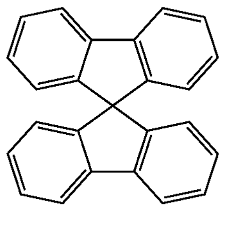

-continued

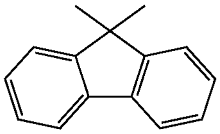

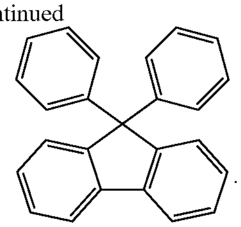

In the description, the term “heterocyclic group” may refer to any functional group or substituent derived from a ring including at least one of boron (B), oxygen (O), sulfur (S), nitrogen (N), phosphorus (P), silicon (Si), or selenium (Se) as a heteroatom. The heterocyclic group may be an aliphatic heterocyclic group or an aromatic heterocyclic group. The aromatic heterocyclic group may be a heteroaryl group. The aliphatic heterocycle and the aromatic heterocycle may each independently be monocyclic or polycyclic.

When the heterocyclic group contains two or more hetero atoms, the two or more hetero atoms may be the same as or different from each other. The heterocyclic group may be a monocyclic heterocyclic group or a polycyclic heterocyclic group, and in some embodiments may be a heteroaryl group. The number of ring-forming carbon atoms in the heterocyclic group may be 2 to 60, 2 to 30, 2 to 20, or 2 to 10.

The number of carbons for forming a ring of the aliphatic heterocyclic group may be 2 to 30, 2 to 20, or 2 to 10. Non-limiting examples of the aliphatic heterocyclic group include an oxirane group, thiirane group, pyrrolidine group, piperidine group, tetrahydrofuran group, tetrahydrothiophene group, thiane group, tetrahydropyran group, 1,4-dioxane group, etc.

When the heteroaryl group contains two or more heteroatoms, the two or more heteroatoms may be the same as or different from each other. The heteroaryl group may be a monocyclic heteroaryl group or a polycyclic heteroaryl group. The number of ring-forming carbon atoms in the heteroaryl group may be 2 to 30, 2 to 20, or 2 to 10. Non-limiting examples of the heteroaryl group include thiophenyl, furanyl, pyrrolyl, imidazolyl, thiazolyl, oxazolyl, oxadiazolyl, triazolyl, pyridyl, bipyridyl, pyrimidyl, triazinyl, triazolyl, acridyl, pyridazinyl, pyrazinyl, quinolinyl, quinazolinyl, quinoxalinyl, phenoxazolyl, phthalazinyl, pyrido pyrimidyl, pyrido pyrazinyl, pyrazino pyrazinyl, isoquinolinyl, indolyl, carbazolyl, N-arylcarbazolyl, N-heteroarylcarbazolyl, N-alkylcarbazolyl, benzoxazolyl, benzimidazolyl, benzothiazolyl, benzocarbazolyl, benzothiophenyl, dibenzothiophenyl, thienothiophenyl, benzofuranyl, phenanthrolinyl, thiazolyl, isoxazolyl, oxadiazolyl, thiadiazolyl, phenothiazolyl, phenothiazinyl, dibenzosilolyl, dibenzofuranyl, etc.

In the description, the above description of the aryl group may be applied to an arylene group, except that the arylene group is a divalent group. The above description of the heteroaryl group may be applied to a heteroarylene group, except that the heteroarylene group is a divalent group.

In the description, the number of carbon atoms in an amino group is not specifically limited, but may be 1 to 30. The term “amino group” may refer to an alkyl amino group, an aryl amino group, or a heteroaryl amino group. Non-limiting examples of the amino group include a methylamino group, a dimethylamino group, a phenylamino group, a diphenylamino group, a naphthylamino group, a 9-methylanthracenylamino group, a triphenylamino group, etc.

In the description, the alkenyl group may be linear or branched. The number of carbon atoms is not specifically limited, and may be 2 to 30, 2 to 20, or 2 to 10. Non-limiting examples of the alkenyl group include a vinyl group, a 1-butenyl group, a 1-pentenyl group, a 1,3-butadienyl aryl group, a styrenyl group, a styryl vinyl group, etc.

In the description, the number of carbon atoms in the amine group is not specifically limited, but may be 1 to 30. The amine group may be an alkyl amine group or an aryl amine group. Non-limiting examples of the amine group include, but are not limited to, a methylamine group, dimethylamine group, phenylamine group, diphenylamine group, naphthylamine group, 9-methyl-anthracenylamine group, triphenylamine group, etc.

In the description, the alkyl group in the alkylamine group may be the same as the alkyl group generally described above.

In the description, the aryl group in the arylamine group may be the same as the aryl group generally described above.

In the description, the term “direct linkage” may refer to a single bond.

In the description, “—*” refers to a point of connection (e.g., a bond).

Hereinafter, an organic electroluminescence device according to an embodiment of the present disclosure and an amine compound included therein will be explained with reference to the drawings.

Figure 2:
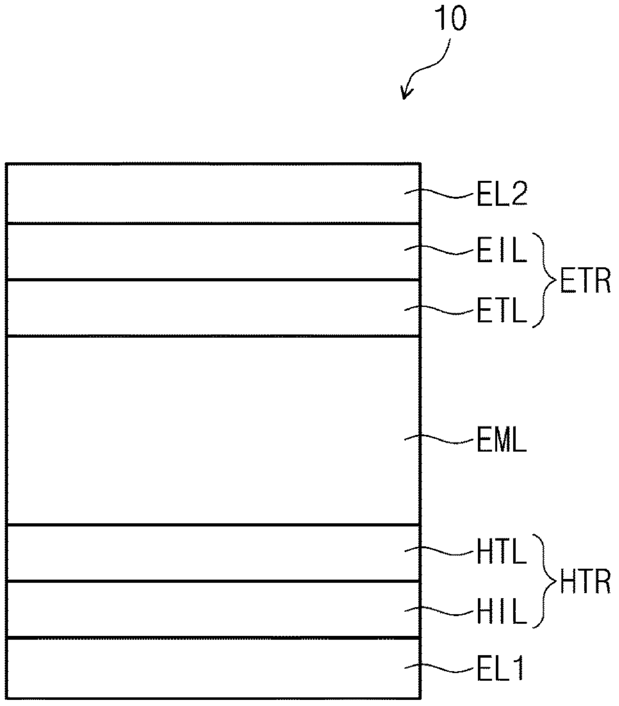
FIG. 2 is a schematic cross-sectional view illustrating an organic electroluminescence device according to an embodiment of the present disclosure.
Figure 3:
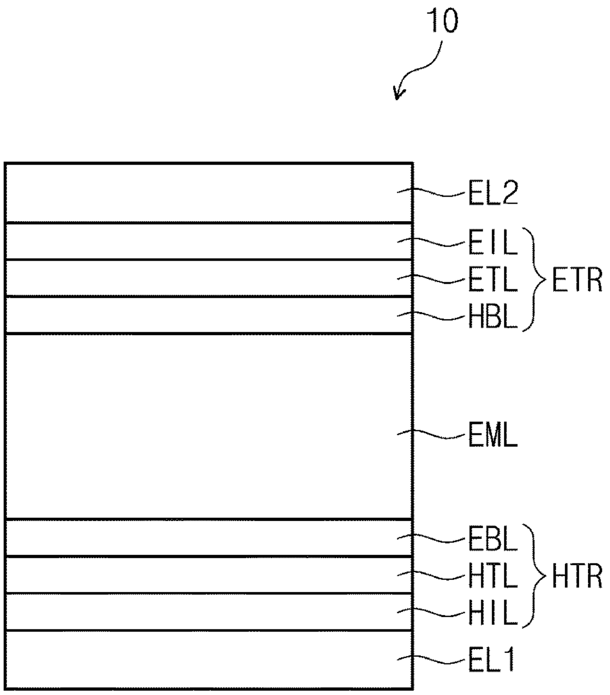
FIG. 3 is a schematic cross-sectional view illustrating an organic electroluminescence device according to an embodiment of the present disclosure.
Figure 4:
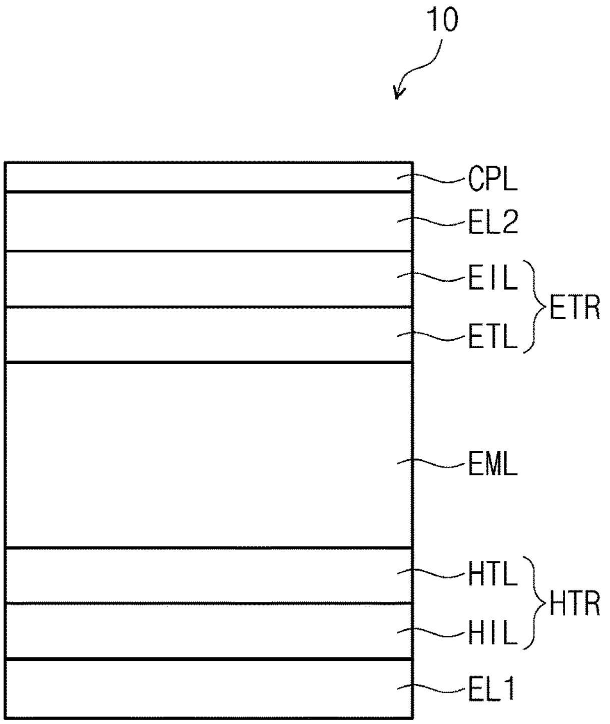
FIG. 4 is a schematic cross-sectional view illustrating an organic electroluminescence device according to an embodiment of the present disclosure.

FIGS. 1 to 4 are schematic cross-sectional views illustrating an organic electroluminescence device according to an embodiment of the present disclosure. Referring to FIGS. 1 to 4, in an organic electroluminescence device 10 according to an embodiment, a first electrode EL1 and a second electrode EL2 are disposed to face each other and an emission layer EML is disposed between the first electrode EL1 and the second electrode EL2.

in some embodiments, the organic electroluminescence device 10 of an embodiment may further include a plurality of functional layers between the first electrode EL1 and the second electrode EL2 in addition to the emission layer EML. The plurality of functional layers may include a hole transport region HTR and an electron transport region ETR. For example, the organic electroluminescence device 10 according to an embodiment may include the first electrode EL1, the hole transport region HTR, the emission layer EML, the electron transport region ETR, and the second electrode EL2, which are sequentially stacked. In some embodiments, the organic electroluminescence device 10 of an embodiment may include a capping layer CPL disposed on the second electrode EL2.

The organic electroluminescence device 10 of an embodiment may include a compound of an embodiment, which will be described later, in the hole transfer region HTR disposed between the first electrode EL1 and the second electrode EL2. However, embodiments are not limited thereto, and the organic electroluminescence device 10 of an embodiment may include a compound according to an embodiment not only in the hole transport region HTR but also in the emission layer EML or electron transport region ETR, which are among the plurality of functional layers disposed between the first electrode EL1 and the second electrode EL2, or in the capping layer CPL disposed on the second electrode EL2.

The first electrode EL1 may have conductivity (e.g., may be conductive). The first electrode EL1 may be formed of a metal alloy and/or a conductive compound. The first electrode EL1 may be an anode. In some embodiments, the first electrode EL1 may be a pixel electrode. The first electrode EL1 may be a transmissive electrode, a transflective electrode, or a reflective electrode. When the first electrode EL1 is a transmissive electrode, the first electrode EL1 may include a transparent metal oxide (such as indium tin oxide (ITO), indium zinc oxide (IZO), zinc oxide (ZnO), and/or indium tin zinc oxide (ITZO)). When the first electrode EL1 is a transflective electrode or a reflective electrode, the first electrode EL1 may include silver (Ag), magnesium (Mg), copper (Cu), aluminum (Al), platinum (Pt), palladium (Pd), gold (Au), nickel (Ni), neodymium (Nd), iridium (Ir), chromium (Cr), lithium (Li), calcium (Ca), LiF/Ca, LiF/AI, molybdenum (Mo), titanium (Ti), a compound thereof, or any mixture thereof (e.g., a mixture of Ag and Mg). In some embodiments, the first electrode EL1 may have a multilayer structure including a reflective layer and/or a transflective layer formed of the above-described materials, and a transparent conductive layer formed of ITO, IZO, ZnO, ITZO, etc. For example, the first electrode EL1 may have a three-layer structure of ITO/Ag/ITO, but embodiments of the present disclosure are not limited thereto. The thickness of the first electrode EL1 may be about 1,000 Å to about 10,000 Å, for example, about 1,000 Å to about 3,000 Å.

The hole transport region HTR may be provided on the first electrode EL1. The hole transport region HTR may include at least one of a hole injection layer HIL, a hole transport layer HTL, a hole buffer layer, or an electron blocking layer EBL. The thickness of the hole transport region HTR may be, for example, about 50 Å to about 15,000 Å.

The hole transport region HTR may have a single layer formed of a single material, a single layer formed of a plurality of different materials, or a multilayer structure including a plurality of layers formed of a plurality of different materials.

For example, the hole transport region HTR may have a single layer structure of a hole injection layer HIL or a hole transport layer HTL, or a single layer structure formed of a hole injection material and a hole transport material. In some embodiments, the hole transport region HTR may have a single layer structure formed of a plurality of different materials, or a structure of hole injection layer HIL/hole transport layer HTL, hole injection layer HIL/hole transport layer HTL/hole buffer layer, hole injection layer HIL/hole buffer layer, hole transport layer HTL/hole buffer layer, or hole injection layer HIL/hole transport layer HTL/electron blocking layer EBL, which may be sequentially laminated on the first electrode EL1, but embodiments are not limited thereto.

The hole transport region HTR may be formed using any suitable method (such as a vacuum deposition method, a spin coating method, a cast method, a Langmuir-Blodgett (LB) method, an inkjet printing method, a laser printing method, and/or a laser induced thermal imaging (LITI) method).

The hole transport region HTR may include the amine compound of an embodiment. For example, the hole injection layer HIL and/or the hole transport layer HTL may include the amine compound of an embodiment.

The amine compound of an embodiment contains (includes) a fluorene group, an aryl group having 6 to 60 ring-forming carbon atoms that is substituted to the fluorene group, a heteroaryl group having 2 to 60 ring-forming carbon atoms that is substituted to the fluorene group, and at least one amine group that is substituted to the fluorene group. For example, the amine compound may have a structure in which the above-mentioned substituents are substituted to a core including the fluorene group.

In an embodiment, the amine compound may include an aryl group, a heteroaryl group, and at least one amine group as substituents of the fluorene group. The aryl group and the heteroaryl group may each be connected to the 9-position carbon of the fluorene group. The aryl group substituted at the 9-position carbon of the fluorene group may be an aryl group in which all the carbons of the aryl group are substituted with deuterium (e.g., may be a deuterated aryl group). For example, the aryl group substituted at the 9-position carbon of the fluorene group may be a phenyl group that is substituted with deuterium, a naphthyl group that is substituted with deuterium, or a biphenyl group that is substituted with deuterium. The heteroaryl group substituted at the 9-position carbon of the fluorene group may be a dibenzoheterole group. For example, the heteroaryl group substituted to the 9-position carbon of the fluorene group may be a fused polycyclic heteroaryl group in which three rings are fused. In some embodiments, the heteroaryl group substituted at the 9-position carbon of the fluorene group may be a substituted or unsubstituted dibenzothiophene group, a substituted or unsubstituted dibenzofuran group, or a substituted or unsubstituted carbazole group.

At least one amine group may be connected to at least one carbon among positions 1 through 8 of the fluorene group. In an embodiment, the amine group may be a tertiary amine. The fluorene group may be connected to the nitrogen atom of the amine group, and the nitrogen atom may include two substituents that are each independently a substituted or unsubstituted aryl group having 6 to 60 ring-forming carbon atoms, or a substituted or unsubstituted heteroaryl group having 3 to 60 ring-forming carbon atoms. In some embodiments, the amine group nitrogen atom substituents may each independently be an unsubstituted phenyl group, an unsubstituted biphenyl group, or an unsubstituted naphthyl group.

An amine compound according to an embodiment may be represented Formula 1:

Formula 1

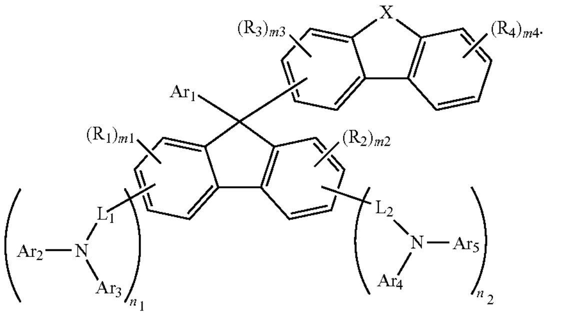

In Formula 1, X may be O, S, or $NAr_6$. For example, the heteroaryl group may be a substituted or unsubstituted dibenzofuran group, a substituted or unsubstituted dibenzothiophene group, or a substituted or unsubstituted carbazole group.

$L_1$ and $L_2$ may each independently be a direct linkage, a substituted or unsubstituted arylene group having 6 to 60 ring-forming carbon atoms, or a substituted or unsubstituted heteroarylene group having 2 to 60 ring-forming carbon atoms. For example, $L_1$ and $L_2$ may be a direct linkage.

$n_1$ and $n_2$ may each independently be 0 or 1, and at least one of $n_1$ or $n_2$ may be 1. For example, the amine compound of an embodiment may include one or two substituted amine groups.

$R_1$ to $R_4$ may each independently be a hydrogen atom, a deuterium atom, a halogen atom, a substituted or unsubstituted alkyl group having 1 to 20 carbon atoms, a substituted or unsubstituted aryl group having 6 to 60 ring-forming carbon atoms, or a substituted or unsubstituted heteroaryl group having 2 to 60 ring-forming carbon atoms, and/or may be bonded to an adjacent group to form a ring. For example, $R_1$ to $R_4$ may each independently be a hydrogen atom.

$m_1$, $m_2$, and $m_4$ may each independently be an integer of 0 to 4, and $m_3$ may be an integer of 0 to 3. For example, $m_1$ to $m_4$ may each be 0.

$Ar_1$ may be a phenyl group substituted with deuterium, a naphthyl group substituted with deuterium, or a biphenyl group substituted with deuterium. For example, $Ar_1$ may be represented by at least one of Formula $t_1$ to Formula $t_5$:

Formula $t_1$

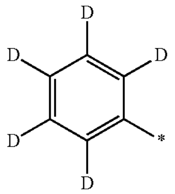

Formula $t_2$

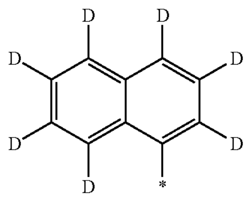

Formula $t_3$

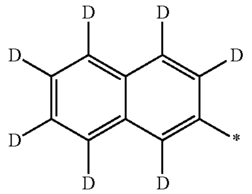

Formula $t_4$

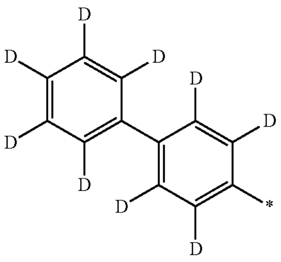

-continued

Formula $t_5$

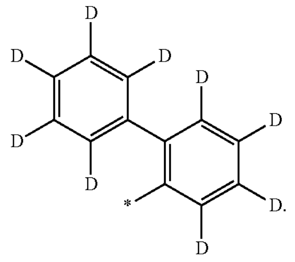

$Ar_2$ to $Ar_6$ may each independently be a substituted or unsubstituted aryl group having 6 to 60 ring-forming carbon atoms, or a substituted or unsubstituted heteroaryl group having 3 to 60 ring-forming carbon atoms. For example, $Ar_2$ to $Ar_4$ and $Ar_6$ may each be an unsubstituted phenyl group. $Ar_5$ may each be an unsubstituted phenyl group, an unsubstituted biphenyl group, or an unsubstituted naphthyl group. However, embodiments are not limited thereto.

In an embodiment, the amine compound represented by Formula 1 may be represented by at least one of Formula 1-1 to Formula 1-3:

Formula 1-1

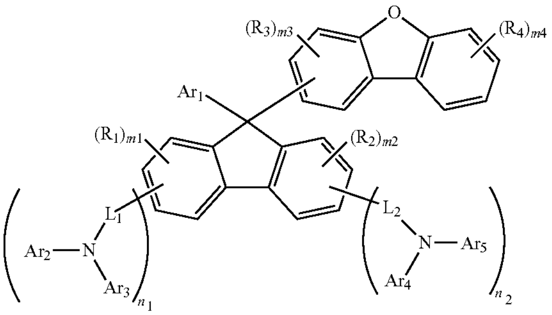

Formula 1-2

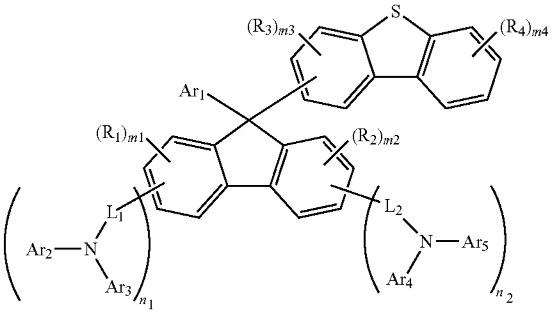

-continued

Formula 1-3

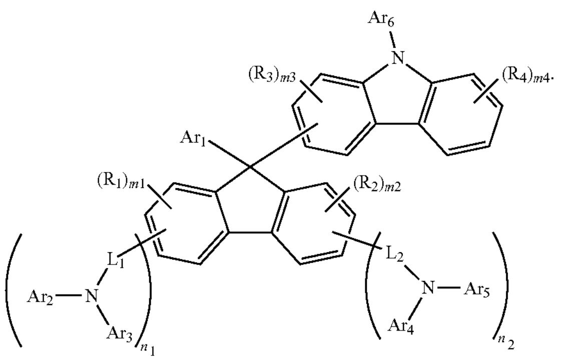

Formula 1-1 to Formula 1-3 are embodiments of Formula 1 in which X is specified. For example, Formula 1-1 to Formula 1-3 are formulae in which X is specified as O, S, and $NAr_6$, respectively. For example, Formula 1-1 includes a dibenzofuran group in the amine compound. Formula 1-2 includes a dibenzothiophene group in the amine compound. Formula 1-3 includes a carbazole group in the amine compound.

In Formula 1-1 to Formula 1-3, $L_1$, $L_2$, $R_1$ to $R_4$, $m_1$ to $m_4$, $Ar_1$ to $Ar_6$, $n_1$ and $n_2$ may each independently be the same as defined in Formula 1.

In an embodiment, the amine compound represented by Formula 1 may be represented by at least one of Formula 2-1 to Formula 2-5:

Formula 2-1

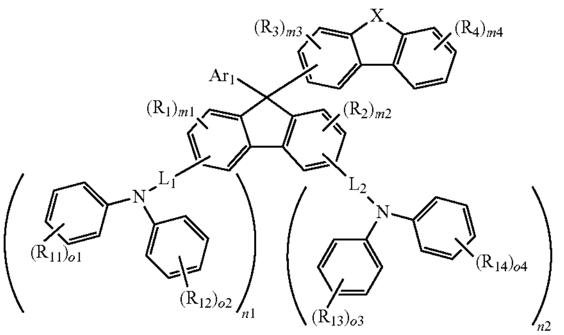

Formula 2-2

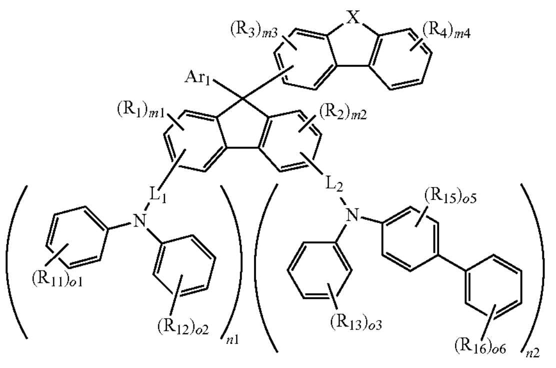

-continued

Formula 2-3

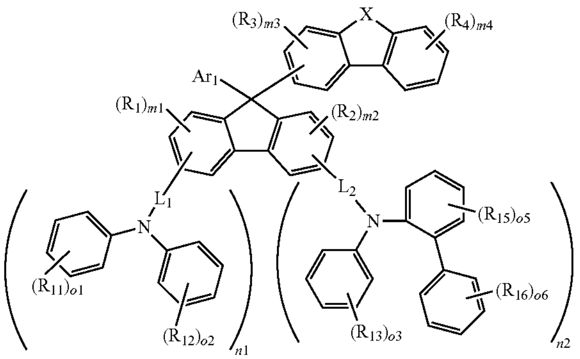

Formula 2-4

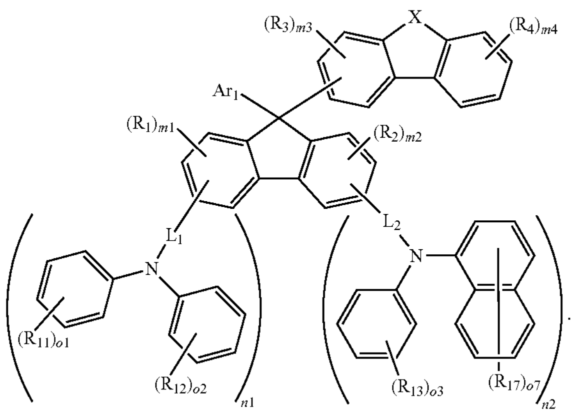

Formula 2-5

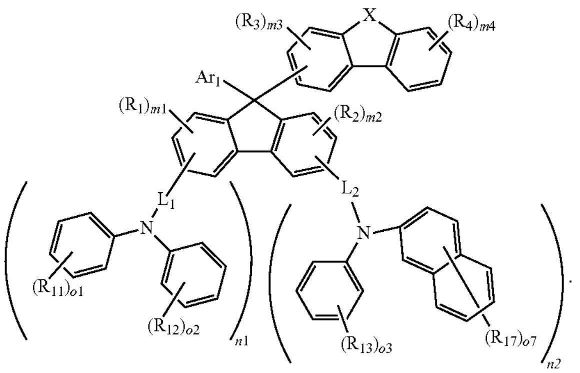

Formula 2-1 to Formula 2-5 are embodiments of Formula 1 in which $Ar_2$ to $Ar_5$ are specified. For example, in Formula 2-1, $Ar_2$ to $Ar_5$ are each independently a phenyl group. In Formula 2-2 and Formula 2-3, $Ar_2$ to $Ar_4$ are each independently a phenyl group and $Ar_5$ is as a biphenyl group. In Formula 2-2 and Formula 2-3, $Ar_5$ is a biphenyl group in which the nitrogen atom of the amine is connected to the para-position and ortho-position, respectively, with respect to the single bond connecting the two phenyl groups of the biphenyl group. In Formula 2-4 and Formula 2-5, $Ar_2$ to $Ar_4$ are each independently a phenyl group, and $Ar_5$ is a naphthyl group.

In Formula 2-1 to Formula 2-5, $R_{11}$ to $R_{17}$ may each independently be a hydrogen atom, a deuterium atom, a halogen atom, a substituted or unsubstituted alkyl group having 1 to 20 carbon atoms, a substituted or unsubstituted aryl group having 6 to 60 ring-forming carbon atoms, or a substituted or unsubstituted heteroaryl group having 2 to 60 ring-forming carbon atoms, and/or may be bonded to an adjacent group to form a ring. For example, $R_{11}$ to $R_{17}$ may each be hydrogen atoms. However, embodiments are not limited thereto.

$o_1$ to $o_4$ and $o_6$ may each independently be an integer of 0 to 5. $o_5$ may be an integer of 0 to 4. $o_7$ may be an integer of 0 to 7. For example, $o_1$ to $o_7$ may be 0. However, embodiments are not limited thereto.

In Formula 2-1 to Formula 2-5, X, $R_1$ to $R_4$, $L_1$, $L_2$, $n_1$, $n_2$, $m_1$ to $m_4$ and $Ar_1$ may each independently be the same as defined in Formula 1.

In an embodiment, the amine compound represented by Formula 1 may be represented by Formula 3-1:

Formula 3-1

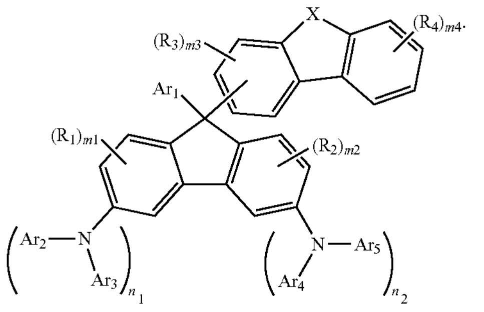

Formula 3-1 is a formula in which the amine groups are substituted to the fluorene group at specified positions. In Formula 3-1, the two amine groups may be respectively connected to the 3-position carbon and 6-position carbons. However, embodiments are not limited thereto.

In Formula 3-1, X, $Ar_1$ to $Ar_5$, $R_1$ to $R_4$, $n_1$, $n_2$, and $m_1$ to $m_4$ may each independently be the same as defined in Formula 1.

In an embodiment, the amine compound represented by Formula 1 may be represented by at least one of Formula 4-1 and Formula 4-2:

Formula 4-1

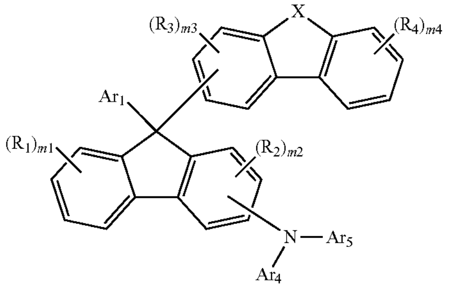

-continued

Formula 4-2

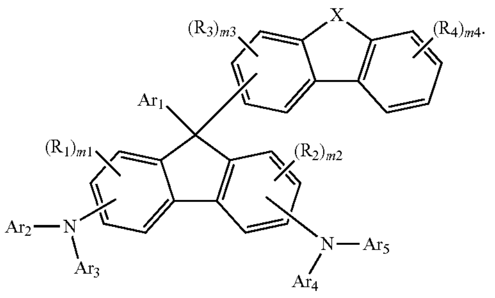

Formula 4-1 is an embodiment of Formula 1 in which $n_1$ is 0, and $n_2$ is 1. The amine compound represented by Formula 4-1 may include one amine group substituted to the fluorene group.

Formula 4-2 is an embodiment of Formula 1 in which $n_1$ and $n_2$ are each 1. The amine compound represented by Formula 4-2 may include two amine groups substituted to the fluorene group.

In Formula 4-1 and Formula 4-2, X, $Ar_1$ to $Ar_5$, $R_1$ to $R_4$, and $m_1$ to $m_4$ may each independently be the same as defined in Formula 1.

In an embodiment, the amine compound represented by Formula 1 may include at least one of the compounds represented by Compound Group 1:

Compound Group 1

1

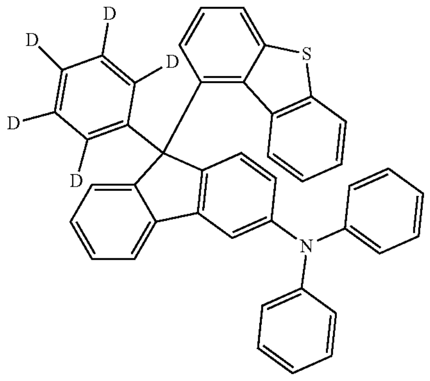

2

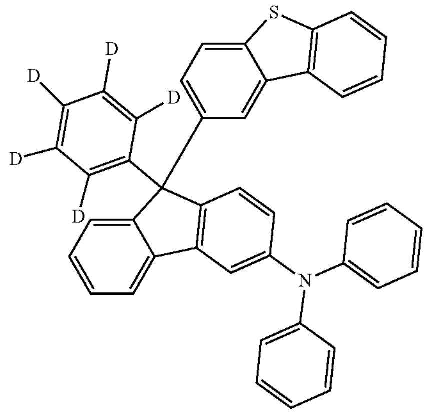

-continued
3
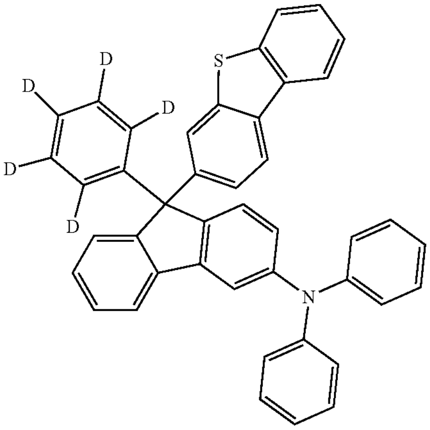
4
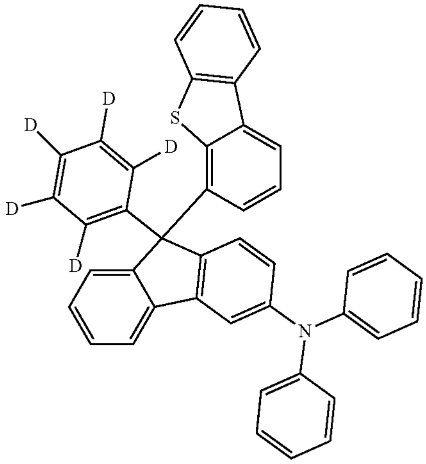
5
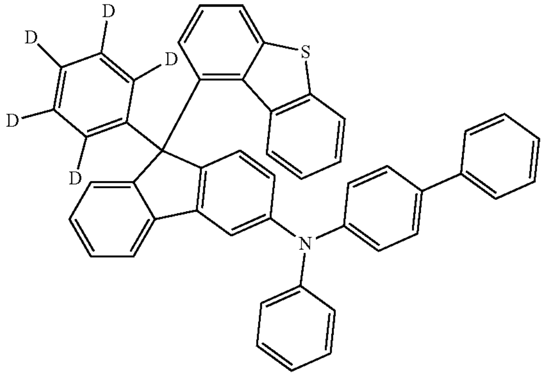
-continued
6
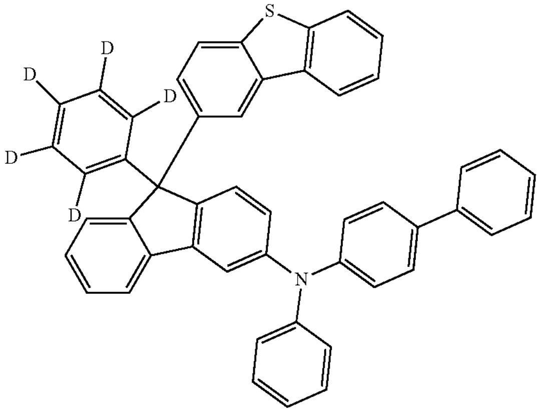
7
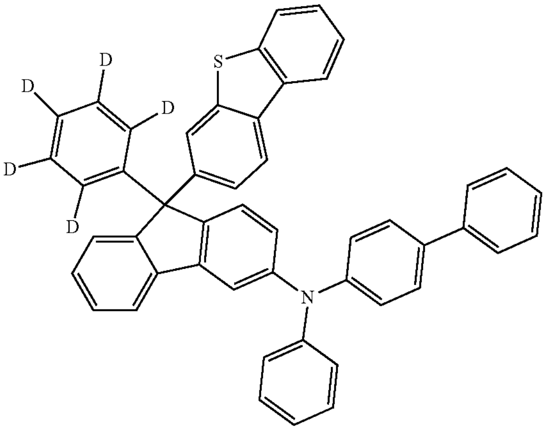
8
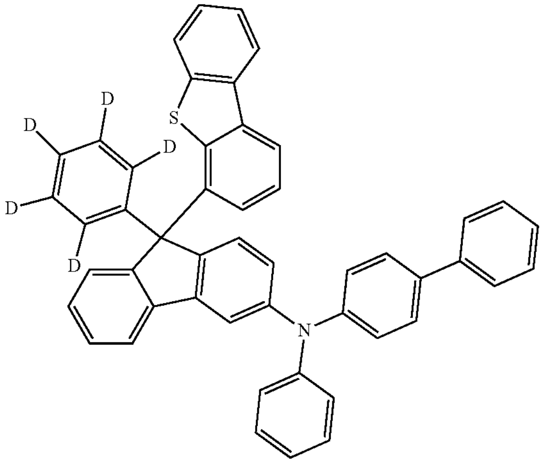

-continued
9
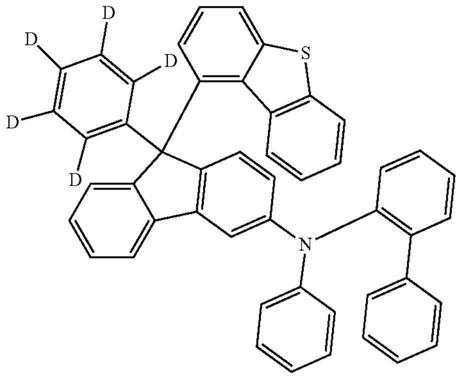
10
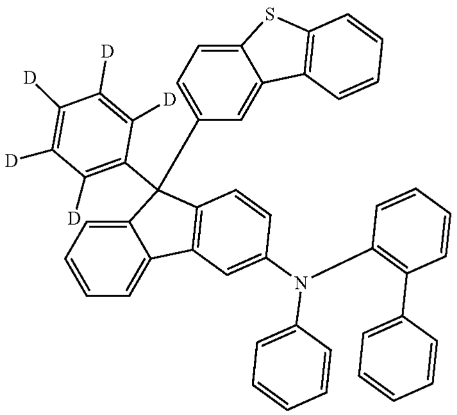
11
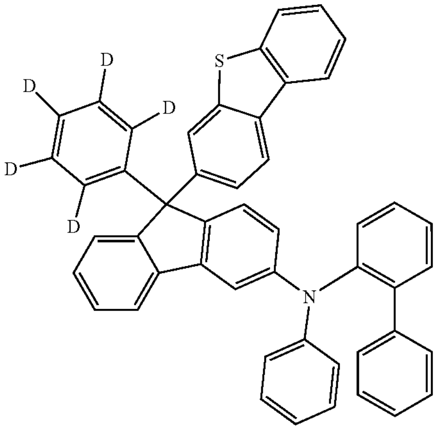
-continued
12
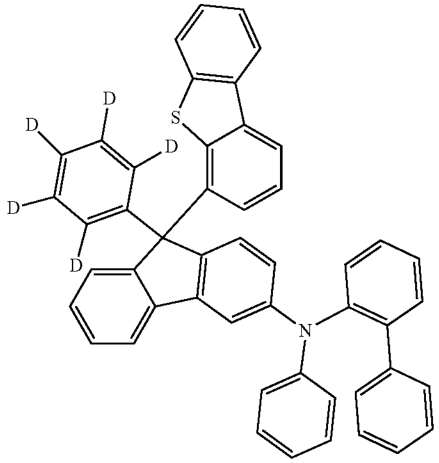
13
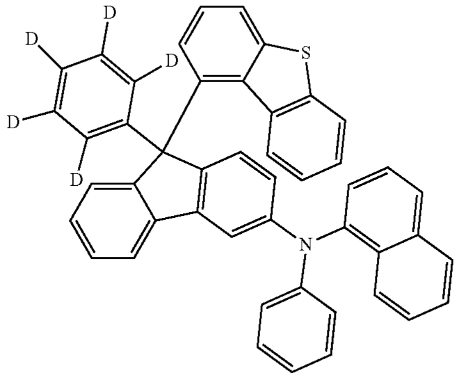
14
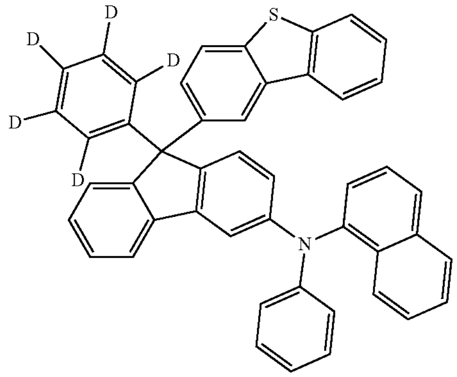
15
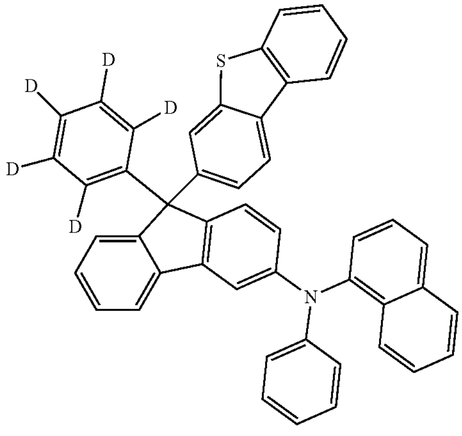

-continued
16
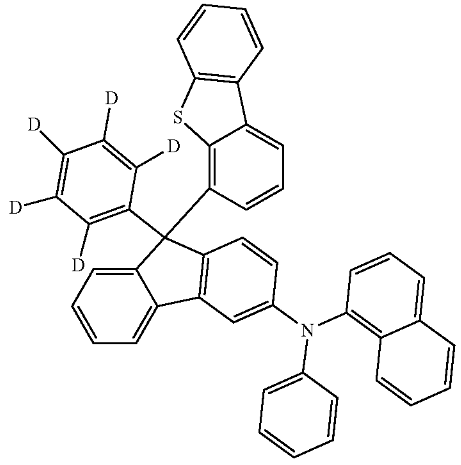
17
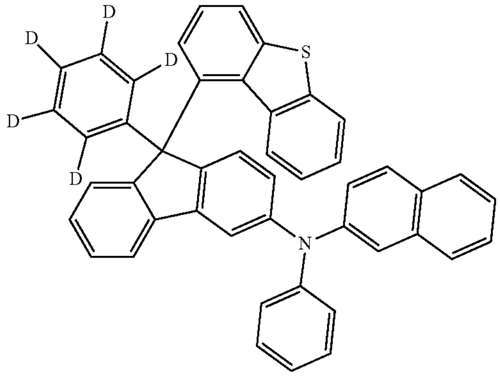
18
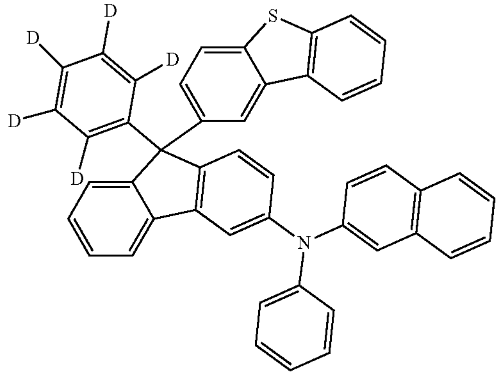
19
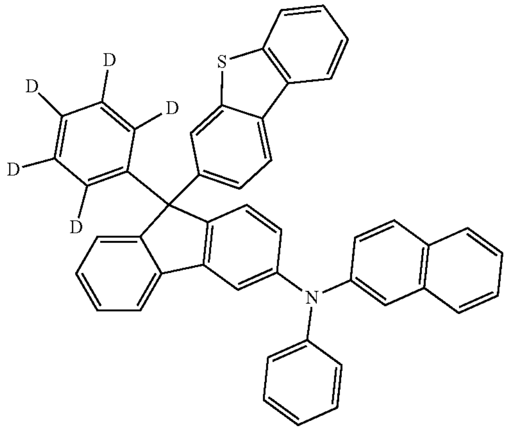
-continued
20
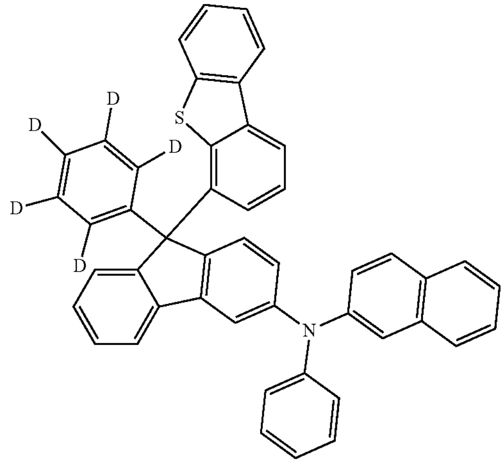
21
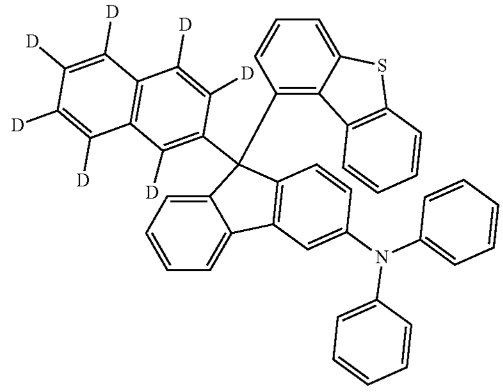
22
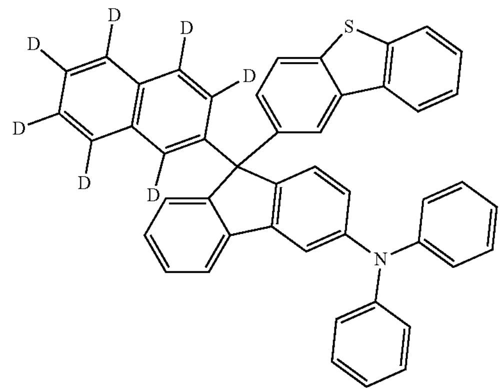

-continued
23
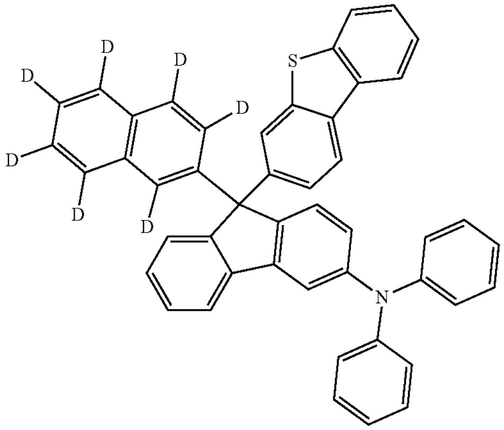
24
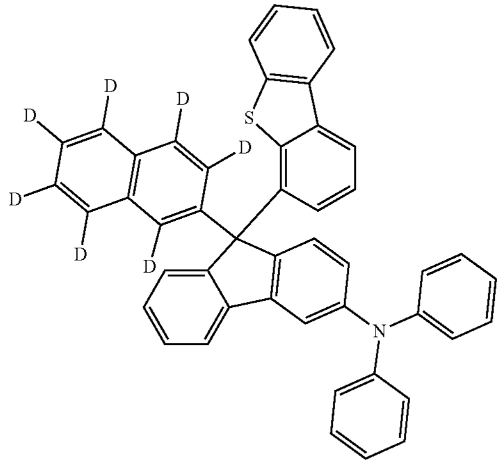
25
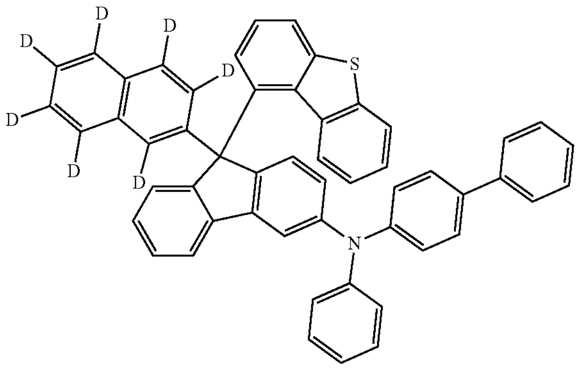
-continued
26
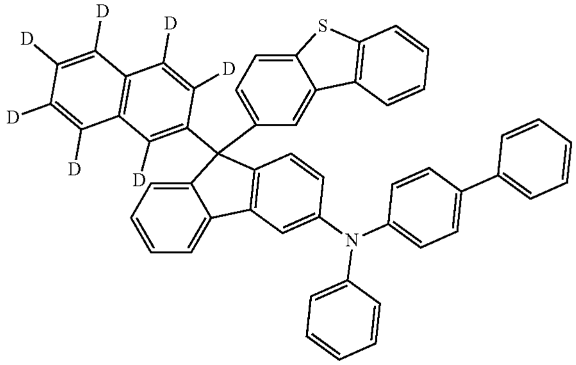
27
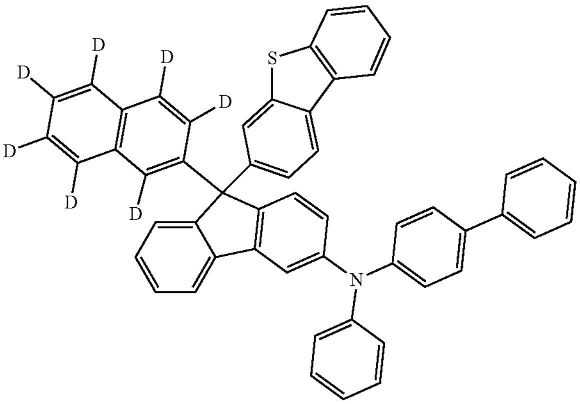
28
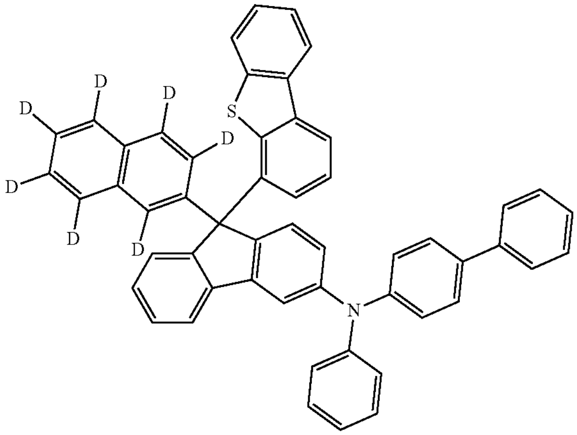
29
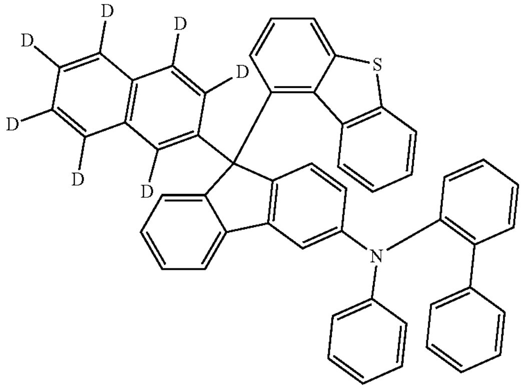

-continued
30
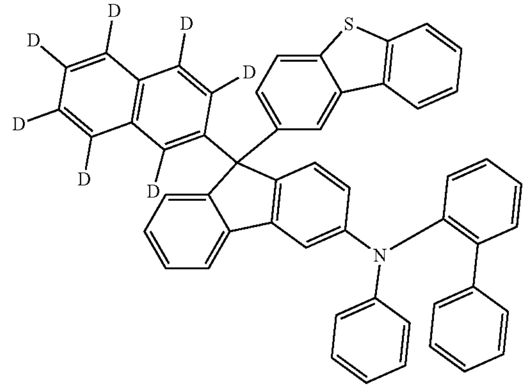
31
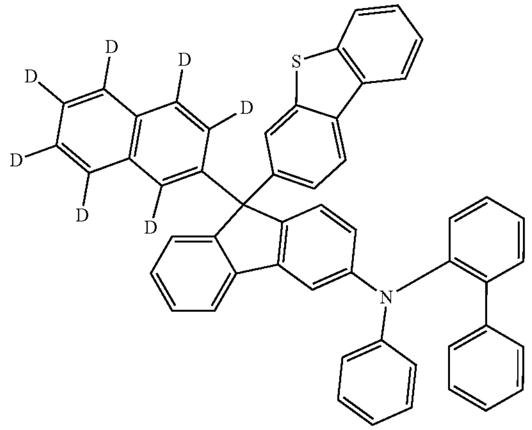
32
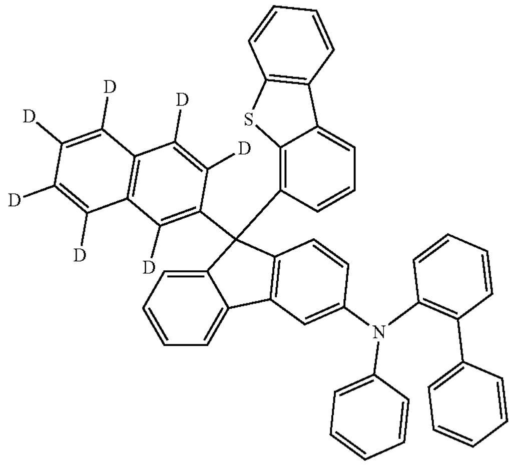
-continued
33
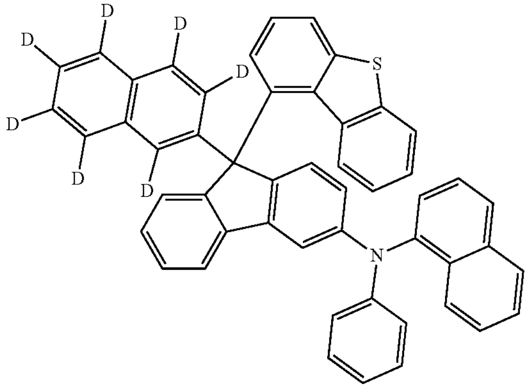
34
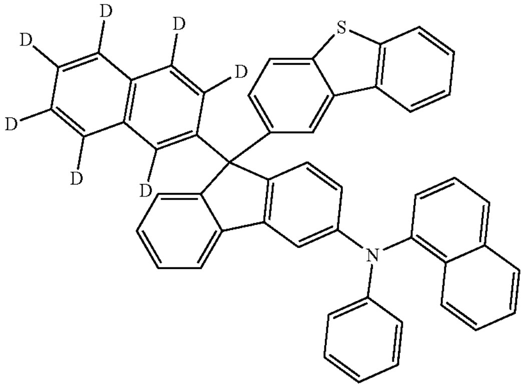
35
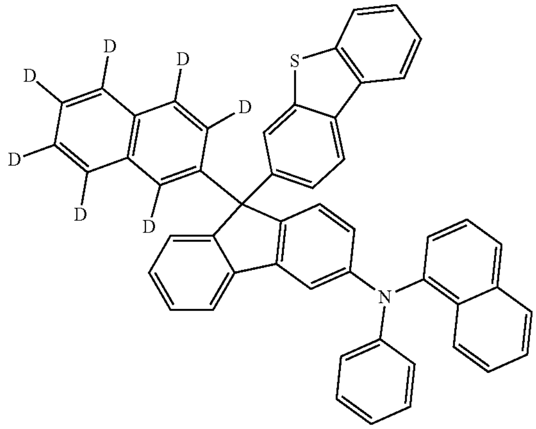

-continued
36
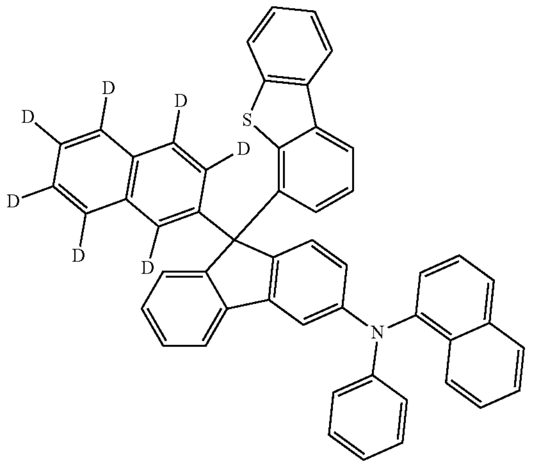
37
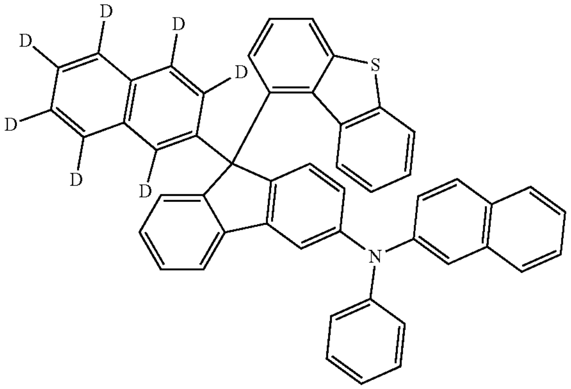
38
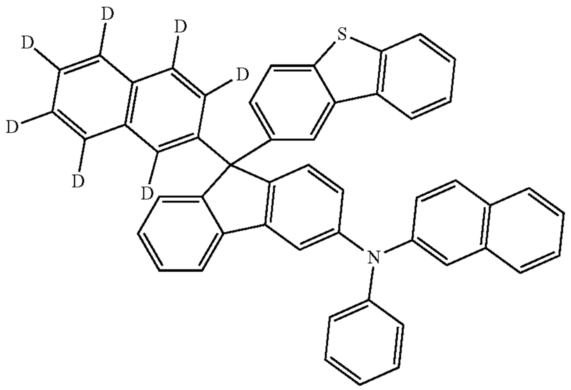
-continued
39
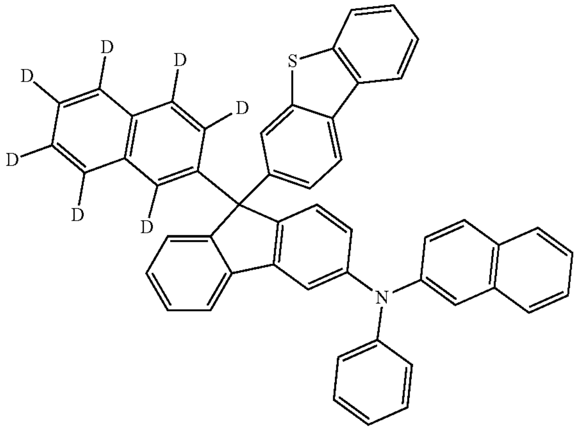
40
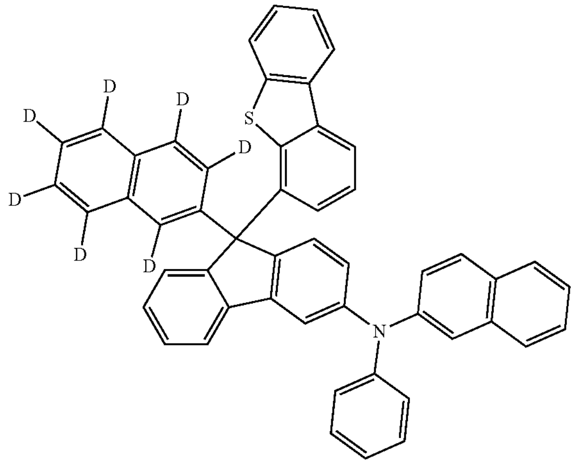
41
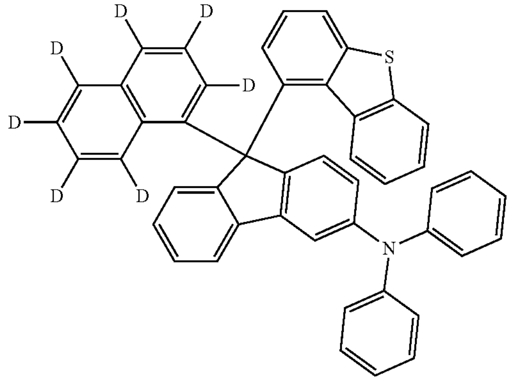

-continued
42
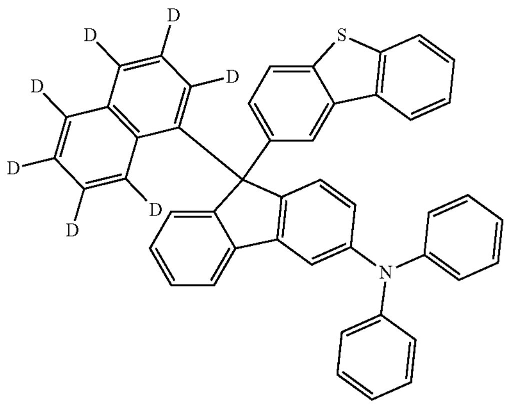
43
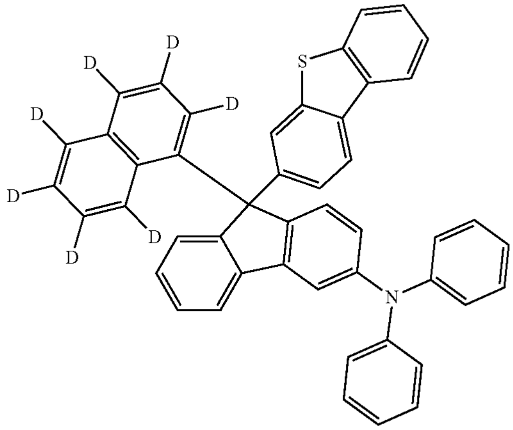
44
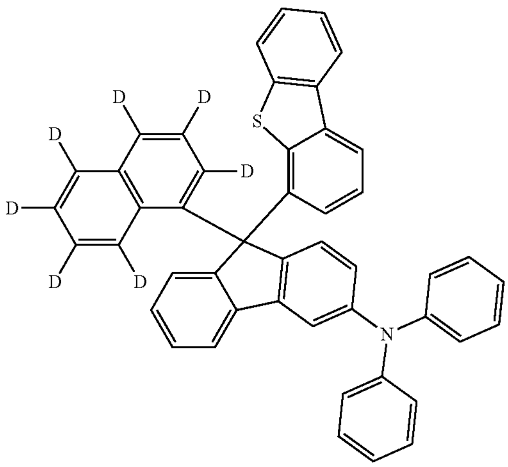
-continued
45
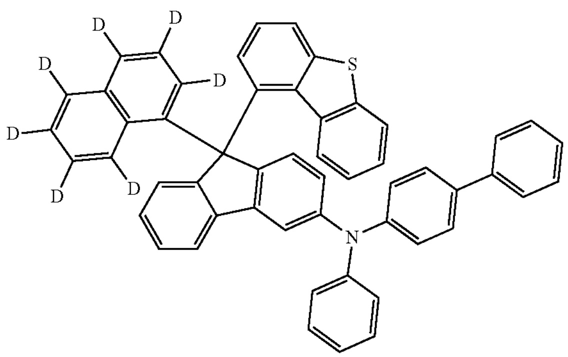
46
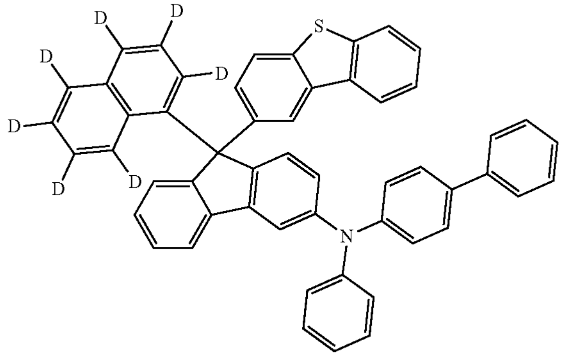
47
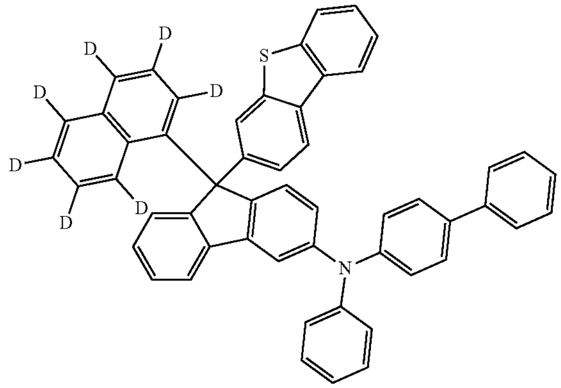
48
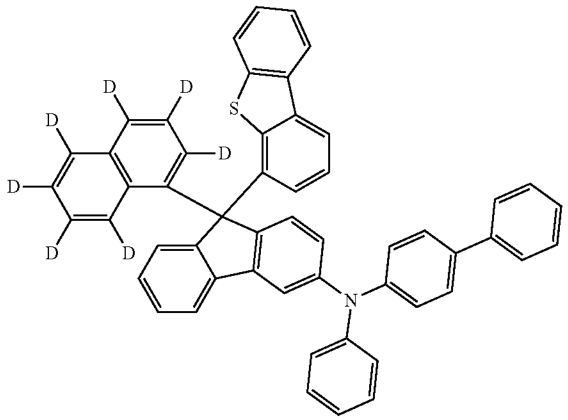

-continued
49
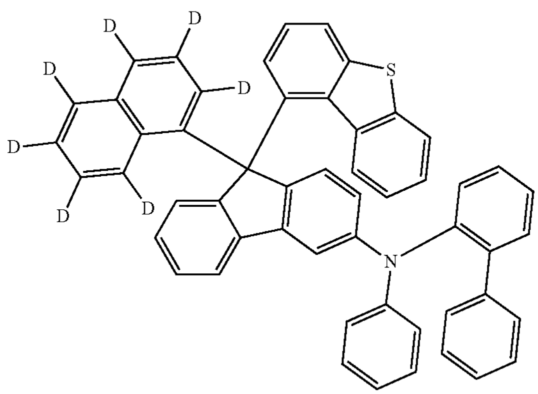
50
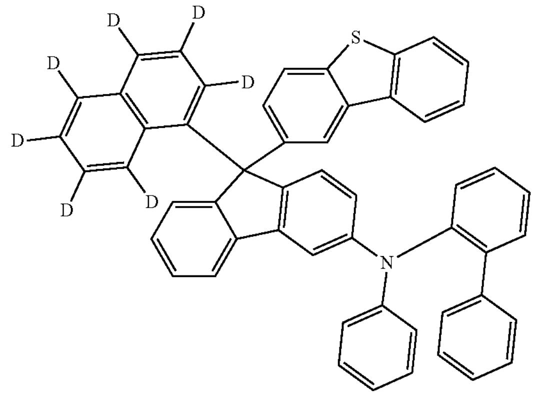
51
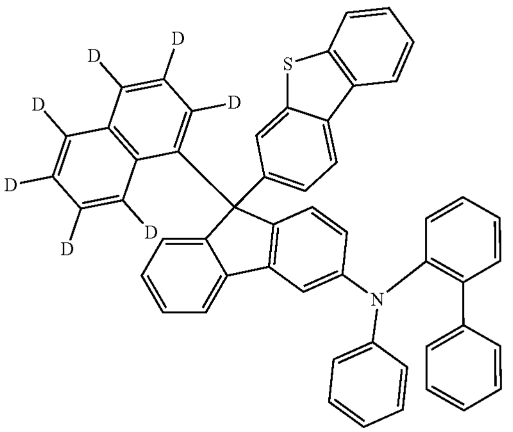
-continued
52
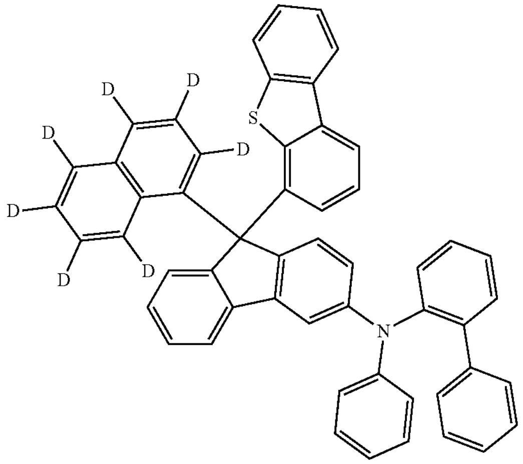
53
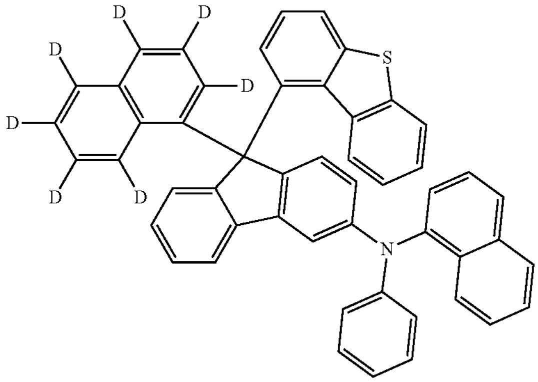
54
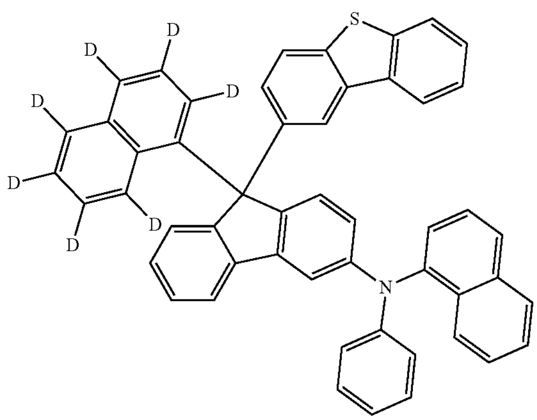

-continued
55
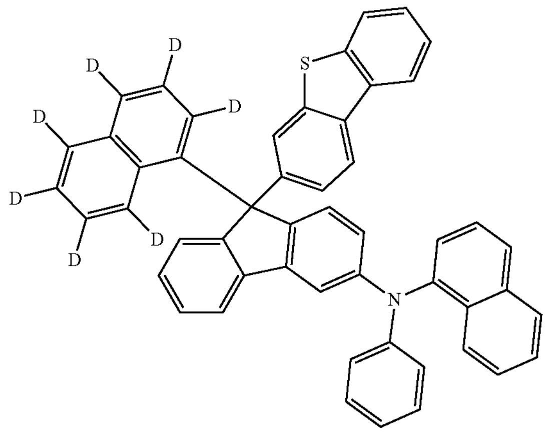
56
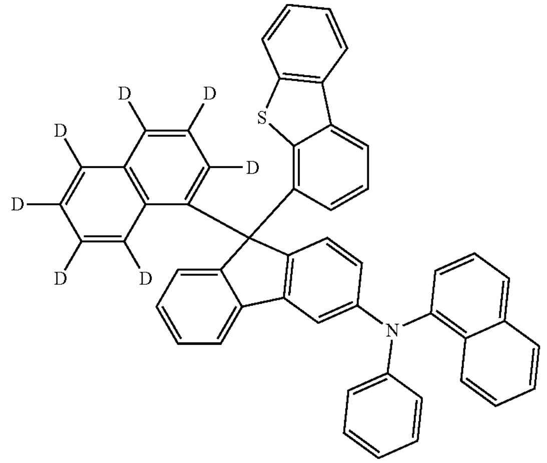
57
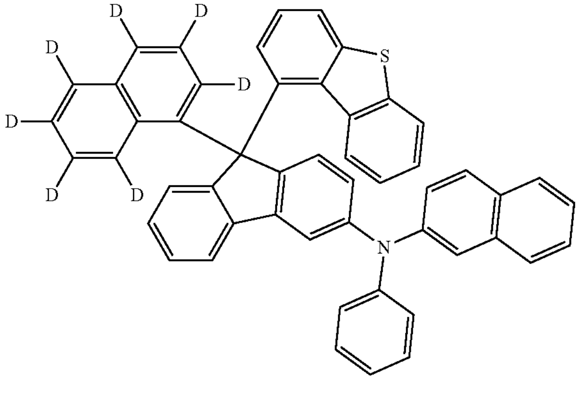
-continued
58
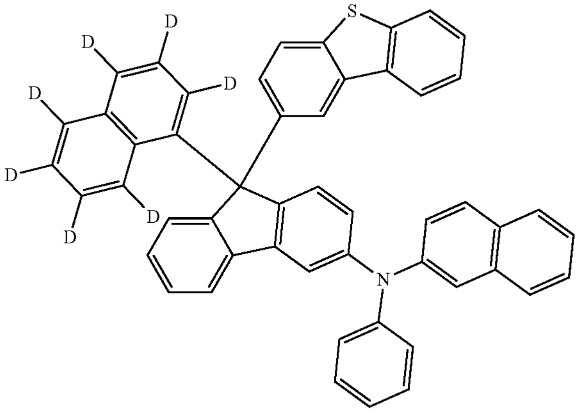
59
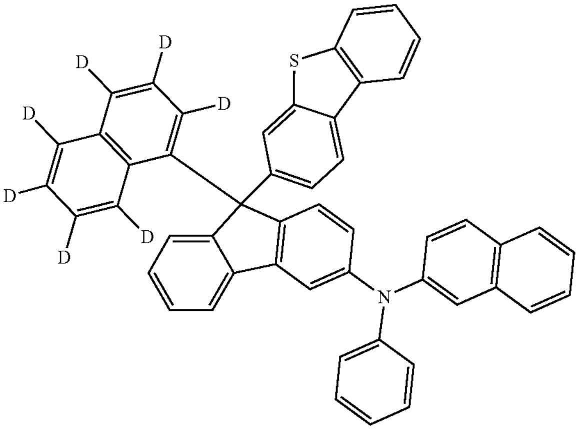
60
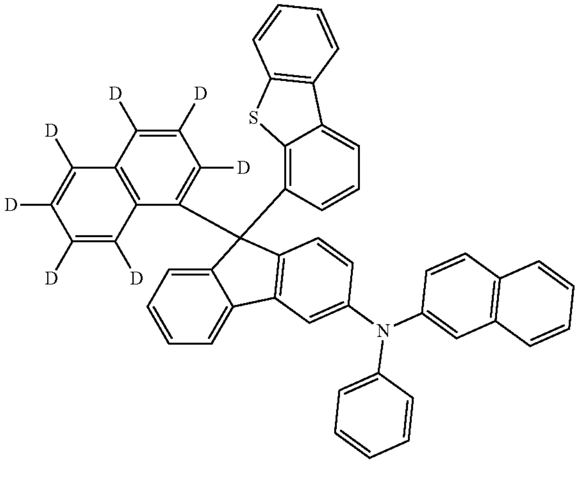

-continued
61
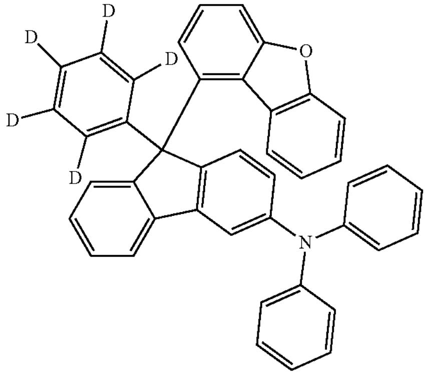
62
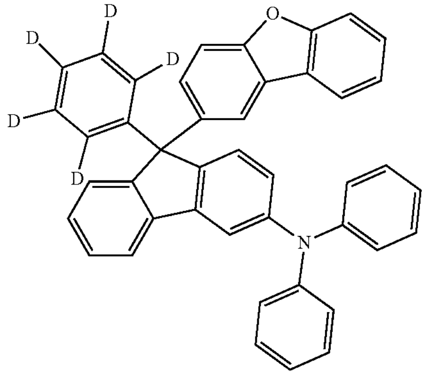
63
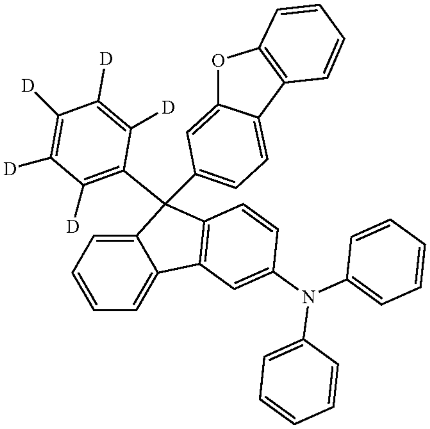
64
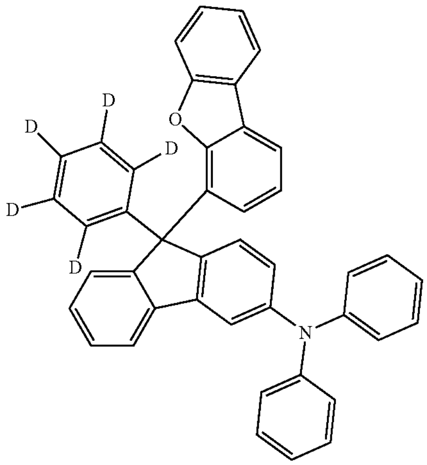
-continued
65
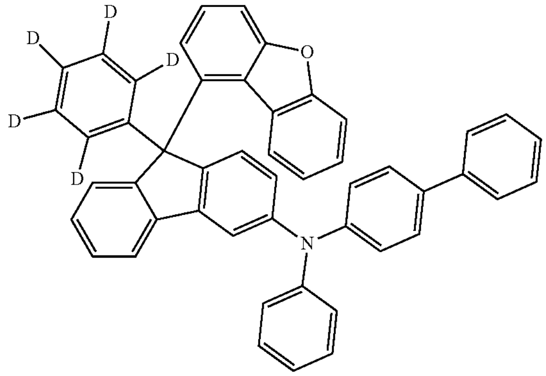
66
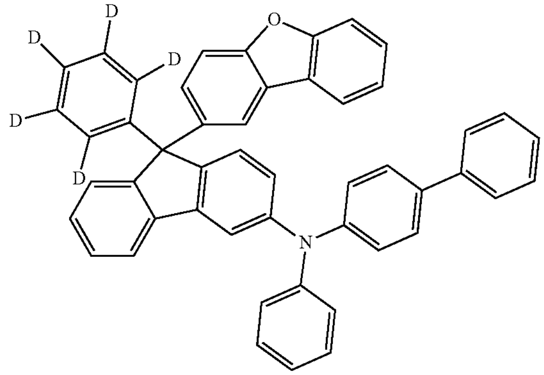
67
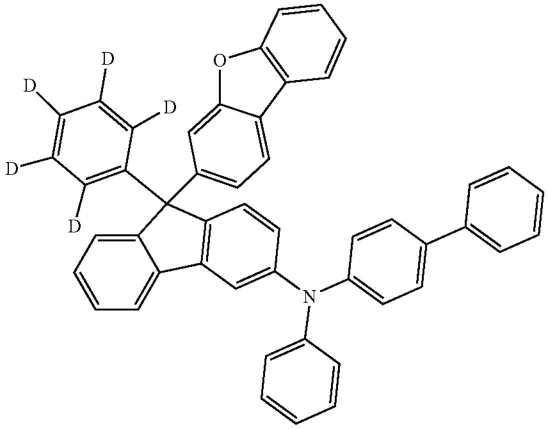

-continued
68
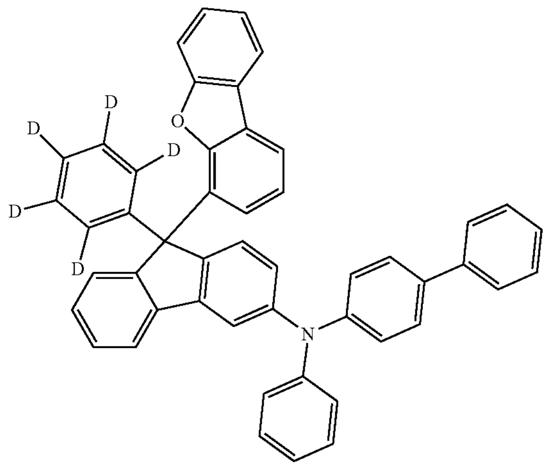
69
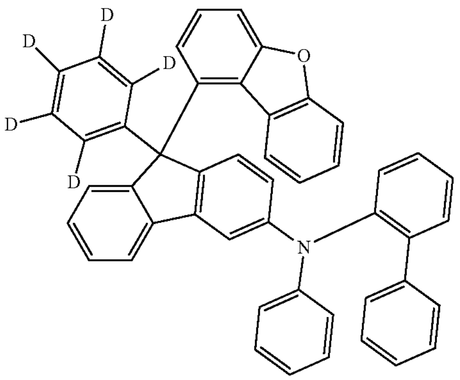
70
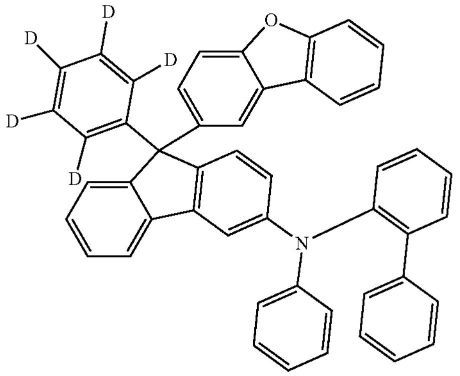
71
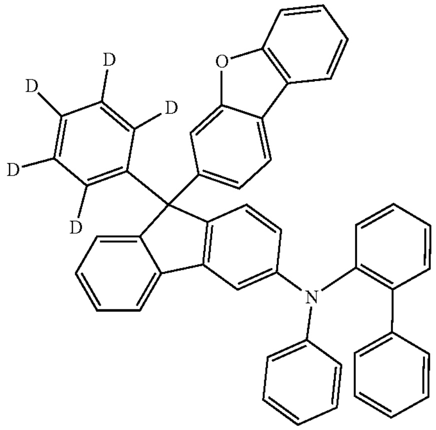
72
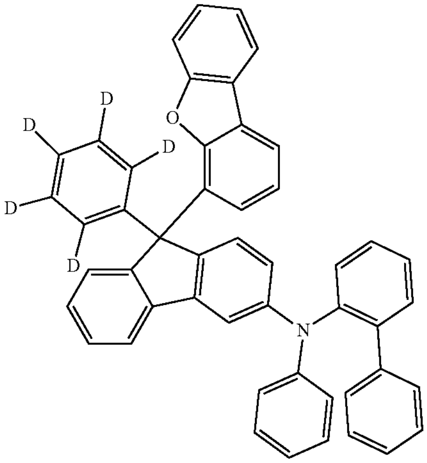
73
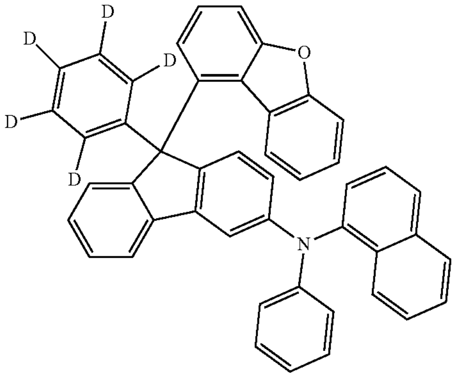
74
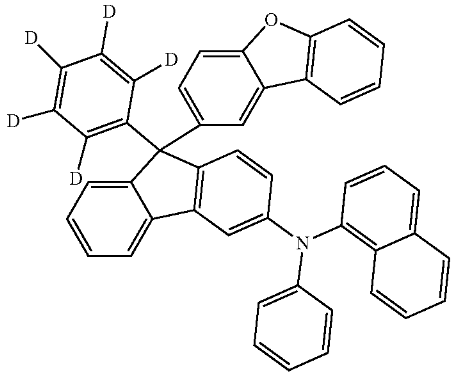

-continued
75
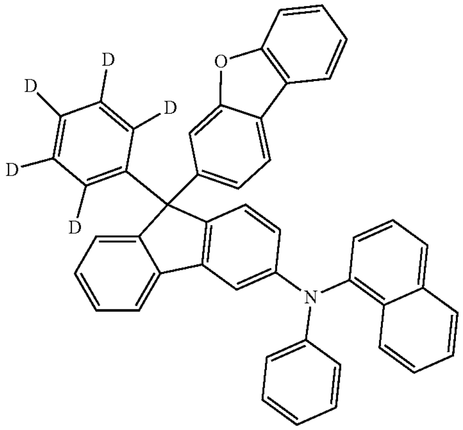
76
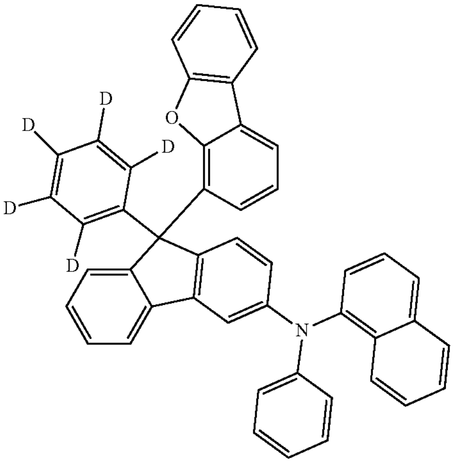
77
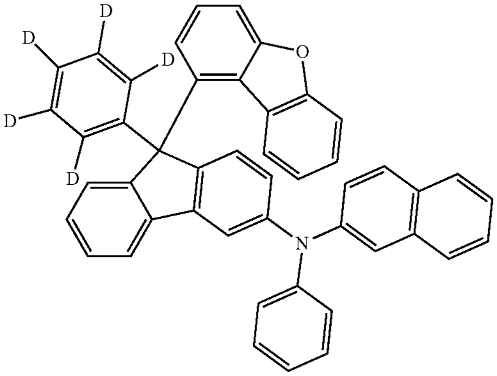
78
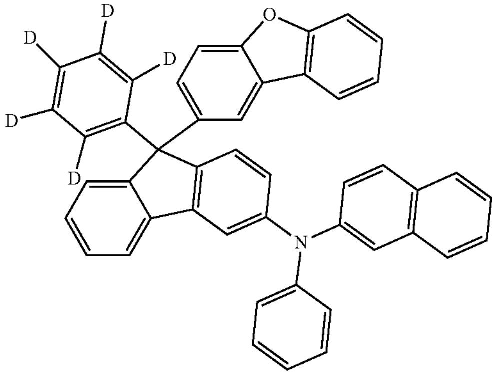
-continued
79
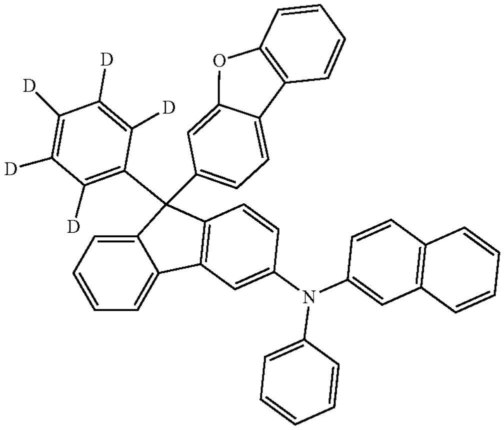
80
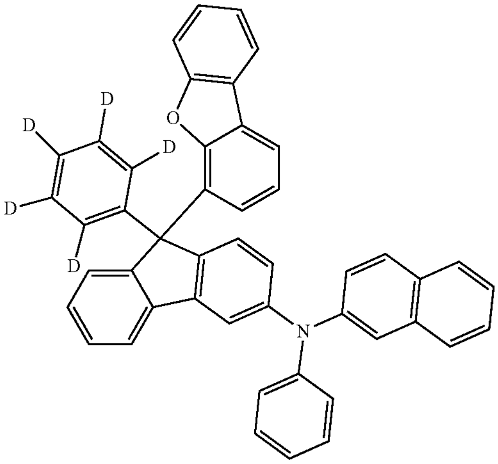
81
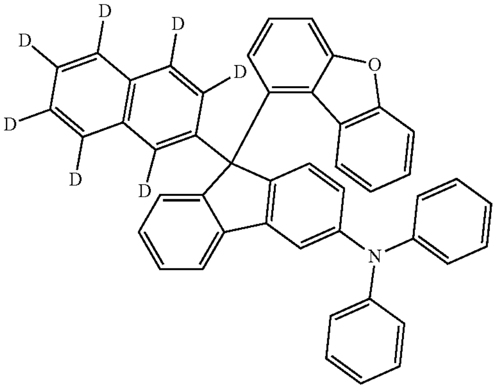

-continued
82
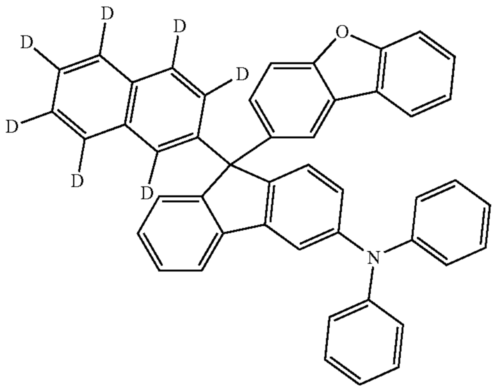
83
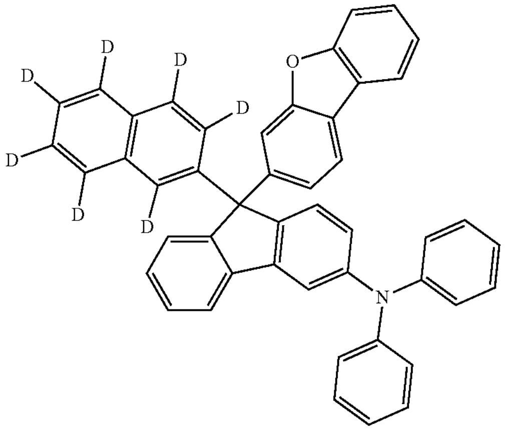
84
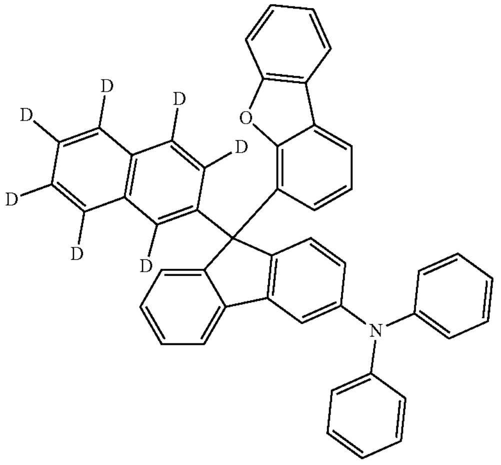
-continued
85
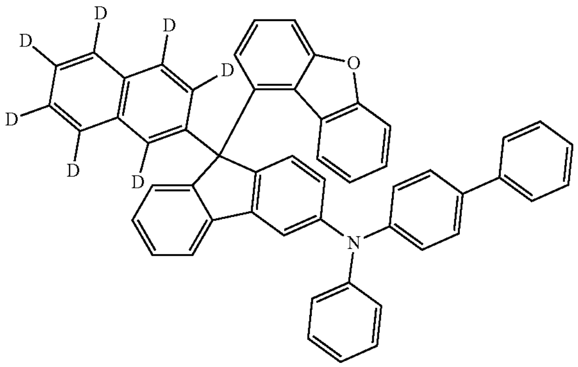
86
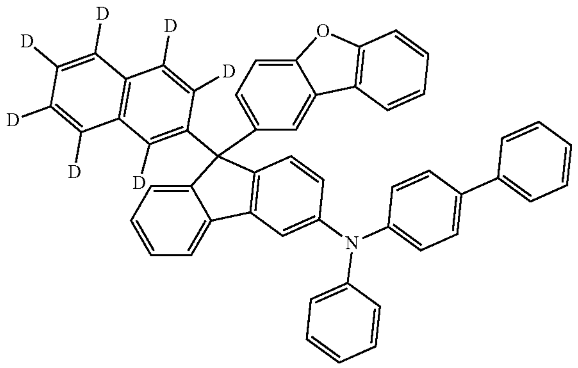
87
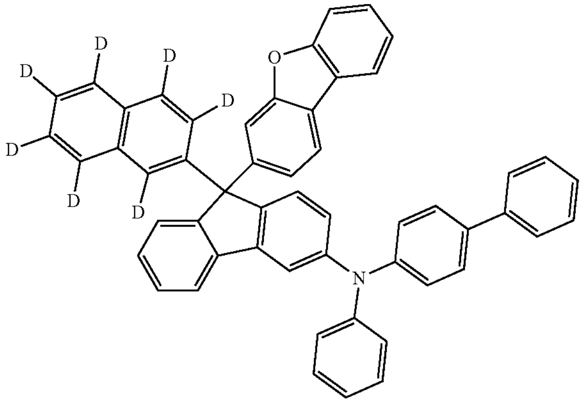
88
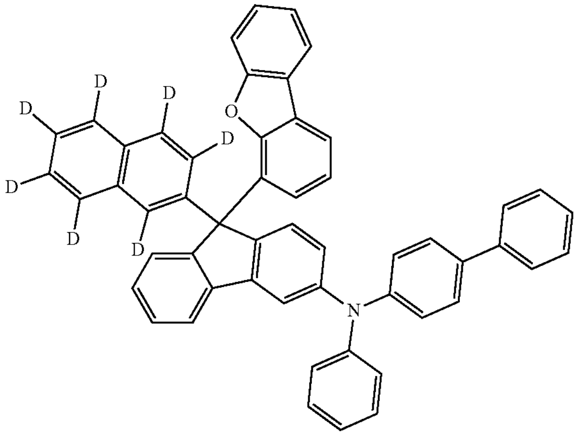

-continued
89
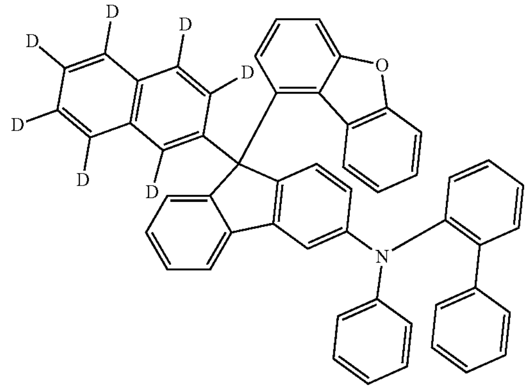
90
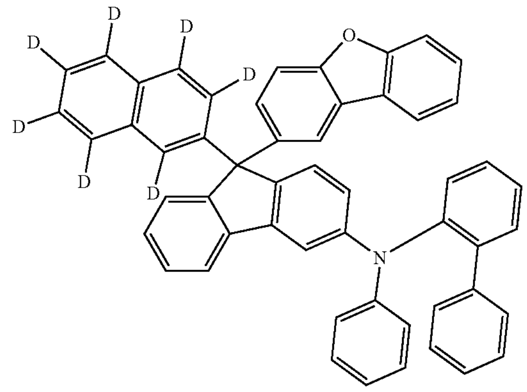
91
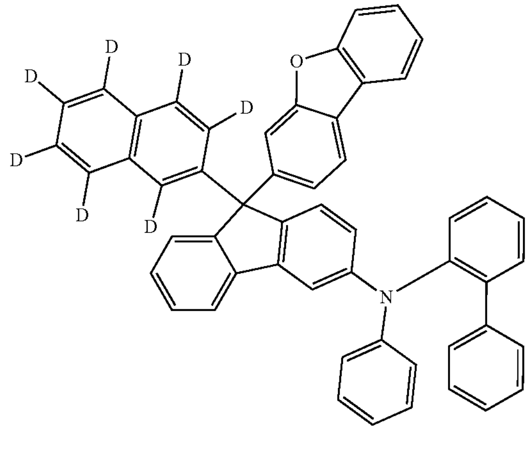
-continued
92
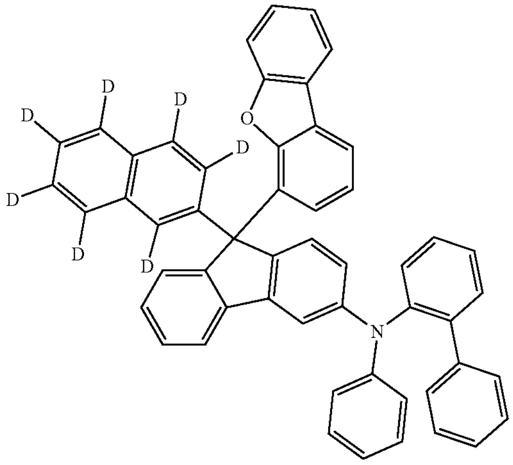
93
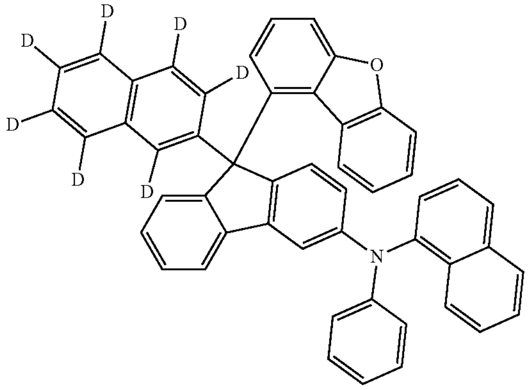
94
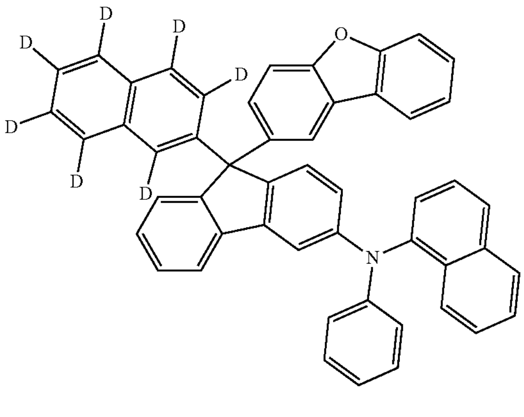

-continued
95
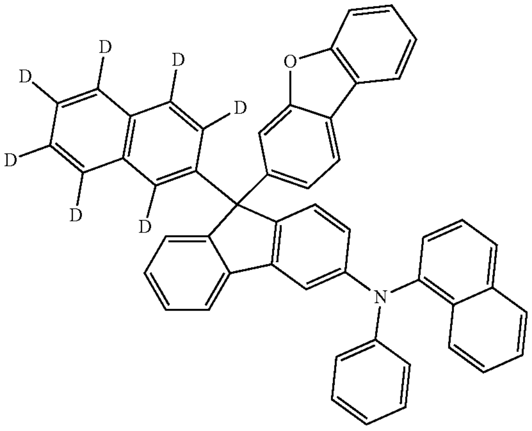
96
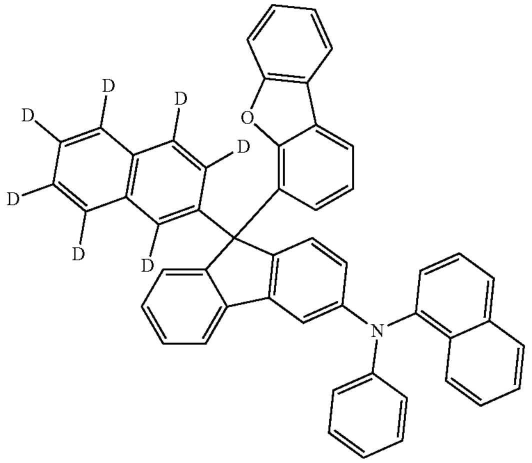
97
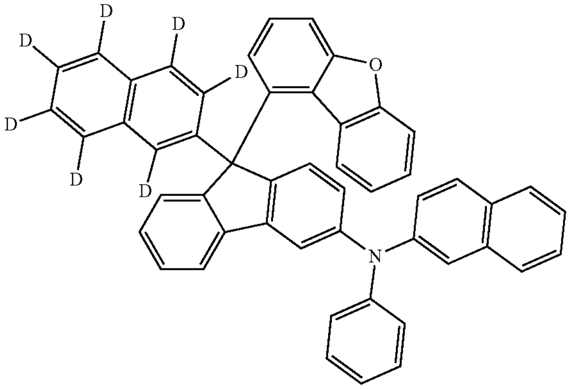
-continued
98
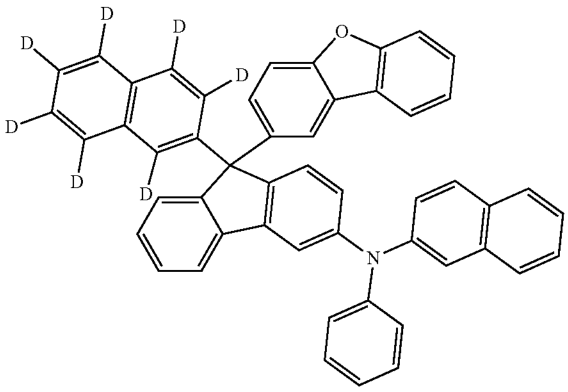
99
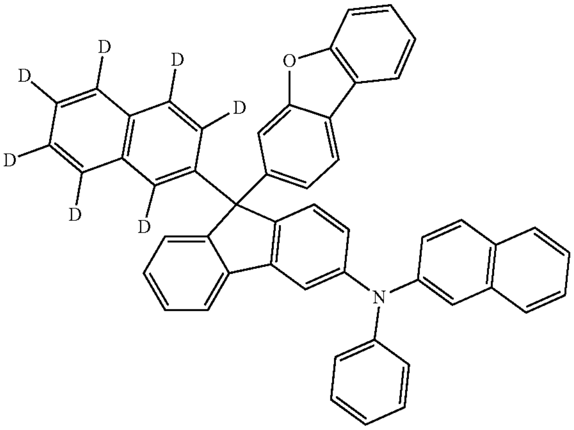
100
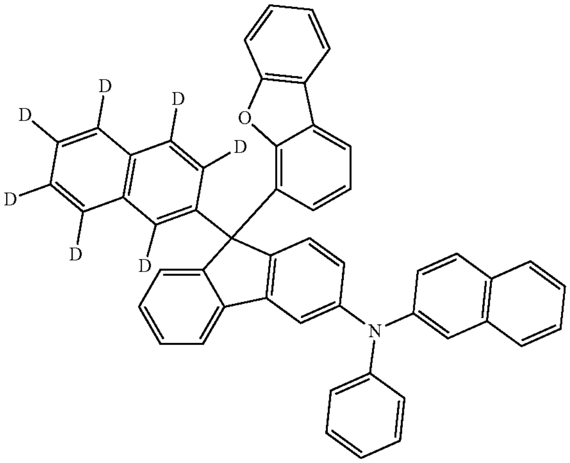

-continued
101
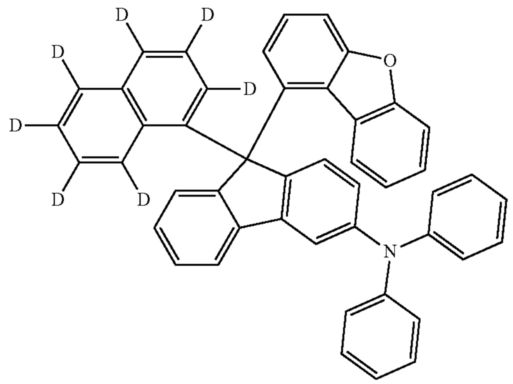
102
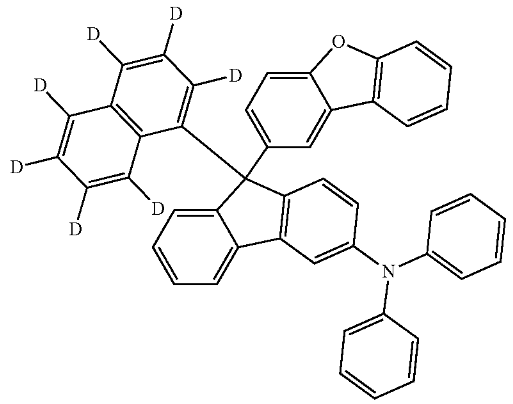
103
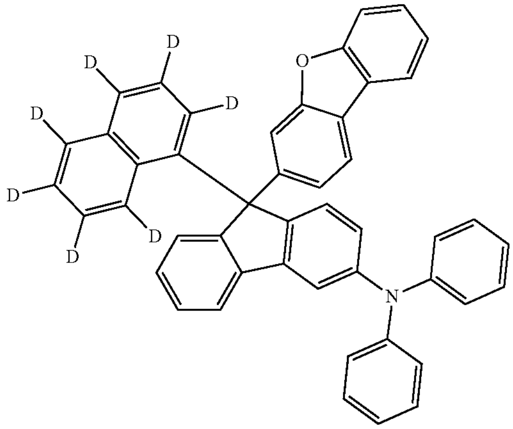
-continued
104
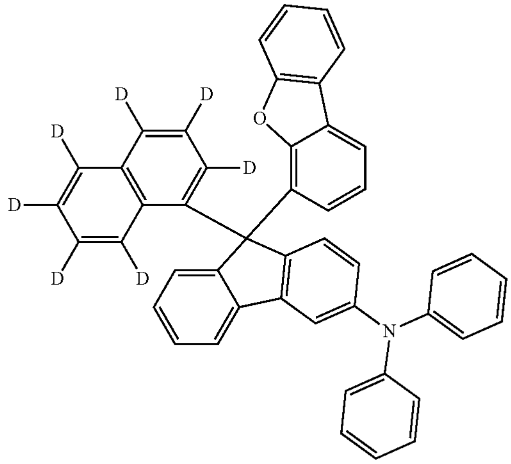
105
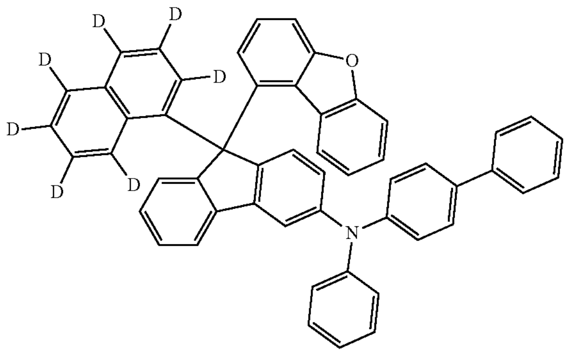
106
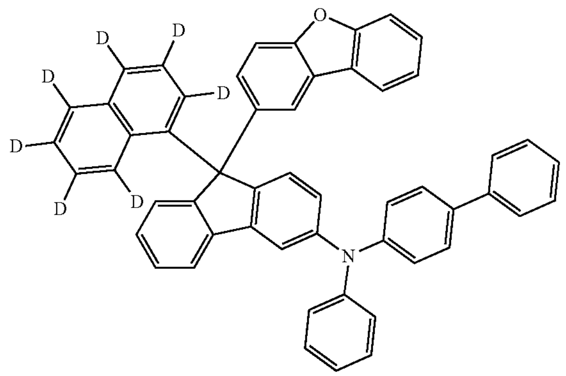
107
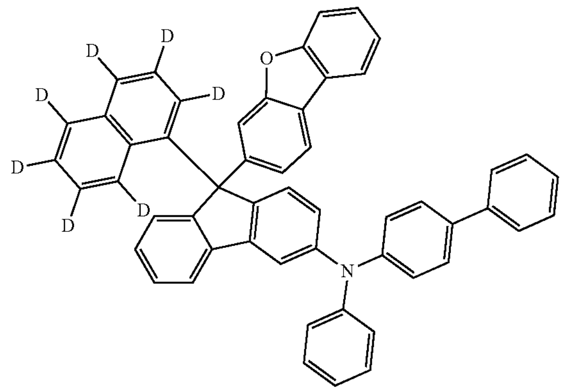

-continued
108
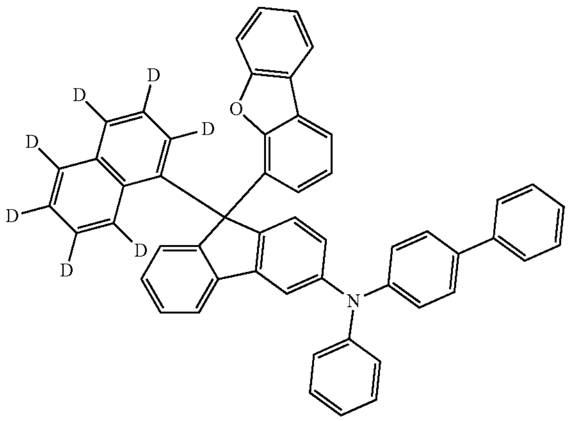
109
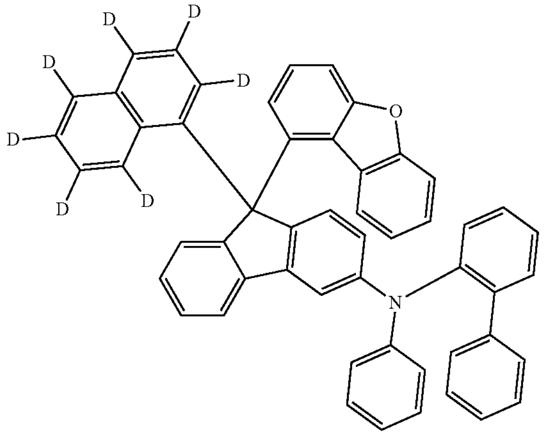
110
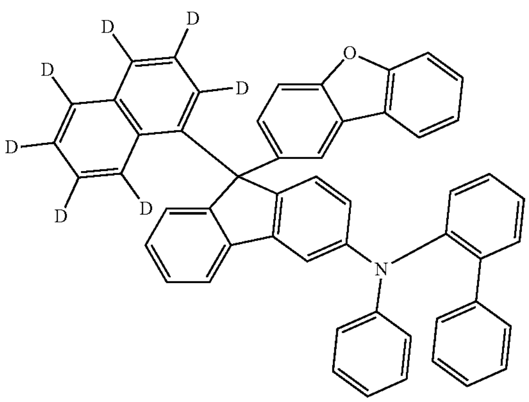
-continued
111
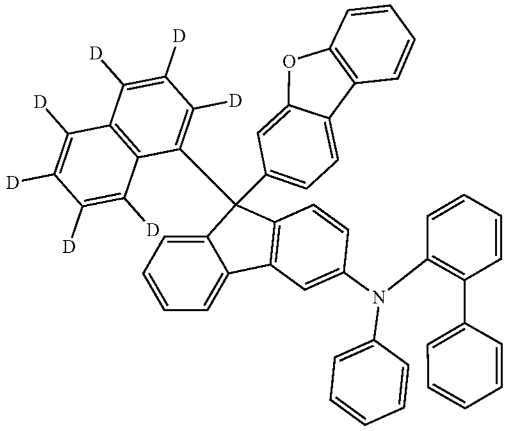
112
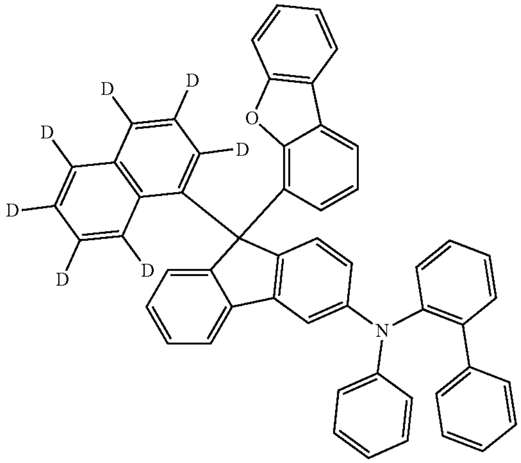
113
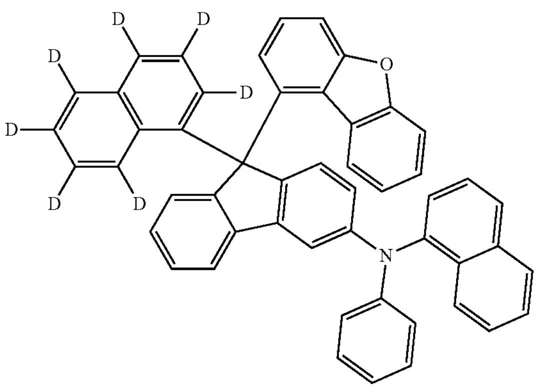

-continued
114
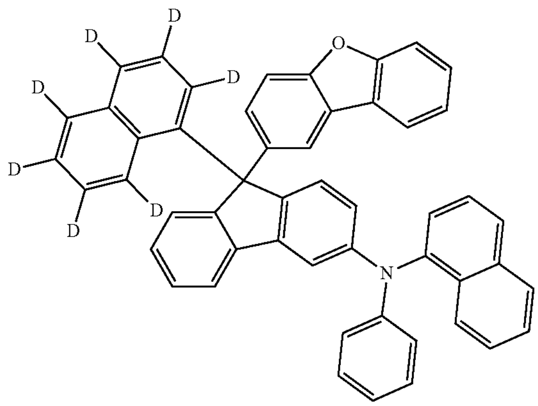
115
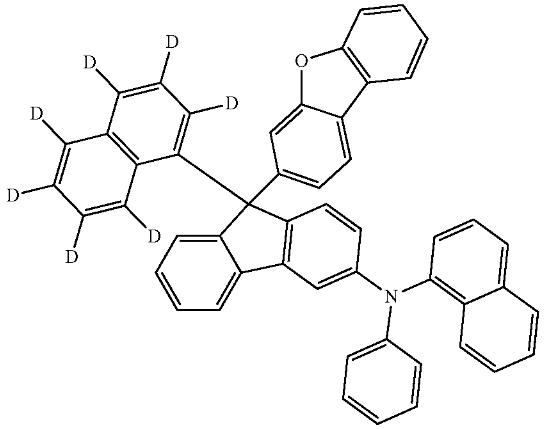
116
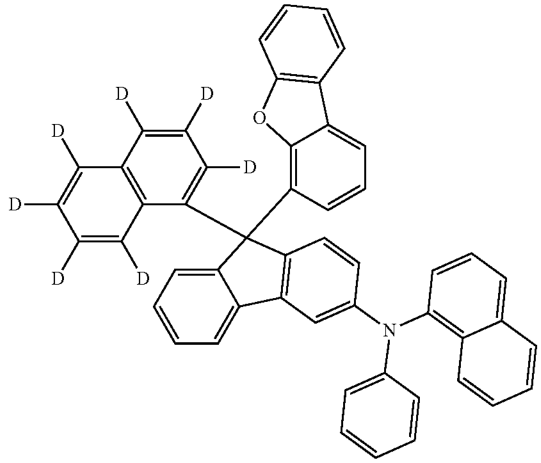
-continued
117
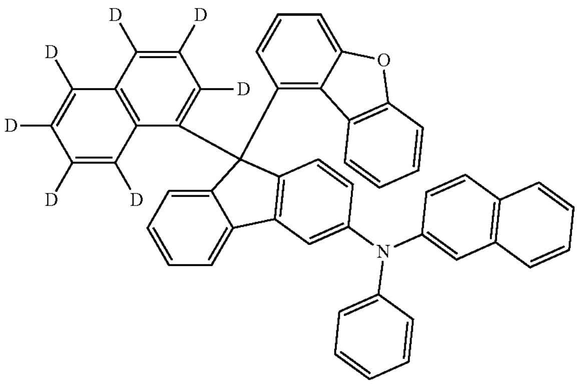
118
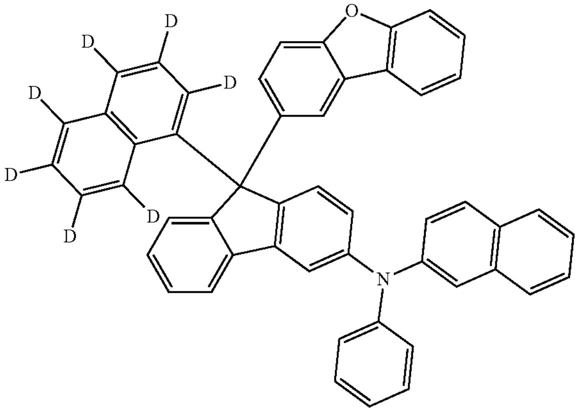
119
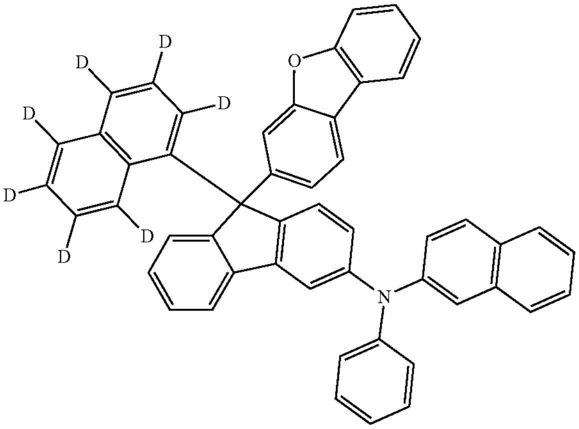

-continued
120
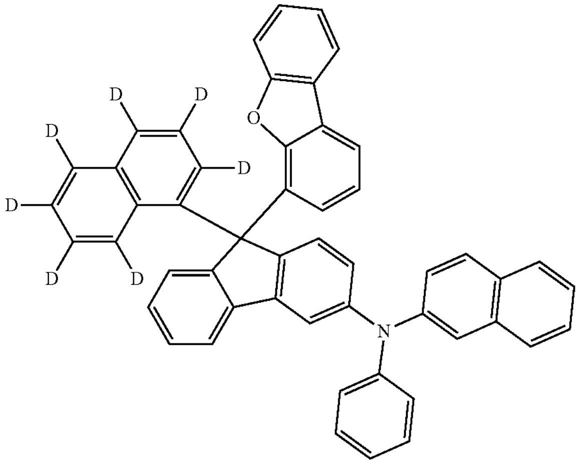
121
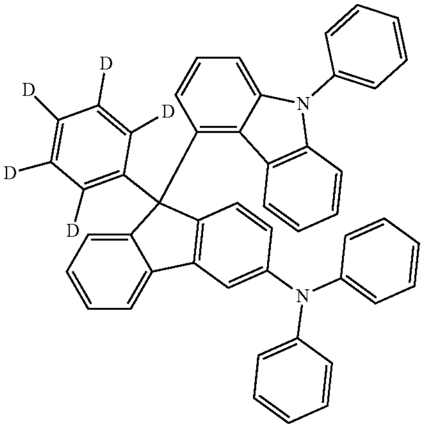
122
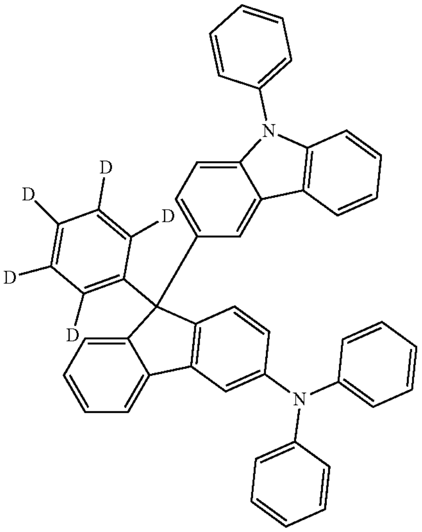
-continued
123
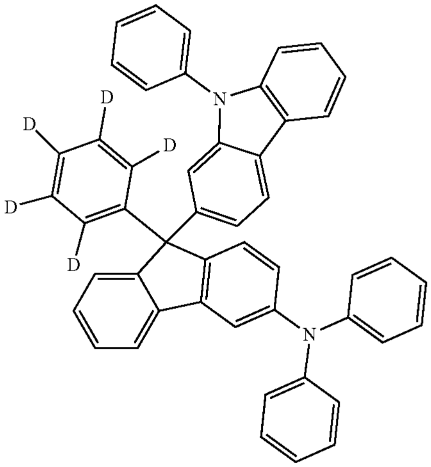
124
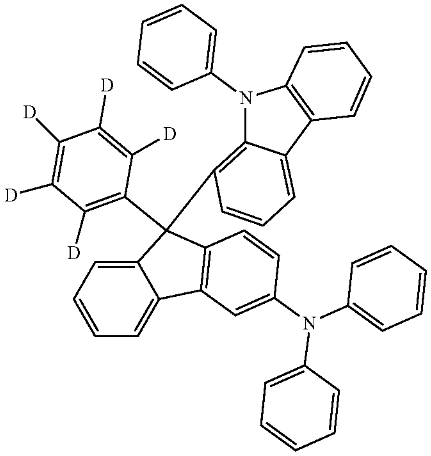
125
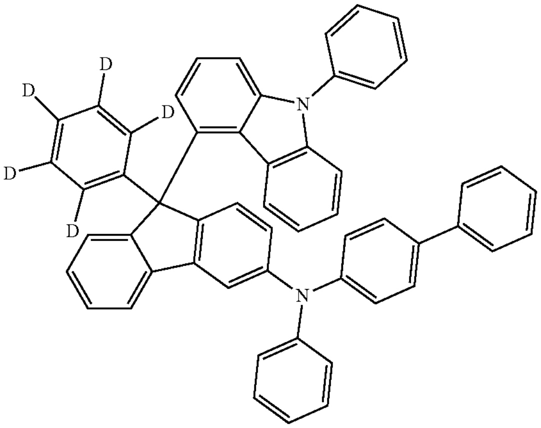

-continued
126
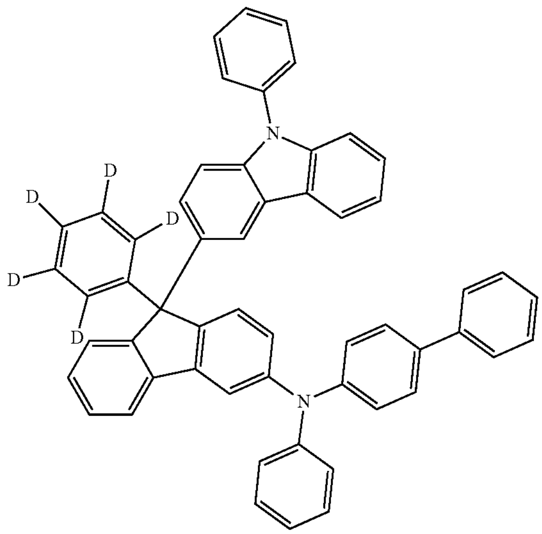
127
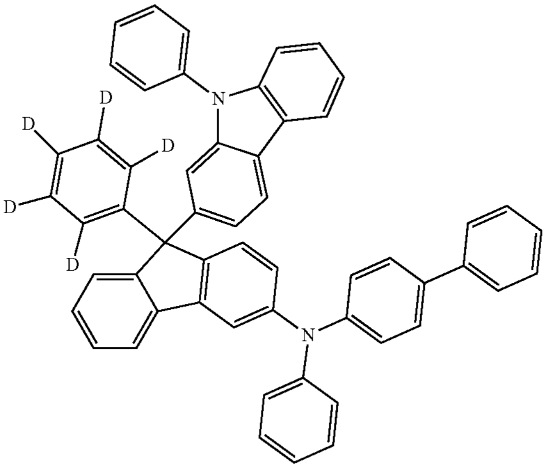
128
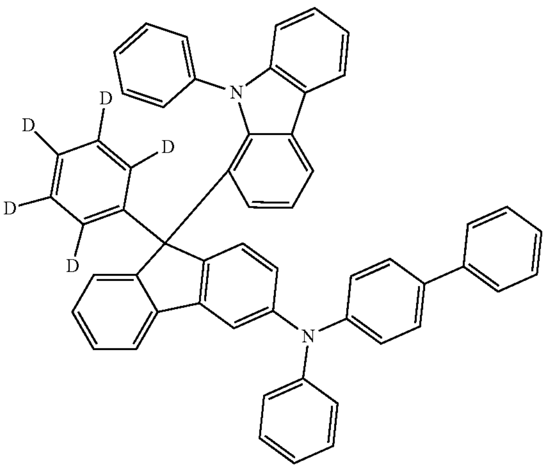
-continued
129
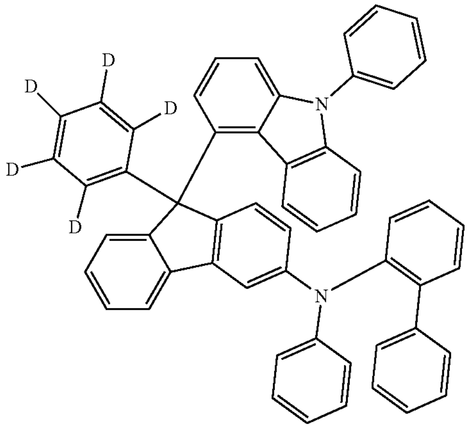
130
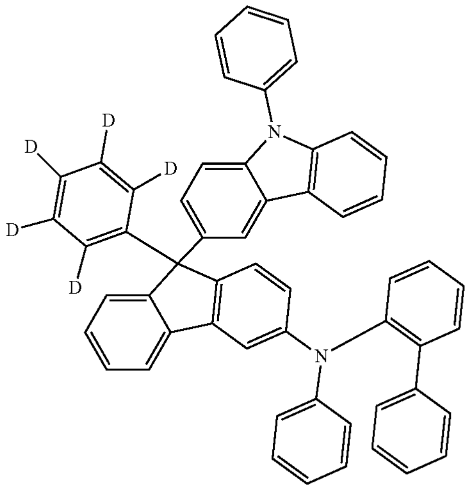
131
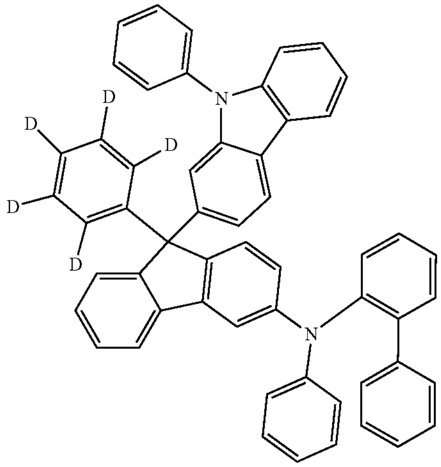

-continued
132
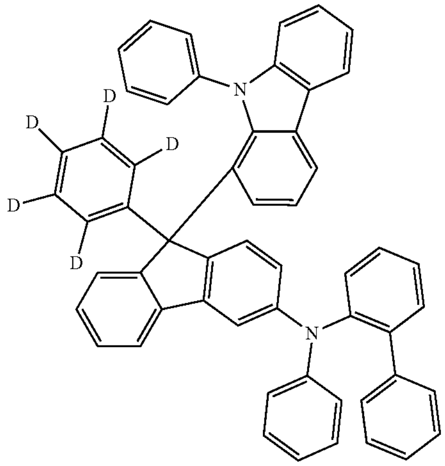
133
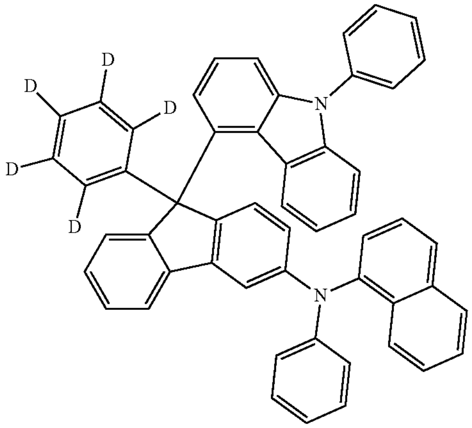
134
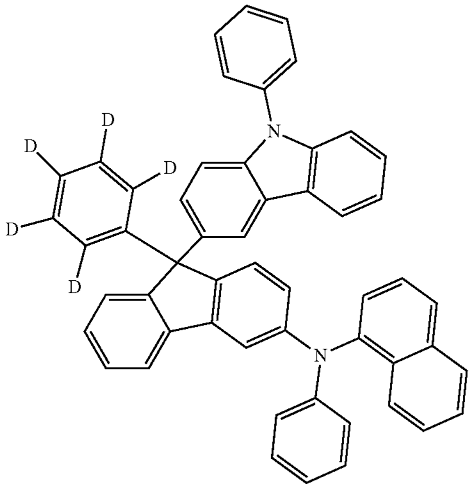
-continued
135
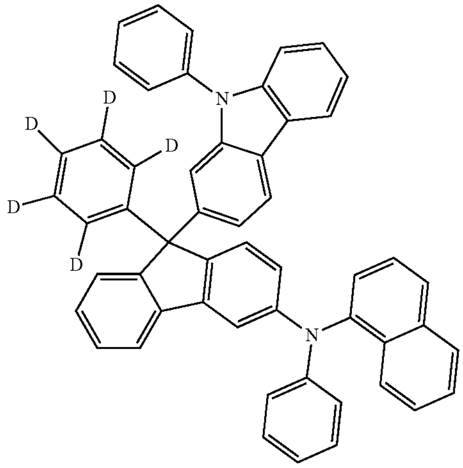
136
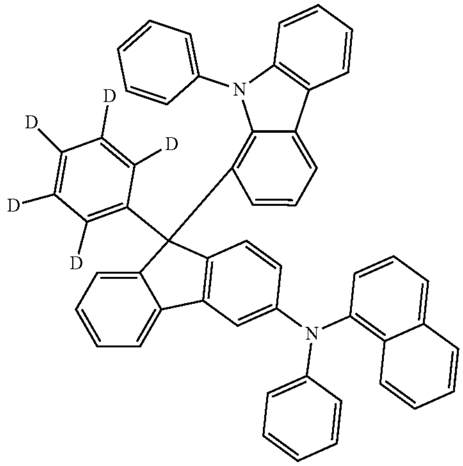
137
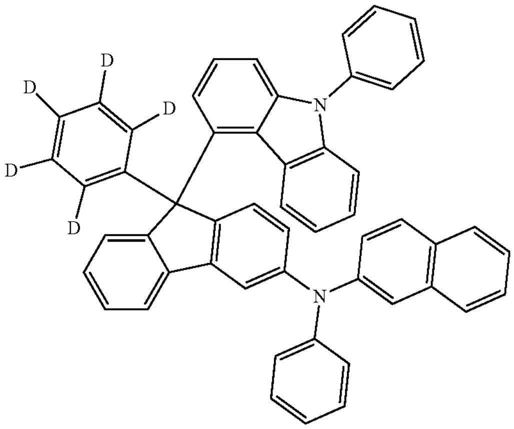

-continued
138
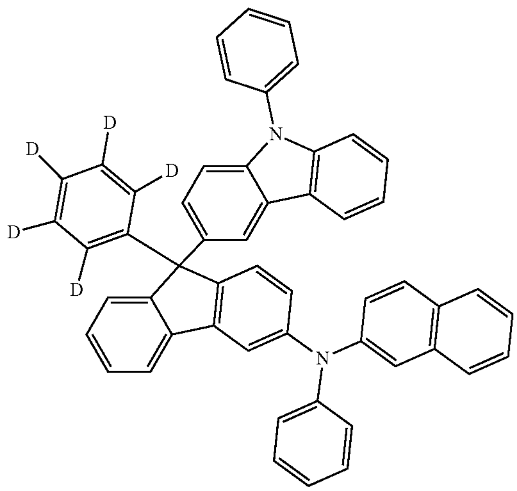
139
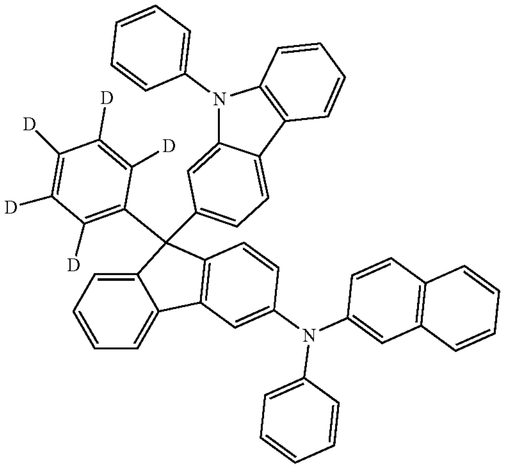
140
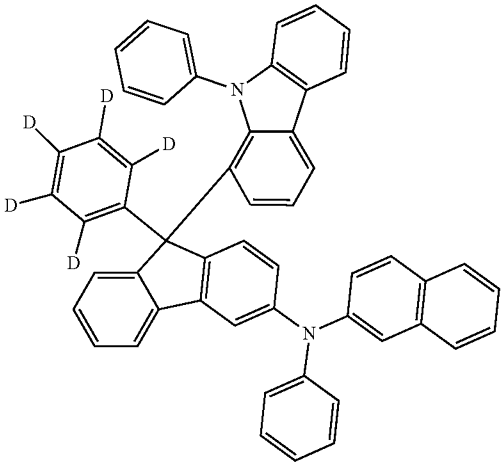
-continued
141
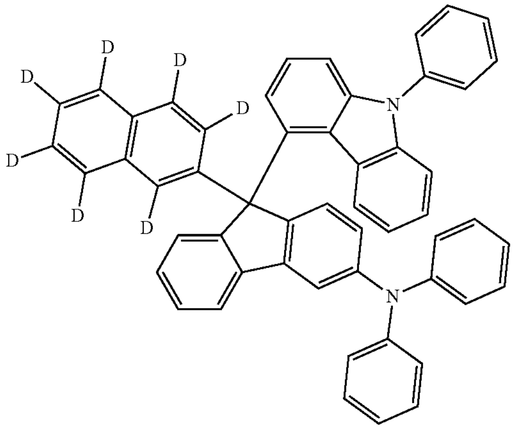
142
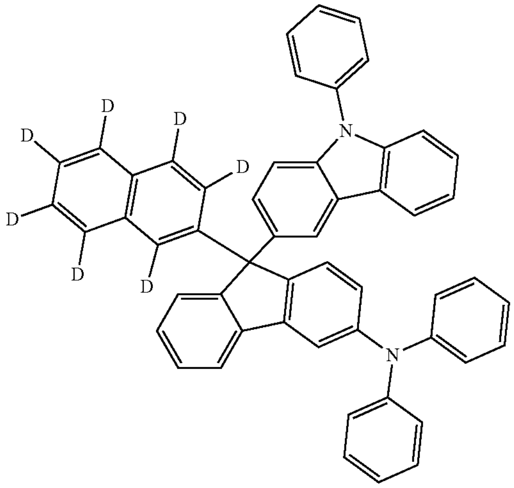
143
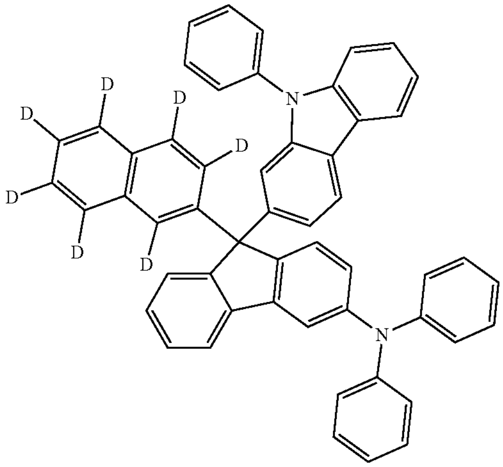

-continued
144
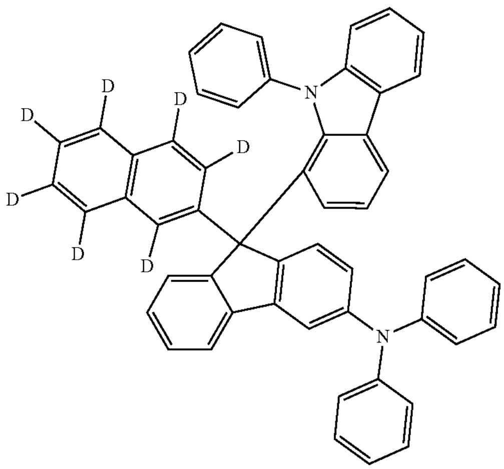
145
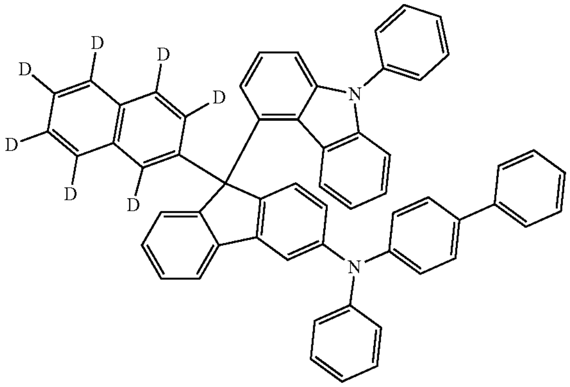
146
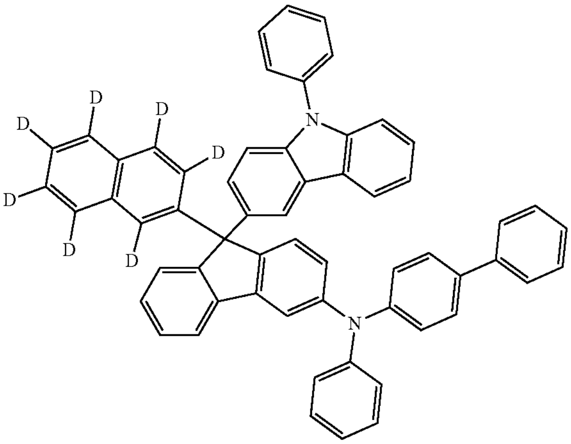
-continued
147
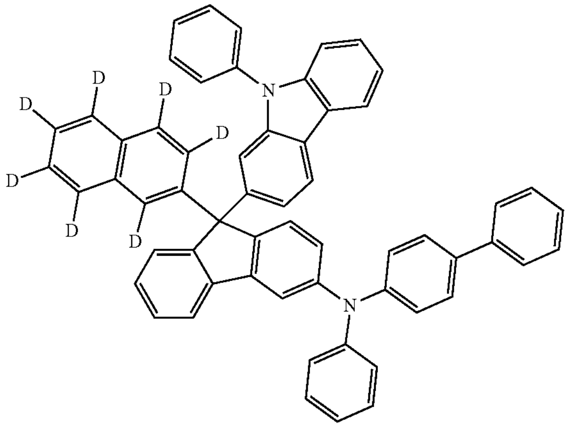
148
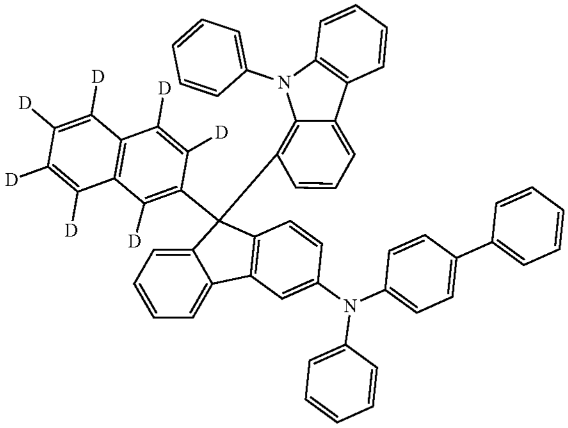
149
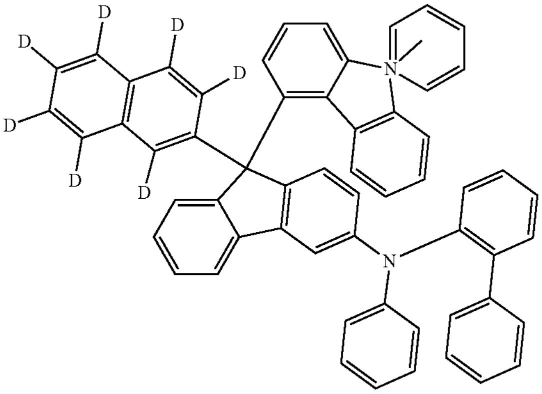

-continued
150
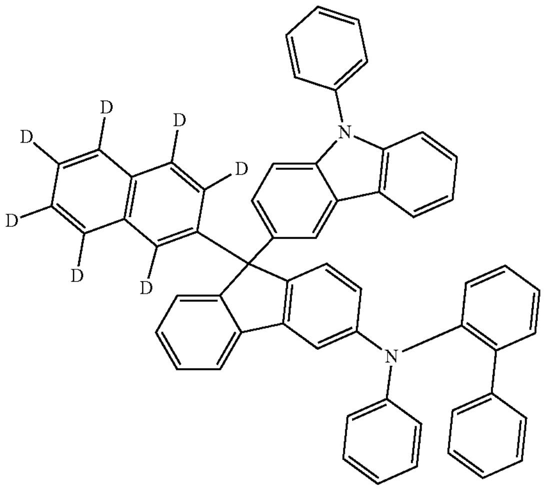
151
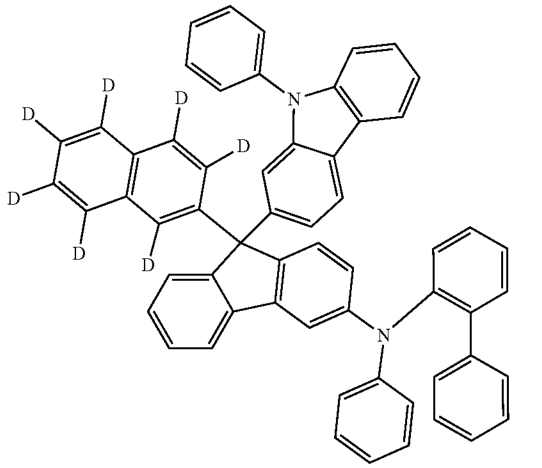
152
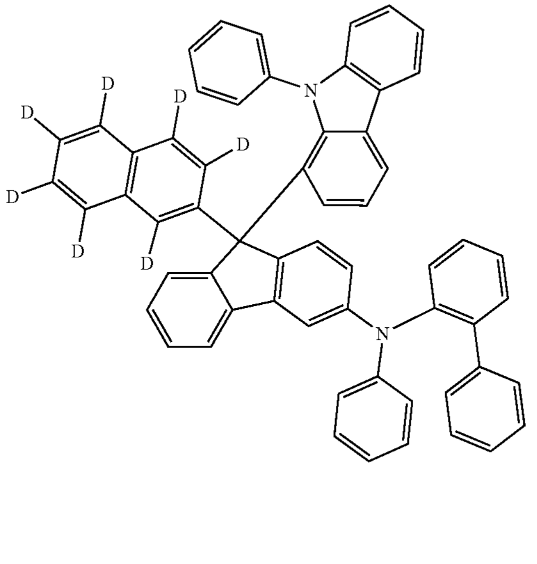
-continued
153
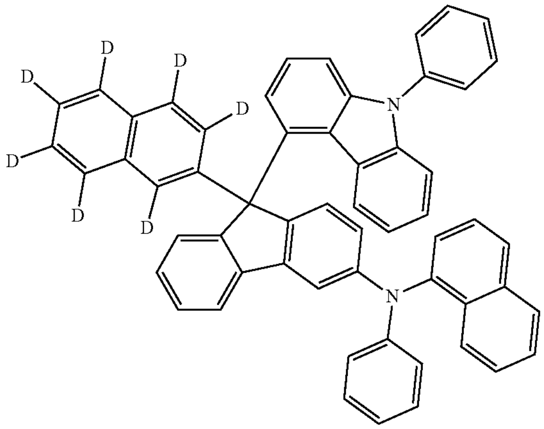
154
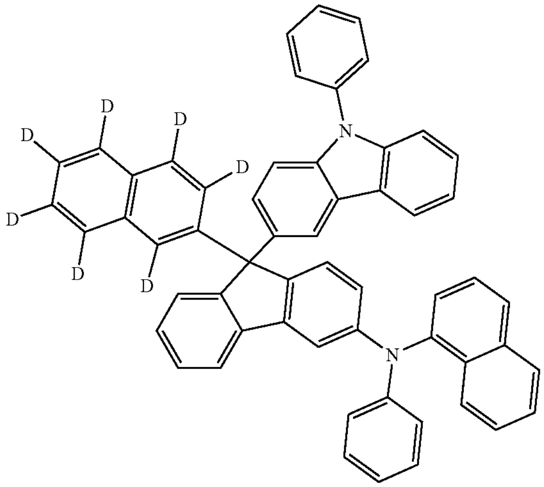
155
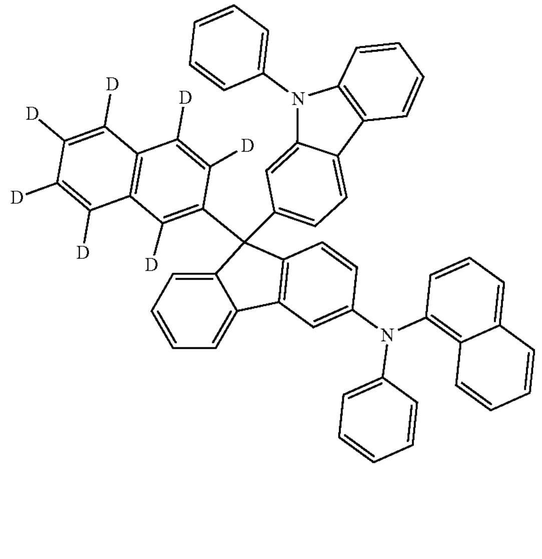

-continued
156
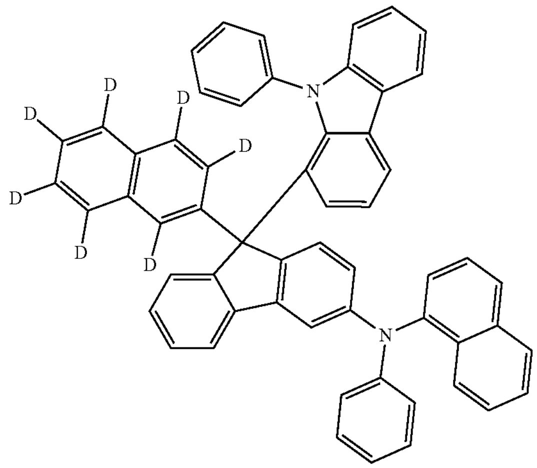
157
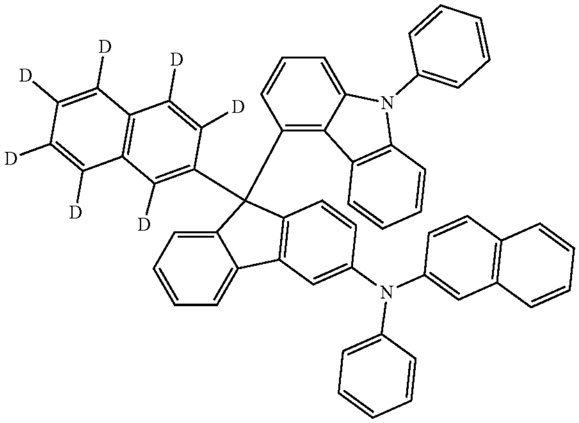
158
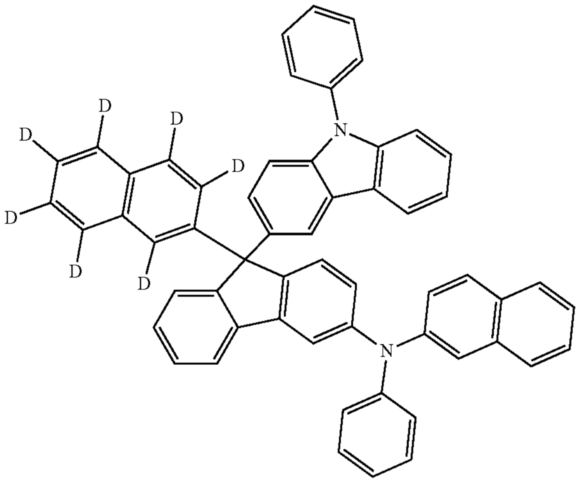
-continued
159
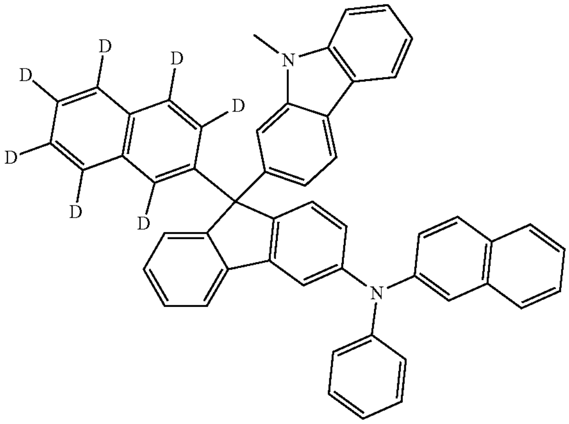
160
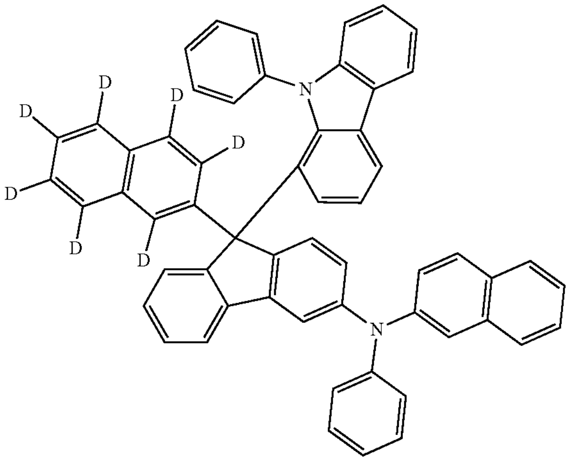
161
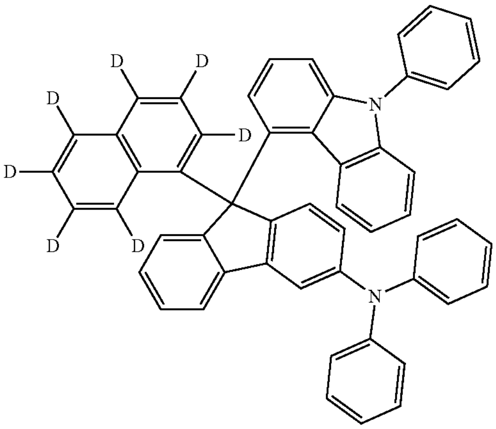

-continued
162
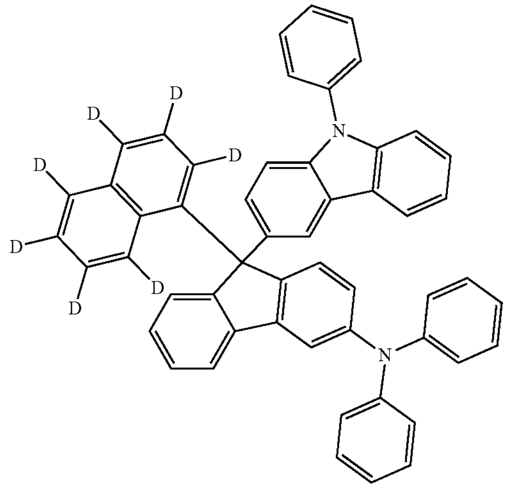
163
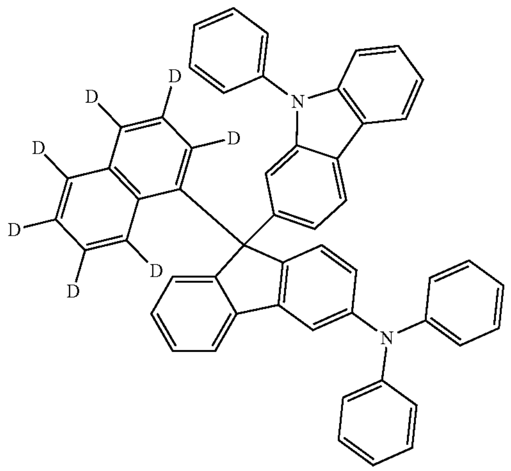
164
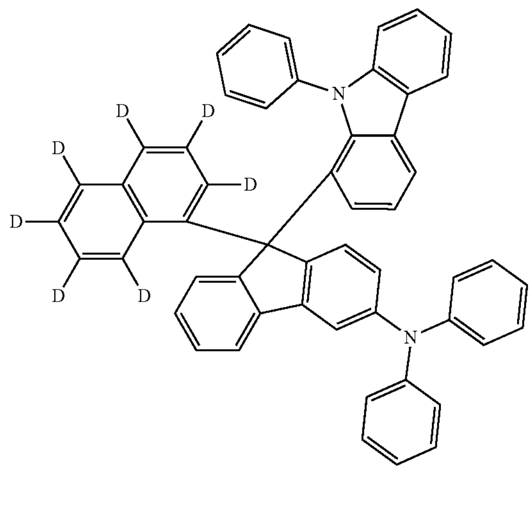
-continued
165
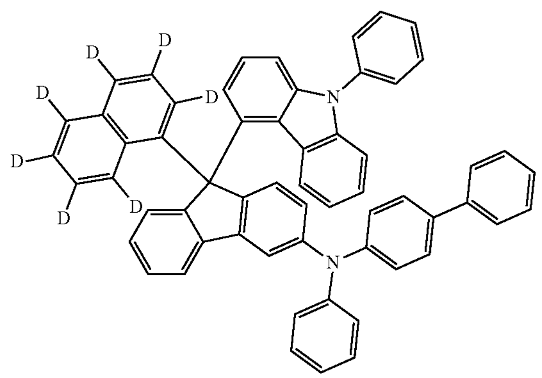
166
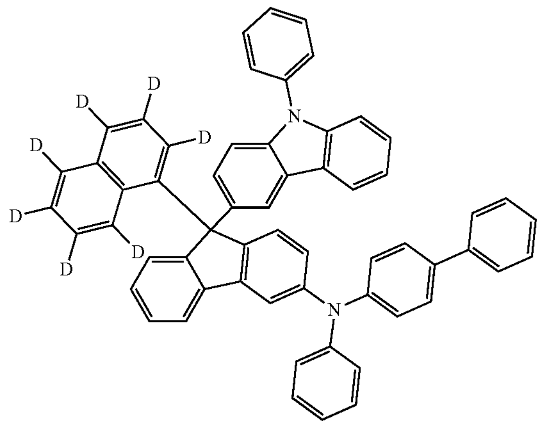
167
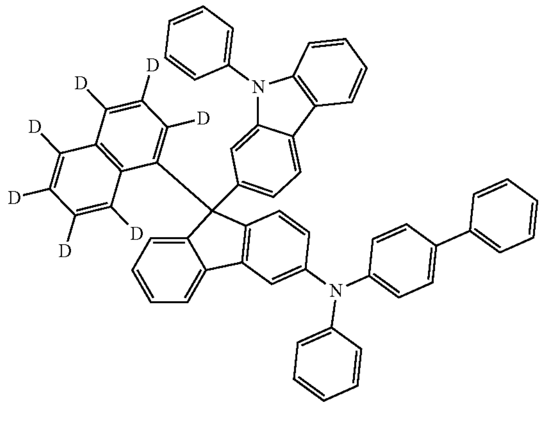

-continued
168
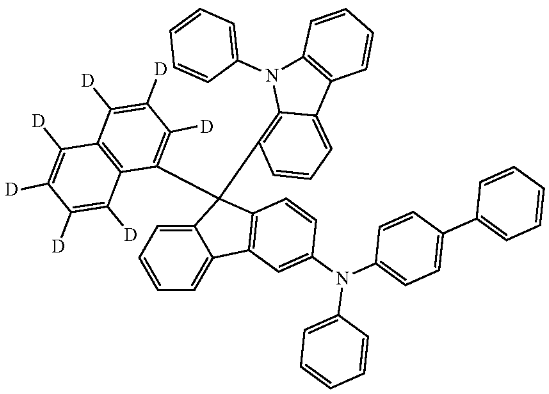
169
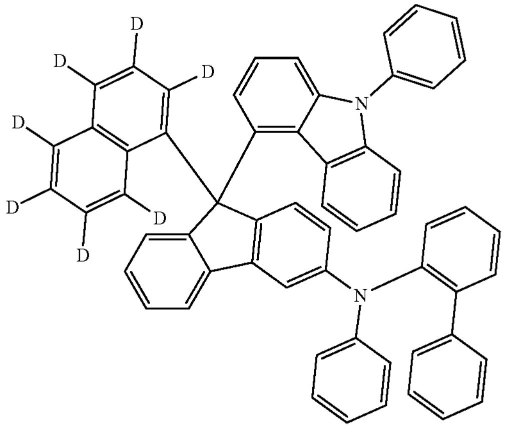
170
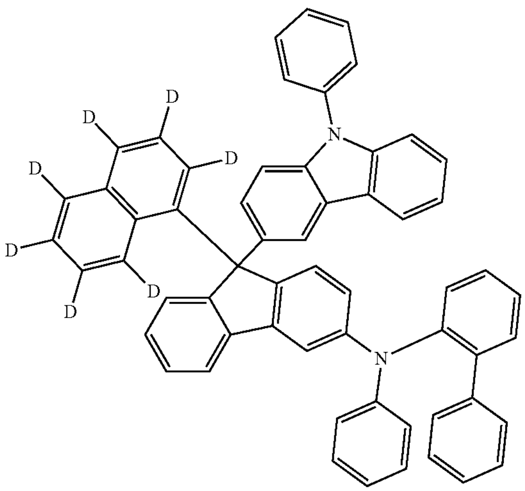
-continued
171
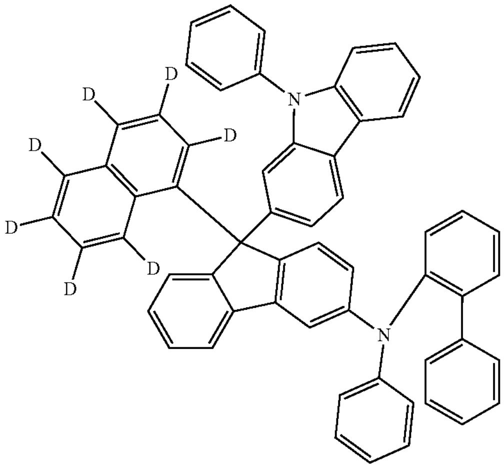
172
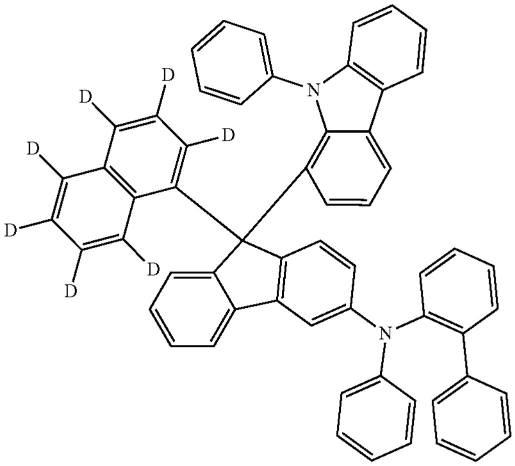
173
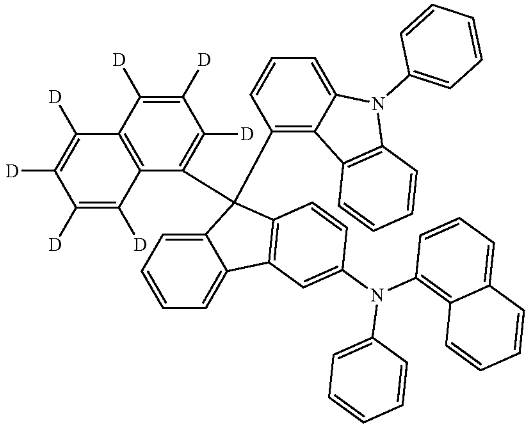

-continued
174
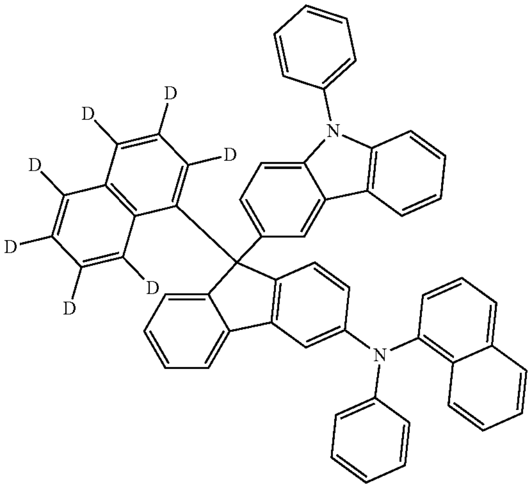
173
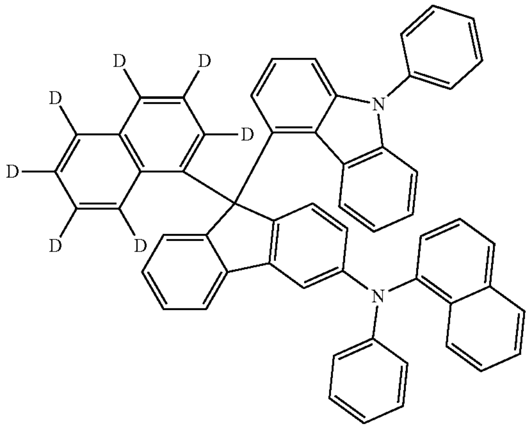
174
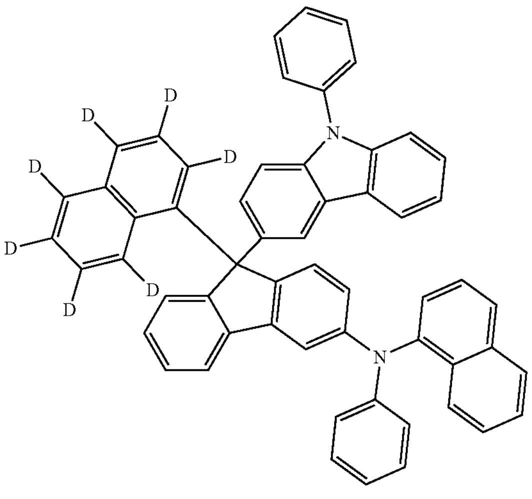
-continued
177
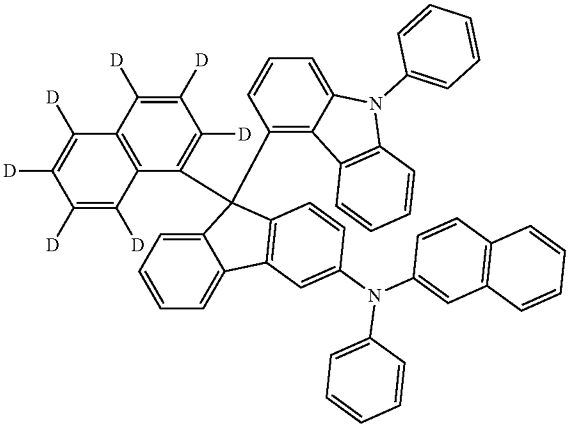
178
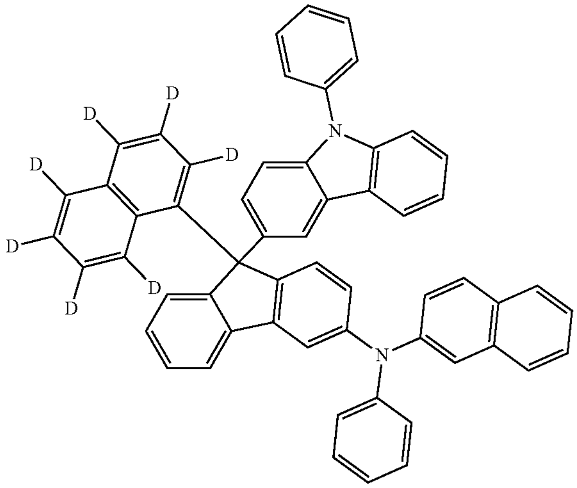
179
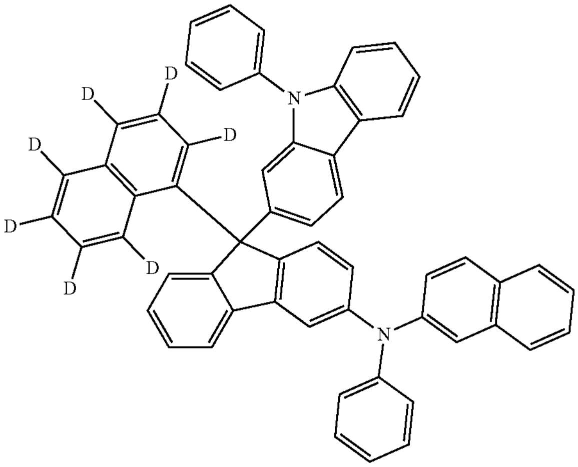

-continued
180
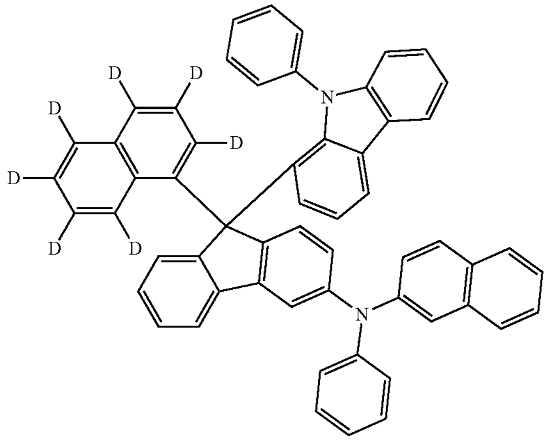
181
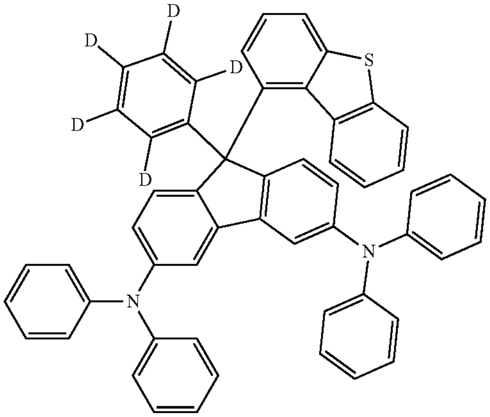
182
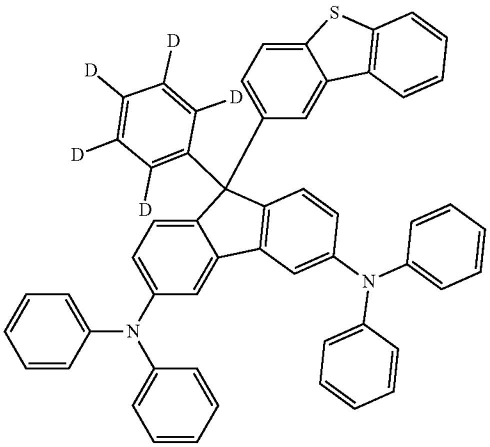
-continued
183
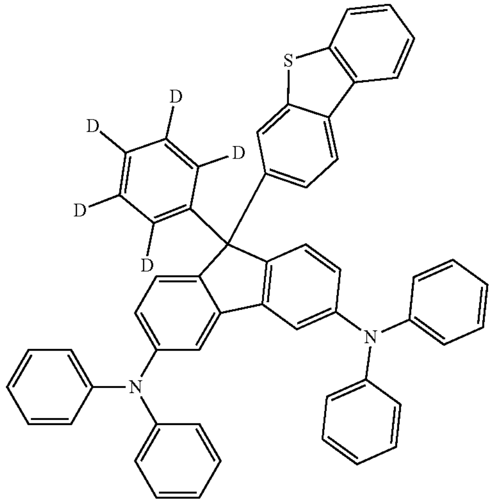
184
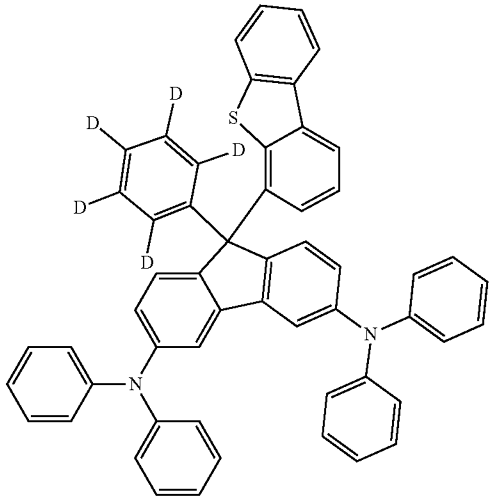
185
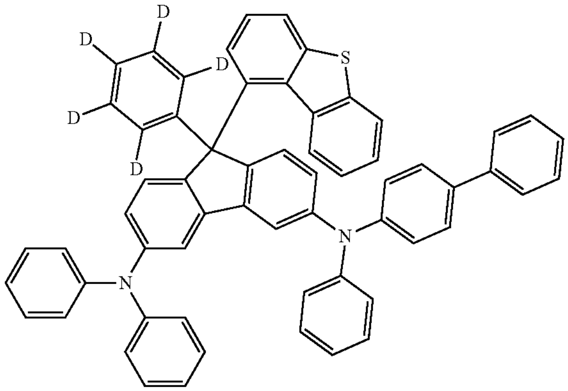

-continued
186
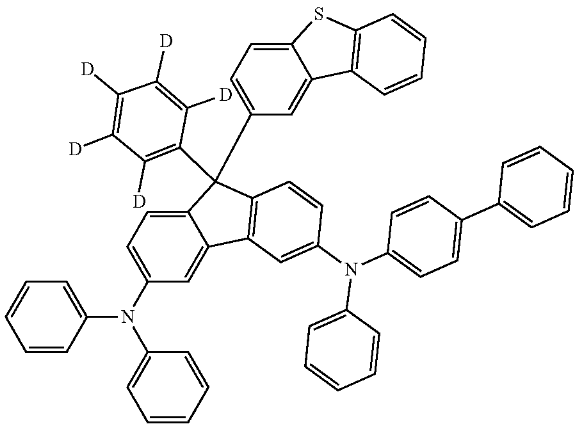
187
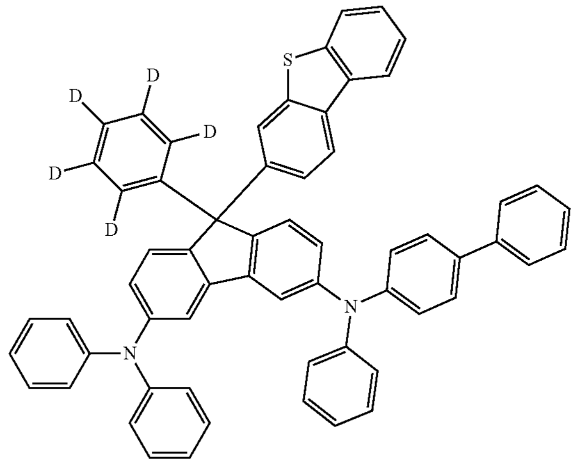
188
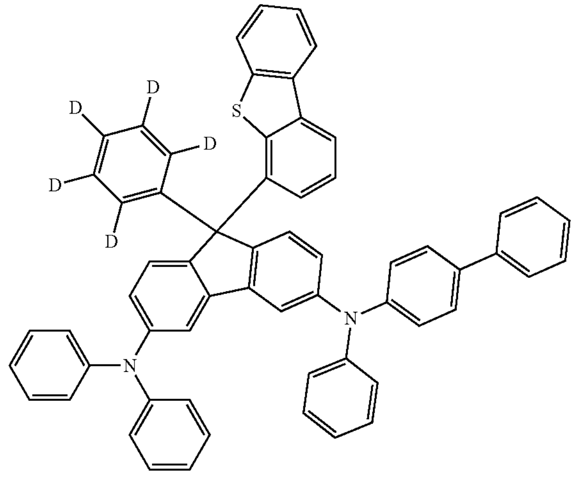
-continued
189
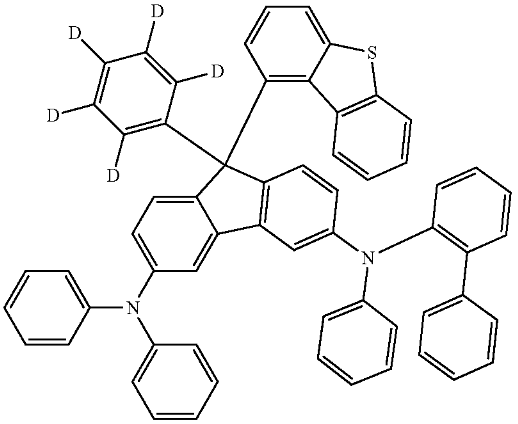
190
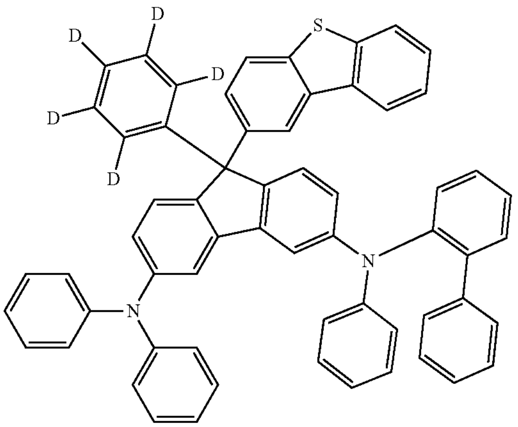
191
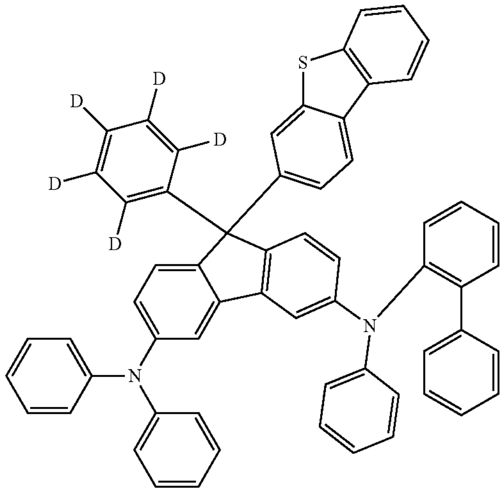

-continued
192
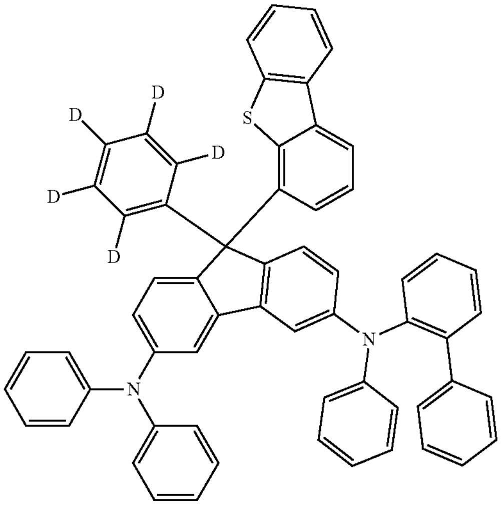
193
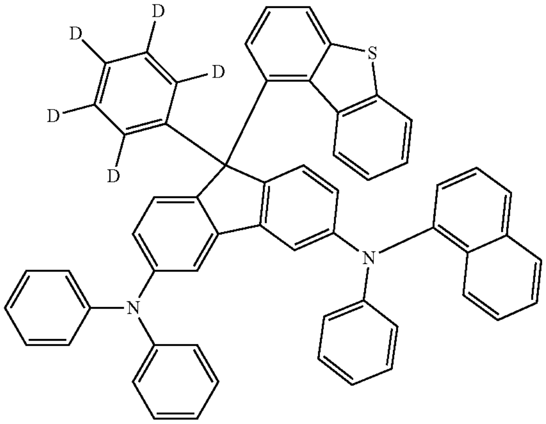
194
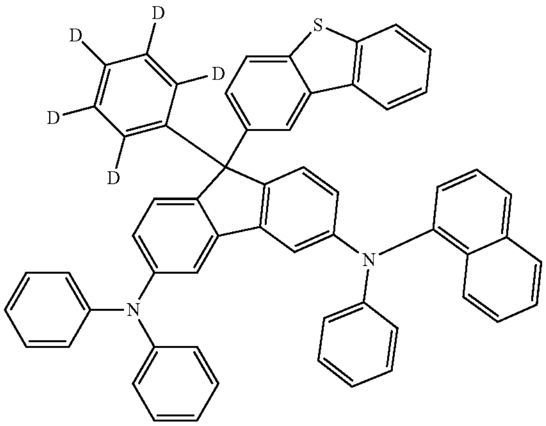
-continued
195
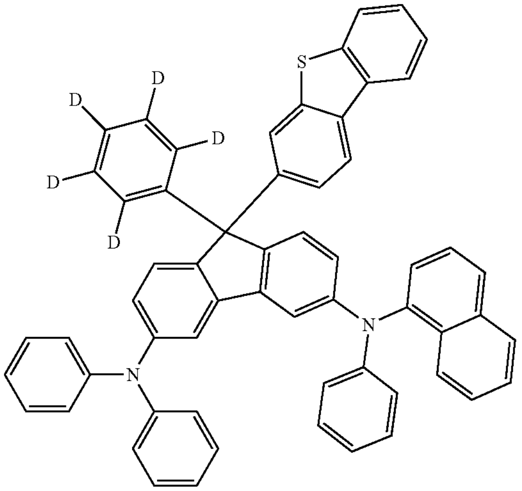
196
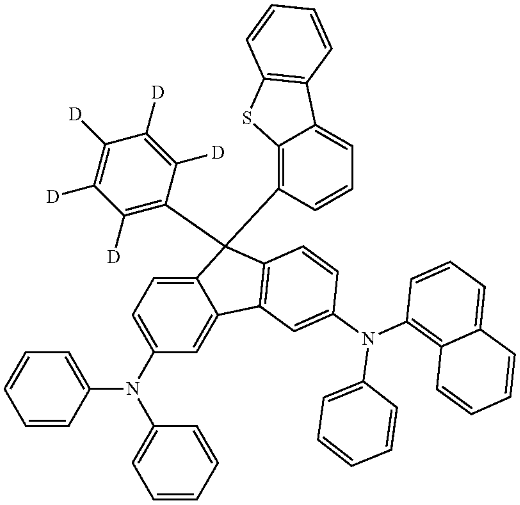
197
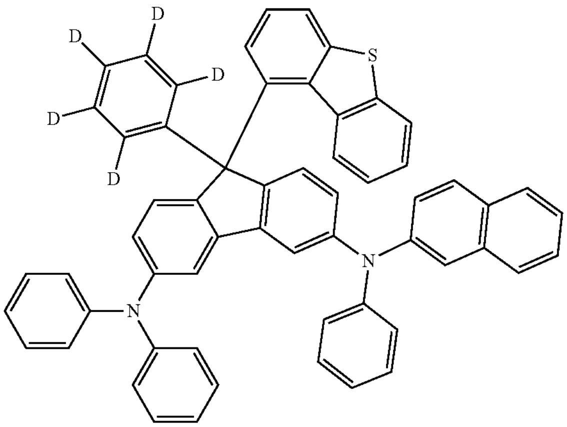

-continued
198
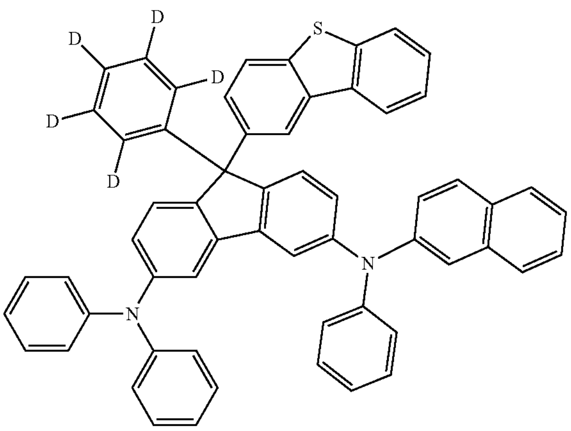
199
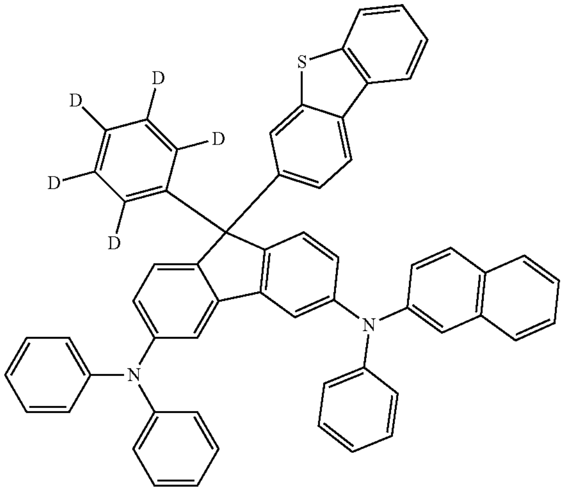
200
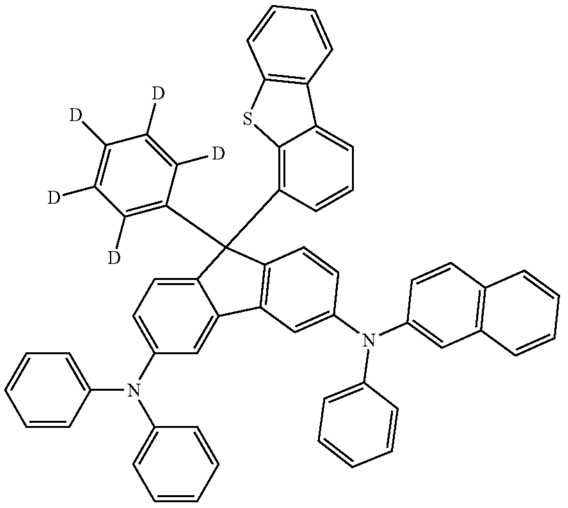
-continued
201
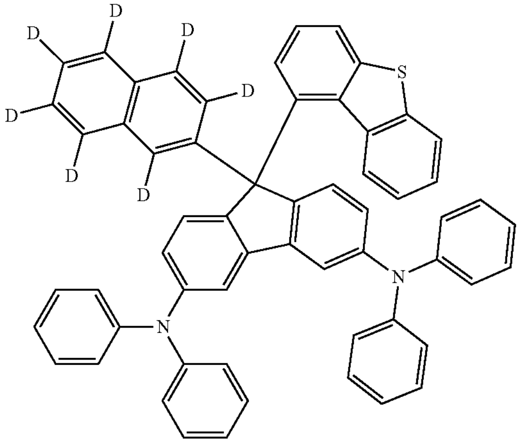
202
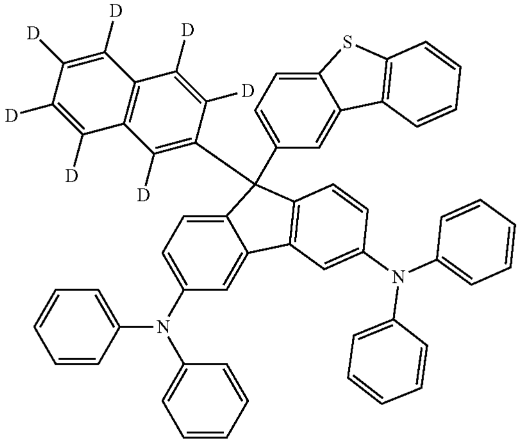
203
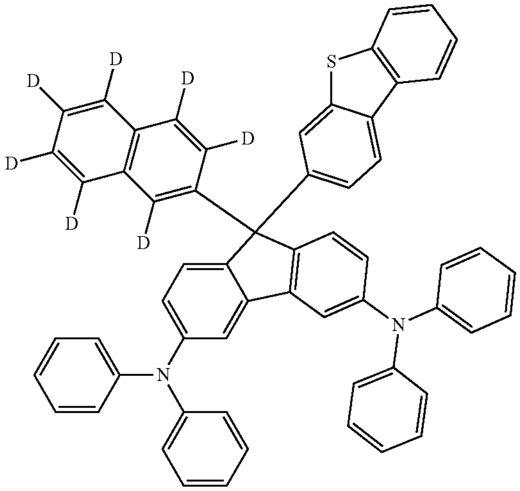

-continued
204
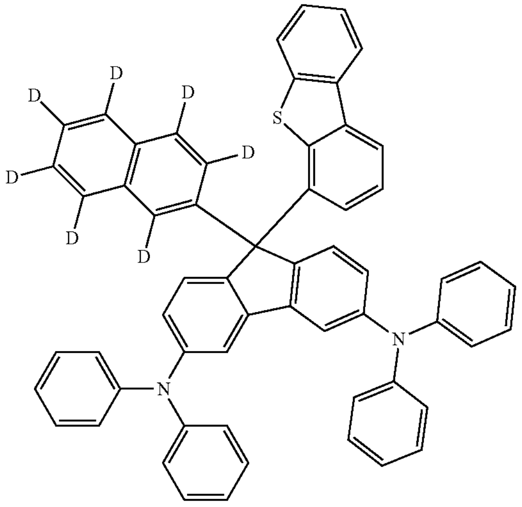
205
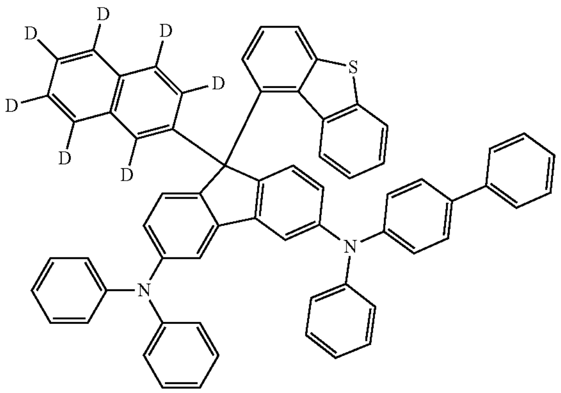
206
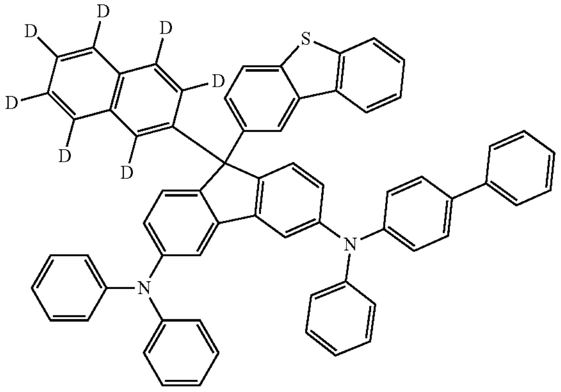
-continued
207
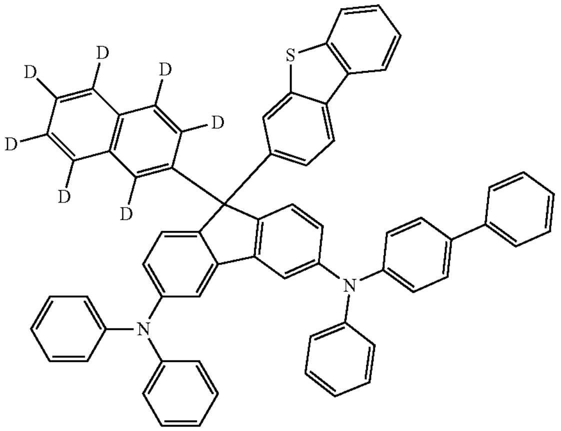
208
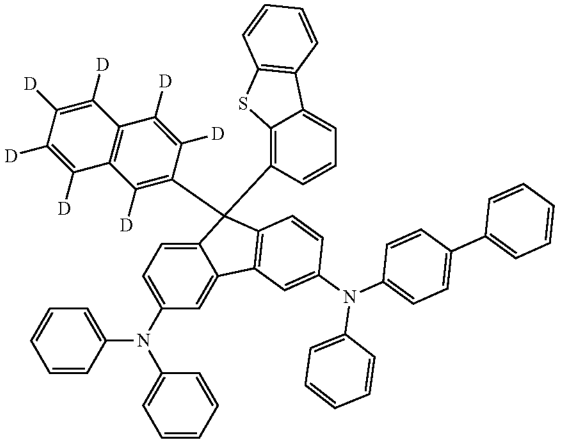
209
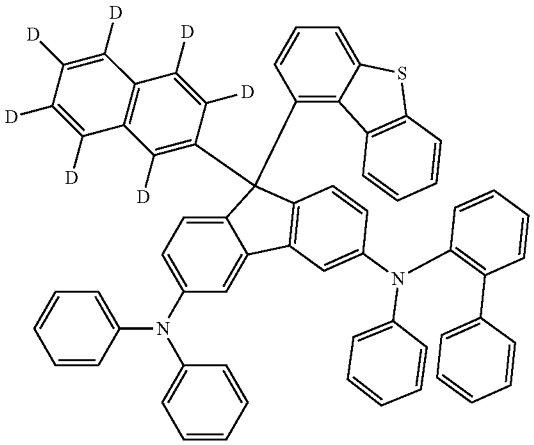

-continued
210
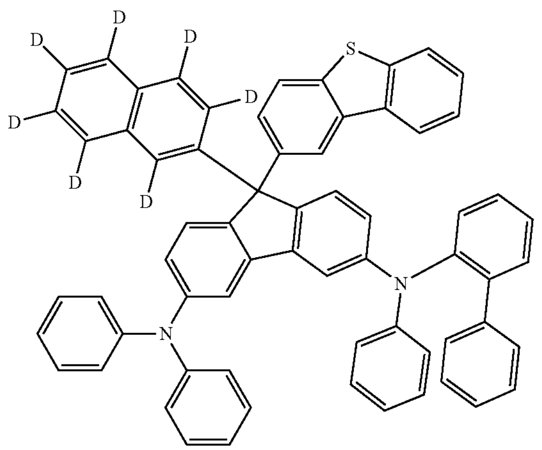
211
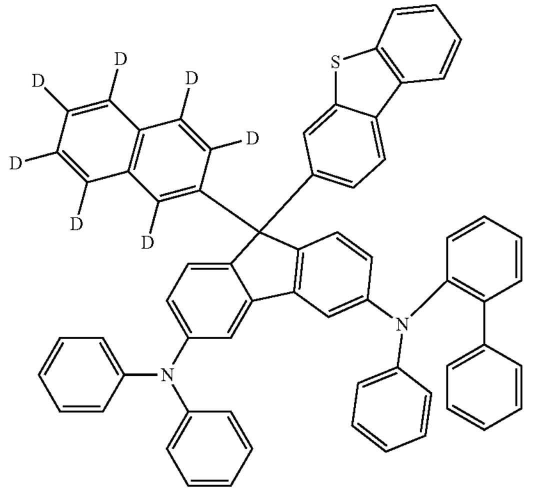
212
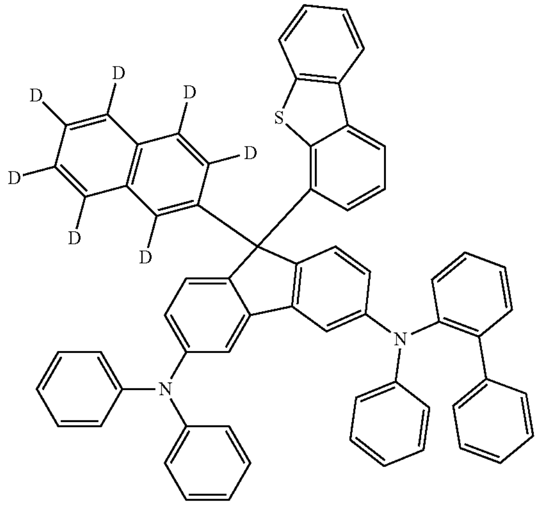
-continued
213
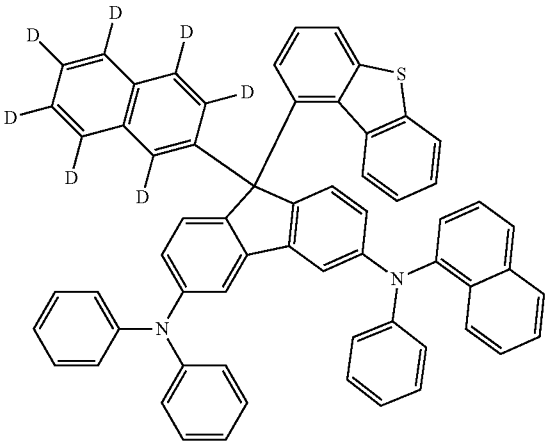
214
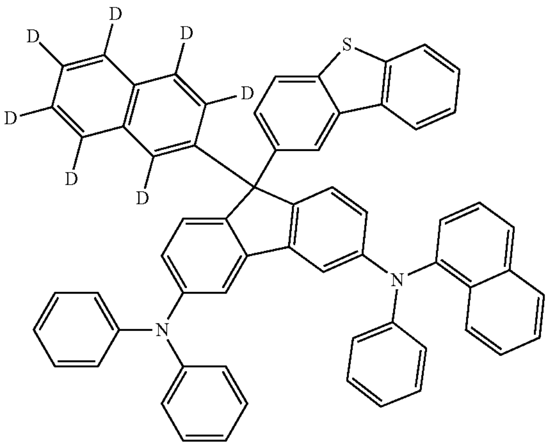
215
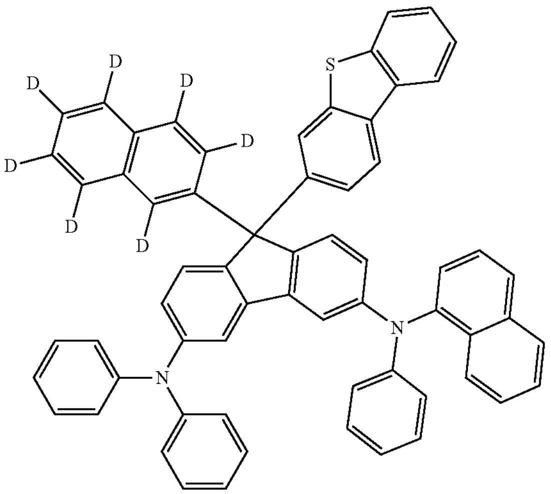

-continued
216
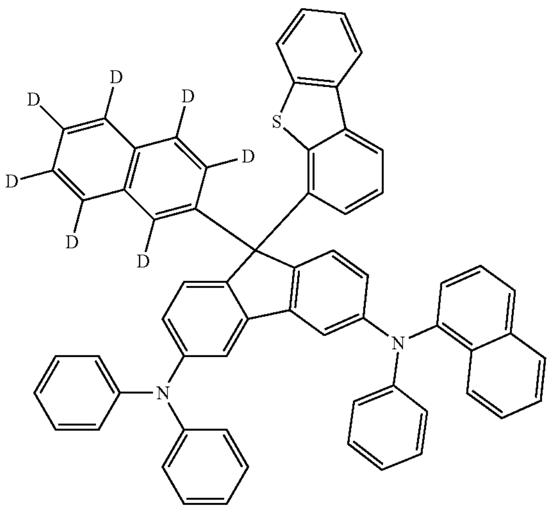
217
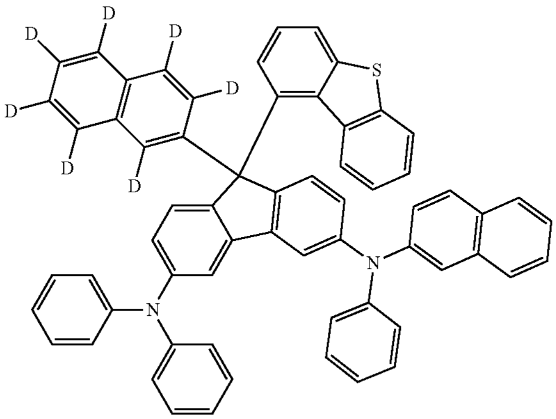
218
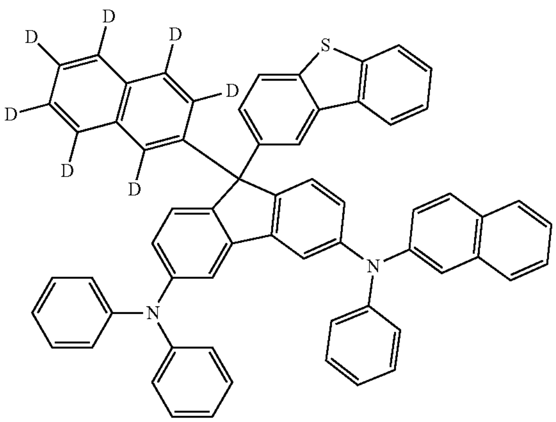
-continued
219
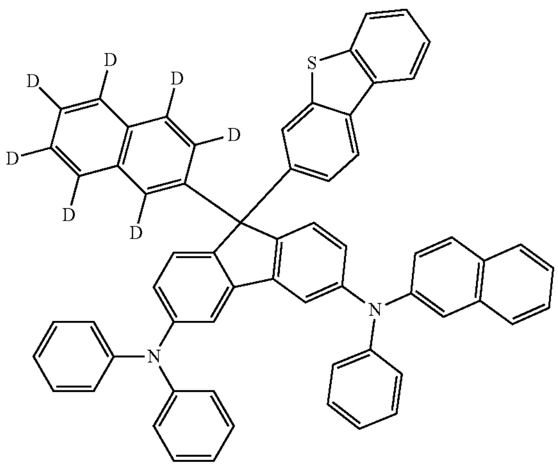
220
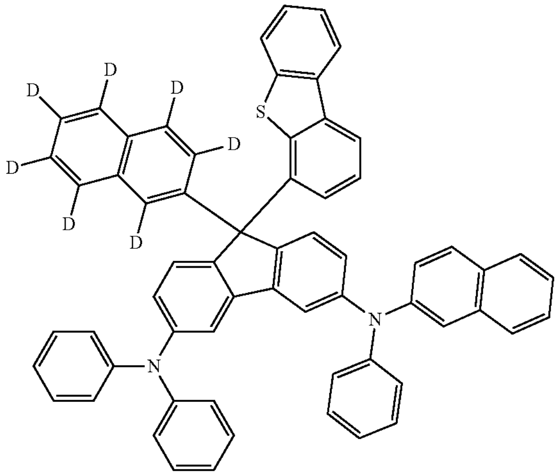
221
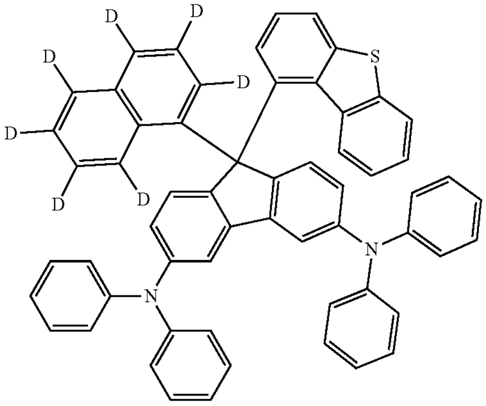

-continued
222
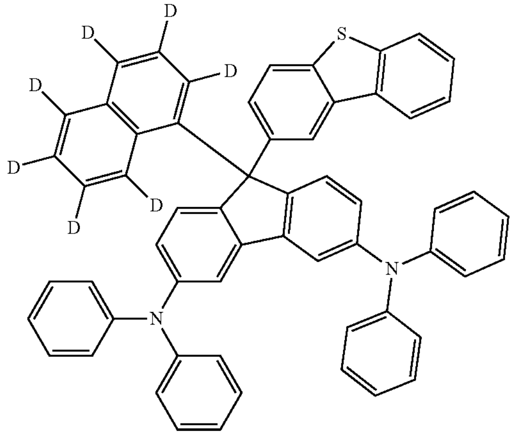
223
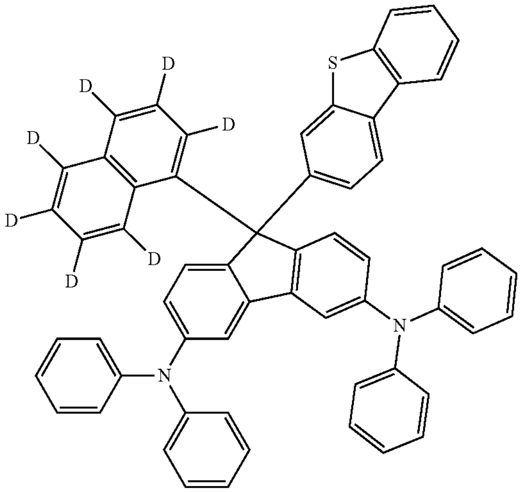
224
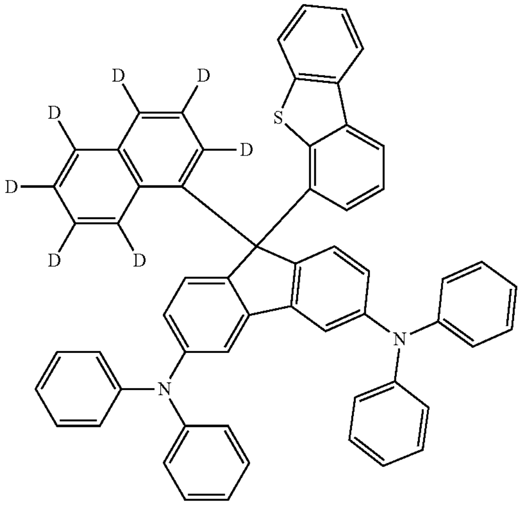
-continued
225
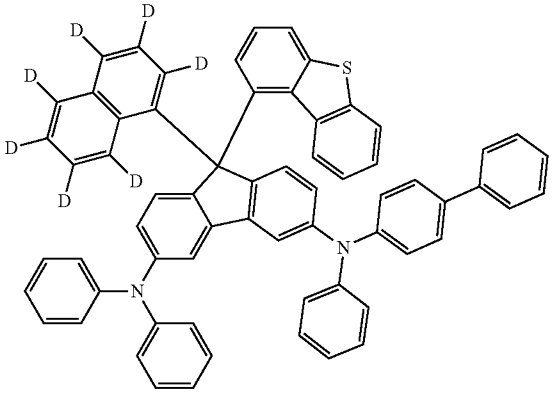
226
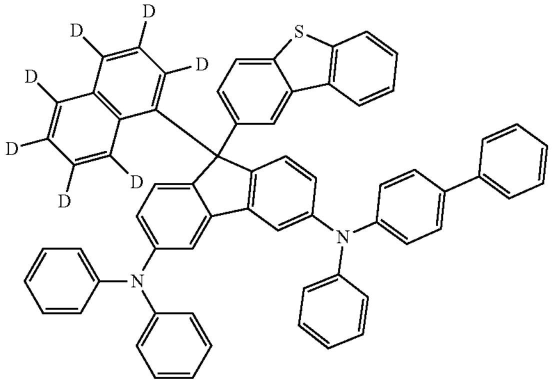
227
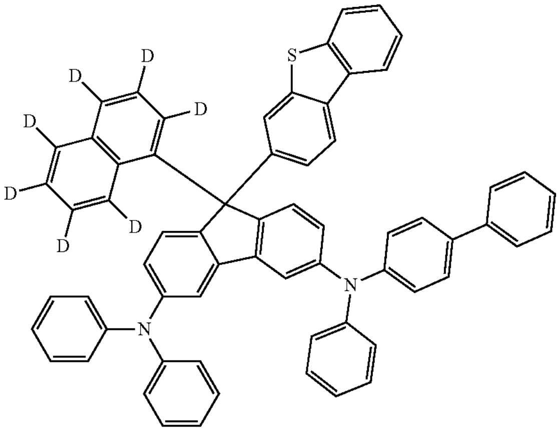

-continued
228
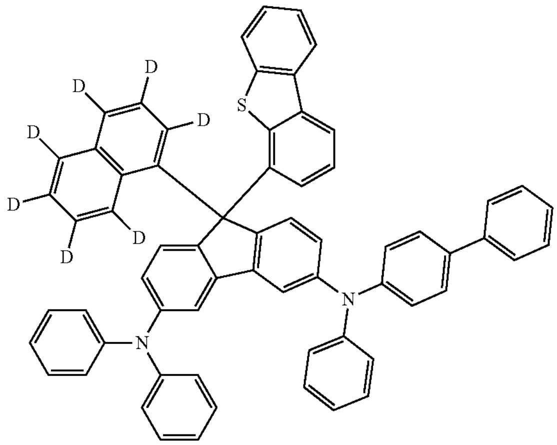
229
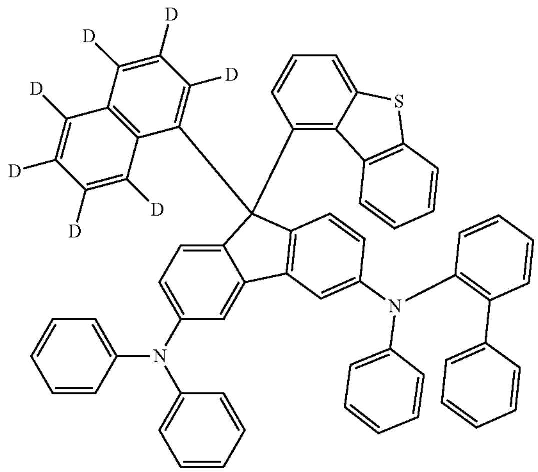
230
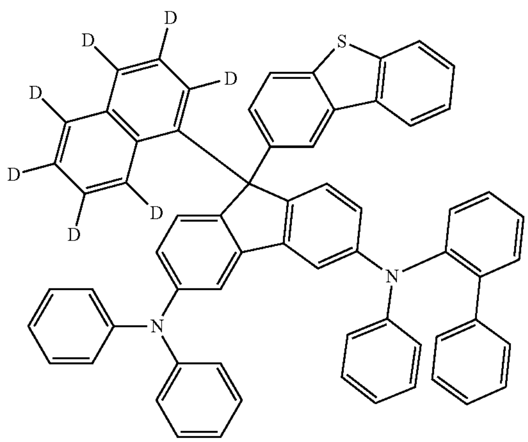
-continued
231
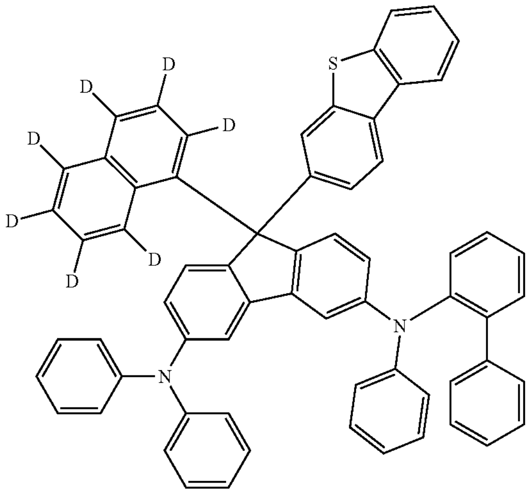
232
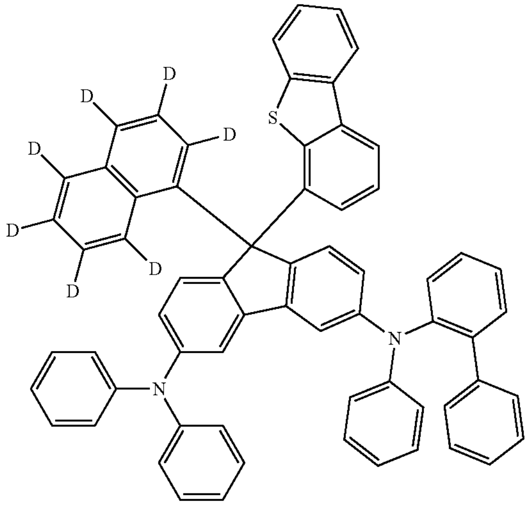
233
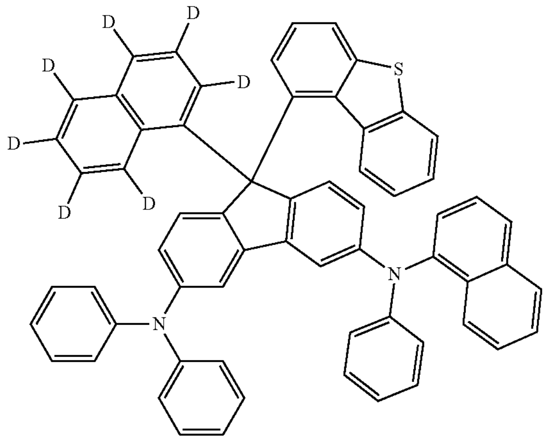

-continued
234
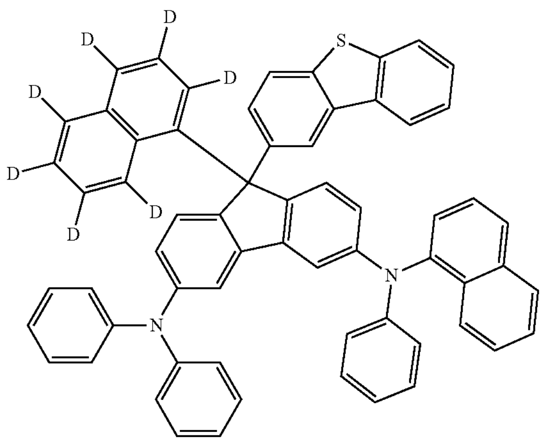
235
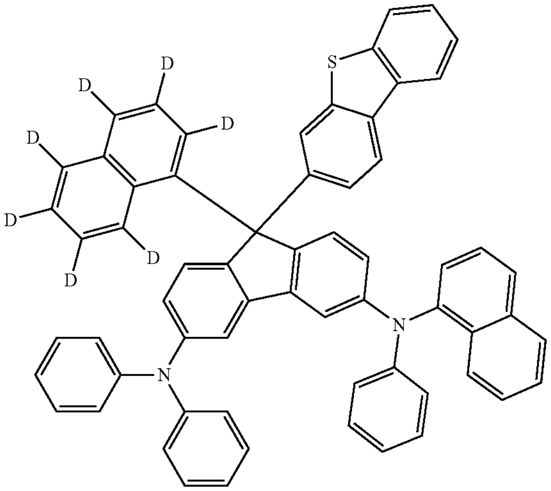
236
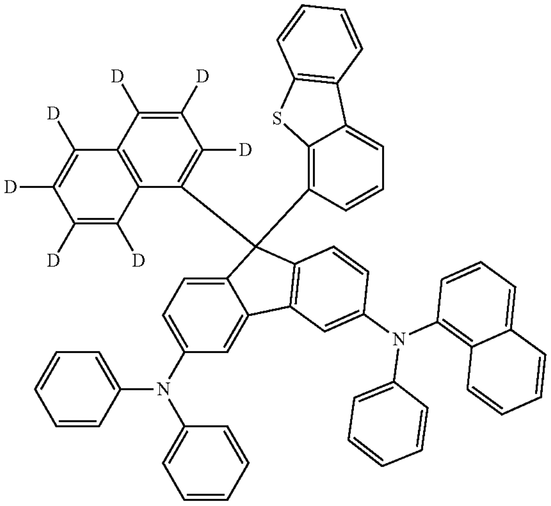
-continued
237
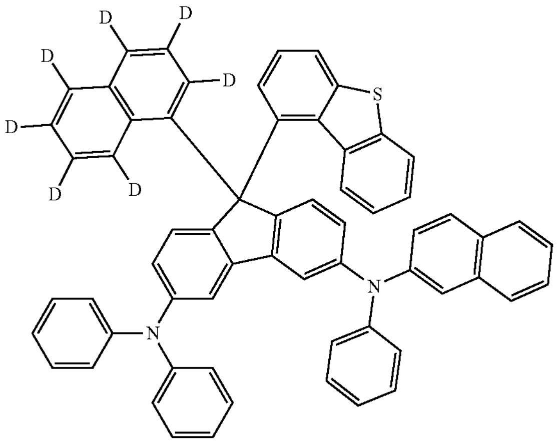
238
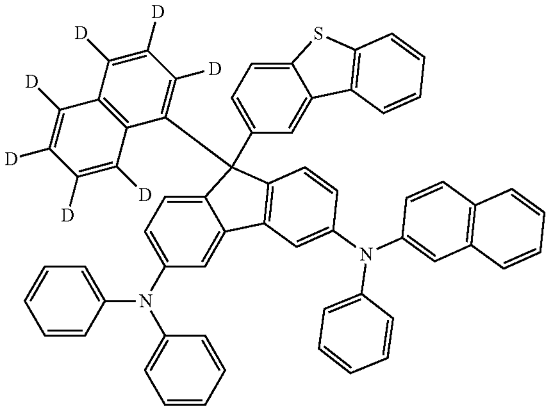
239
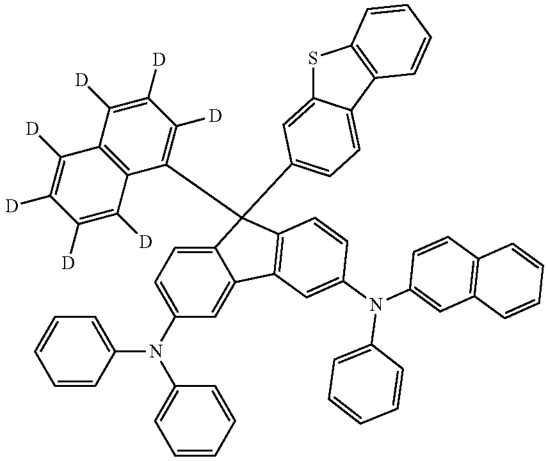

-continued
240
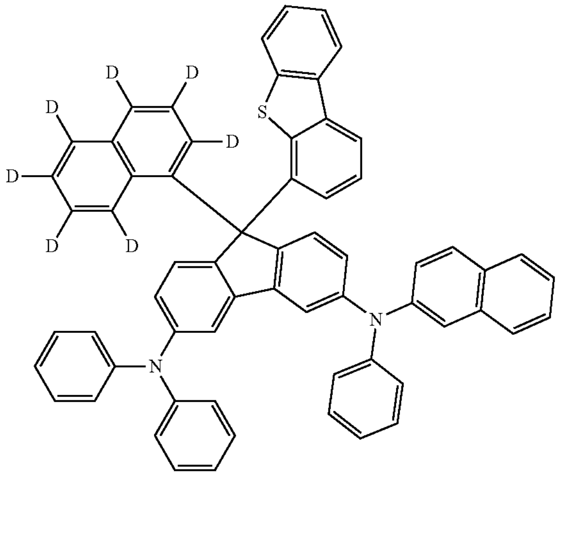
241
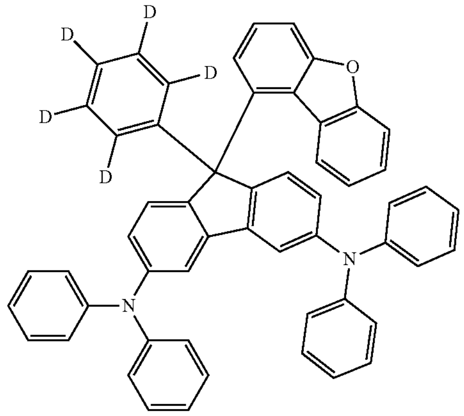
242
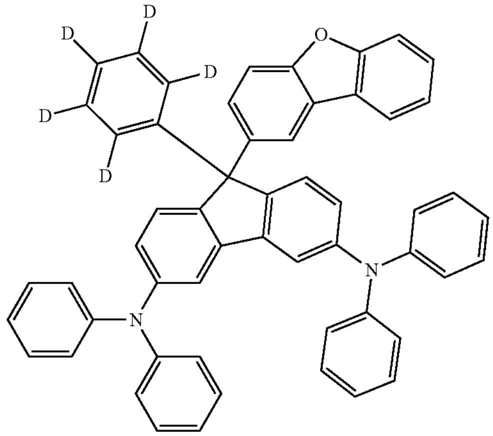
-continued
243
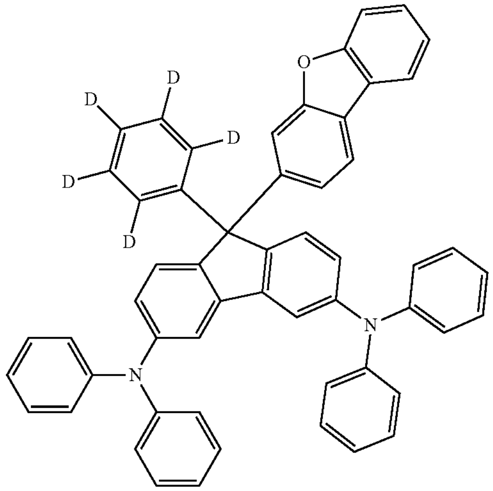
244
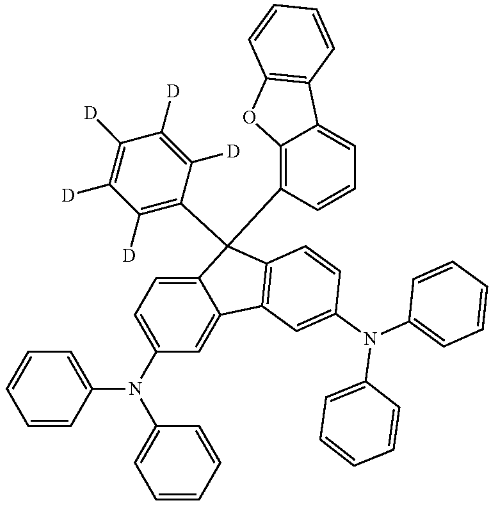
245
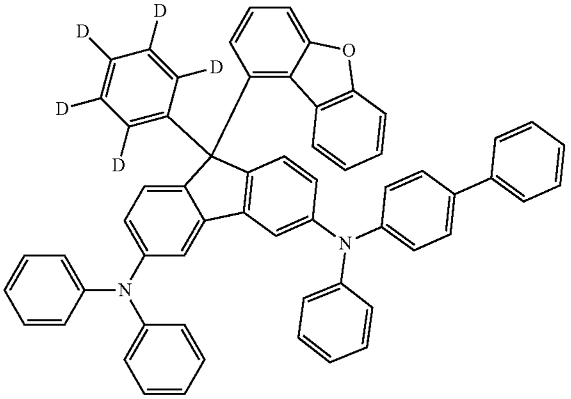

-continued
246
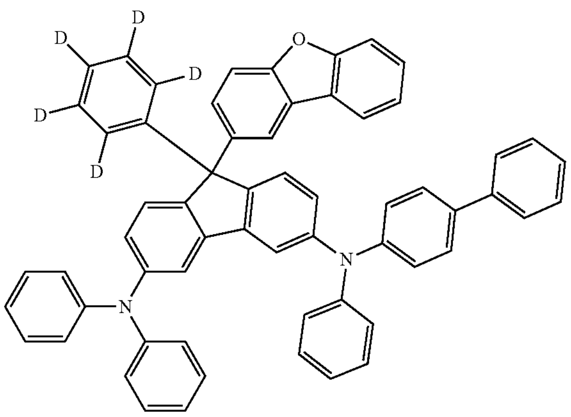
247
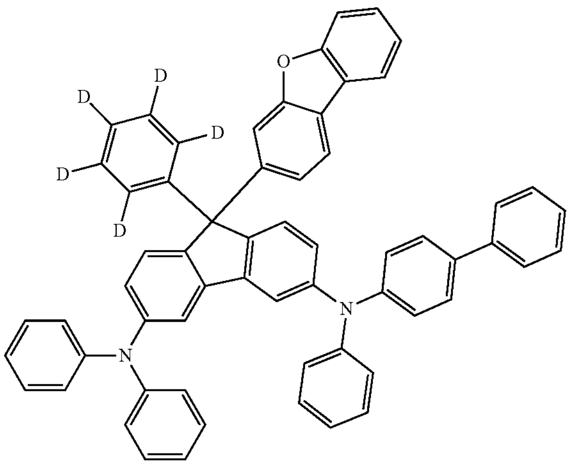
248
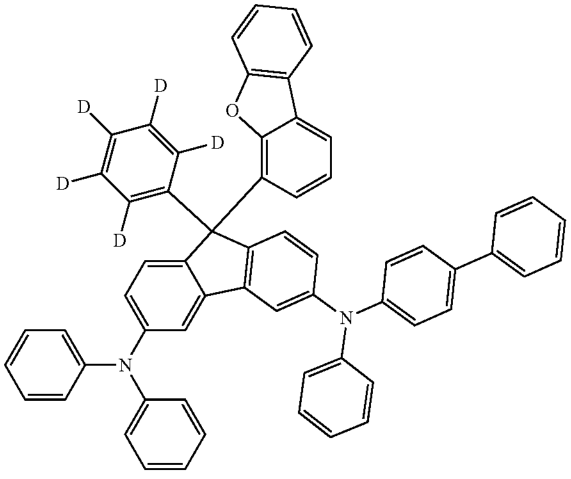
-continued
249
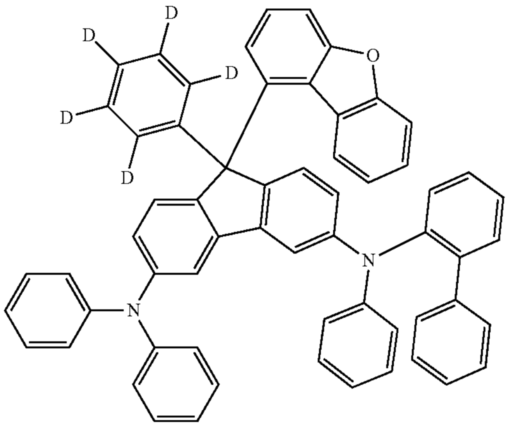
250
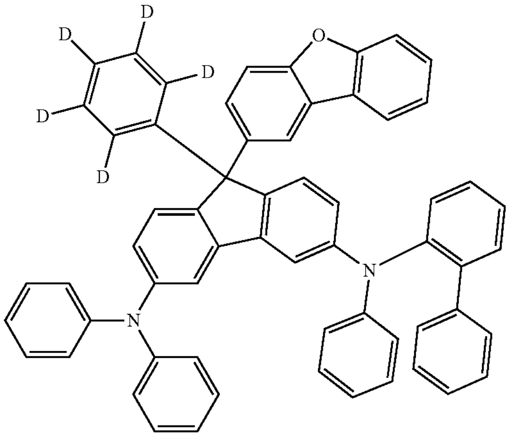
251
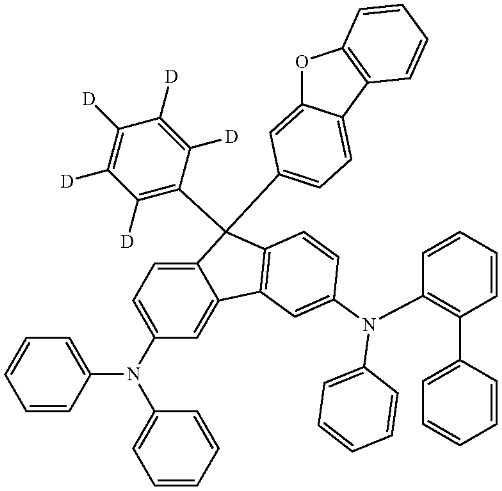

-continued
252
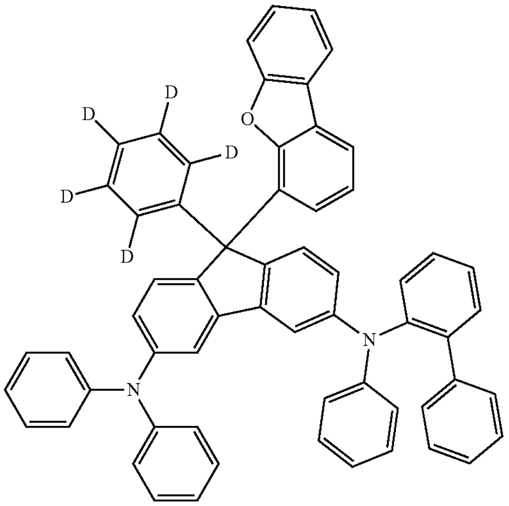
253
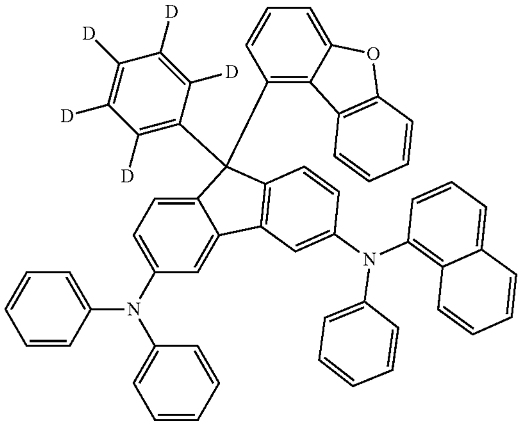
254
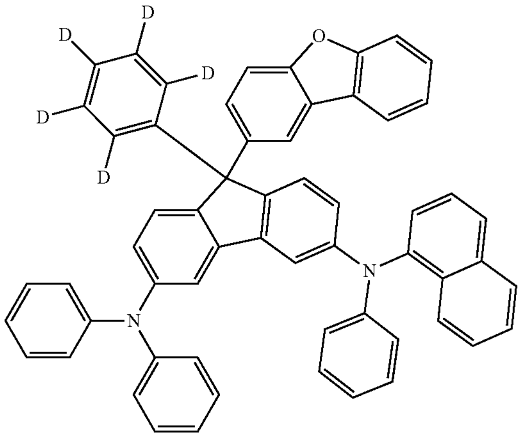
-continued
255
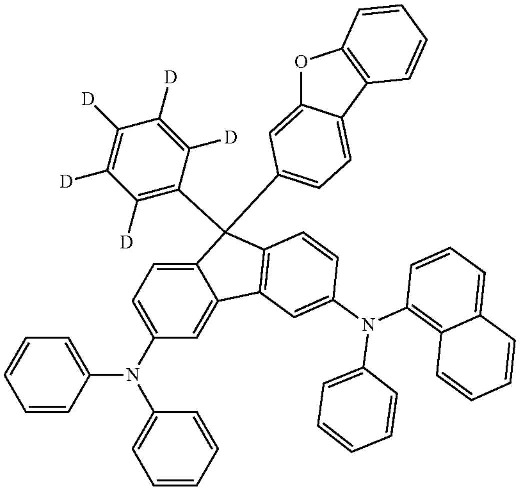
256
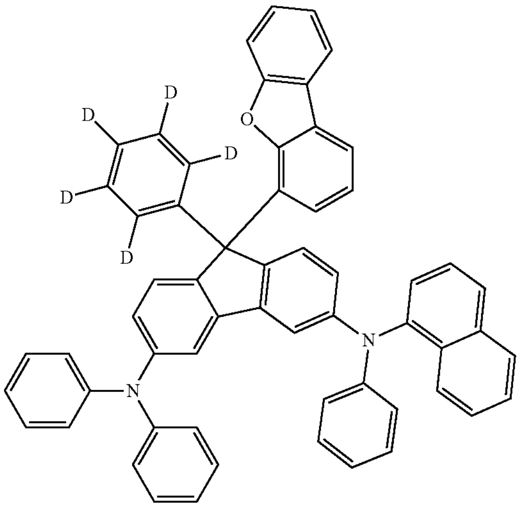
257
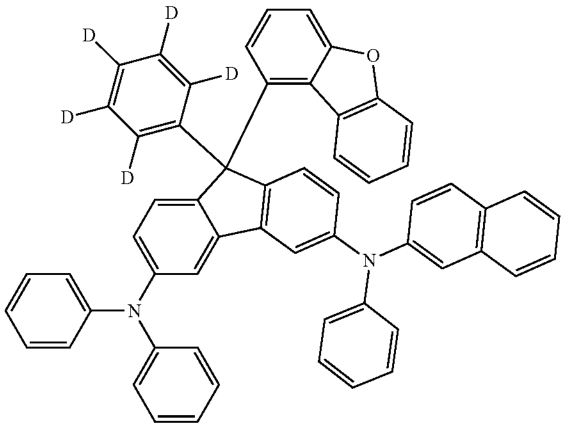

-continued
258
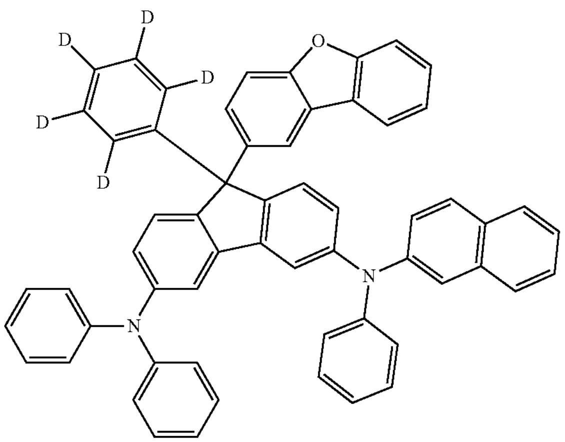
259
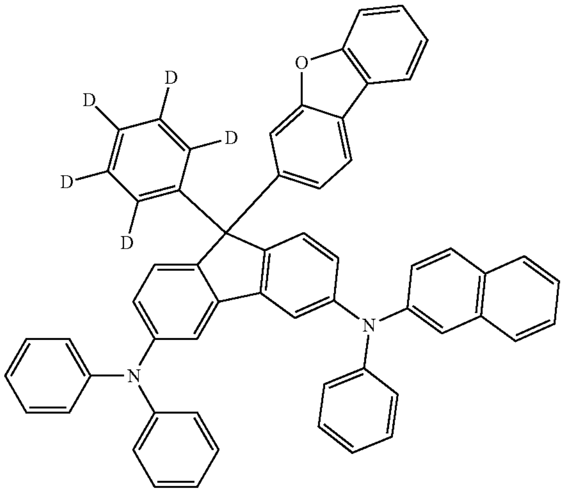
260
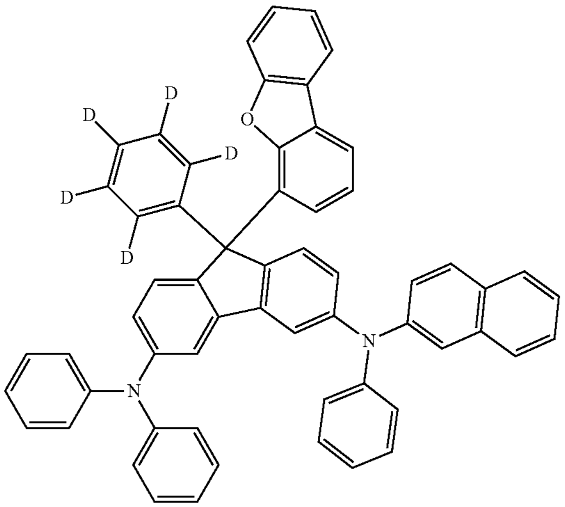
-continued
261
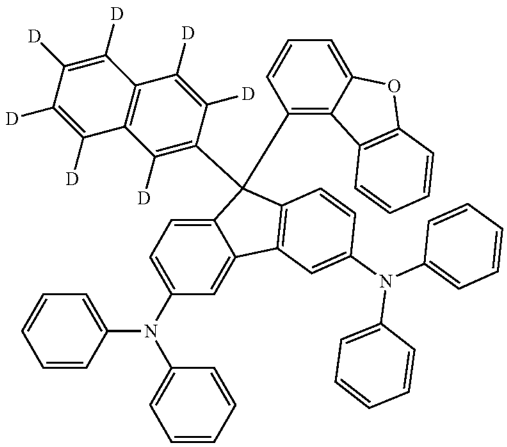
262
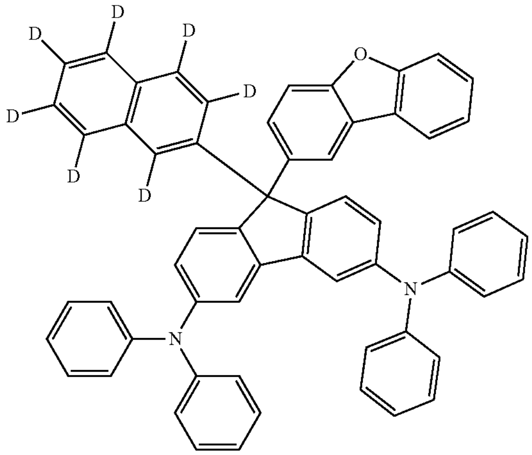
263
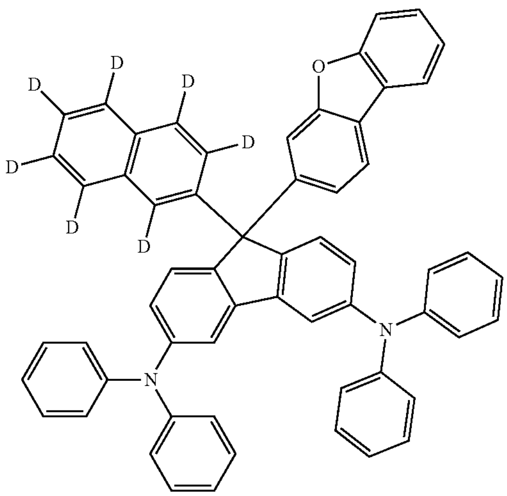

-continued
264
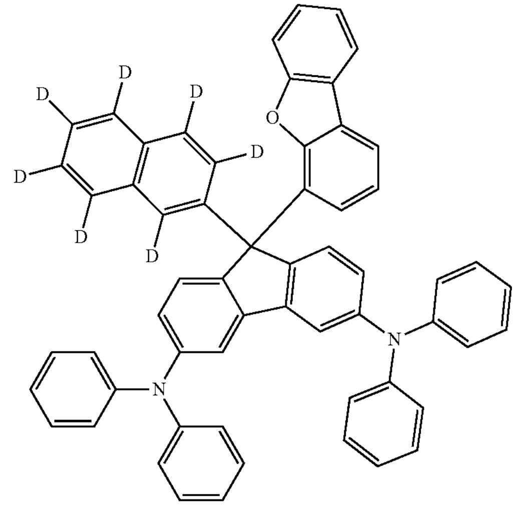
265
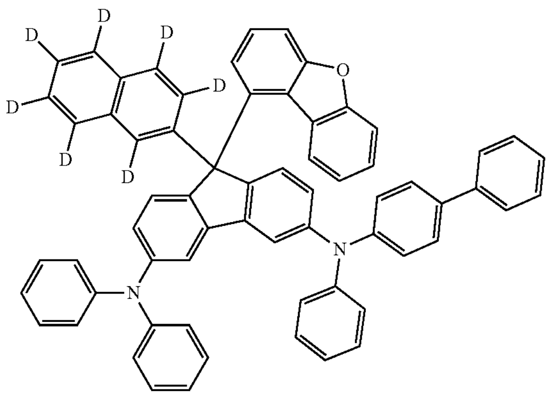
266
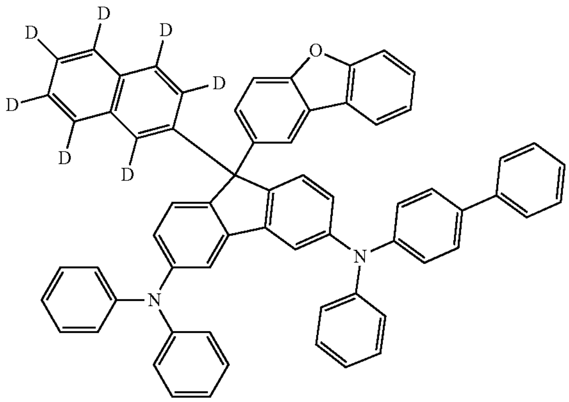
-continued
267
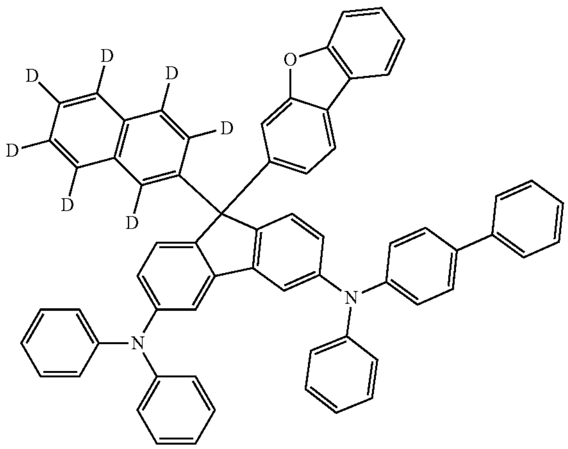
268
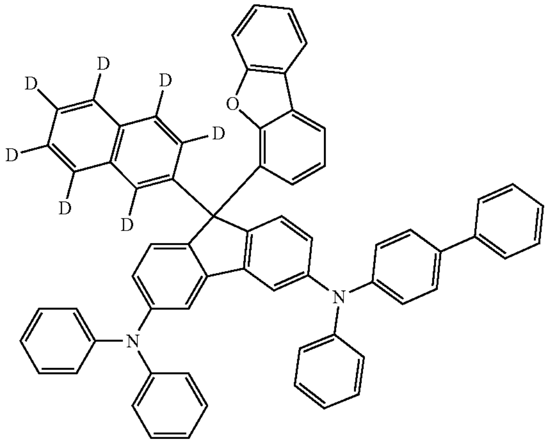
269
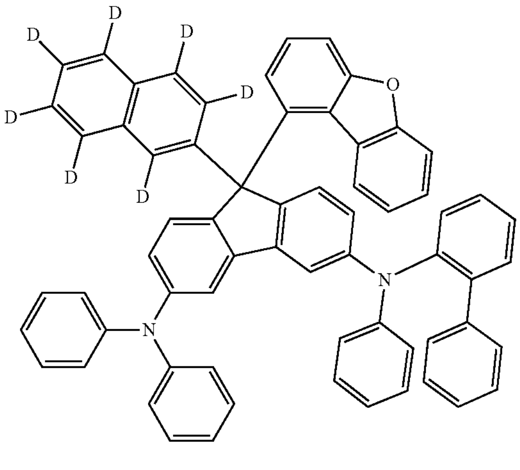

-continued
270
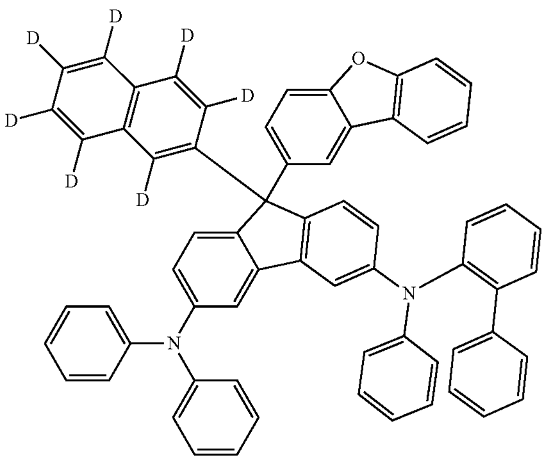
271
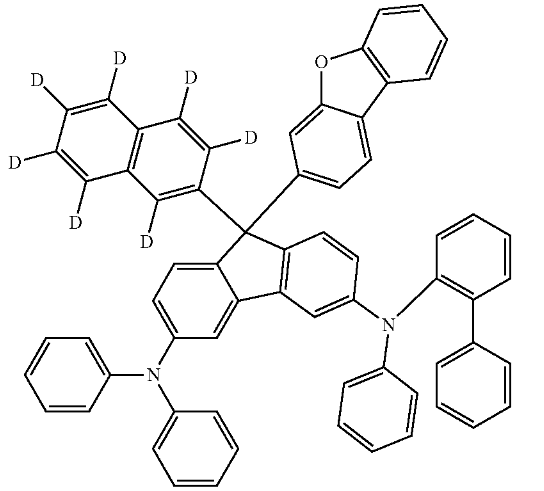
272
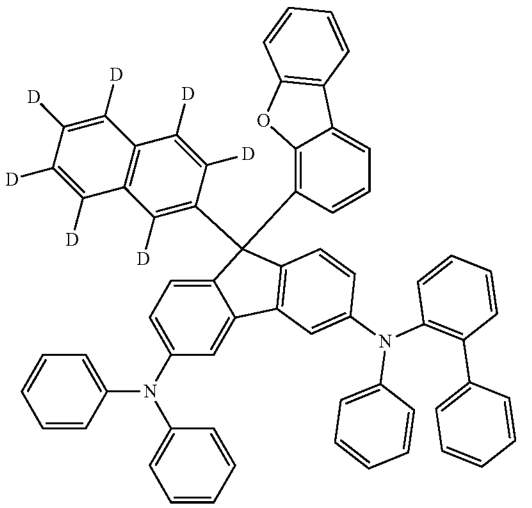
-continued
273
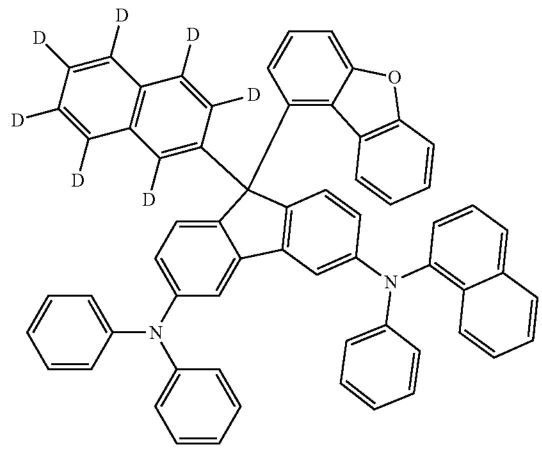
274
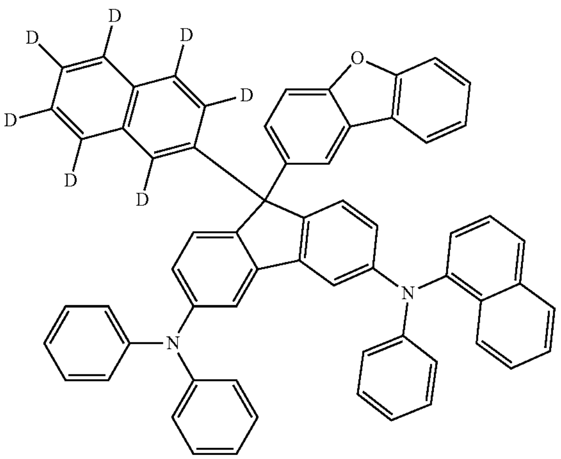
275
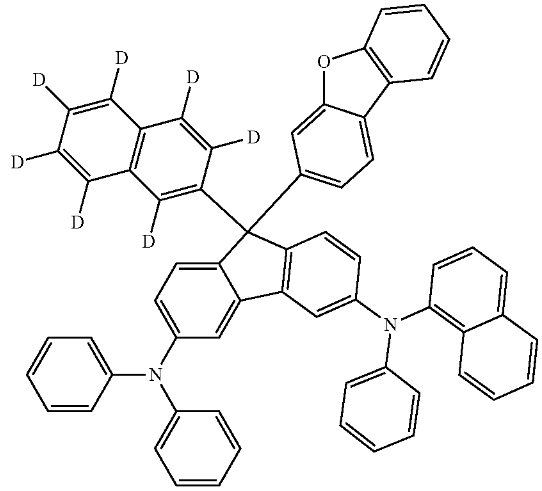

-continued
276
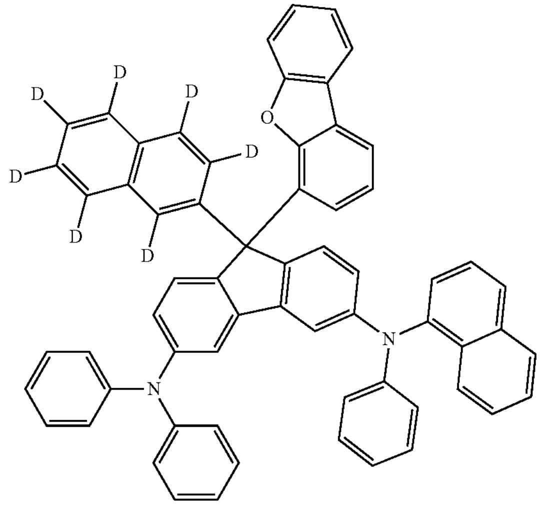
277
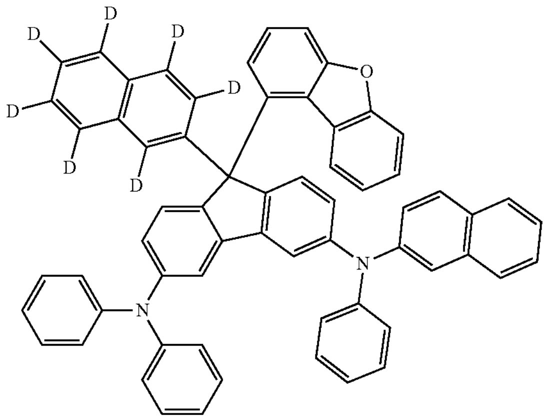
278
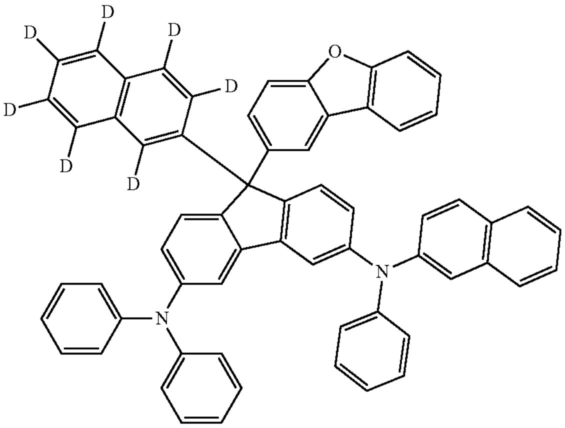
-continued
279
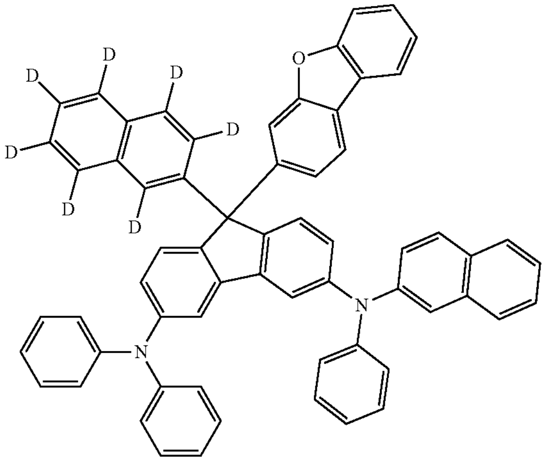
280
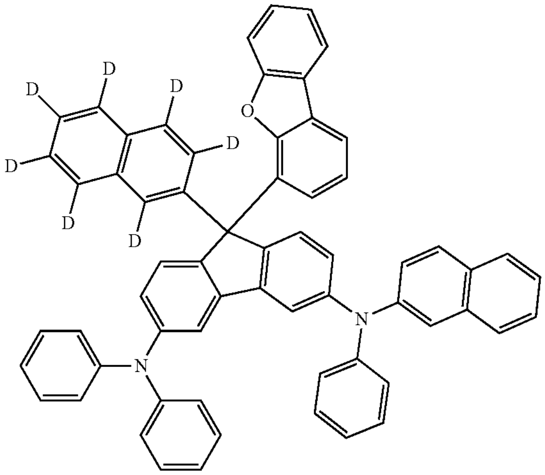
281
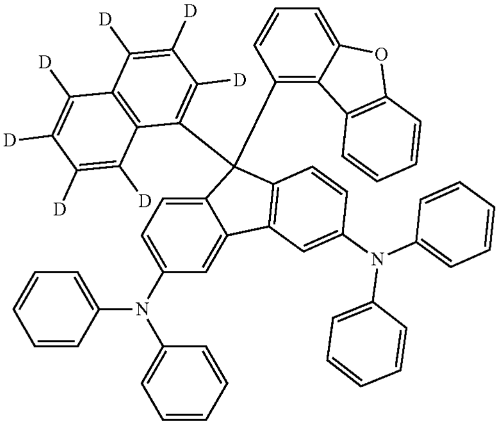

-continued
282
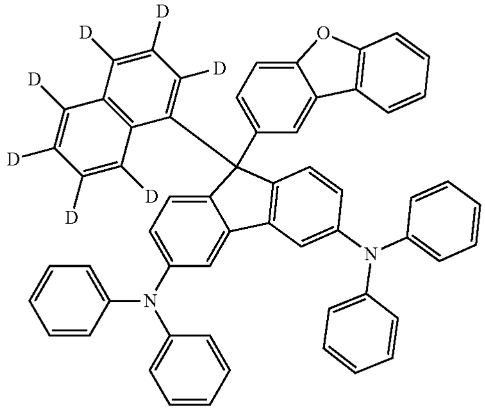
283
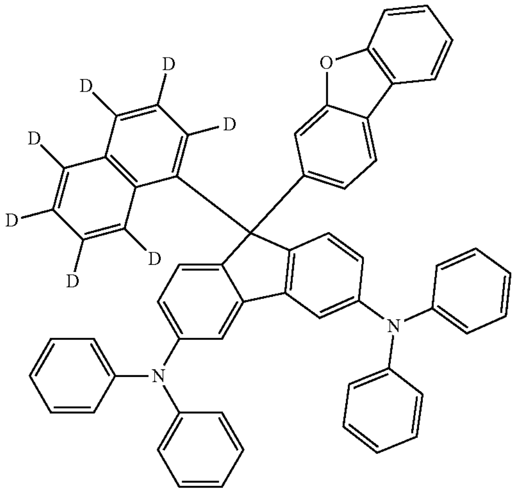
284
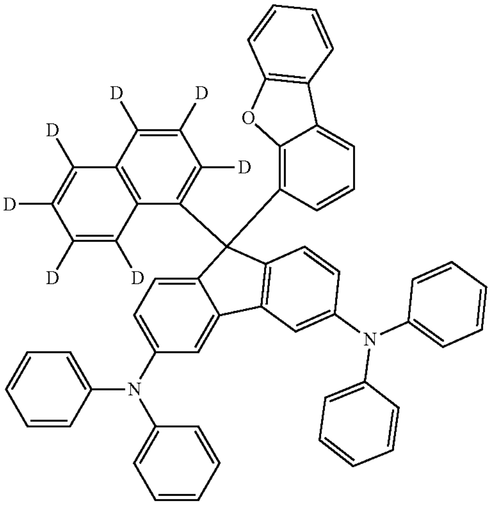
-continued
285
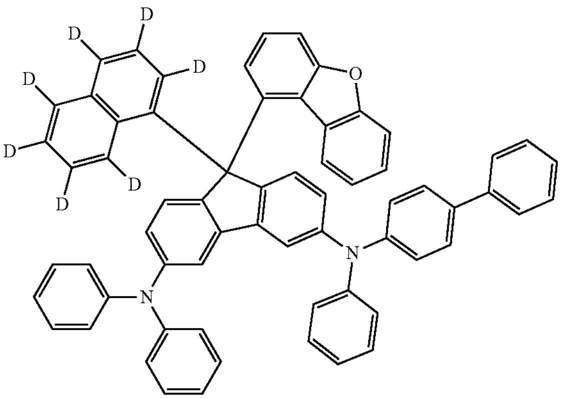
286
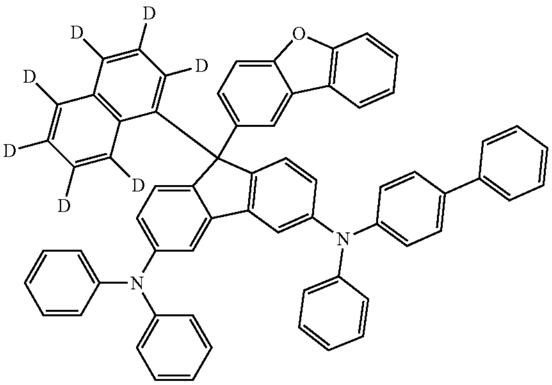
287
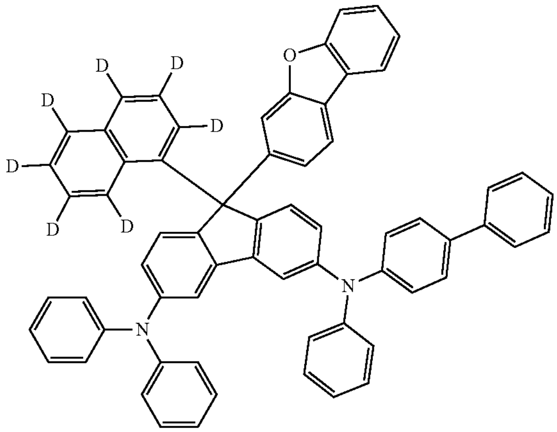

-continued
288
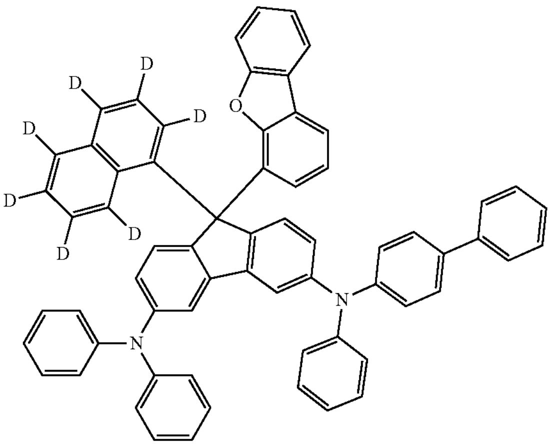
289
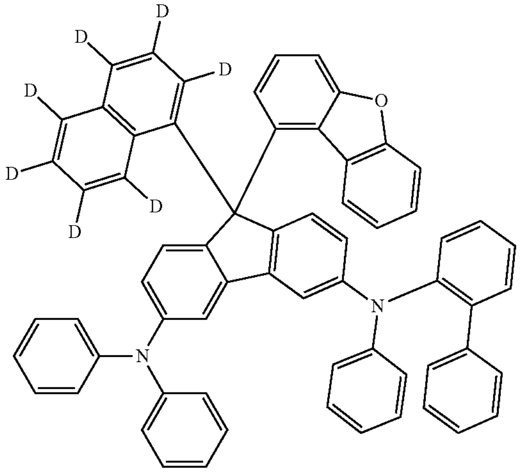
290
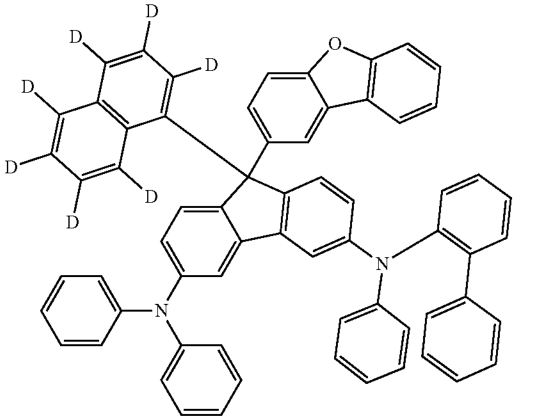
-continued
291
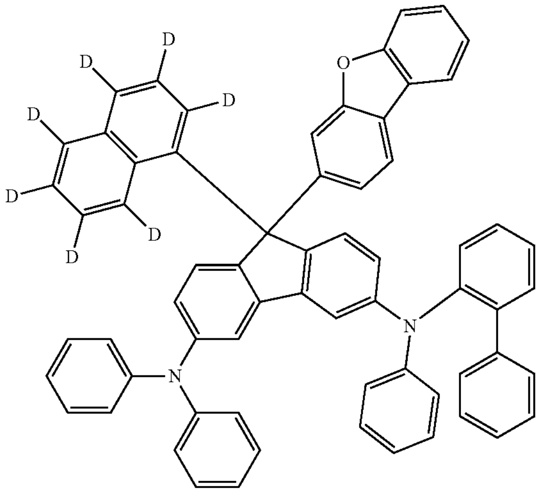
292
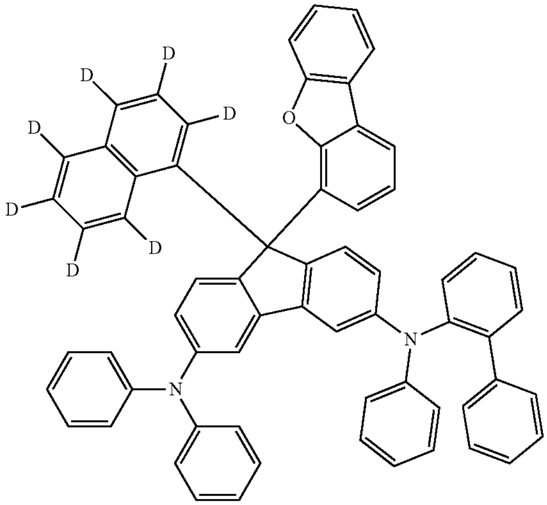
293
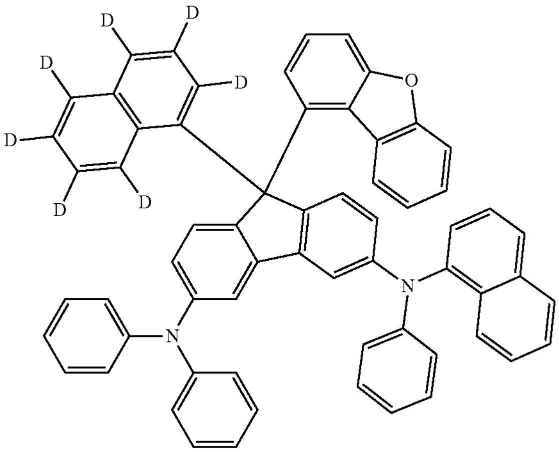

-continued
294
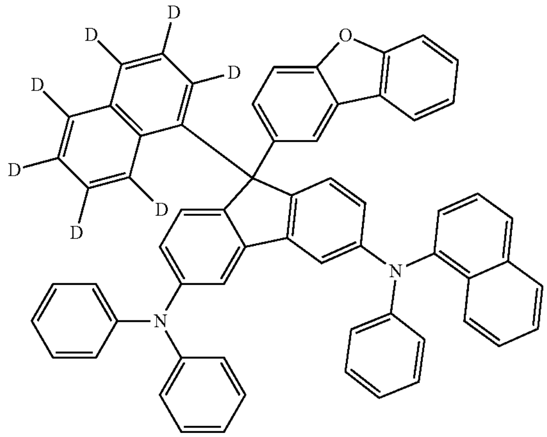
295
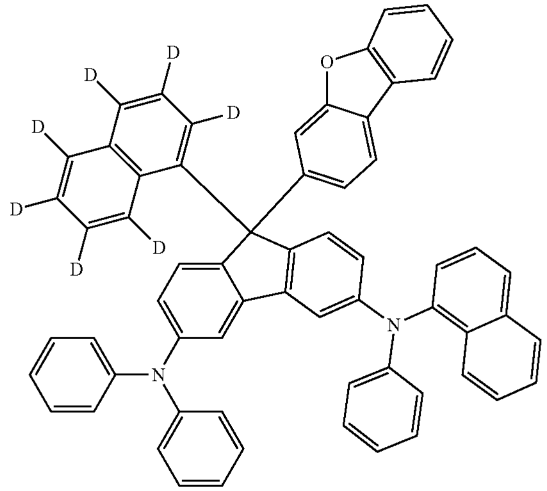
296
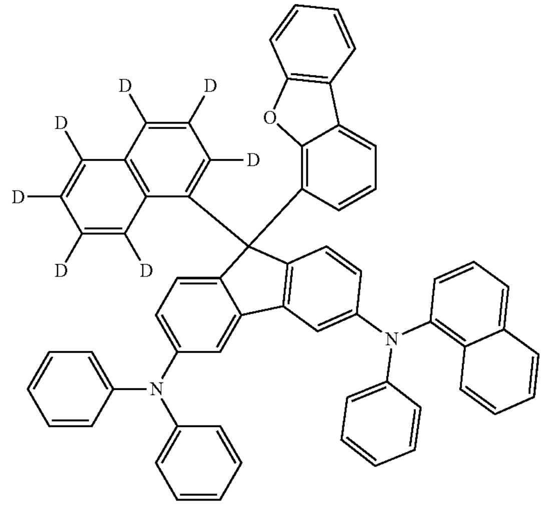
-continued
297
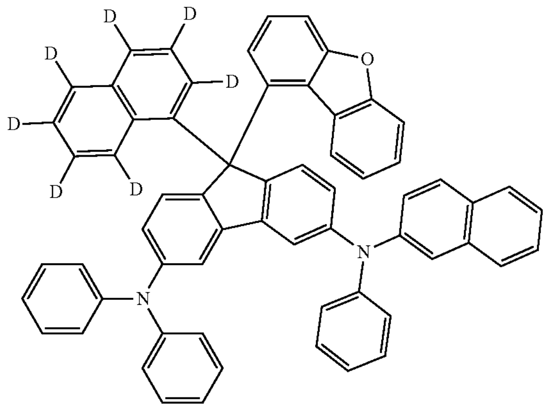
298
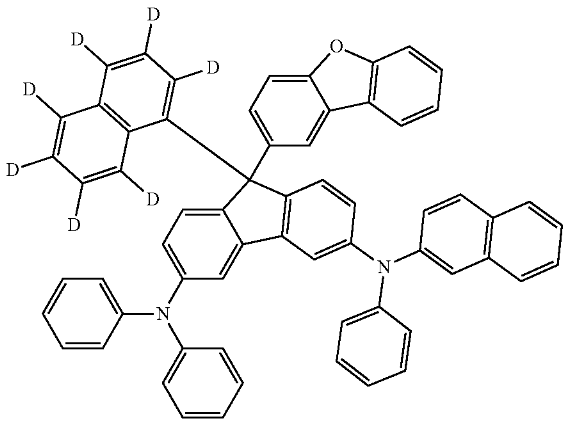
299
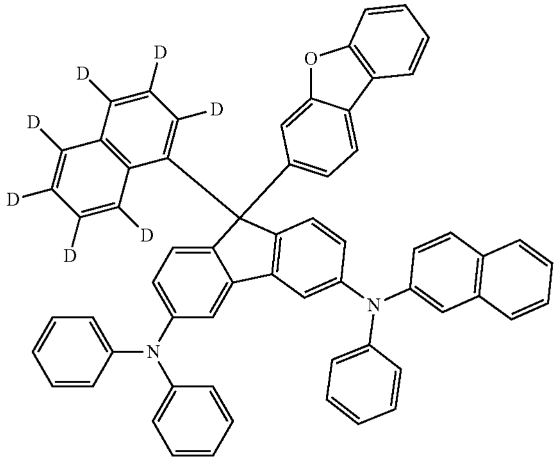

-continued
300
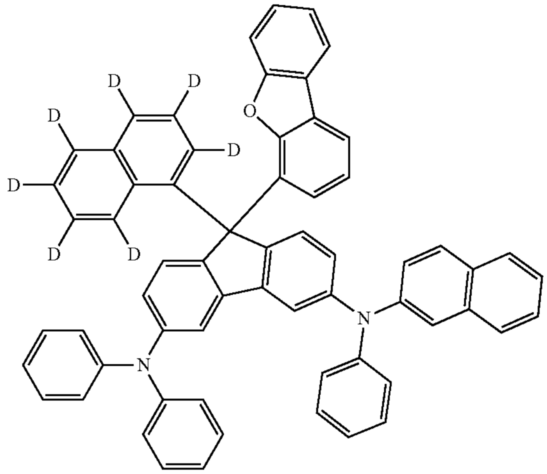
301
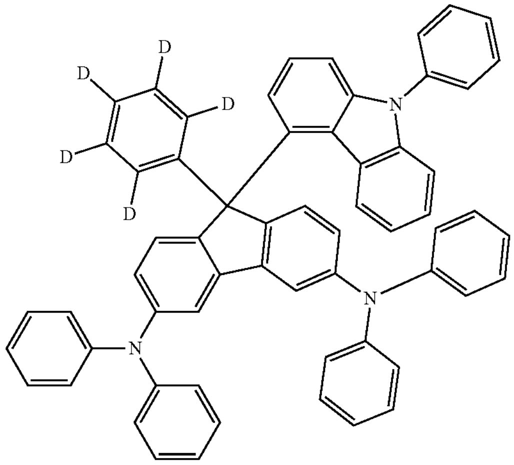
302
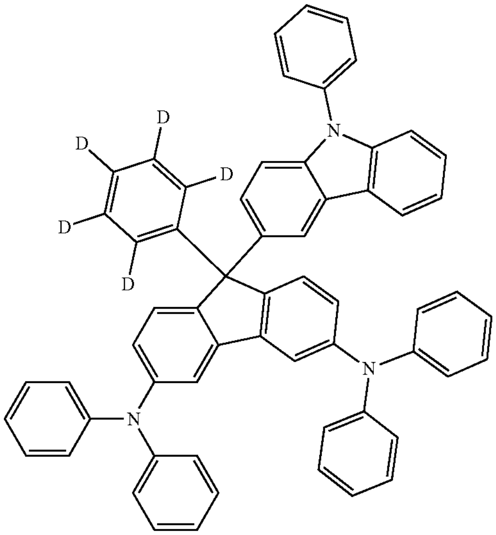
-continued
303
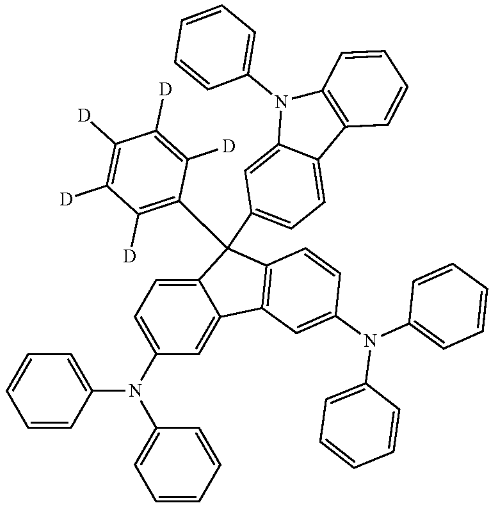
304
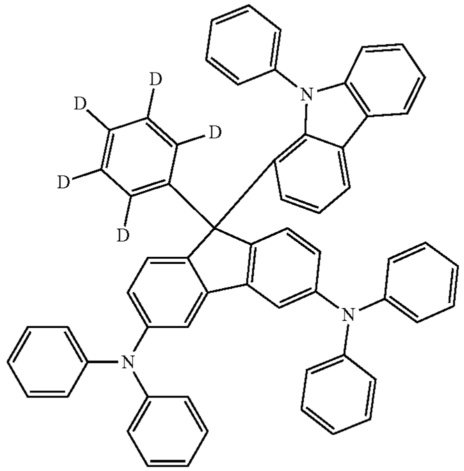
305
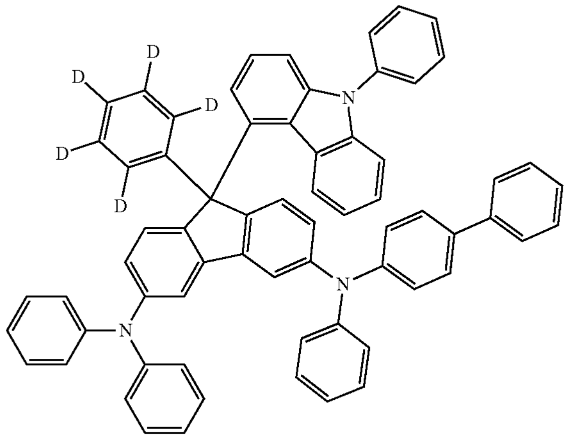

-continued
306
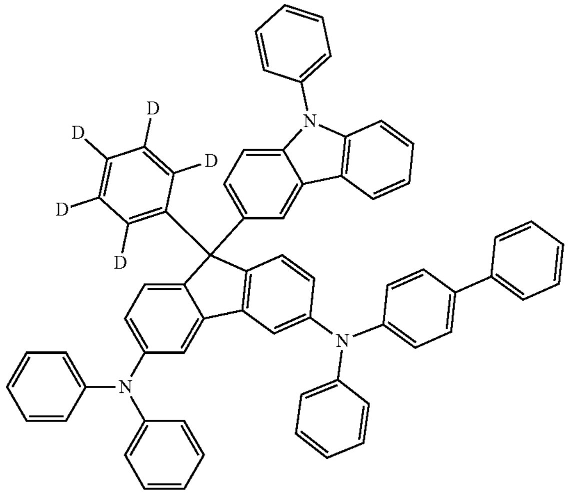
307
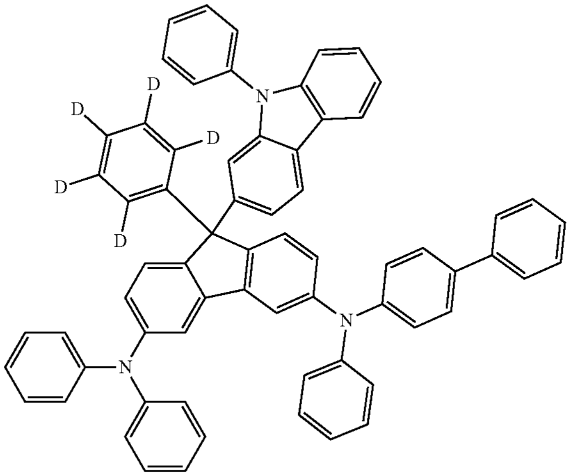
308
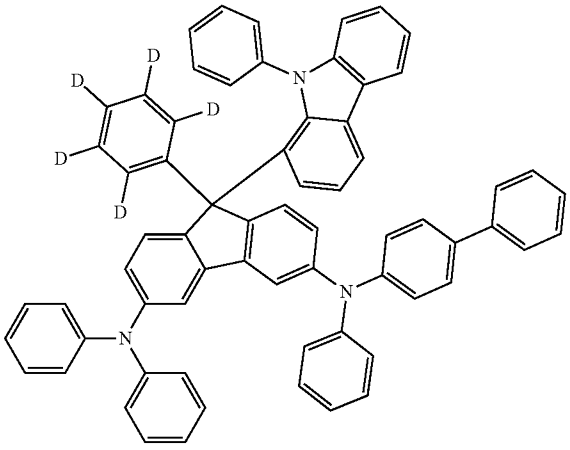
-continued
309
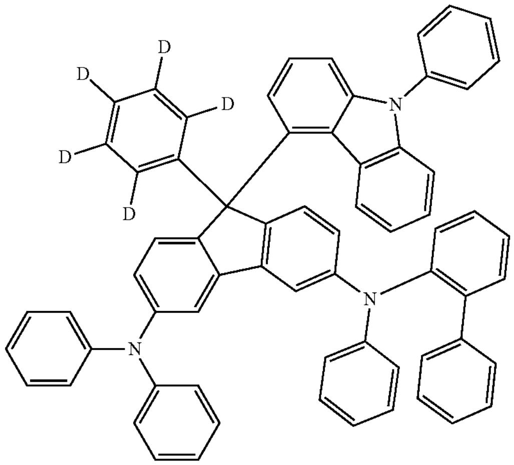
310
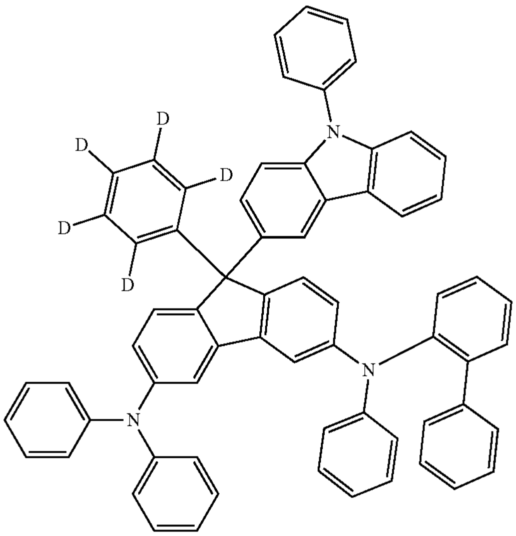
311
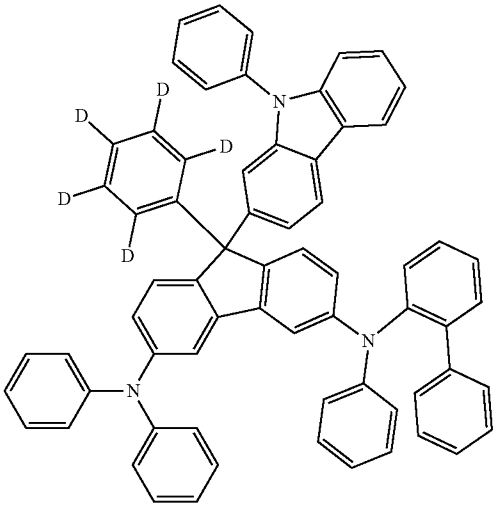

-continued
312
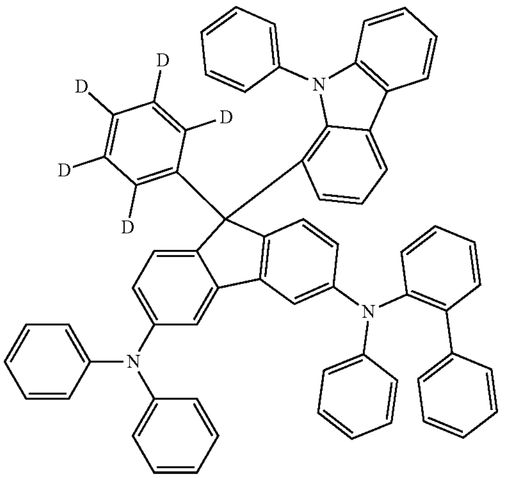
313
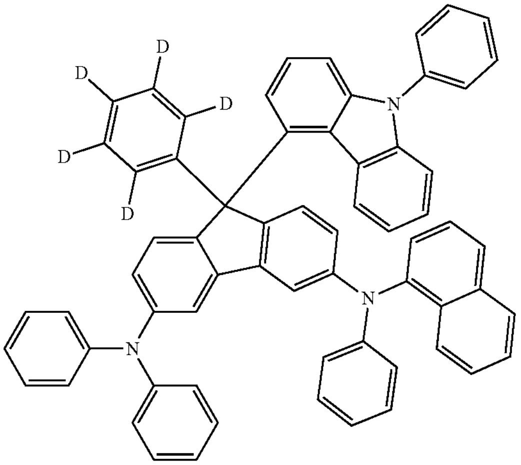
314
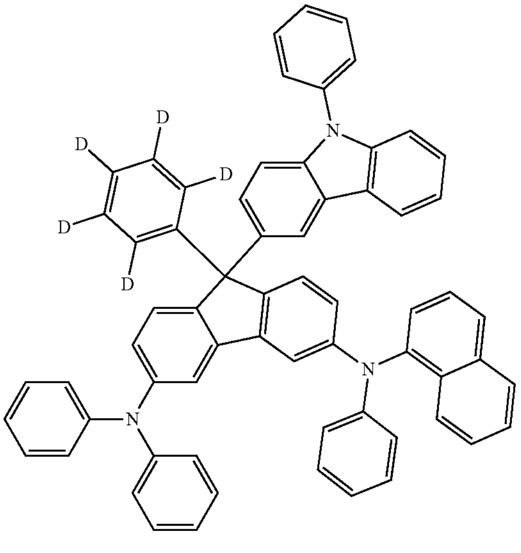
-continued
315
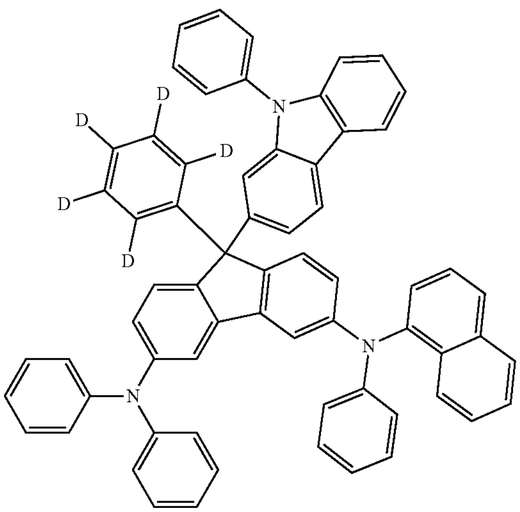
316
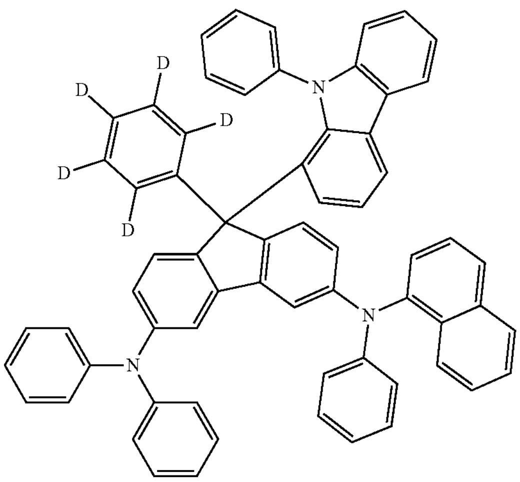
317
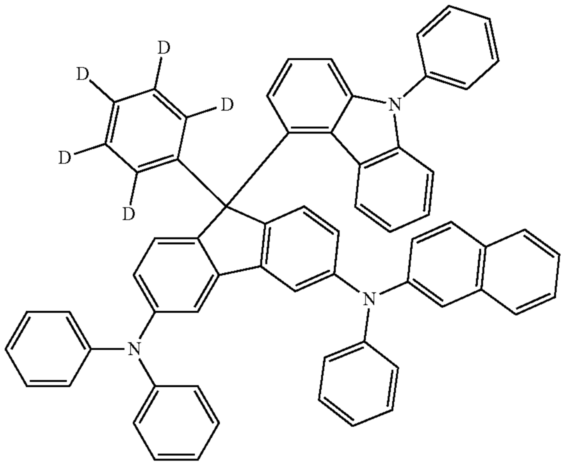

-continued
318
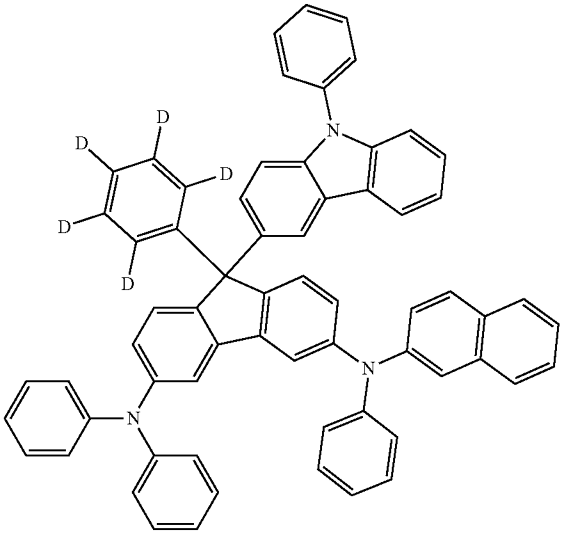
319
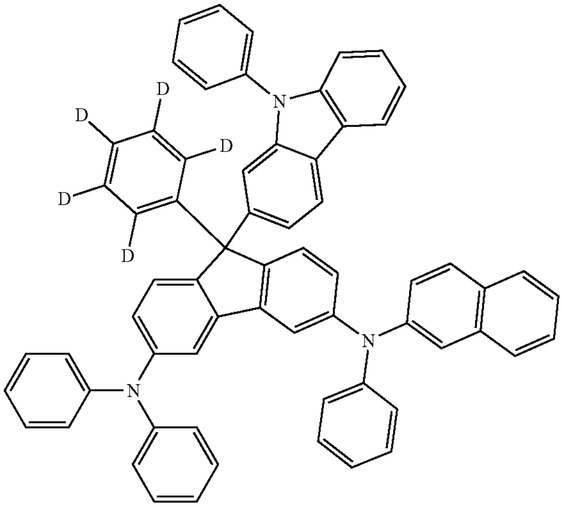
320
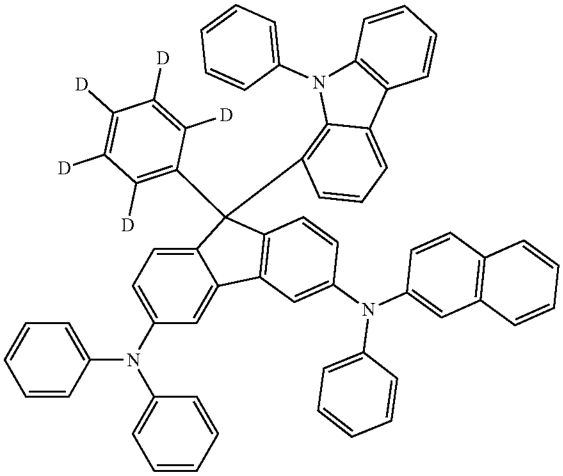
-continued
321
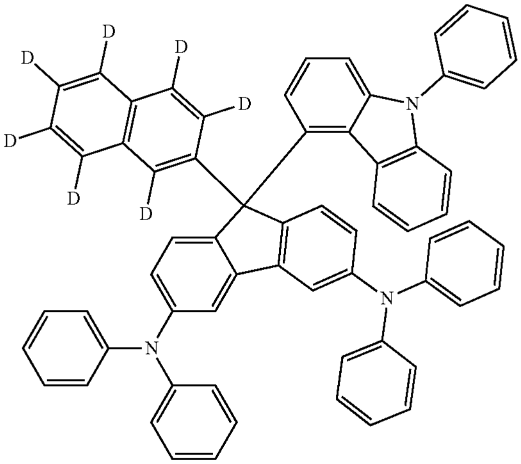
322
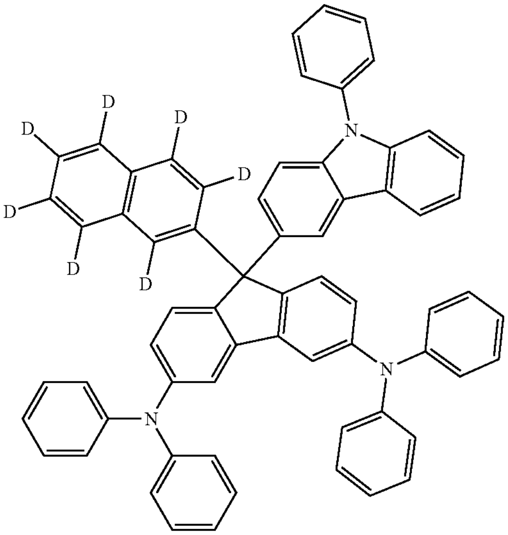
323
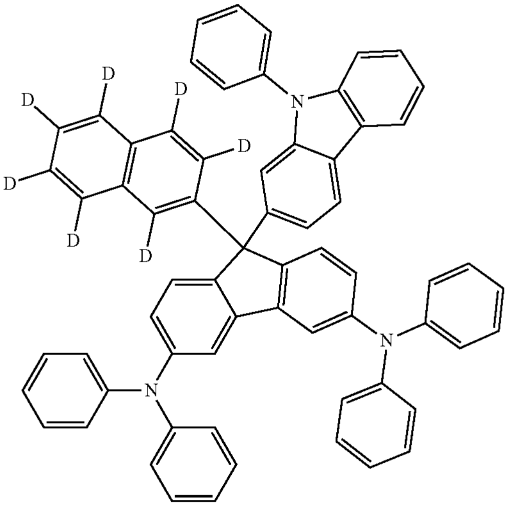

-continued
324
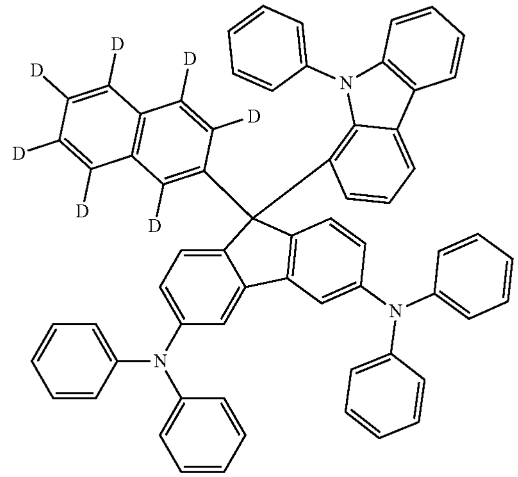
325
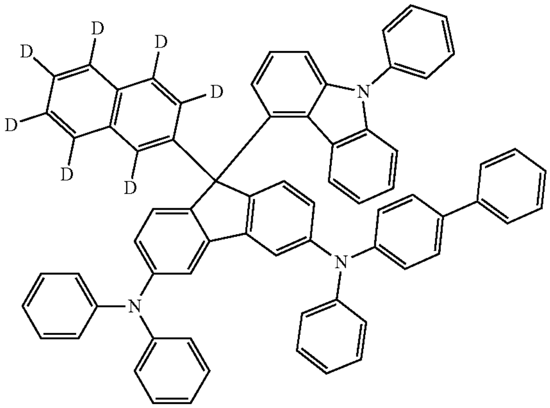
326
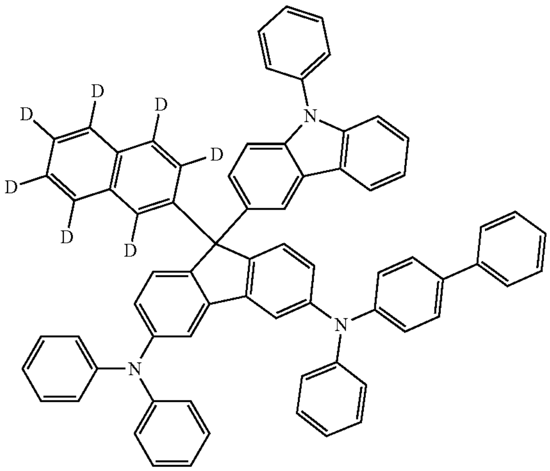
-continued
327
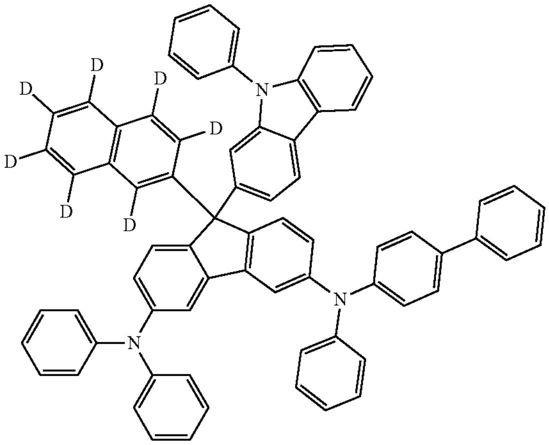
328
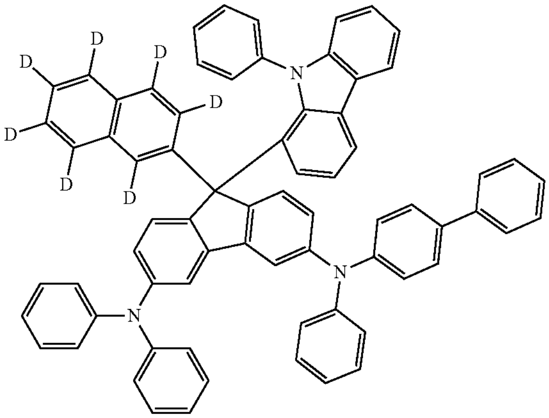
329
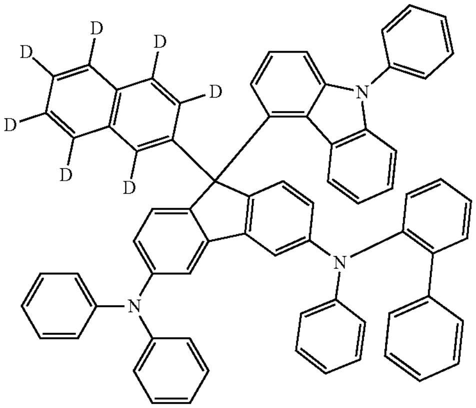

-continued
330
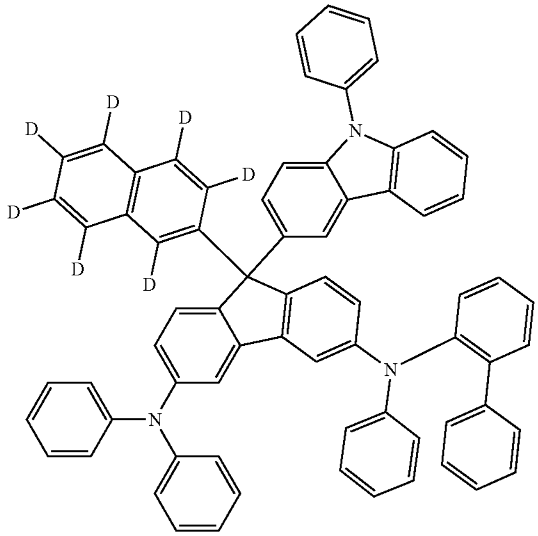
331
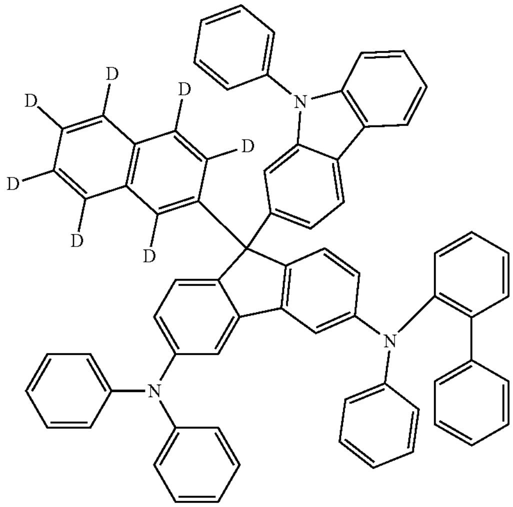
332
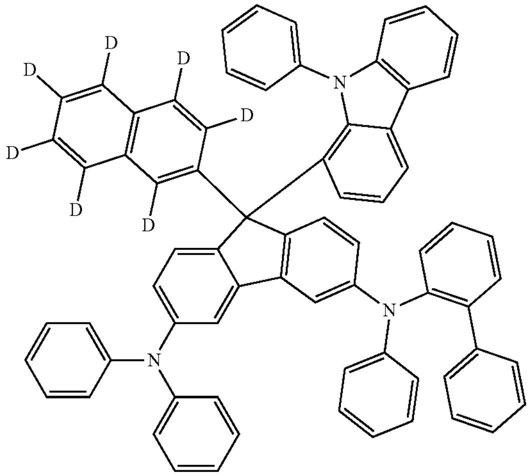
-continued
333
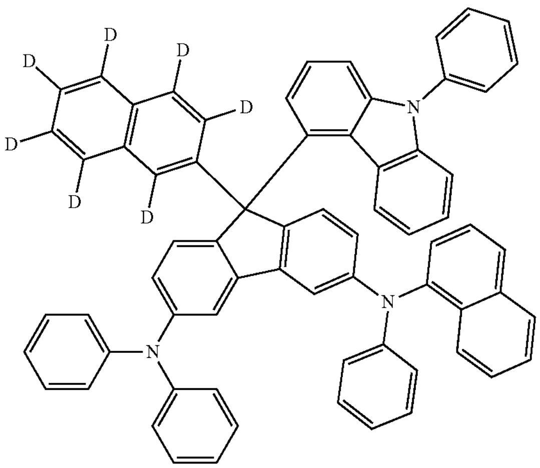
334
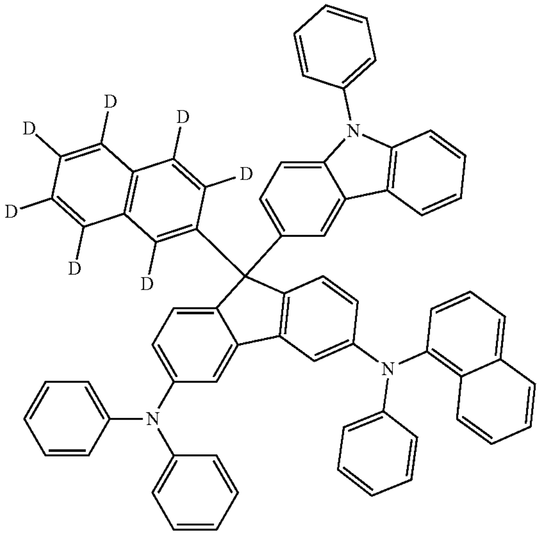
335
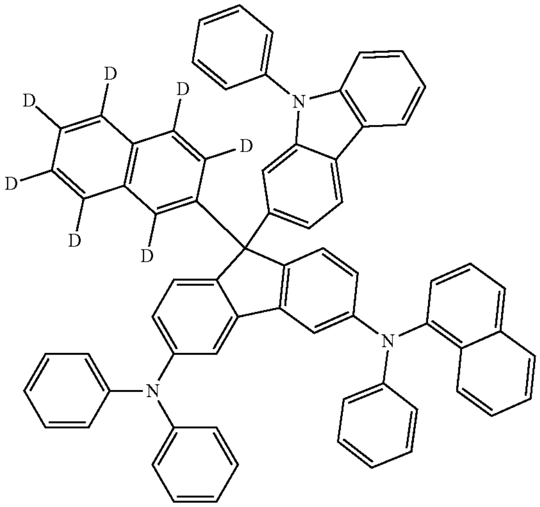

-continued
336
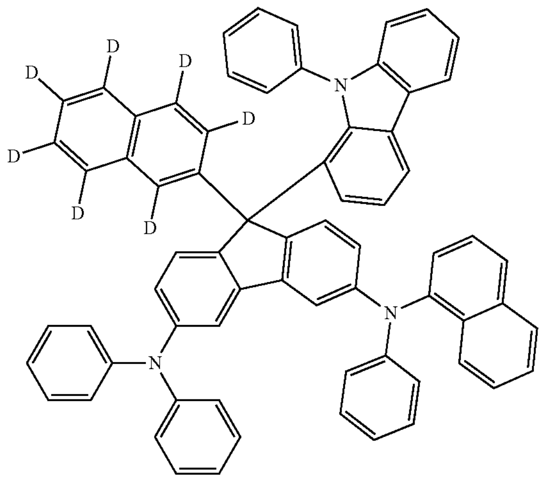
339
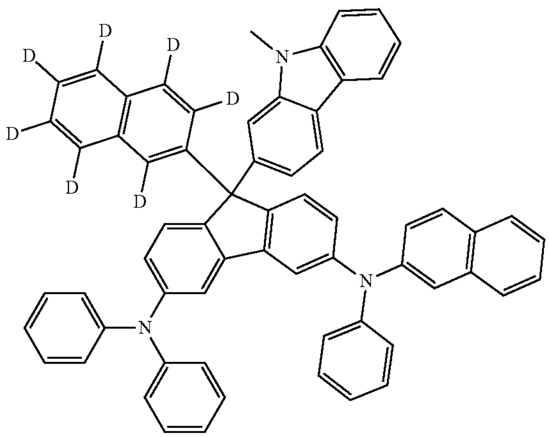
340
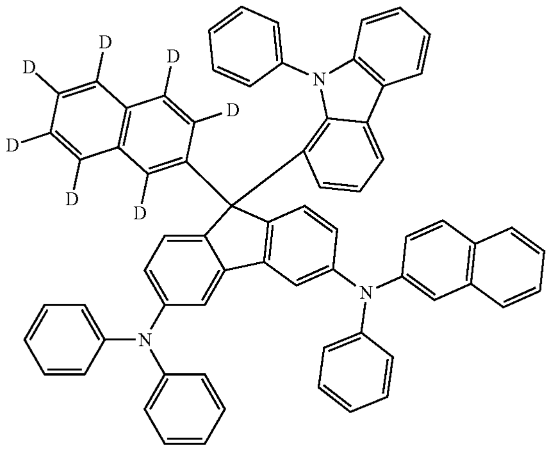
-continued
341
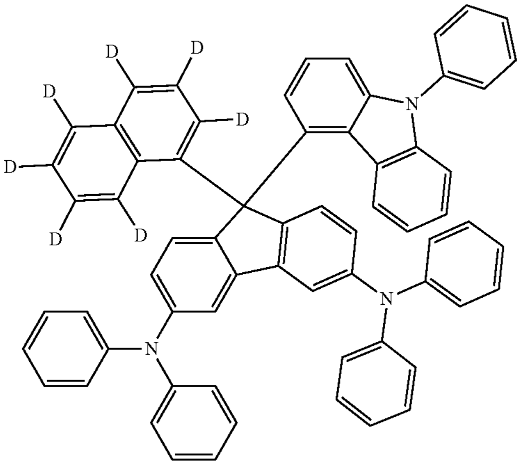
342
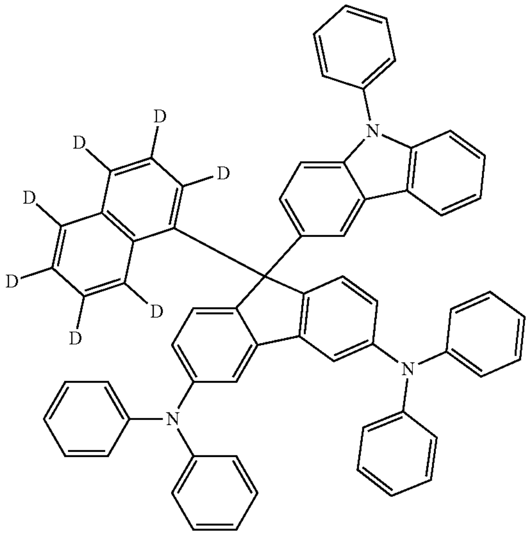
343
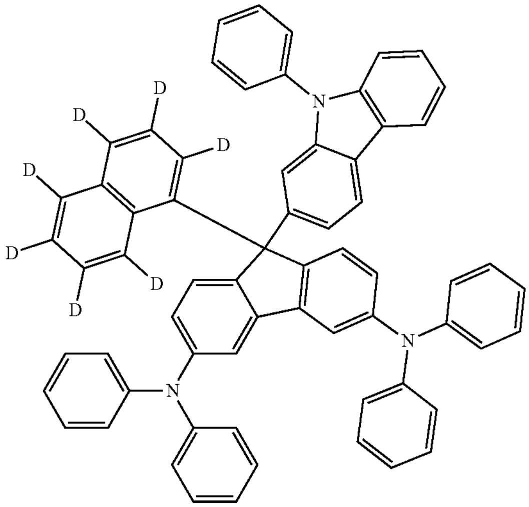

-continued
344
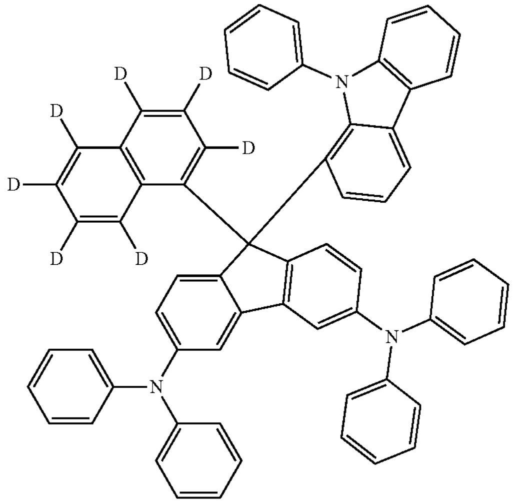
345
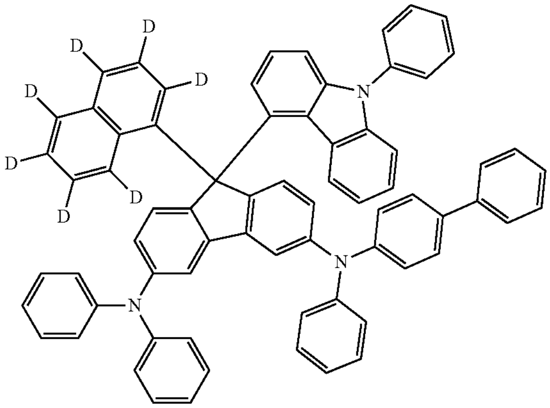
346
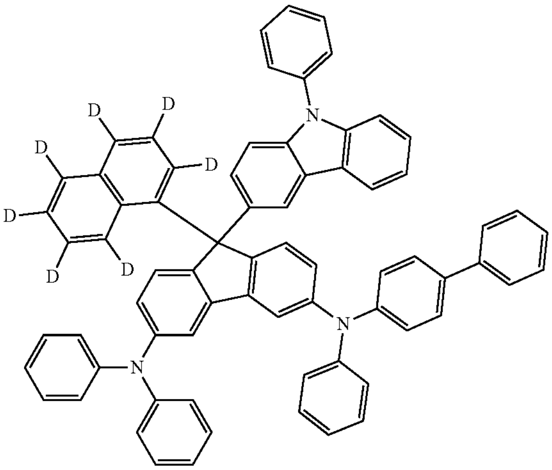
-continued
347
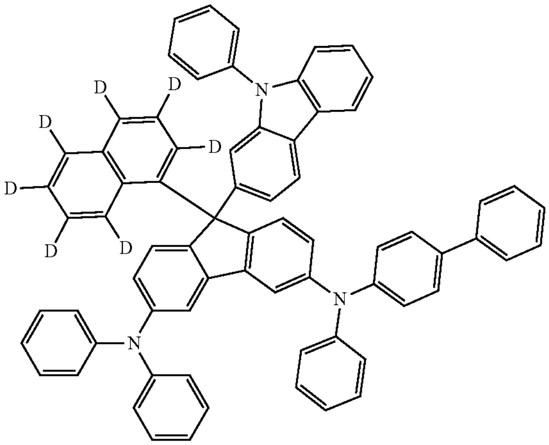
348
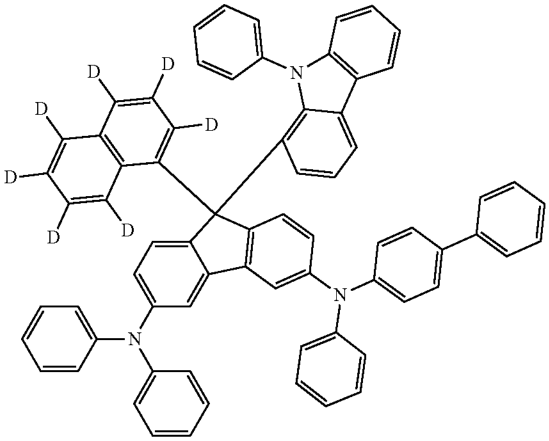
349
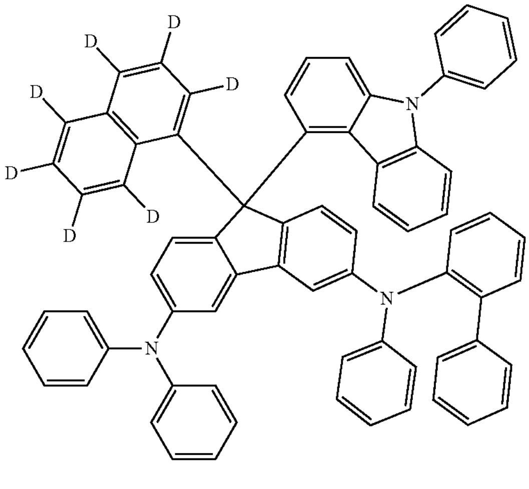

-continued
350
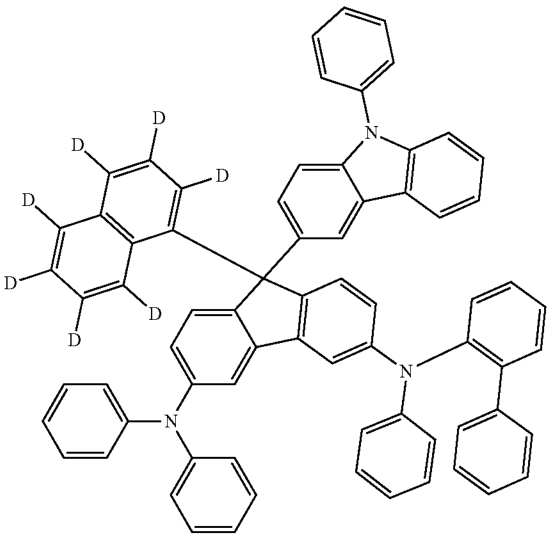
351
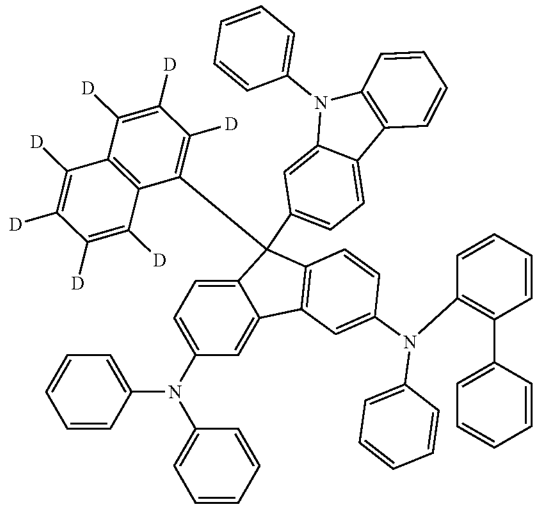
352
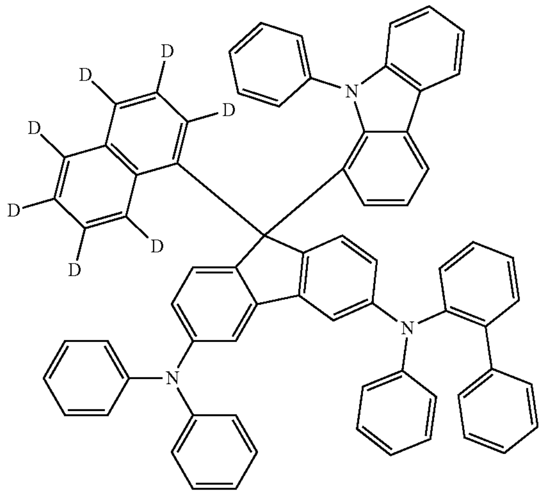
-continued
353
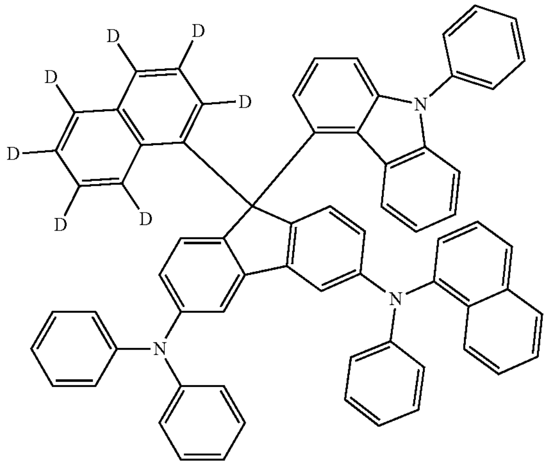
354
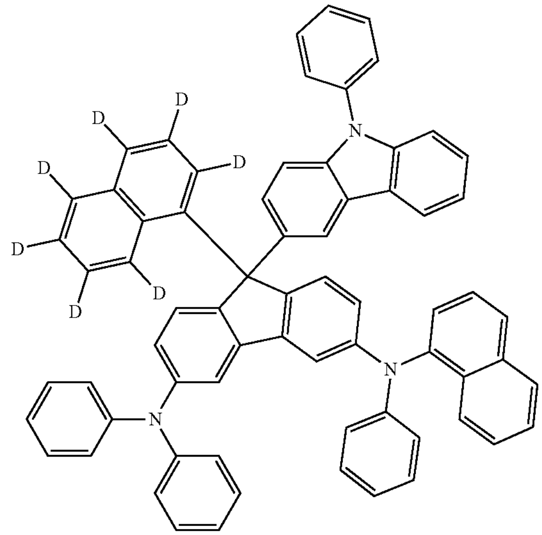
355
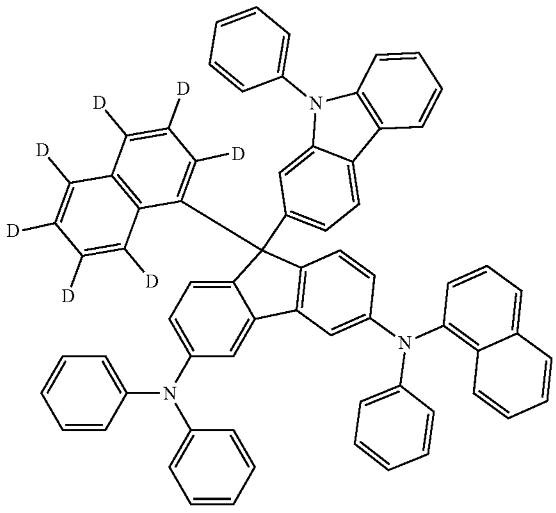

-continued
356
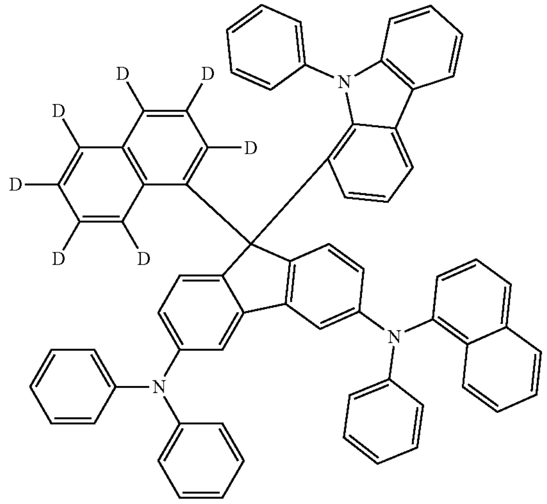
357
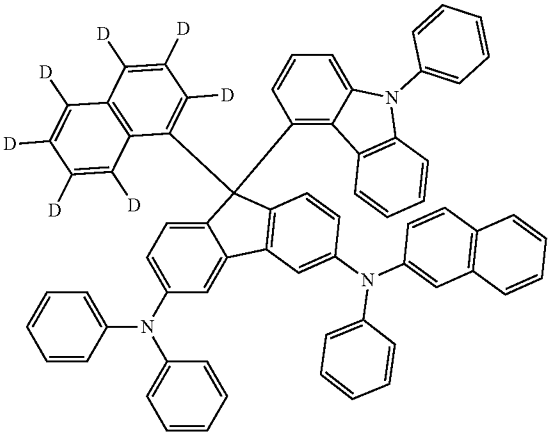
358
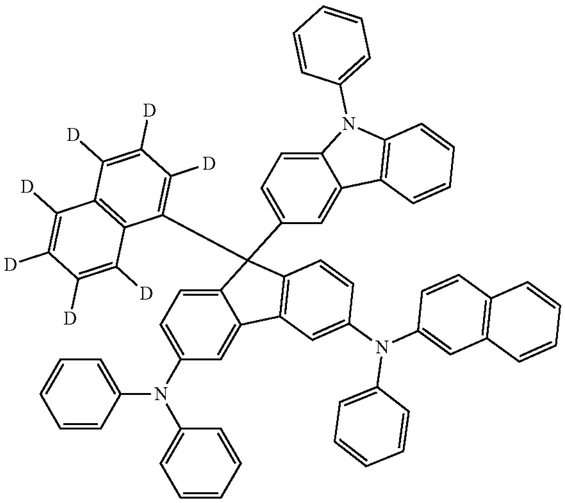
-continued
359
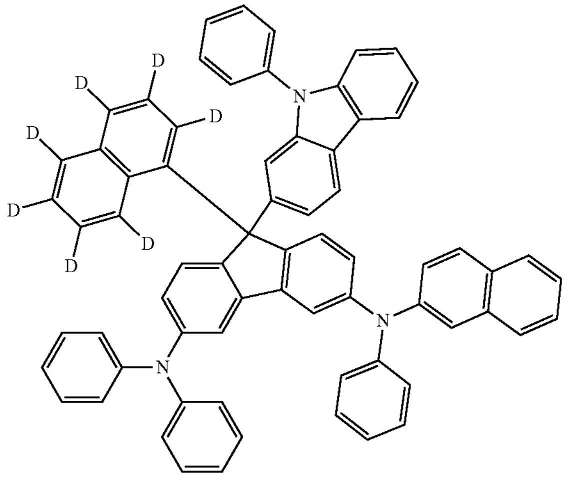
360
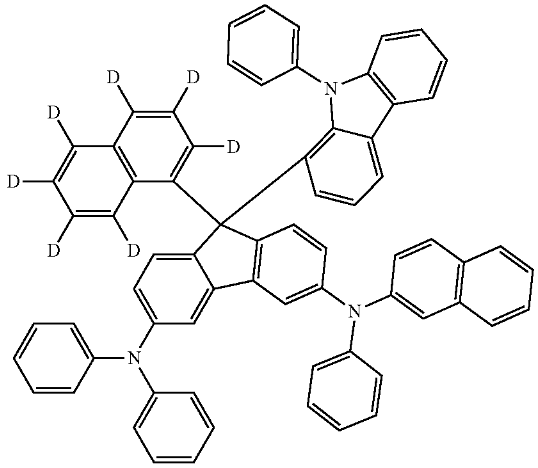
175
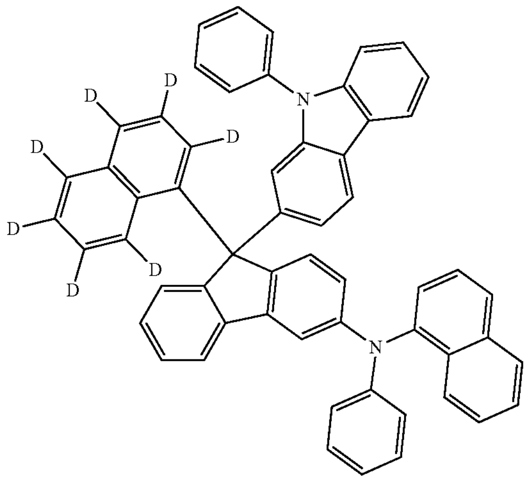

-continued

176

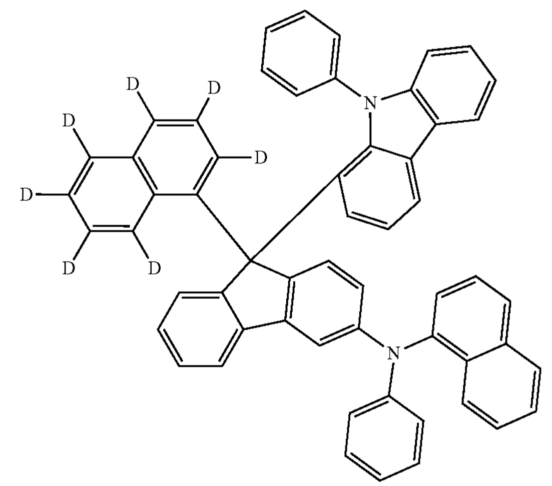

337

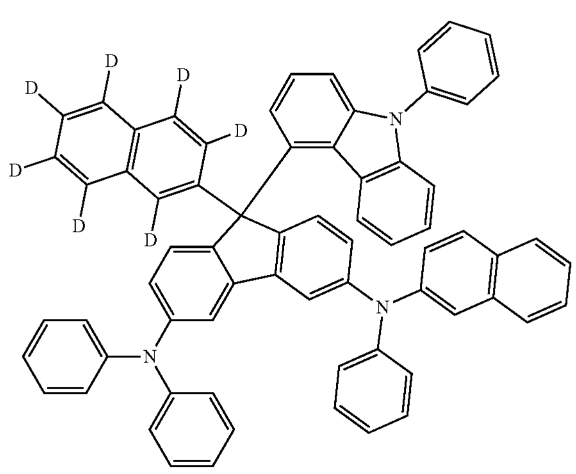

338

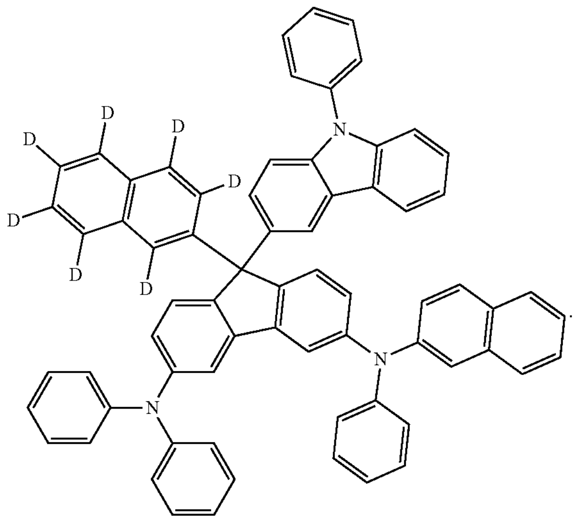

In the organic electroluminescence device 10 of an embodiment illustrated in FIGS. 1 to 4, the hole transport region HTR may include an amine compound represented by Formula 1. For example, the hole transport layer HTL and/or the hole injection layer HIL may include the amine compound represented by Formula 1 as a material. However, embodiments are not limited thereto.

The hole transport region HTR may include one or two or more of the amine compounds represented by Compound Group 1 as described above. The hole transport region HTR may further include any suitable material in the art, in addition to the above-described amine compounds.

The hole injection layer HIL may include, for example, a phthalocyanine compound (such as copper phthalocyanine); N,N'-diphenyl-N,N'-bis-[4-(phenyl-m-tolyl-amino)-phenyl]-biphenyl-4,4'-diamine (DNTPD), 4,4',4"-[tris(3-methylphenyl)phenylamino]triphenylamine] (m-MTDATA), 4,4',4"-tris(N,N-diphenylamino)triphenylamine (TDATA), 4,4',4"-tris{N,-(2-naphthyl)-N-phenylamino)-triphenylamine (2-TNATA), poly(3,4-ethylene dioxythiophene)/poly(4-styrenesulfonate) (PEDOT/PSS), polyaniline/dodecylbenzenesulfonic acid (PANI/DBSA), polyaniline/camphor sulfonic acid (PANI/CSA), polyaniline/poly(4-styrene sulfonate) (PANI/PSS), N,N'-di(naphthalene-1-yl)-N,N'-diphenyl-benzidine (NPB), triphenylamine-containing polyether ketone (TPAPEK), 4-isopropyl-4'-methyldiphenyliodonium tetrakis(pentafluorophenyl)borate, dipyrazino[2,3-f: 2',3'-h]quinoxaline-2,3,6,7,10,11-hexacarbonitrile (HAT-CN), etc.

The hole transport layer HTL may include, for example, carbazole derivatives (such as N-phenyl carbazole and/or polyvinyl carbazole), fluorene derivatives, N,N'-bis(3-methylphenyl)-N,N'-diphenyl-[1,1-biphenyl]-4,4'-diamine (TPD), triphenylamine derivatives (such as 4,4',4"-tris(N-carbazolyl)triphenylamine (TCTA)), N,N'-di(naphthalene-1-yl)-N,N'-diphenyl-benzidine (NPB), 4,4'-cyclohexylidene bis[N,N-bis(4-methylphenyl]benzenamine] (TAPC), 4,4'-bis[N,N'-(3-tolyl)amino]-3,3'-dimethylbiphenyl (HMTPD), 1,3-Bis(N-carbazolyl)benzene (mCP), etc.

The thickness of the hole transport region HTR may be about 100 Å to about 10,000 Å, for example, about 100 Å to about 5,000 Å. The thickness of the hole injection layer HIL may be, for example, about 30 Å to about 1,000 Å, and the thickness of the hole transport layer HTL may be about 30 Å to about 1,000 Å. For example, the thickness of the electron blocking layer EBL may be about 10 Å to about 1,000 Å. When the thicknesses of the hole transport region HTR, the hole injection layer HIL, the hole transport layer HTL, and the electron blocking layer EBL satisfy the above-described ranges, satisfactory hole transport properties may be achieved without a substantial increase in driving voltage.

The hole transport region HTR may further include, in addition to the above-described materials, a charge generating material to increase conductivity. The charge generating material may be dispersed substantially uniformly or non-uniformly in the hole transport region HTR. The charge generating material may be, for example, a p-dopant. The p-dopant may be a quinone derivative, metal oxide, and/or cyano group-containing compound, but is not limited thereto. Non-limiting examples of the p-dopant include, but are not limited to, quinone derivatives (such as tetracyanoquinodimethane (TCNQ) and/or 2,3,5,6-tetrafluoro-tetracyanoquinodimethane (F4-TCNQ)), and metal oxides (such as tungsten oxides and/or molybdenum oxides).

The hole transport region HTR may further include at least one of a hole buffer layer or an electron blocking layer EBL, in addition to the hole injection layer HIL and the hole transport layer HTL. The hole buffer layer may compensate for a resonance distance of the wavelength of light emitted from an emission layer EML to increase light emission efficiency. Materials included in the hole transport region HTR may also be included in the hole buffer layer. The electron blocking layer EBL may prevent or reduce electrons from being injected from the electron transport region ETR to the hole transport region HTR.

The emission layer EML is provided on the hole transport region HTR. The thickness of the emission layer EML may be, for example, about 100 Å to about 1000 Å, or about 100 Å to about 300 Å. The emission layer EML may have a single layer formed of a single material, a single layer formed of a plurality of different materials, or a multilayer structure having a plurality of layers formed of a plurality of different materials.

In the organic electroluminescence device 10 of an embodiment, the emission layer EML may include anthracene derivatives, pyrene derivatives, fluoranthene derivatives, chrysene derivatives, dihydrobenzanthracene derivatives, and/or triphenylene derivatives. For example, the emission layer EML may include anthracene derivatives and/or pyrene derivatives.

The emission layer EML may include anthracene derivatives represented by Formula A:

Formula A

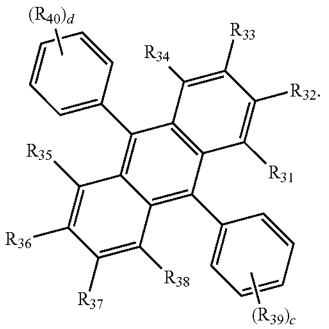

In Formula A, $R_{31}$ to $R_{40}$ may each independently be a hydrogen atom, a deuterium atom, a halogen atom, a substituted or unsubstituted silyl group, a substituted or unsubstituted alkyl group having 1 to 10 carbon atoms, a substituted or unsubstituted aryl group having 6 to 30 ring-forming carbon atoms, or a substituted or unsubstituted heteroaryl group having 2 to 30 ring-forming carbon atoms, or may be bonded to an adjacent group to form a ring. In some embodiments, $R_{31}$ to $R_{40}$ may be bonded to an adjacent group to form a saturated hydrocarbon ring or an unsaturated hydrocarbon ring.

In Formula A, c and d may each independently be an integer of 0 to 5.

Formula A may be represented by at least one of Compound 4-1 to Compound 4-6:

4-1

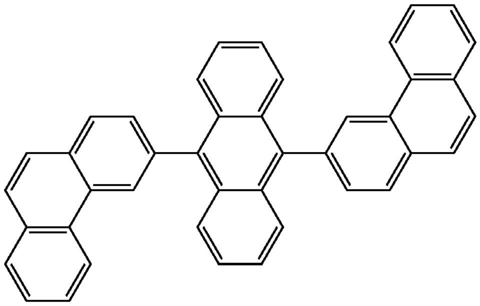

-continued 4-2

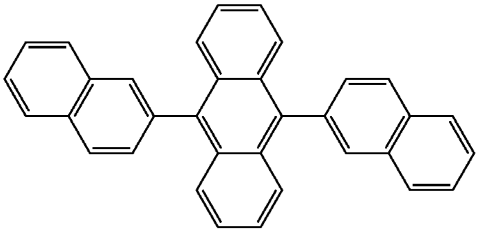

4-3

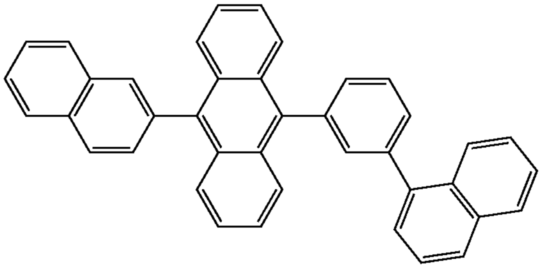

4-4

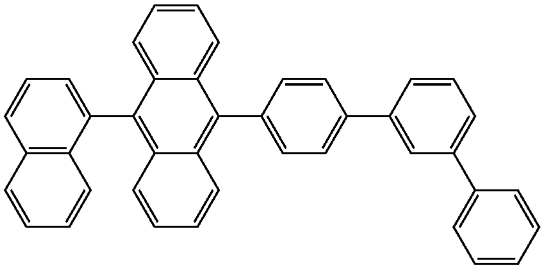

4-5

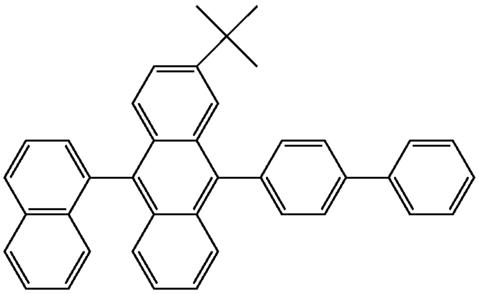

4-6

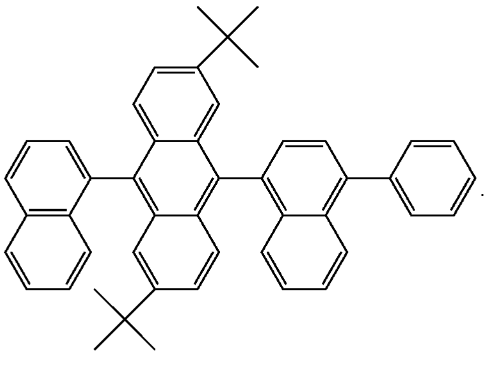

The emission layer EML may further include any suitable material in the art as a host material. For example, the emission layer EML may include, as a host material, at least one of bis[2-(diphenylphosphino)phenyl] ether oxide (DPEPO), 4,4'-bis(carbazol-9-yl)biphenyl (CBP), 1,3-bis (carbazol-9-yl)benzene (mCP), 2,8-Bis(diphenylphosphoryl)dibenzo[b,d]furan (PPF), 4,4',4"-tris(carbazol-9-yl)-triphenylamine (TcTa), or 1,3,5-tris(1-phenyl-1H-benzo[d] imidazole-2-yl)benzene (TPBi). However, embodiments are not limited thereto, and for example, tris(8-hydroxyquinolino)aluminum ($Alq_3$), 4,4'-bis(N-carbazolyl)-1,1'-biphenyl (CBP), poly(n-vinylcarbazole (PVK), 9,10-di(naphthalene-2-yl)anthracene (ADN), 4,4',4"-tris(carbazol-9-yl)-triphenylamine (TcTa), 1,3,5-tris(N-phenylbenzimidazol-2-Abenzene (TPBi), 3-tert-butyl-9,10-di(naphth-2-yl) anthracene (TBADN), distyrylarylene (DSA), 4,4'-bis(9-carbazolyl)-2,2'-dimethyl-biphenyl (CDBP), 2-methyl-9,10-bis(naphthalen-2-yl)anthracene (MADN), hexaphenylcyclotriphosphazene (CP1), 1,4-bis(triphenylsilyl)benzene (UGH2), hexaphenylcyclotrisiloxane ($DPSiO_3$), octaphenylcyclotetra siloxane ($DPSiO_4$), 2,8-bis(diphenylphosphoryl)dibenzofuran (PPF), etc. may be used as a host material.

In an embodiment, the emission layer EML may include, as a dopant material, styryl derivatives (e.g., 1,4-bis[2-(3-N-ethylcarbazolyl)vinyl]benzene (BCzVB), 4-(di-p-tolylamino)-4'-[(di-p-tolylamino)styryl]stilbene (DPAVB), and N-(4-((E)-2-(6-((E)-4-(diphenylamino)styryl)naphthalen-2-yl)vinyl)phenyl)-N-phenylbenzenamine (N-BDAVBi), perylene and the derivatives thereof (e.g., 2,5,8,11-tetra-t-butylperylene (TBP)), pyrene and the derivatives thereof (e.g., 1-dipyrene, 1,4-dipyrenylbenzene, 1,4-bis(N,N-diphenylamino)pyrene), 4,4'-bis[2-(4-(N,N-diphenylamino)phenyl)vinyl]piphenyl (DPAVBi) etc.

The emission layer EML may include any suitable phosphorescence dopant material. For example, a metal complex including iridium (Ir), platinum (Pt), osmium (Os), aurum (Au), titanium (Ti), zirconium (Zr), hafnium (Hf), europium (Eu), terbium (Tb), and/or thulium (Tm) may be used as a phosphorescence dopant. For example, iridium(III) bis(4,6-difluorophenylpyridinato-N,C2') (Flrpic), bis(2,4-difluorophenylpyridinato) (Fir6), and/or platinum octaethyl porphyrin (PtOEP) may be used as a phosphorescence dopant. However, embodiments are not limited thereto.

The emission layer EML may further include any suitable phosphorescence host material, for example, bis(4-(9H-carbazol-9-yl)phenyl)diphenylsilane (BCPDS).

When the emission layer EML is to emit red light, the emission layer EML may further include, for example, a fluorescent material (such as tris(dibenzoylmethanato) phenanthroline europium (PBD: $Eu(DBM)_3(Phen)$) and/or perylene). When the emission layer EML is to emit red light, a dopant included in the emission layer EML may be, for example, a metal complex or organometallic compound (such as bis(1-phenylisoquinoline) acetylacetonate iridium (PIQIr(acac)), bis(1-phenylquinoline) acetylacetonate iridium (PQIr(acac)), tris(1-phenylquinoline) iridium (PQIr), and/or octaethylporphyrin platinum (PtOEP)), rubrene and derivatives thereof, and/or 4-dicyanomethylene-2-(p-dimethylaminostyryl)-6-methyl-4H-pyran (DCM) and derivatives thereof.

When the emission layer EML is to emit green light, the emission layer EML may further include, for example, a fluorescent material (such as tris(8-hydroxyquinolino) aluminum ($Alq_3$)). When the emission layer EML is to emit green light, a dopant included in the emission layer EML may be, for example, a metal complex or organometallic compound (such as fac-tris(2-phenylpyridine) iridium ($Ir(ppy)_3$)), and/or coumarins and derivatives thereof.

When the emission layer EML is to emit blue light, the emission layer EML may further include, for example, a fluorescent material including any one selected from the group consisting of spiro-DPVBi, spiro-6P, distyryl-benzene (DSB), distyryl-arylene (DSA), polyfluorene (PFO)-based polymer, and poly(p-phenylene vinylene) (PPV)-based polymer. When the light emitting layer EML is to emit blue light, a dopant included in the emission layer EML may be selected from a metal complex or organometallic compound (such as $(4,6\text{-F2ppy})_2Irpic$), perylene and derivatives thereof, etc.

In the organic electroluminescence device 10 of an embodiment illustrated in FIGS. 1 to 4, the electron transport region ETR is provided on the emission layer EML. The electron transport region ETR may include at least one of a hole blocking layer HBL, an electron transport layer ETL, or an electron injection layer EIL, but embodiments are not limited thereto.

The electron transport region ETR may have a single layer formed of a single material, a single layer formed of a plurality of different materials, or a multilayer structure including a plurality of layers formed of a plurality of different materials.

For example, the electron transport region ETR may have a single layer structure of an electron injection layer EIL or an electron transport layer ETL, or may have a single layer structure formed of an electron injection material and an electron transport material. In some embodiments, the electron transport region ETR may have a single layer structure formed of a plurality of different materials, or may have a structure in which an electron transport layer ETL/electron injection layer EIL and a hole blocking layer HBL/electron transport layer ETL/electron injection layer EIL are stacked in order from the emission layer EML, but is not limited thereto. The thickness of the electron transport region ETR may be, for example, about 1000 Å to about 1,500 Å.

The electron transport region ETR may be formed using any suitable method (such as a vacuum deposition method, a spin coating method, a cast method, a Langmuir-Blodgett (LB) method, an inkjet printing method, a laser printing method, a laser induced thermal imaging (LITI) method, etc.)

When the electron transport region ETR includes an electron transport layer ETL, the electron transport region ETR may include an anthracene-based compound. However, embodiments are not limited thereto, and the electron transport region may include, for example, tris(8-hydroxyquinolinato)aluminum ($Alq_3$), 1,3,5-tri[(3-pyridyl)-phen-3-yl] benzene, 2,4,6-tris(3-(pyridin-3-yl)biphenyl-3-yl)-1,3,5-triazine,2-(4-(N-phenylbenzimidazolyl-1-yl phenyl)-9,10-dinaphthylanthracene, 1,3,5-tri(1-phenyl-1H-benzo[d] imidazol-2-yl)phenyl (TPBi), 2,9-dimethyl-4,7-diphenyl-1,10-phenanthroline (BCP), 4,7-diphenyl-1,10-phenanthroline (Bphen), 3-(4-biphenylyl)-4-phenyl-5-tert-butylphenyl-1,2,4-triazole (TAZ), 4-(naphthalen-1-yl)-3,5-diphenyl-4H-1,2,4-triazole (NTAZ), 2-(4-biphenylyl)-5-(4-tert-butylphenyl)-1,3,4-oxadiazole (tBu-PBD), bis(2-methyl-8-quinolinolato-N1,O8)-(1,1-biphenyl-4-olato) aluminum (BAlq), beryllium bis(benzoquinolin-10-olate) (Bebq2), 9,10-di(naphthalene-2-yl)anthracene (ADN), 1,3-Bis[3,5-di(pyridin-3-yl)phenyl]benzene (BmPyPhB), or a mixture thereof. The thickness of the electron transport layers ETL may be about 100 Å to about 1,000 Å, for example, about 150 Å to about 500 Å. When the thickness of the electron transport layers ETL satisfies the above-described range, satisfactory electron transport characteristics may be obtained without a substantial increase in driving voltage.

When the electron transport region ETR includes the electron injection layer EIL, the electron transport region ETR may be formed using a metal halide (such as LiF, NaCl, CsF, RbCl, RbI, and/or CuI), a lanthanide metal (such as Yb), a metal oxide (such as $Li_2O$ and/or BaO), or lithium quinolate (Liq), etc., but embodiments of the present disclosure are not limited thereto. The electron injection layer EIL may also be formed of a mixture of an electron transport material and an insulating organo-metal salt. The organo-metal salt may be a material having an energy band gap of about 4 eV or more. In some embodiments, the organo-metal salt may include, for example, metal acetates, metal benzoates, metal acetoacetates, metal acetylacetonates and/or metal stearates. The thickness of the electron injection layers EIL may be about 1 Å to about 100 Å, and about 3 Å to about 90 Å. When the thickness of the electron injection layers EIL satisfies the above-described range, satisfactory electron injection properties may be obtained without a substantial increase in driving voltage.

The electron transport region ETR may include a hole blocking layer HBL as described above. The hole blocking layer HBL may include, for example, at least one of 2,9-dimethyl-4,7-diphenyl-1,10-phenanthroline (BCP) or 4,7-diphenyl-1,10-phenanthroline (Bphen), but is not limited thereto.

The second electrode EL2 is provided on the electron transport region ETR. The second electrode EL2 may be a common electrode and/or a negative electrode. The second electrode EL2 may be a transmissive electrode, a transflective electrode, or a reflective electrode. When the second electrode EL2 is a transmissive electrode, the second electrode EL2 may include a transparent metal oxide, for example, ITO, IZO, ZnO, ITZO, etc.

When the second electrode EL2 is a transflective electrode or a reflective electrode, the second electrode EL2 may include Ag, Mg, Cu, Al, Pt, Pd, Au, Ni, Nd, Ir, Cr, Li, Ca, LiF/Ca, LiF/Al, Mo, Ti, a compound thereof, or a mixture thereof (for example, a mixture of Ag and Mg). In some embodiments, the first electrode EL1 may have a multilayer structure including a reflective layer or a transflective layer formed of the above-described materials, and a transparent conductive layer formed of ITO, IZO, ZnO, ITZO, etc.

In some embodiments, the second electrode EL2 may be connected with an auxiliary electrode. When the second electrode EL2 is connected with the auxiliary electrode, the resistance of the second electrode EL2 may decrease.

In some embodiments, a capping layer CPL may be further disposed on the second electrode EL2 of the organic electroluminescence device 10 according to an embodiment. The capping layer CPL may include, for example, a-NPD, NPB, TPD, m-MTDATA, $Alq_3$, CuPc, N4,N4,N4',N4'-tetra (biphenyl-4-yl) biphenyl-4,4'-diamine (TPD15), 4,4',4"-tris (carbazol sol-9-yl) triphenylamine (TCTA), etc.

The amine compound of an embodiment described above may be included in one or more organic layers, as well as in the hole transport region HTR as a material for the organic electroluminescence device 10. The organic electroluminescence device 10 of an embodiment of the present disclosure may also include the above-described amine compound in at least one organic layer disposed between the first electrode EL1 and the second electrode EL2, or the capping layer CPL disposed on the second electrode EL2.

Hereinafter, with reference to Examples and Comparative Examples, an amine compound according to an embodiment of this present disclosure and an organic electroluminescence device of an embodiment will be described in more detail. The Examples below are provided only for the understanding of this present disclosure, and the scope of the present disclosure is not limited thereto.

Synthesis of Amine Compound

An amine compound according to an embodiment of the present disclosure may be synthesized, for example, as follows. However, a synthetic method of the amine compound according to an embodiment of the present disclosure is not limited thereto.

1. Synthesis of Compound 4

Reaction Formula 1

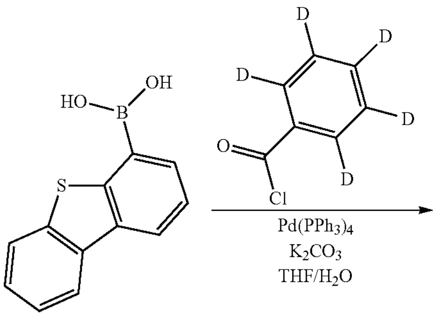

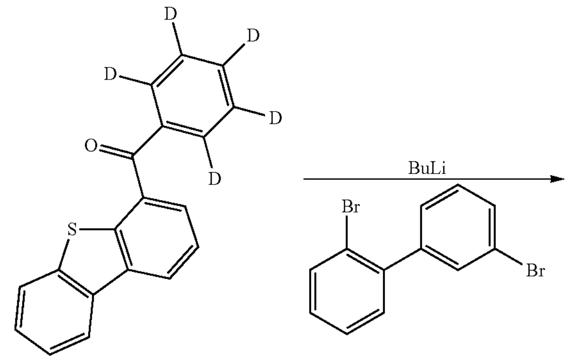

4-1

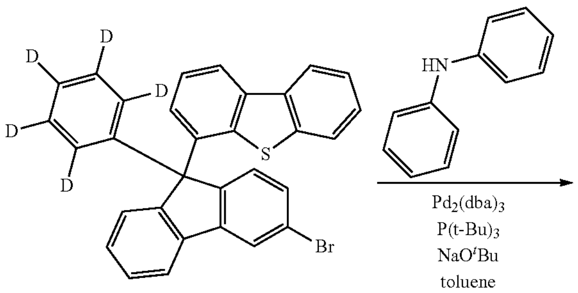

4-2

-continued

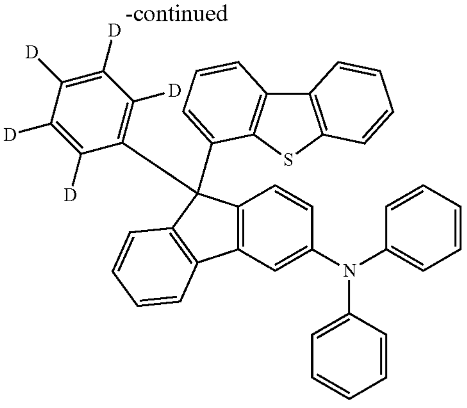

4

1-1. Synthesis of Intermediate Compound 4-1

Dibenzo[b,d]thiophen-4-ylboronic acid (2.28 g), $Pd(PPh_3)_4$ (0.56 g), $K_2CO_3$ (3.45 g), and benzoyl-$d^5$ chloride (1.88 g) were dissolved in $THF/H_2O$ (100 m L/25 mL), and then stirred at 80° C. for 12 hours. This reaction solution was cooled to room temperature and then quenched with water, followed by extracting an organic layer three times with ethyl ether. The separated organic layer was dried with anhydrous magnesium sulfate and distilled at reduced pressure to obtain residues. The obtained residues were separated and purified by column chromatography to obtain Compound 4-1 (1.85 g, yield: 63%).

1-2. Synthesis of Intermediate Compound 4-2

Compound 2,3'-dibromo-1,1'-biphenyl (3.12 g) was dissolved in THF (50 mL), and then 2.5 M n-BuLi (4.8 mL) was added dropwise at −78° C. Compound 4-1 (2.93 g) was dissolved in THF (50 mL), and then the mixture was added dropwise to the prepared solution. The resultant mixture was stirred at −78° C. for 1 hour, and then stirred at room temperature for 2 hours. The reaction was quenched with water followed by extracting an organic layer three times with ethyl ether. The separated organic layer was dried with anhydrous magnesium sulfate and distilled at reduced pressure to obtain residues. The obtained residues were separated and purified by column chromatography to obtain Compound 4-2 (4.07 g, yield: 60%).

1-3. Synthesis of Compound 4

Compound 4-2 (5.08 g), diphenylamine (1.69 g), $Pd_2(dba)_3$ (0.46 g), $P(t-Bu)_3$ (0.21 g), and NaOtBu (2.44 g) were dissolved in toluene (50 mL), and then stirred at 80° C. for 1 hour. This reaction solution was cooled to room temperature and then quenched with water, followed by extracting an organic layer three times with ethyl ether. The separated organic layer was dried with anhydrous magnesium sulfate and distilled at reduced pressure to obtain residues. The obtained residues were separated and purified by column chromatography to obtain Compound 4 (4.24 g, yield: 71%).

2. Synthesis of Compound 24

Reaction Formula 2

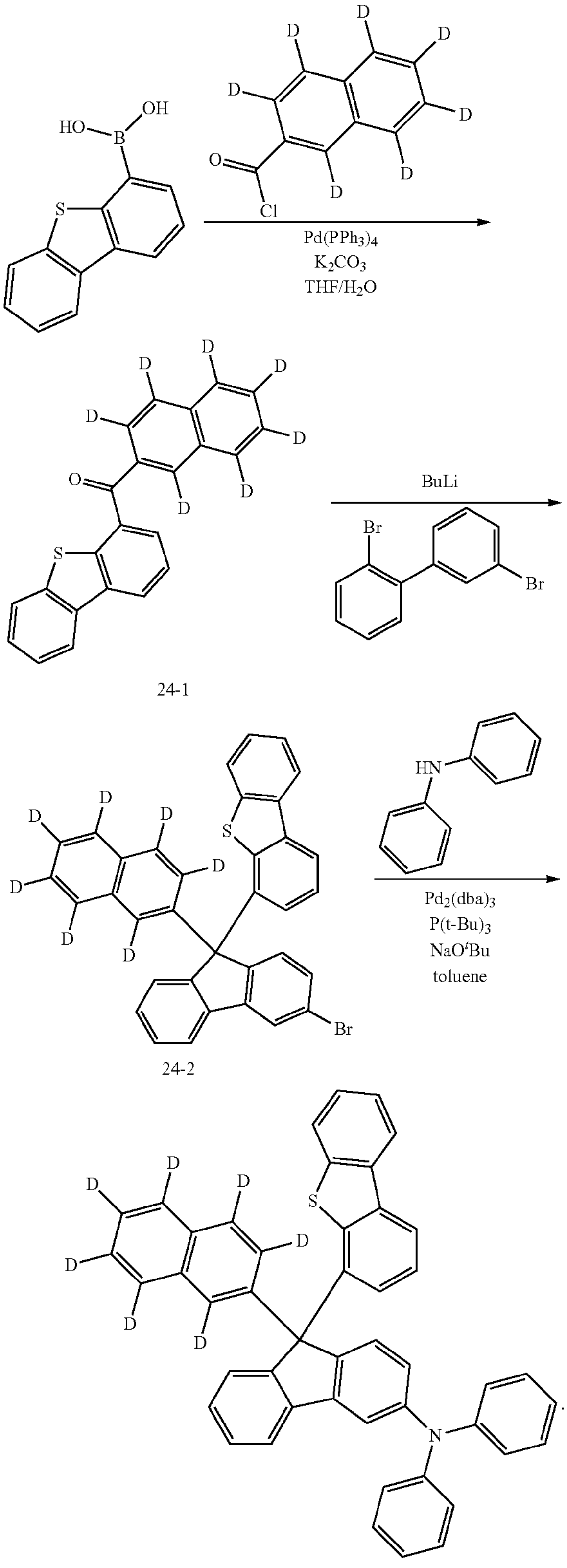

24-1

24-2

24

Compound 24 was obtained by performing substantially the same method as the synthetic method of Compound 4, except that 2-naphthoyl-d 7 chloride (1.97 g) was used instead of benzoyl-d 5 chloride (4.98 g, yield: 77%).

3. Synthesis of Compound 64

Reaction Formula 3

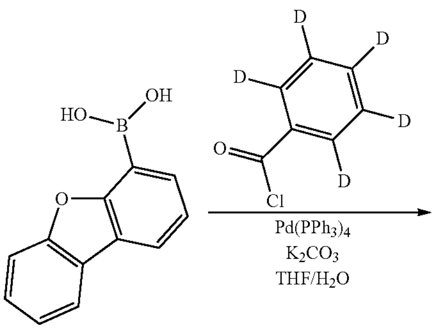

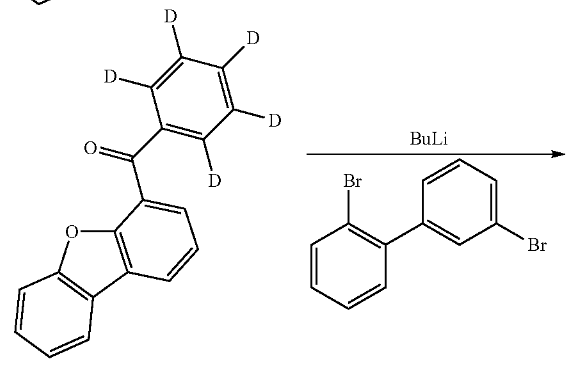

64-1

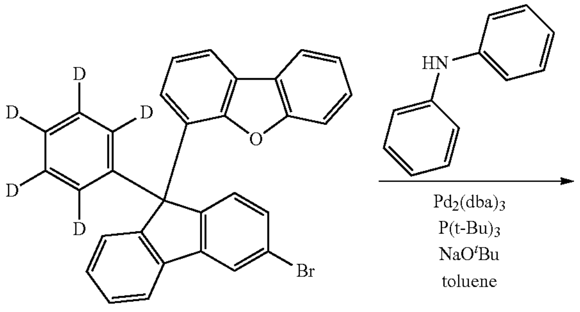

64-2

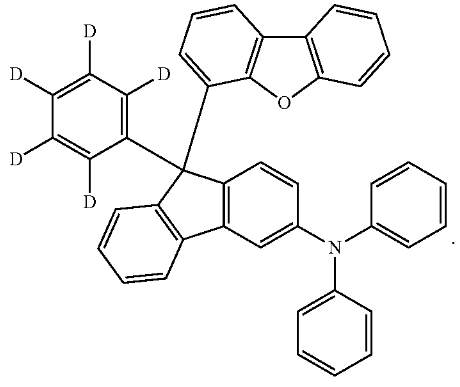

64

Compound 64 was obtained by performing substantially the same method as the synthetic method of Compound 4, except that dibenzo[b,d]furan-4-ylboronic acid (2.12 g) was used instead of dibenzo[b,d]thiophen-4-ylboronic acid (4.06 g, yield: 70%).

4. Synthesis of Compound 84

Reaction Formula 4

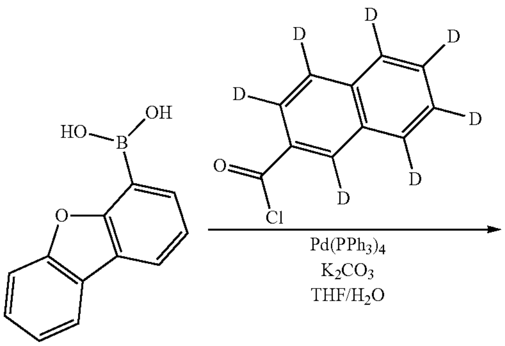

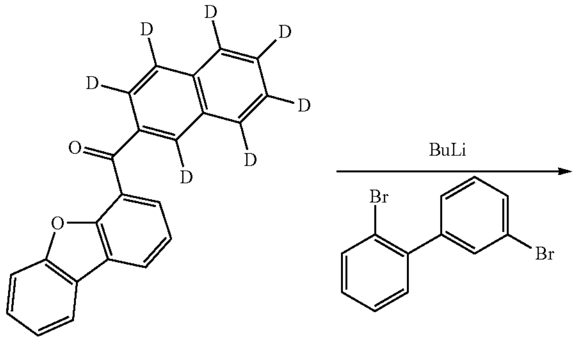

84-1

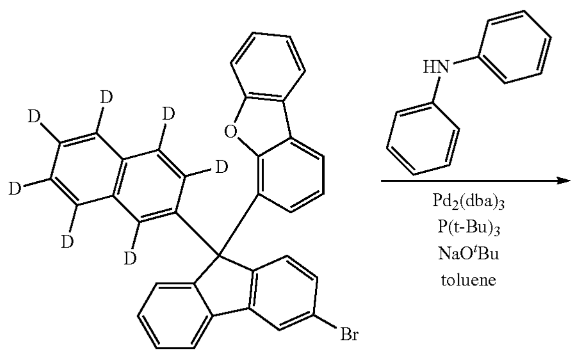

84-2

-continued

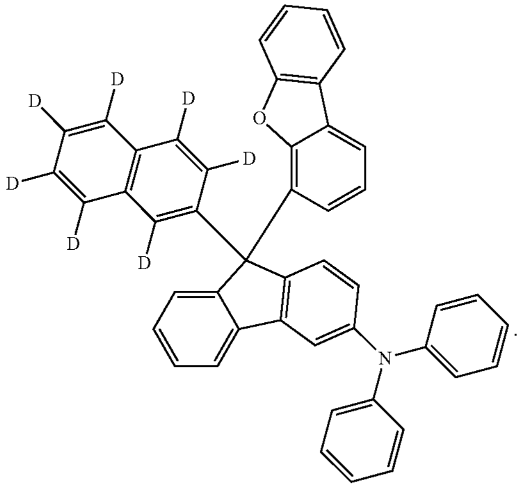

84

Compound 84 was obtained by performing substantially the same method as the synthetic method of Compound 64, except that 2-naphthoyl-d 7 chloride (1.97 g) was used instead of benzoyl-d 5 chloride (4.23 g, yield: 67%).

5. Synthesis of Compound 124

Reaction Formula 5

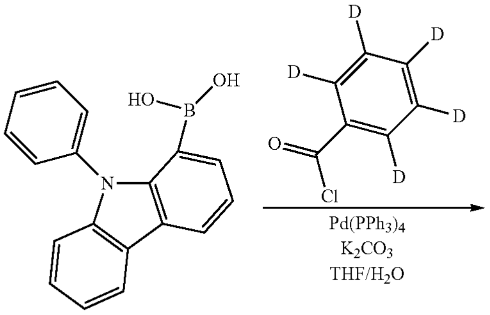

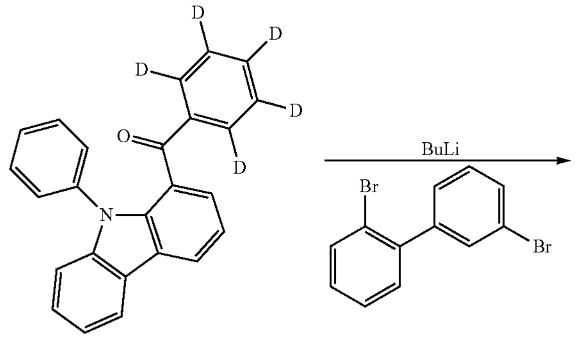

-continued

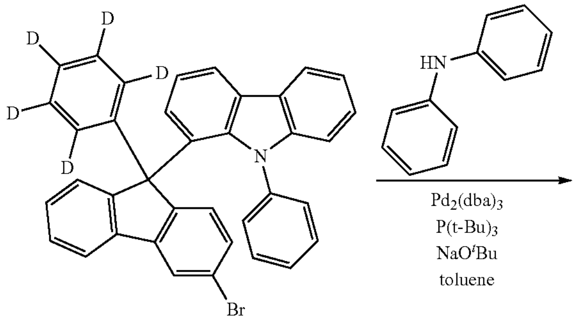

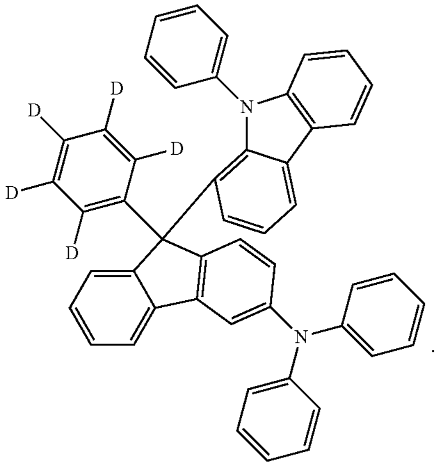

124

Compound 124 was obtained by performing substantially the same method as the synthetic method of Compound 4, except that (9-phenyl-9H-carbazol-1-yl)boronic acid (2.87 g) was used instead of dibenzo[b,d]thiophen-4-ylboronic acid (4.25 g, yield:65%).

6. Synthesis of Compound 144

Reaction Formula 6

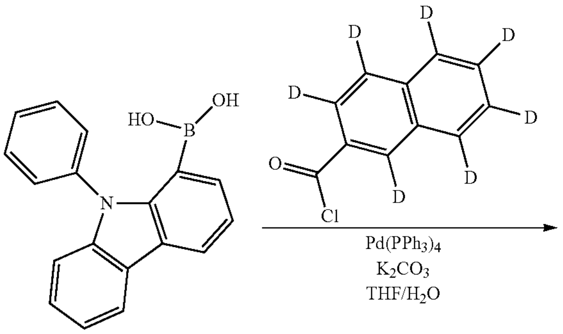

-continued

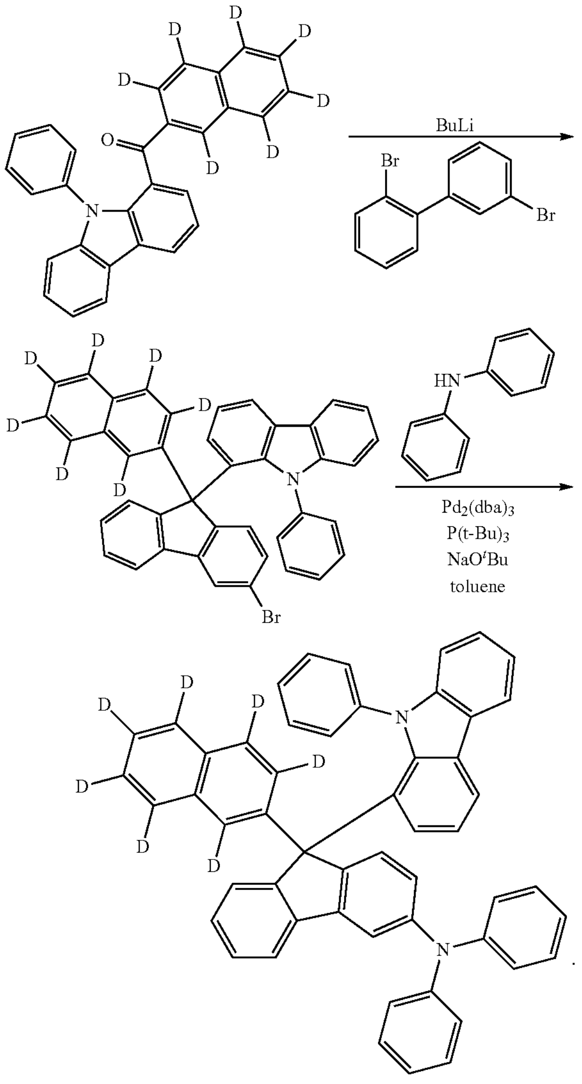

144

Compound 144 was obtained by performing substantially the same method as the synthetic method of Compound 124, except that 2-naphthoyl-d 7 chloride (1.97 g) was used instead of benzoyl-d 5 chloride (4.31 g, yield: 61%).

7. Synthesis of Compound 184

Reaction Formula 7

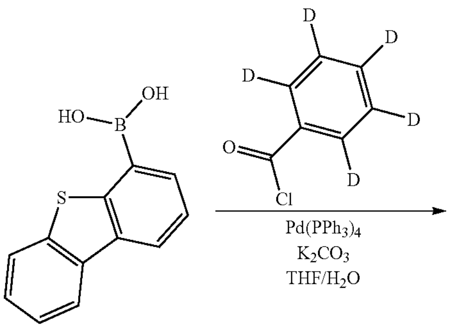

-continued

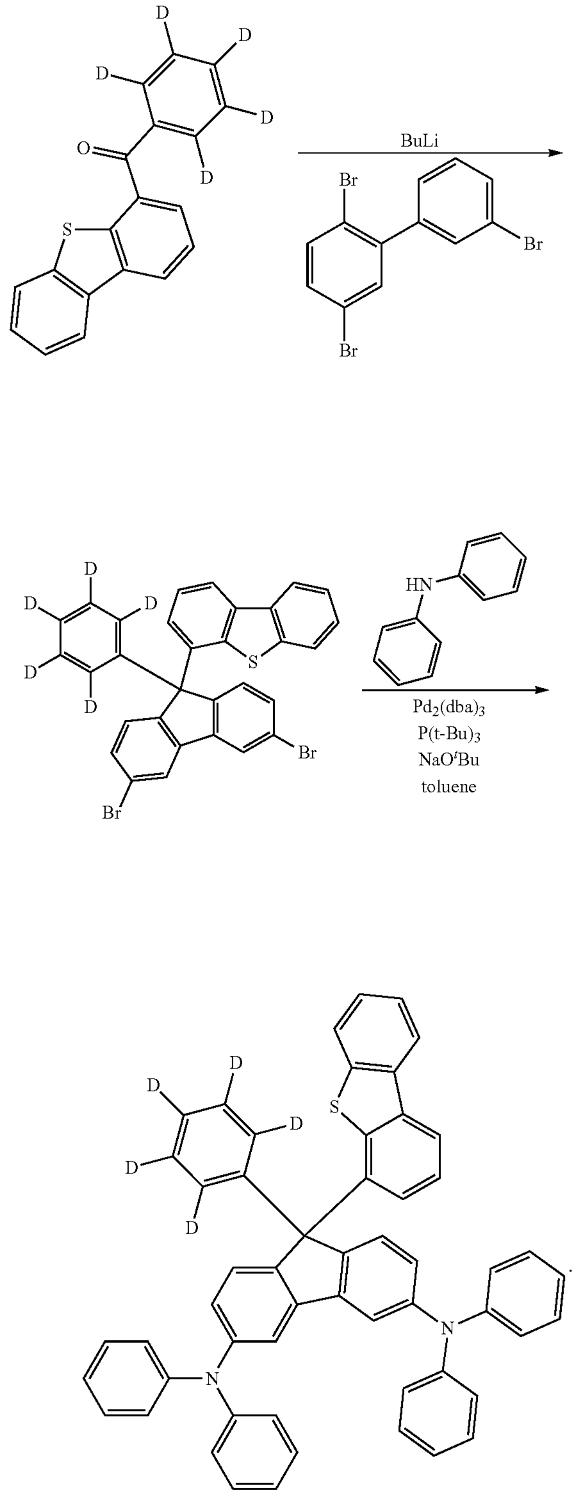

184

Compound 184 was obtained by performing substantially the same method as the synthetic method of Compound 4, except that 2,5,3'-tribromo-1,1'-biphenyl (3.12 g) was used instead of 2,3'-dibromo-1,1'-biphenyl; and diphenylamine, $Pd_2(dba)_3$, $P(t\text{-}Bu)_3$, and NaOtBu were used two times more (5.04 g, yield: 66%).

8. Synthesis of Compound 204

Reaction Formula 8

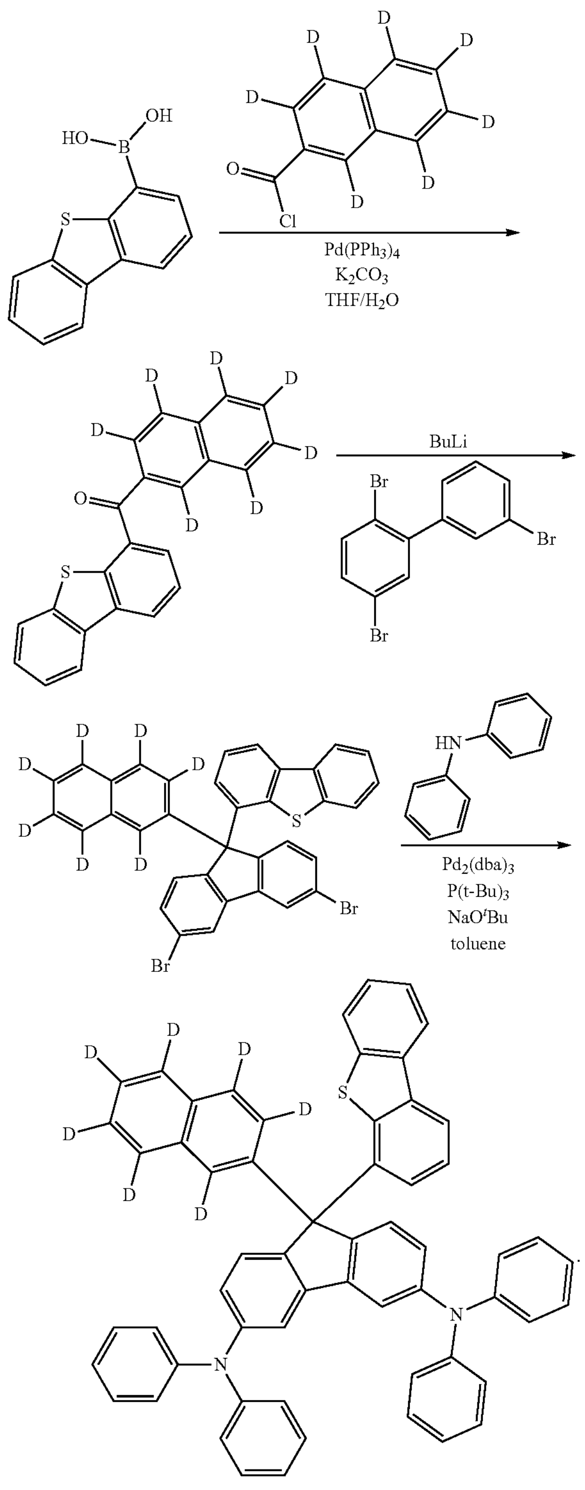

204

Compound 204 was obtained by performing substantially the same method as the synthetic method of Compound 184, except that 2-naphthoyl-d 7 chloride (1.97 g) was used instead of benzoyl-d 5 chloride (5.79 g, yield: 71%).

9. Synthesis of Compound 244

Reaction Formula 9

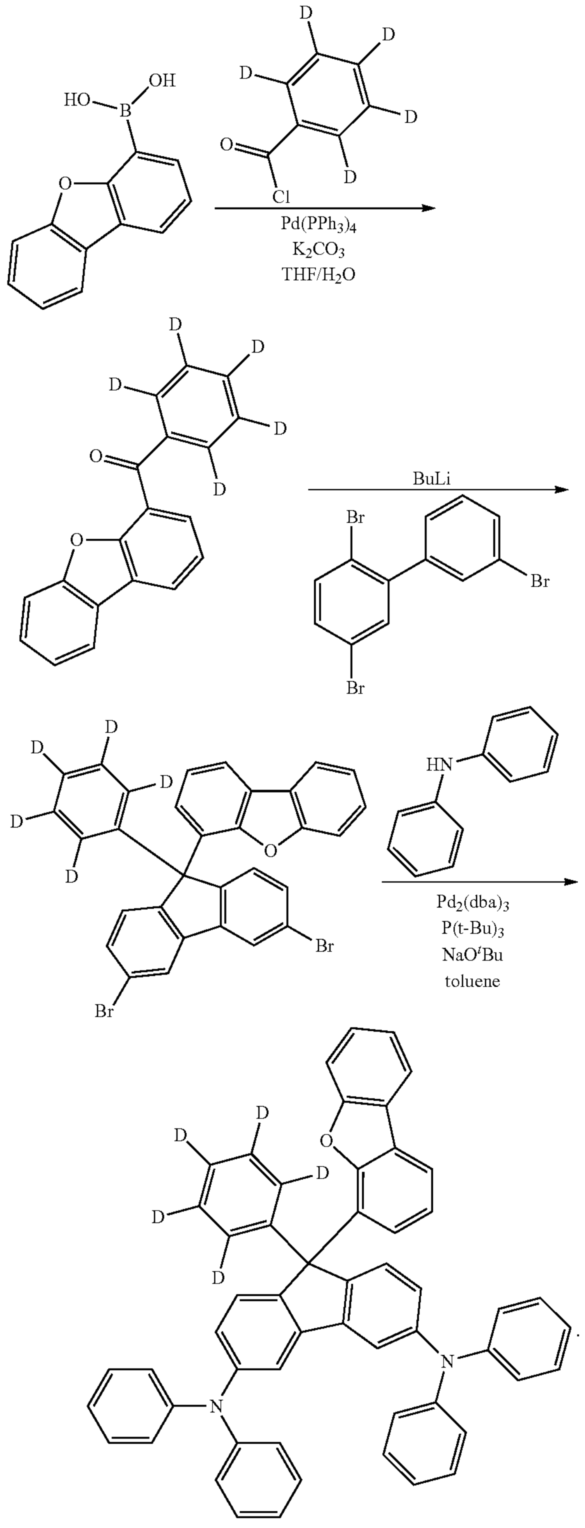

244

Compound 244 was obtained by performing substantially the same method as the synthetic method of Compound 184, except that dibenzo[b,d]furan-4-ylboronic acid (2.12 g) was used instead of dibenzo[b,d]thiophen-4-ylboronic acid (5.29 g, yield: 69%).

10. Synthesis of Compound 264

Reaction Formula 10

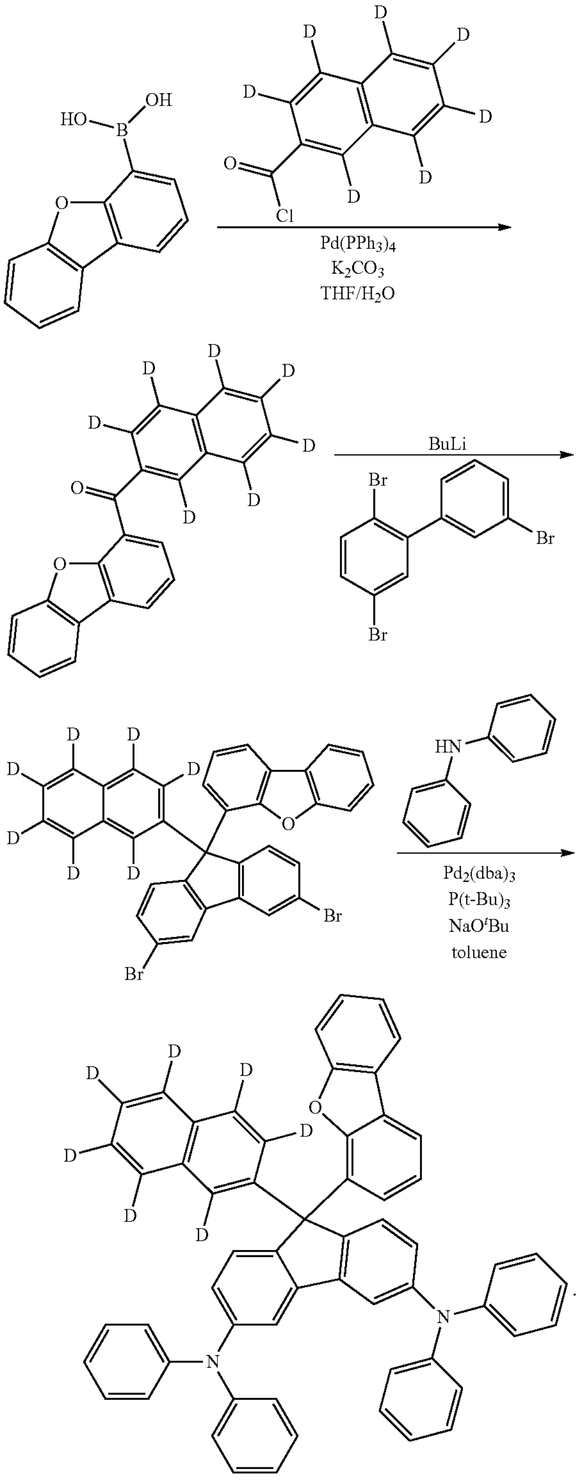

264

Compound 204 was obtained by performing substantially the same method as the synthetic method of Compound 184, except that 2-naphthoyl-d 7 chloride (1.97 g) was used instead of benzoyl-d 5 chloride (6.16 g, yield: 77%).

$^{1}$H NMR and MS/FAB of the Synthesized Compounds are shown in Table 1:

TABLE 1

| Compound number | $^{1}$H NMR | MS/FAB |
|---|---|---|
| Compound 4 | 8.45 (d, 1H), 8.35 (d, 1H), 7.93-7.90 (dd, 2H), 7.62-7.49 (m, 6H), 7.38 (dd, 1H), 7.28-7.24 (m, 6H), 7.08-7.00 (m, 7H) | 597.23 |
| Compound 24 | 8.45 (d, 1H), 8.35 (d, 1H), 7.93-7.90 (dd, 2H), 7.62-7.49 (m, 6H), 7.38 (dd, 1H), 7.28-7.24 (m, 6H), 7.08-7.00 (m, 7H) | 649.26 |
| Compound 64 | 7.98 (d, 1H), 7.90-7.88 (d, 2H), 7.62 (s, 1H), 7.55-7.50 (m, 3H), 7.38-7.24 (m, 9H), 7.09-7.00 (m, 8H) | 581.26 |
| Compound 84 | 7.98 (d, 1H), 7.90-7.88 (d, 2H), 7.62 (s, 1H), 7.55-7.50 (m, 3H), 7.38-7.24 (m, 9H), 7.09-7.00 (m, 8H) | 633.28 |
| Compound 124 | 8.45 (d, 1H), 8.19 (d, 1H) 7.90 (d, 1H), 7.62-7.50 (m, 10H), 7.38 (dd, 1H), 7.28-7.20 (m, 7H), 7.08-6.98 (m, 8H) | 656.30 |
| Compound 144 | 8.45 (d, 1H), 8.19 (d, 1H) 7.90 (d, 1H), 7.62-7.50 (m, 10H), 7.38 (dd, 1H), 7.28-7.20 (m, 7H), 7.08-6.98 (m, 8H) | 708.33 |
| Compound 184 | 8.45 (d, 1H), 8.35 (d, 1H), 7.93 (s, 1H), 7.62-7.49 (m, 7H), 7.28-7.24 (m, 9H), 7.08-7.00 (m, 14H) | 764.31 |
| Compound 204 | 8.45 (d, 1H), 8.35 (d, 1H), 7.93 (s, 1H), 7.62-7.49 (m, 7H), 7.28-7.24 (m, 9H), 7.08-7.00 (m, 14H) | 816.34 |
| Compound 244 | 7.98 (d, 1H), 7.88 (d, 1H), 7.62 (s, 2H), 7.51 (m, 3H), 7.39-7.24 (m, 11H), 7.09-7.00 (m, 15H) | 748.33 |
| Compound 264 | 7.98 (d, 1H), 7.88 (d, 1H), 7.62 (s, 2H), 7.51 (m, 3H), 7.39-7.24 (m, 11H), 7.09-7.00 (m, 15H) | 800.36 |

(Manufacture and Evaluation of Organic Electroluminescence Device Including Amine Compound)

The emission characteristics of organic electroluminescence devices including the amine compound of an embodiment in a hole transport region were evaluated as follows. The method for manufacturing the organic electroluminescence device for the evaluation of the device is described below.

The amine compounds of Compounds 4, 24, 64, 84, 124, 144, 184, 204, 244 and 264 as described above were used as hole transport layer materials to manufacture the organic electroluminescence devices of examples 1 to 10. Comparative Examples 1 to 4 are the organic electroluminescence devices manufactured by using each of Comparative Example Compounds C1, C2, C3, and C4 as a hole transport region material.

Compounds used in Examples 1 to 10 and Comparative Examples 1 to 4 are as follows.
Example Compounds
4
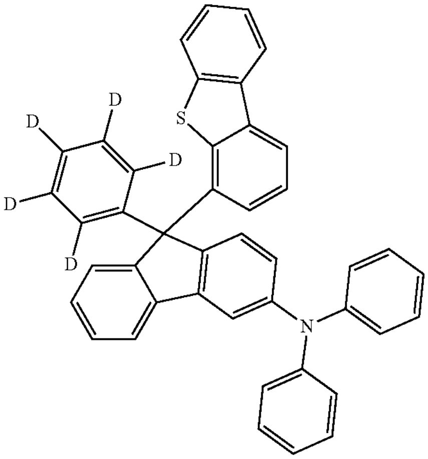
24
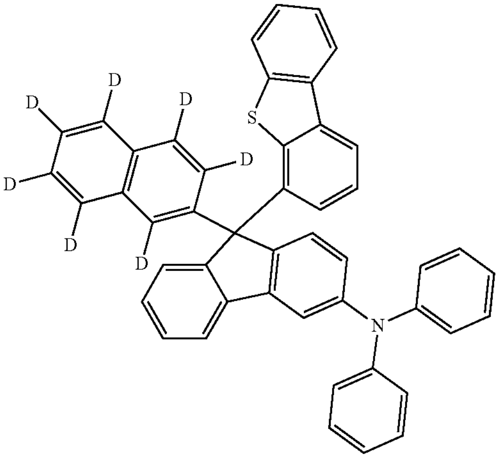
64
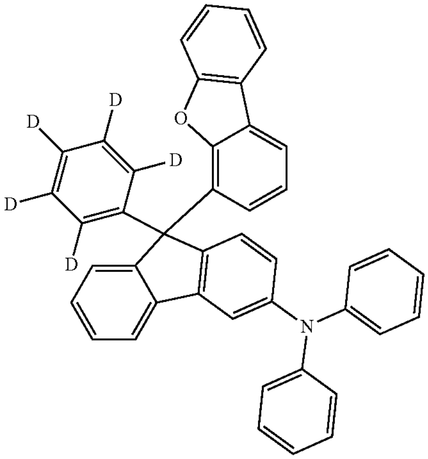
-continued
84
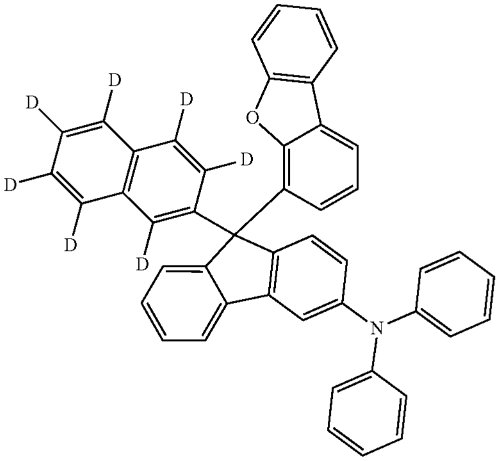
124
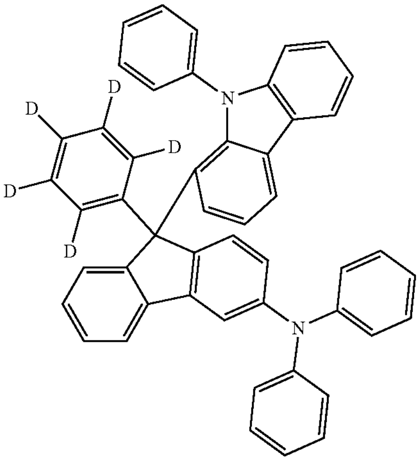
144
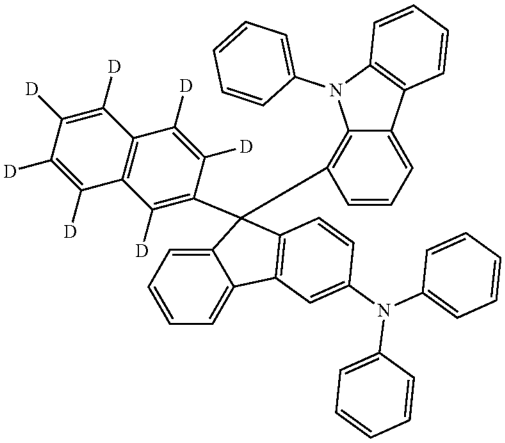

-continued
184
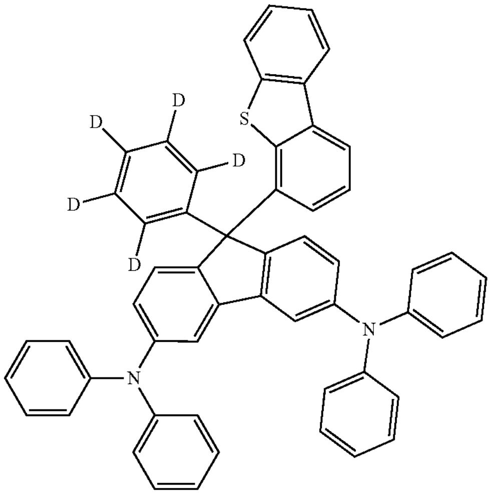
204
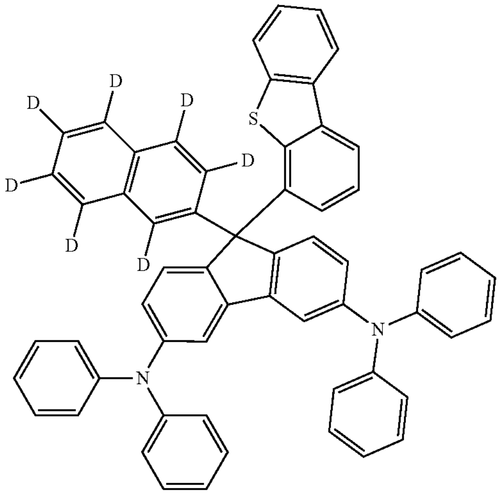
244
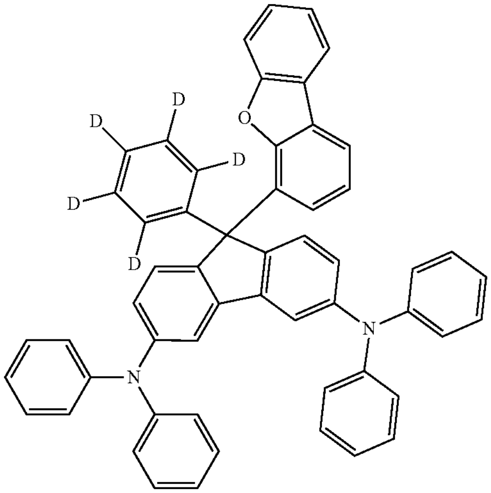
-continued
244
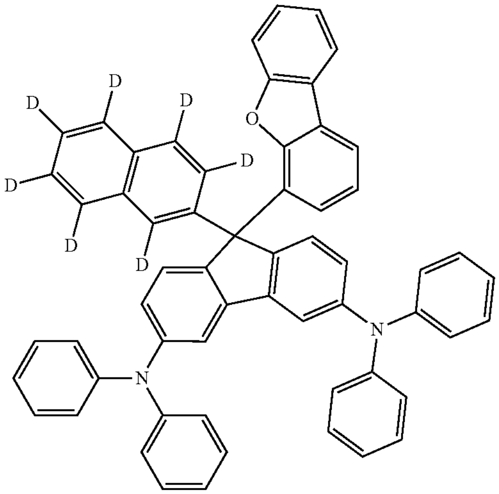
Comparative Example Compounds
C1
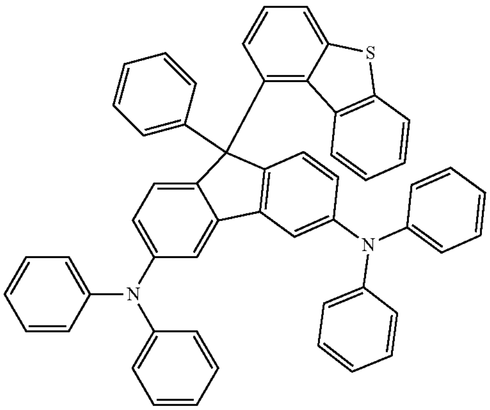
C2
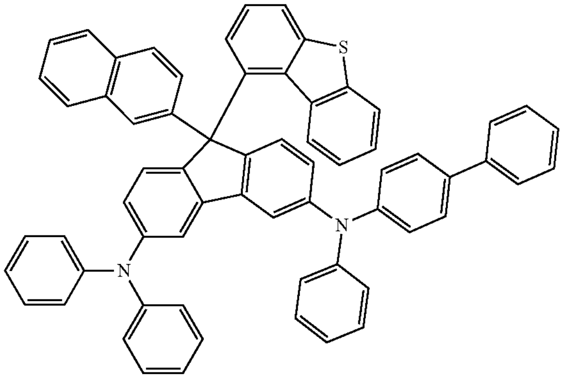

-continued

C3

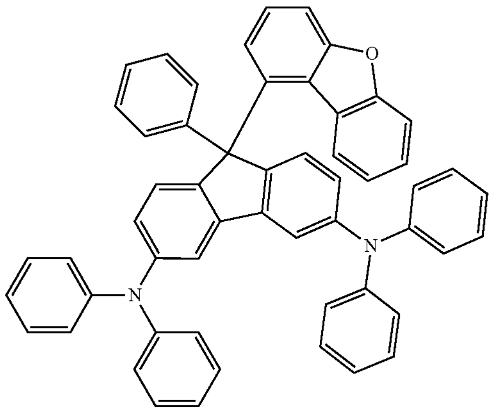

C4

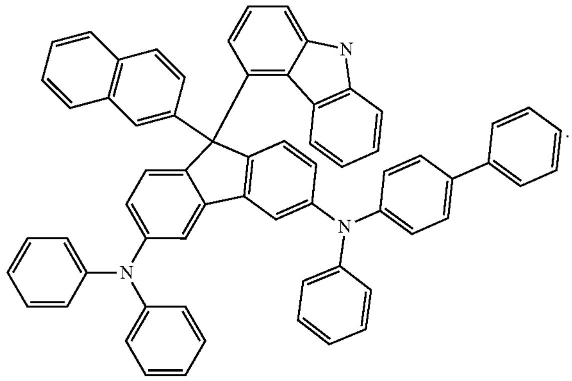

Manufacture of Organic Electroluminescence Device

Organic electroluminescence devices including an amine Example Compound or a Comparative Example Compound in a hole transport region were manufactured via the following method.

For an anode, an ITO glass substrate of about 15 Ω/$cm^2$ (about 1,200 Å) made by Corning Co. was cut to a size of 50 mm×50 mm×0.7 mm, cleansed by ultrasonic waves in isopropyl alcohol and pure water for about 5 minutes, and then cleansed by ultraviolet irradiation for about 30 minutes and exposure to ozone. The ITO glass substrate was installed on a vacuum deposition apparatus.

On the ITO glass substrate, 2-TNATA was deposited in vacuum to a thickness of about 600 Å to form a hole injection layer, and on the hole injection layer, the Example Compound or Comparative Compound was deposited in vacuum to a thickness of about 300 Å to form a hole transport layer.

On the hole transport layer, 9,10-di(naphthalen-2-yl)anthracene (hereinafter, DNA) as a blue fluorescent host and 4,4'-bis[2-(4-(N,N-diphenylamino)phenyl)vinyl]piphenyl (hereinafter, DPAVBi) as a blue fluorescent dopant were co-deposited at a weight ratio of 98:2 to form an emission layer having a thickness of about 300 Å.

Then, $Alq_3$ was deposited on the emission layer to form an electron transport layer having a thickness of about 300 Å, and LiF (which is an alkaline metal halide) was deposited on the electron transport layer to form an electron injection layer having a thickness of about 10 Å. Next, Al was deposited in vacuum to a thickness of about 3,000 Å to form an LiF/AI cathode electrode, thereby manufacturing an organic electroluminescence device.

The materials of each layer used in the manufacture of the organic electroluminescence devices are as follows.

Functional Layer Compound

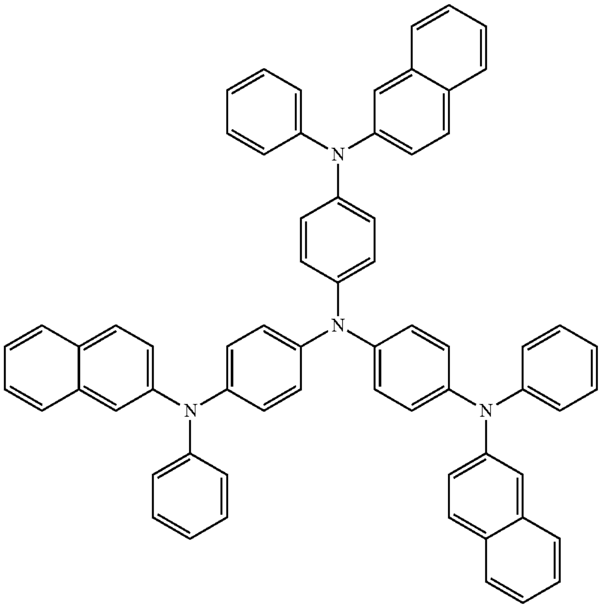

2-TNATA

-continued

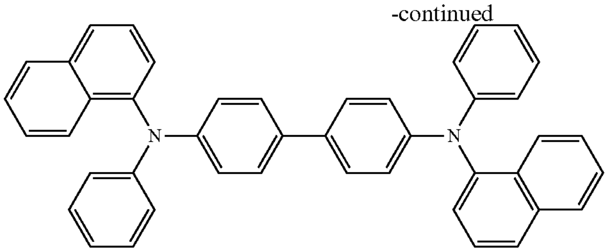

NPB

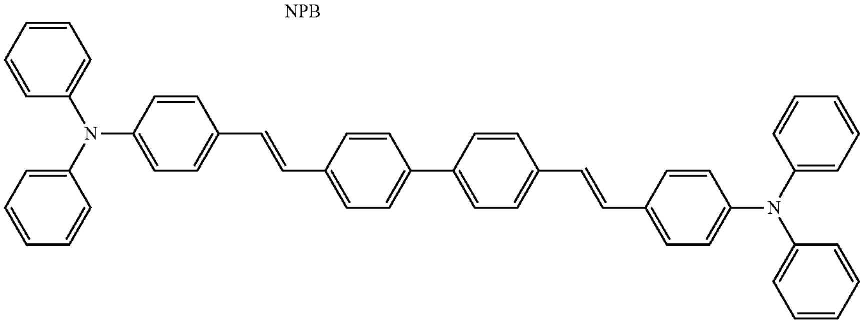

DPAVBi

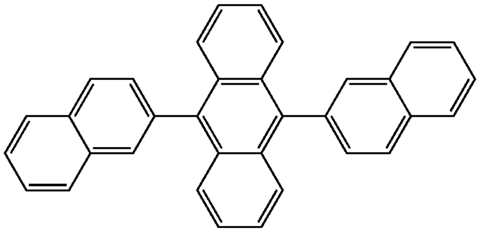

.

DNA

Evaluation of Organic Electroluminescence Device Characteristics

The characteristics of the manufactured organic electroluminescence devices were evaluated using a brightness distribution measurement device. The driving voltage, brightness, efficiency, luminous wavelength, and service life (Tao, unit: time) of the organic electroluminescence devices according to the Examples and Comparative Examples were measured. The driving voltage (V), current efficiency (cd/A) at a current density of 50 mA/$cm^2$, and brightness (cd/$m^2$) of each of the manufactured organic electroluminescence devices are shown in Table 2. The half service life (which is the time taken to reduce the brightness to 50% with respect to a brightness of 5,000 nit) is also shown in Table 2. The half service life was measured by continuous driving at a current density of 100 mA/$cm^2$. The brightness spectrum of each of the Examples and Comparative Examples was measured with a spectroradiometer. A luminous peak, (e.g., the maximum luminous wavelength) was determined from the measured brightness spectrum.

TABLE 2

| Device manu-factured examples | Hole transport material | Drive voltage (V) | Current density (mA/$cm^2$) | Brightness (cd/$m^2$) | Efficiency (cd/A) | Luminous color | Half service life (hr @ 100 mA/$cm^2$) |
|---|---|---|---|---|---|---|---|
| Comparative Example 1 | Comparative Example 1 | 4.71 | 50 | 3145 | 6.29 | Blue | 320 |
| Comparative Example 2 | Comparative Example 2 | 4.63 | 50 | 3150 | 6.30 | Blue | 342 |
| Comparative Example 3 | Comparative Example 3 | 4.86 | 50 | 3270 | 6.54 | Blue | 351 |
| Comparative Example 4 | Comparative Example 4 | 4.82 | 50 | 3105 | 6.21 | Blue | 333 |
| Example 1 | Compound 4 | 4.35 | 50 | 3705 | 7.41 | Blue | 375 |
| Example 2 | Compound 24 | 4.15 | 50 | 3480 | 6.96 | Blue | 374 |
| Example 3 | Compound 64 | 4.36 | 50 | 3740 | 7.48 | Blue | 381 |
| Example 4 | Compound 84 | 4.24 | 50 | 3520 | 7.04 | Blue | 388 |

TABLE 2-continued

| Device manu-factured examples | Hole transport material | Drive voltage (V) | Current density ($mA/cm^2$) | Brightness ($cd/m^2$) | Efficiency (cd/A) | Luminous color | Half service life (hr @ 100 $mA/cm^2$) |
|---|---|---|---|---|---|---|---|
| Example 5 | Compound 124 | 4.15 | 50 | 3640 | 7.28 | Blue | 369 |
| Example 6 | Compound 144 | 4.13 | 50 | 3900 | 7.80 | Blue | 394 |
| Example 7 | Compound 184 | 4.00 | 50 | 3610 | 7.22 | Blue | 379 |
| Example 8 | Compound 204 | 4.21 | 50 | 3430 | 6.86 | Blue | 398 |
| Example 9 | Compound 244 | 4.36 | 50 | 3455 | 6.91 | Blue | 378 |
| Example 10 | Compound 264 | 4.45 | 50 | 3280 | 6.56 | Blue | 380 |

Referring to the results of Table 2, when the amine compound according to an embodiment of the present disclosure is applied to the hole transport layer HTL of the organic electroluminescence device 10, it is confirmed that high efficiency, high brightness, low driving voltage, and a long service life of the device may be achieved. Referring to the results of Examples 1 to 10 and Comparative Examples 1 to 4, it is confirmed that the Examples (each including the amine compound containing a fluorene group, an deuterated aryl group substituted to the fluorene group, a heteroaryl group substituted to the fluorene group, and at least one amine group substituted to the fluorene group) each show high efficiency, high brightness, low driving voltage, and long service life characteristics compared to Comparative Examples each including the amine compound not containing the fluorene group and the aryl group which is substituted with deuterium.

In comparison, Comparative Examples 1 to 4 emit light in a blue wavelength region, but have low luminous efficiency and service life characteristics compared to the Examples. In addition, Comparative Examples 1 to 4 show higher driving voltages than the Examples.

The amine compound of an embodiment includes an aryl group substituted to the fluorene group, where all the carbons of the aryl group are substituted with deuterium, and thus provides excellent service life characteristics when applied to a device, compared to Comparative Example Compounds that do not include the aryl group substituted with deuterium. In addition, the amine compound of an embodiment may include a fused polycyclic compound (such as a fluorene group, a dibenzofuran group, a dibenzothiophene group, and/or a carbazole group) to thus improve heat resistance and durability against a high temperature environment. The organic electroluminescence device including the amine compound of an embodiment is capable of achieving high efficiency, high brightness, low driving voltage, and a long service life due to having a stable structure in which heat resistance and durability are improved.

The organic electroluminescence device of an embodiment may have high efficiency and increased service life characteristics.

The amine compound of an embodiment may be applied to an emission layer of the organic electroluminescence device to contribute to efficiency and a long service life of the organic electroluminescence device.

As used herein, the terms "substantially," "about," and similar terms are used as terms of approximation and not as terms of degree, and are intended to account for the inherent deviations in measured or calculated values that would be recognized by those of ordinary skill in the art.

Any numerical range recited herein is intended to include all sub-ranges of the same numerical precision subsumed within the recited range. For example, a range of "1.0 to 10.0" is intended to include all subranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited herein is intended to include all lower numerical limitations subsumed therein and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited herein.

Although described with reference to embodiments of the present disclosure, it will be understood that various changes and modifications of the present disclosure may be made by having ordinary skill in the art without departing from the spirit and technical field of the present disclosure as set forth in the following claims and their equivalents.

What is claimed is:

1. An organic electroluminescence device comprising:
- a first electrode;
- a second electrode facing the first electrode; and
- a plurality of organic layers between the first electrode and the second electrode,
- wherein at least one of the organic layers comprises an amine compound;
- the amine compound comprises a fluorene group; an aryl group having 6 to 60 ring-forming carbon atoms, which is substituted to the fluorene group; a heteroaryl group having 2 to 60 ring-forming carbon atoms, which is substituted to the fluorene group; and at least one aryl amine or heteroaryl amine group which is substituted to the fluorene group;
- all substitutable carbons of the aryl group are substituted with deuterium, and
- wherein the amine group is connected to at least one of 3-position carbon or 6-position carbon of the fluorene group.

2. The organic electroluminescence device of claim 1, wherein the heteroaryl group is a substituted or unsubstituted dibenzofuran group, a substituted or unsubstituted dibenzothiophene group, or a substituted or unsubstituted carbazole group.

3. The organic electroluminescence device of claim 1, wherein the organic layers comprise a hole transport region, an emission layer, and an electron transport region, and the hole transport region comprises the amine compound.

4. The organic electroluminescence device of claim 1, wherein the amine compound is represented by Formula 1:

Formula 1

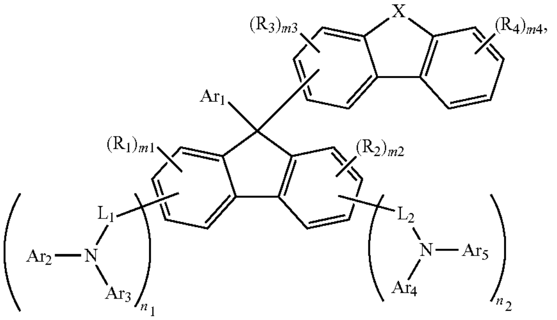

wherein, in Formula 1,

X is O, S, or $NAr_6$;

$L_1$ and $L_2$ are each independently a direct linkage, a substituted or unsubstituted arylene group having 6 to 60 ring-forming carbon atoms, or a substituted or unsubstituted heteroarylene group having 2 to 60 ring-forming carbon atoms;

$R_1$ to $R_4$ are each independently a hydrogen atom, a deuterium atom, a halogen atom, a substituted or unsubstituted alkyl group having 1 to 20 carbon atoms, a substituted or unsubstituted aryl group having 6 to 60 ring-forming carbon atoms, or a substituted or unsubstituted heteroaryl group having 2 to 60 ring-forming carbon atoms, and/or are optionally bonded to an adjacent group to form a ring;

$m_1$, $m_2$, and $m_4$ are each independently an integer of 0 to 4;

$m_3$ is an integer of 0 to 3;

$Ar_1$ is a phenyl group substituted with deuterium, a naphthyl group substituted with deuterium, or a biphenyl group substituted with deuterium;

$Ar_2$ to $Ar_6$ are each independently a substituted or unsubstituted aryl group having 6 to 60 ring-forming carbon atoms, or a substituted or unsubstituted heteroaryl group having 3 to 60 ring-forming carbon atoms; and $n_1$ and $n_2$ are each independently 0 or 1; and at least one of $n_1$ or $n_2$ is 1.

5. The organic electroluminescence device of claim 4, wherein the amine compound represented by Formula 1 is represented by at least one of Formula 1-1 to Formula 1-3:

Formula 1-1

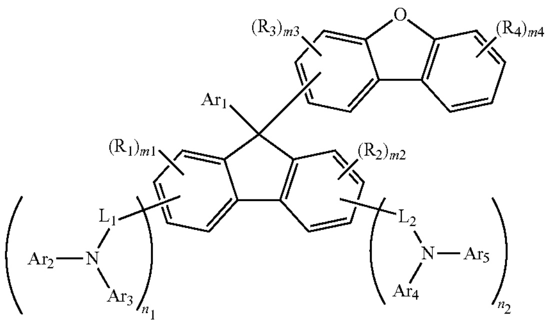

-continued

Formula 1-2

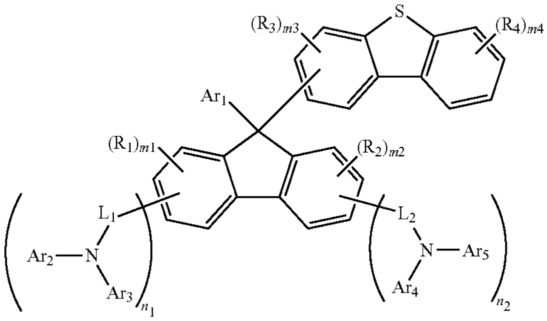

Formula 1-3

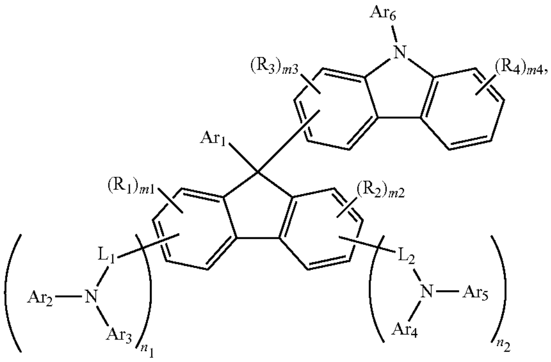

wherein, in Formula 1-1 to Formula 1-3, $L_1$, $L_2$, $R_1$ to $R_4$, $m_1$ to $m_4$, $Ar_1$ to $Ar_6$, $n_1$ and $n_2$ are each independently the same as defined in Formula 1.

6. The organic electroluminescence device of claim 4, wherein the amine compound represented by Formula 1 is represented by at least one of Formula 2-1 to Formula 2-5:

Formula 2-1

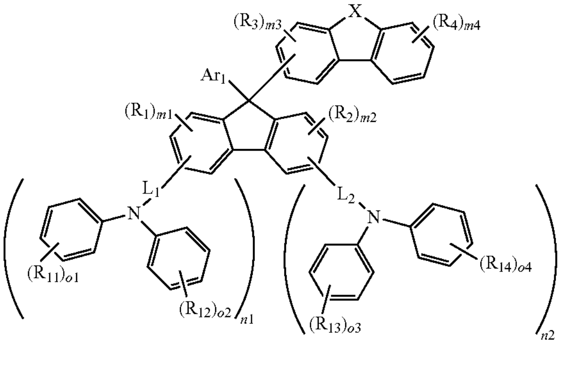

-continued

Formula 2-2

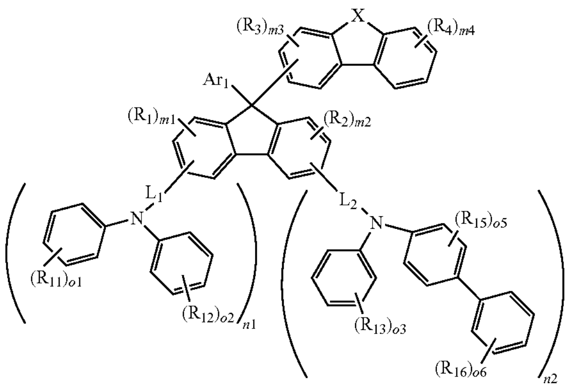

Formula 2-3

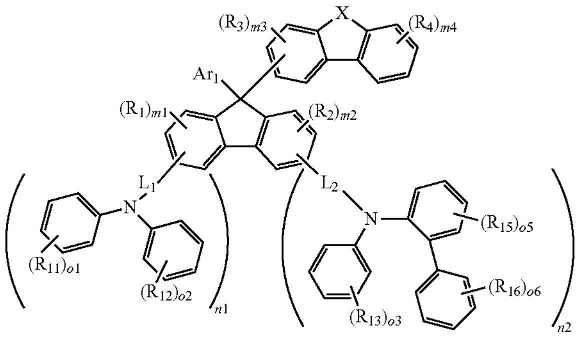

Formula 2-4

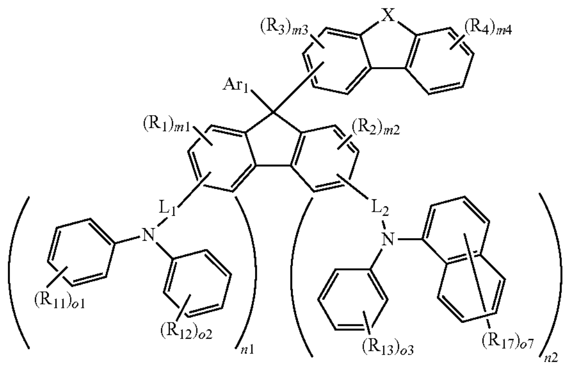

Formula 2-5

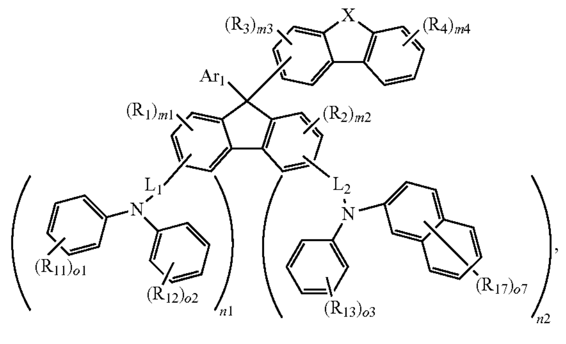

wherein, in Formula 2-1 to Formula 2-5, $R_{11}$ to $R_{17}$ are each independently a hydrogen atom, a deuterium atom, a halogen atom, a substituted or unsubstituted alkyl group having 1 to 20 carbon atoms, a substituted or unsubstituted aryl group having 6 to 60 ring-forming carbon atoms, or a substituted or unsubstituted heteroaryl group having 2 to 60 ring-forming carbon atoms, and/or are optionally bonded to an adjacent group to form a ring;

$o_1$ to $o_4$ and $o_6$ are each independently an integer of 0 to 5;

$o_5$ is an integer of 0 to 4;

$o_7$ is an integer of 0 to 7; and

X, $R_1$ to $R_4$, $L_1$, $L_2$, $n_1$, $n_2$, $m_1$ to $m_4$ and $Ar_1$ are each independently the same as defined in Formula 1.

7. The organic electroluminescence device of claim 4, wherein the amine compound represented by Formula 1 is represented by Formula 3-1:

Formula 3-1

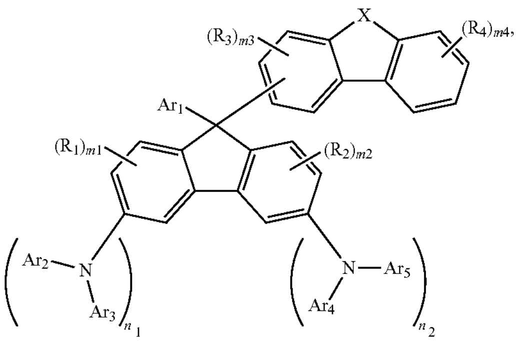

wherein, in Formula 3-1,

X, $Ar_1$ to $Ar_5$, $R_1$ to $R_4$, $n_1$, $n_2$, and $m_1$ to $m_4$ are each independently the same as defined in Formula 1.

8. The organic electroluminescence device of claim 4, wherein the amine compound represented by Formula 1 is represented by at least one of Formula 4-1 and Formula 4-2:

Formula 4-1

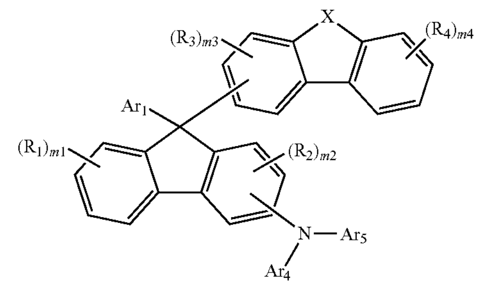

Formula 4-2

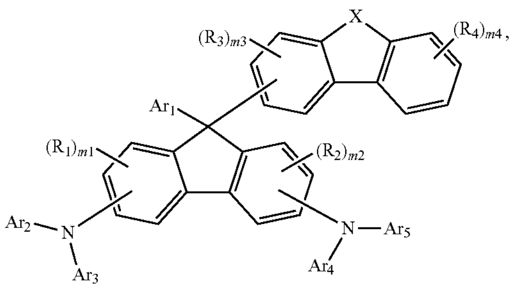

wherein, in Formula 4-1 and Formula 4-2,

X, $Ar_1$ to $Ar_5$, $R_1$ to $R_4$, and $m_1$ to $m_4$ are each independently the same as defined in Formula 1.

9. The organic electroluminescence device of claim 4, wherein X is $NAr_6$, and $Ar_6$ is a substituted or unsubstituted phenyl group.
10. The organic electroluminescence device of claim 4, wherein the amine compound represented by Formula 1 is at least one of the compounds represented by Compound Group 1:
Compound Group 1
1
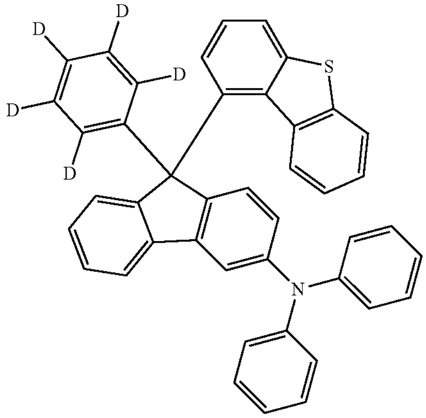
2
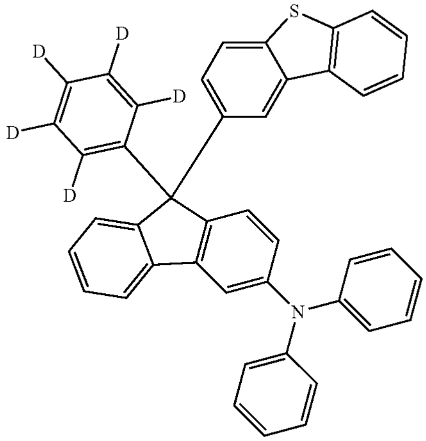
3
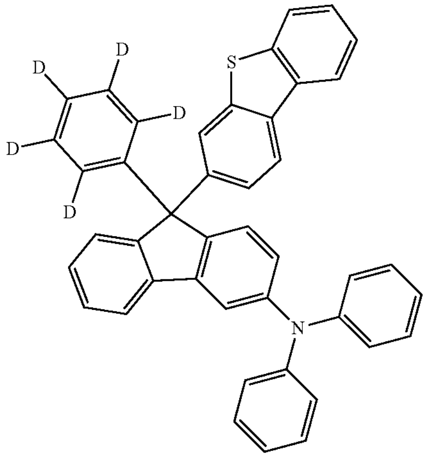
-continued
4
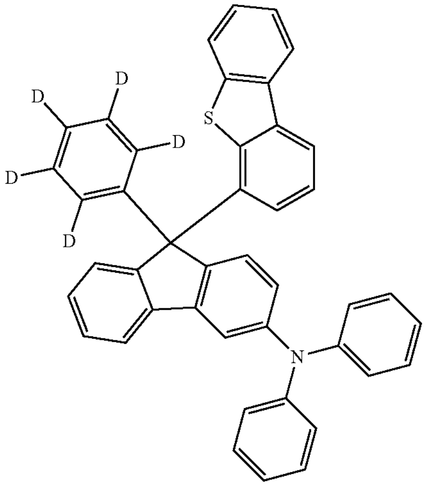
5
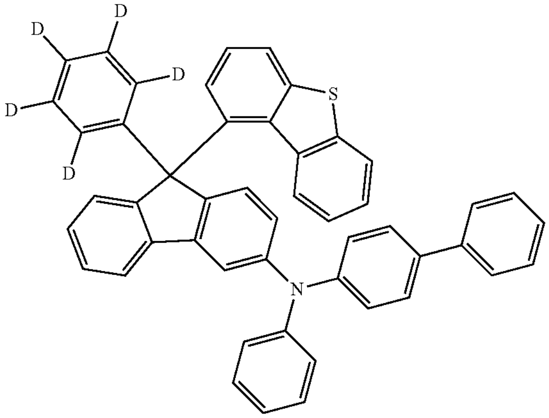
6
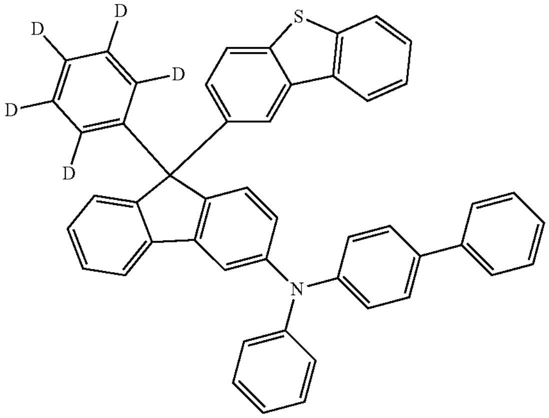

-continued
7
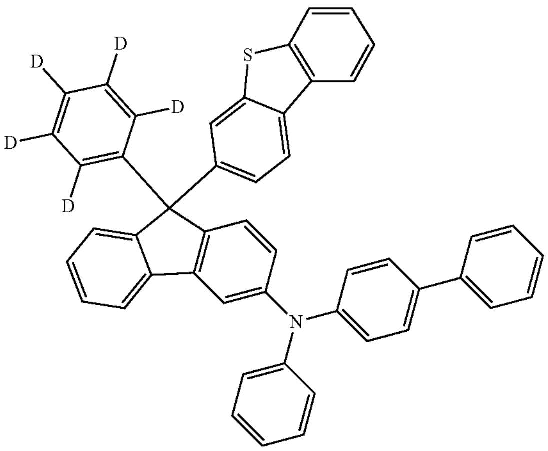
8
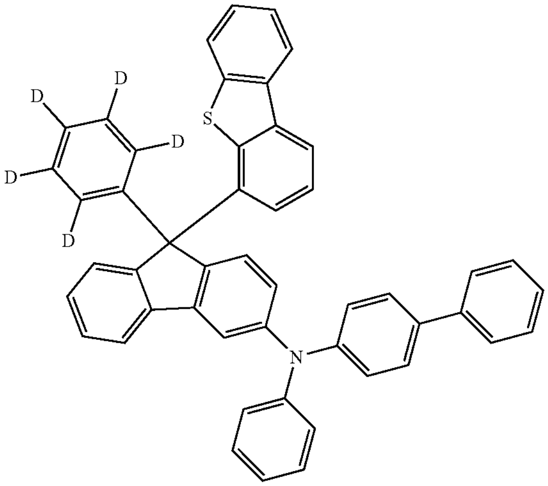
9
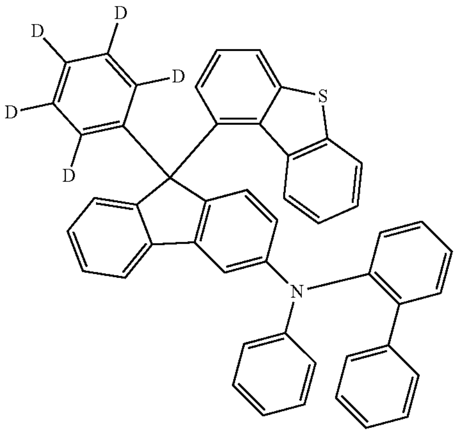
-continued
10
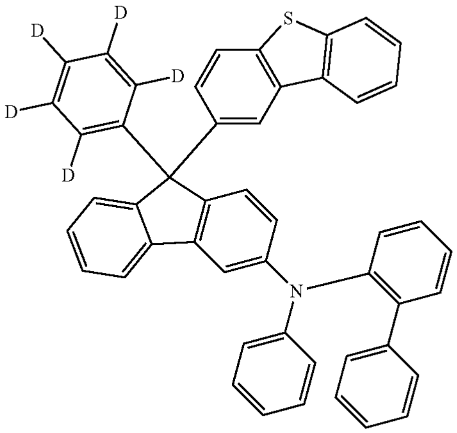
11
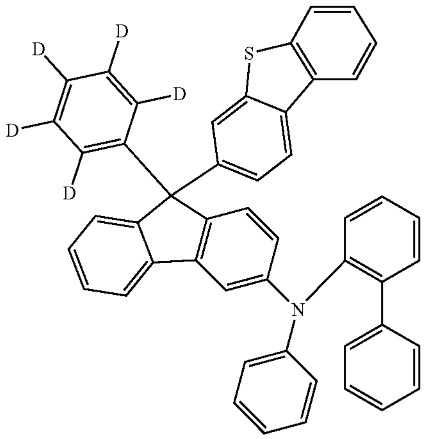
12
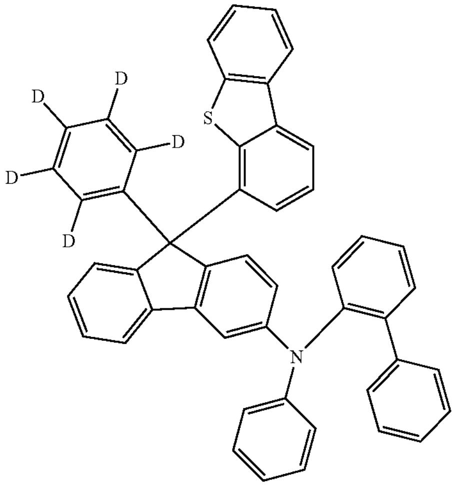

-continued
13
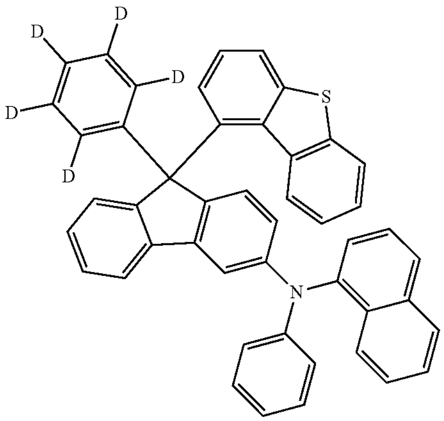
14
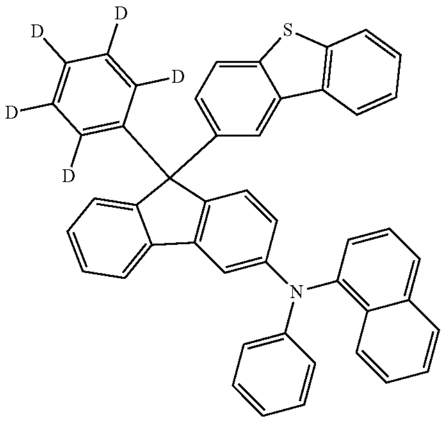
15
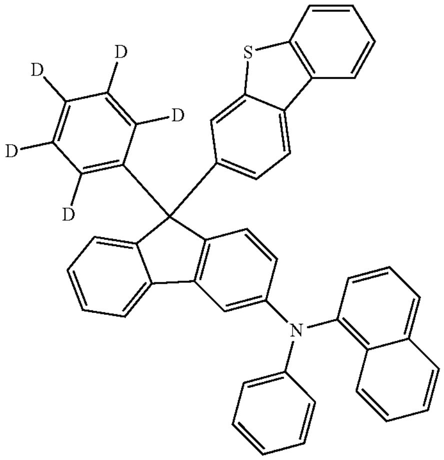
-continued
16
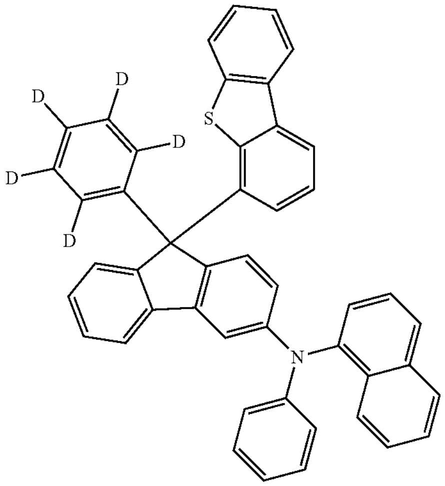
17
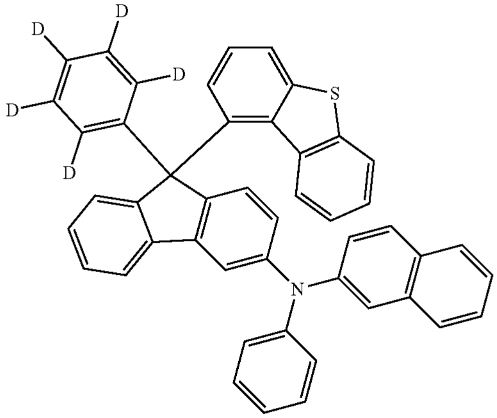
18
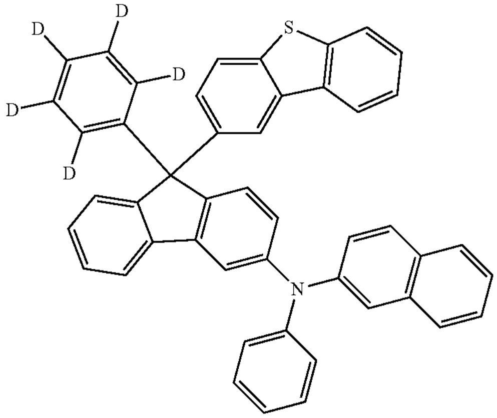

-continued
19
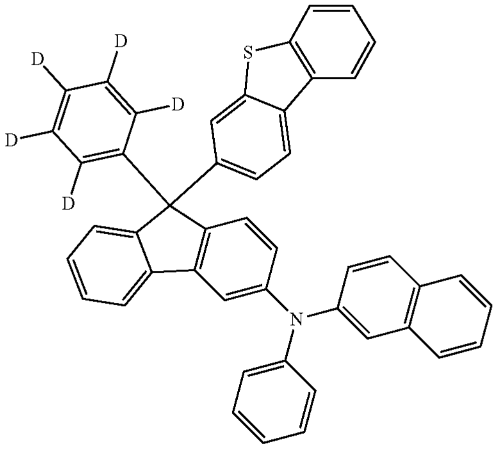
20
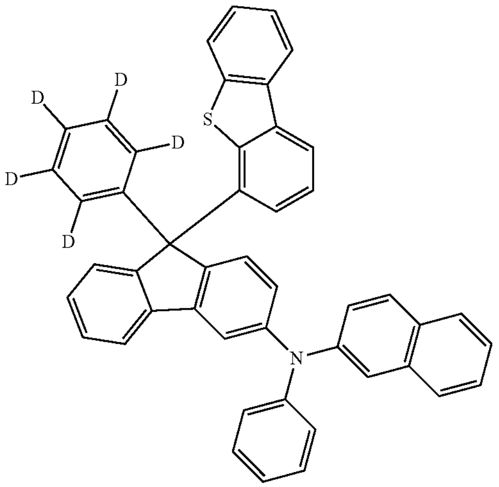
21
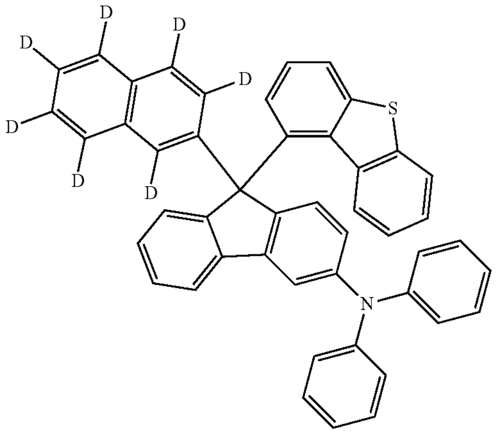
-continued
22
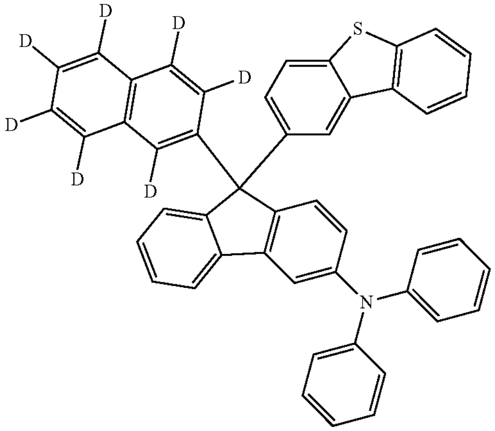
23
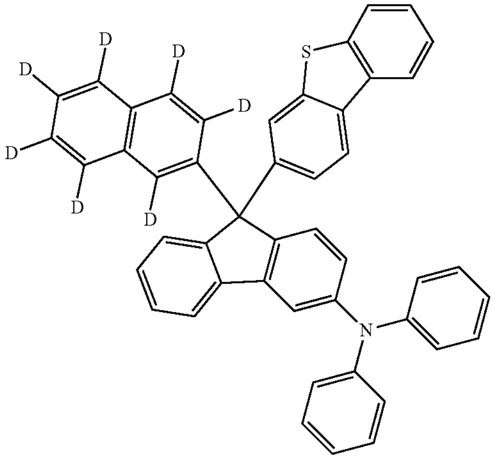
24
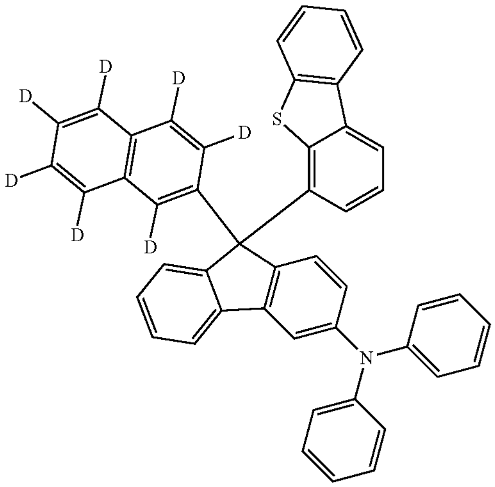

-continued
25
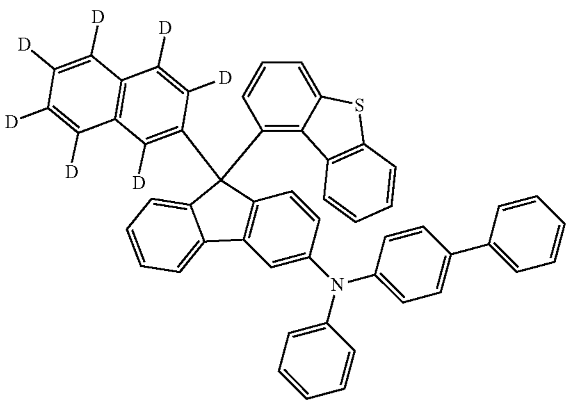
26
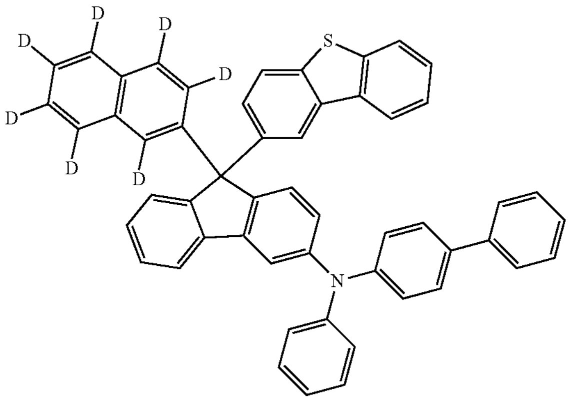
27
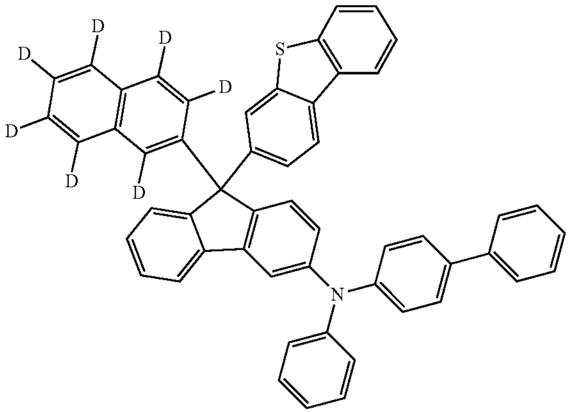
-continued
28
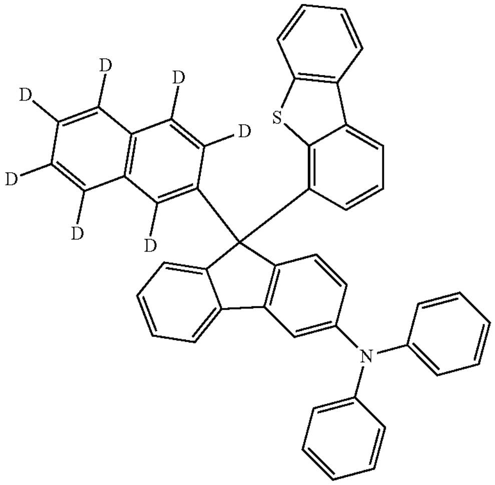
29
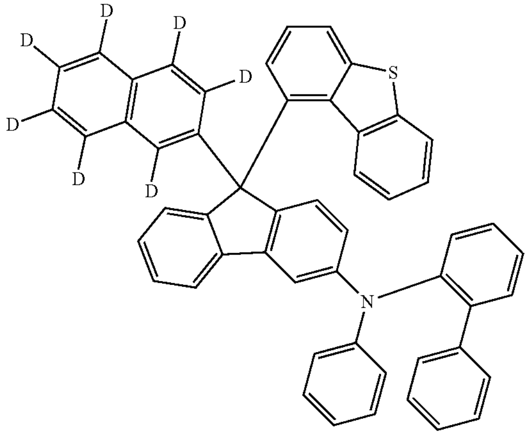
30
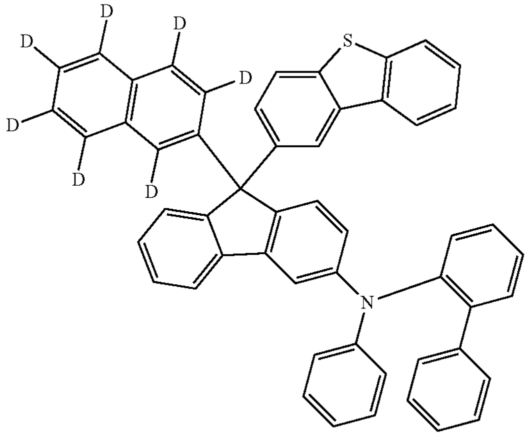

-continued
31
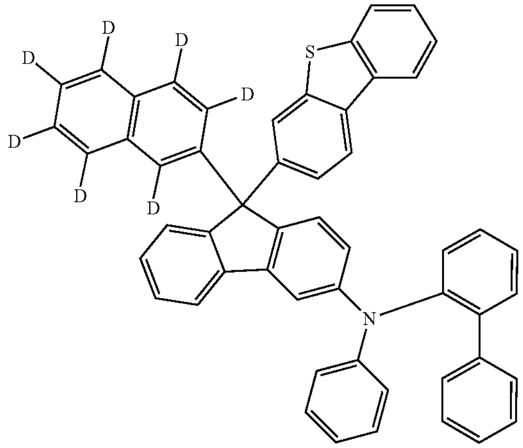
323
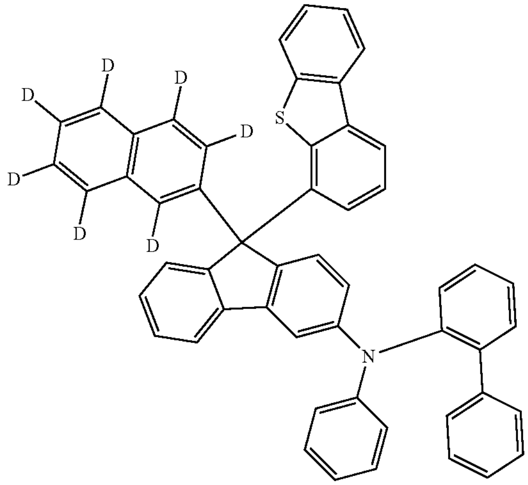
33
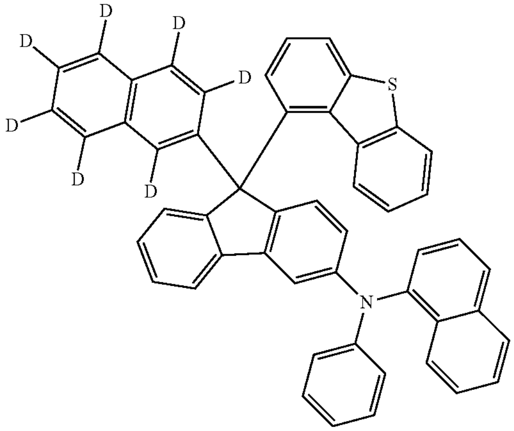
-continued
34
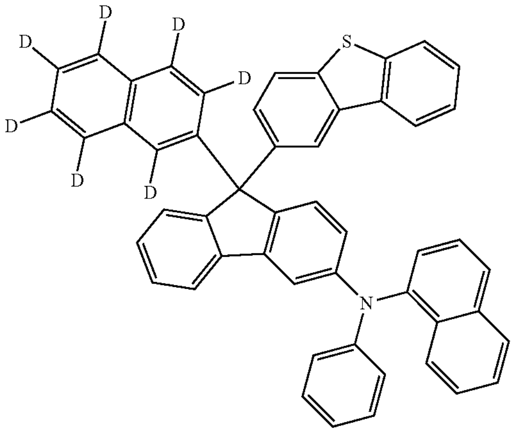
35
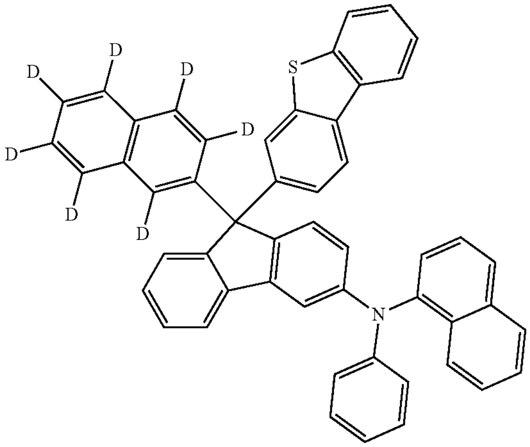
36
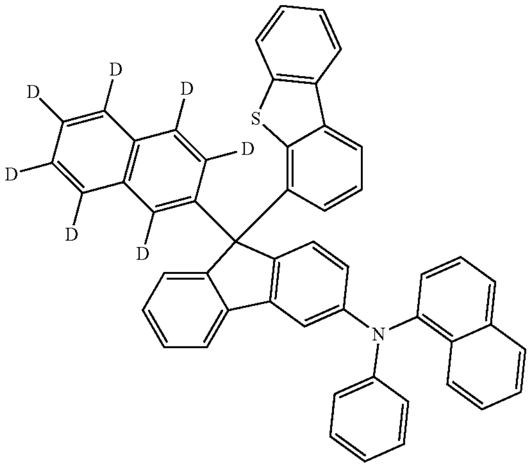

-continued
37
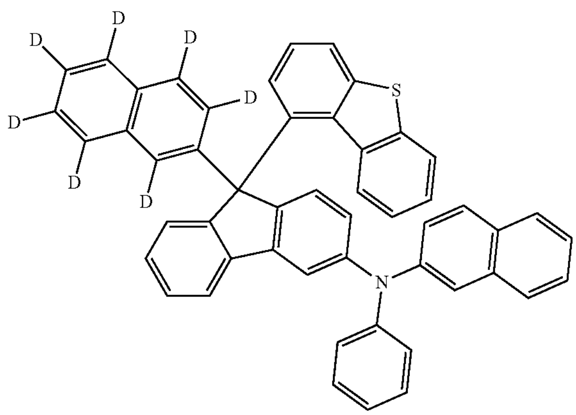
38
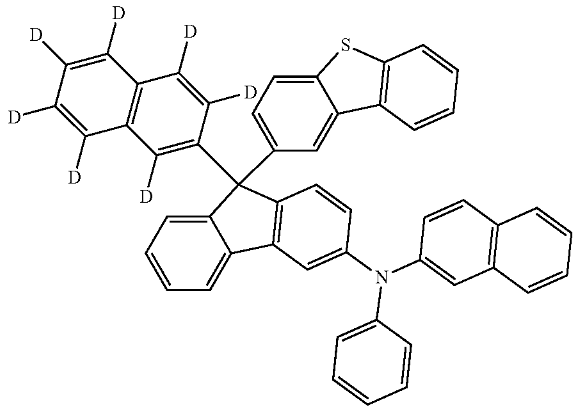
41
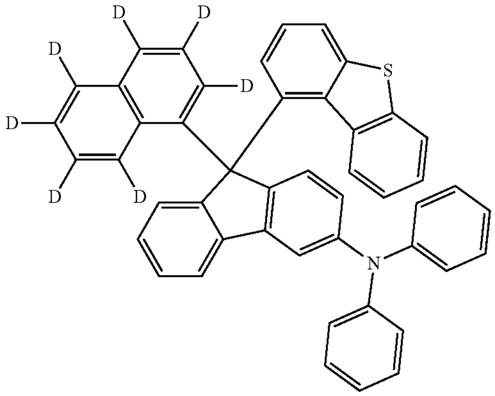
-continued
42
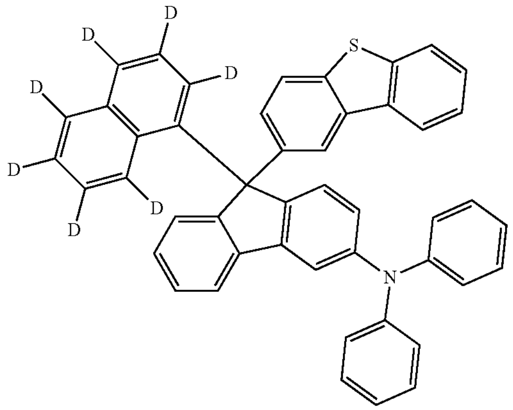
43
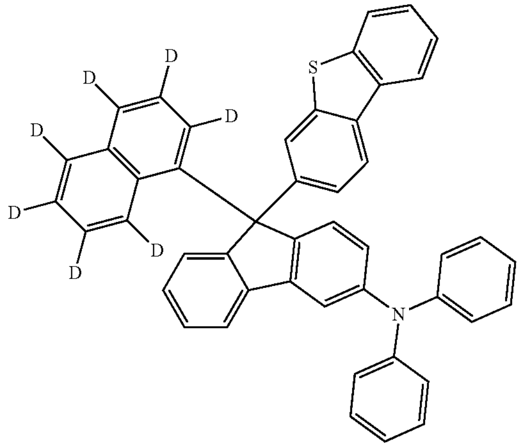
44
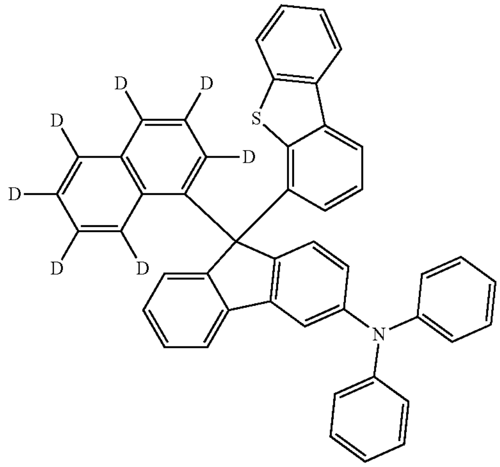

-continued
45
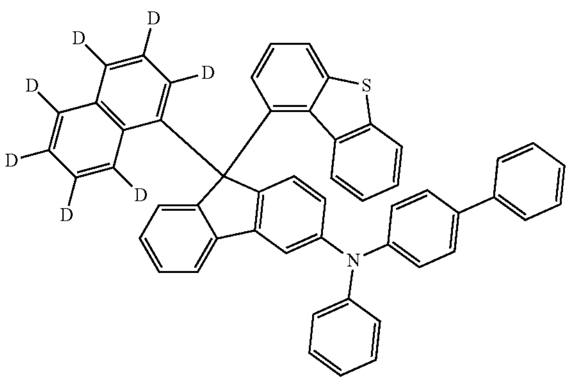
46
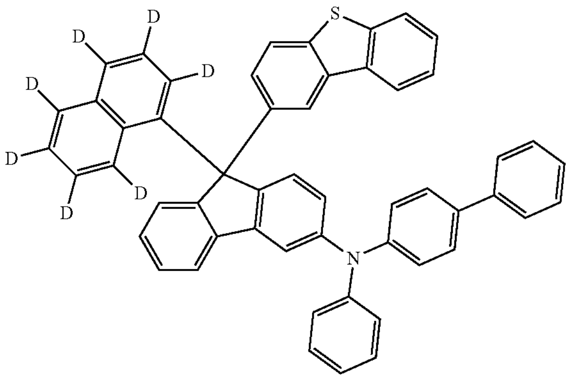
47
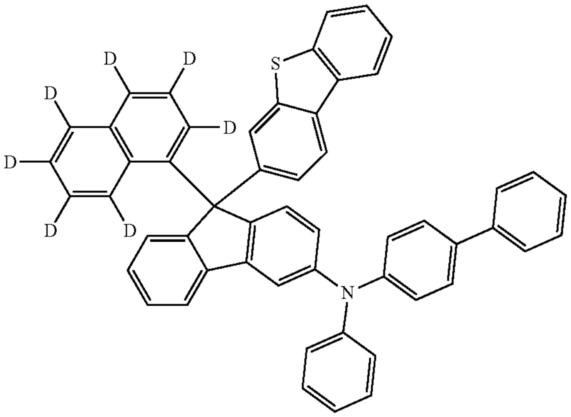
48
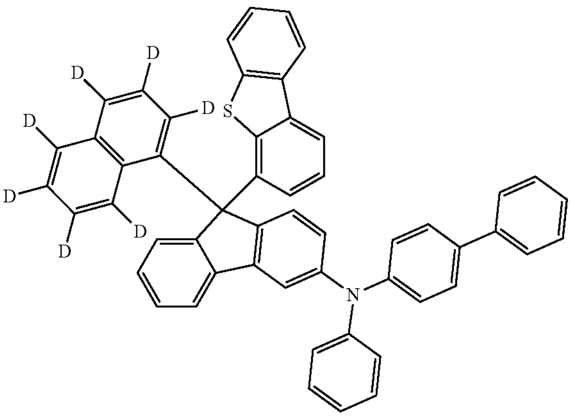
49
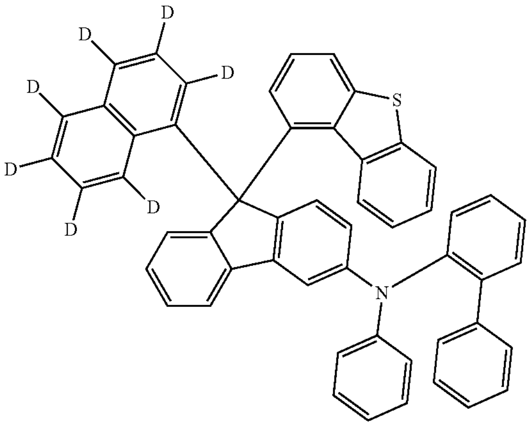
50
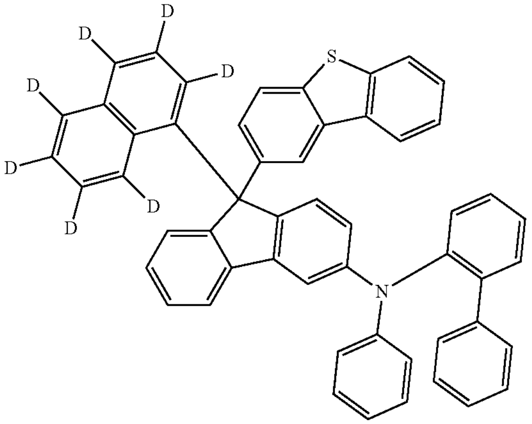

-continued
51
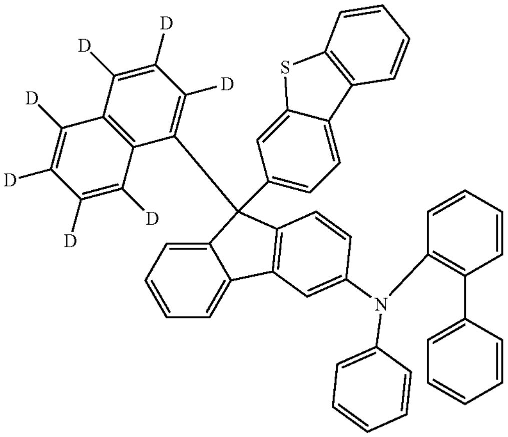
52
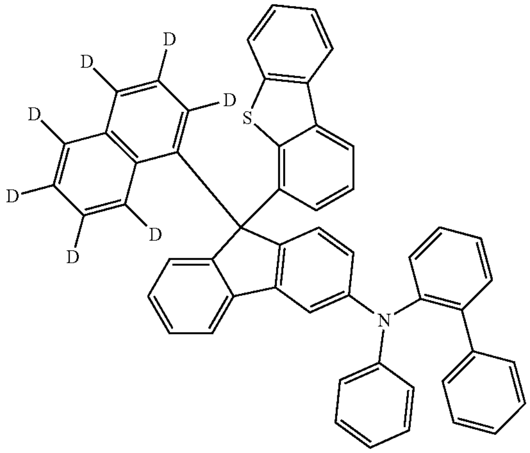
53
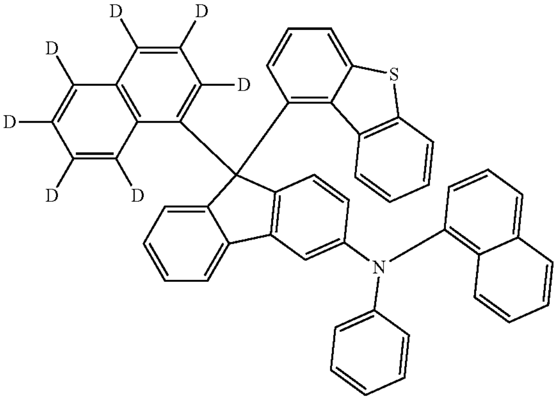
-continued
54
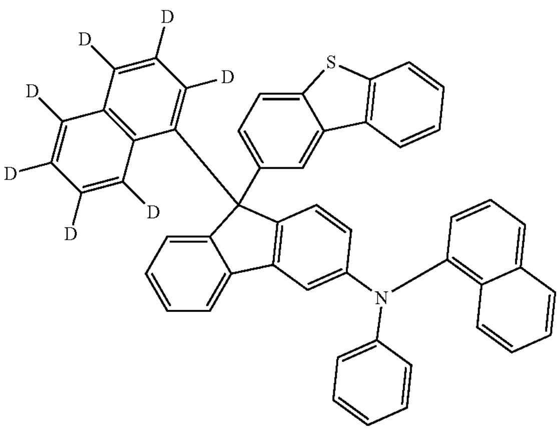
55
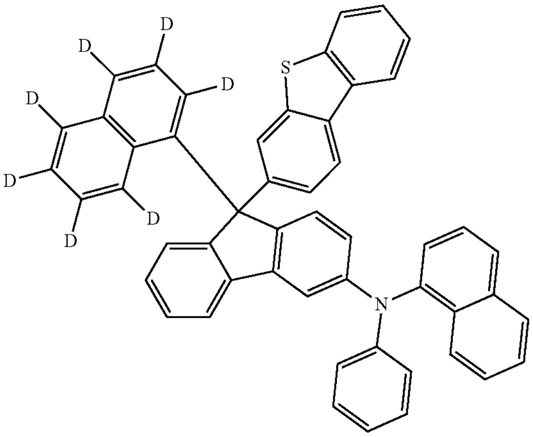
56
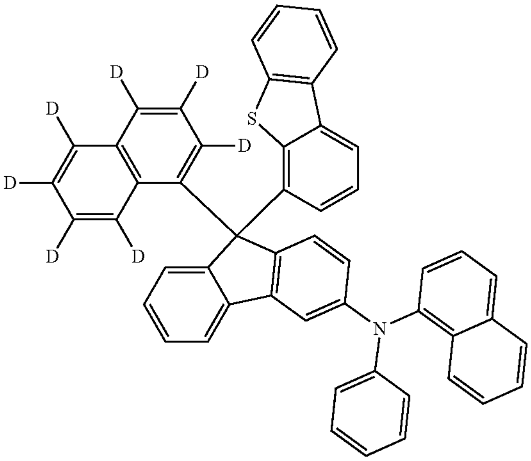

57
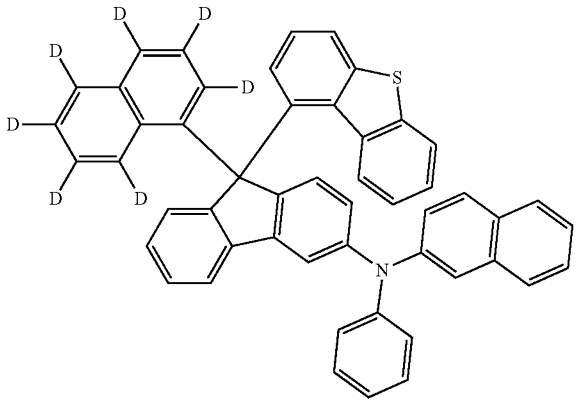
58
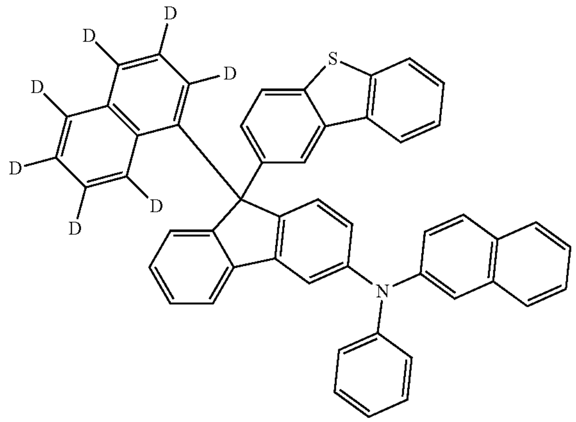
59
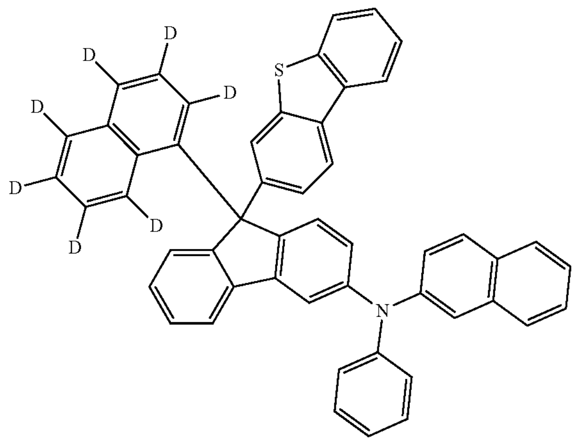
60
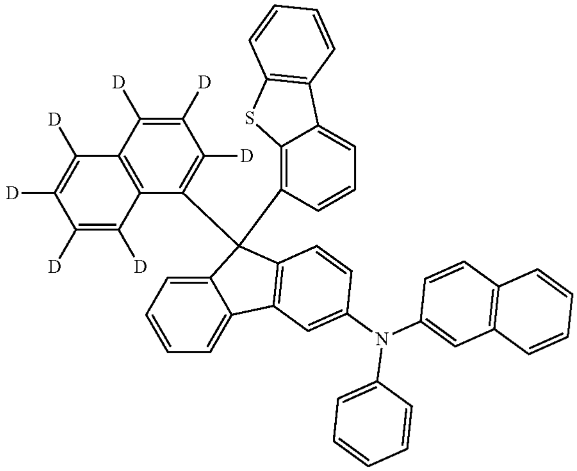
61
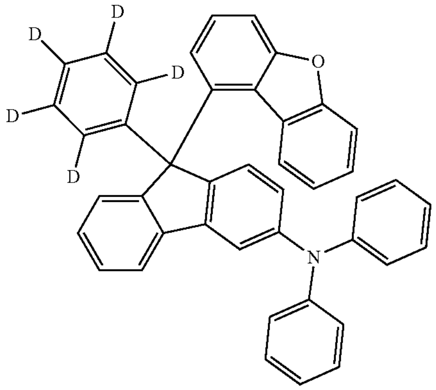
62
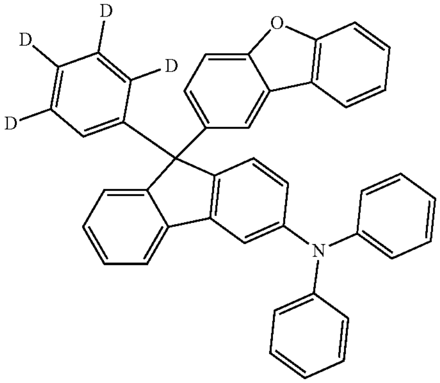

-continued
63
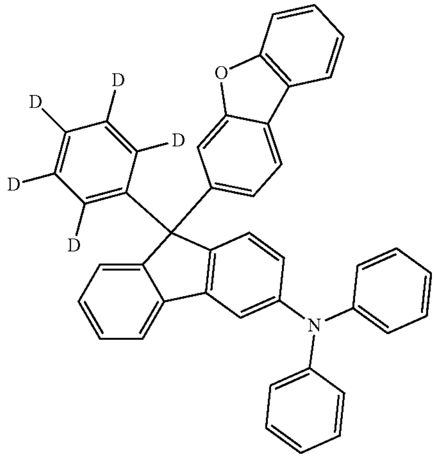
64
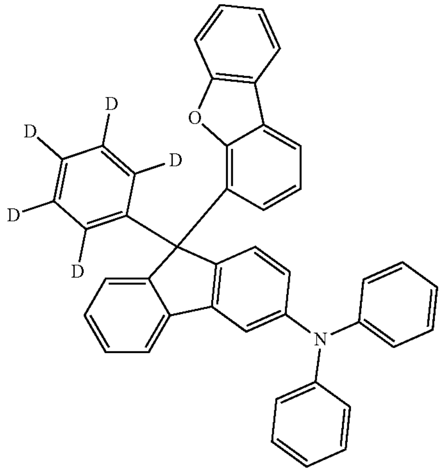
65
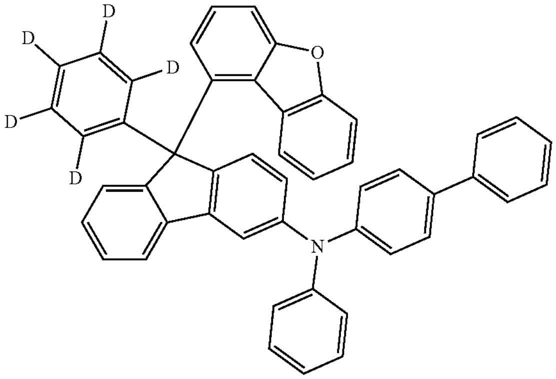
-continued
66
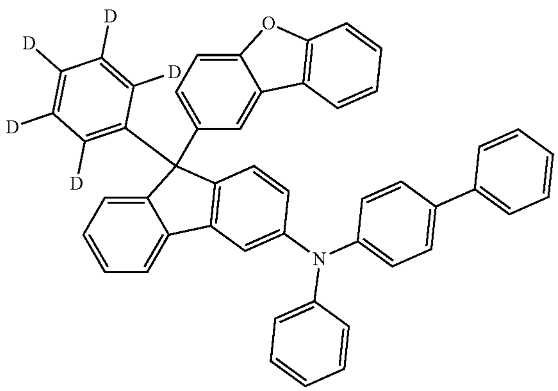
67
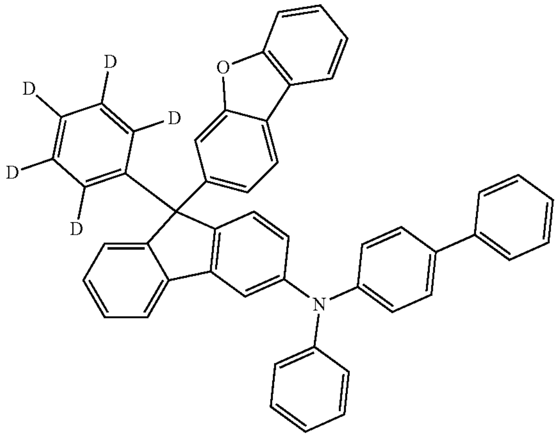
68
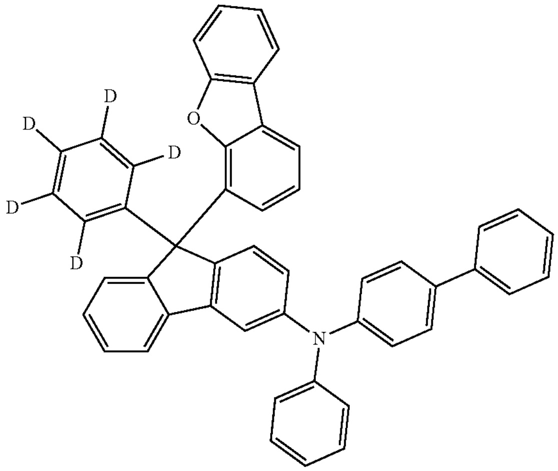

-continued
69
69
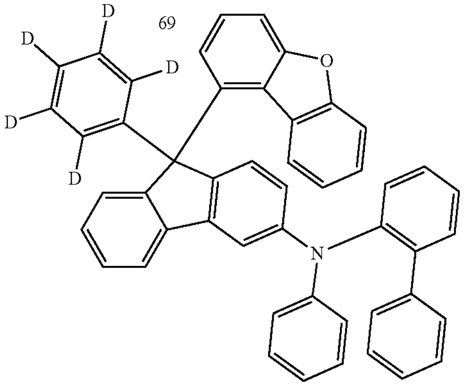
70
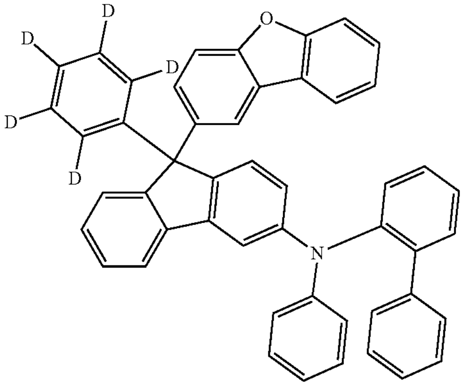
71
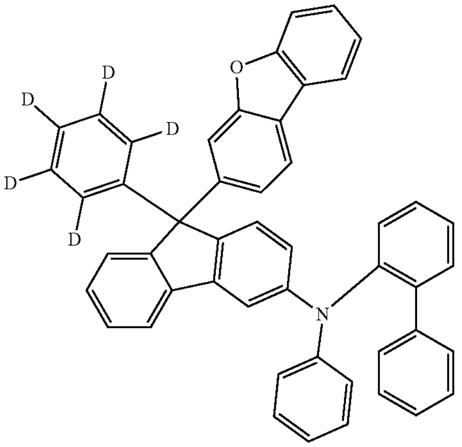
-continued
72
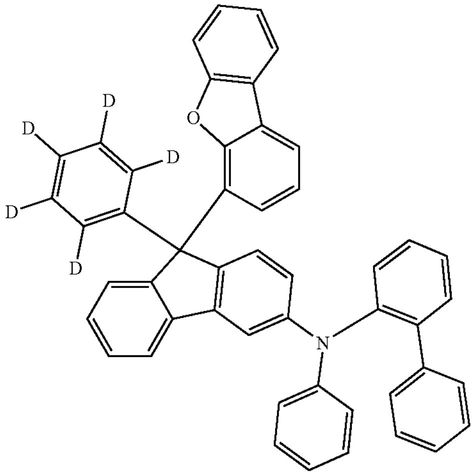
73
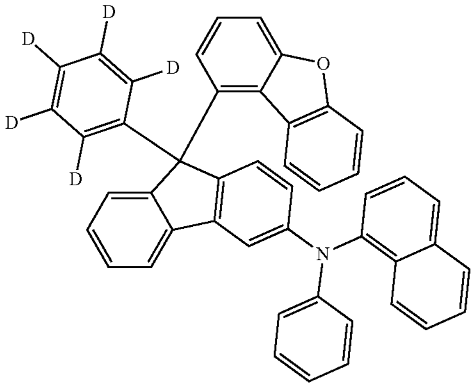
74
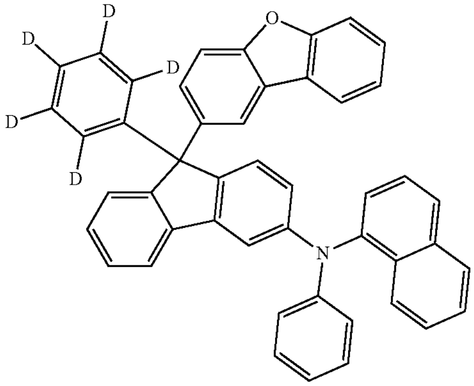

-continued
75
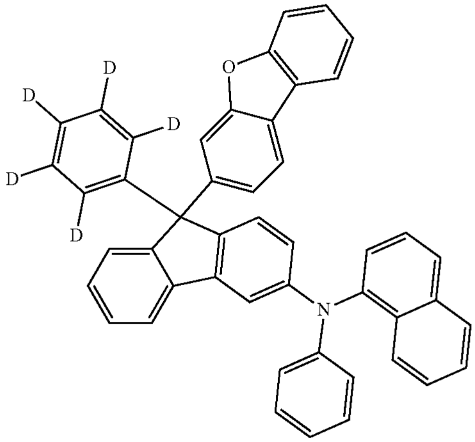
76
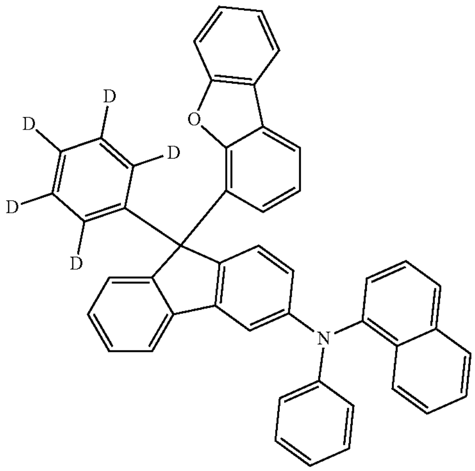
77
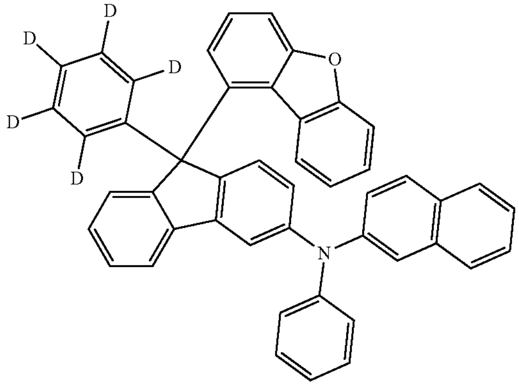
-continued
78
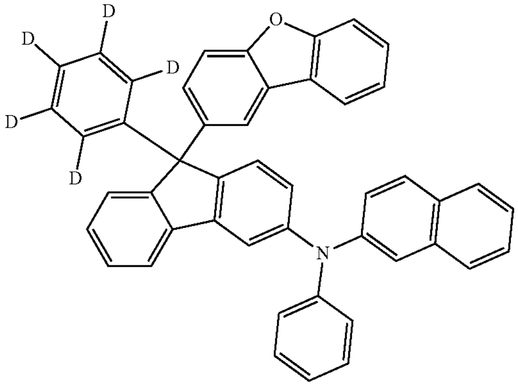
79
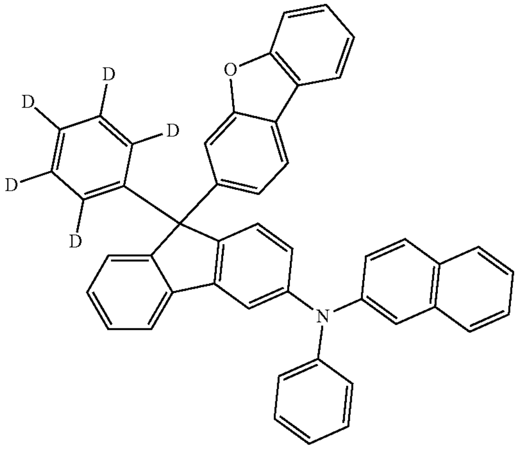
80
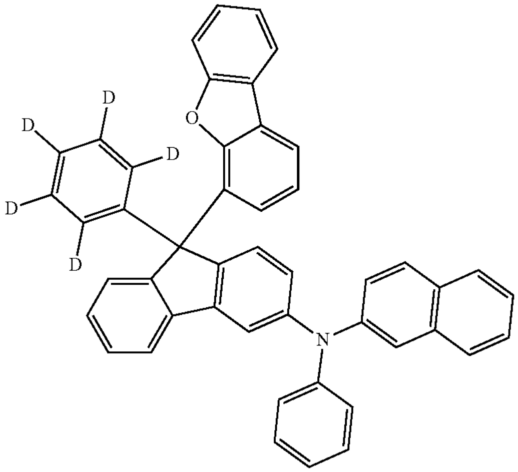

81
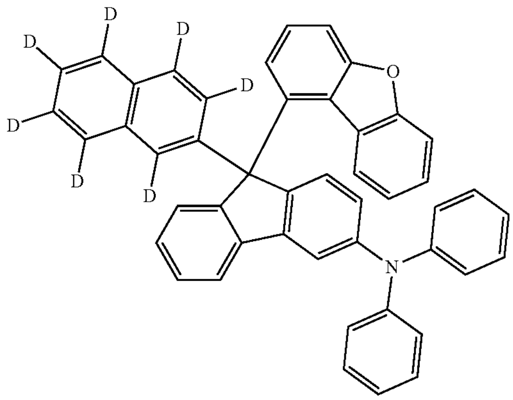
82
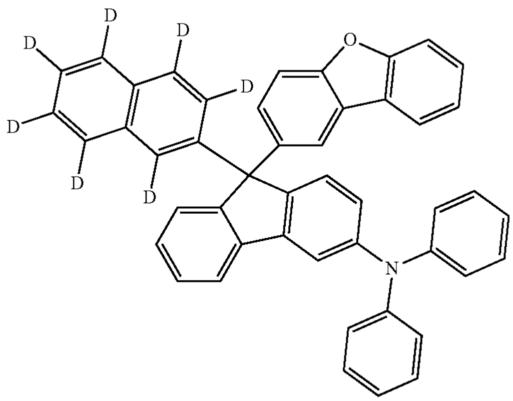
83
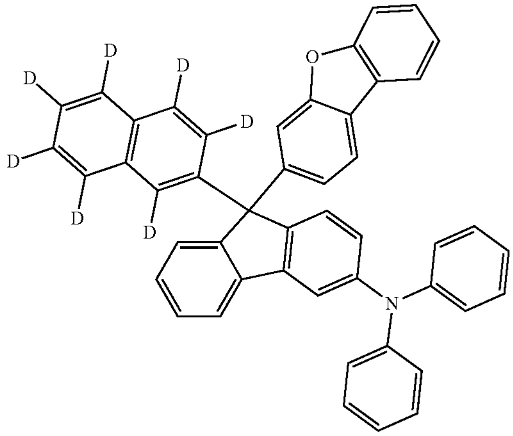
84
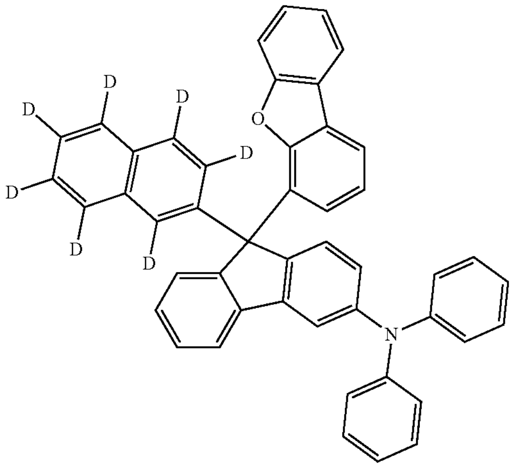
85
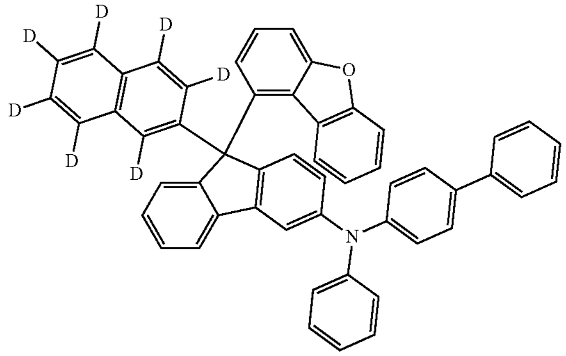
86
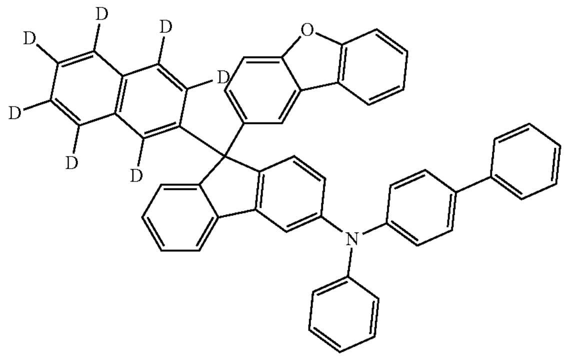
87
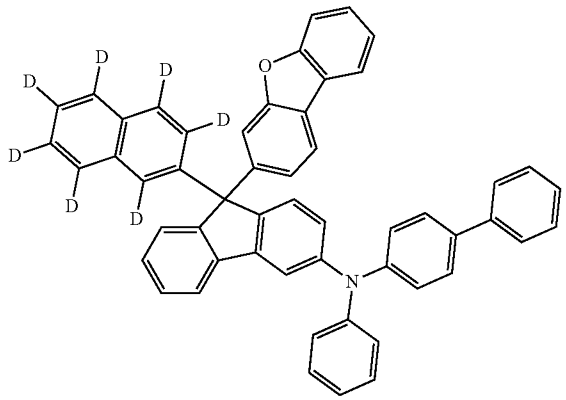

-continued
88
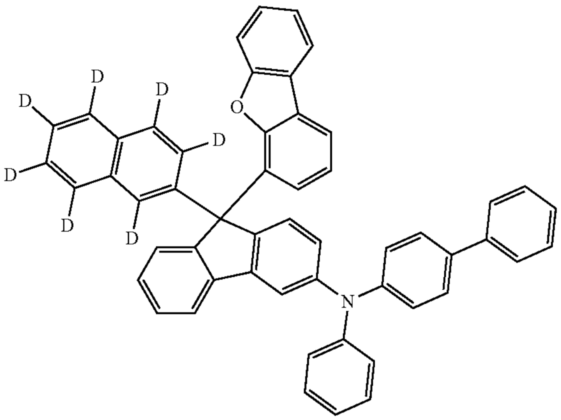
89
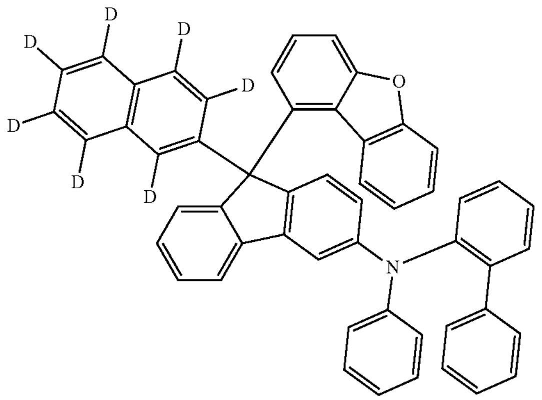
90
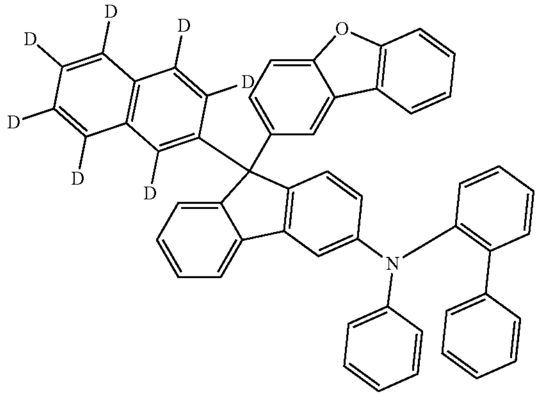
-continued
91
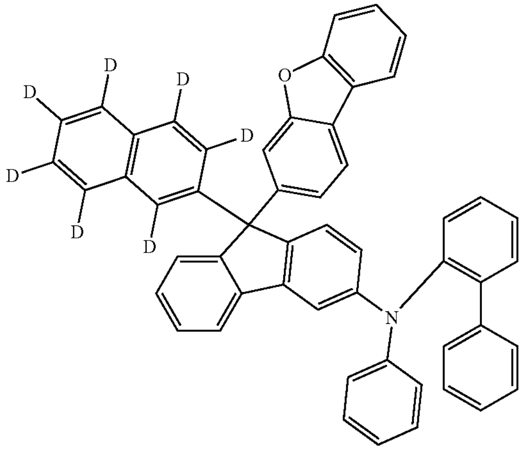
92
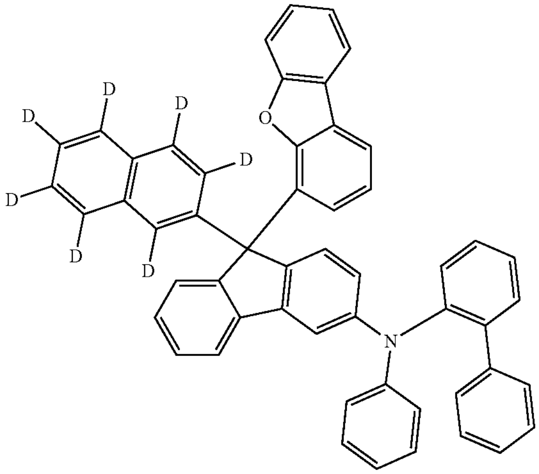
93
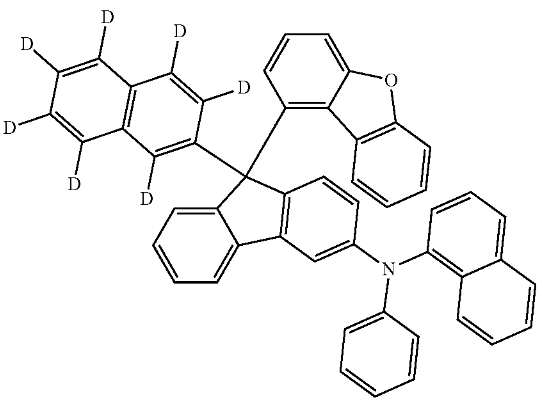

-continued
94
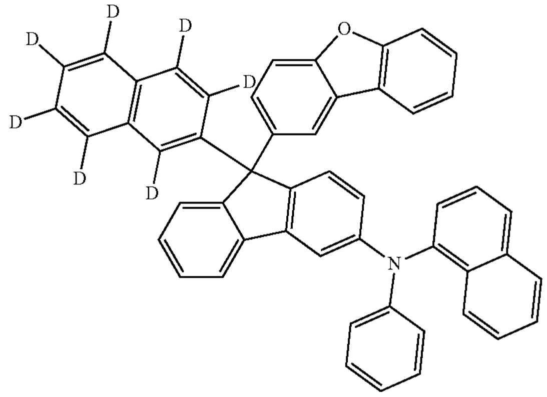
97
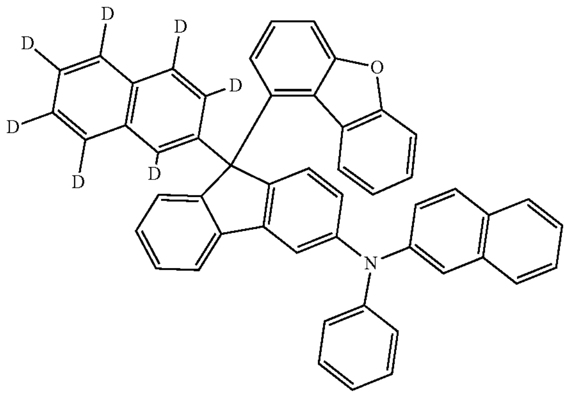
95
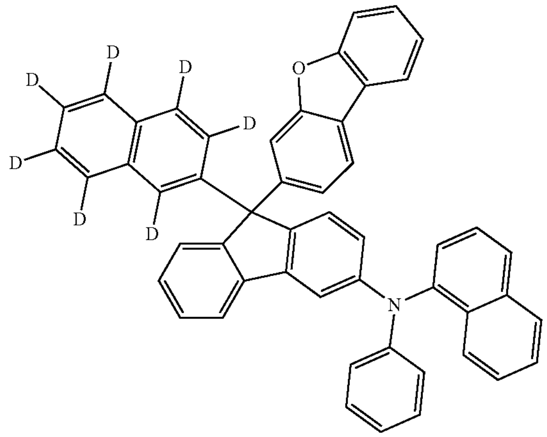
98
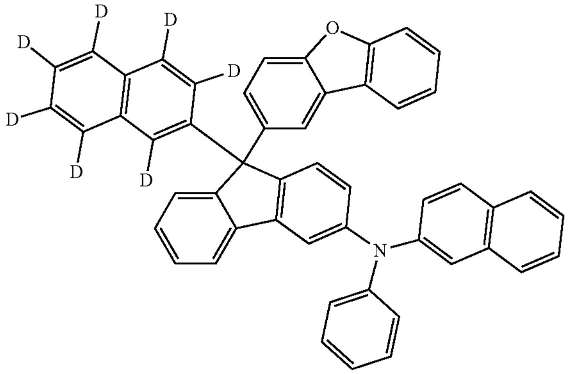
96
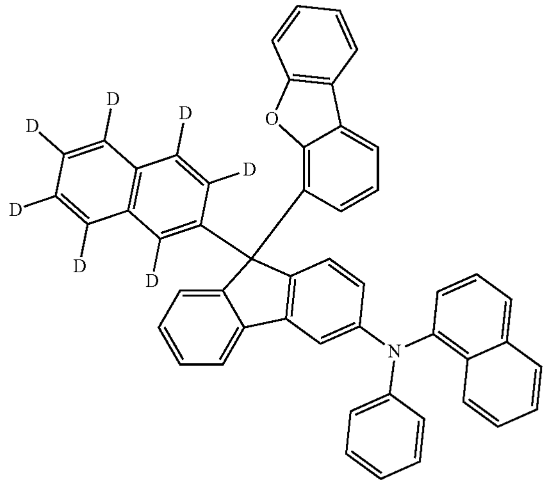
99
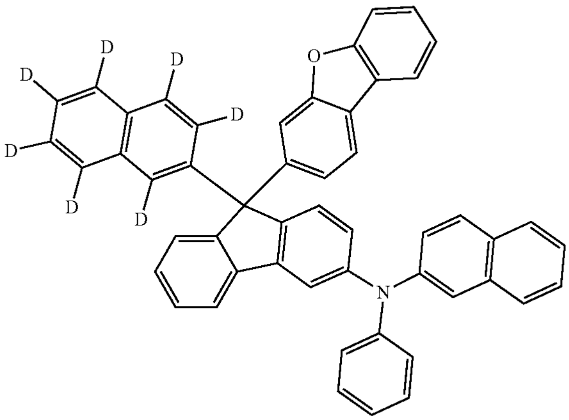

-continued
100
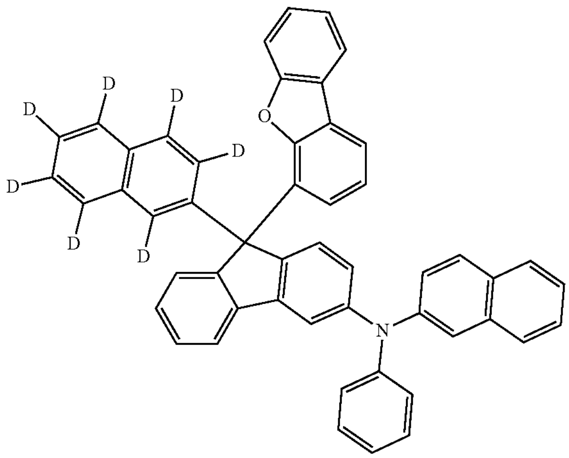
101
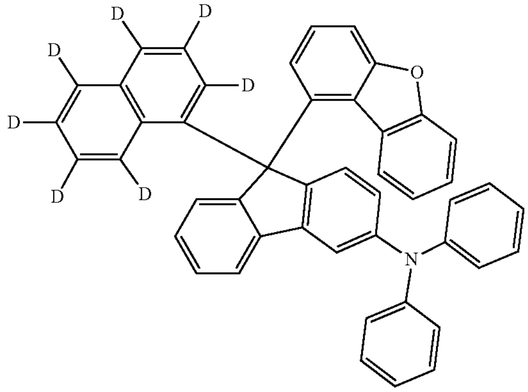
102
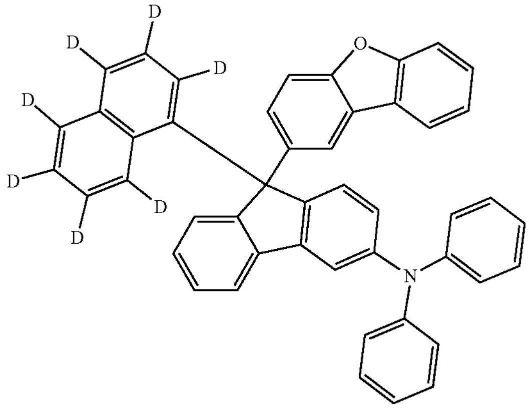
-continued
103
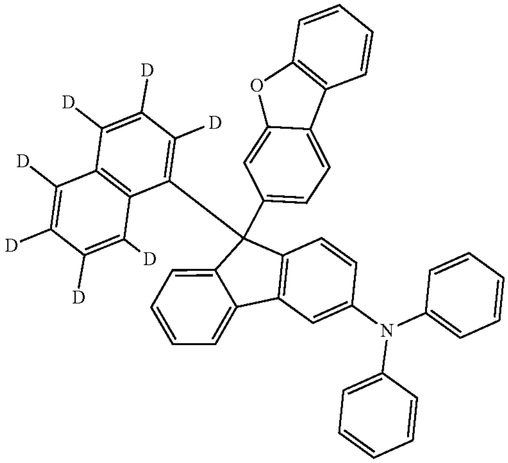
104
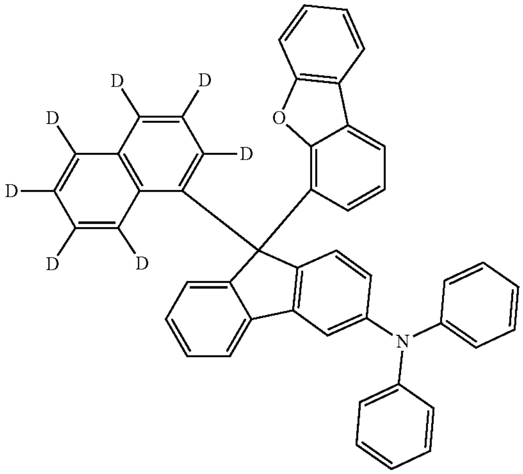
105
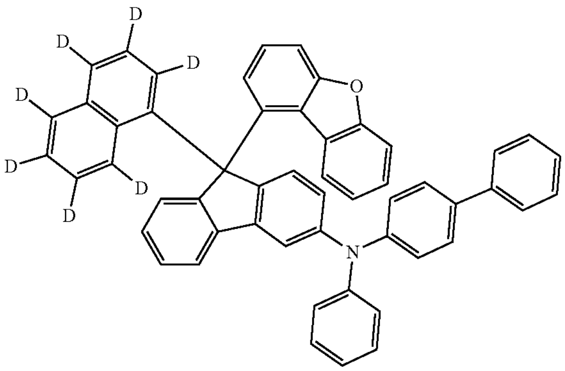

-continued
106
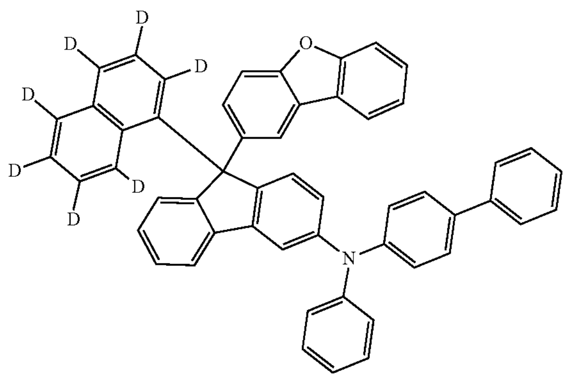
107
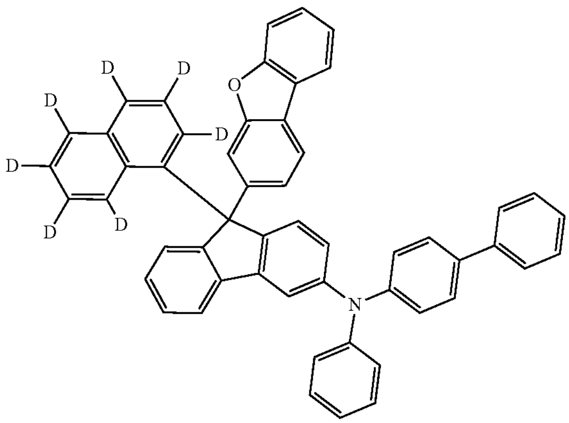
108
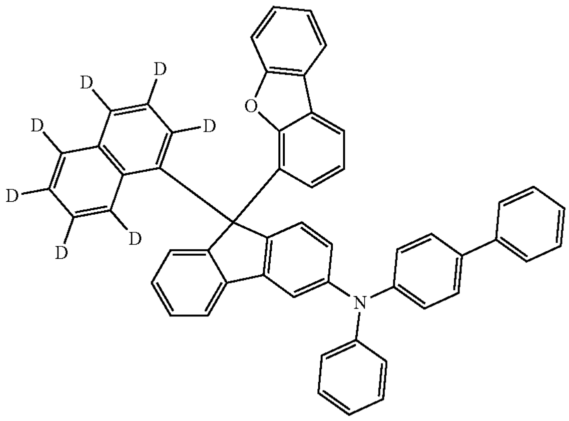
-continued
109
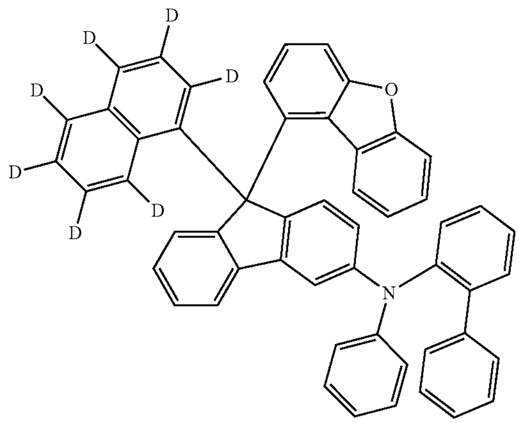
110
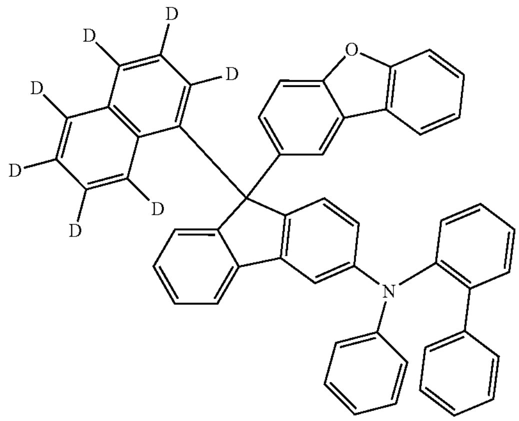
111
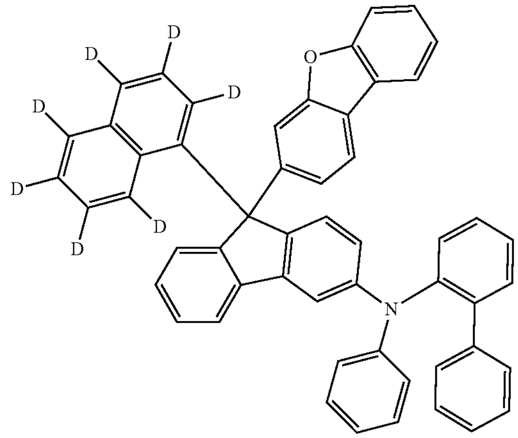

-continued
112
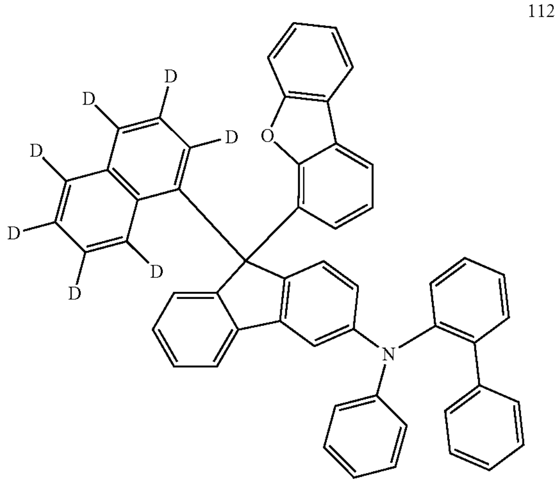
113
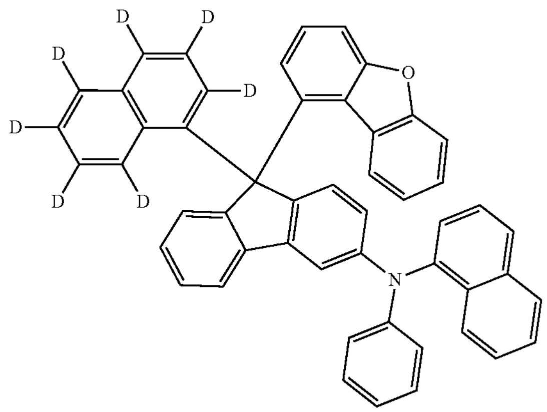
114
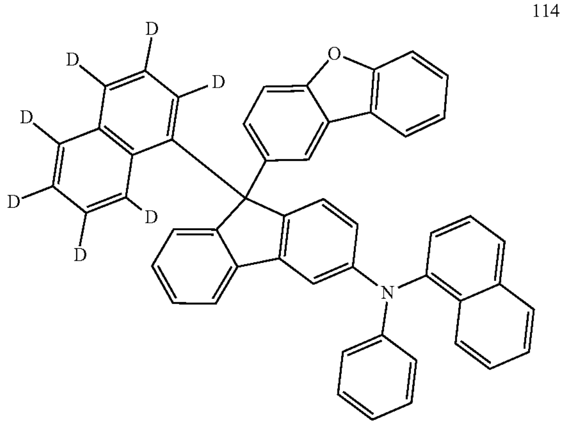
-continued
115
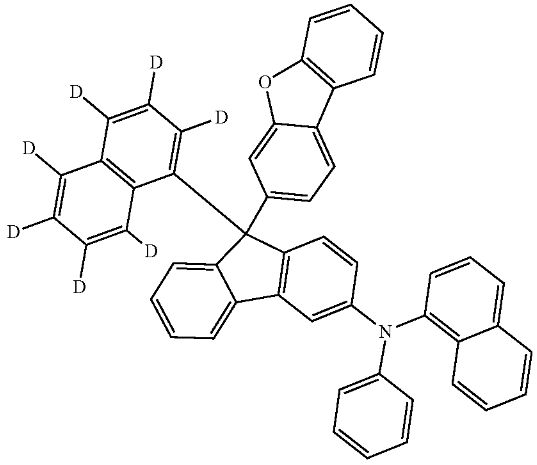
116
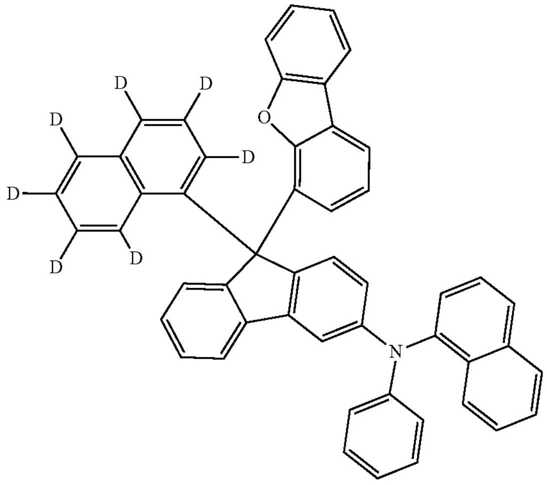
117
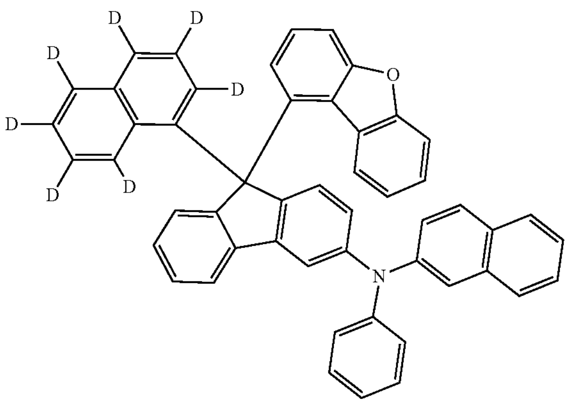

-continued
118
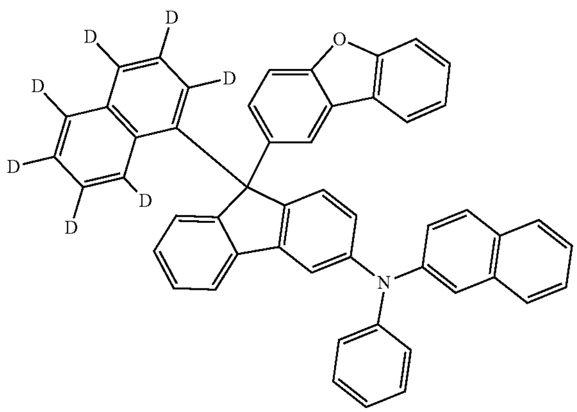
121
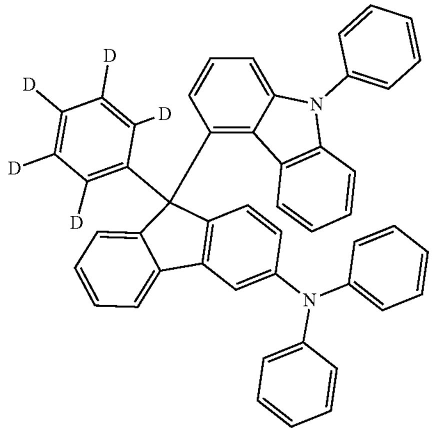
119
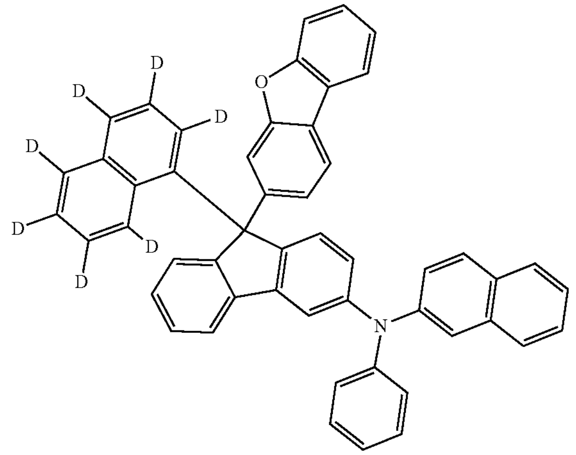
122
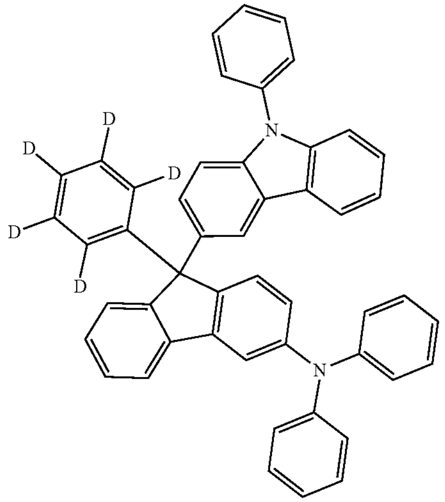
120
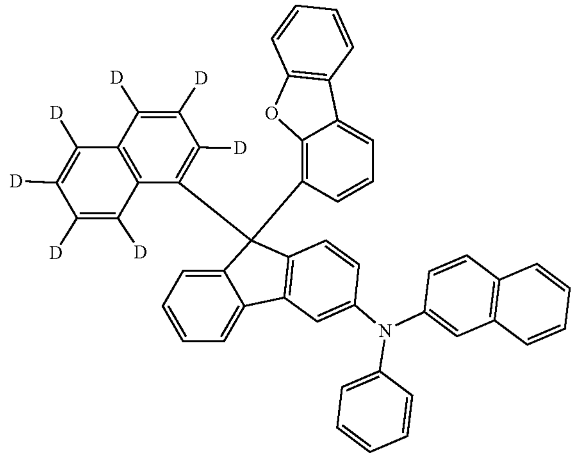
123
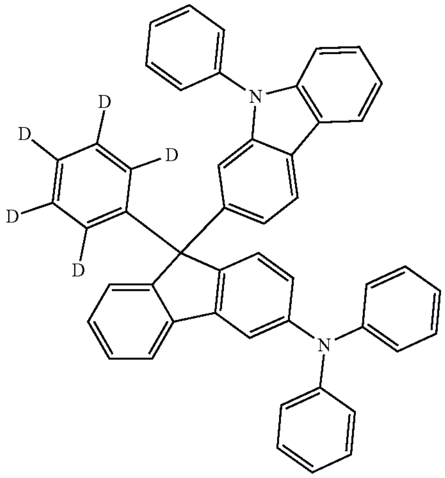

-continued
124
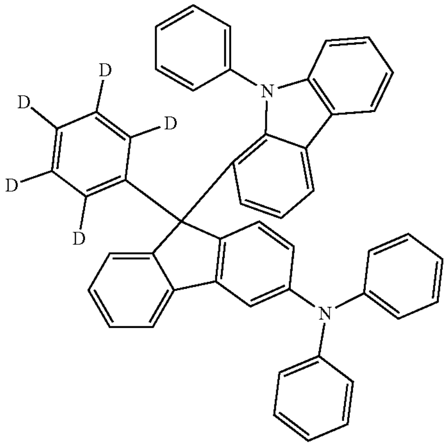
125
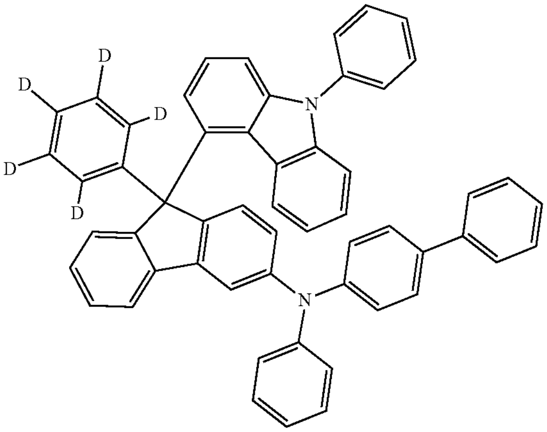
126
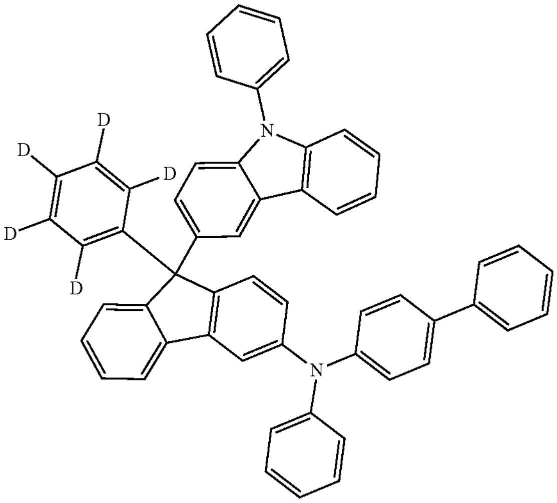
-continued
127
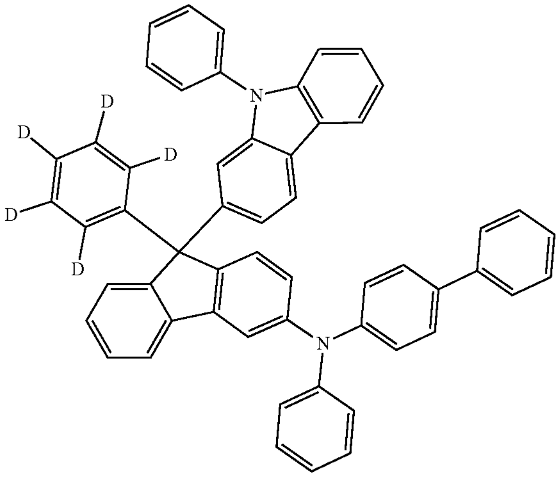
128
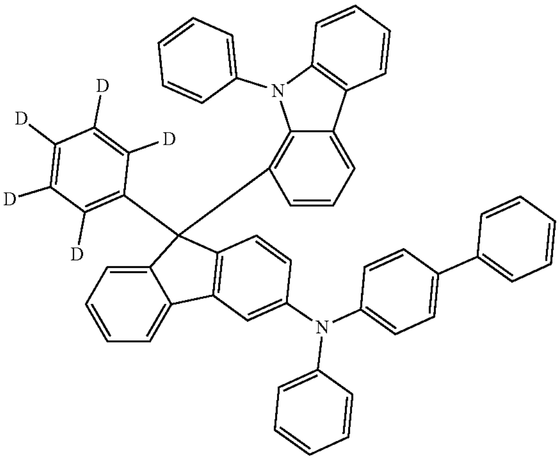
129
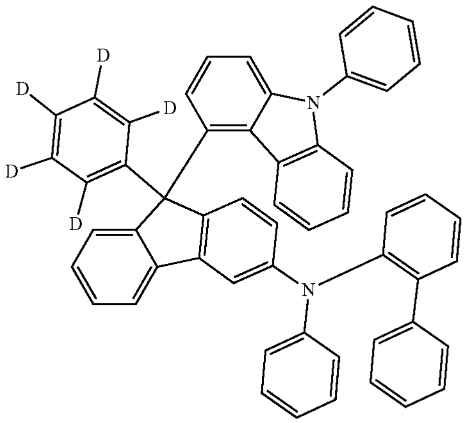

-continued
130
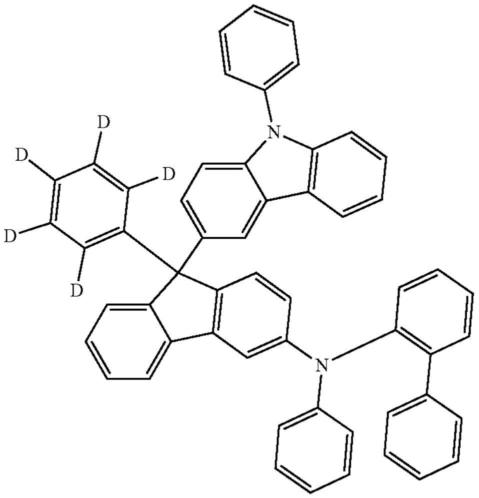
131
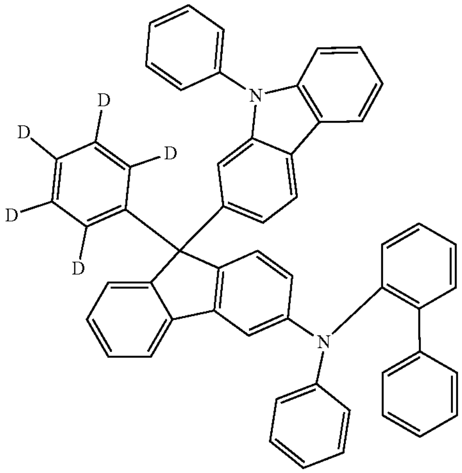
132
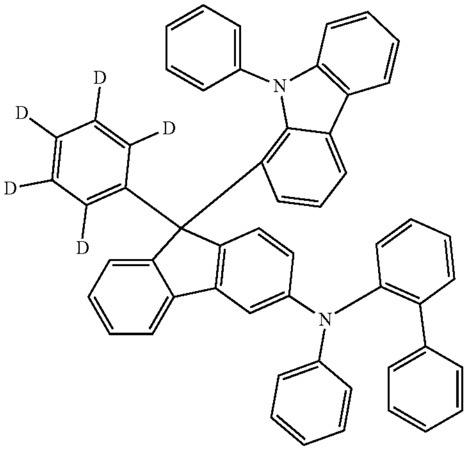
-continued
133
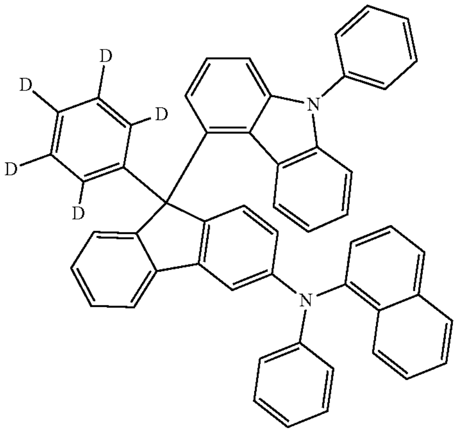
134
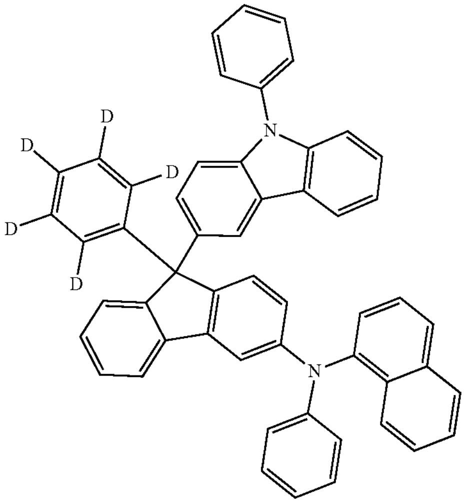
135
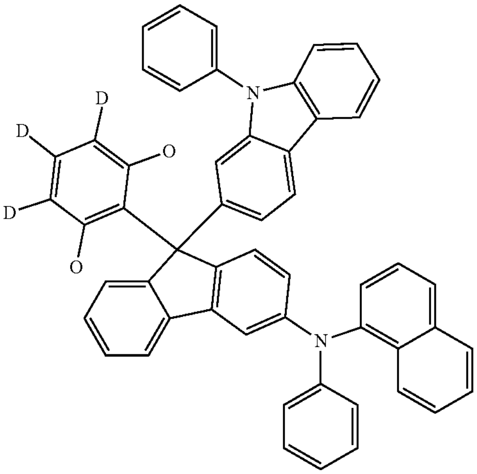

-continued
136
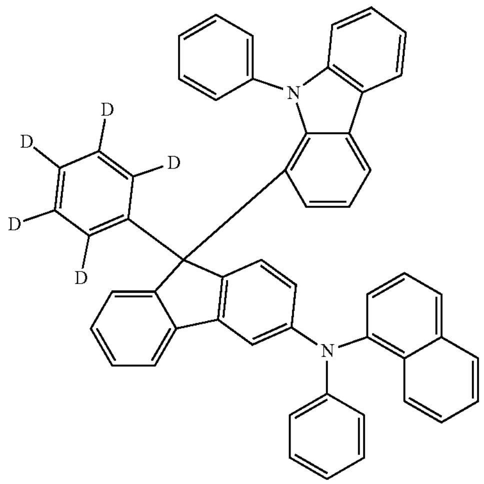
137
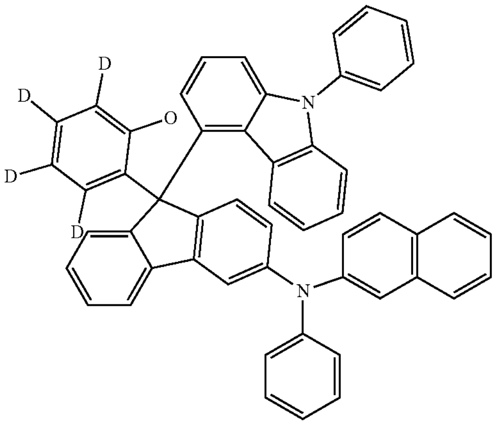
138
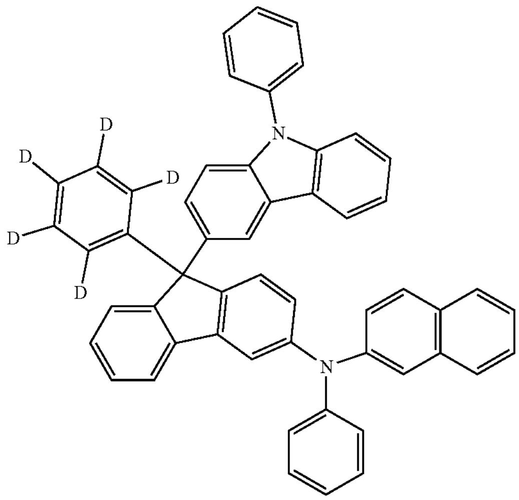
-continued
139
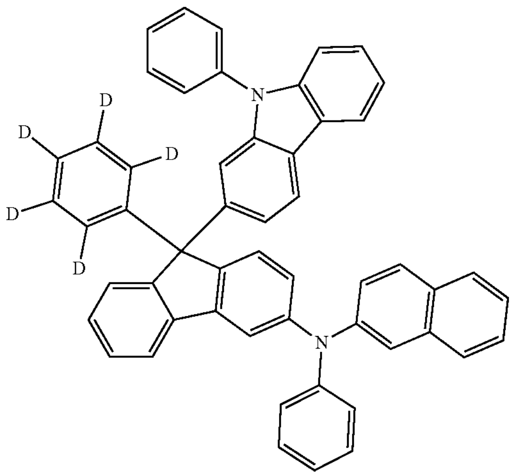
140
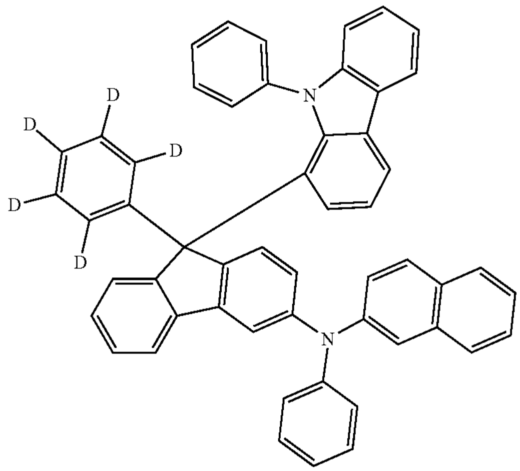
141
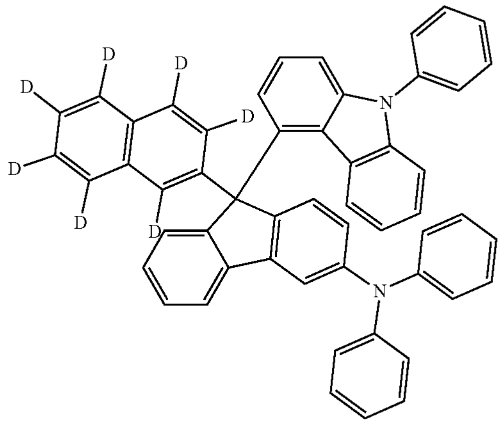

-continued
142
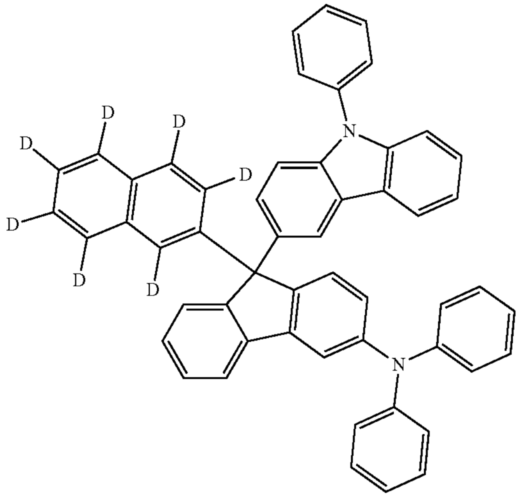
143
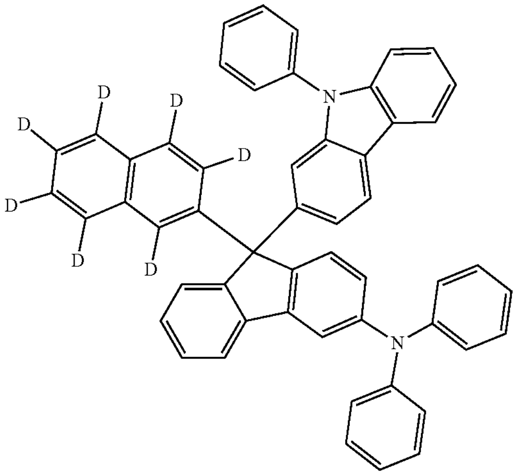
144
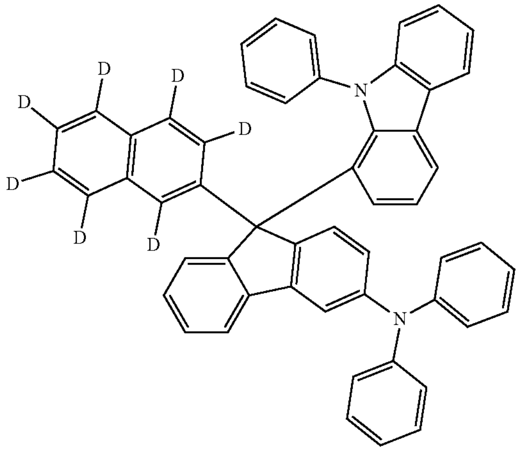
-continued
145
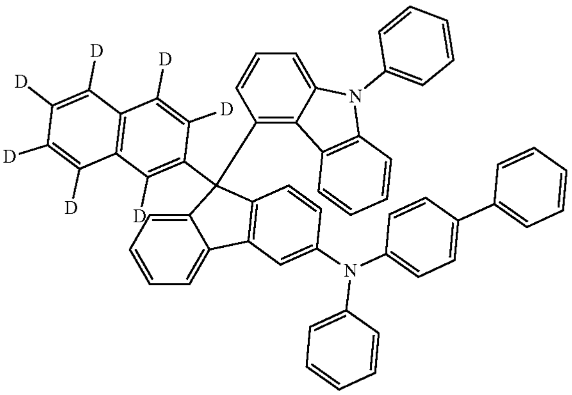
146
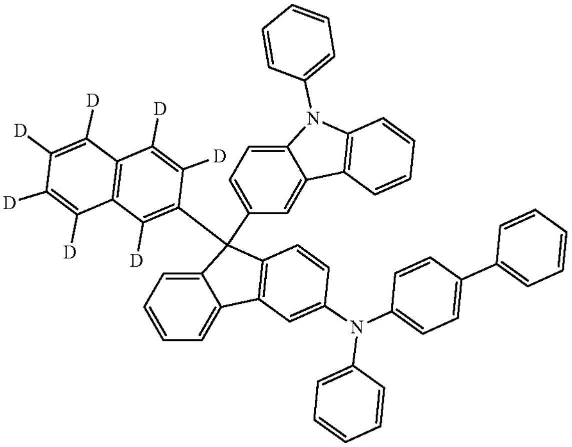
147
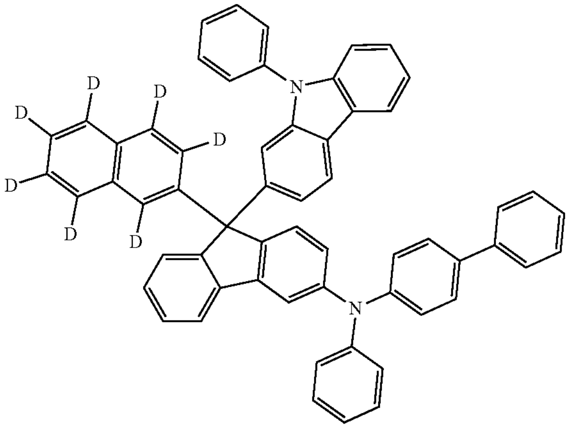

-continued
148
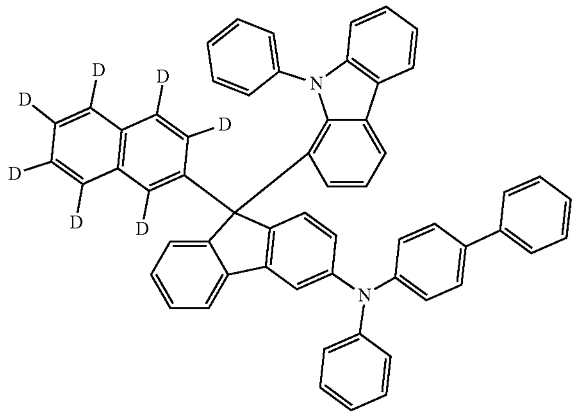
149
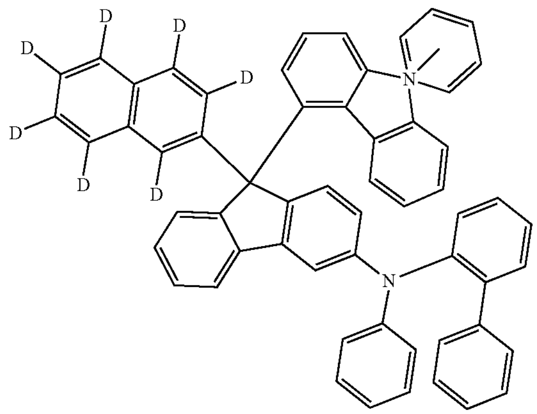
150
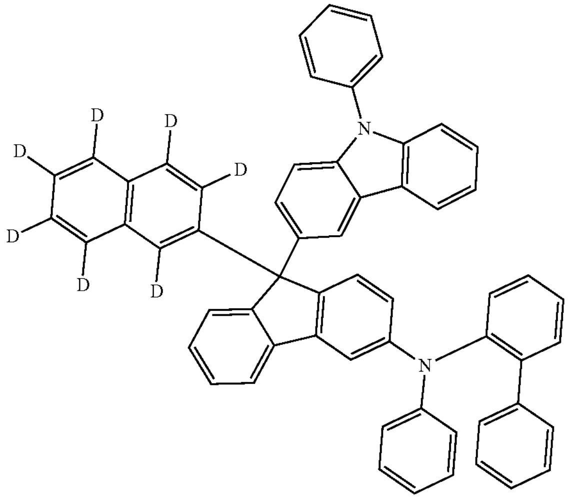
-continued
151
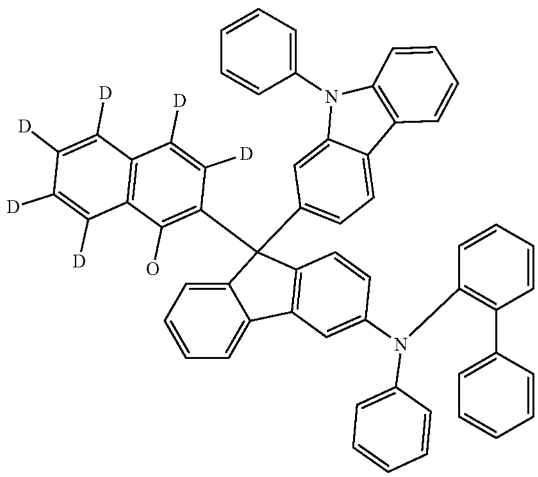
152
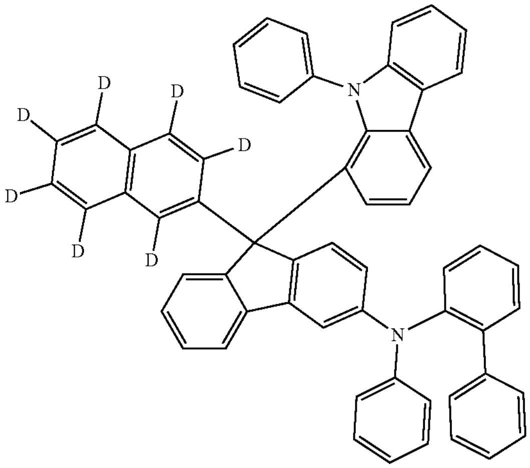
153
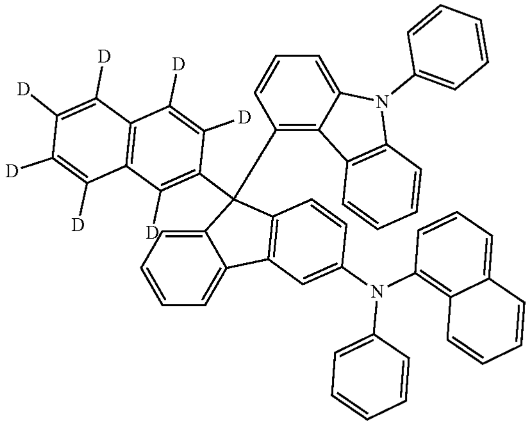

-continued
154
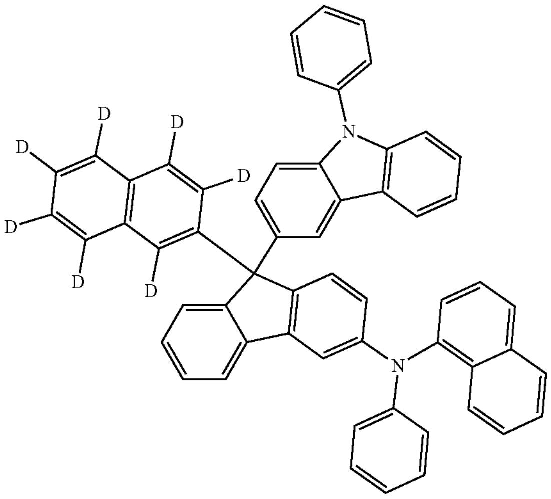
155
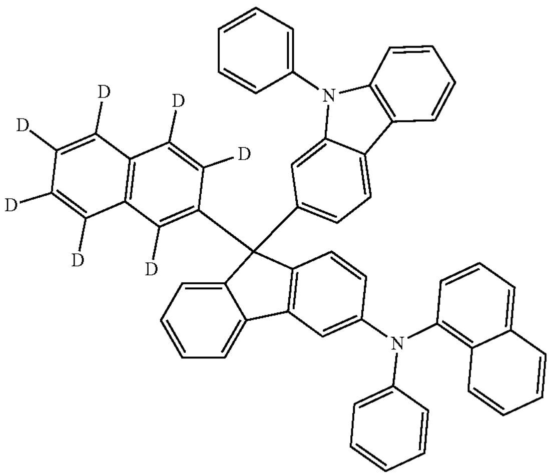
156
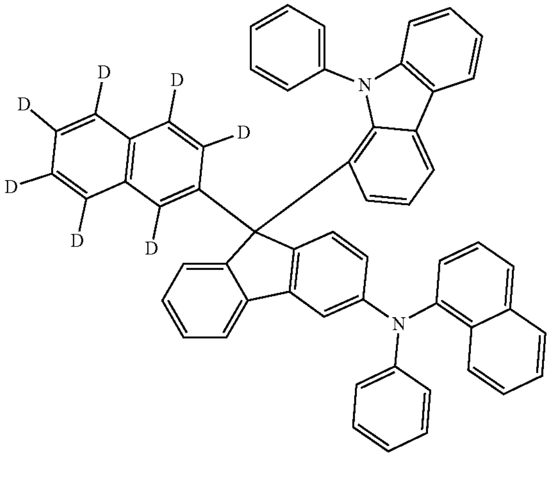
157
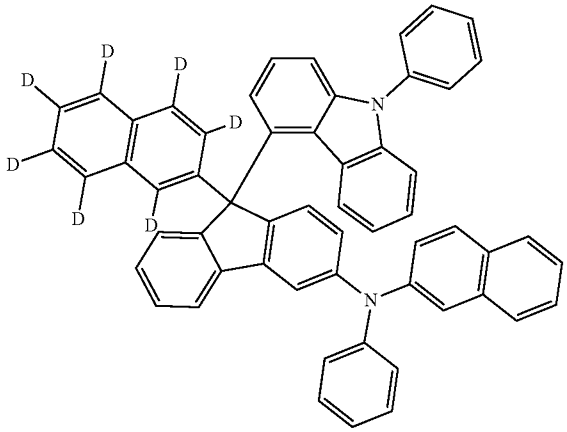
158
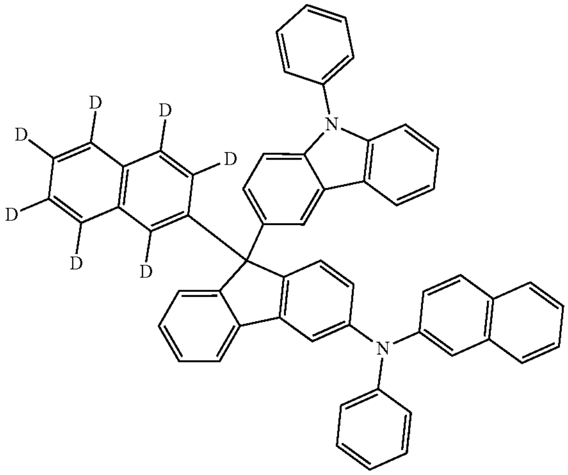
159
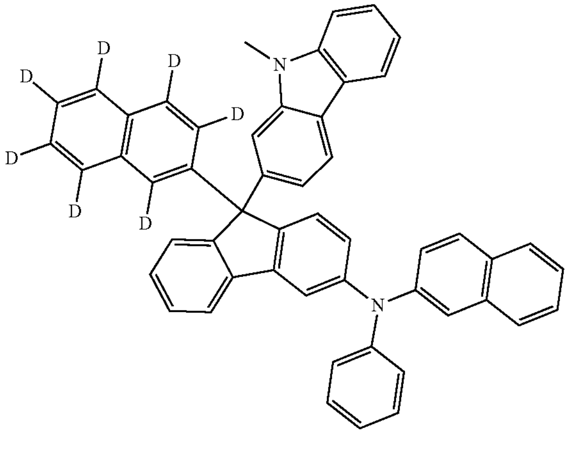

-continued
160
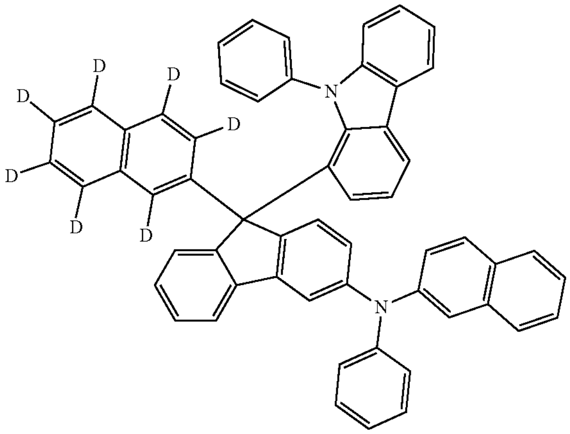
161
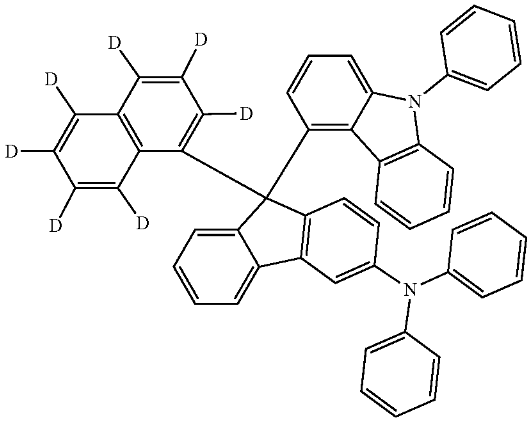
162
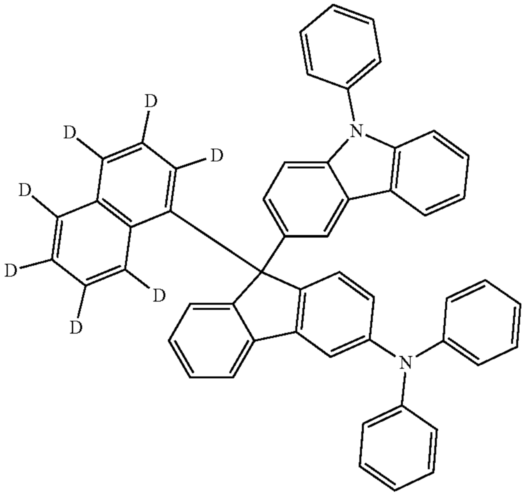
-continued
163
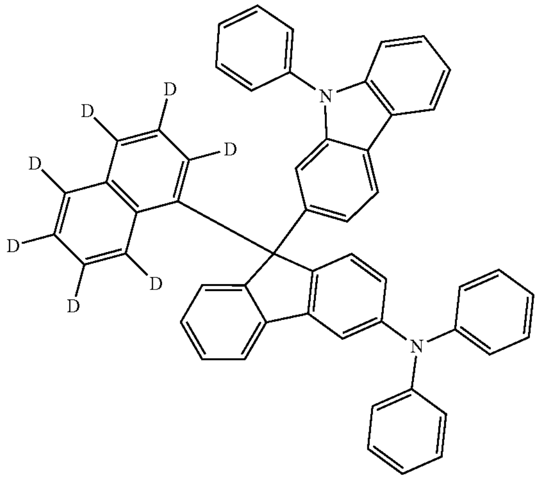
164
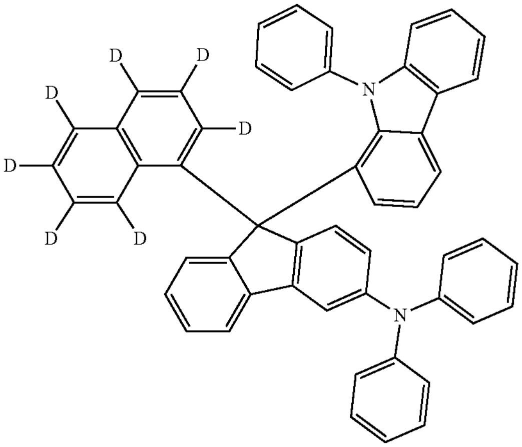
165
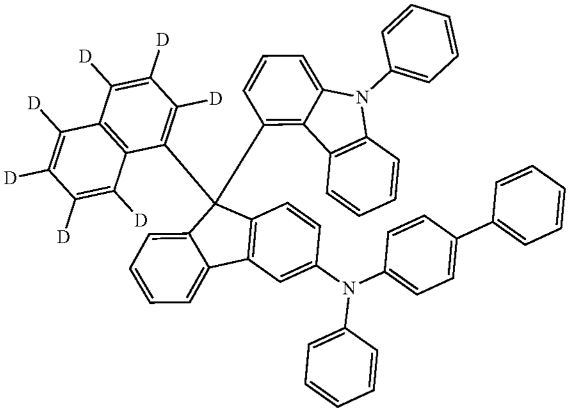

-continued
166
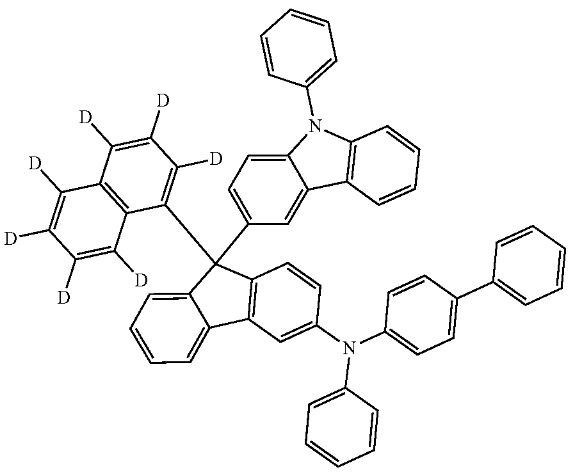
167
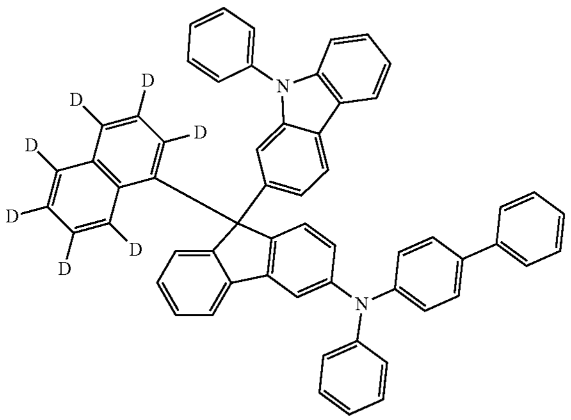
168
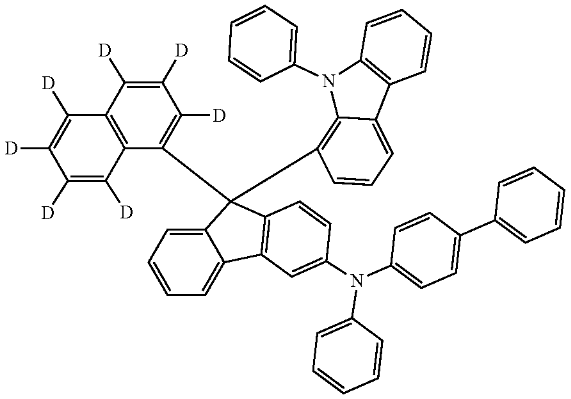
-continued
169
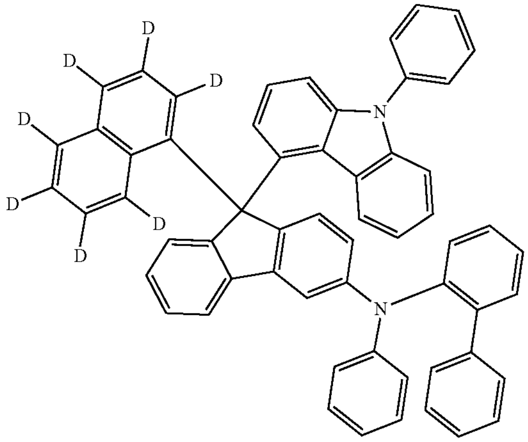
170
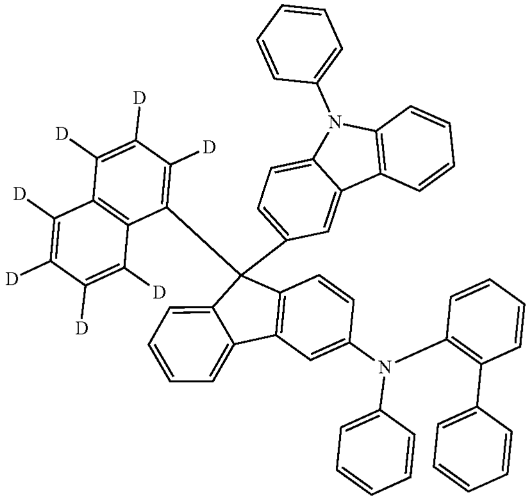
171
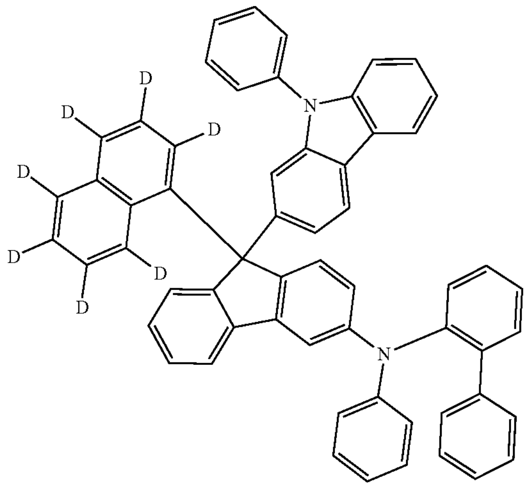

-continued
172
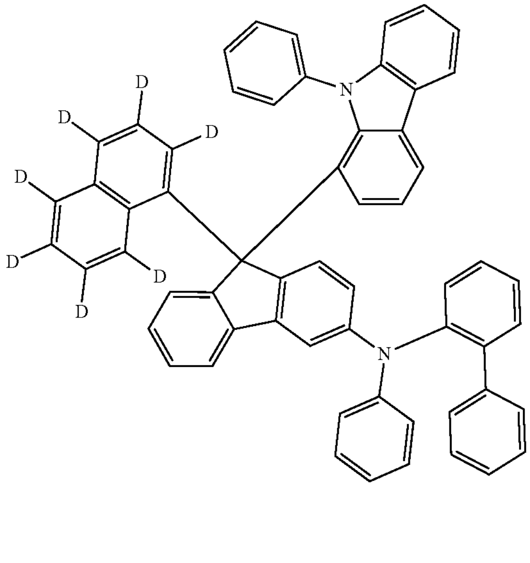
173
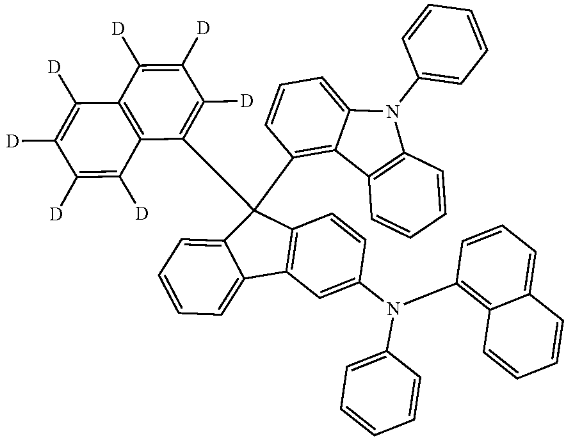
174
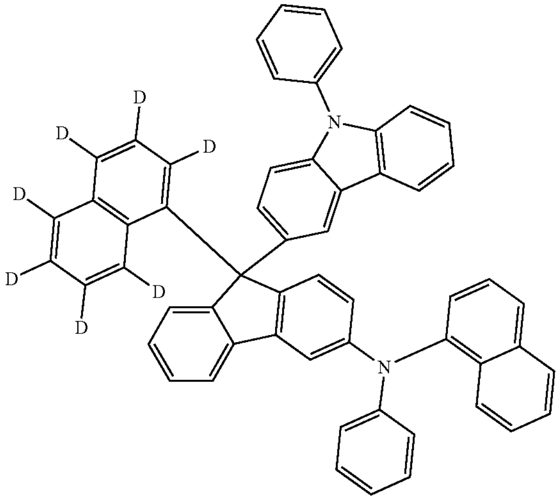
-continued
175
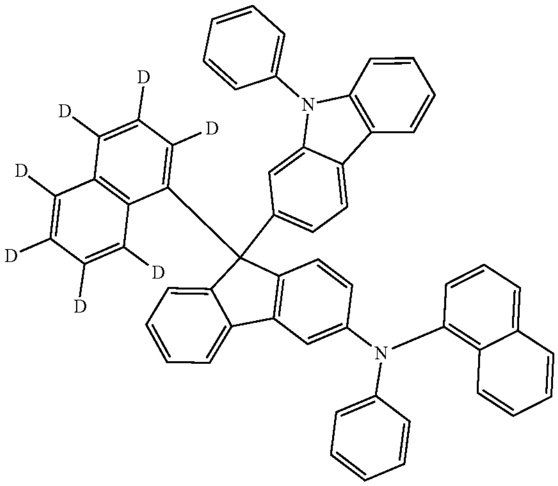
176
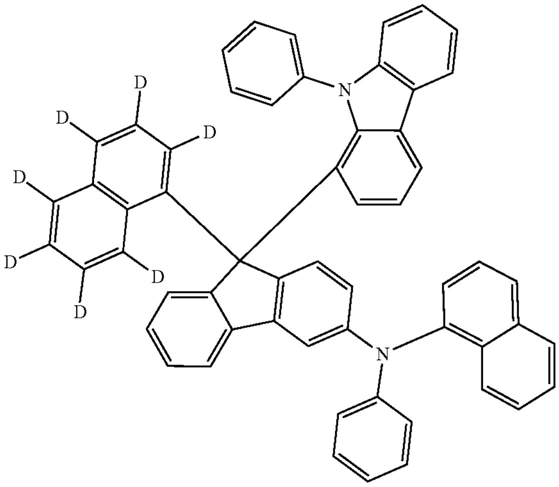
177
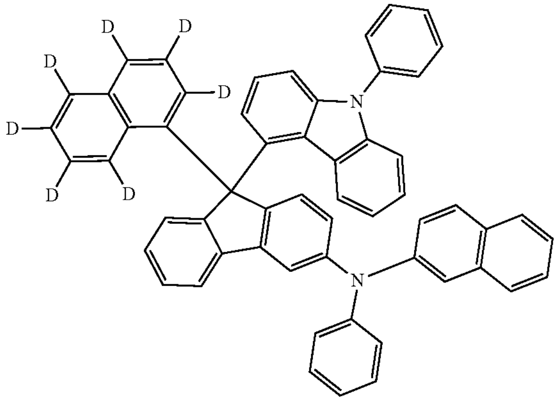

-continued
178
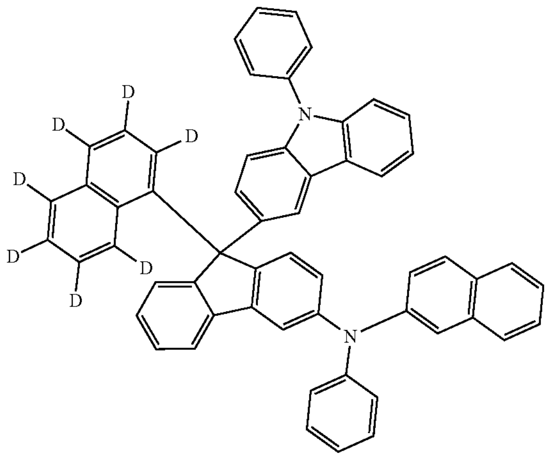
179
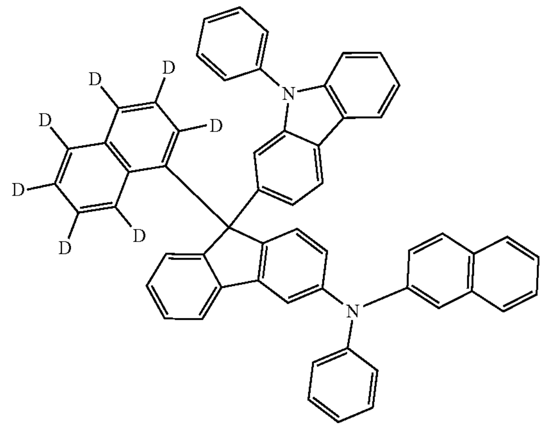
180
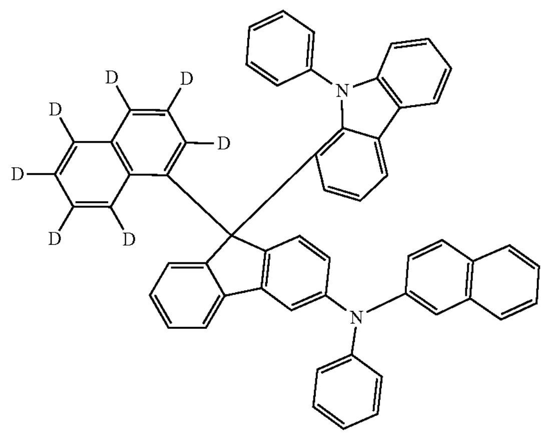
181
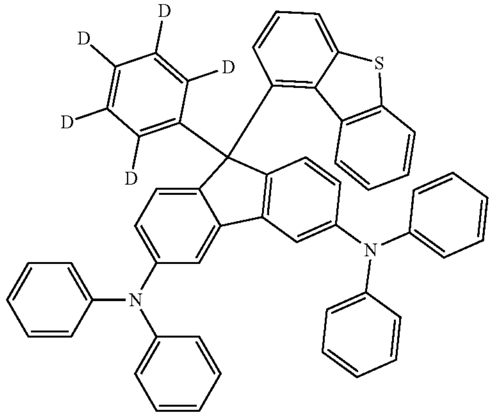
182
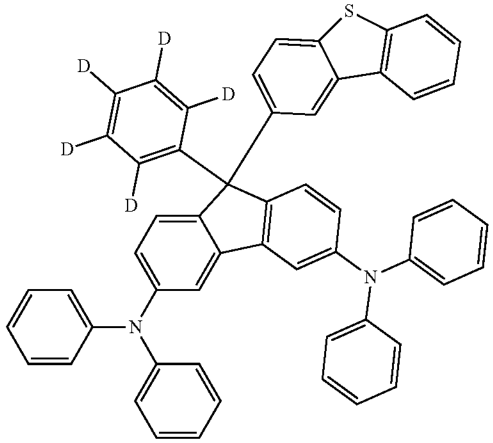
183
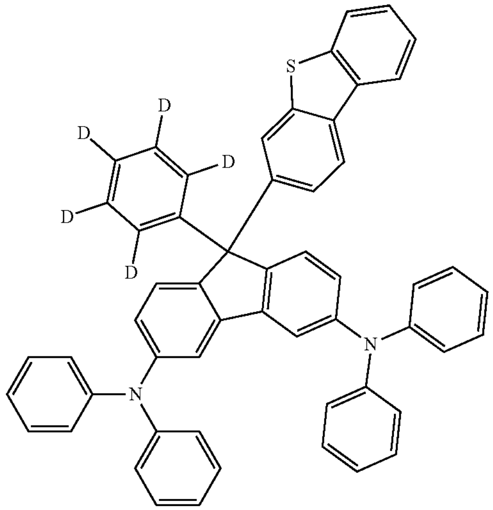

-continued
184
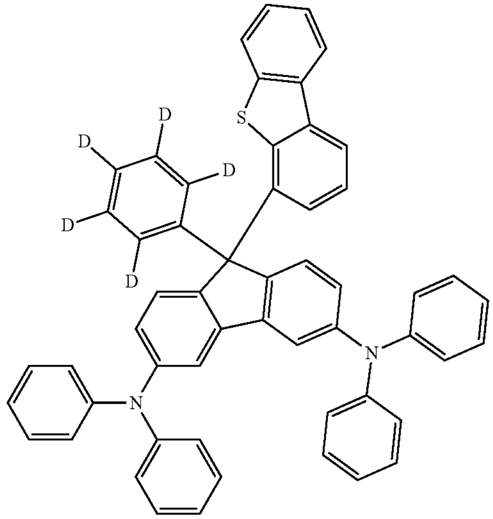
185
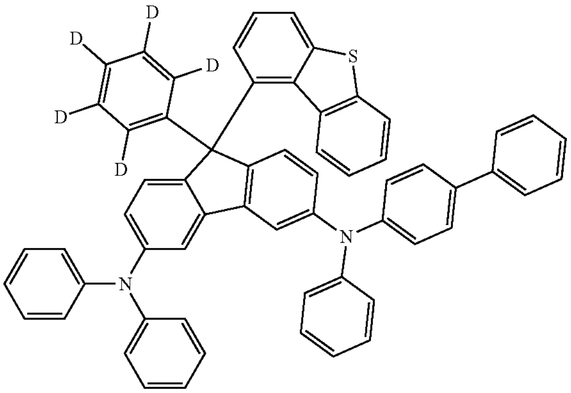
186
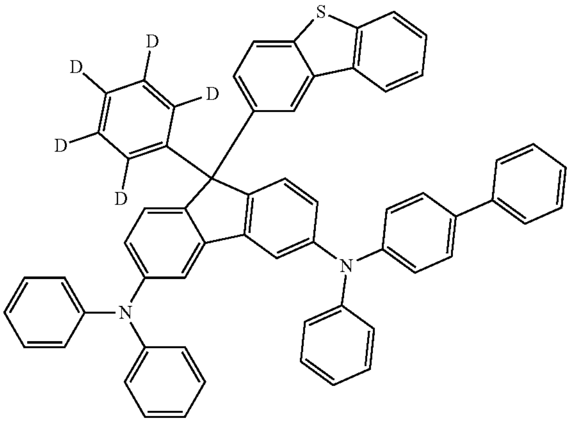
-continued
187
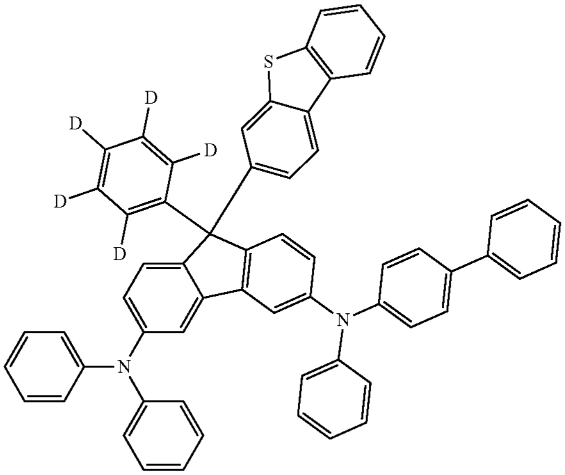
188
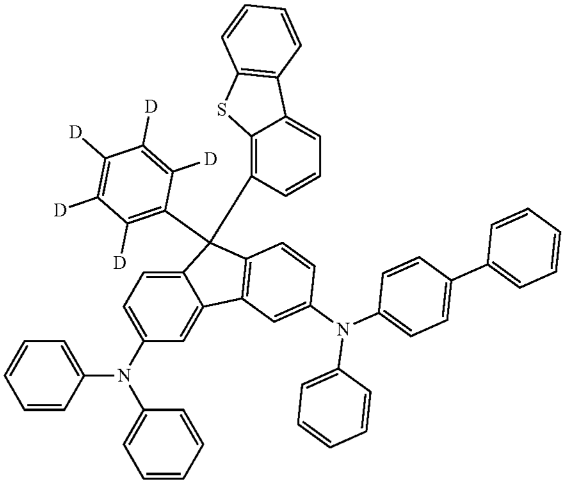
189
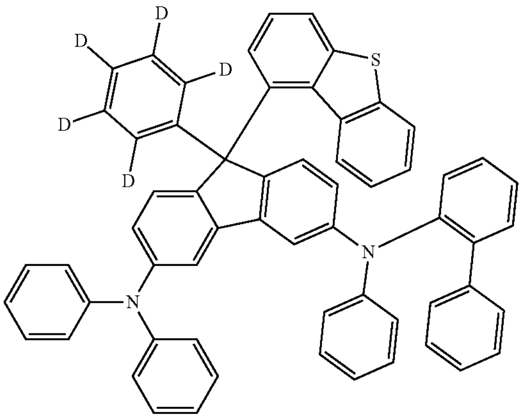

-continued
190
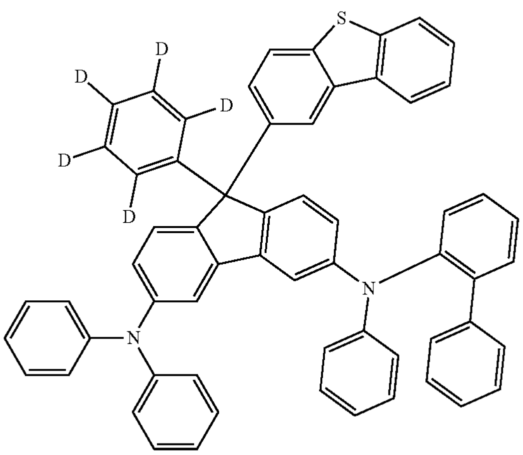
191
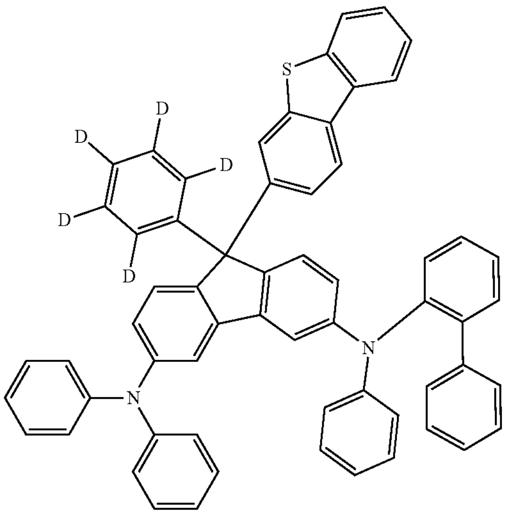
192
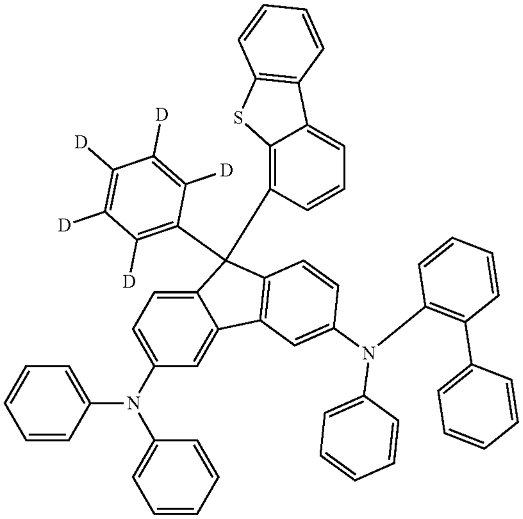
-continued
193
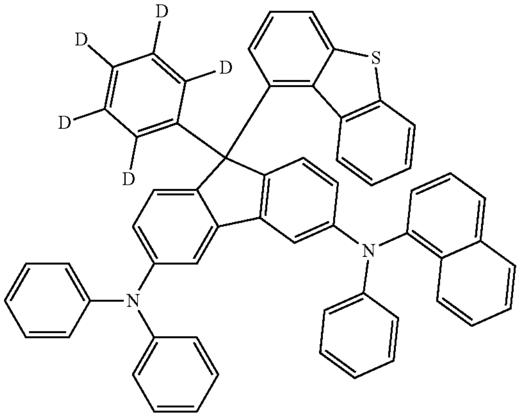
194
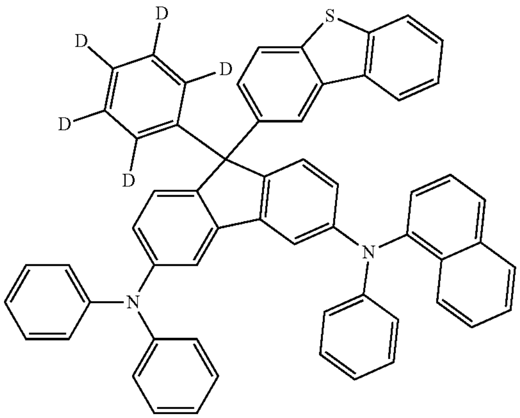
195
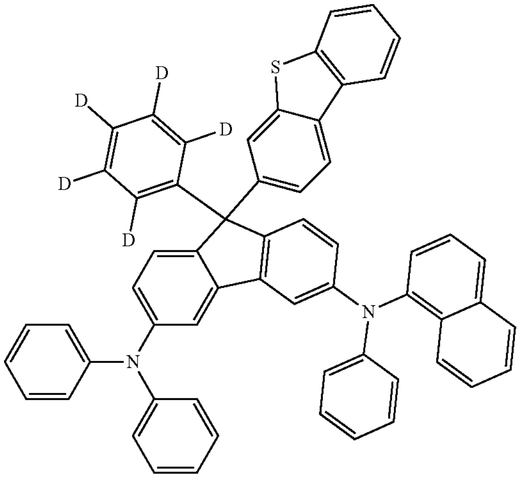

-continued
196
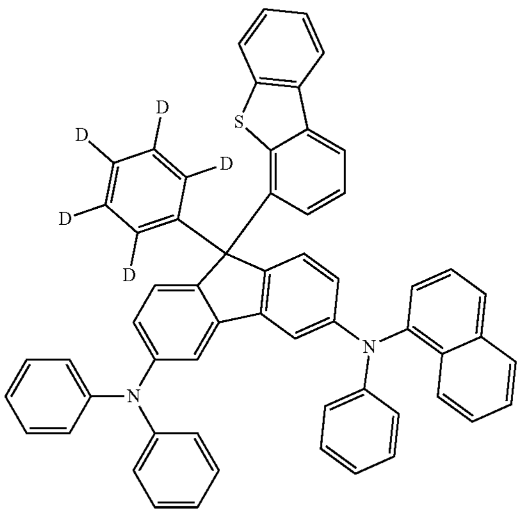
197
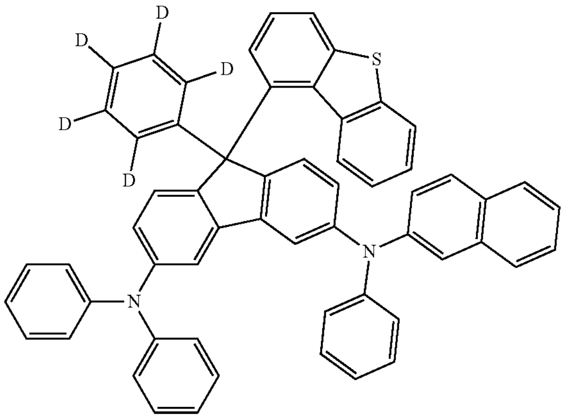
198
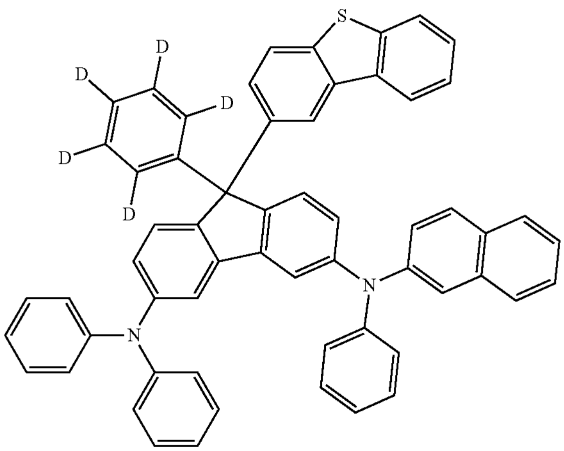
-continued
199
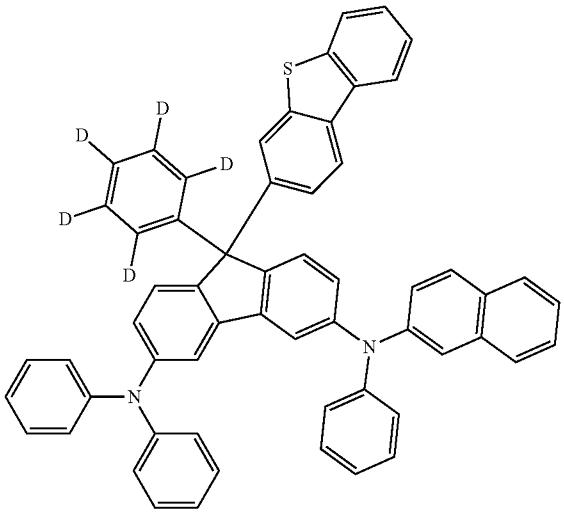
200
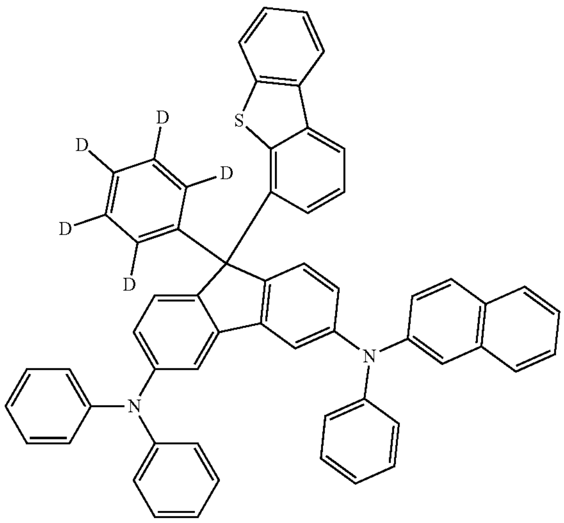
201
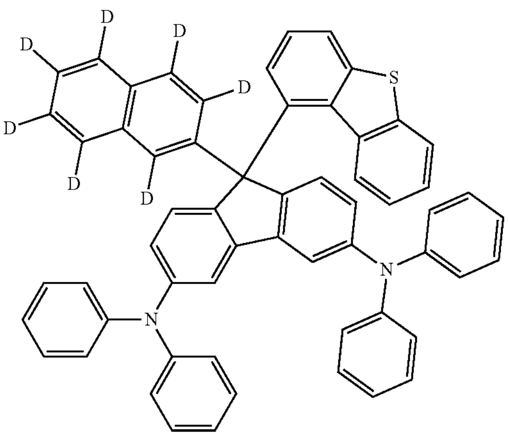

-continued
202
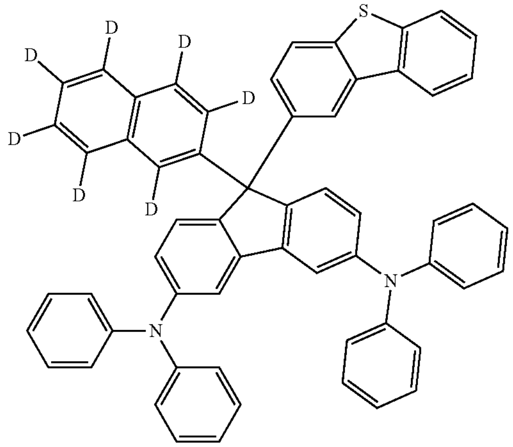
203
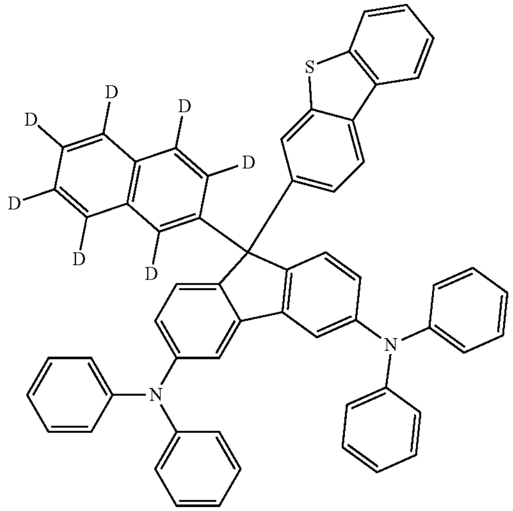
204
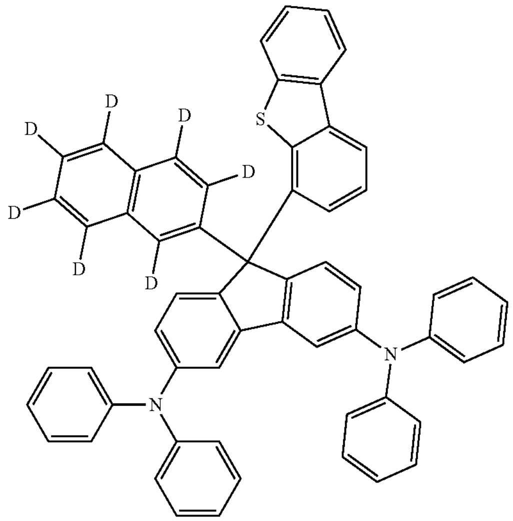
-continued
205
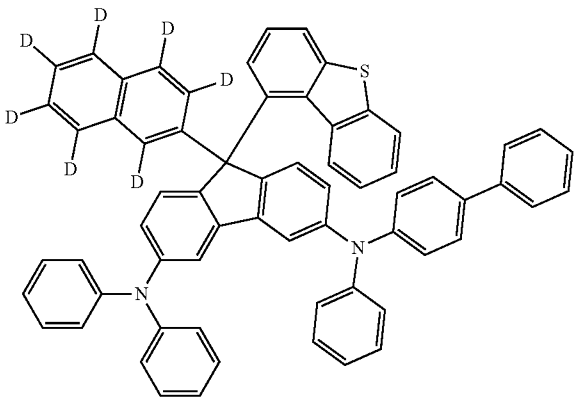
206
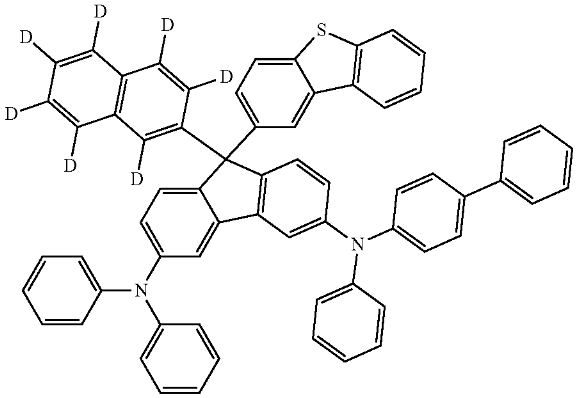
207
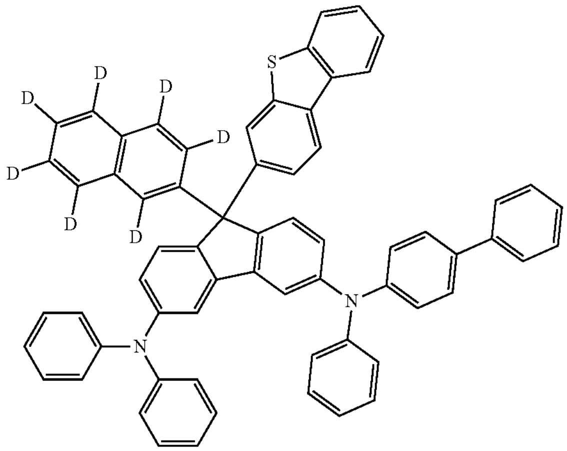

-continued
208
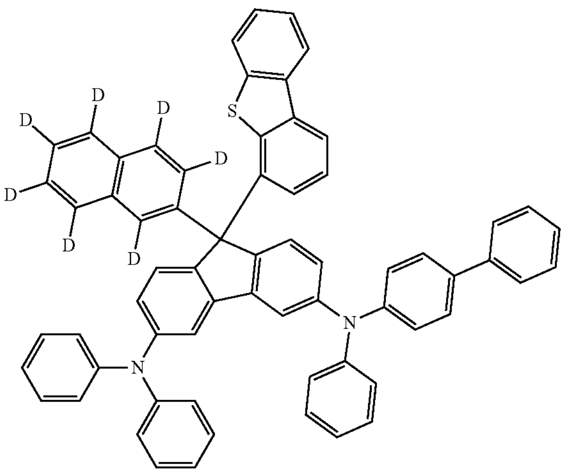
209
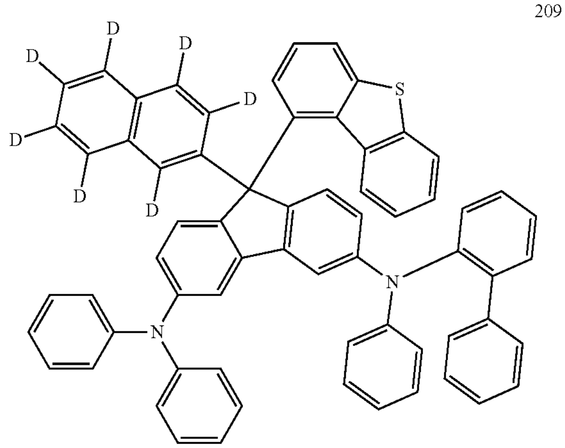
210
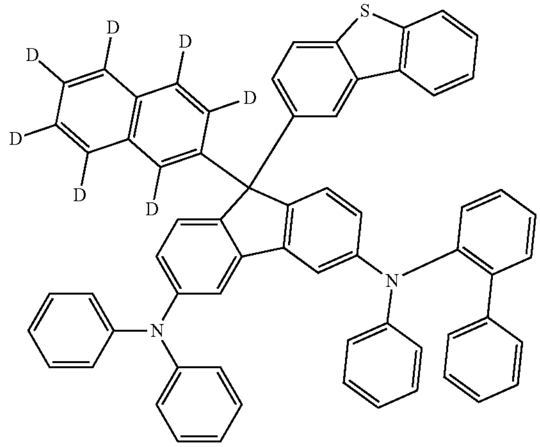
-continued
211
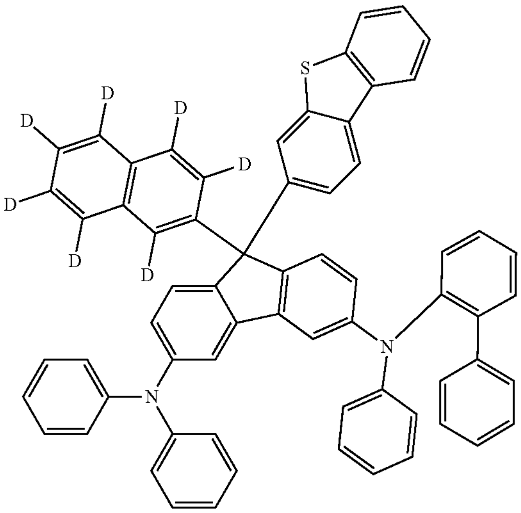
212
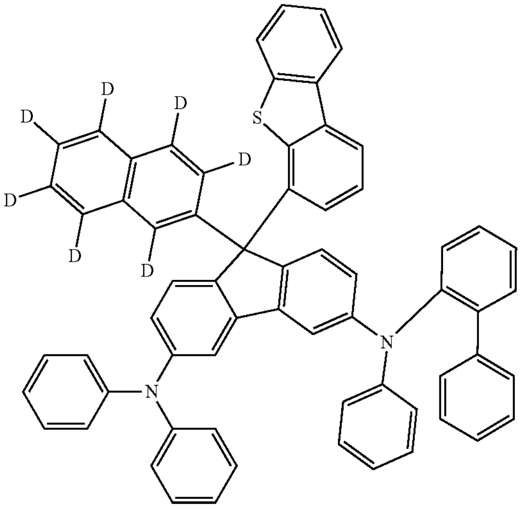
213
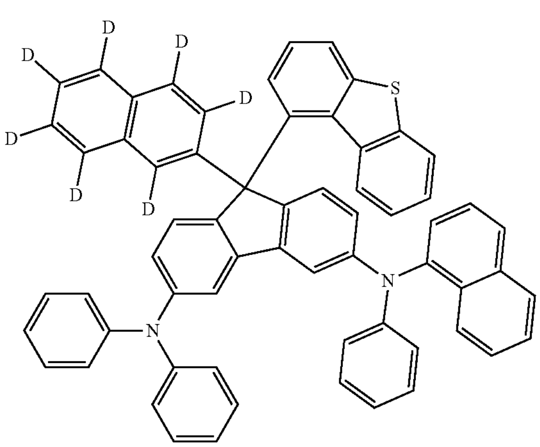

-continued
214
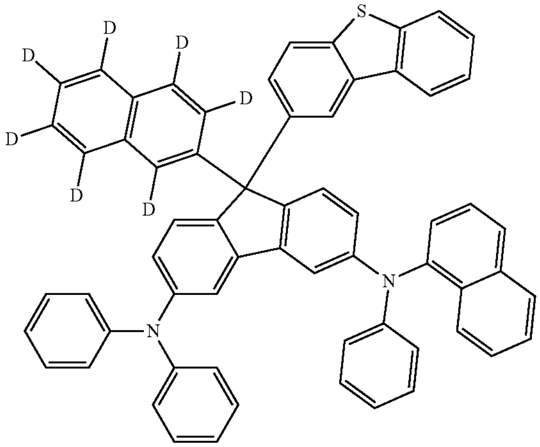
215
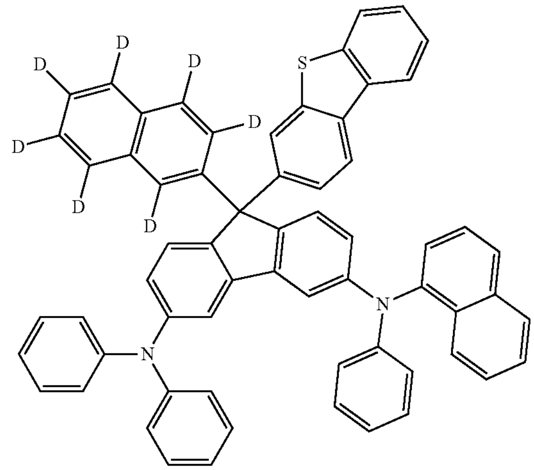
216
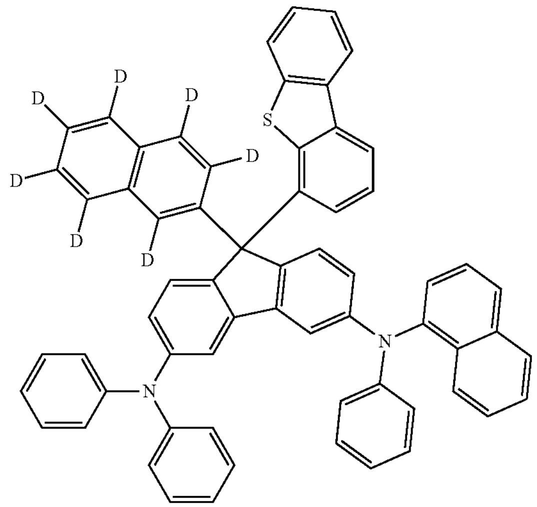
-continued
217
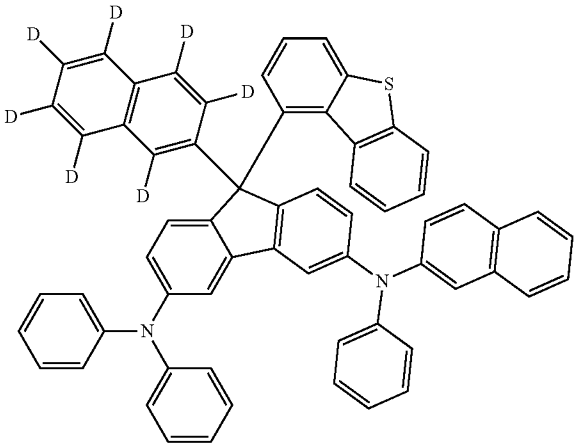
218
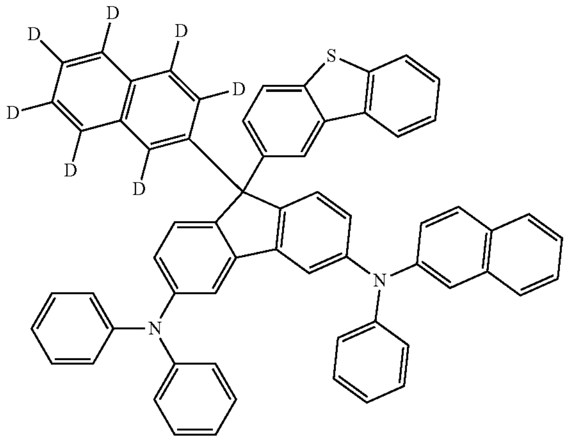
219
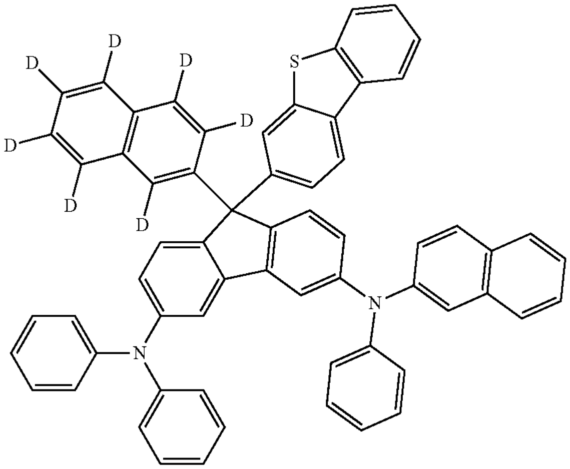

-continued
220
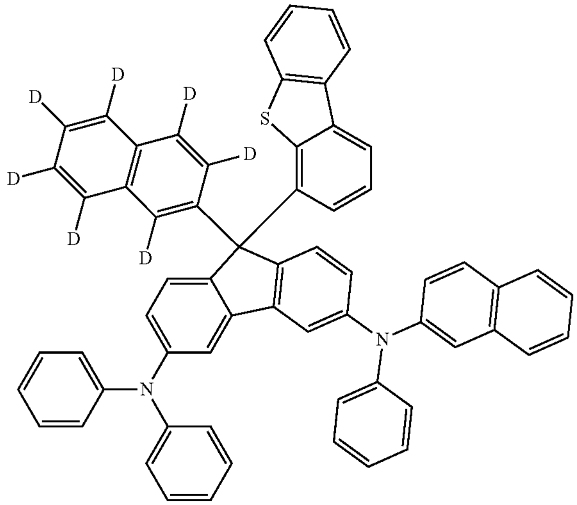
221
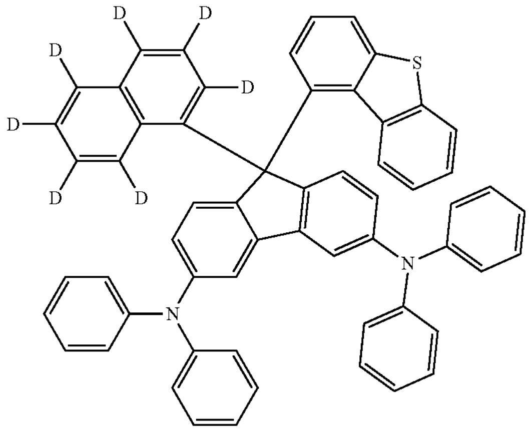
222
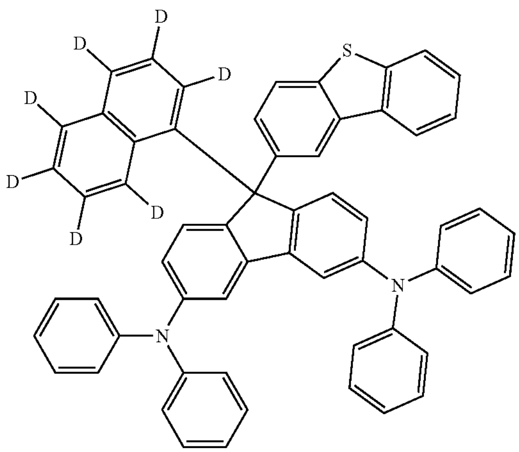
-continued
223
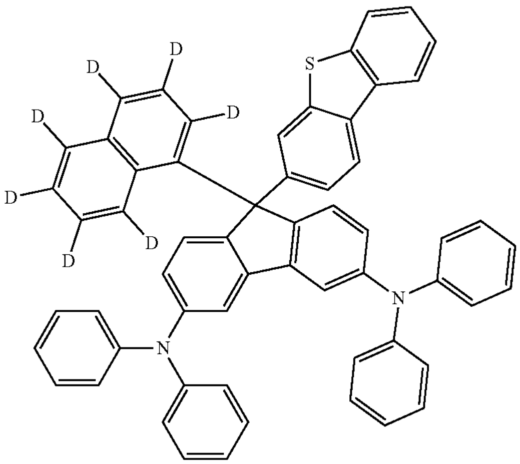
224
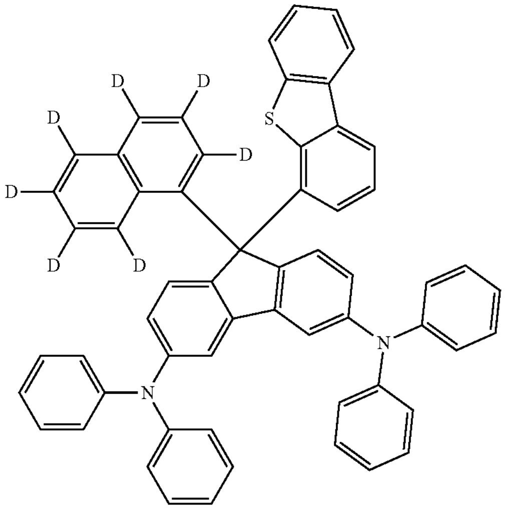
225
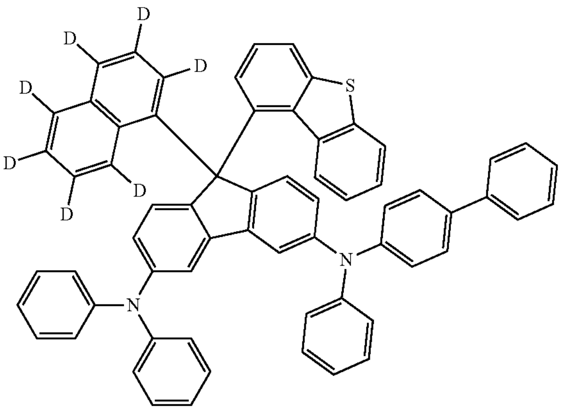

-continued
226
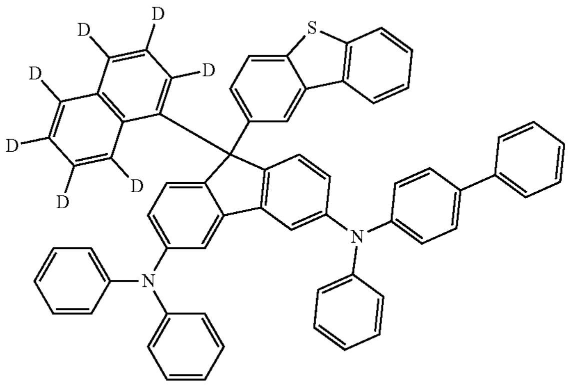
227
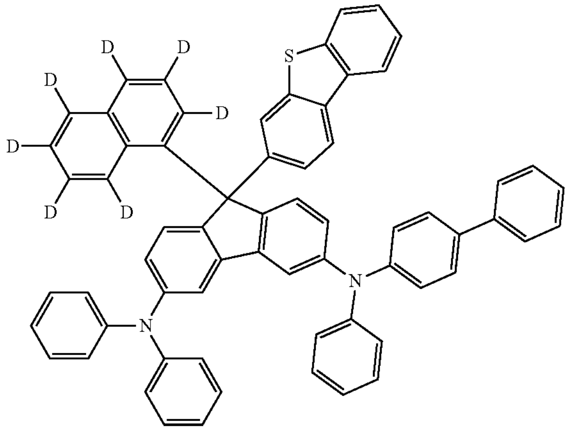
228
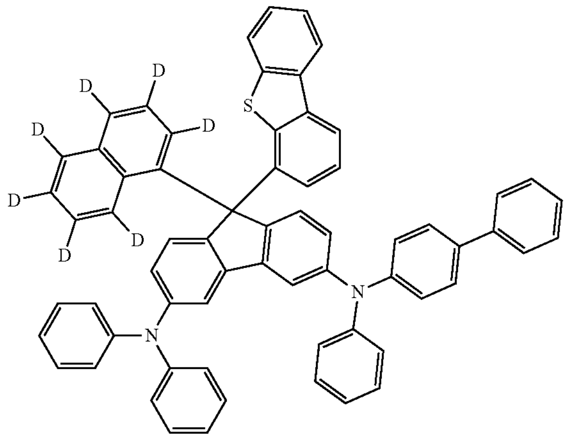
-continued
229
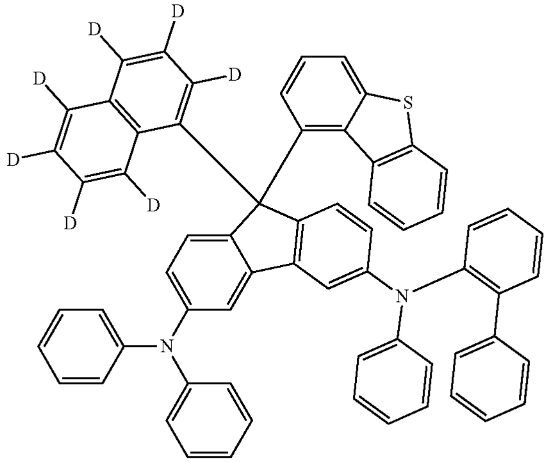
230
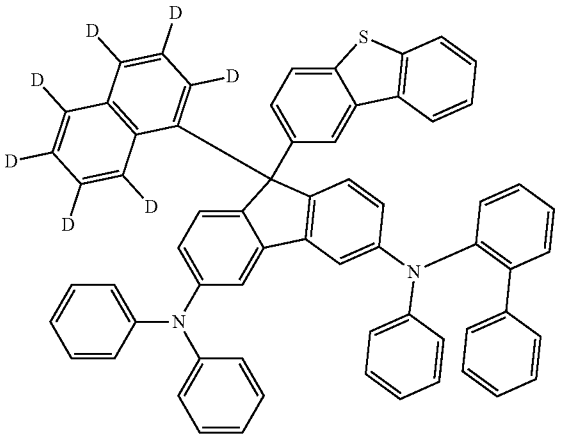
231
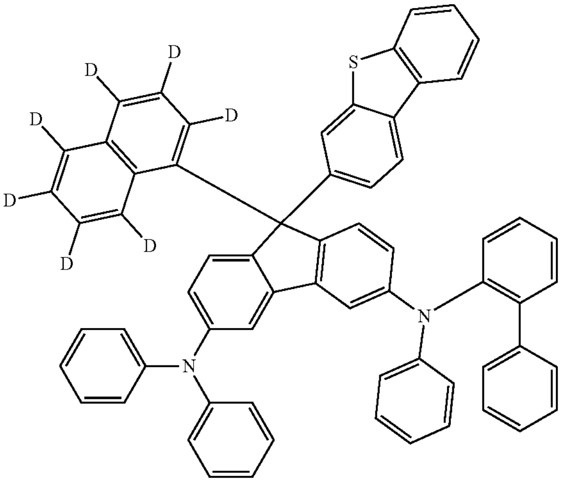

-continued
232
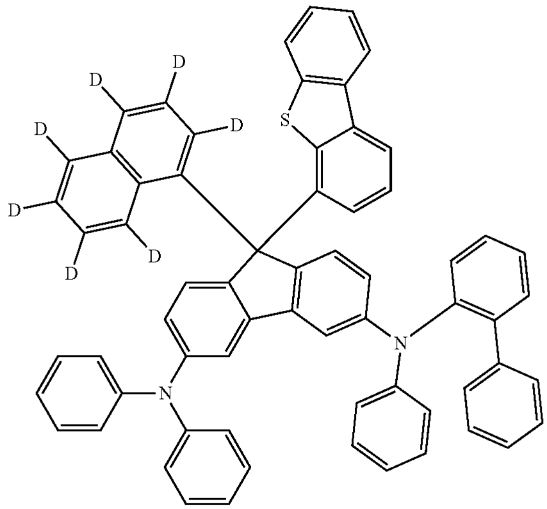
233
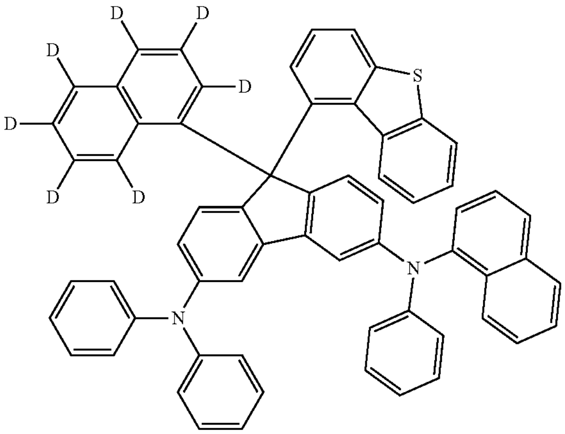
234
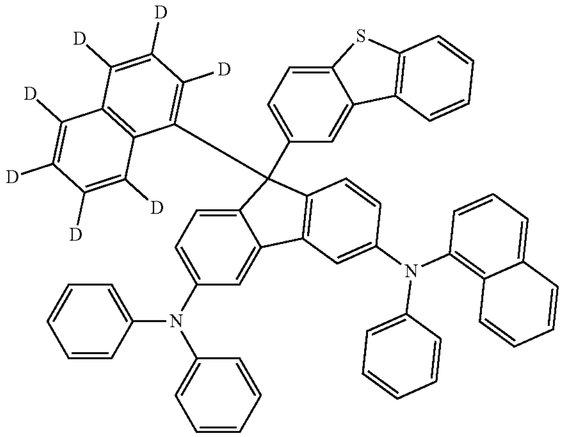
-continued
235
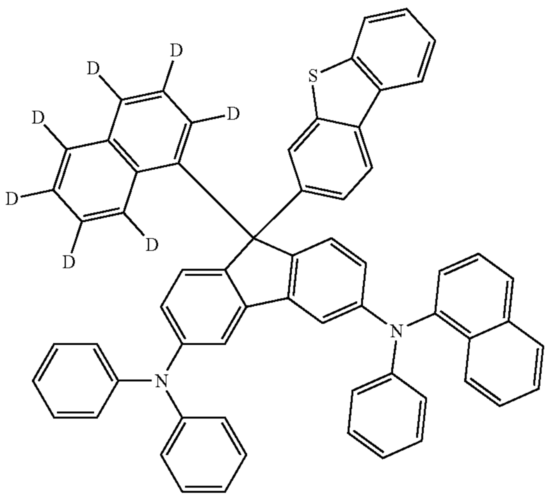
236
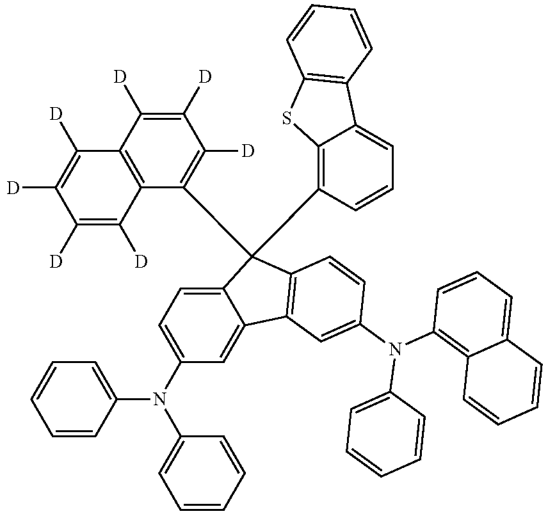
237
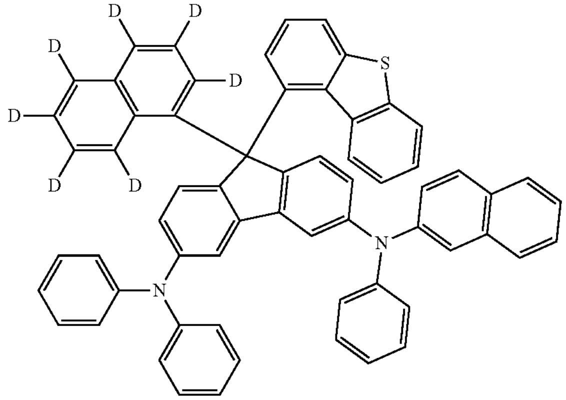

-continued
238
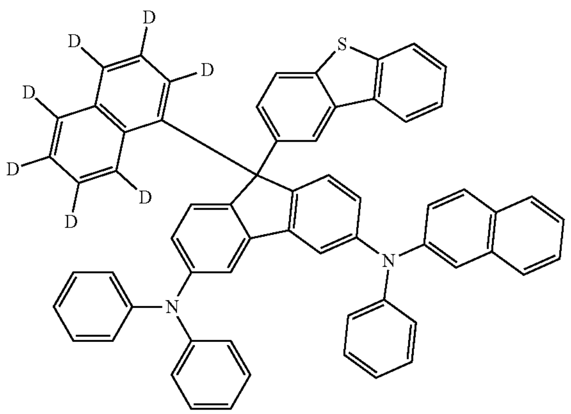
241
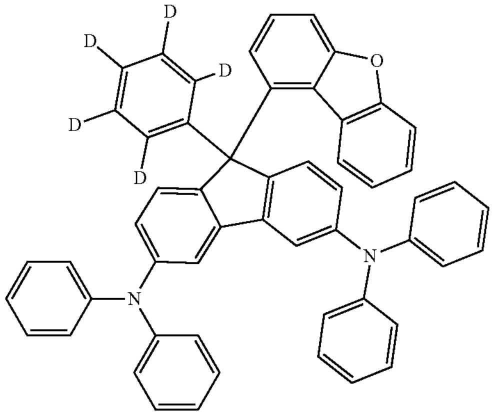
239
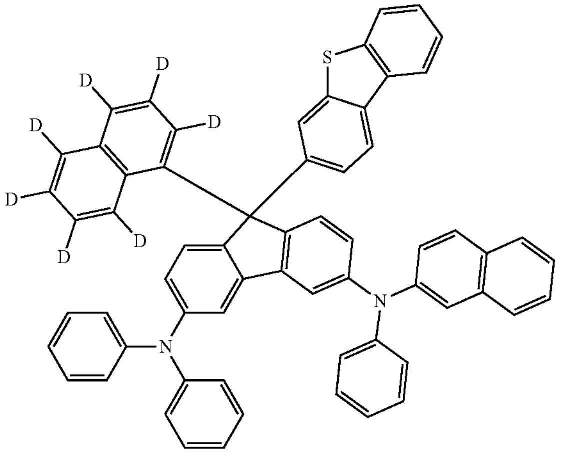
242
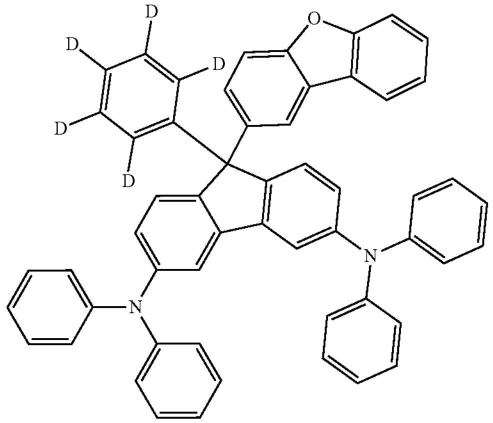
240
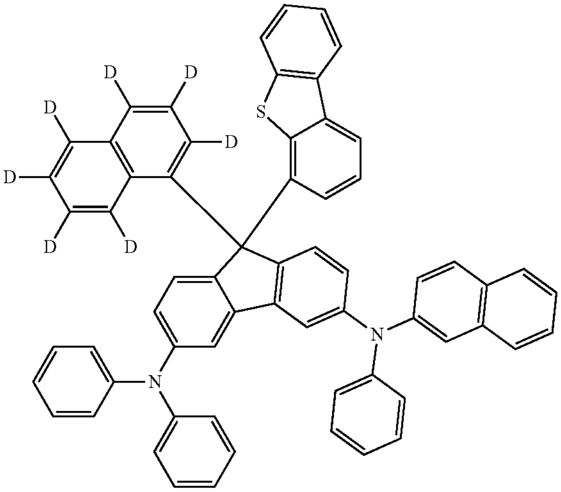
243
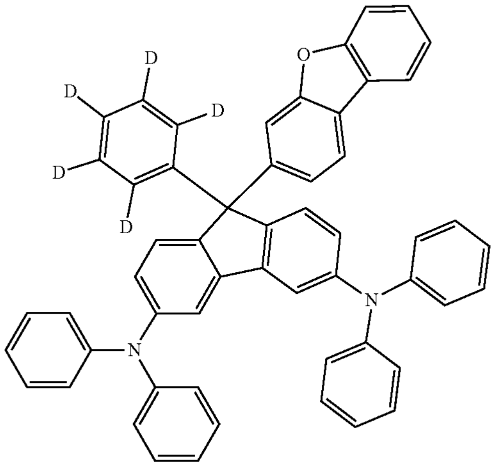

-continued
244
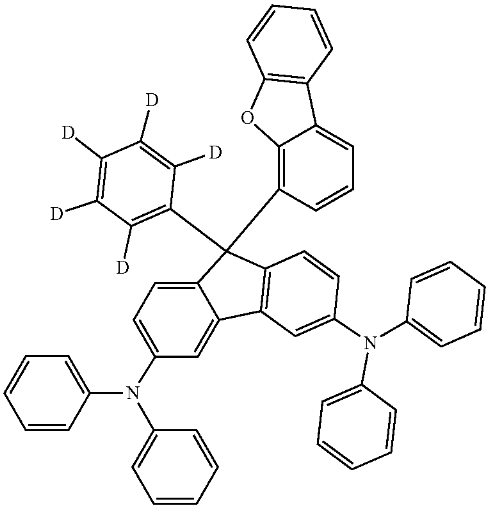
245
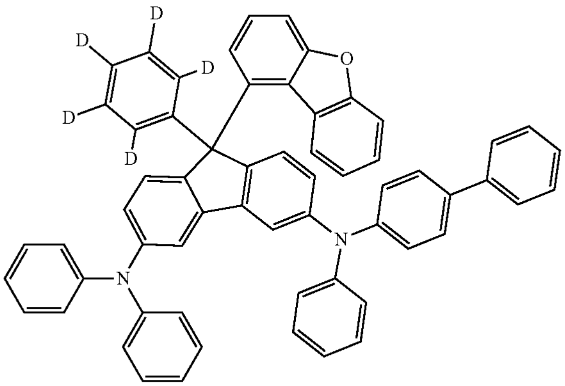
246
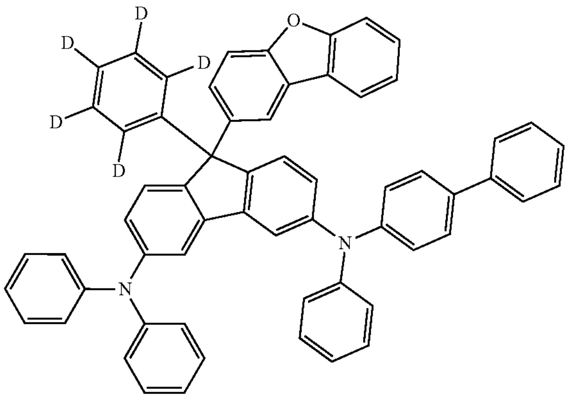
-continued
247
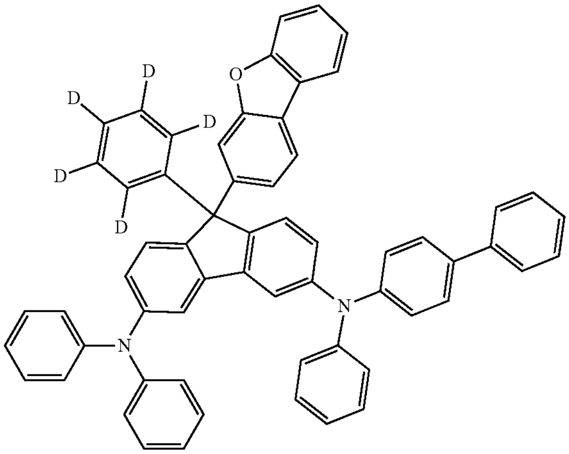
248
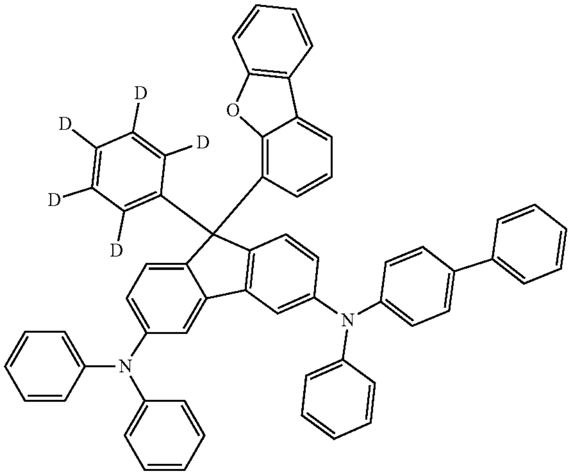
249
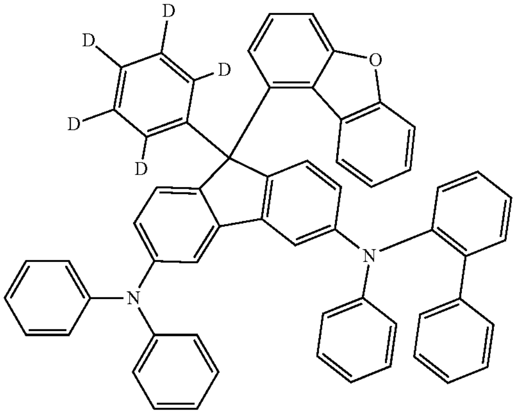

-continued
250
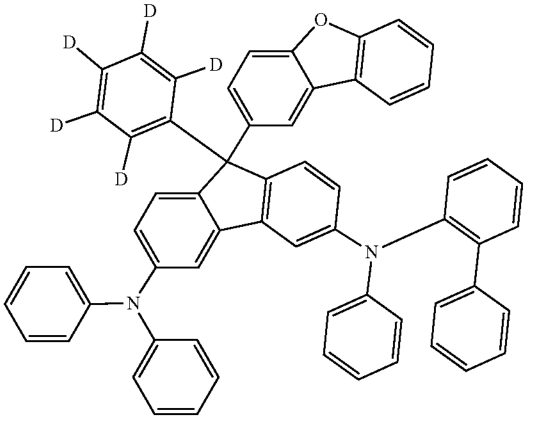
251
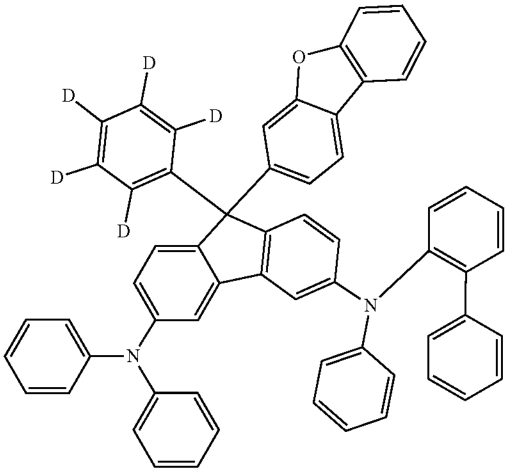
252
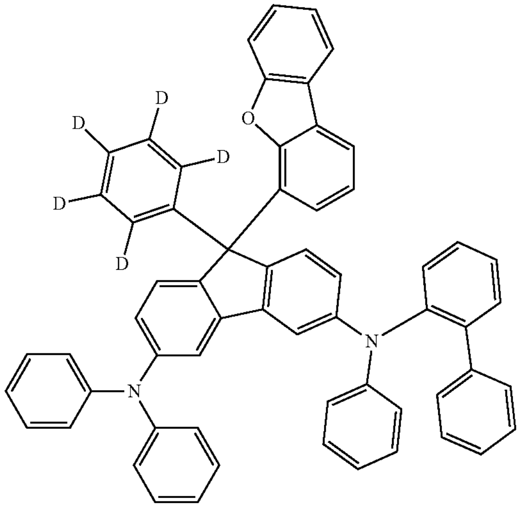
-continued
253
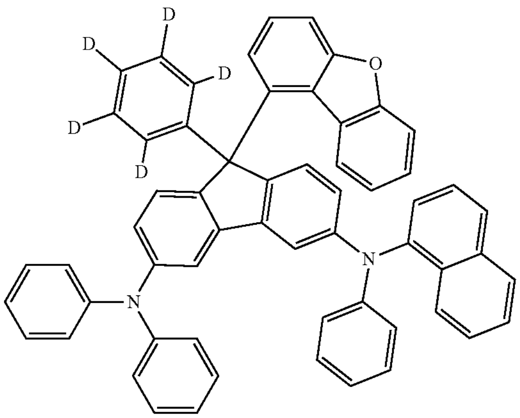
254
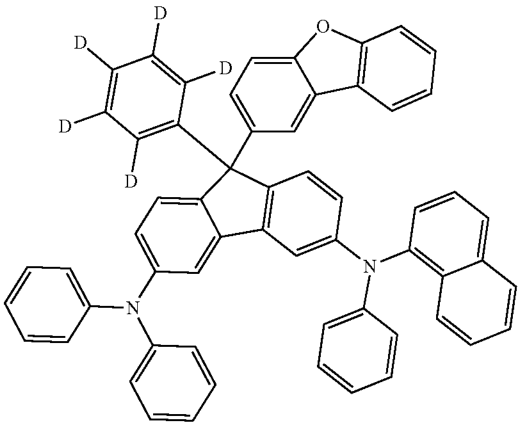
255
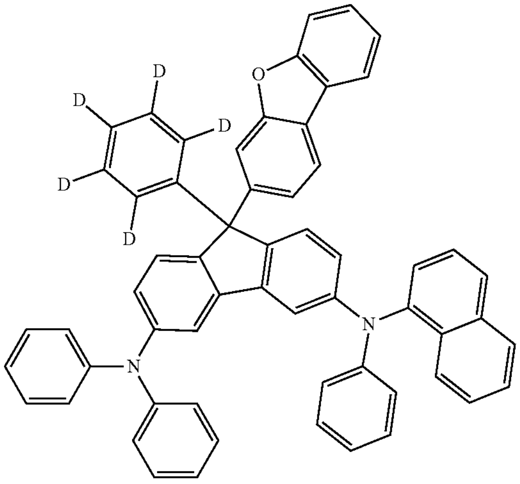

-continued
256
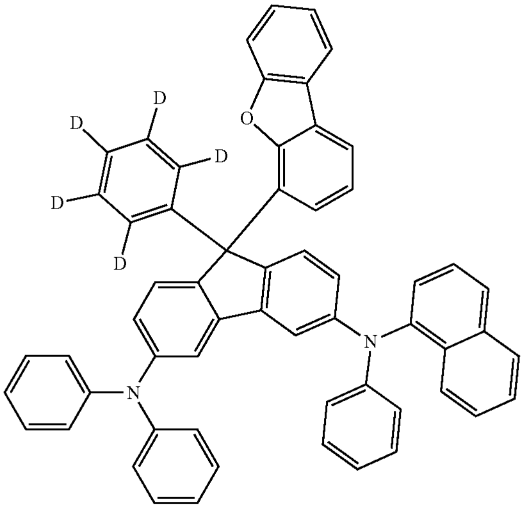
257
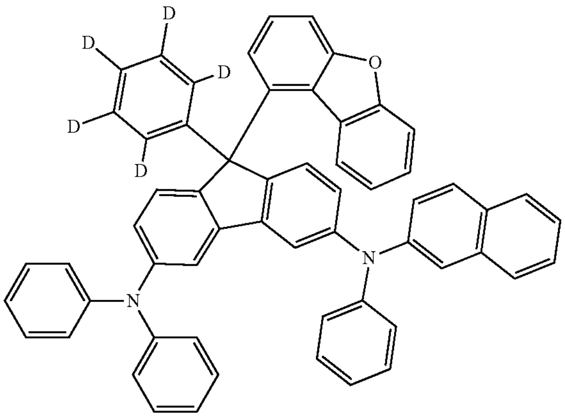
258
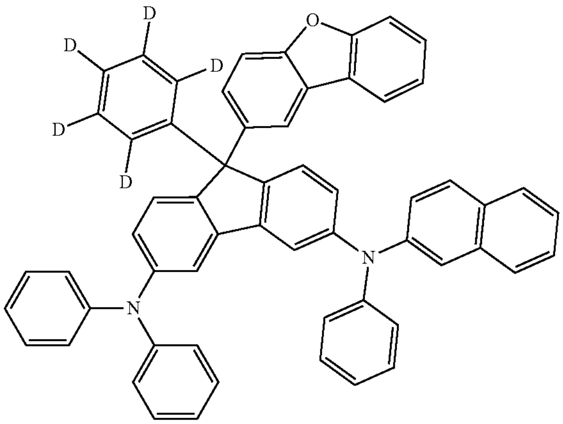
-continued
259
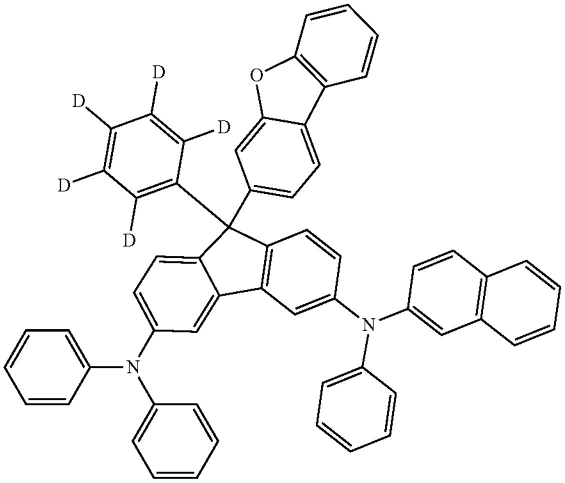
260
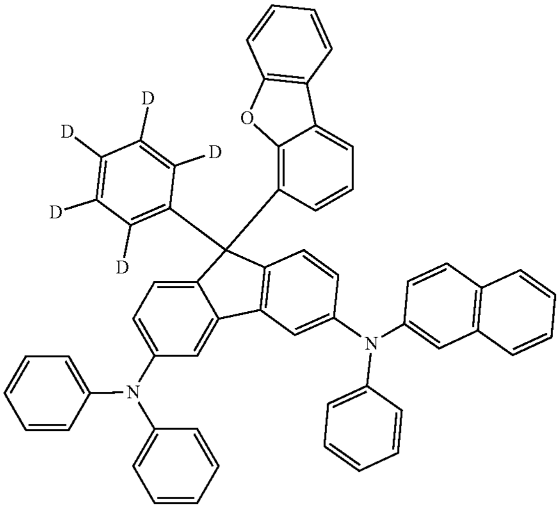
261
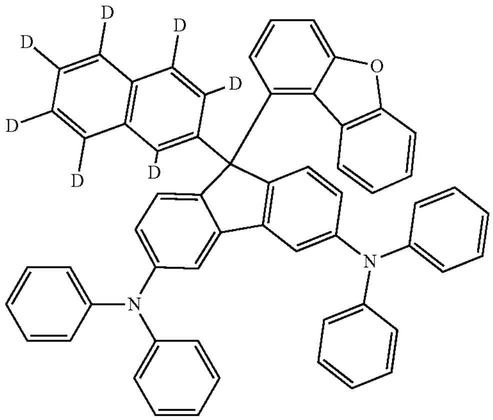

-continued
262
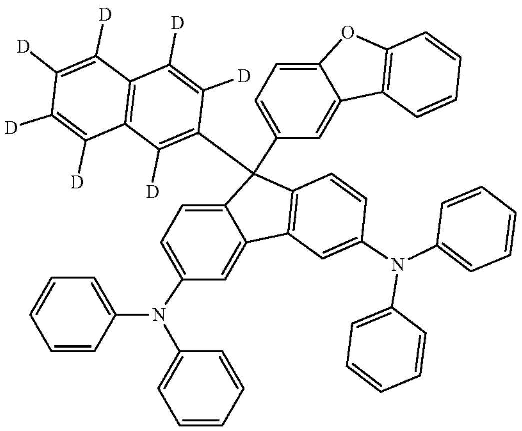
263
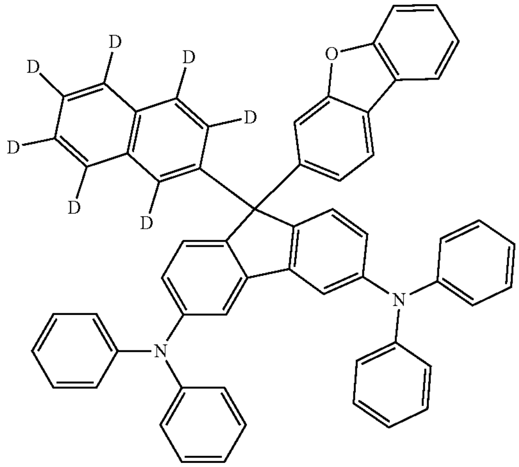
264
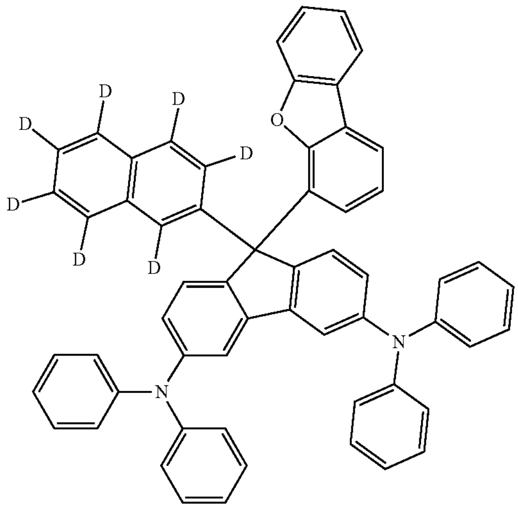
-continued
265
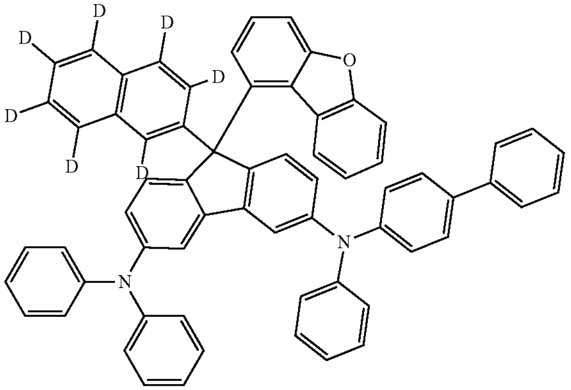
266
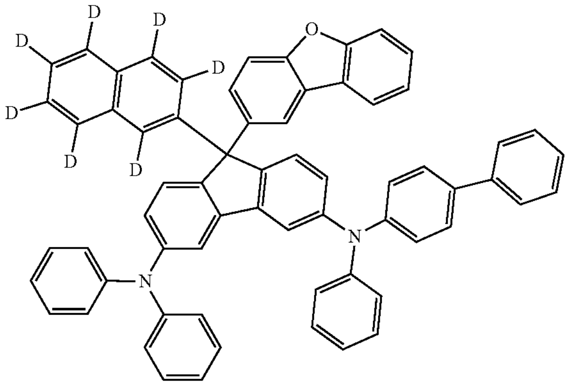
267
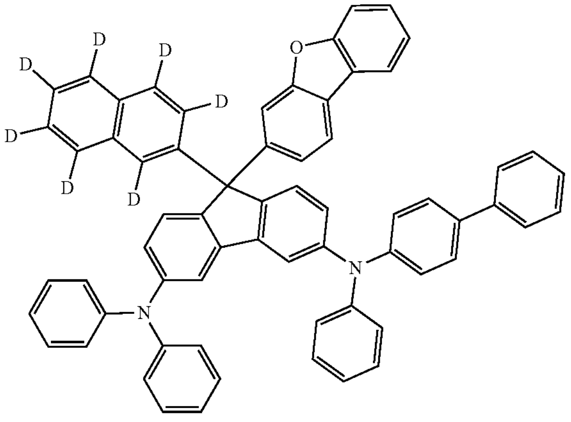

-continued
268
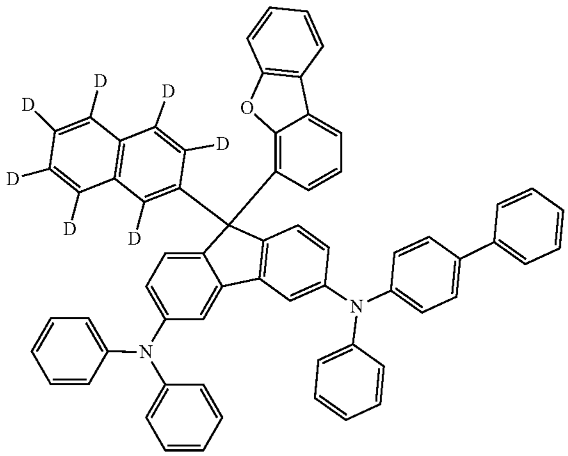
269
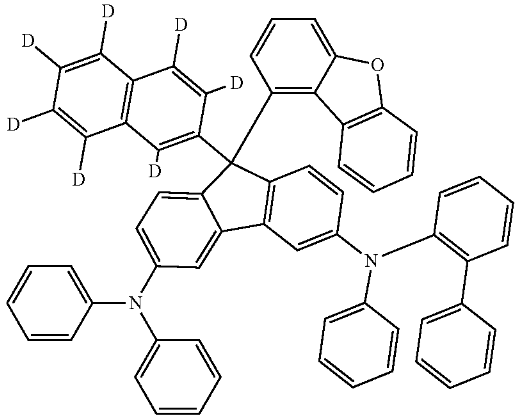
270
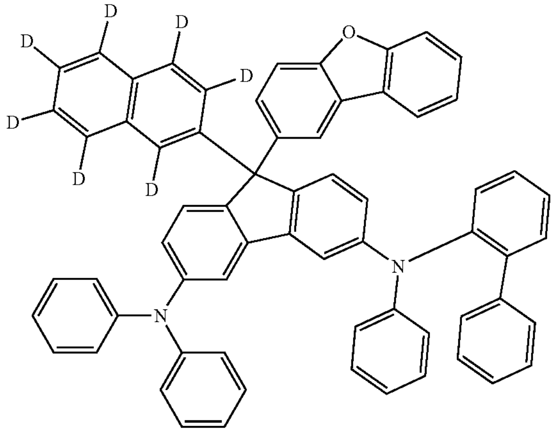
-continued
271
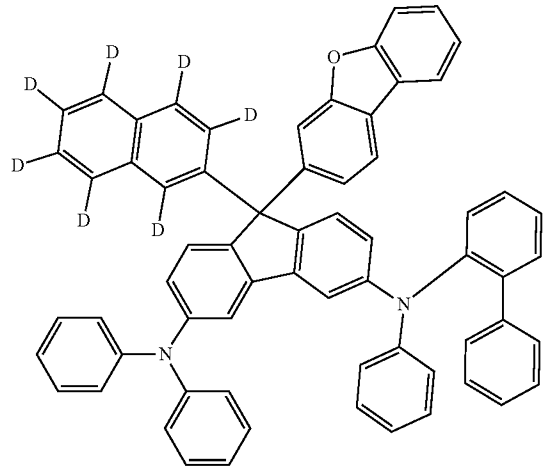
272
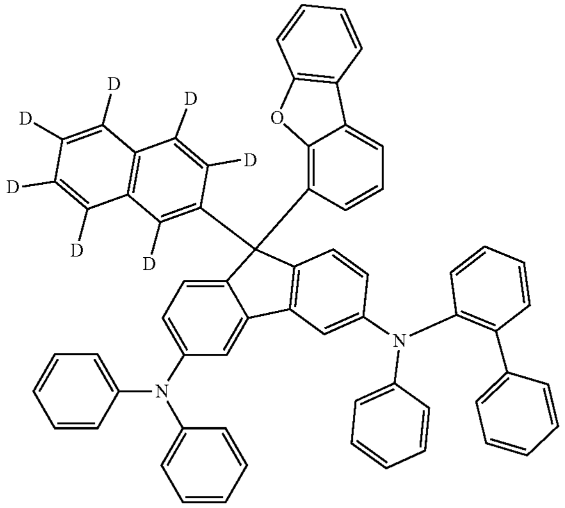
273
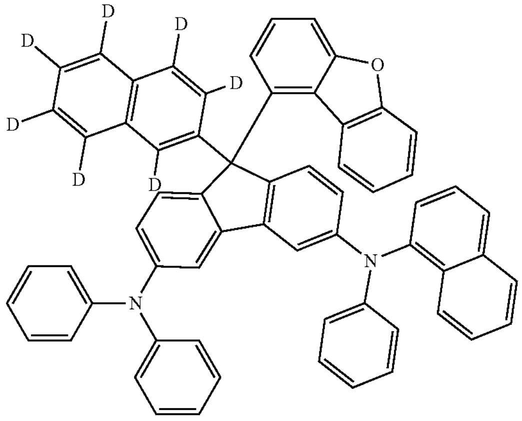

-continued
274
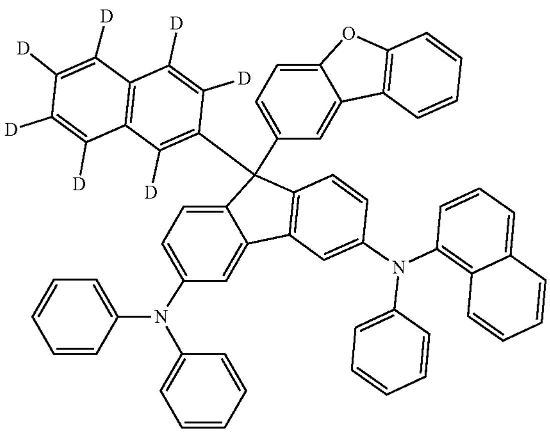
275
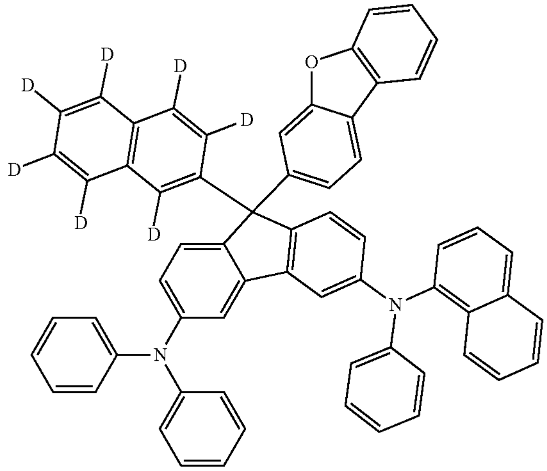
276
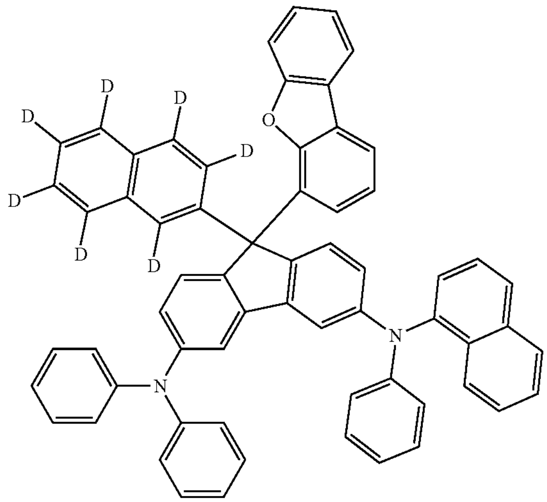
-continued
277
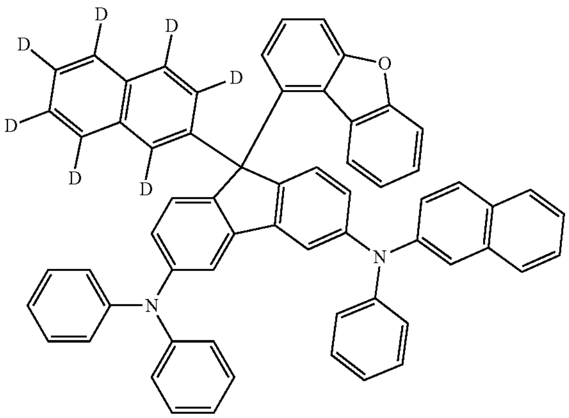
278
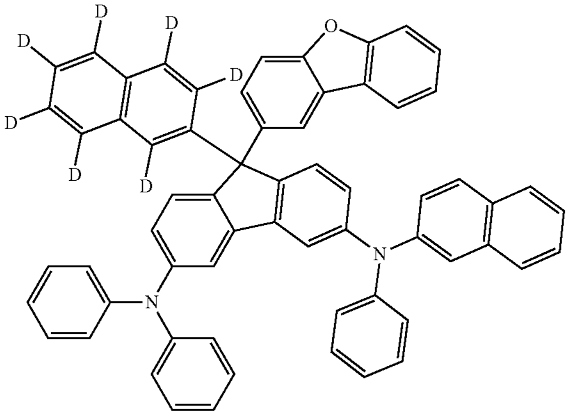
279
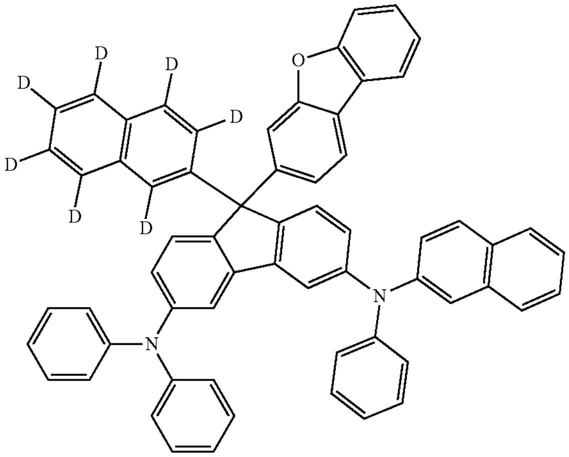

-continued
280
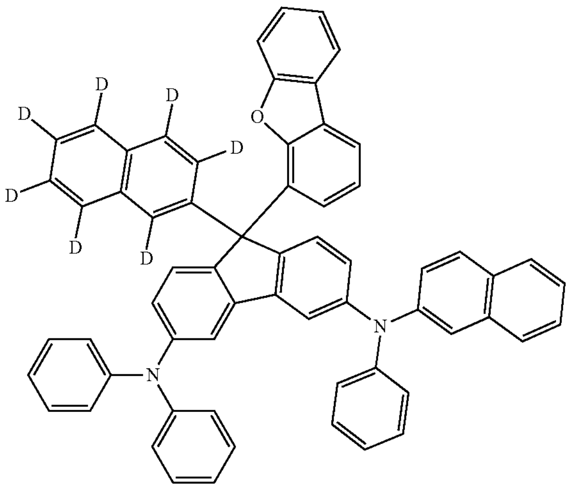
281
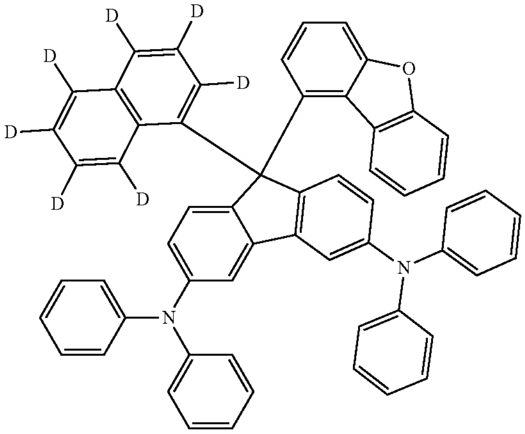
282
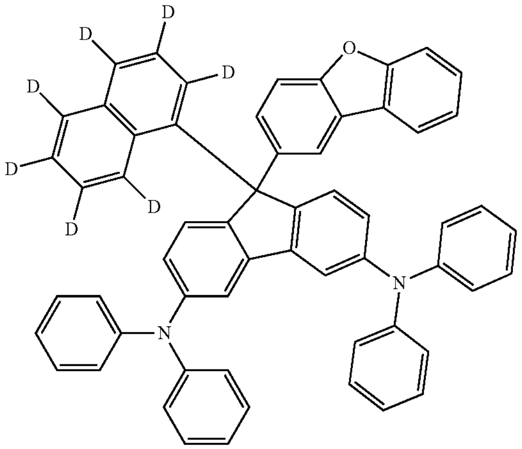
-continued
283
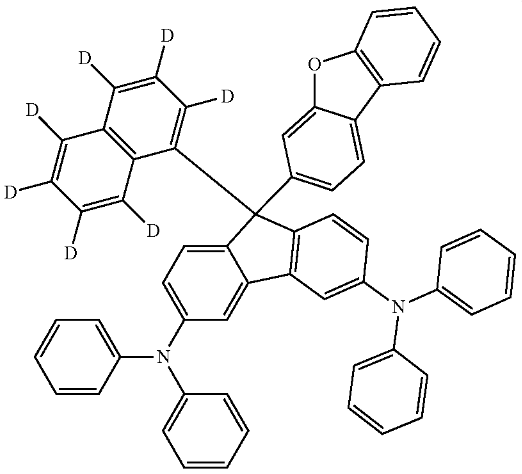
284
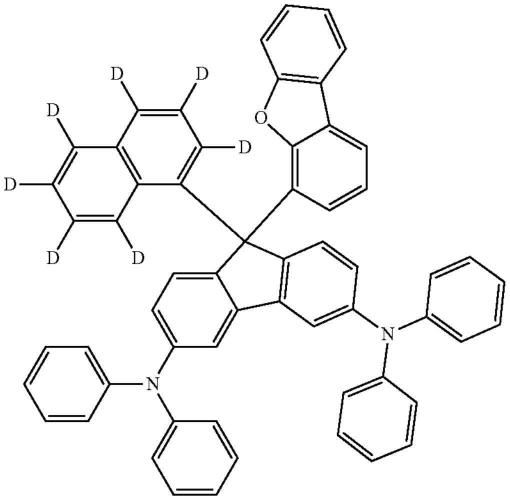
285
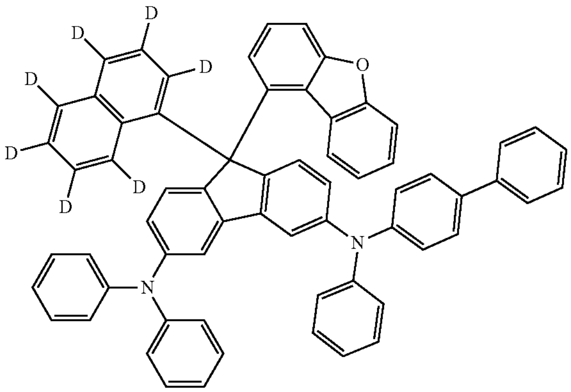

-continued
286
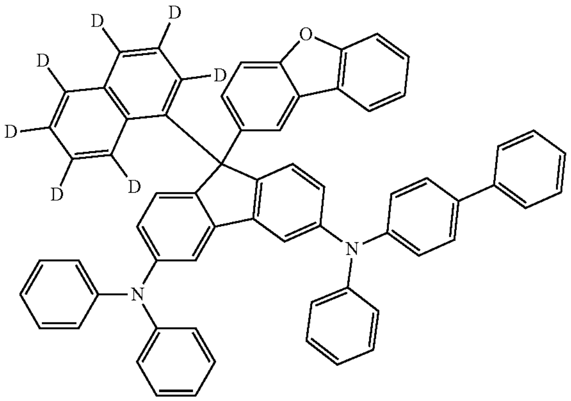
287
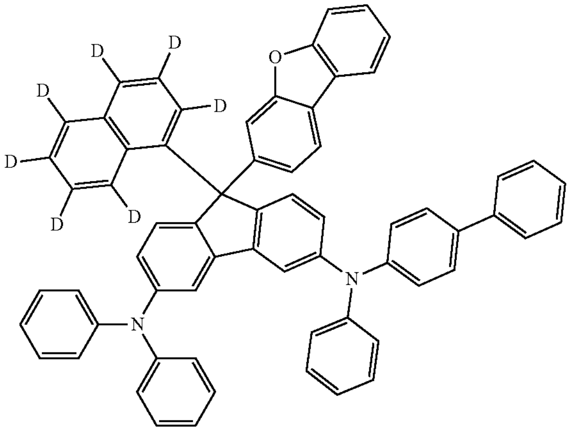
288
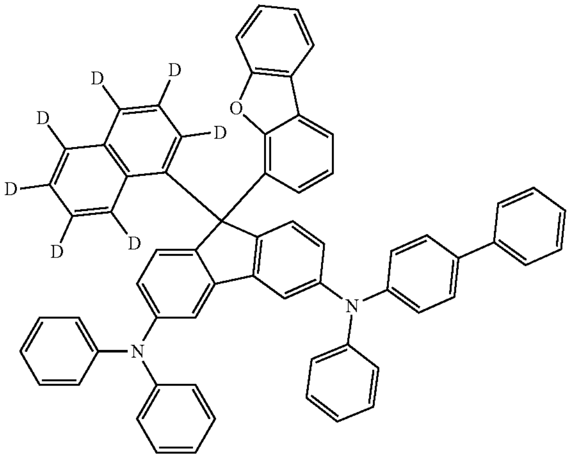
-continued
289
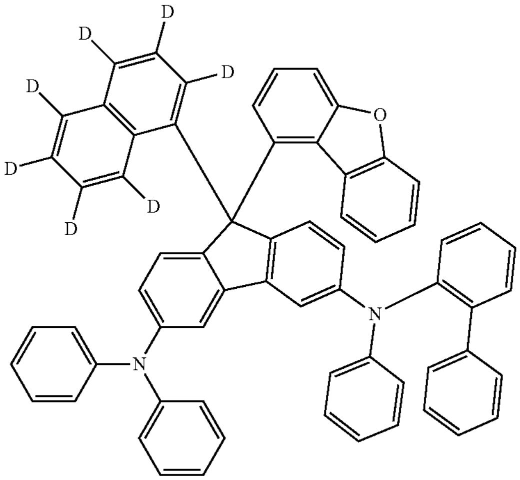
290
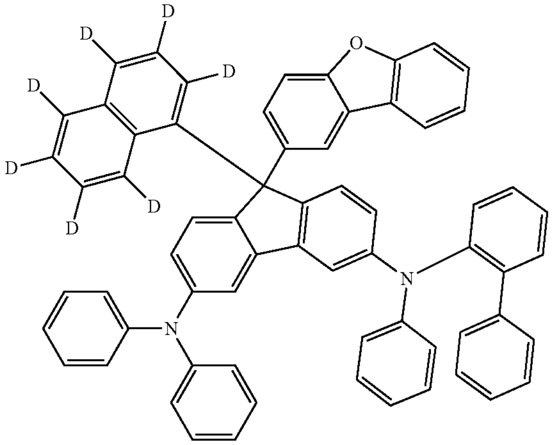
291
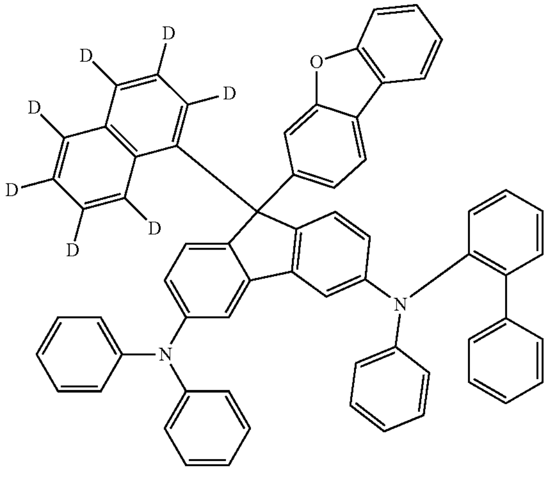

-continued
292
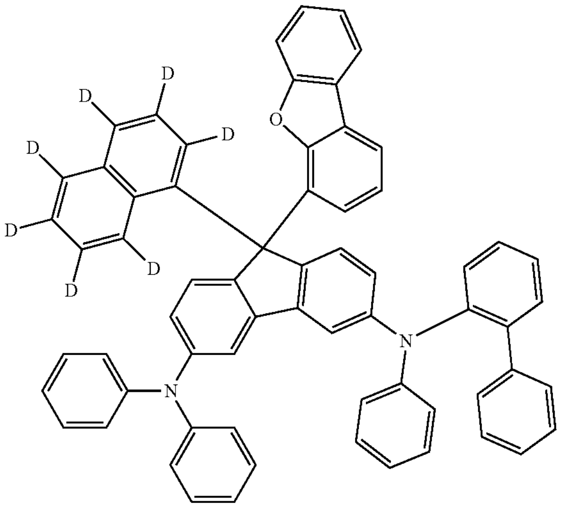
293
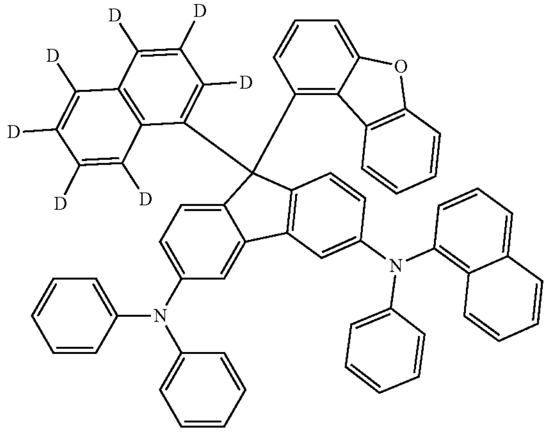
294
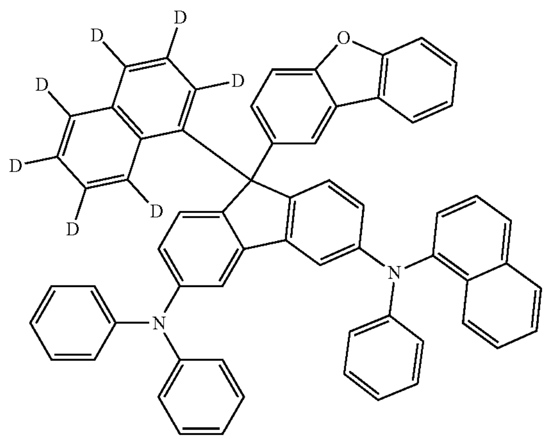
-continued
295
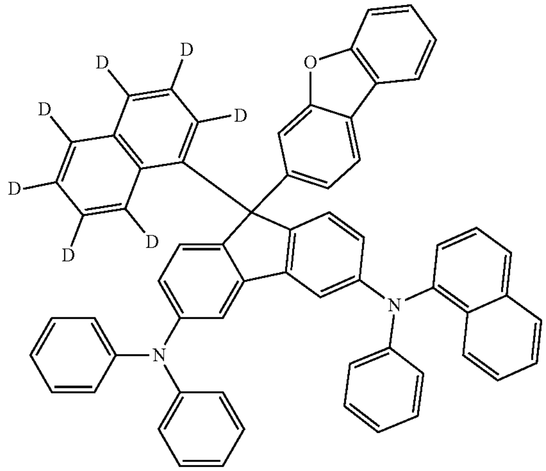
296
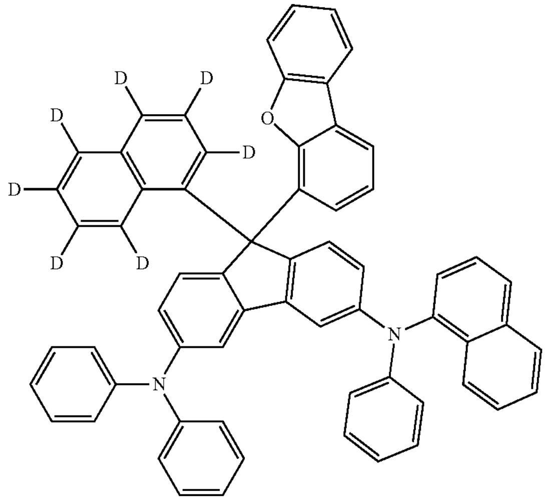
297
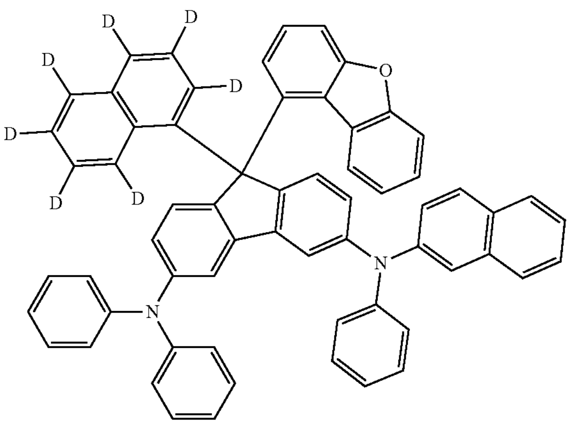

-continued
298
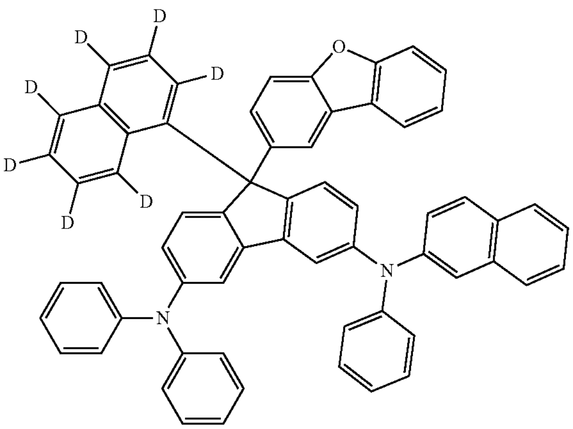
299
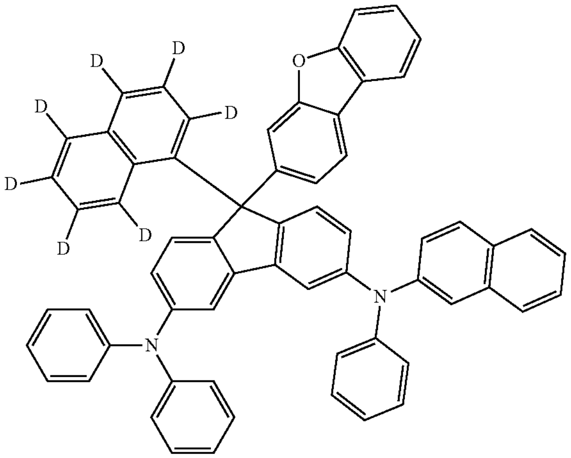
300
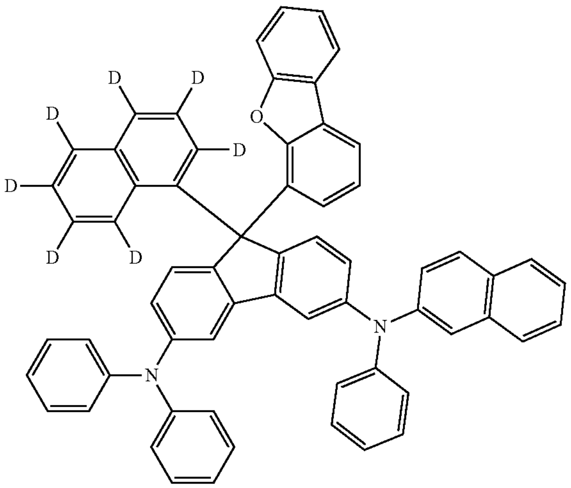
301
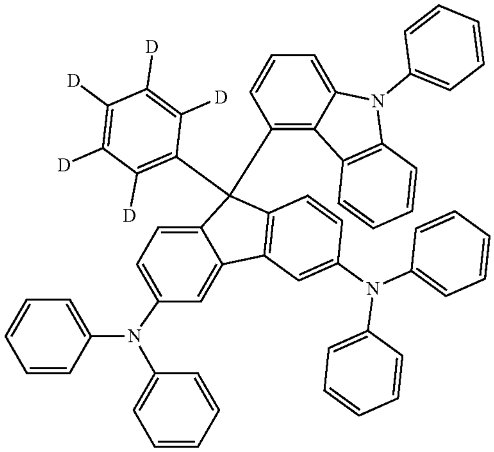
302
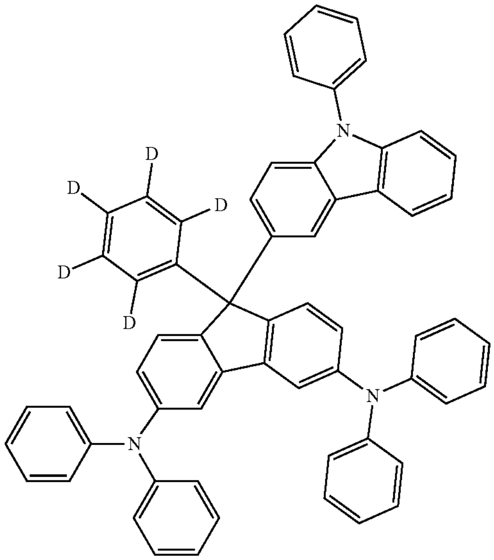
303
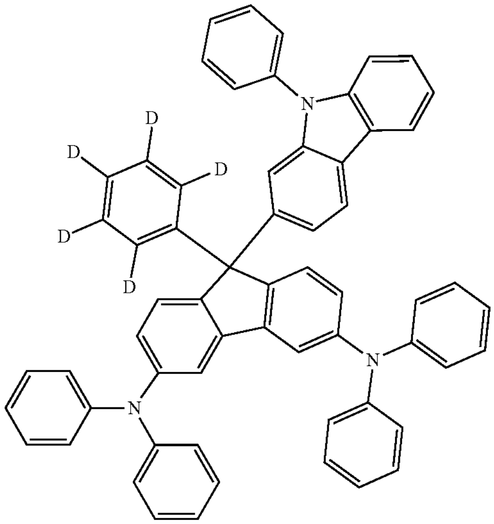

-continued
304
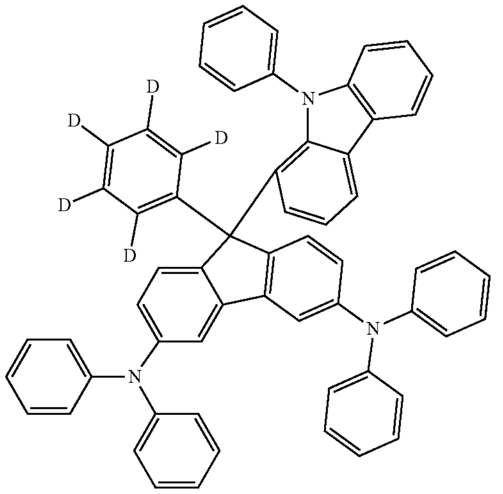
305
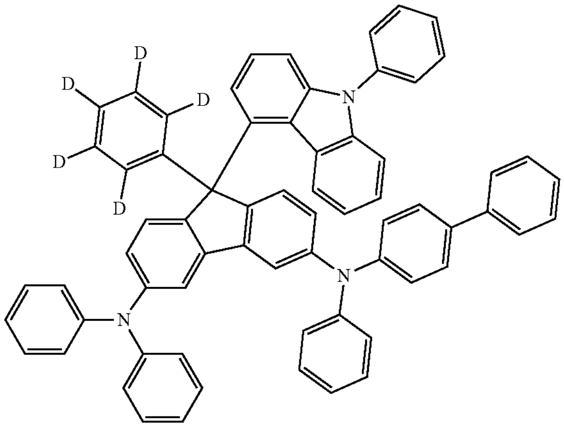
306
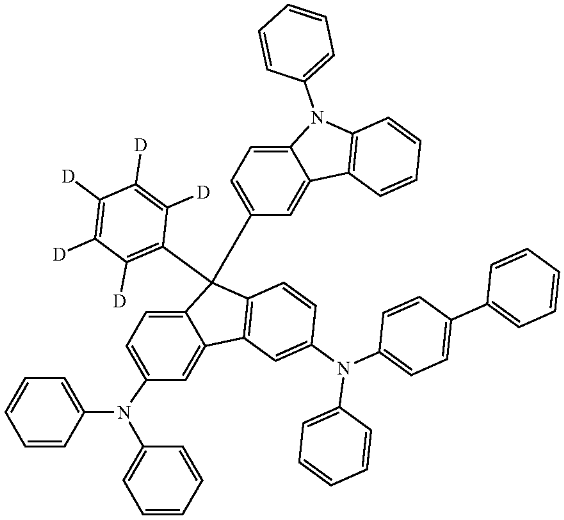
-continued
307
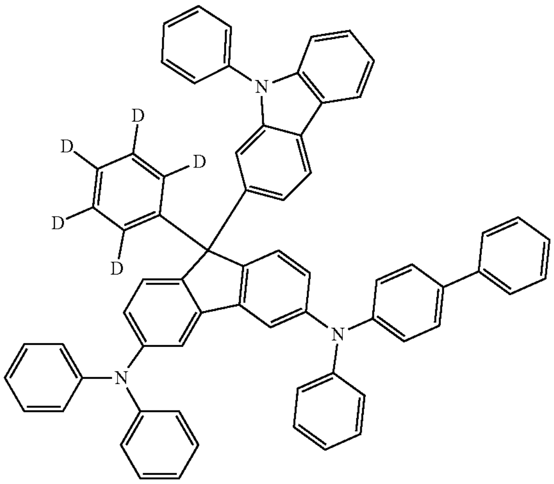
308
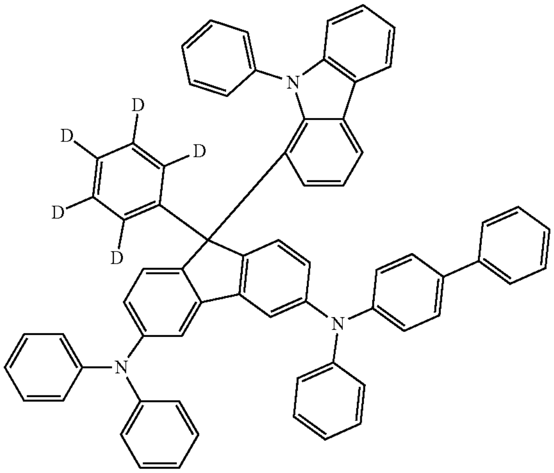
309
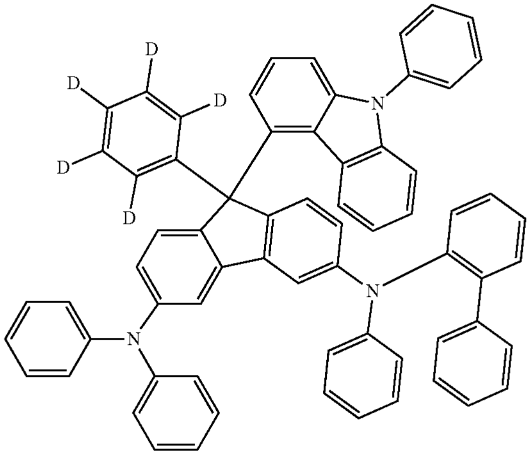

-continued
310
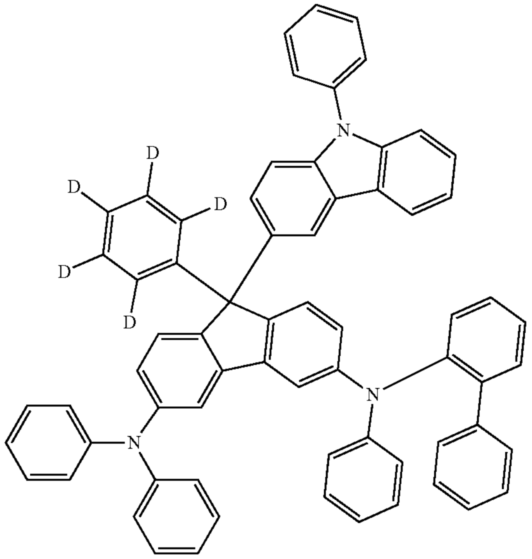
311
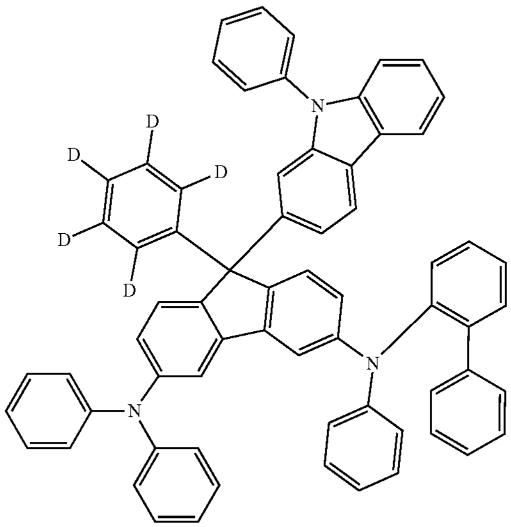
312
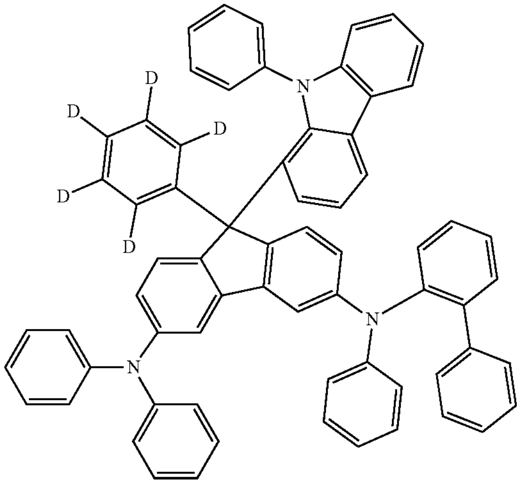
-continued
313
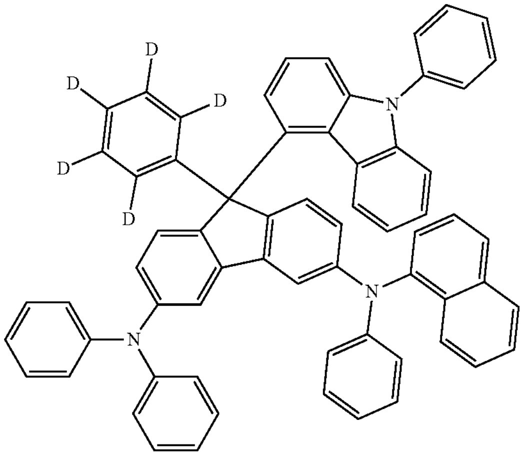
314
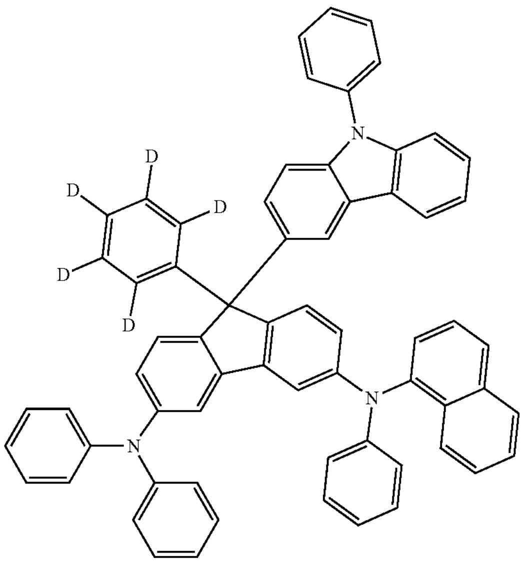
315
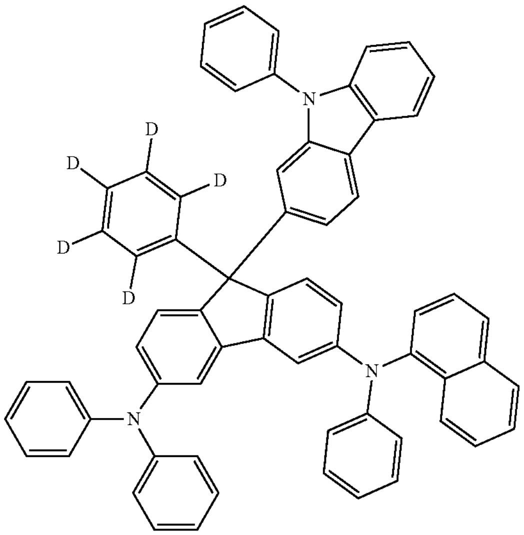

-continued
316
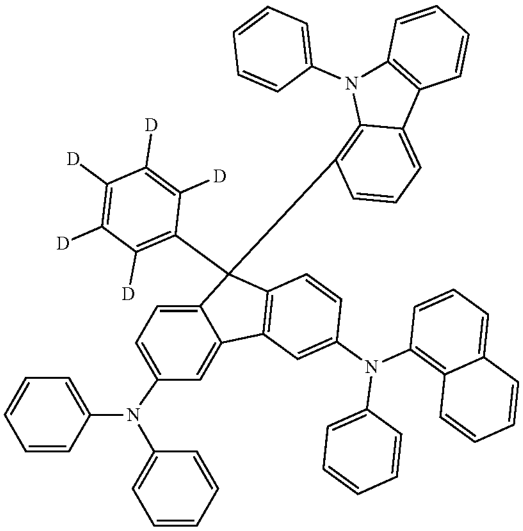
317
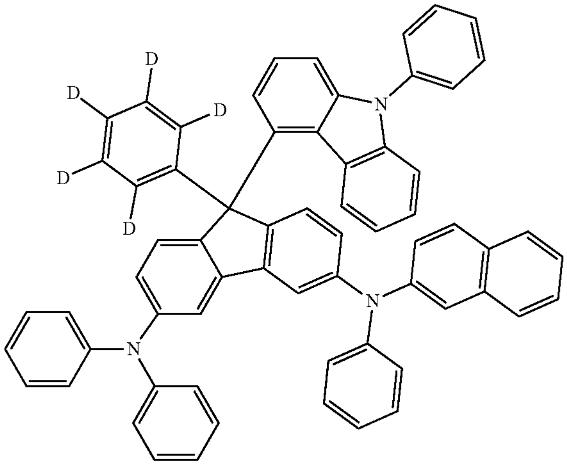
318
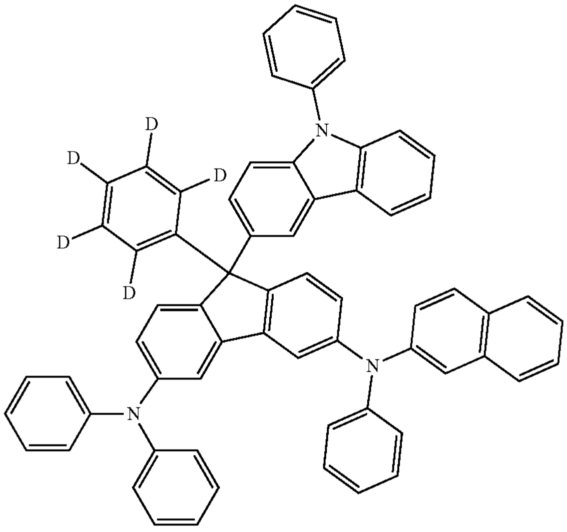
-continued
319
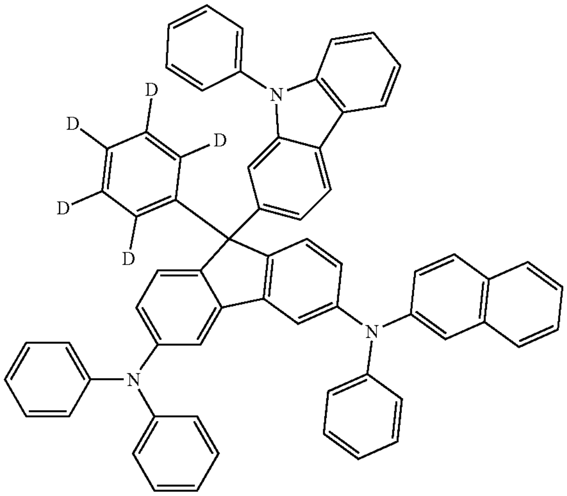
320
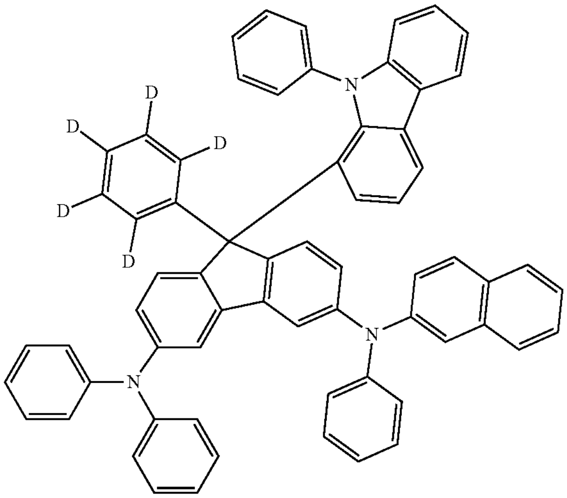
321
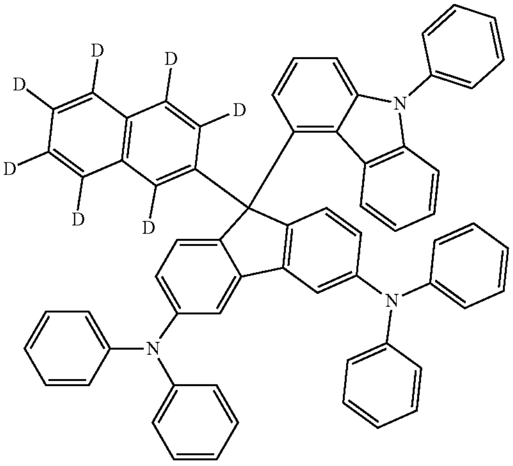

-continued
322
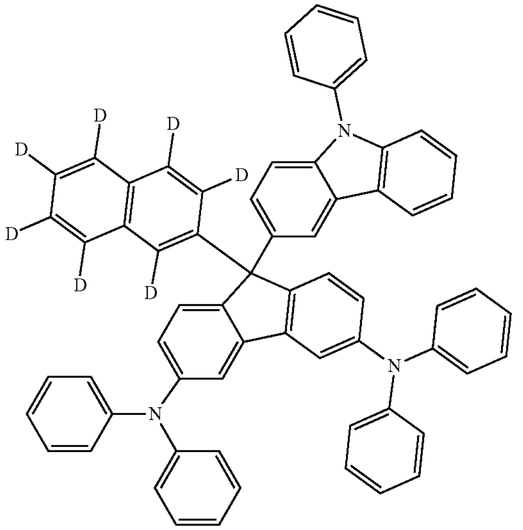
323
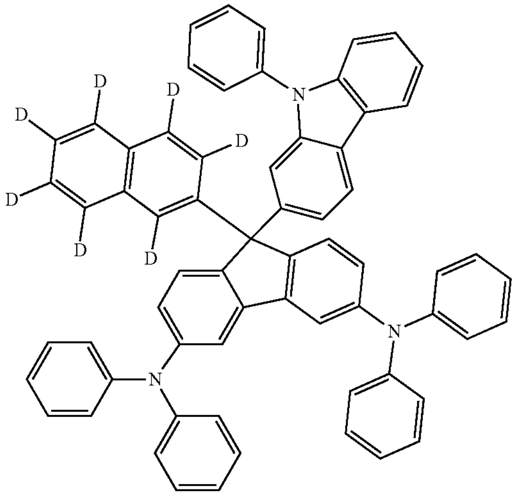
324
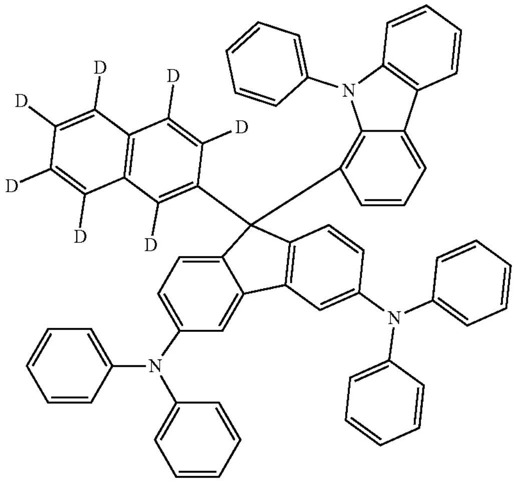
-continued
325
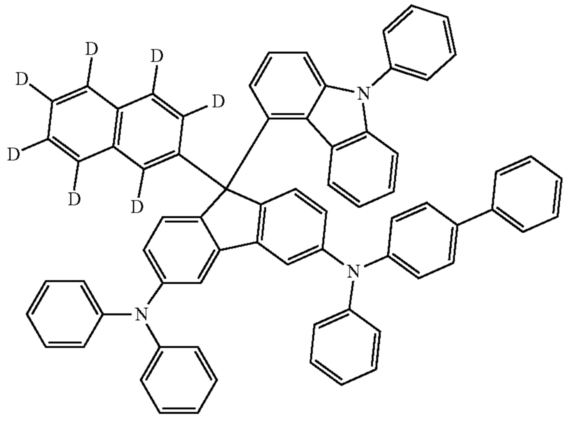
326
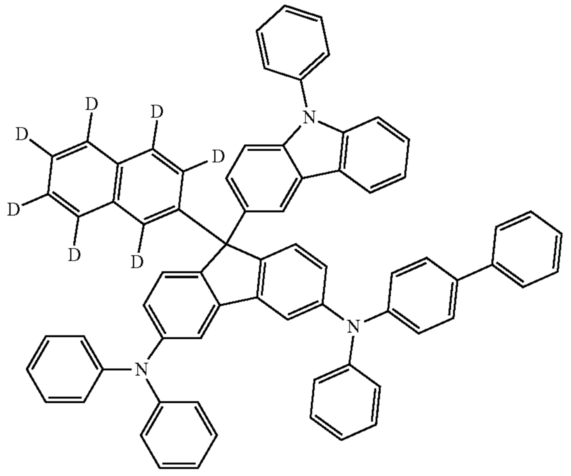
327
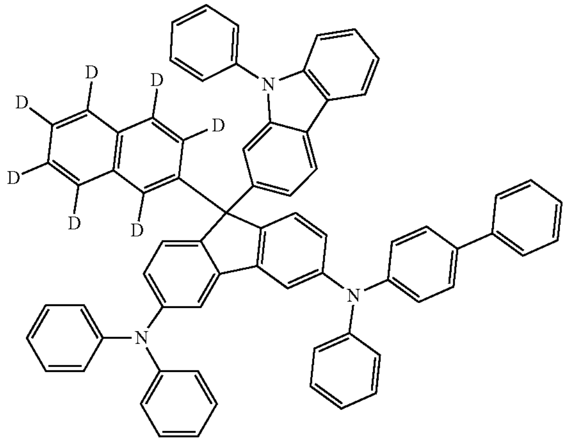

-continued
328
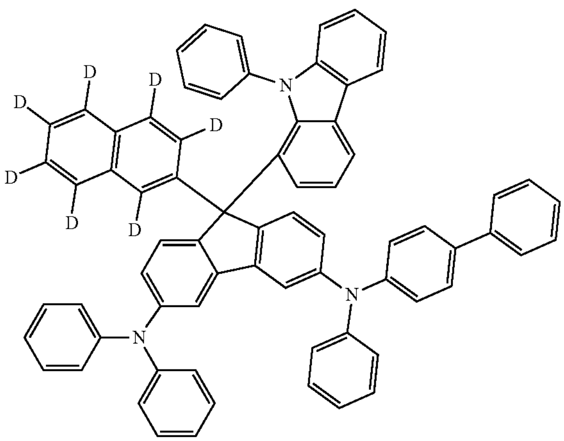
329
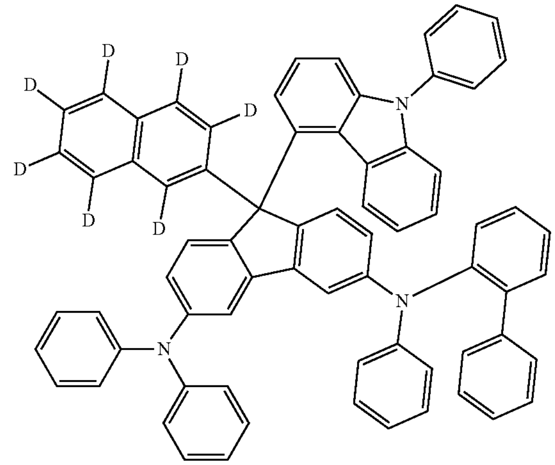
330
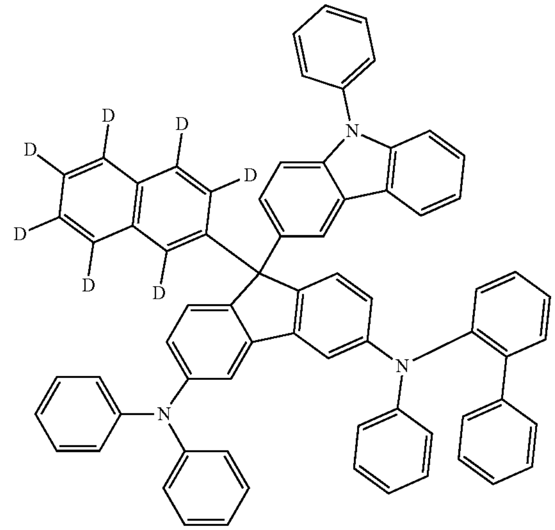
-continued
331
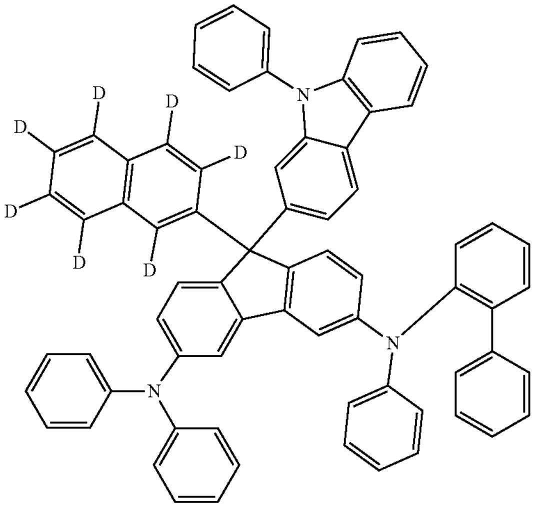
332
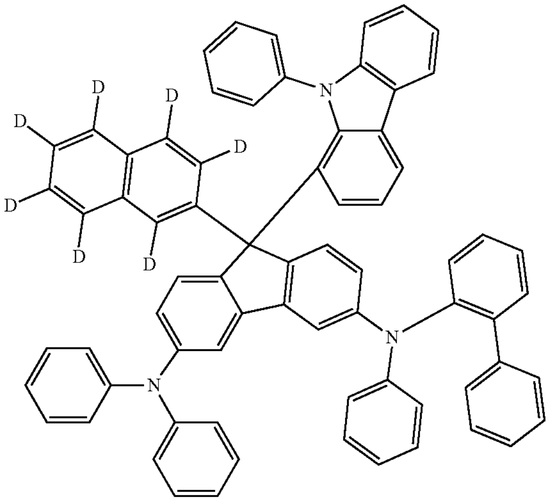
333
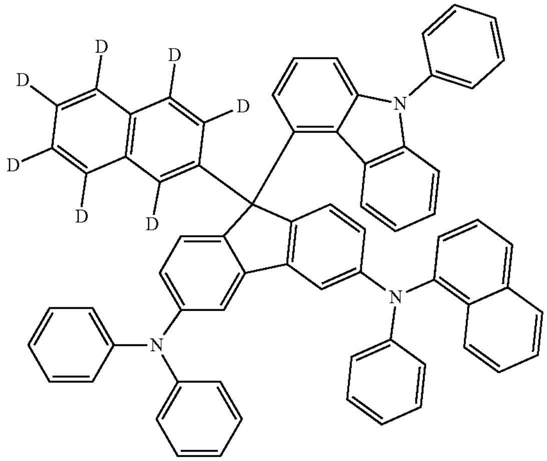

-continued
334
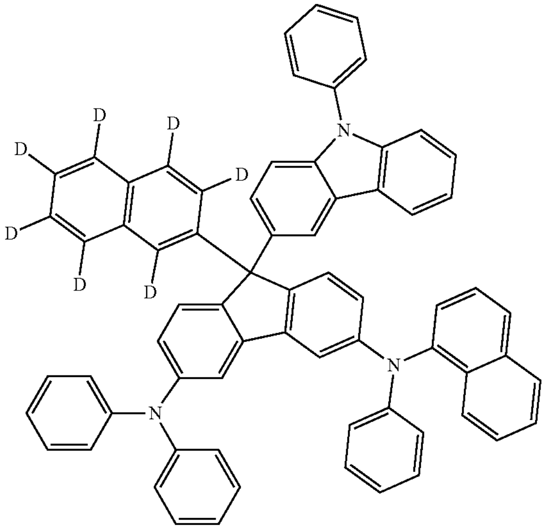
335
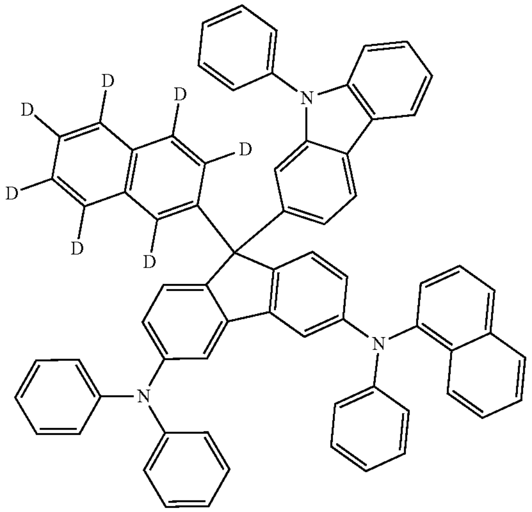
336
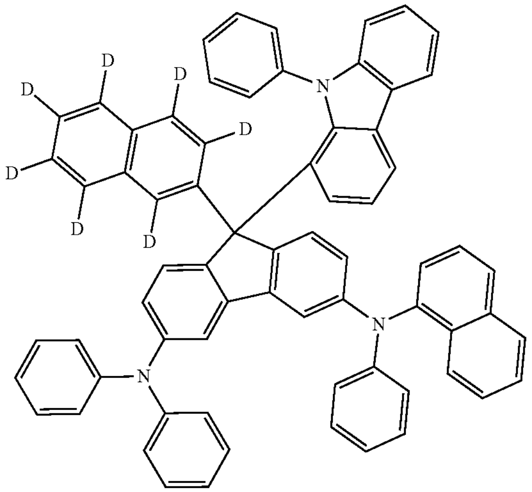
-continued
337
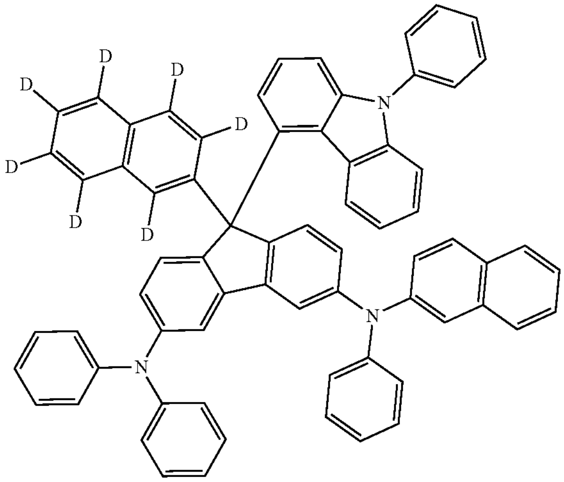
338
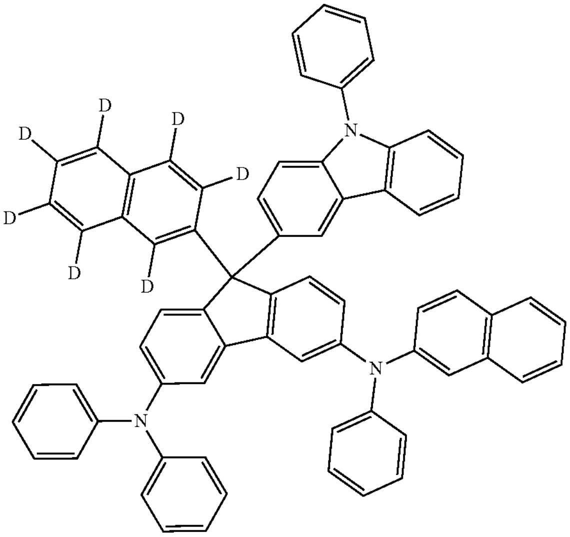
339
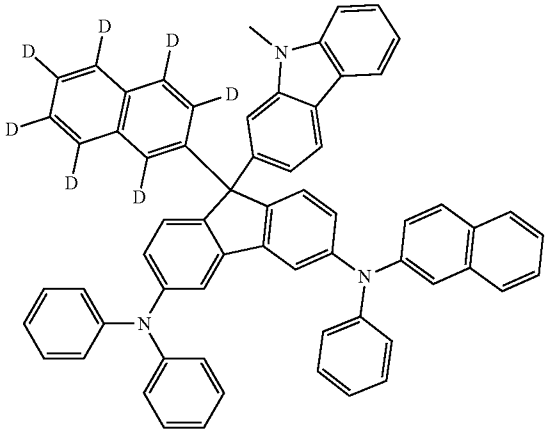

-continued
340
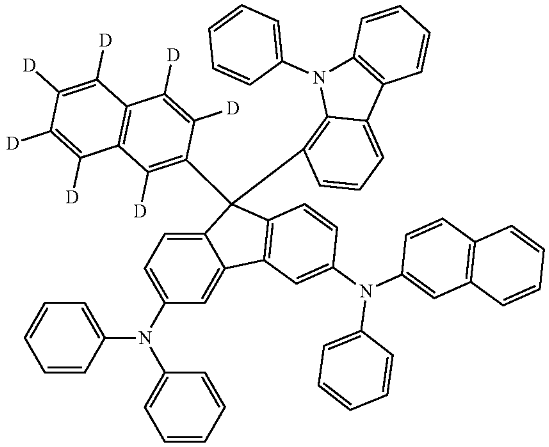
341
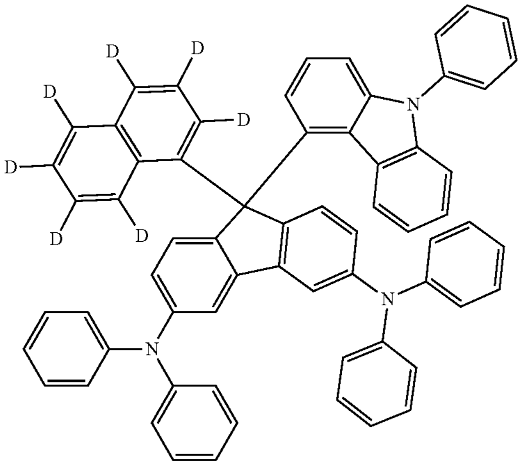
342
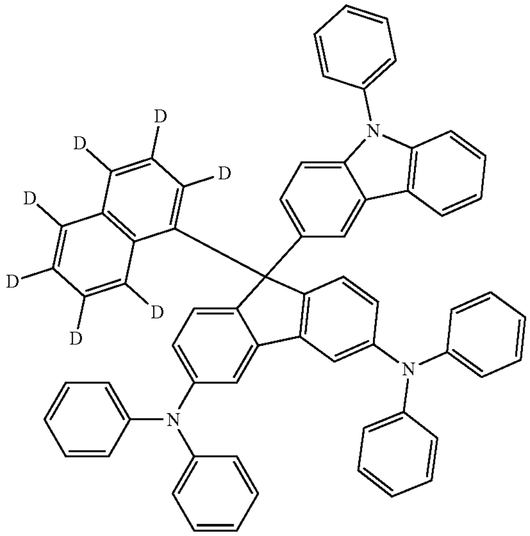
-continued
343
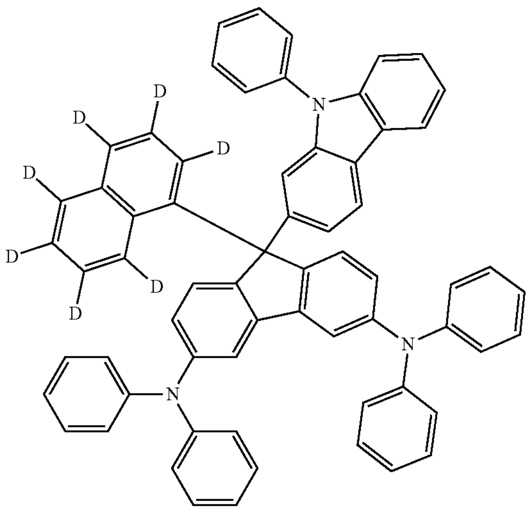
344
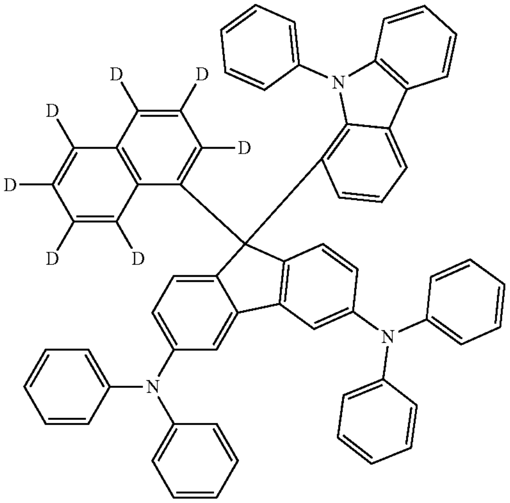
345
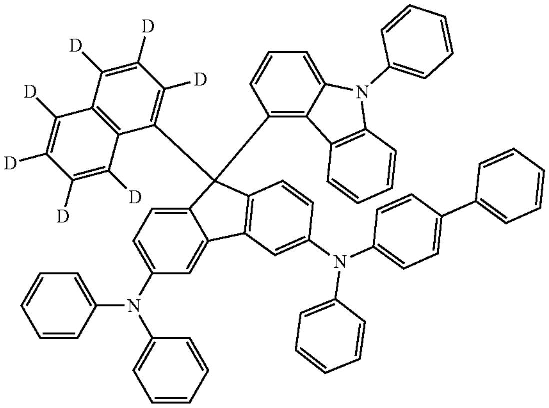

-continued
346
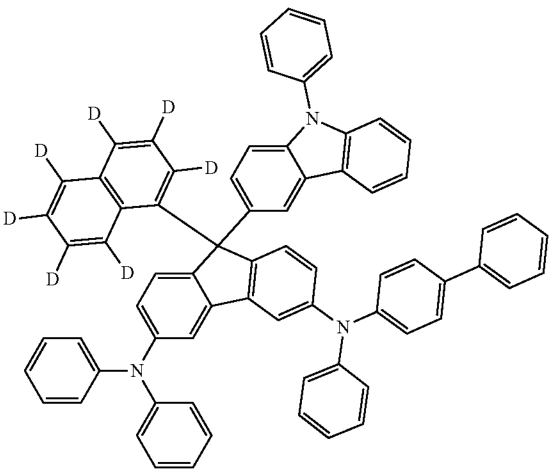
347
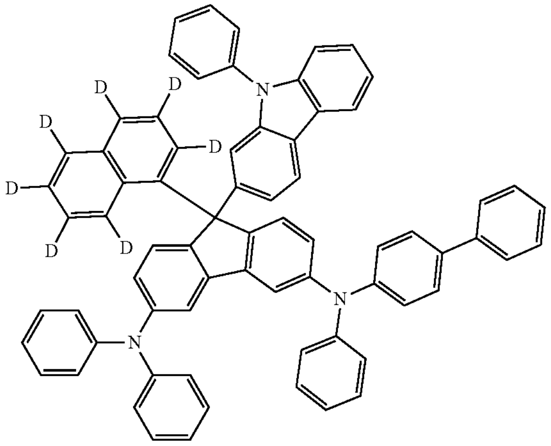
348
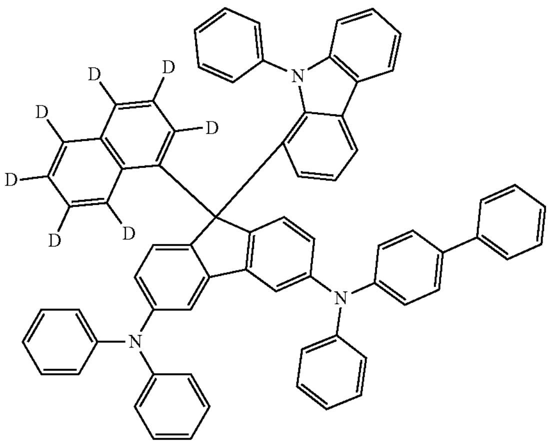
-continued
349
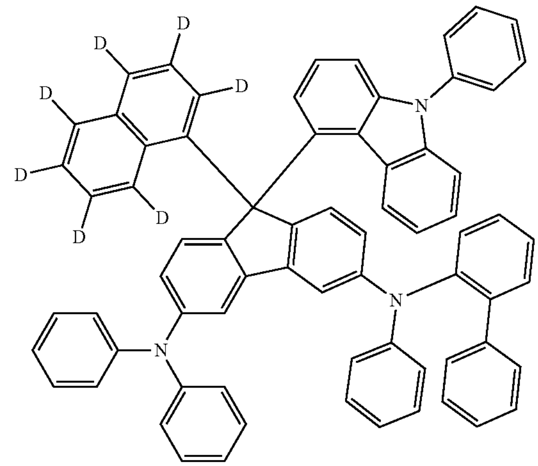
350
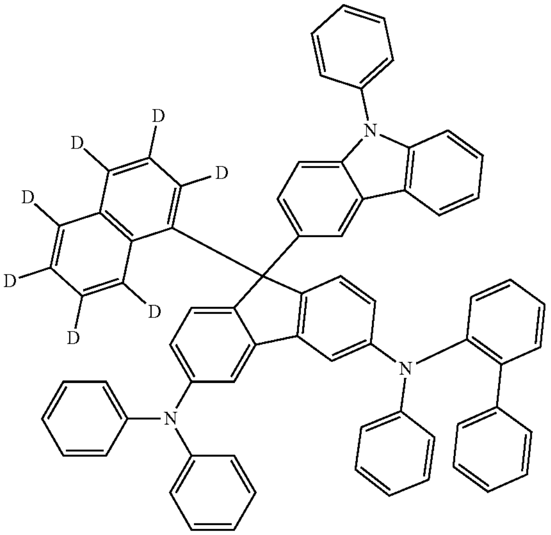
351
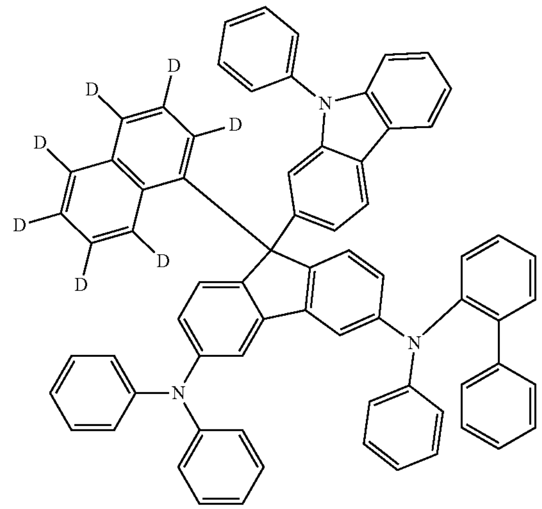

352
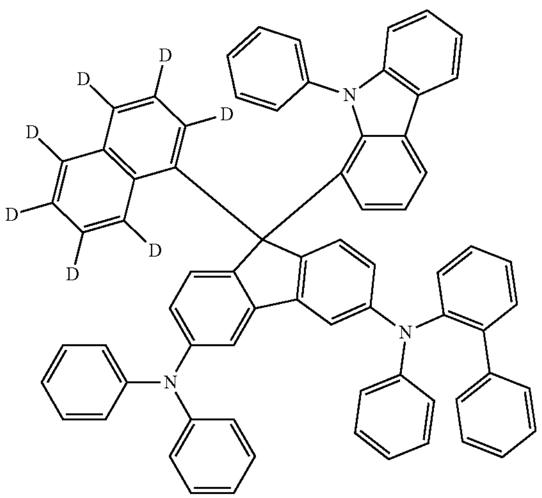
353
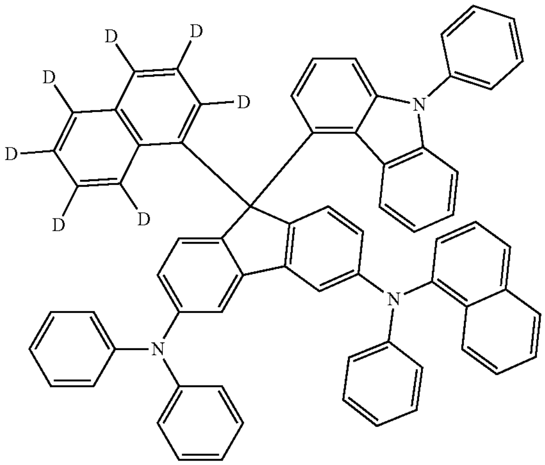
354
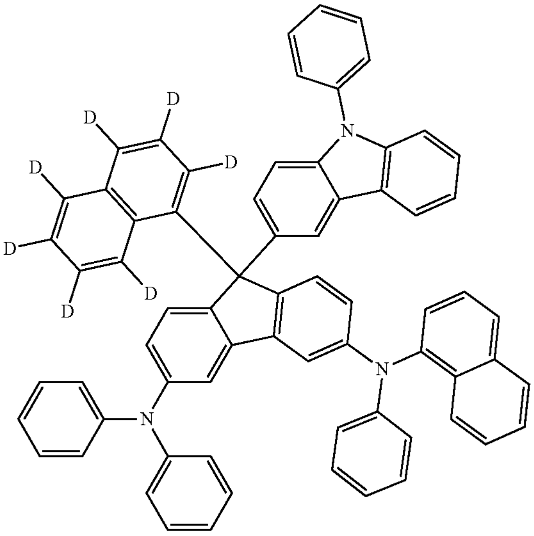
355
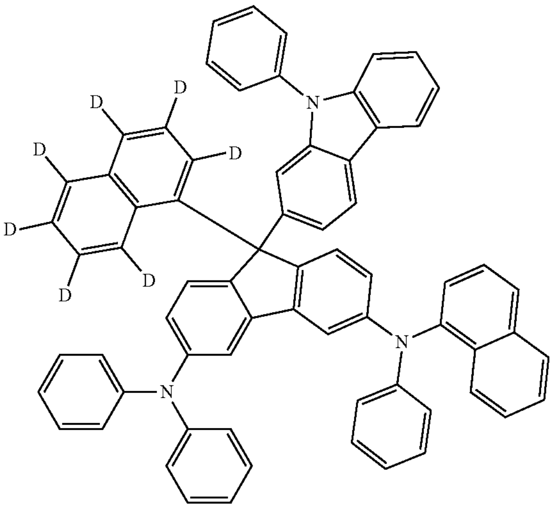
356
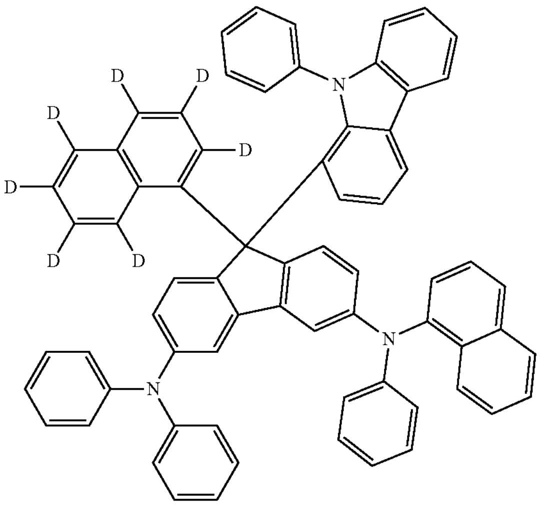
357
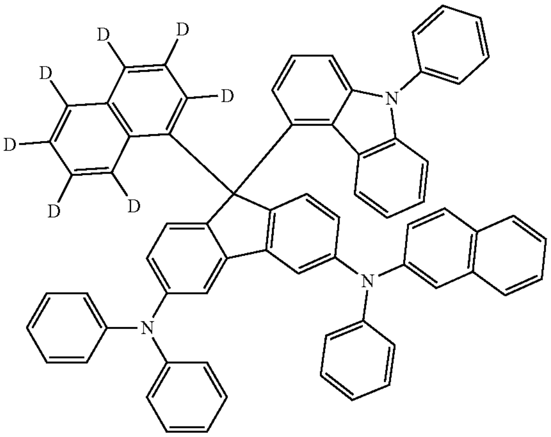

-continued
358
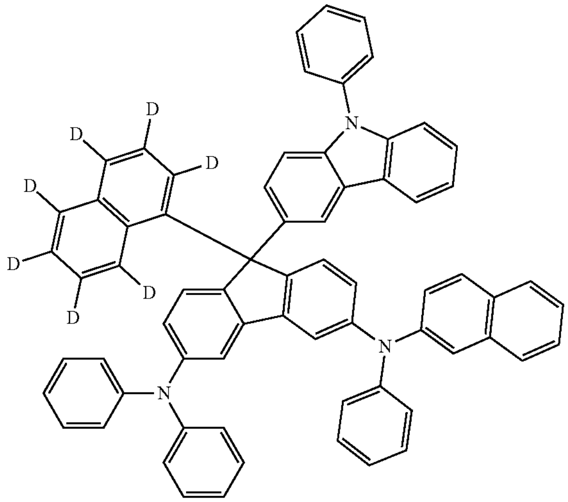
359
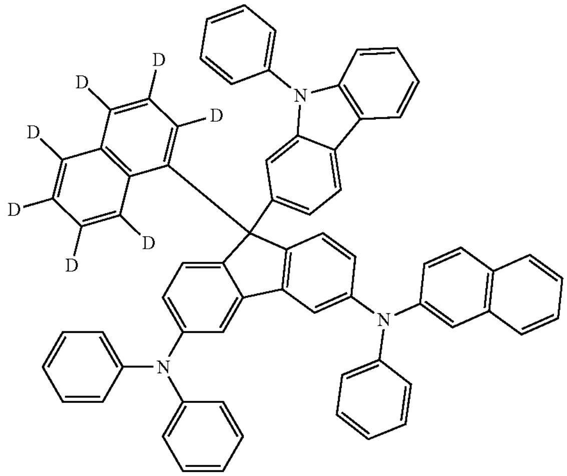
360
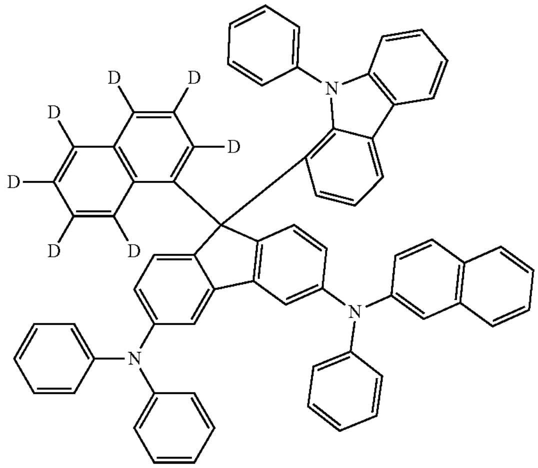
-continued
175
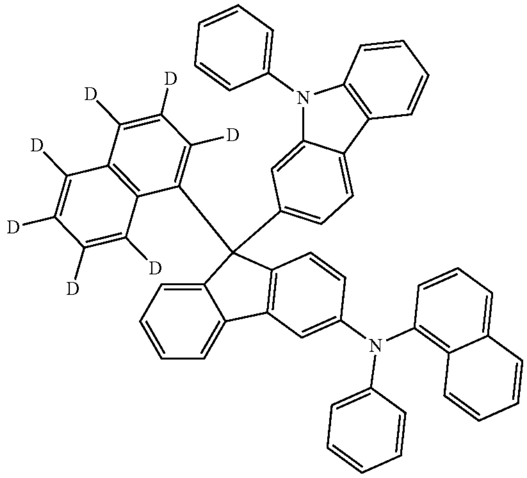
176
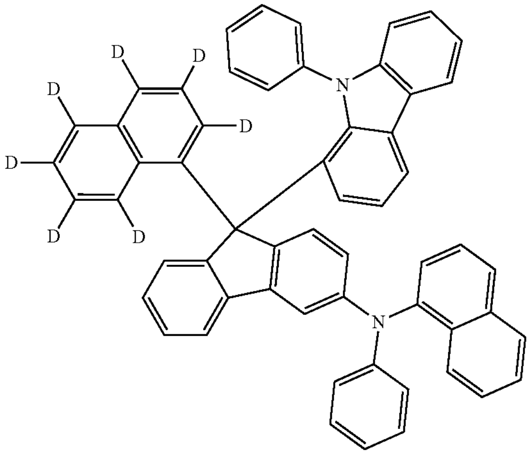
337
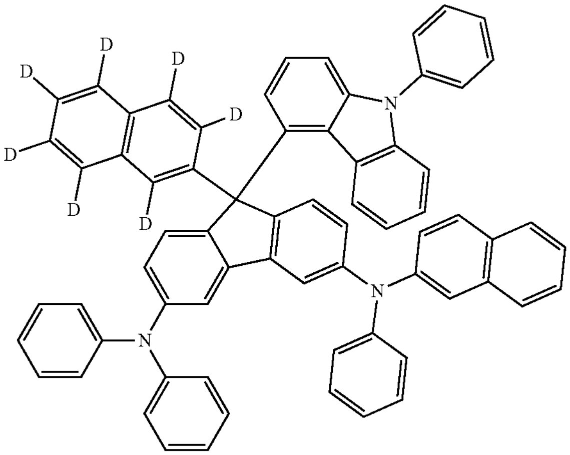

-continued

338

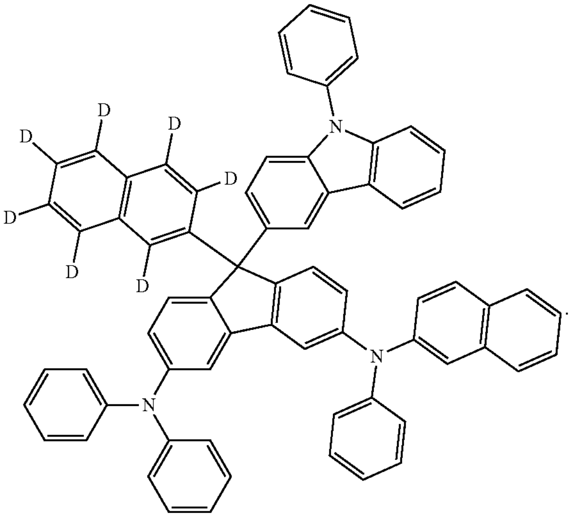

11. An organic electroluminescence device comprising:

a first electrode;

a second electrode facing the first electrode; and a plurality of organic layers between the first electrode and the second electrode, wherein at least one organic layer of the organic layers comprises an amine compound represented by Formula 1:

Formula 1

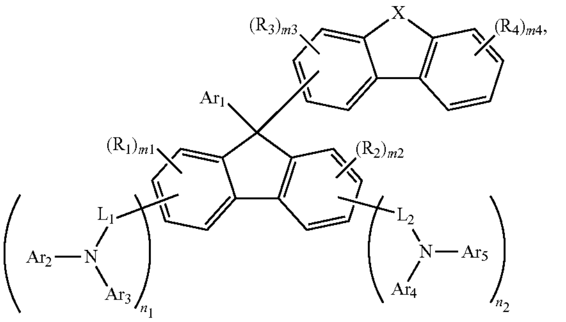

wherein, in Formula 1,

X is O, S, or $NAr_6$;

$L_1$ and $L_2$ are each independently a direct linkage, a substituted or unsubstituted arylene group having 6 to 60 ring-forming carbon atoms, or a substituted or unsubstituted heteroarylene group having 2 to 60 ring-forming carbon atoms;

$R_1$ to $R_4$ are each independently a hydrogen atom, a deuterium atom, a halogen atom, a substituted or unsubstituted alkyl group having 1 to 20 carbon atoms, a substituted or unsubstituted aryl group having 6 to 60 ring-forming carbon atoms, or a substituted or unsubstituted heteroaryl group having 2 to 60 ring-forming carbon atoms, and/or are optionally bonded to an adjacent group to form a ring;

$m_1$, $m_2$, and $m_4$ are each independently an integer of 0 to 4;

$m_3$ is an integer of 0 to 3;

$Ar_1$ is a phenyl group substituted with deuterium, a naphthyl group substituted with deuterium, or a biphenyl group substituted with deuterium;

$Ar_2$ to $Ar_6$ are each independently a substituted or unsubstituted aryl group having 6 to 60 ring-forming carbon atoms, or a substituted or unsubstituted heteroaryl group having 3 to 60 ring-forming carbon atoms;

$n_1$ and $n_2$ are each independently 0 or 1;

at least one of $n_1$ or $n_2$ is 1, and wherein the amine group is connected to at least one of 3-position carbon or 6-position carbon of the fluorene group.

12. The organic electroluminescence device of claim 11, wherein the amine compound represented by Formula 1 is represented by at least one of Formula 1-1 to Formula 1-3:

Formula 1-1

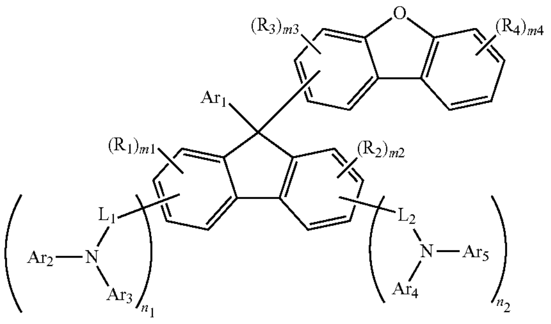

Formula 1-2

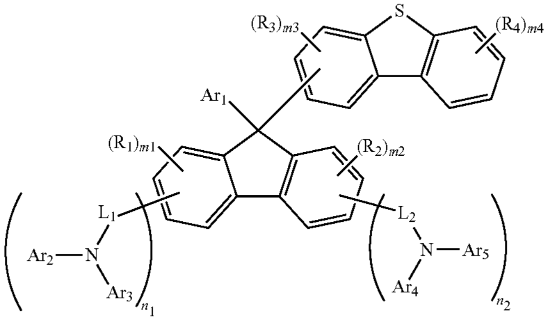

Formula 1-3

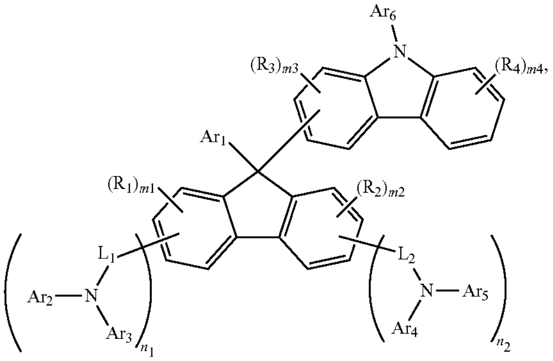

wherein, in Formula 1-1 to Formula 1-3, $L_1$, $L_2$, $R_1$ to $R_4$, $m_1$ to $m_4$, $Ar_1$ to $Ar_6$, $n_1$ and $n_2$ are each independently the same as defined in Formula 1.

13. The organic electroluminescence device of claim 11, wherein the amine compound represented by Formula 1 is represented by at least one of Formula 2-1 to Formula 2-5:

Formula 2-1

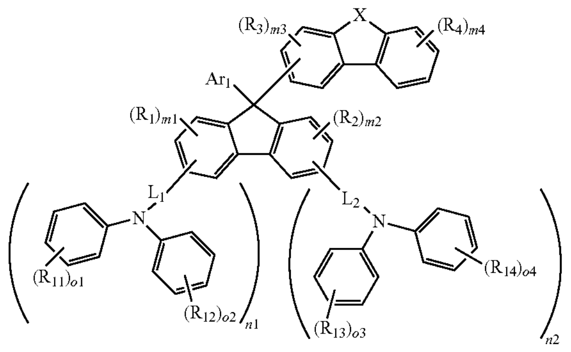

Formula 2-2

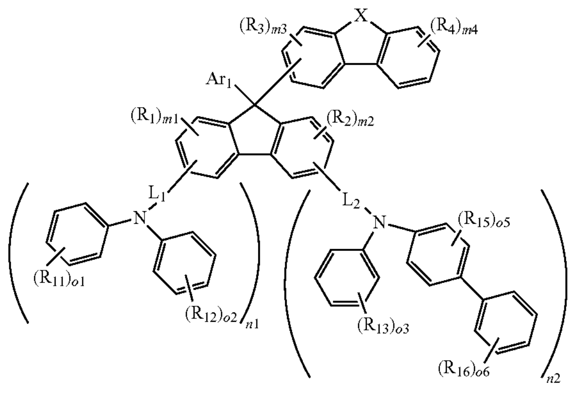

Formula 2-3

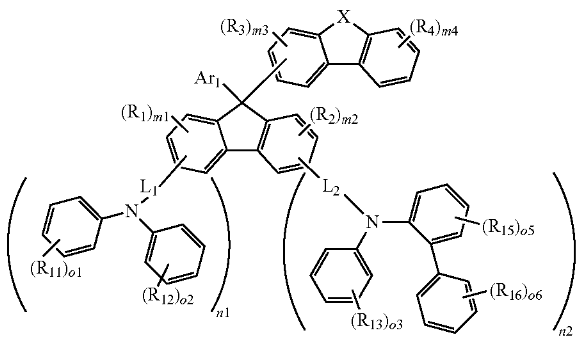

Formula 2-4

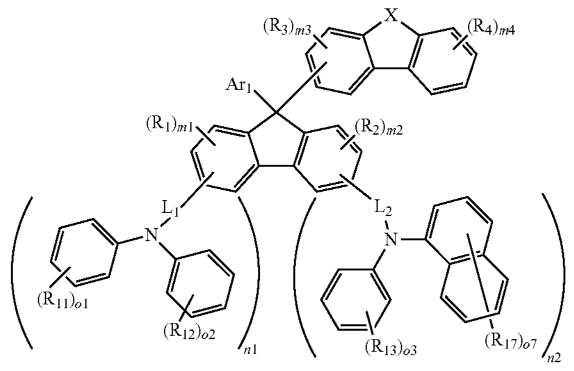

-continued

Formula 2-5

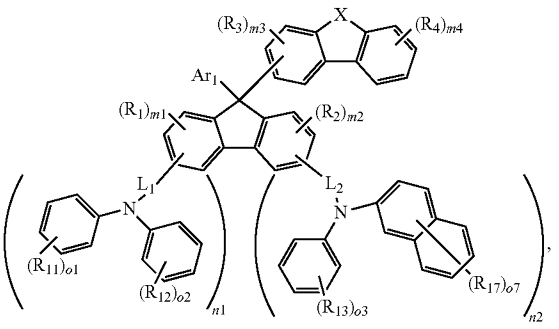

wherein, in Formula 2-1 to Formula 2-5, $R_{11}$ to $R_{17}$ are each independently a hydrogen atom, a deuterium atom, a halogen atom, a substituted or unsubstituted alkyl group having 1 to 20 carbon atoms, a substituted or unsubstituted aryl group having 6 to 60 ring-forming carbon atoms, or a substituted or unsubstituted heteroaryl group having 2 to 60 ring-forming carbon atoms, and/or are optionally bonded to an adjacent group to form a ring;

$o_1$ to $o_4$ and $o_6$ are each independently an integer of 0 to 5;

$o_5$ is an integer of 0 to 4;

$o_7$ is an integer of 0 to 7; and

X, $R_1$ to $R_4$, $L_1$, $L_2$, $n_1$, $n_2$, $m_1$ to $m_4$ and $Ar_1$ are each independently the same as defined in Formula 1.

14. The organic electroluminescence device of claim 11, wherein the amine compound represented by Formula 1 is represented by Formula 3-1:

Formula 3-1

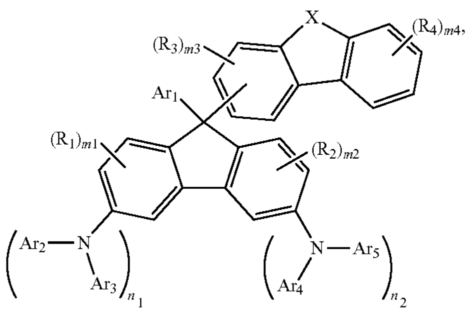

wherein, in Formula 3-1,

X, $Ar_1$ to $Ar_5$, $R_1$ to $R_4$, $n_1$, $n_2$, and $m_1$ to $m_4$ are each independently the same as defined in Formula 1.

15. An amine compound represented by Formula 1:

Formula 1

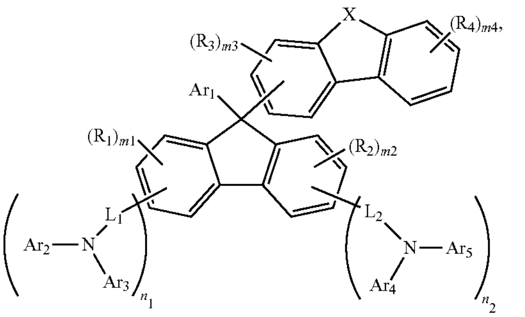

wherein, in Formula 1,

X is O, S, or $NAr_6$;

$L_1$ and $L_2$ are each independently a direct linkage, a substituted or unsubstituted arylene group having 6 to 60 ring-forming carbon atoms, or a substituted or unsubstituted heteroarylene group having 2 to 60 ring-forming carbon atoms;

$R_1$ to $R_4$ are each independently a hydrogen atom, a deuterium atom, a halogen atom, a substituted or unsubstituted alkyl group having 1 to 20 carbon atoms, a substituted or unsubstituted aryl group having 6 to 60 ring-forming carbon atoms, or a substituted or unsubstituted heteroaryl group having 2 to 60 ring-forming carbon atoms, and/or are optionally bonded to an adjacent group to form a ring;

$m_1$, $m_2$, and $m_4$ are each independently an integer of 0 to 4;

$m_3$ is an integer of 0 to 3;

$Ar_1$ is a phenyl group substituted with deuterium, a naphthyl group substituted with deuterium, or a biphenyl group substituted with deuterium;

$Ar_2$ to $Ar_6$ are each independently a substituted or unsubstituted aryl group having 6 to 60 ring-forming carbon atoms, or a substituted or unsubstituted heteroaryl group having 3 to 60 ring-forming carbon atoms;

$n_1$ and $n_2$ are each independently 0 or 1;

at least one of $n_1$ or $n_2$ is 1, and wherein the amine group is connected to at least one of 3-position carbon or 6-position carbon of the fluorene group.

16. The amine compound of claim 15, wherein the amine compound represented by Formula 1 is represented by at least one of Formula 1-1 to Formula 1-3:

Formula 1-1

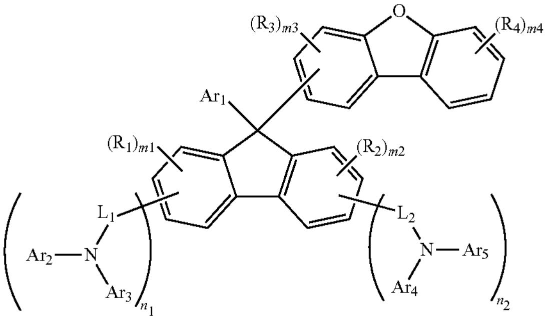

-continued

Formula 1-2

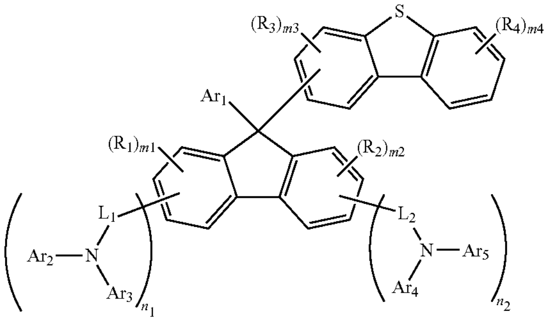

Formula 1-3

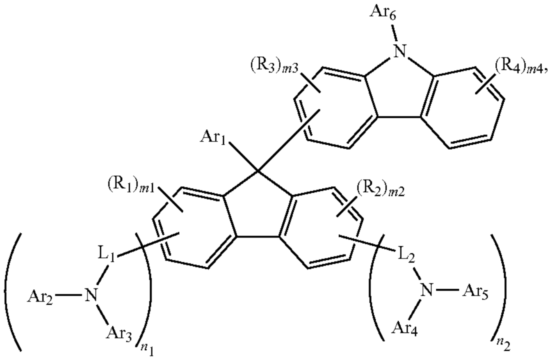

wherein, in Formula 1-1 to Formula 1-3, $L_1$, $L_2$, $R_1$ to $R_4$, $m_1$ to $m_4$, $Ar_1$ to $Ar_6$, $n_1$ and $n_2$ are each independently the same as defined in Formula 1.

17. The amine compound of claim 15, wherein the amine compound represented by Formula 1 is represented by at least one of Formula 2-1 to Formula 2-5:

Formula 2-1

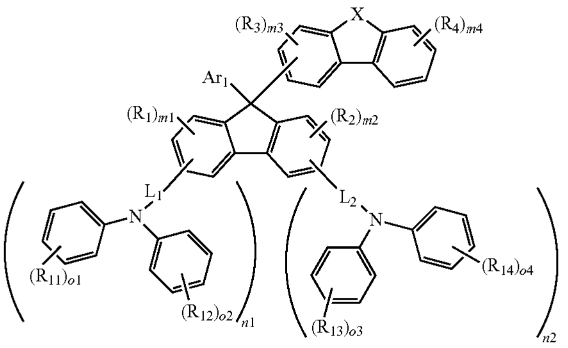

-continued

Formula 2-2

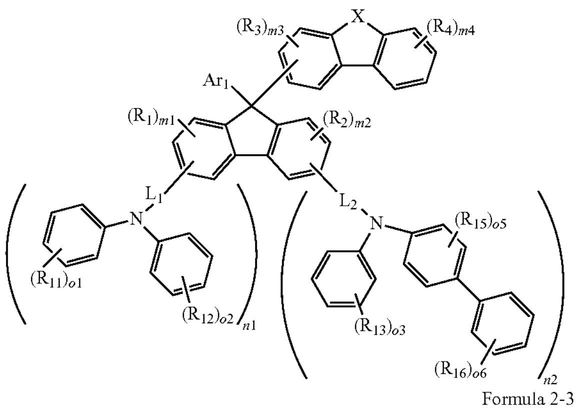

Formula 2-3

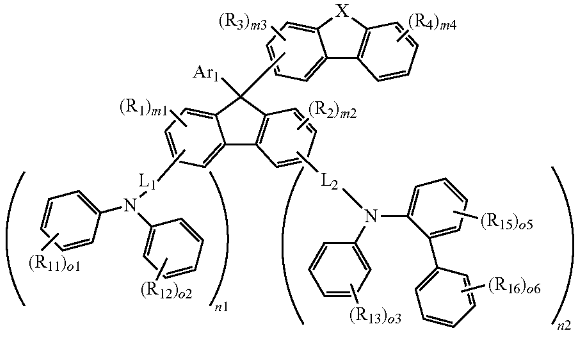

Formula 2-4

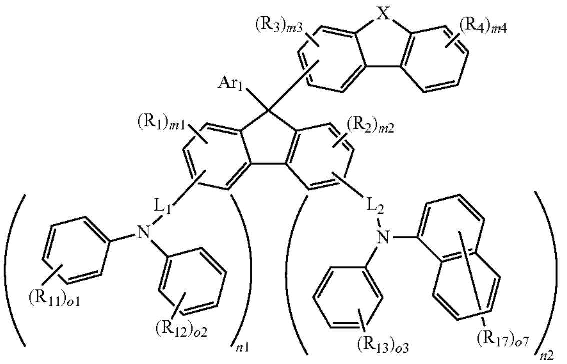

Formula 2-5

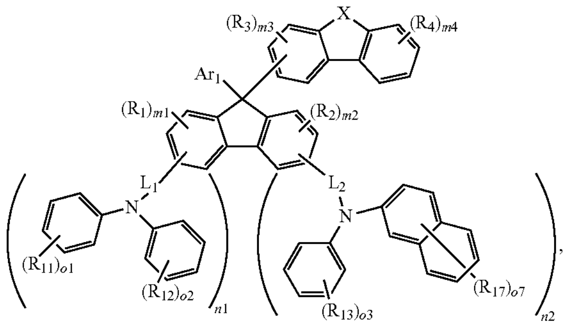

wherein, in Formula 2-1 to Formula 2-5, $R_{11}$ to $R_{17}$ are each independently a hydrogen atom, a deuterium atom, a halogen atom, a substituted or unsubstituted alkyl group having 1 to 20 carbon atoms, a substituted or unsubstituted aryl group having 6 to 60 ring-forming carbon atoms, or a substituted or unsubstituted heteroaryl group having 2 to 60 ring-forming carbon atoms, and/or are optionally bonded to an adjacent group to form a ring;

$o_1$ to $o_4$ and $o_6$ are each independently an integer of 0 to 5;

$o_5$ is an integer of 0 to 4;

$o_7$ is an integer of 0 to 7; and

X, $R_1$ to $R_4$, $L_1$, $L_2$, $n_1$, $n_2$, $m_1$ to $m_4$ and $Ar_1$ are each independently the same as defined in Formula 1.

18. The amine compound of claim 15, wherein the amine compound represented by Formula 1 is represented by Formula 3-1:

Formula 3-1

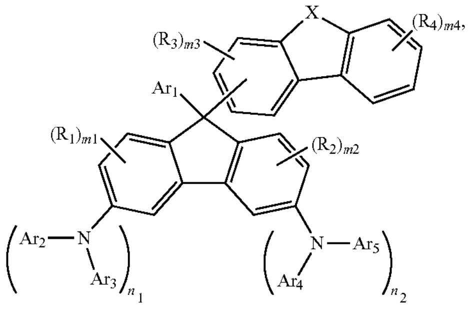

wherein, in Formula 3-1,

X, $Ar_1$ to $Ar_5$, $R_1$ to $R_4$, $n_1$, $n_2$, and $m_1$ to $m_4$ are each independently the same as defined in Formula 1.

19. The amine compound of claim 15, wherein the amine compound represented by Formula 1 comprises at least one of the compounds represented by Compound Group 1:

Compound Group 1

1

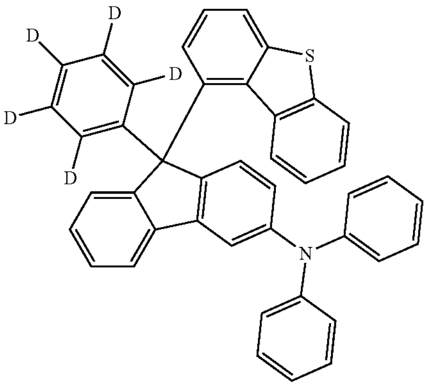

2
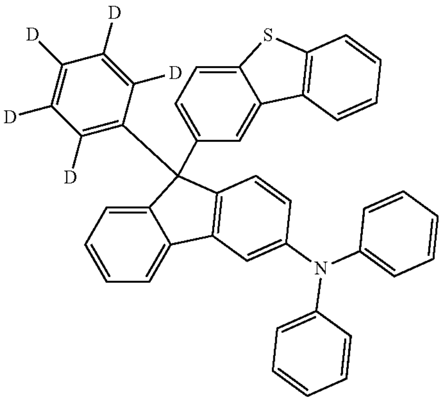
3
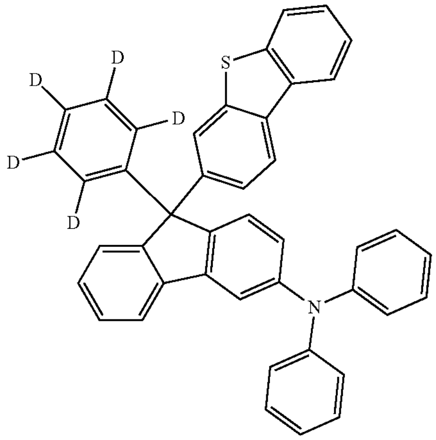
4
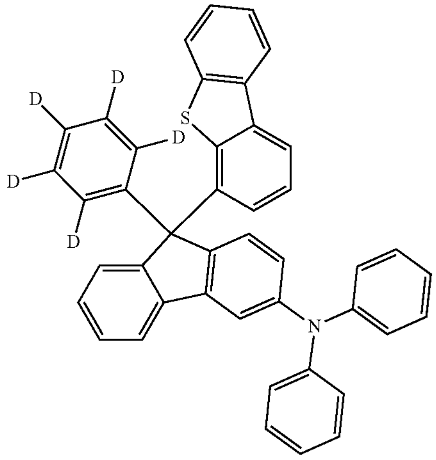
5
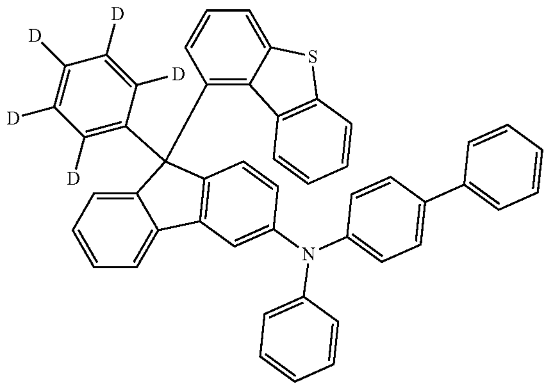
6
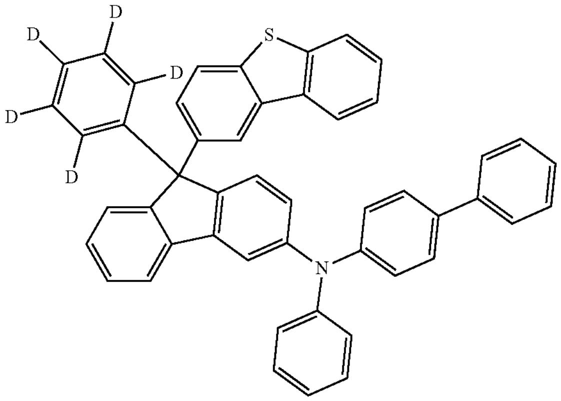
7
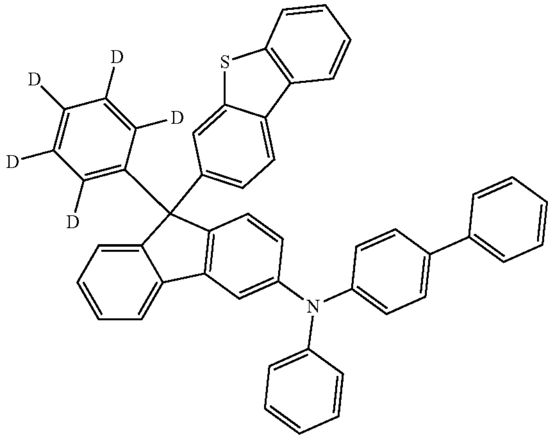

-continued
8
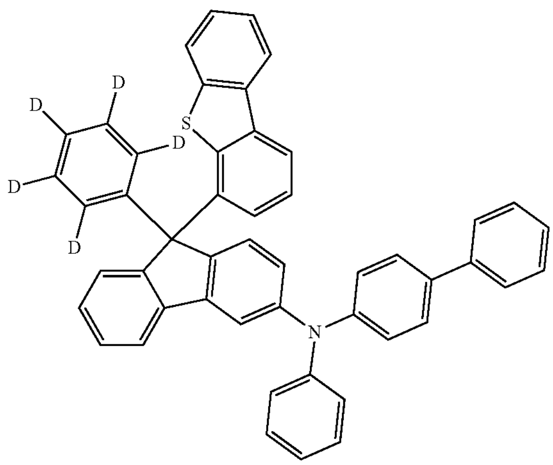
9
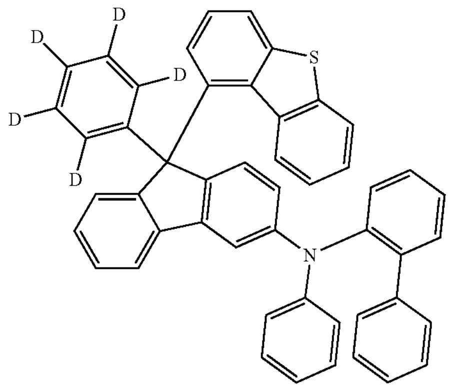
10
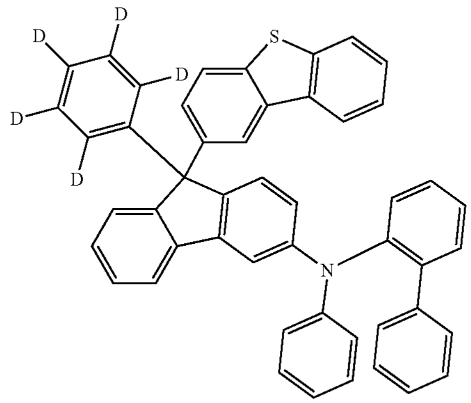
-continued
11
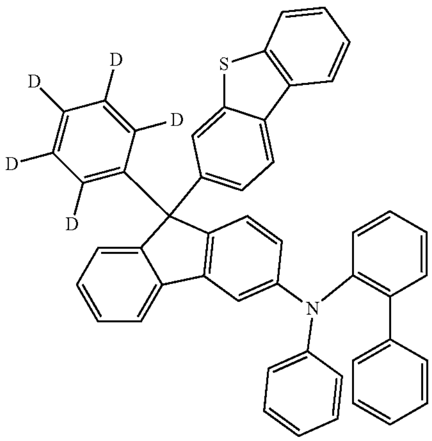
12
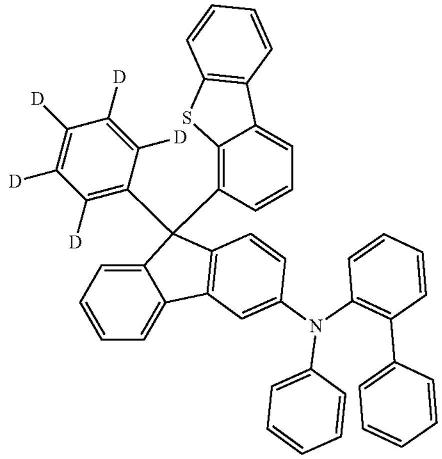
13
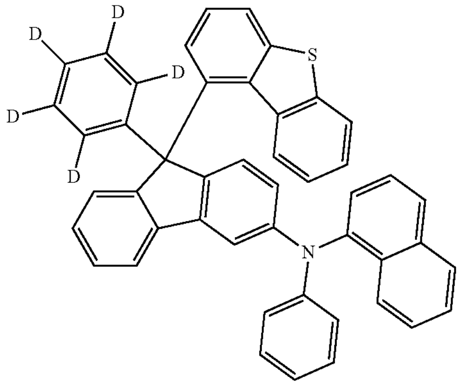

-continued
14
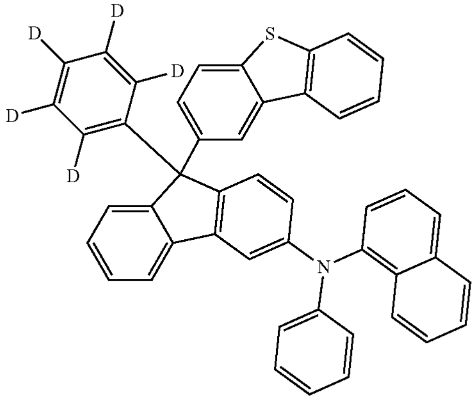
15
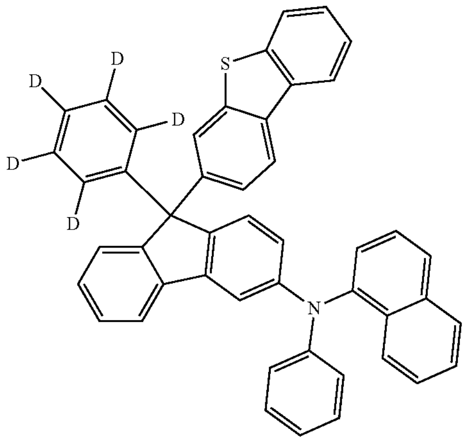
16
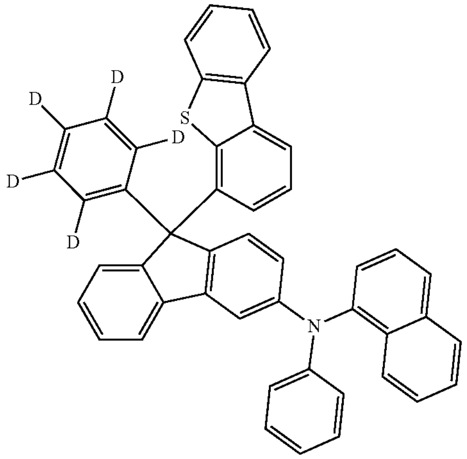
-continued
17
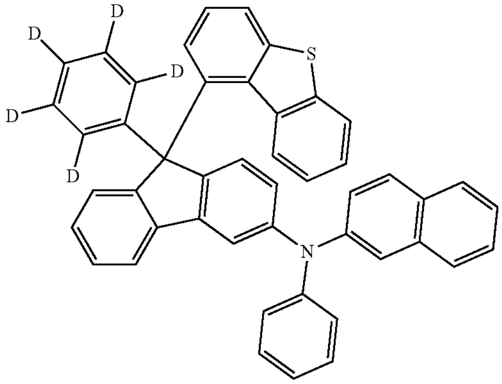
18
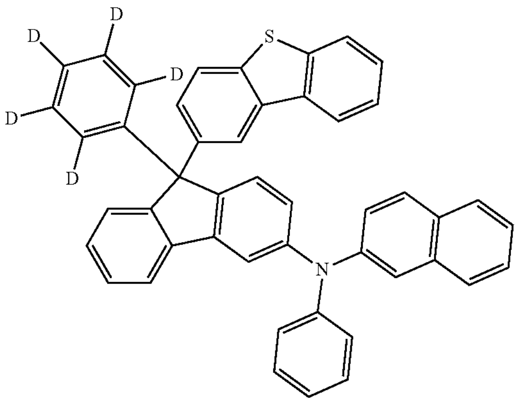
19
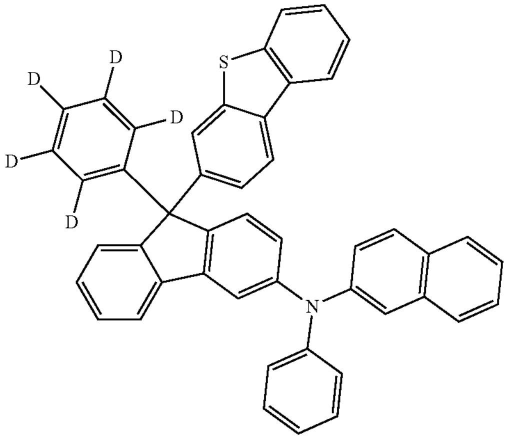

-continued
20
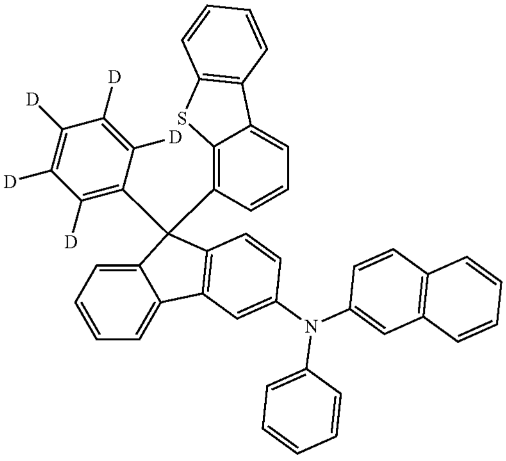
21
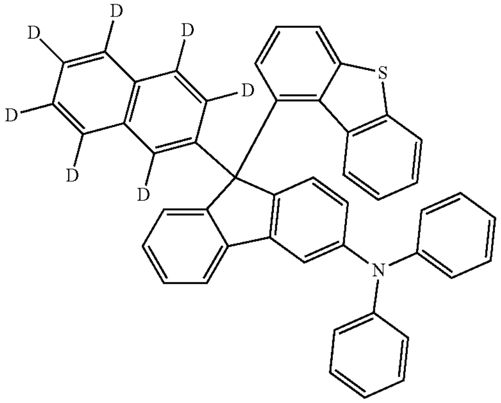
22
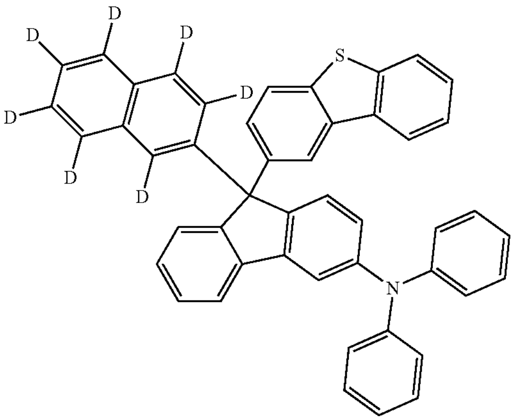
-continued
23
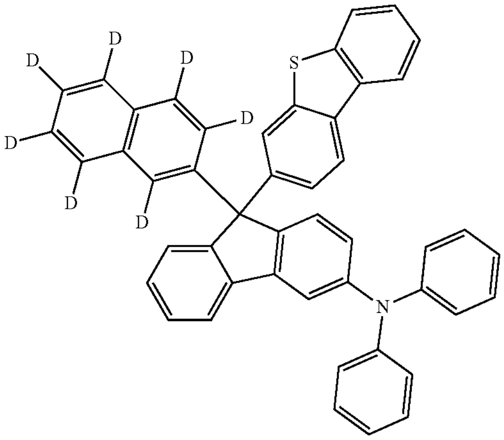
24
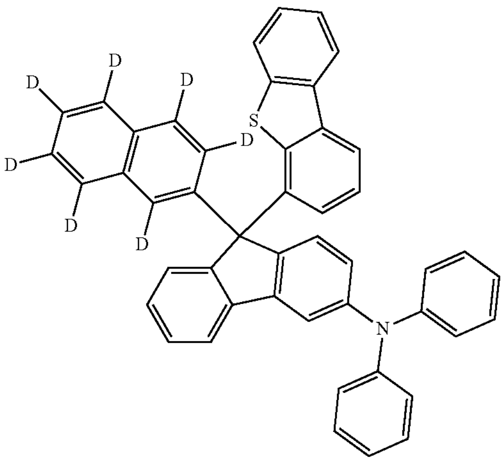
25
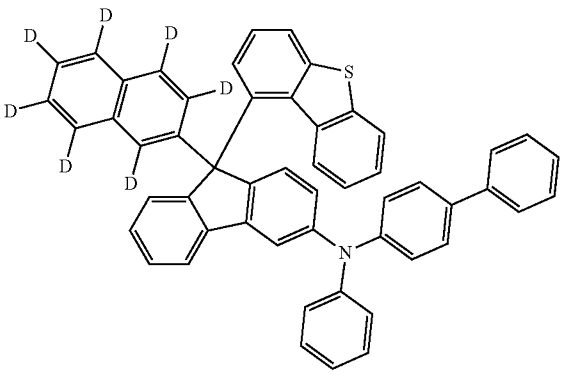

26
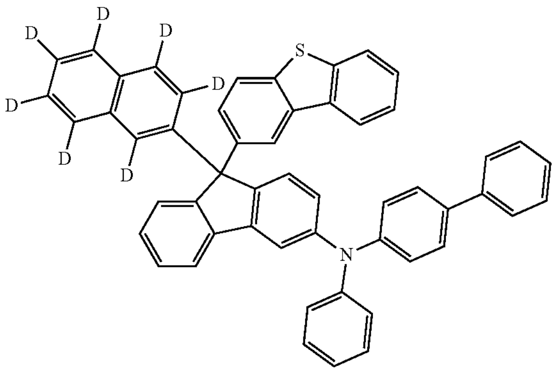
27
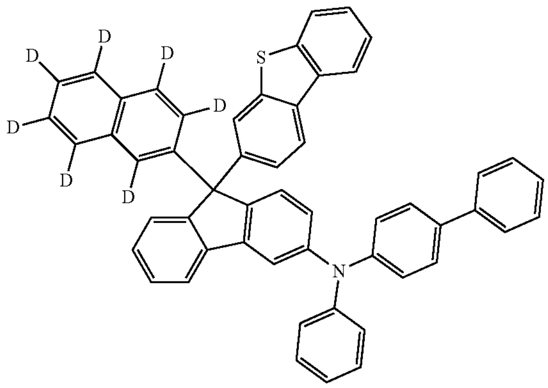
28
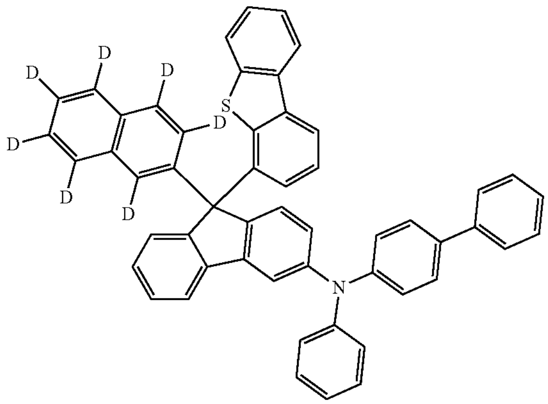
29
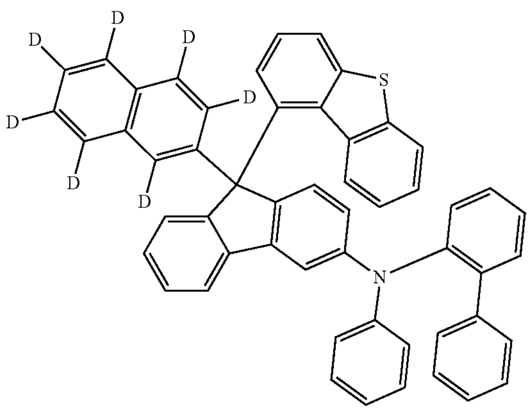
30
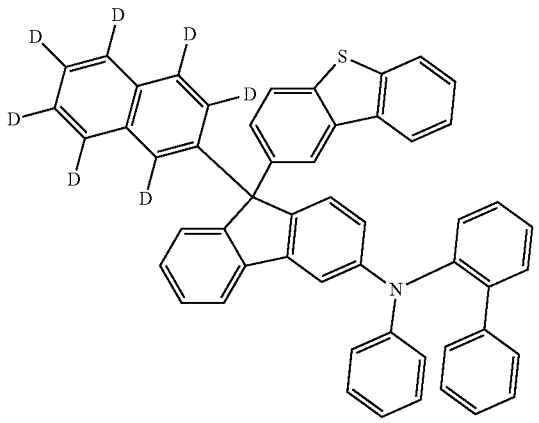
31
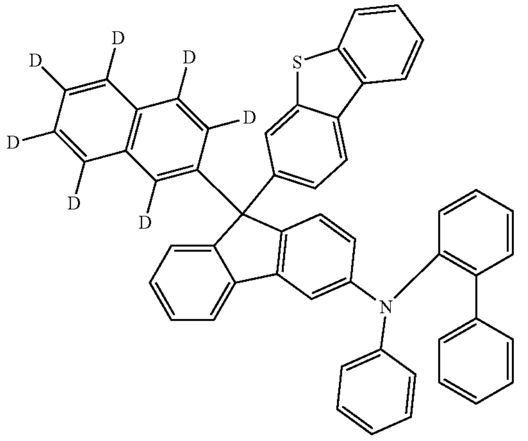
32
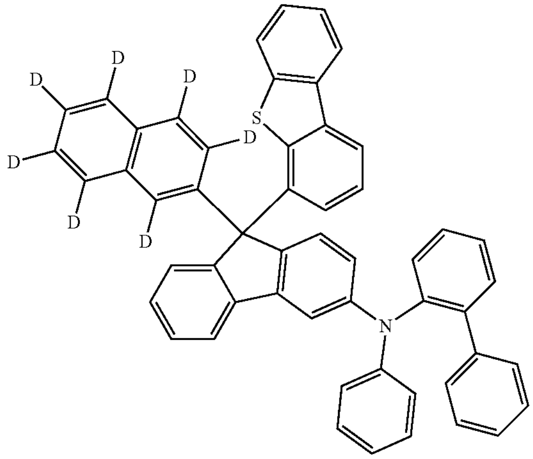

-continued
33
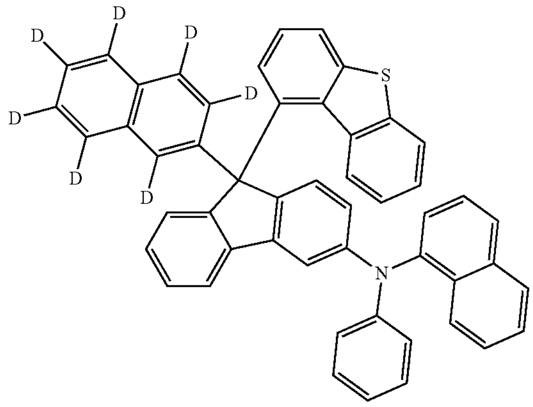
34
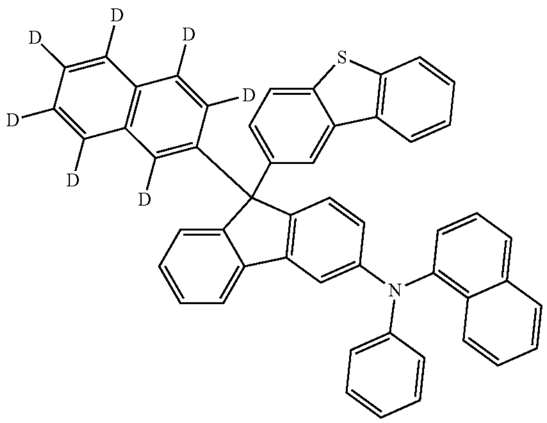
35
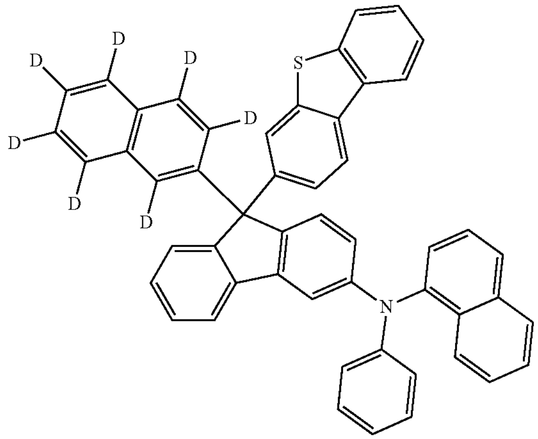
-continued
36
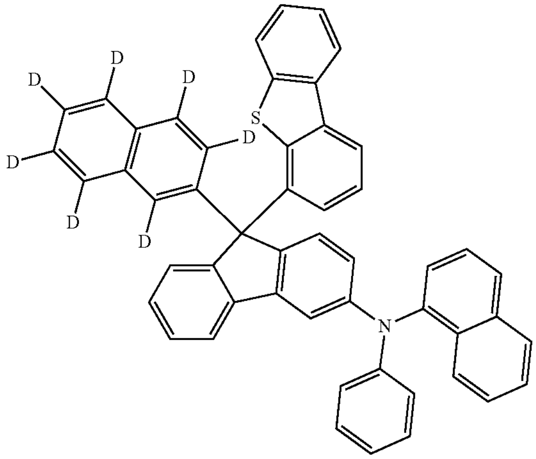
37
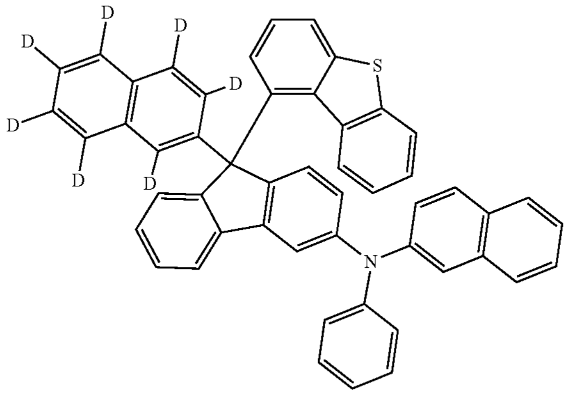
38
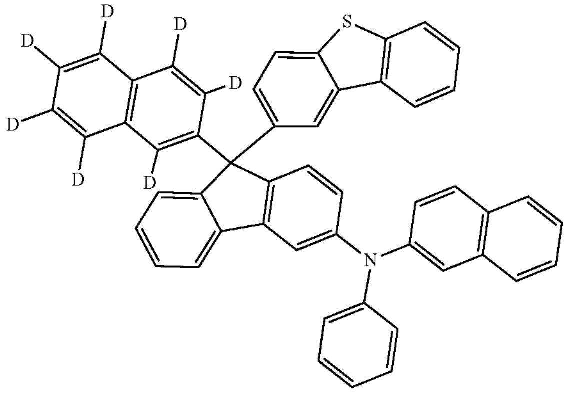

41
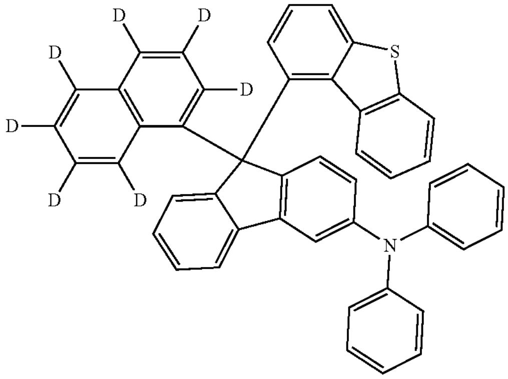
42
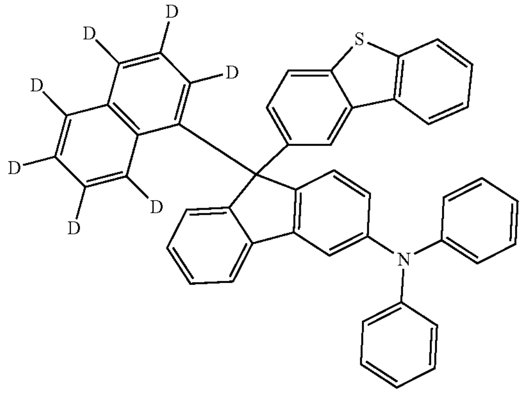
43
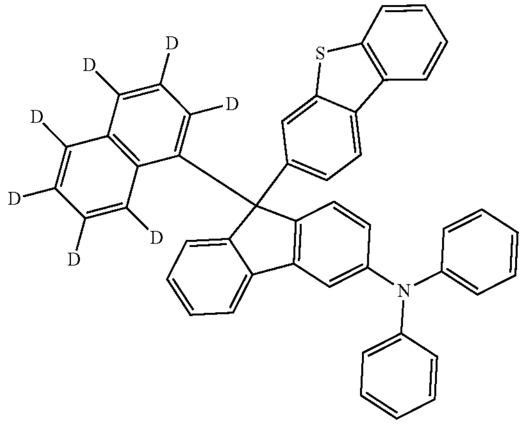
44
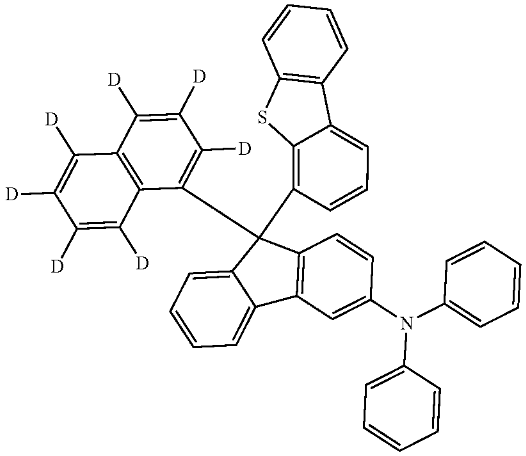
45
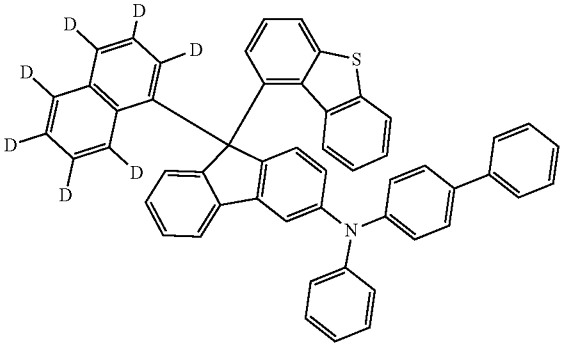
46
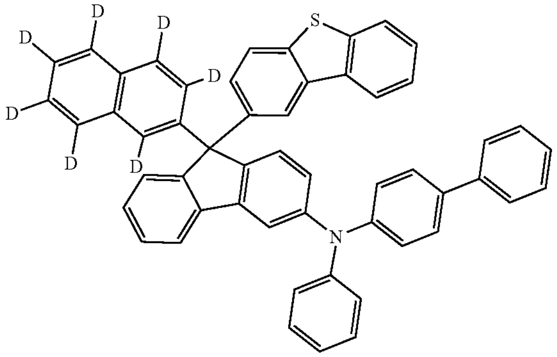
47
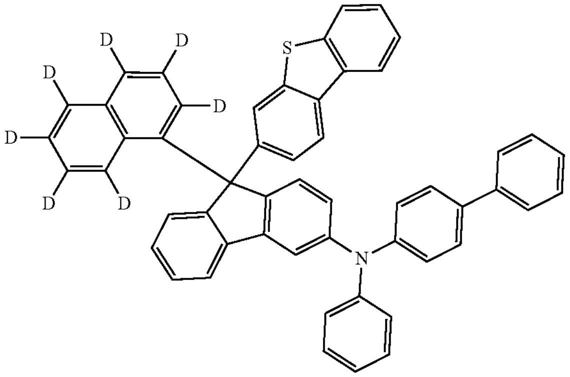

-continued
48
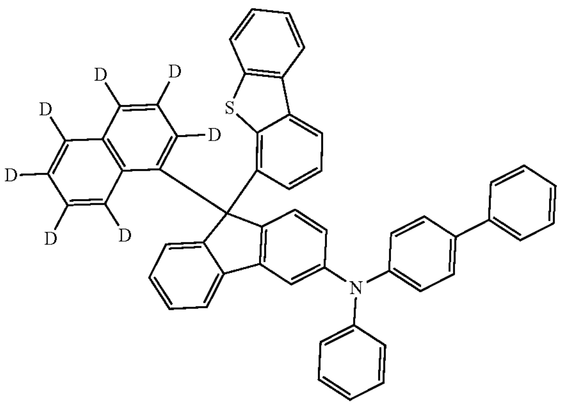
49
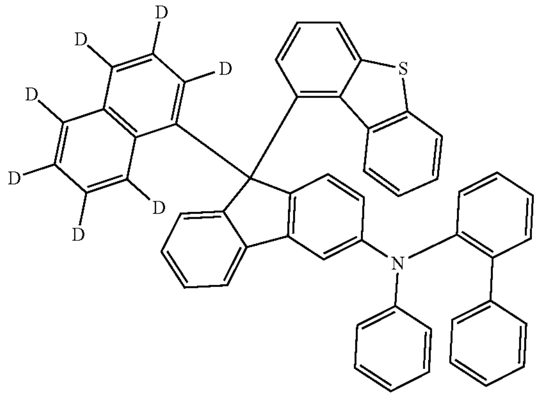
50
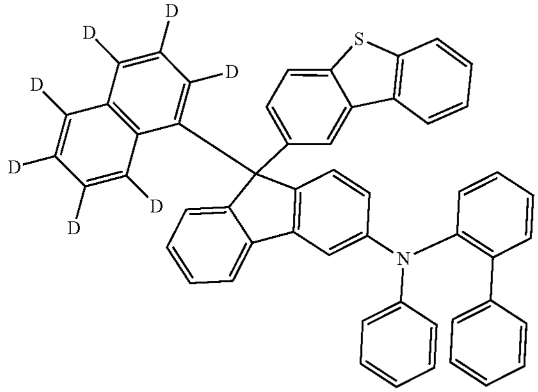
-continued
51
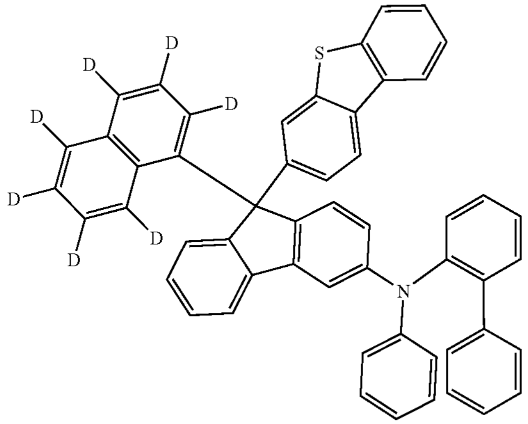
52
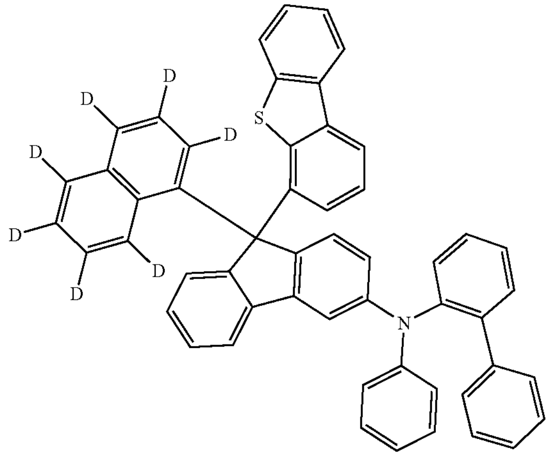
53
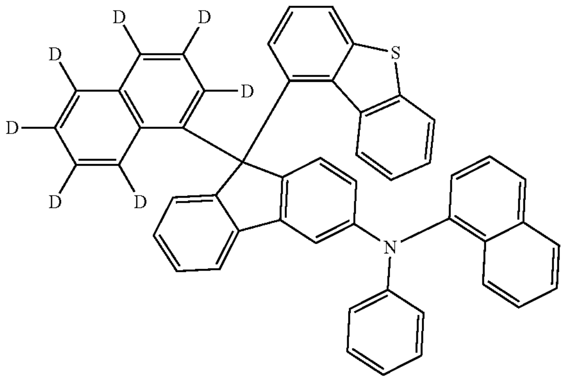

-continued
54
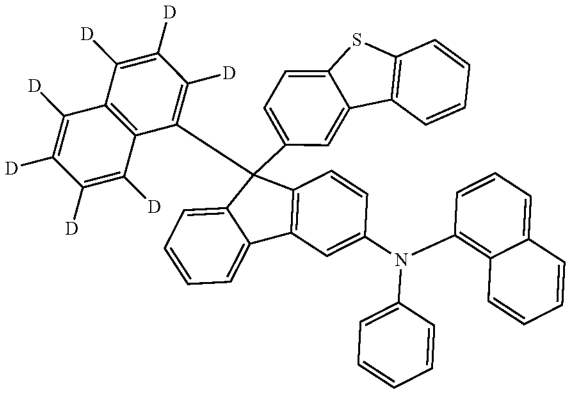
55
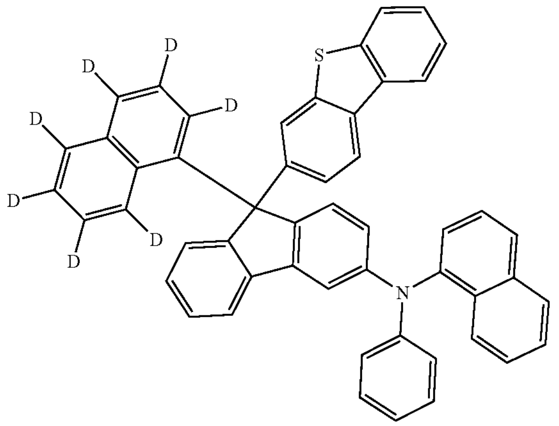
56
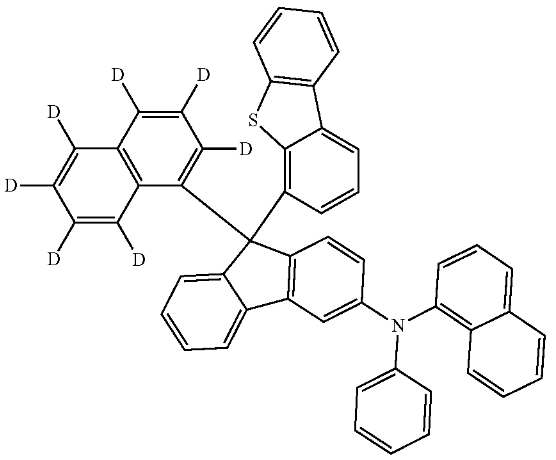
-continued
57
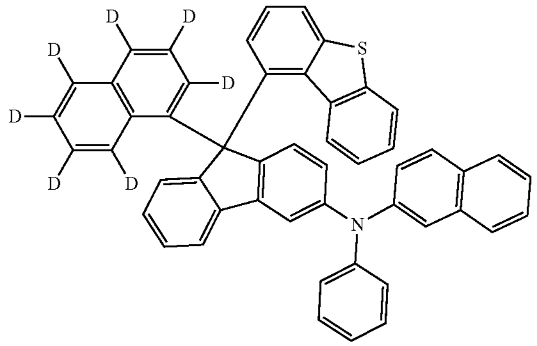
58
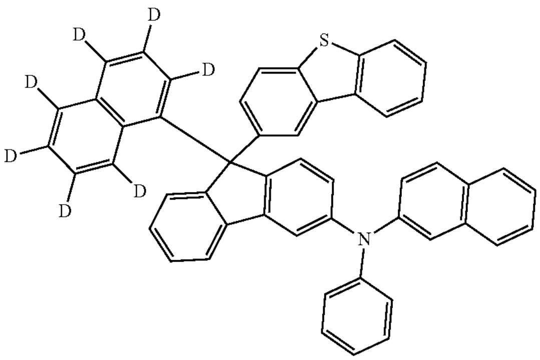
59
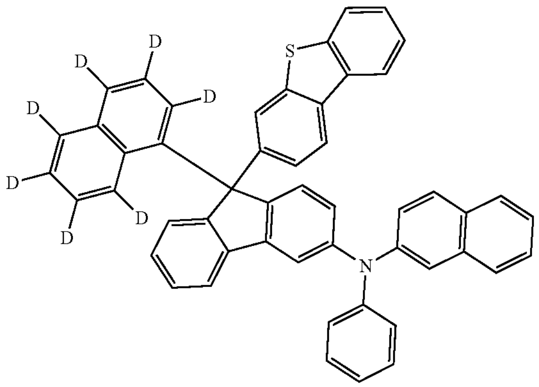
60
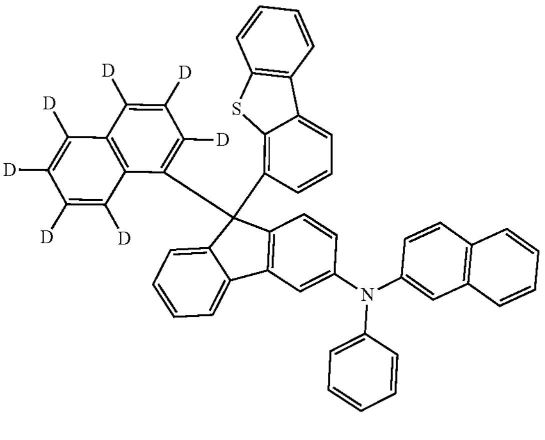

61
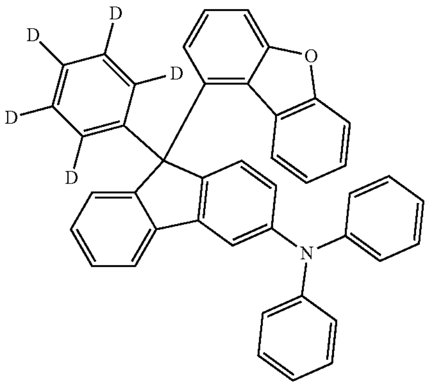
62
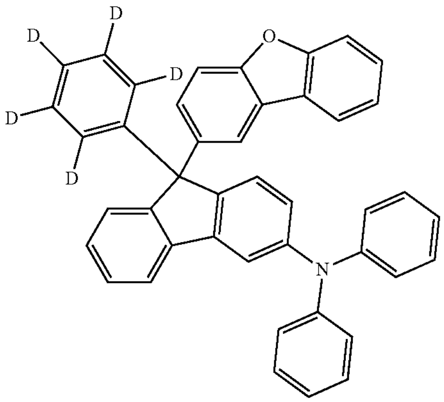
63
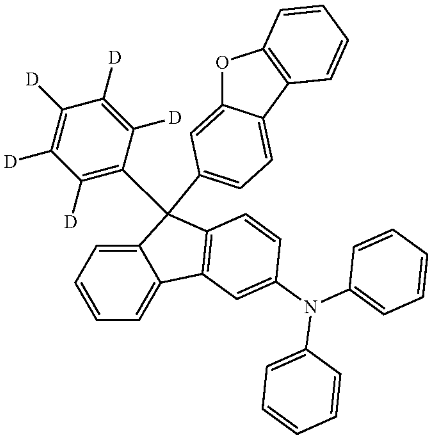
-continued
64
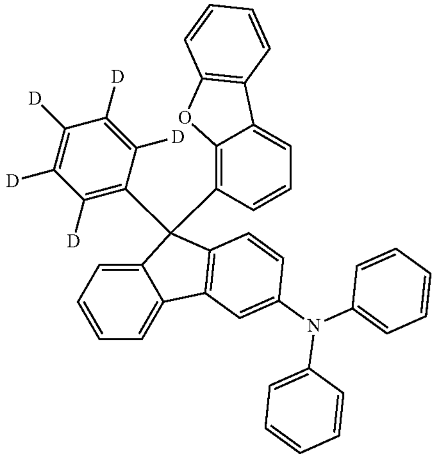
65
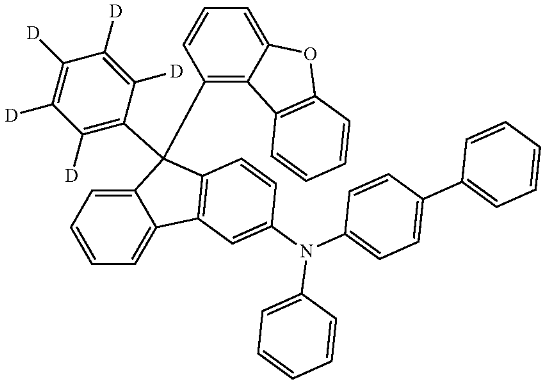
66
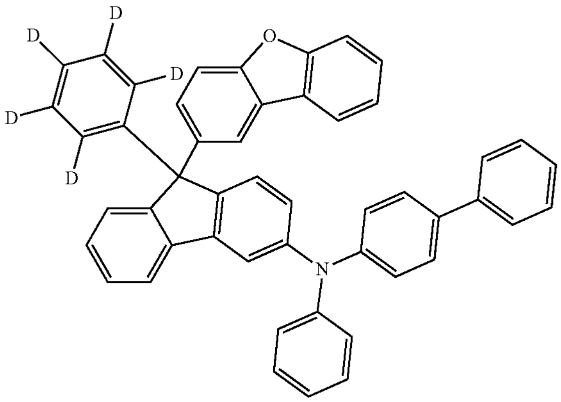

-continued
67
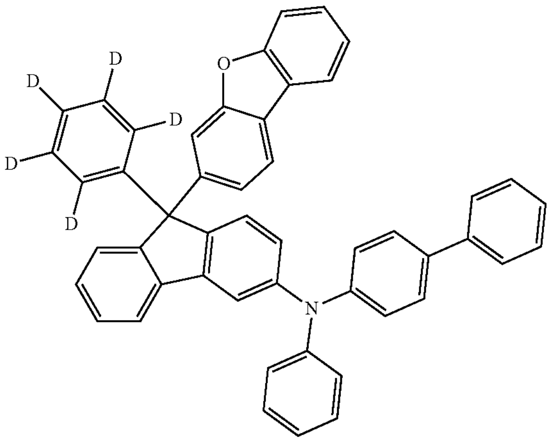
70
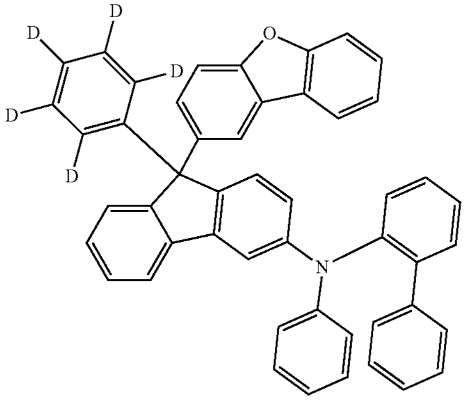
68
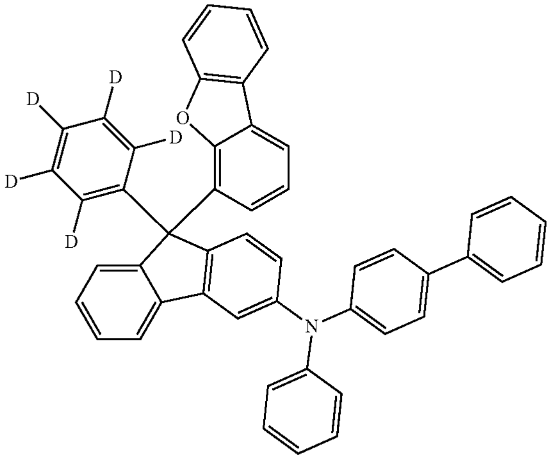
71
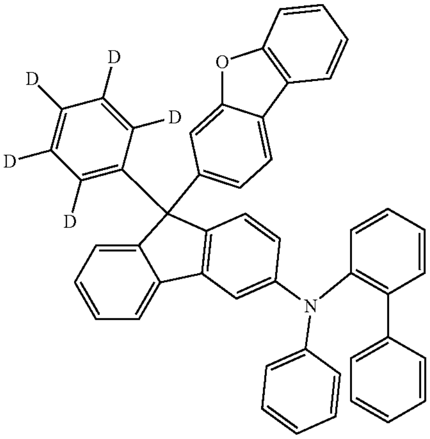
69
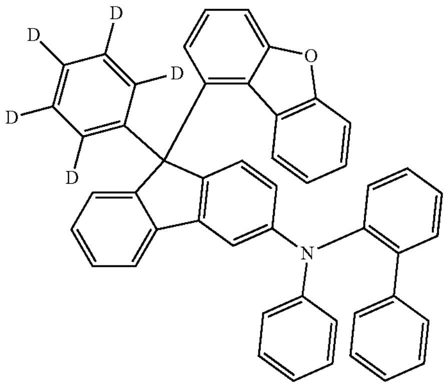
72
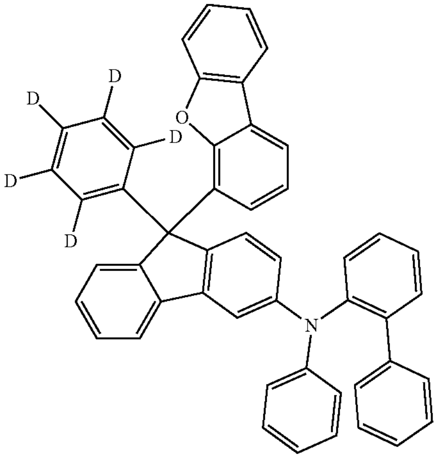

-continued
73
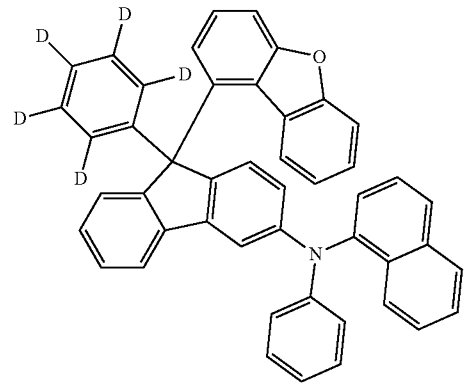
74
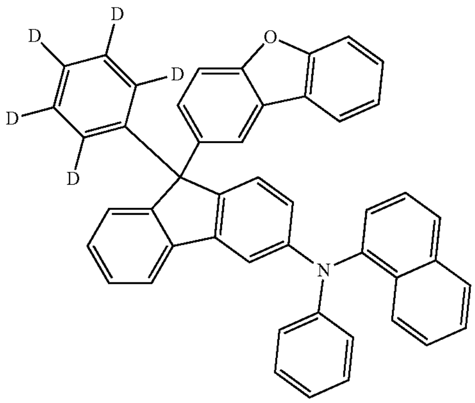
75
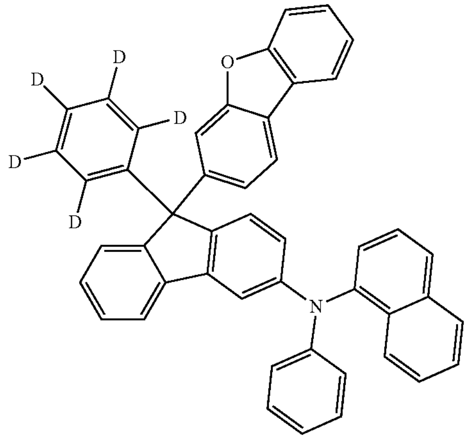
-continued
76
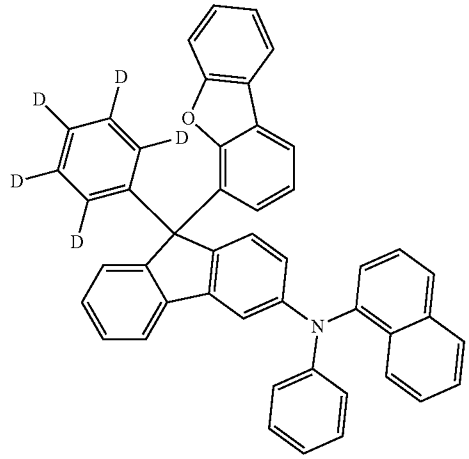
77
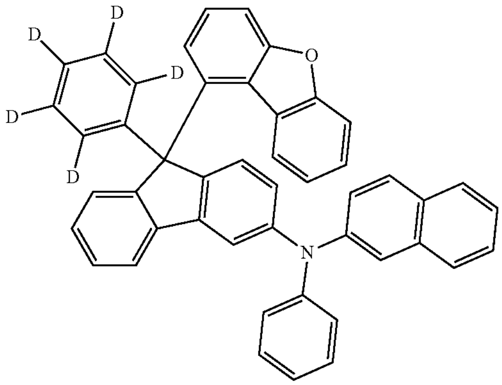
78
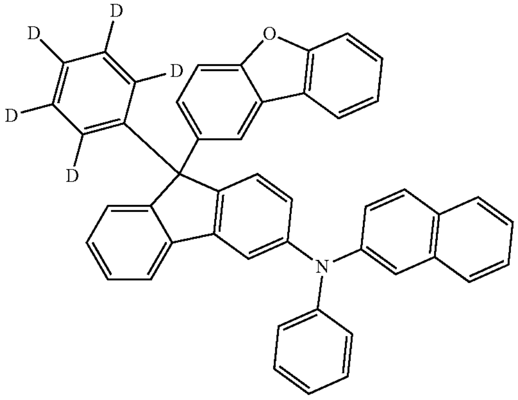

-continued
79
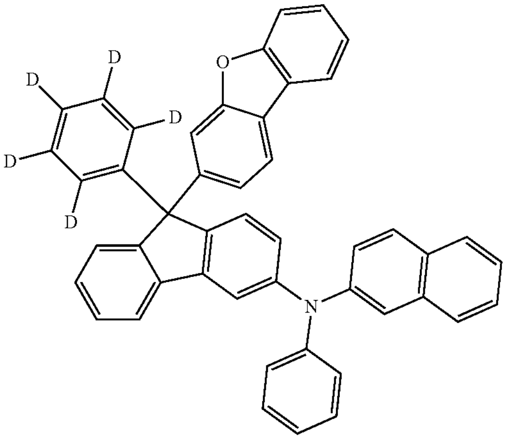
80
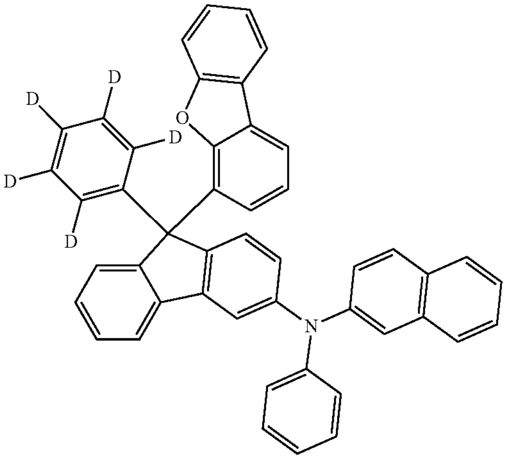
81
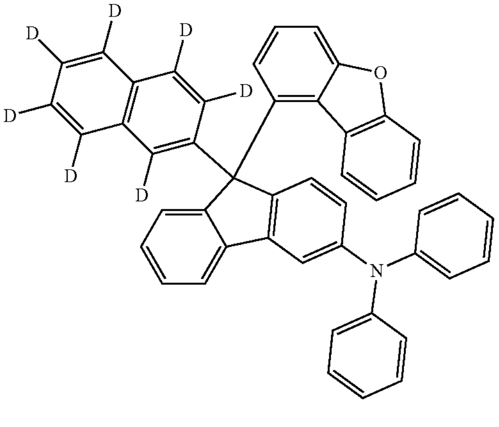
-continued
82
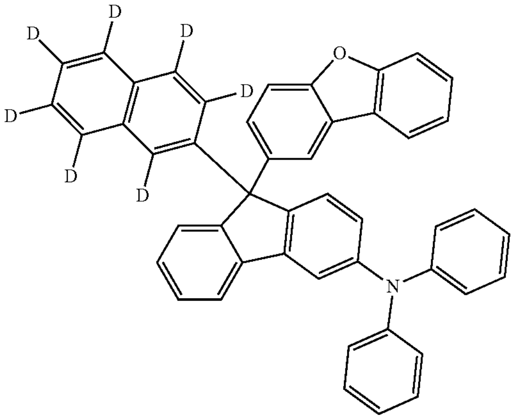
83
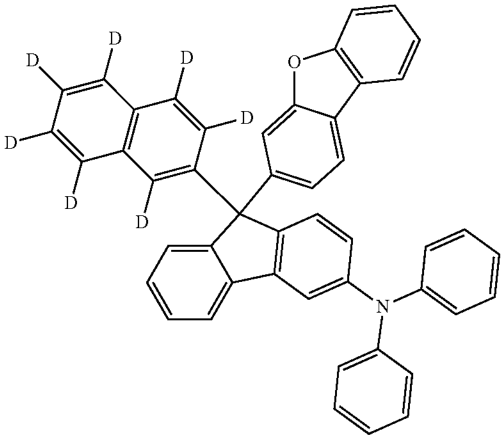
84
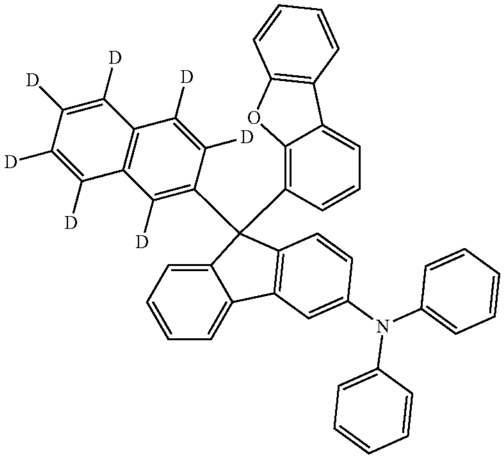

-continued
85
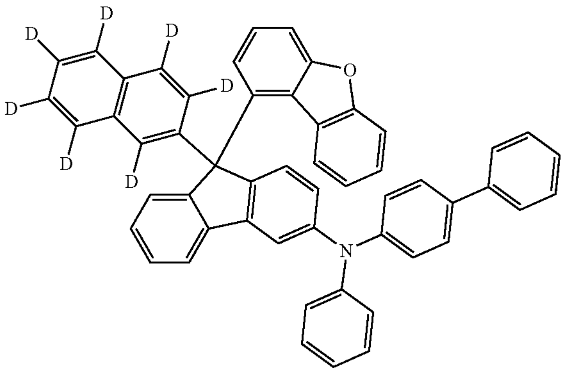
86
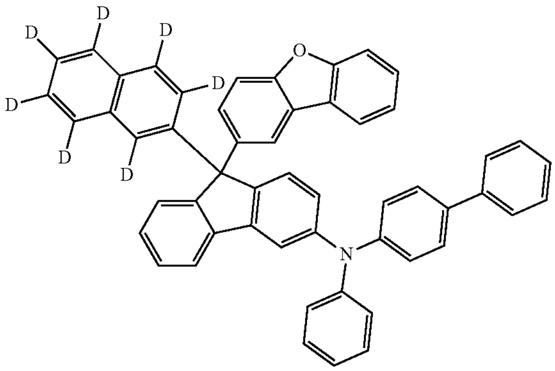
87
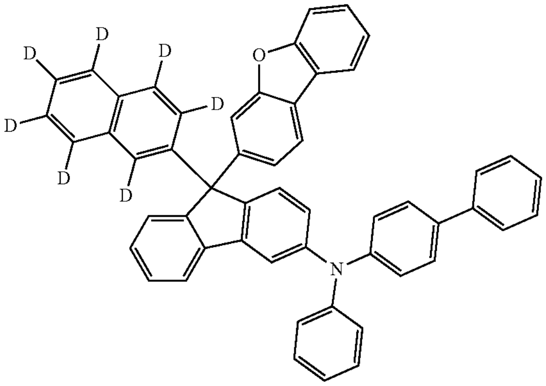
88
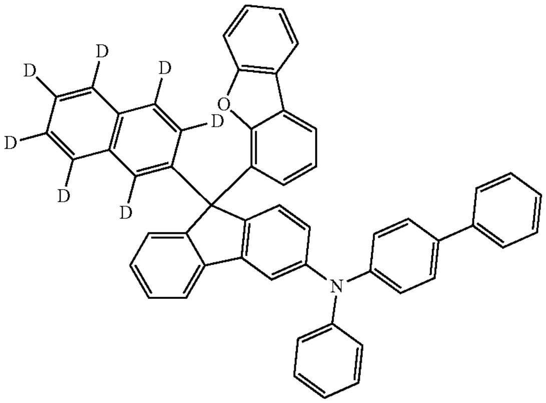
-continued
89
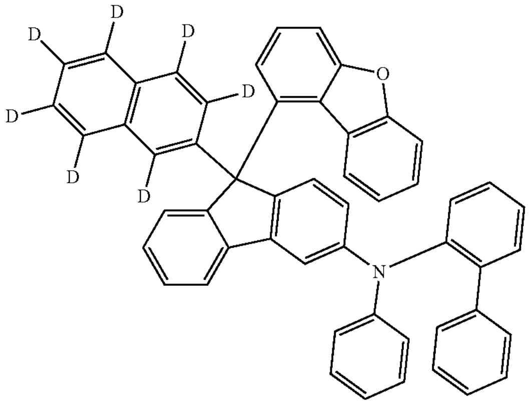
90
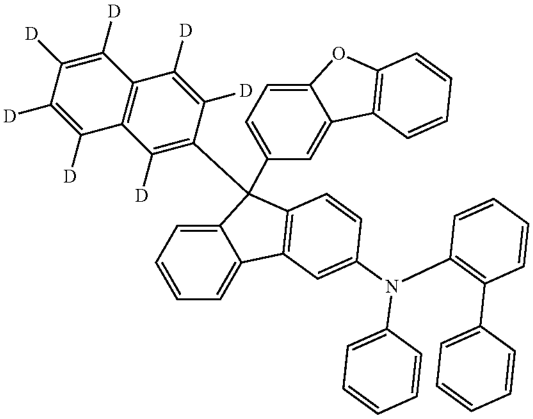
91
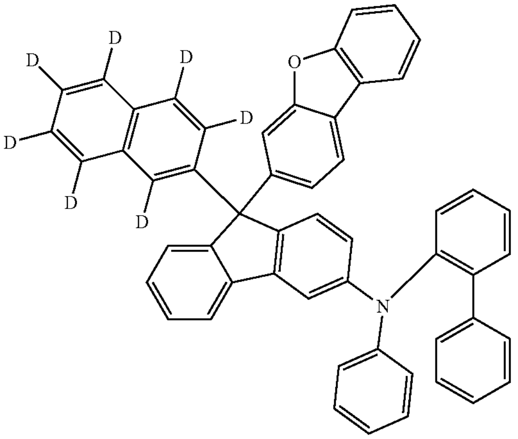

-continued
92
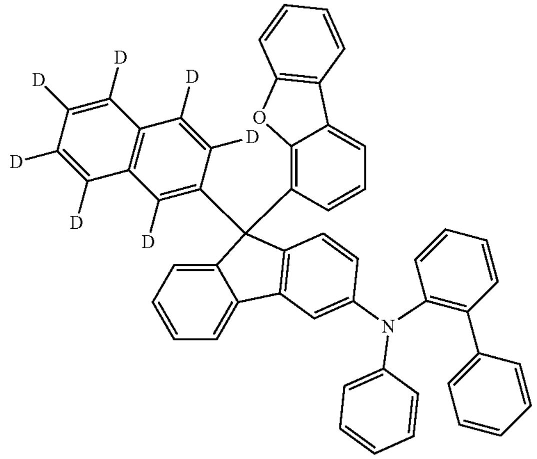
93
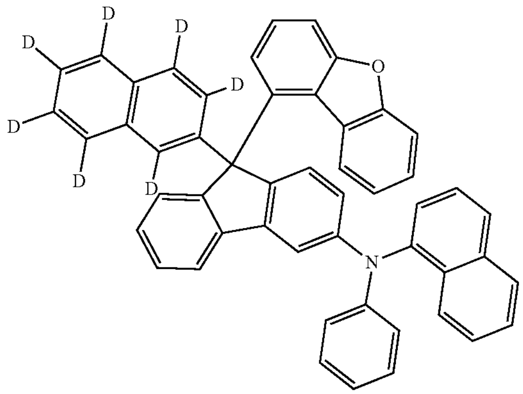
94
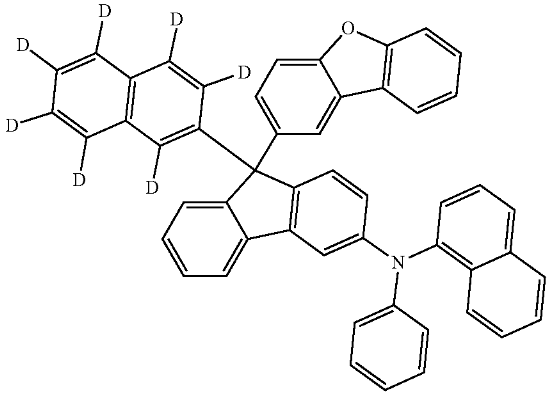
-continued
95
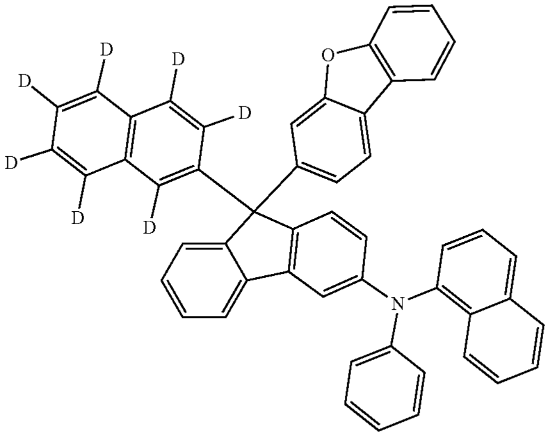
96
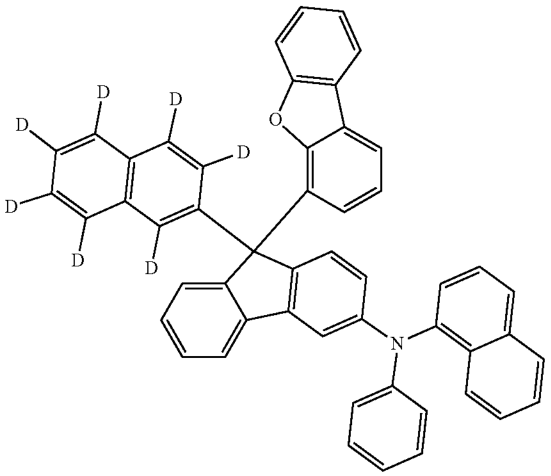
97
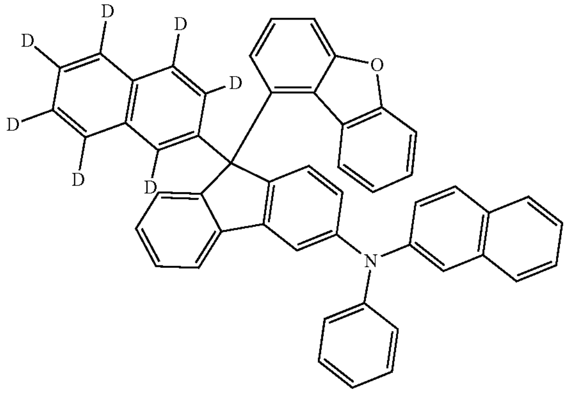

98
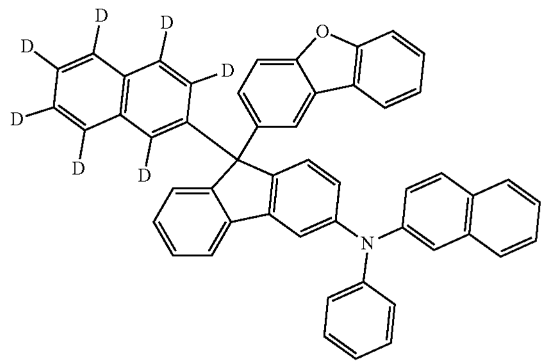
99
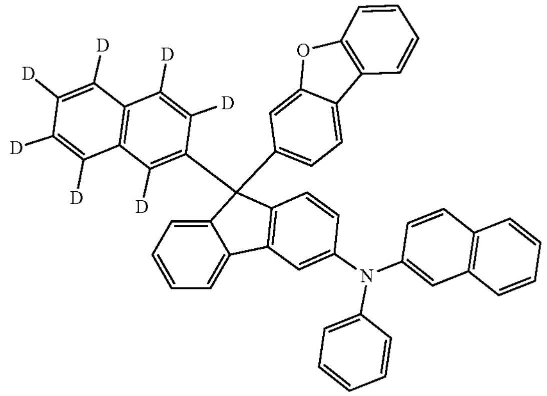
100
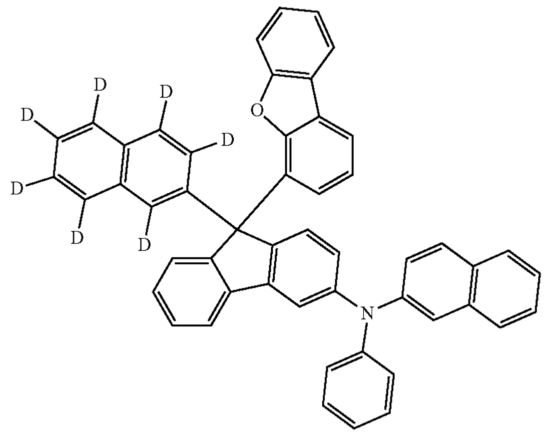
101
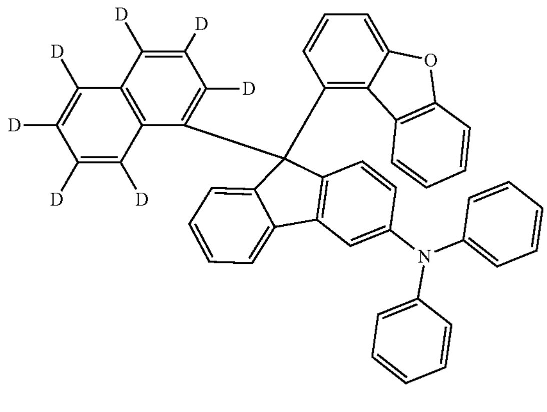
102
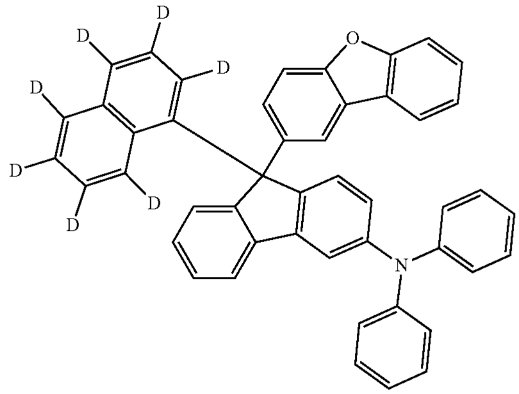
103
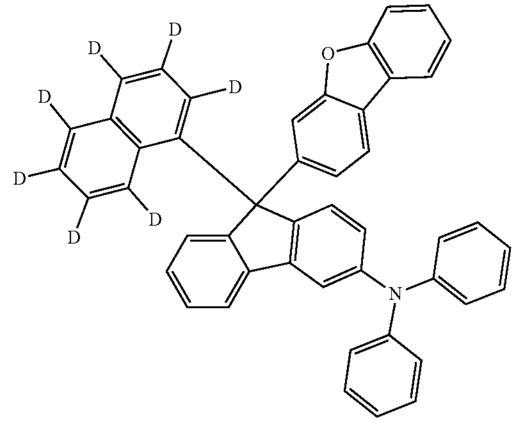
104
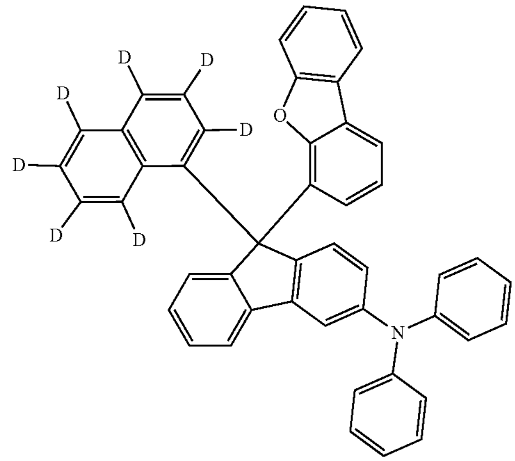

-continued
105
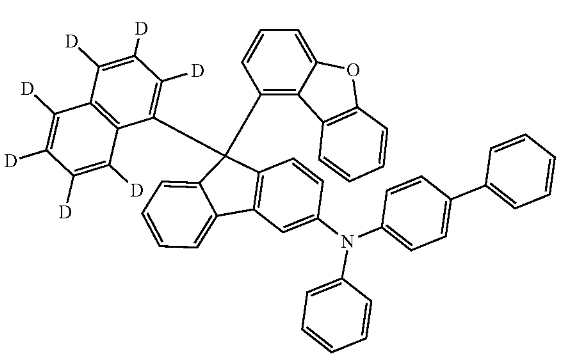
106
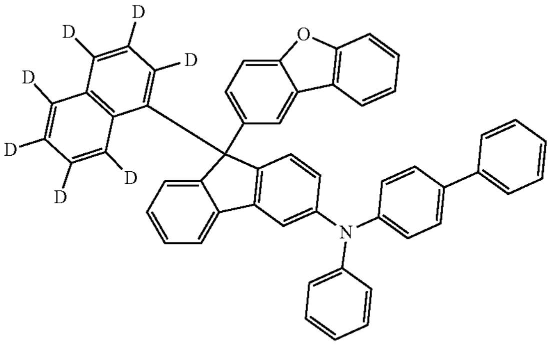
107
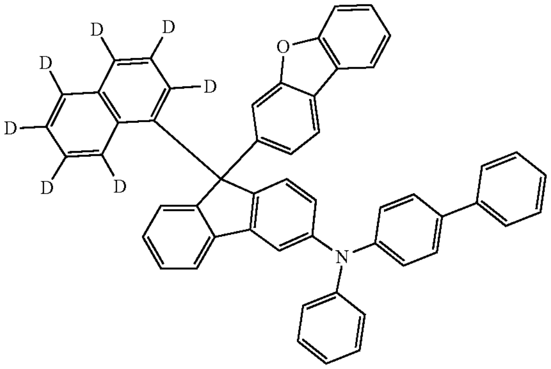
108
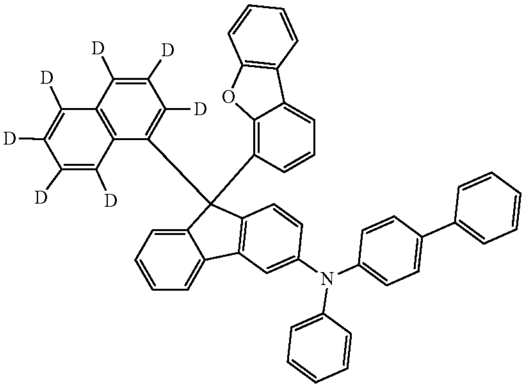
-continued
109
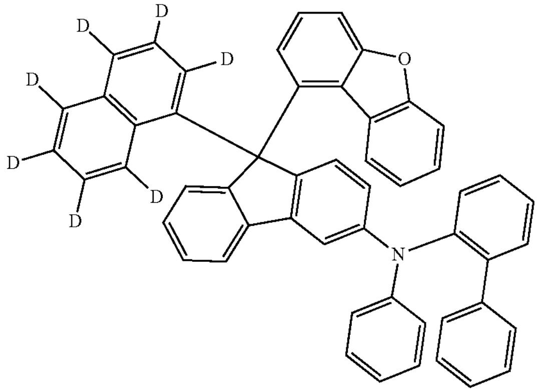
110
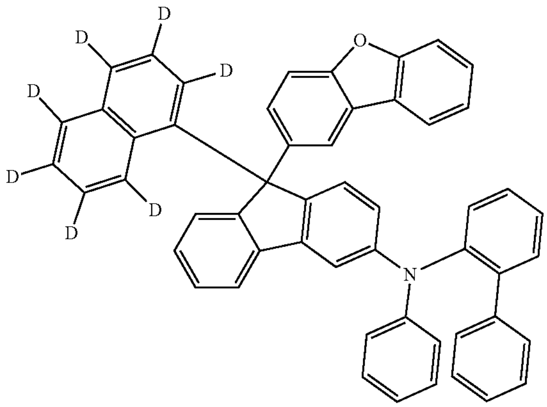
111
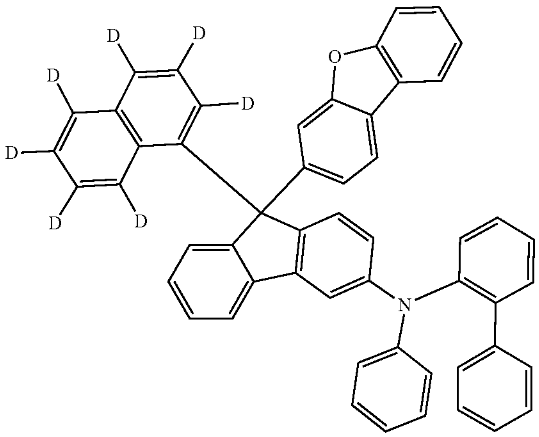

-continued
112
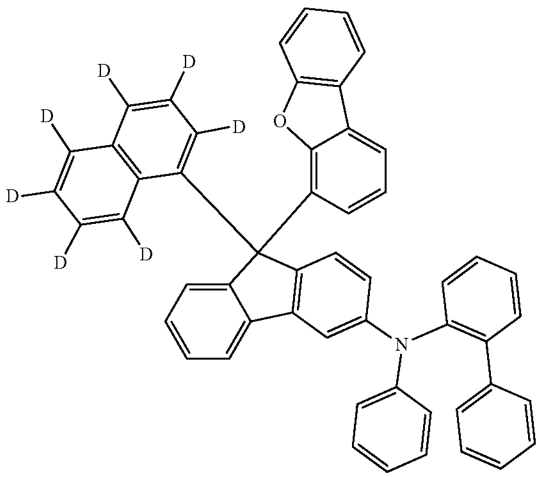
113
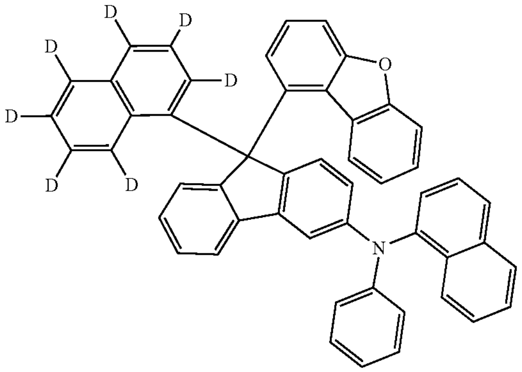
114
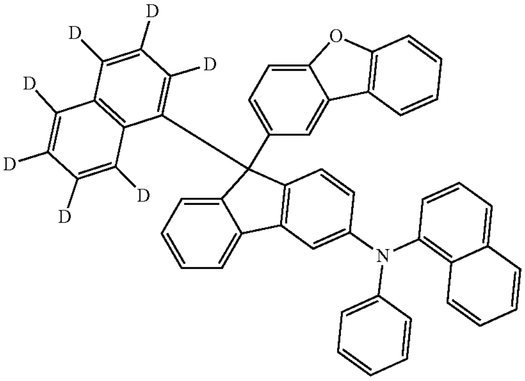
-continued
115
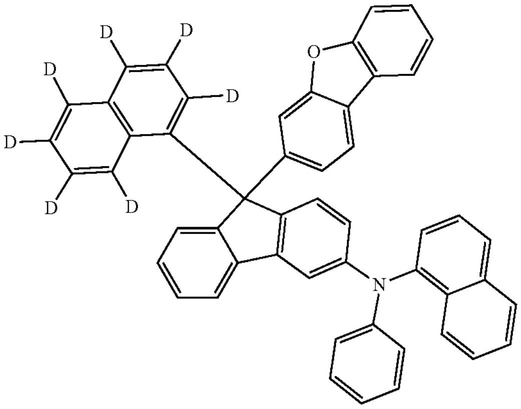
116
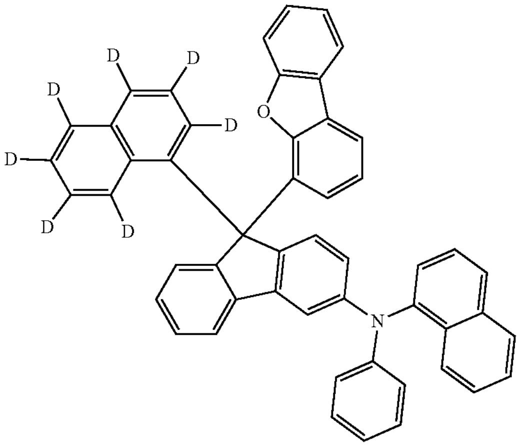
117
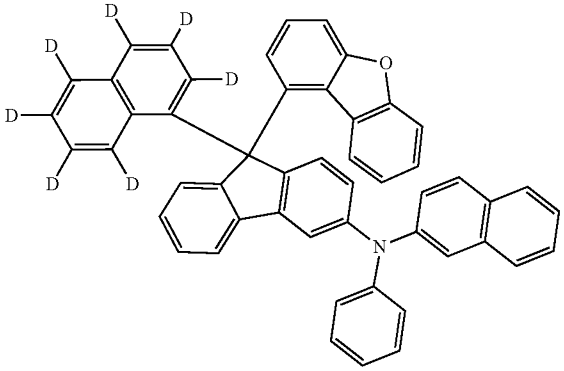

-continued
118
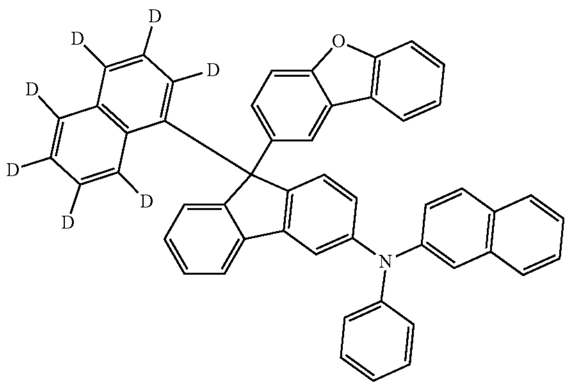
121
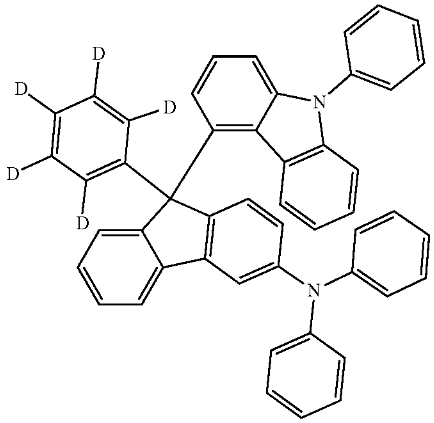
119
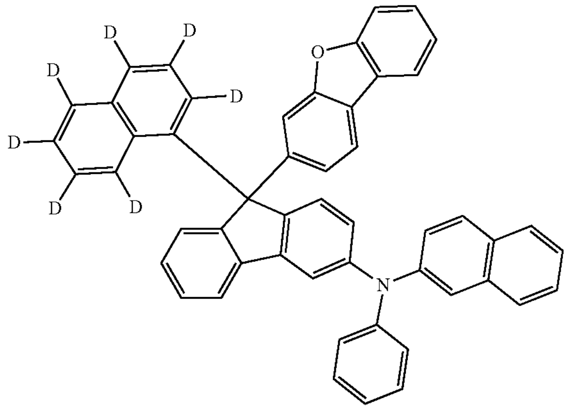
122
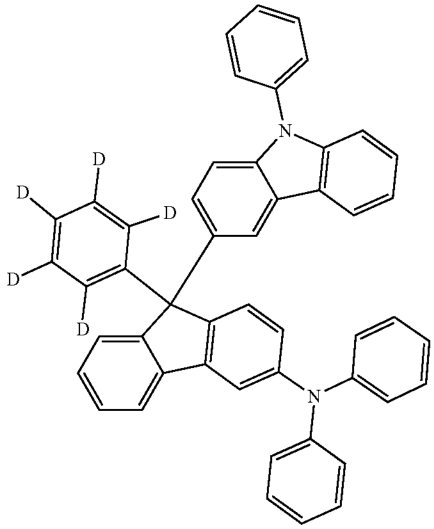
120
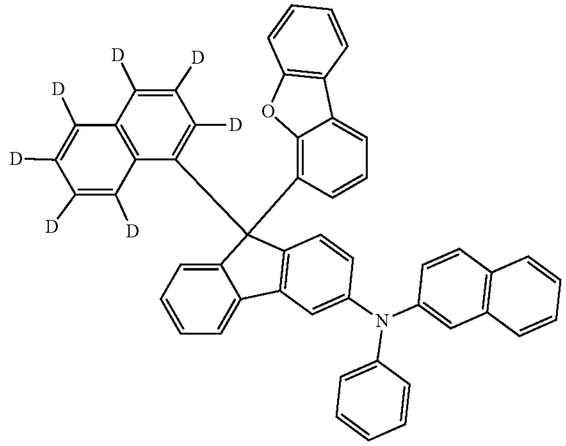
123
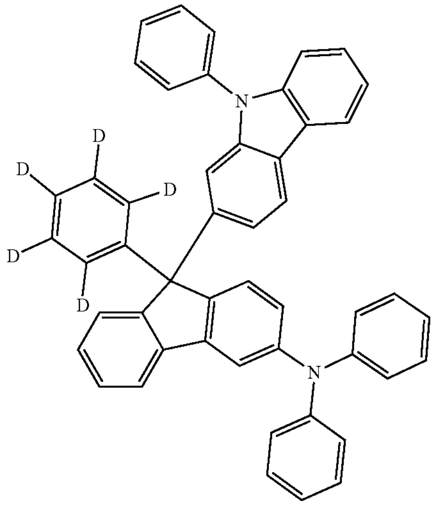

-continued
124
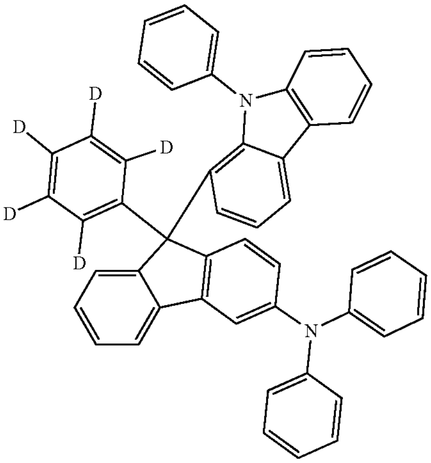
125
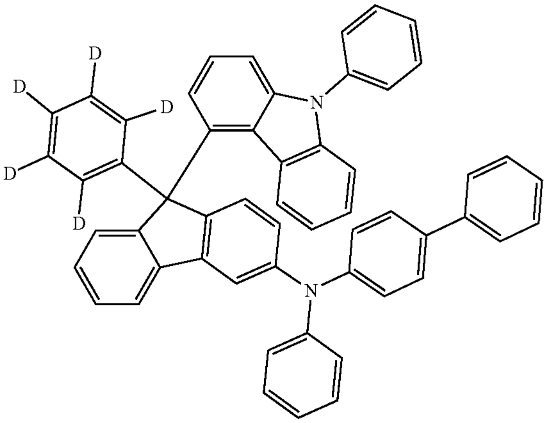
126
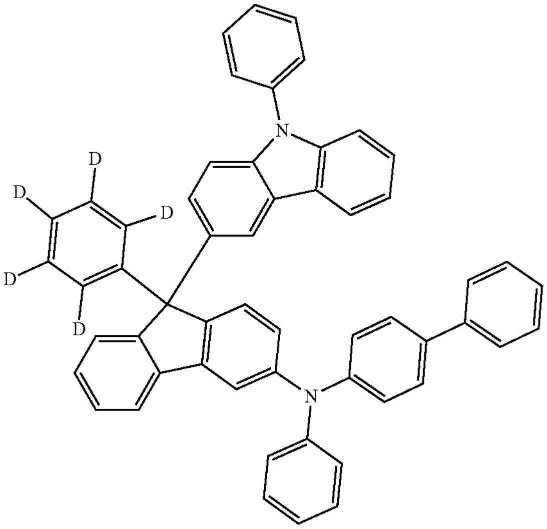
-continued
127
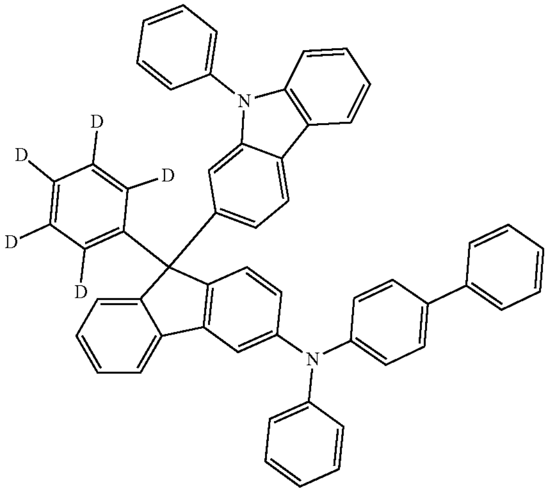
128
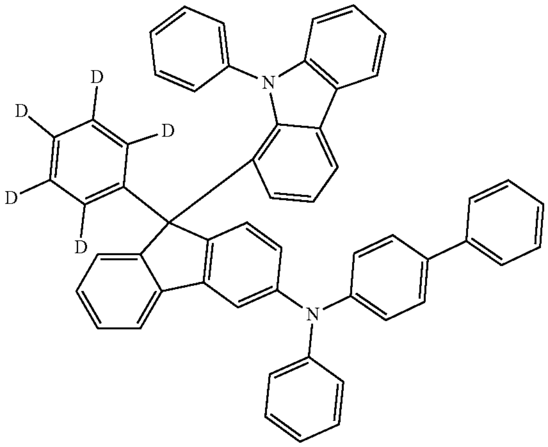
129
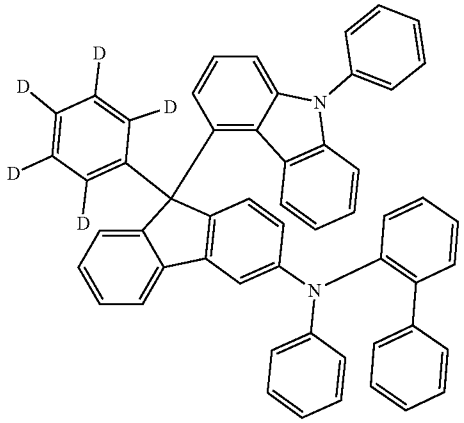

-continued
130
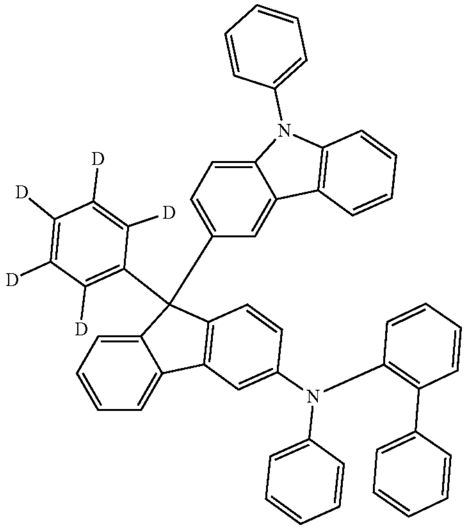
131
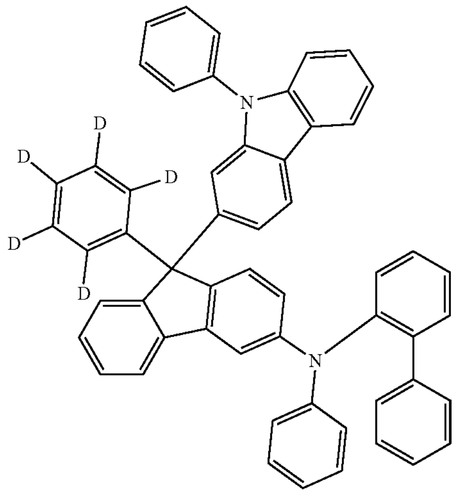
132
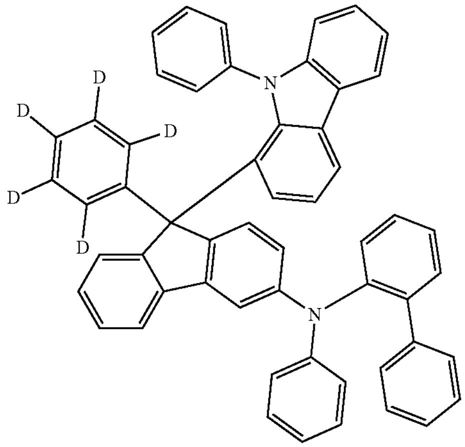
-continued
133
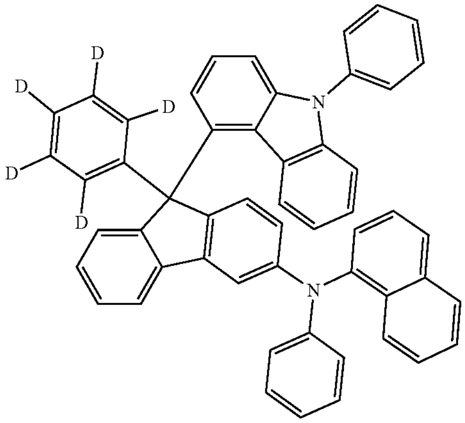
134
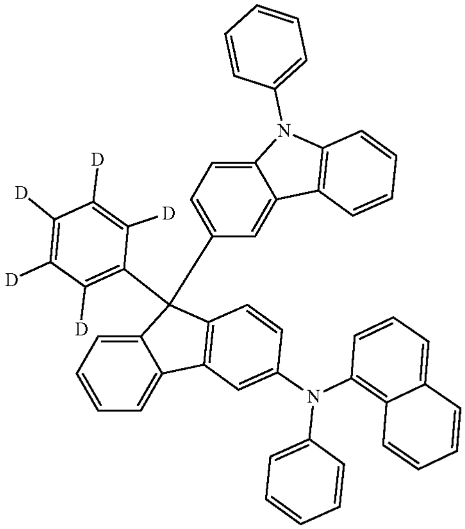
135
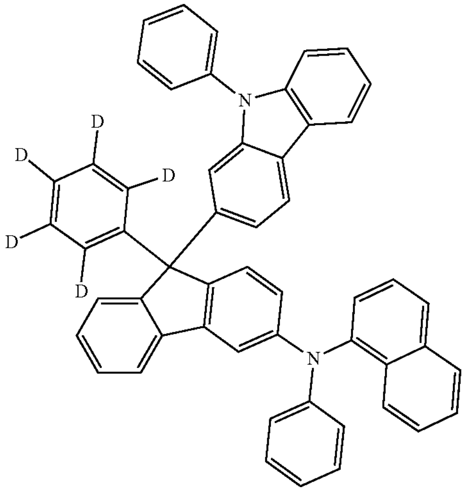

-continued
136
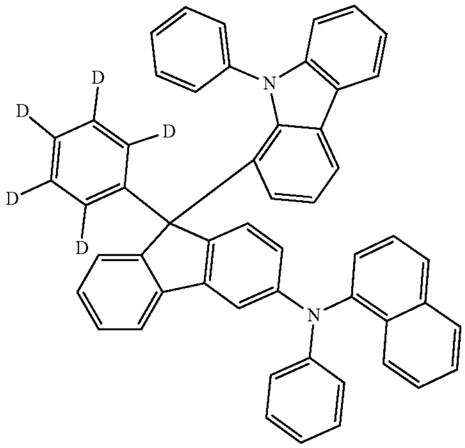
137
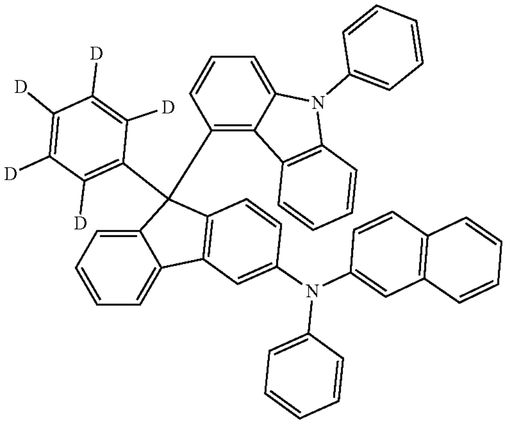
138
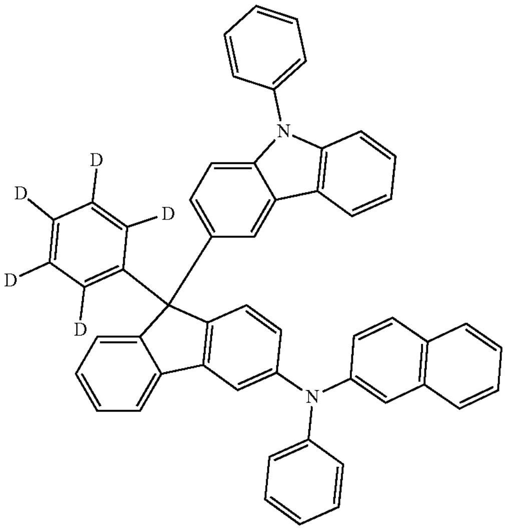
-continued
139
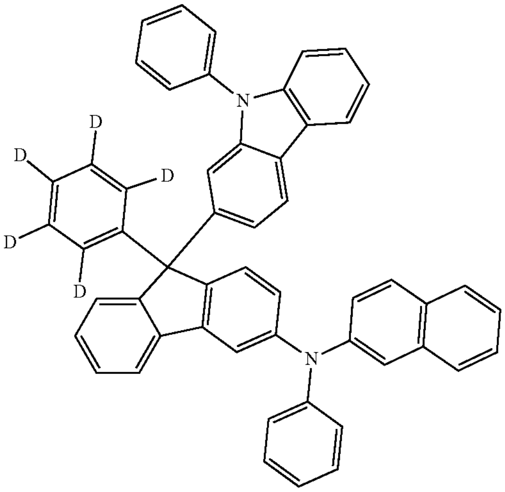
140
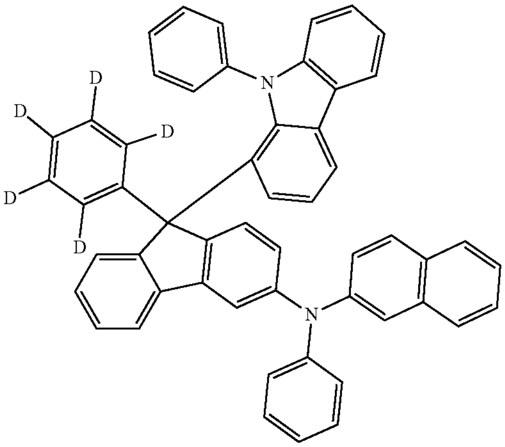
141
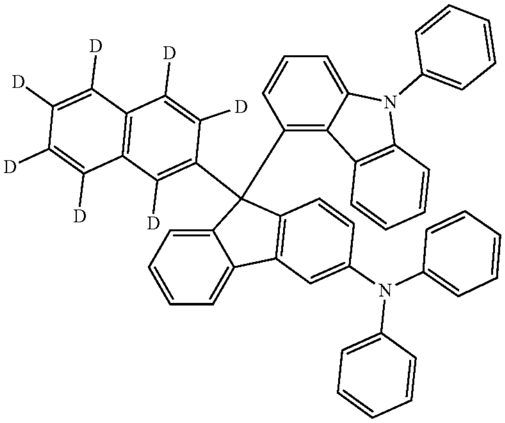

-continued
142
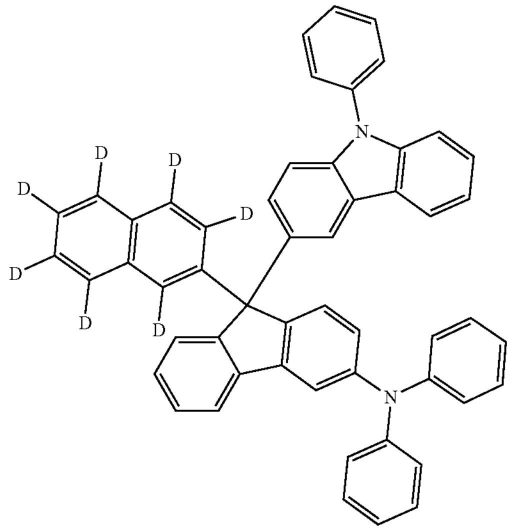
143
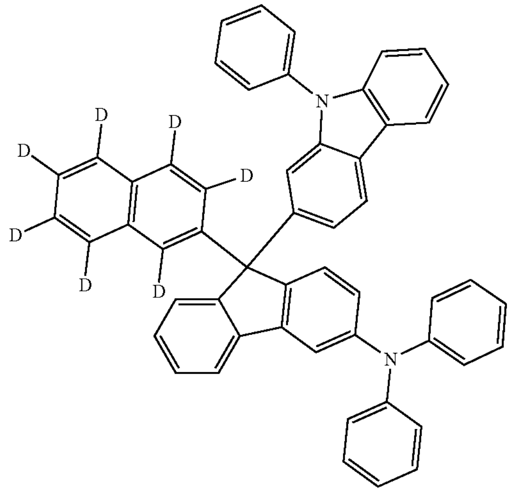
144
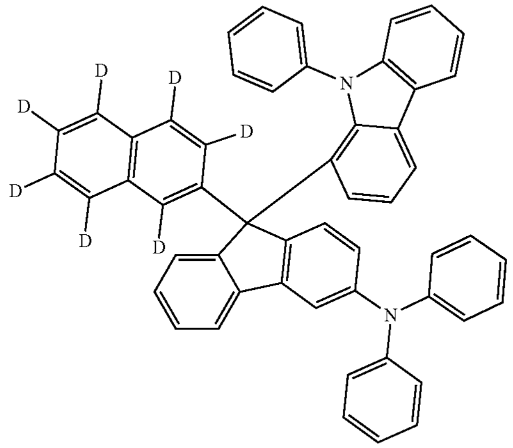
-continued
145
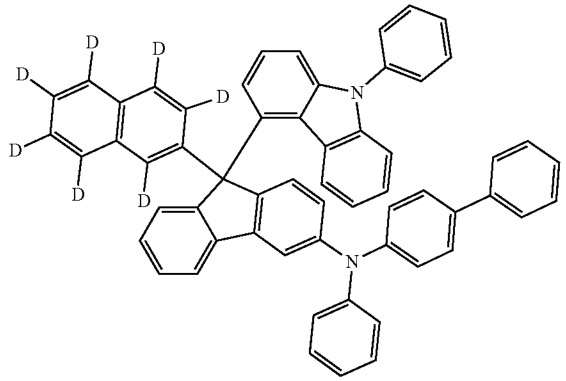
146
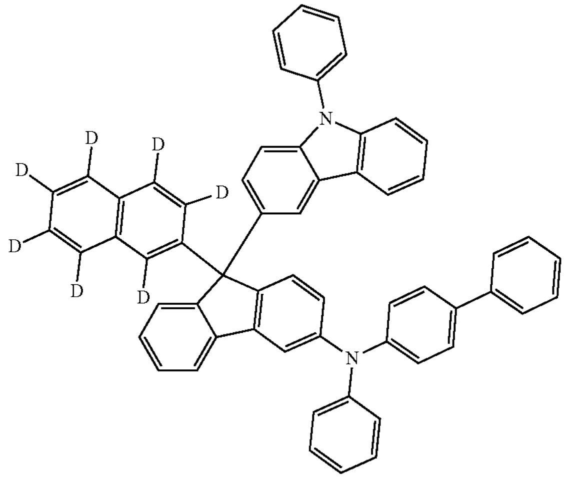
147
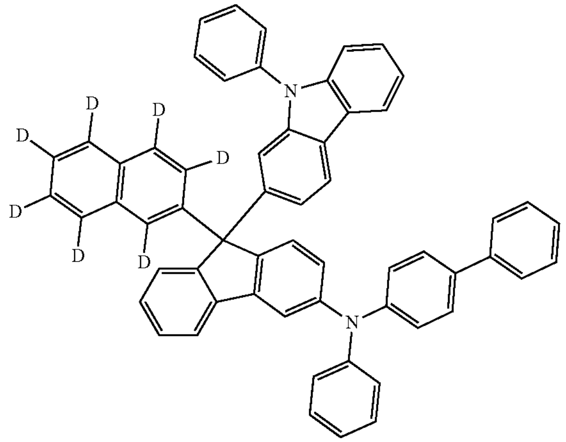

148
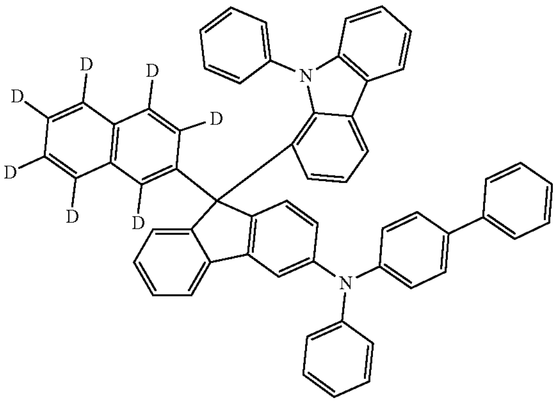
149
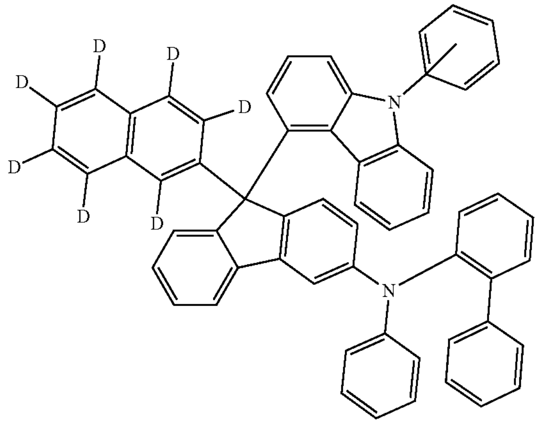
150
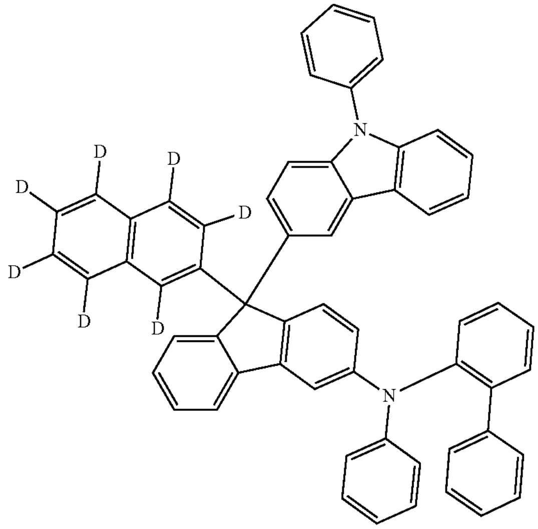
151
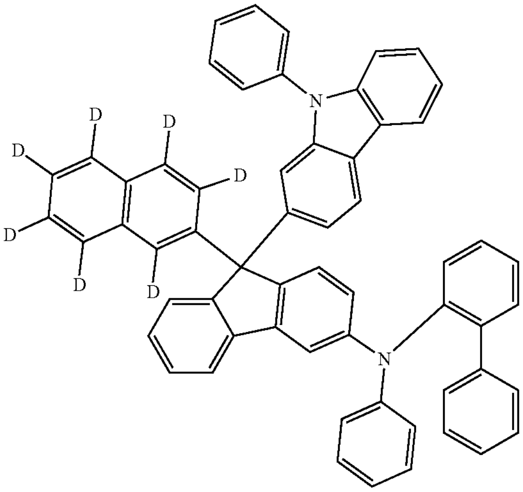
152
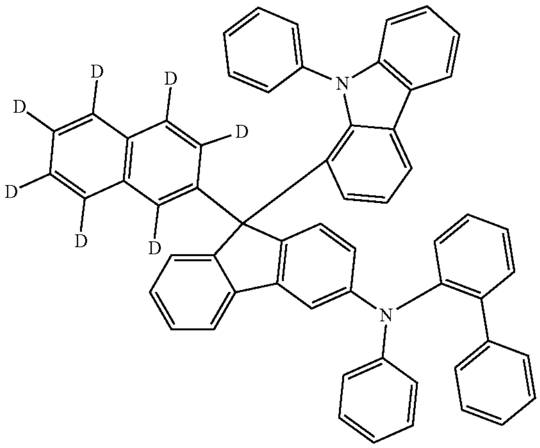
153
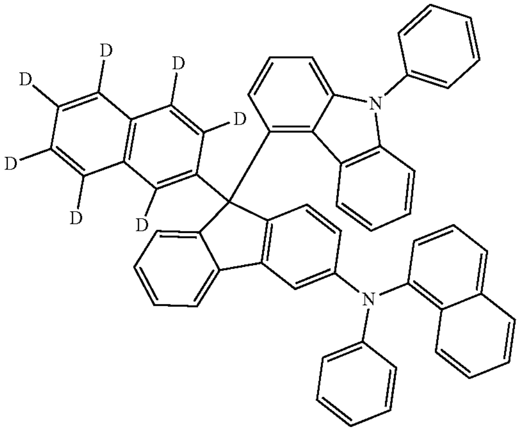

-continued
154
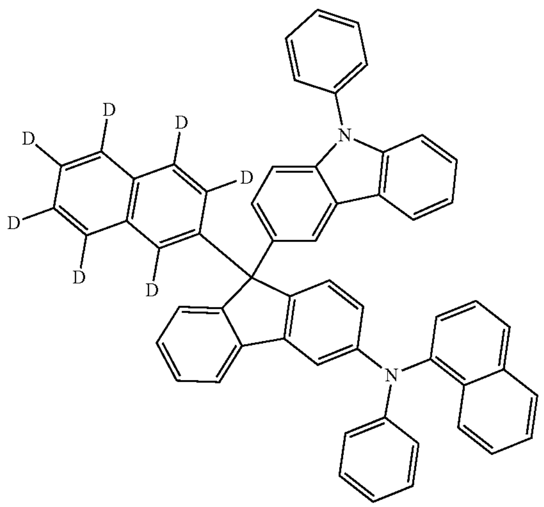
155
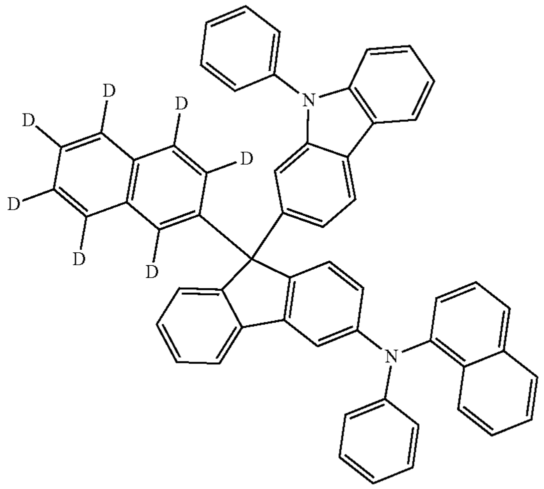
156
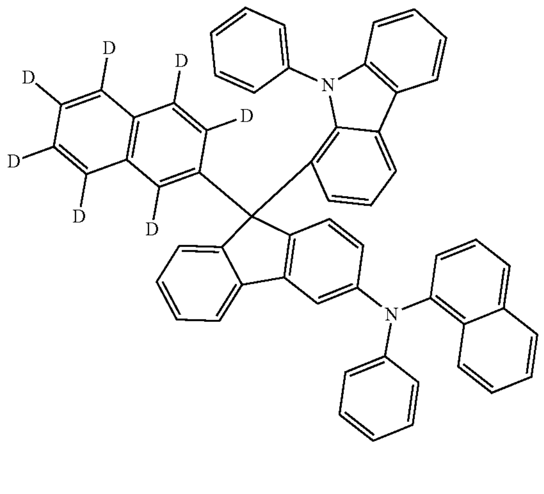
-continued
157
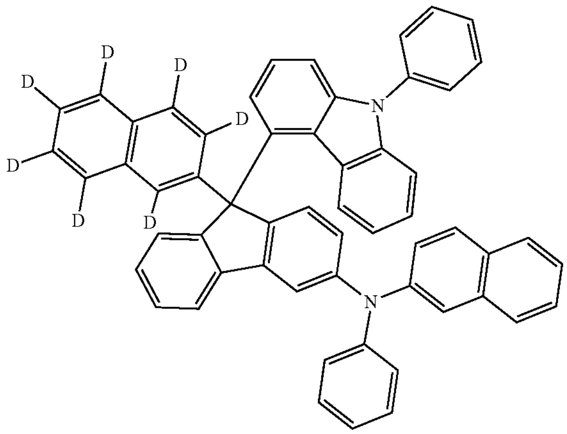
158
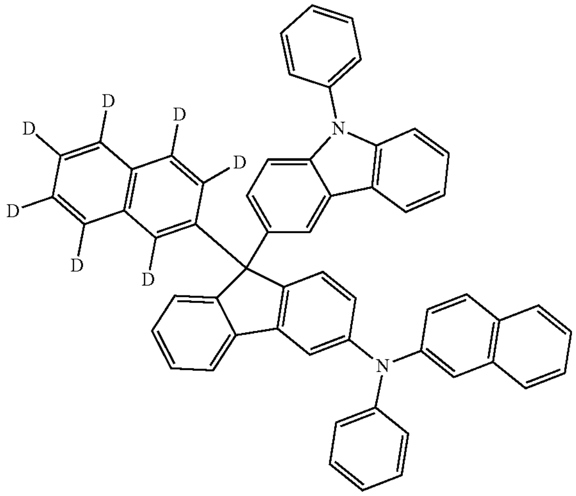
159
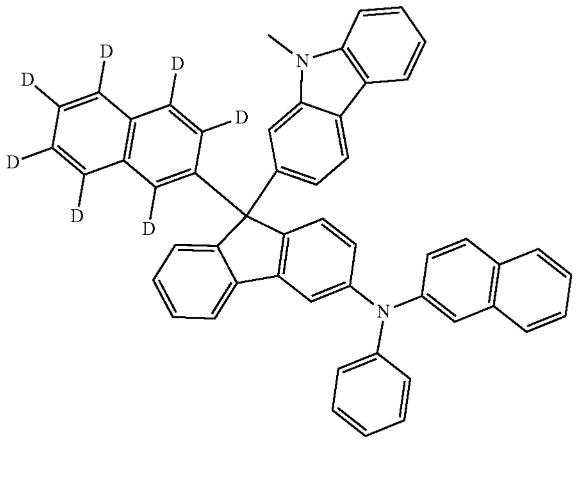

-continued
160
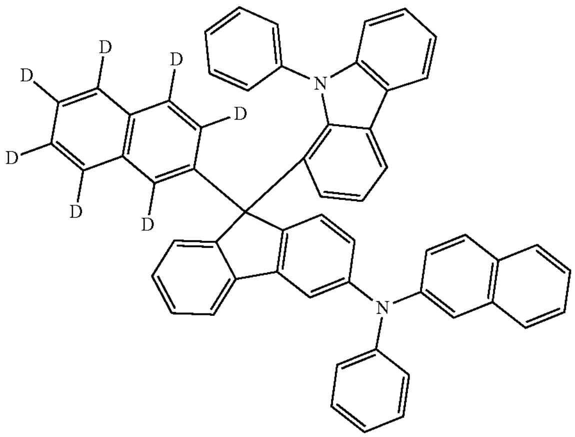
161
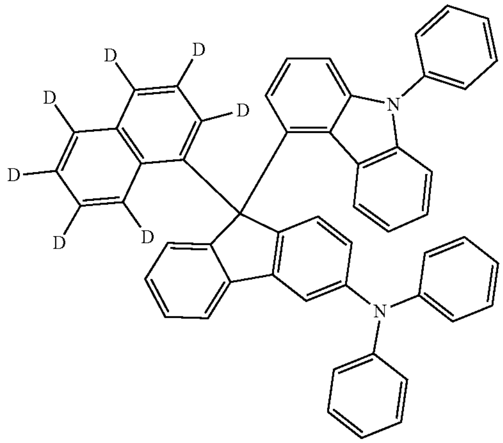
162
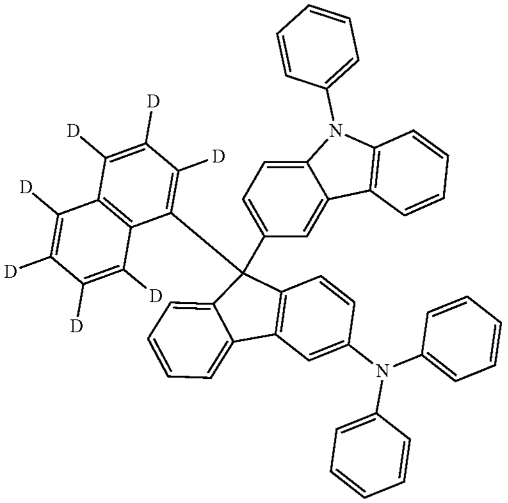
-continued
163
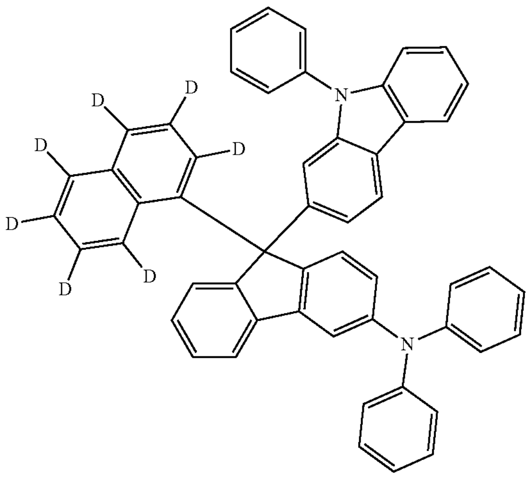
164
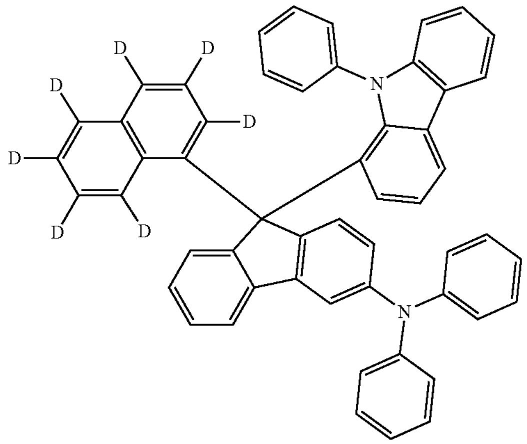
165
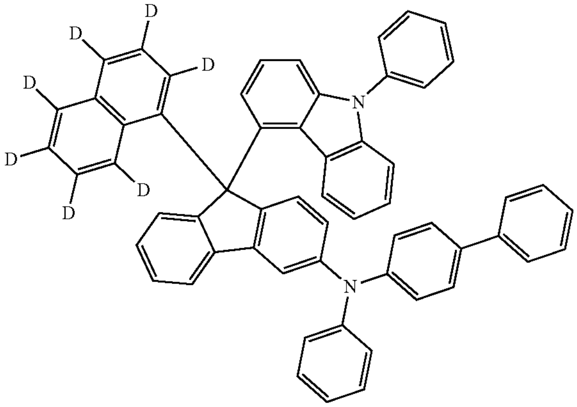

-continued
166
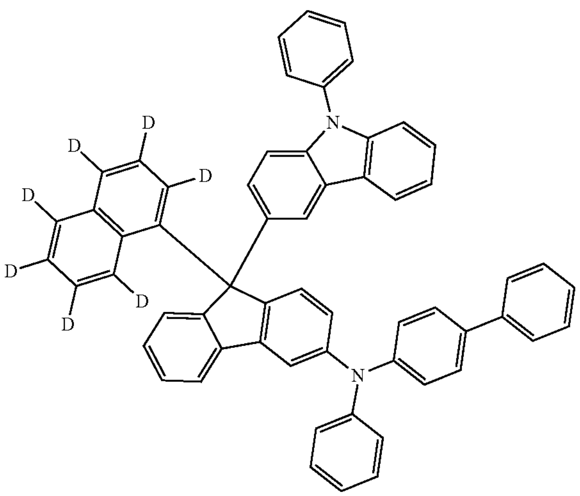
167
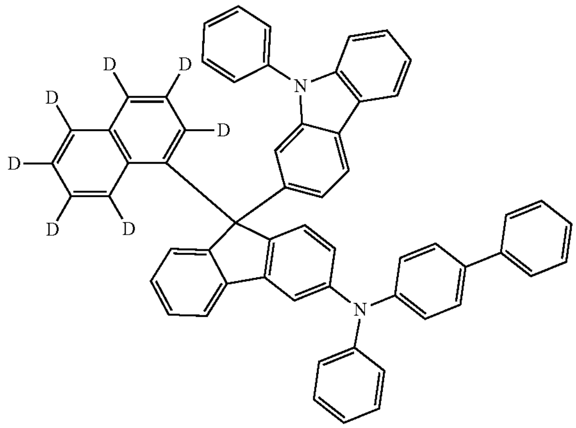
168
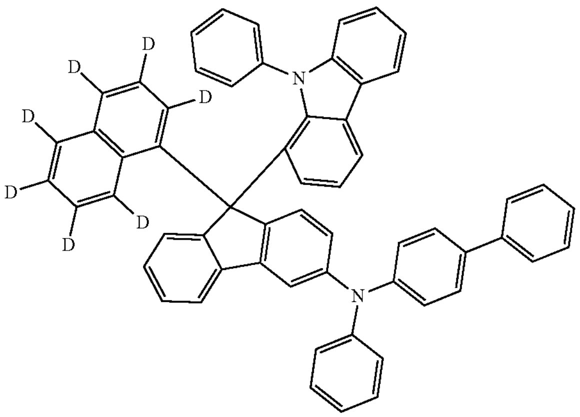
-continued
169
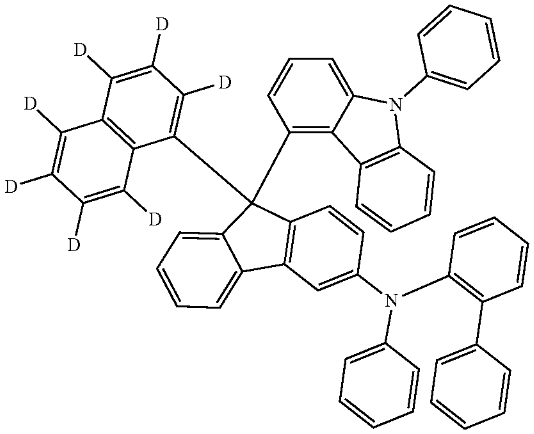
170
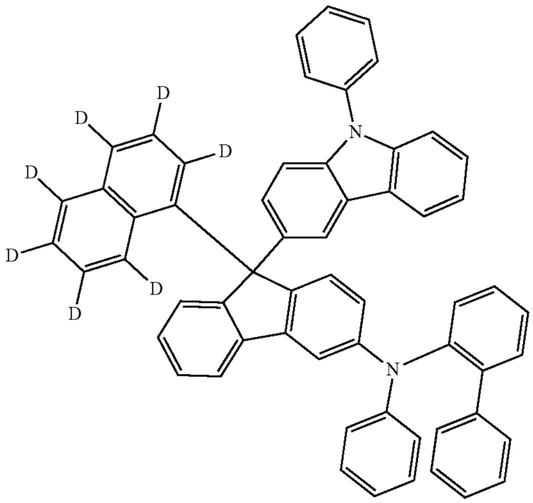
171
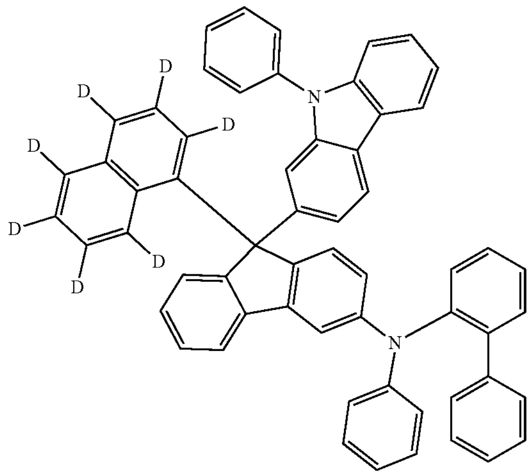

-continued
172
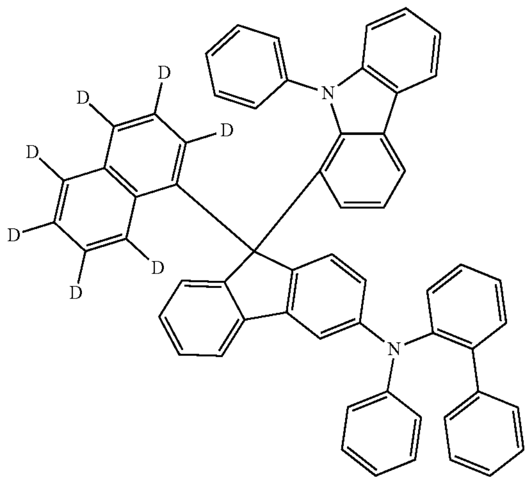
173
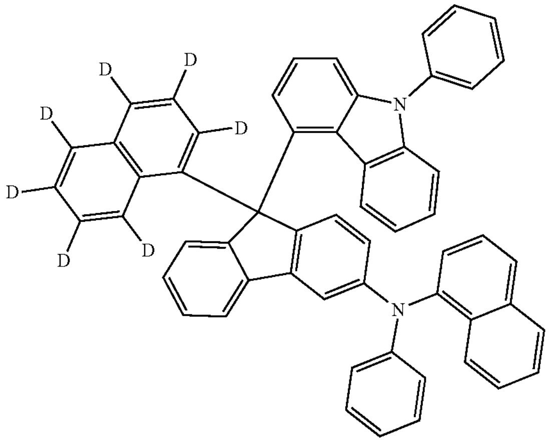
174
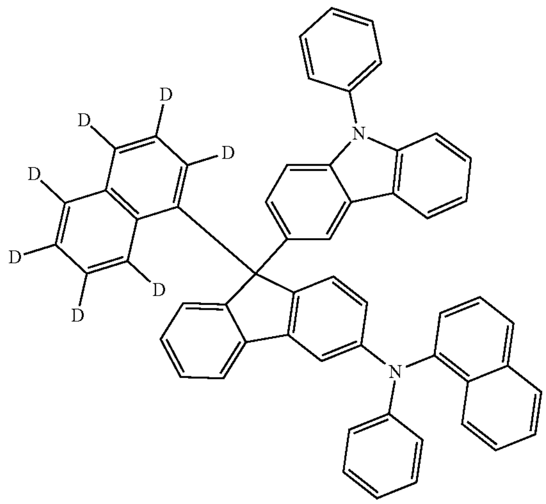
-continued
175
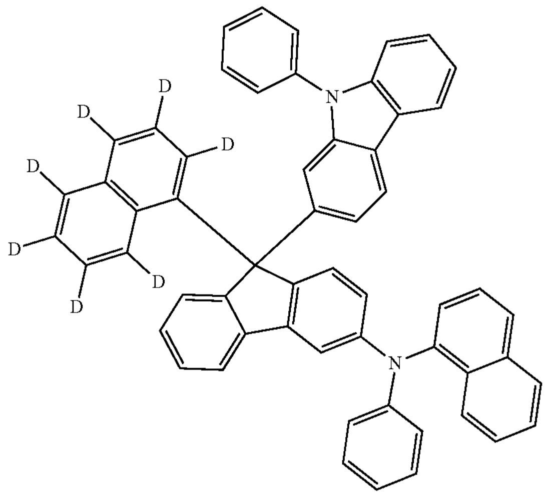
176
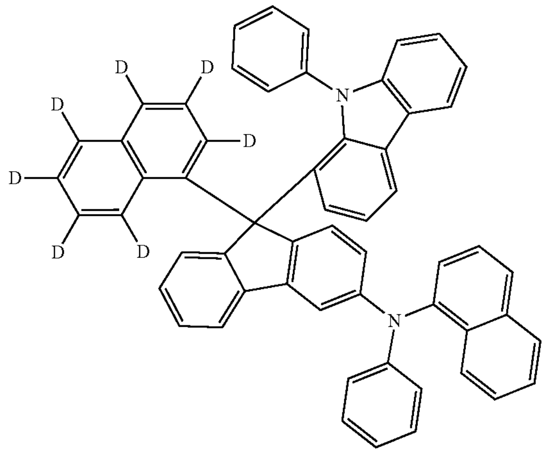
177
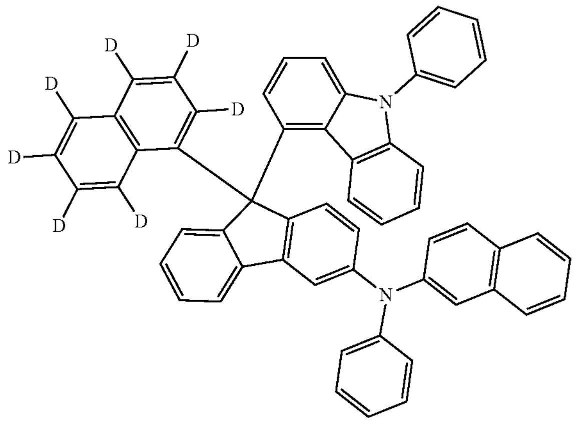

-continued
178
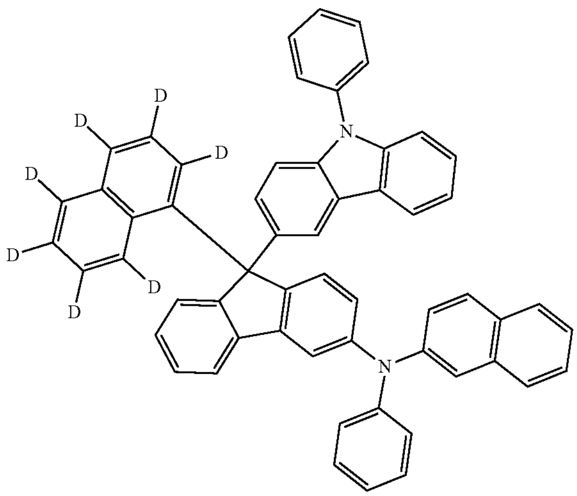
179
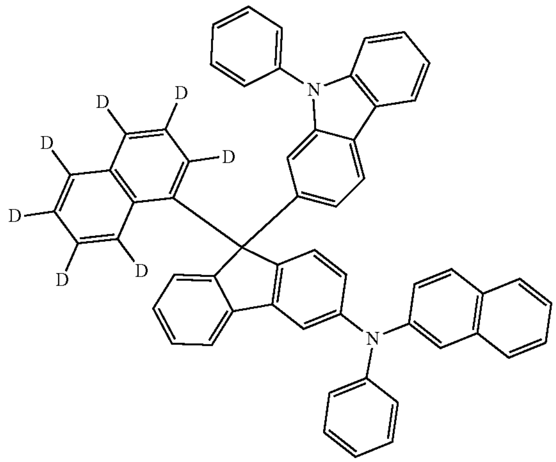
180
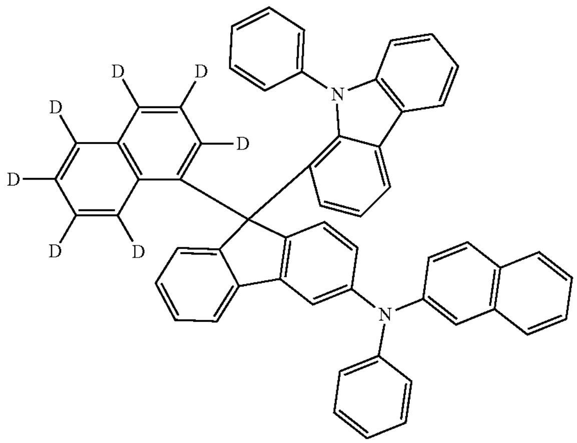
181
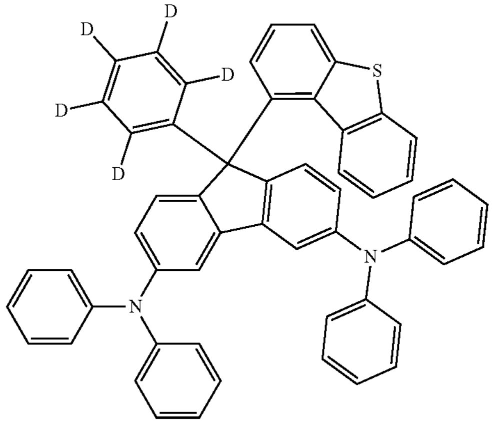
182
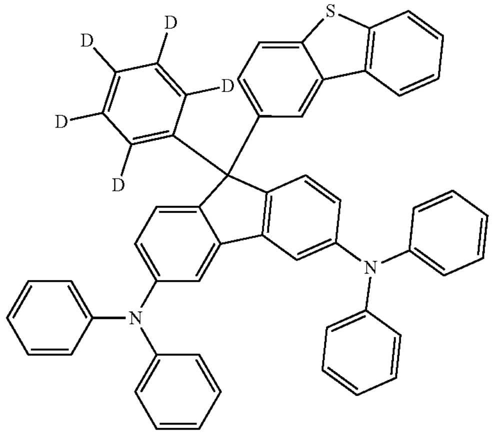
183
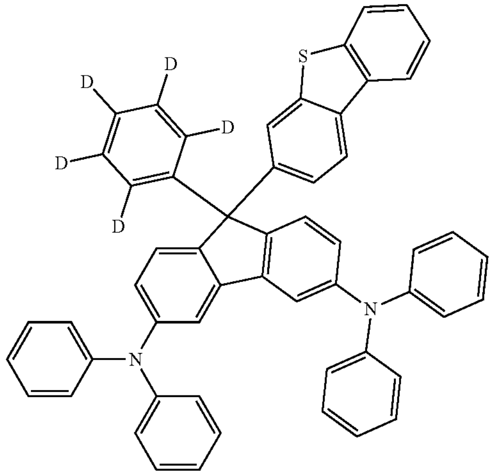

-continued
184
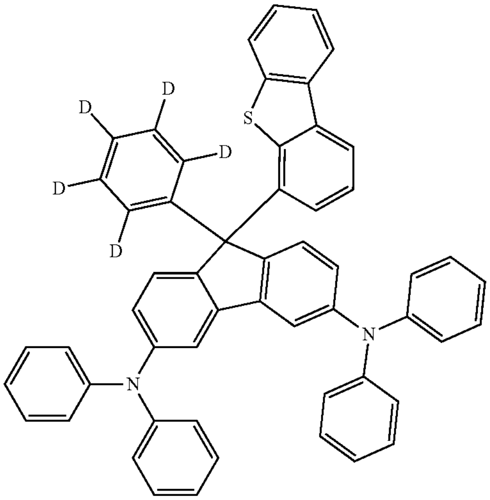
185
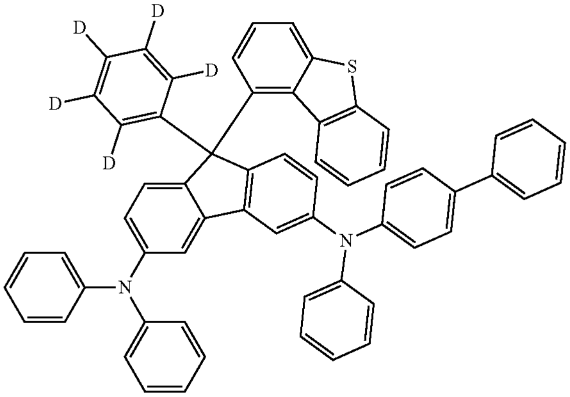
186
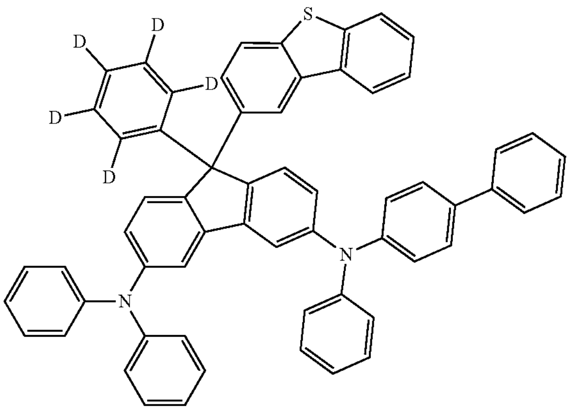
-continued
187
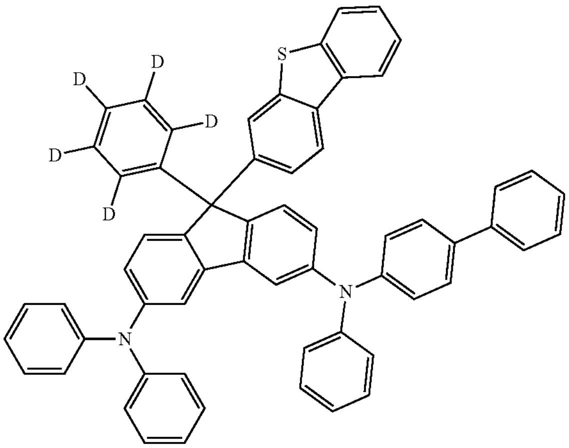
188
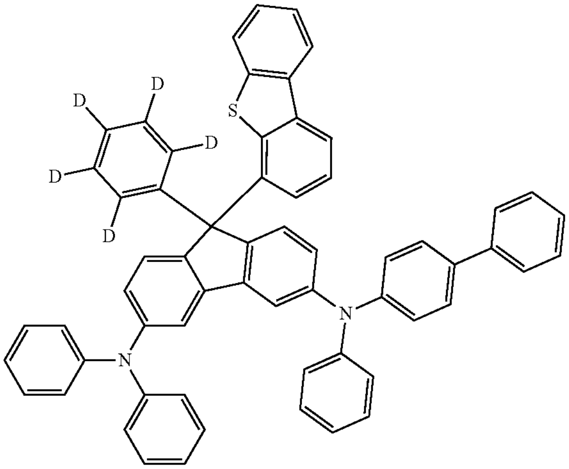
189
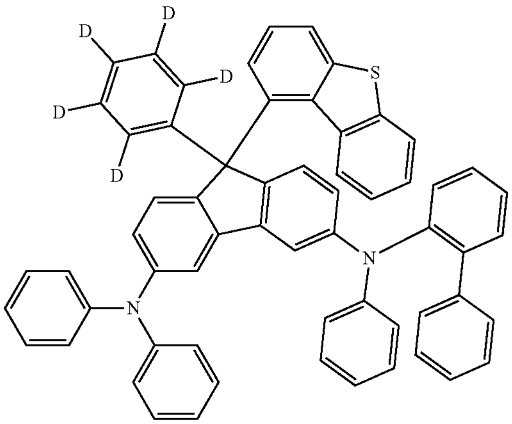

-continued
190
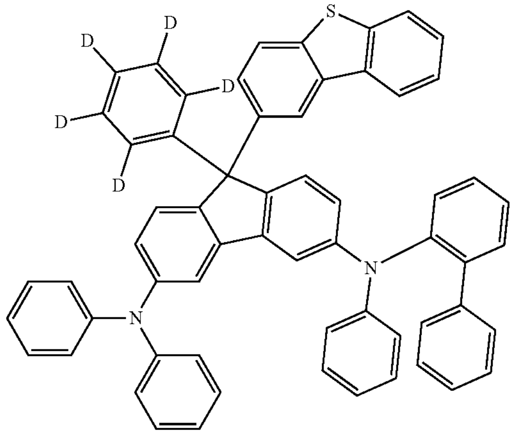
191
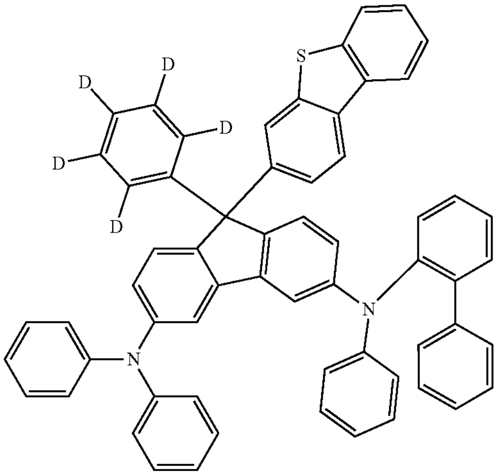
192
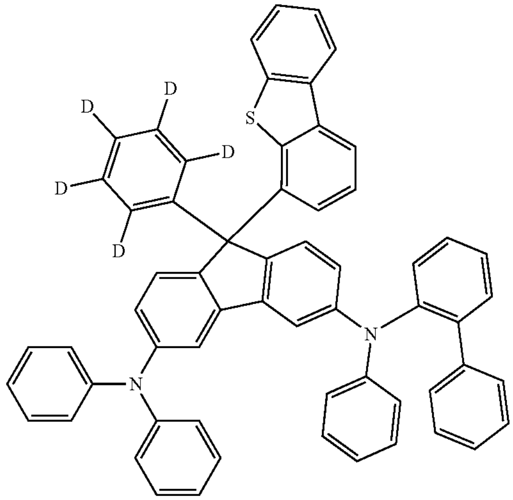
-continued
193
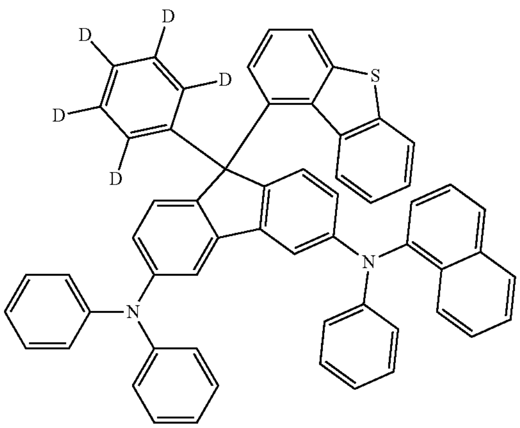
194
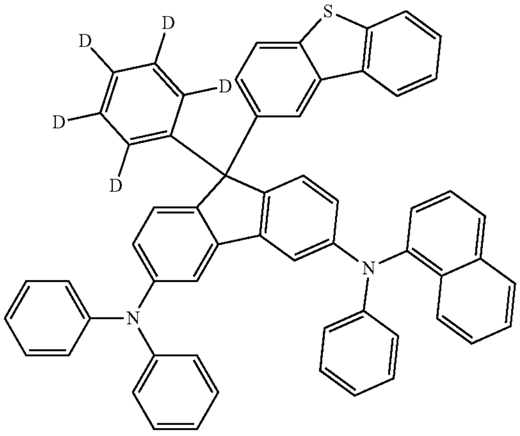
195
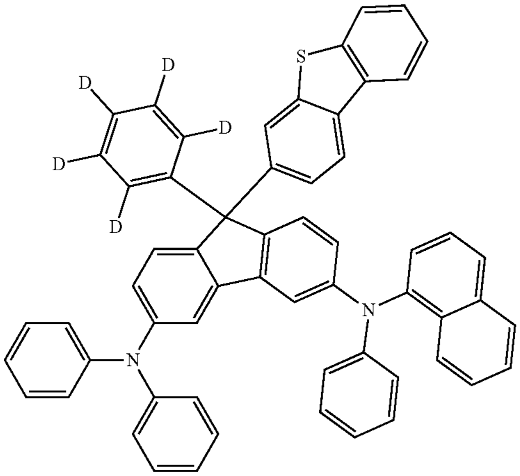

-continued
196
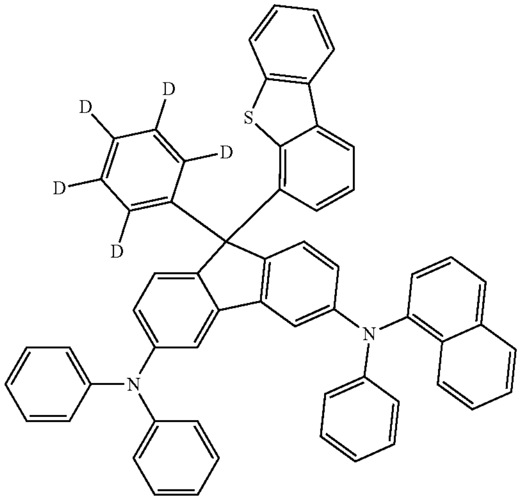
197
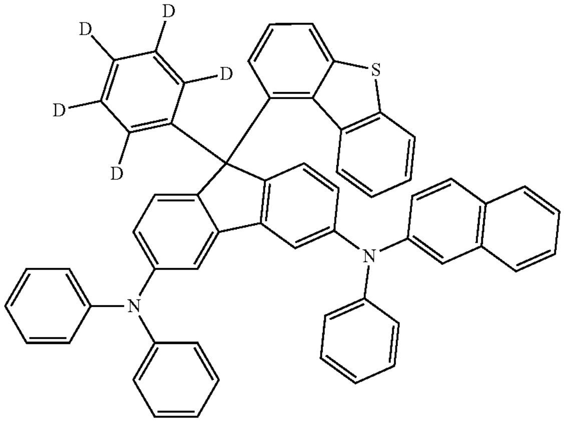
198
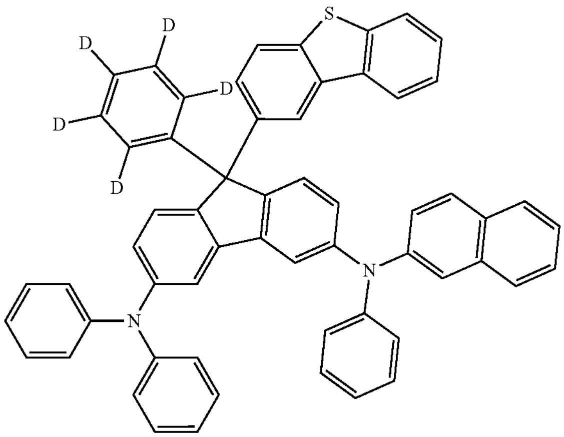
-continued
199
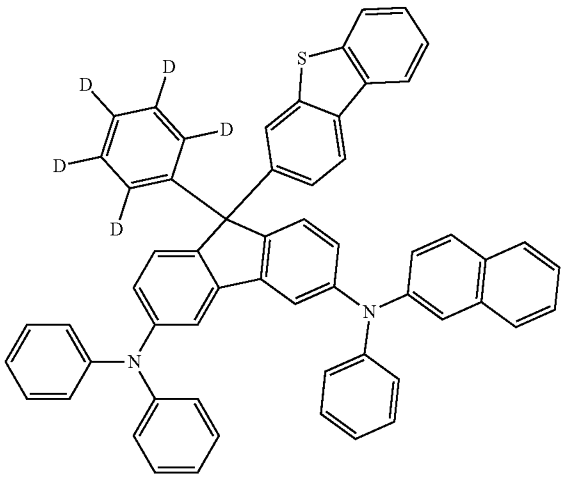
200
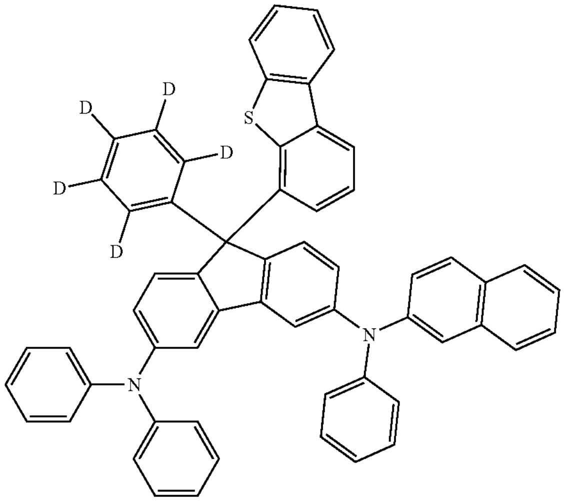
201
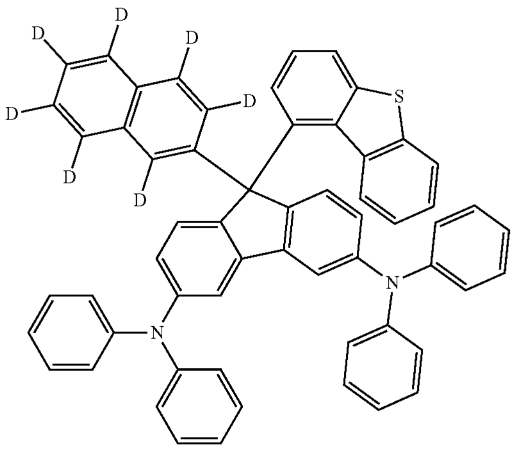

-continued
202
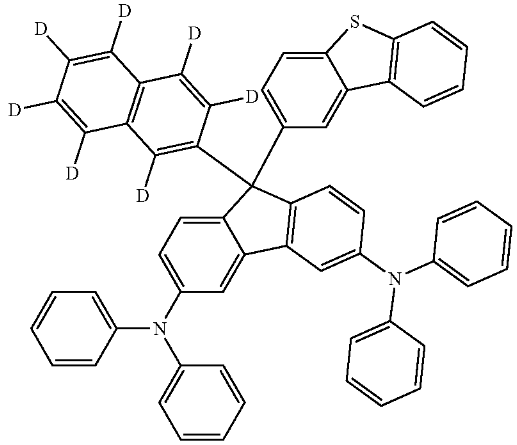
203
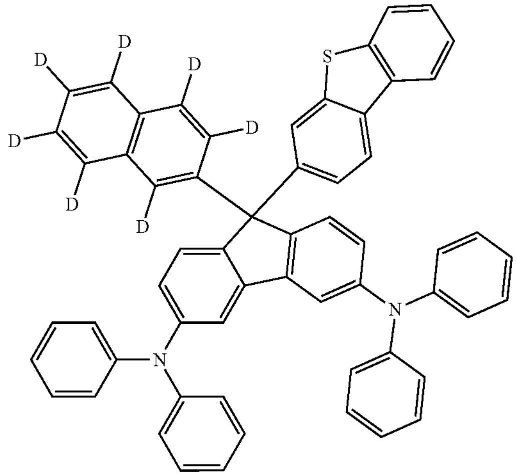
204
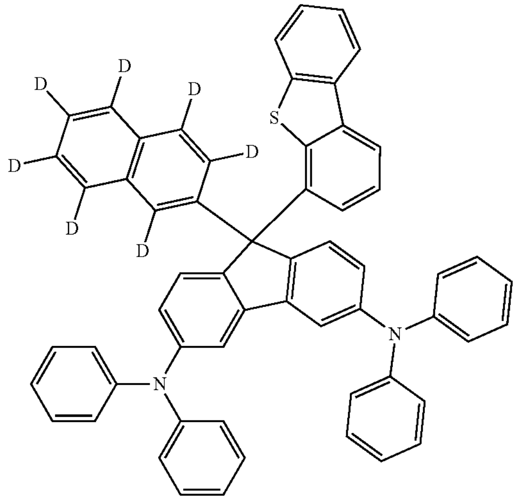
-continued
205
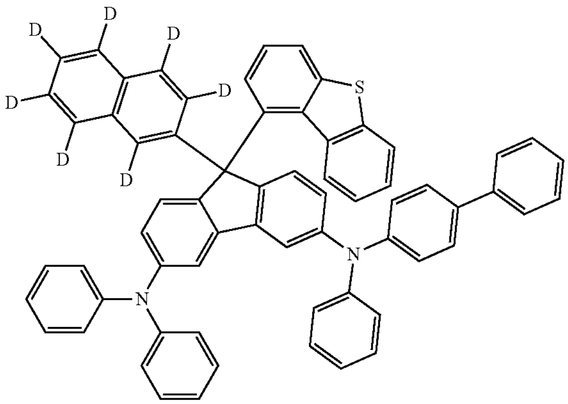
206
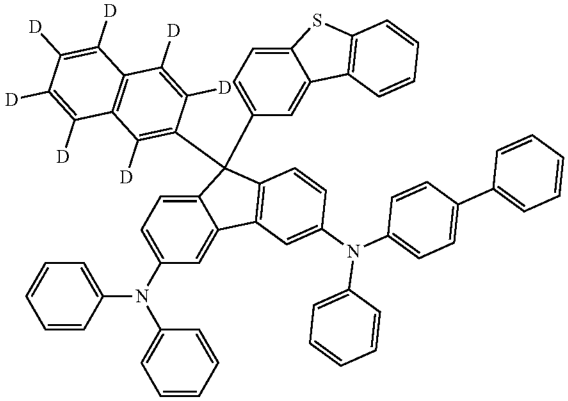
207
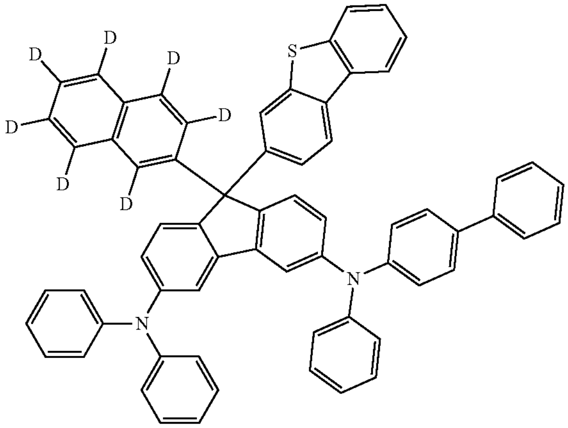

-continued
208
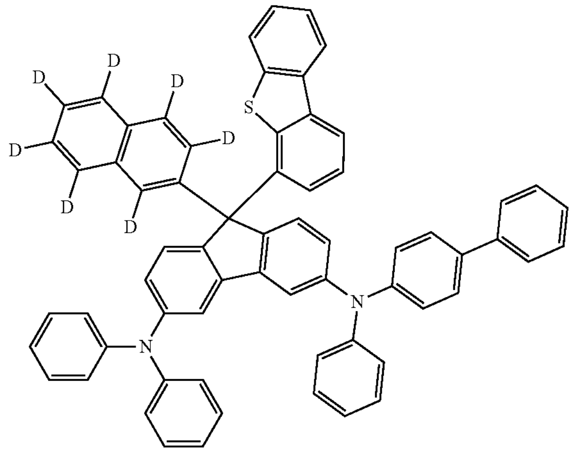
209
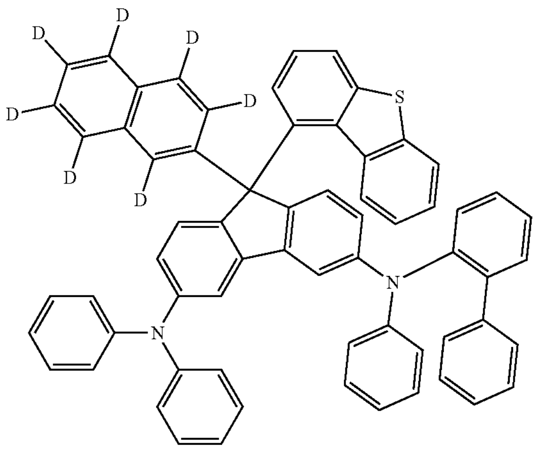
210
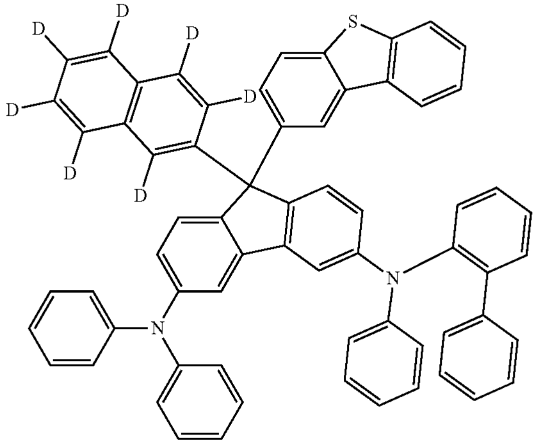
-continued
211
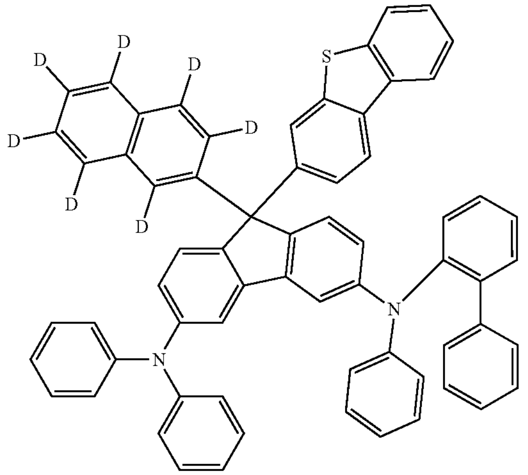
212
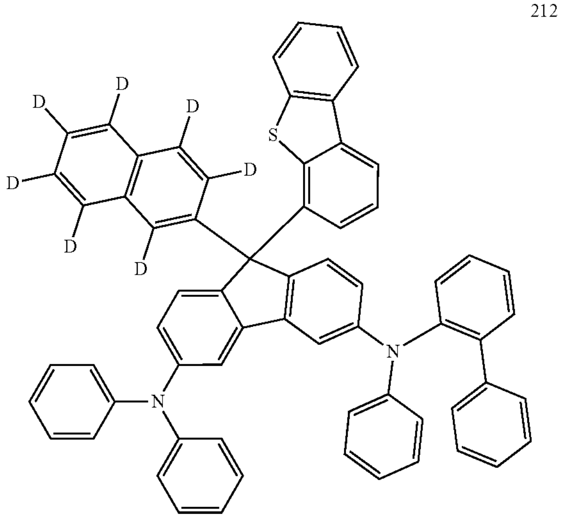 [SMILES: [2H]c1c([2H])c([2H])c2c([2H])c(C3(c4cccc5c4sc4ccccc45)c4ccc(N(c5ccccc5)c5ccccc5)cc4-c4cc(N(c5ccccc5)c5ccccc5-c5ccccc5)ccc43)c([2H])c([2H])c2c1[2H]]
213
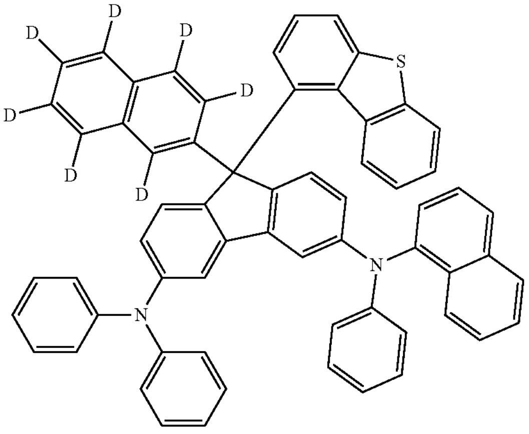

-continued
214
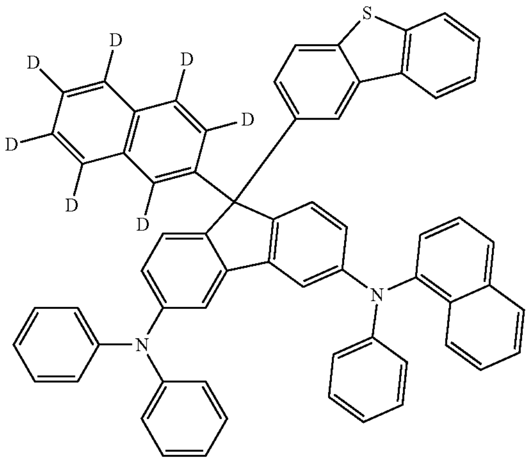
215
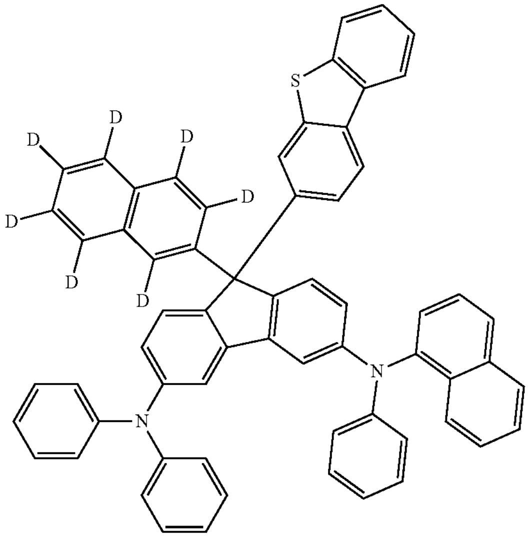
216
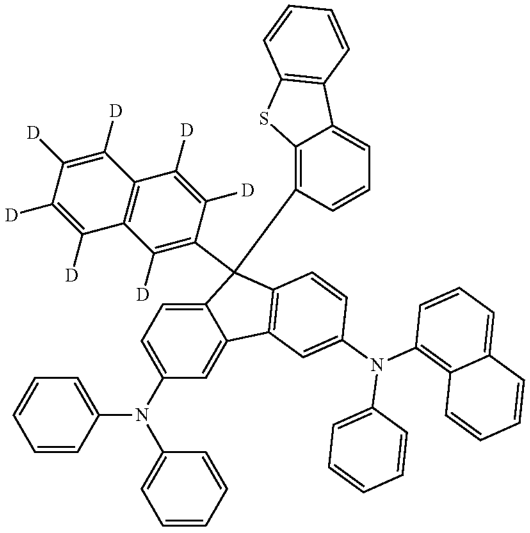
-continued
217
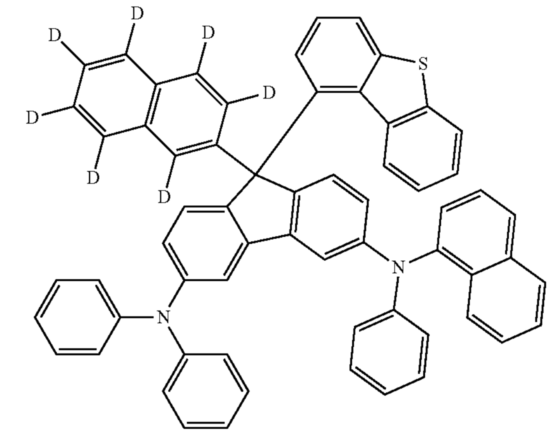
218
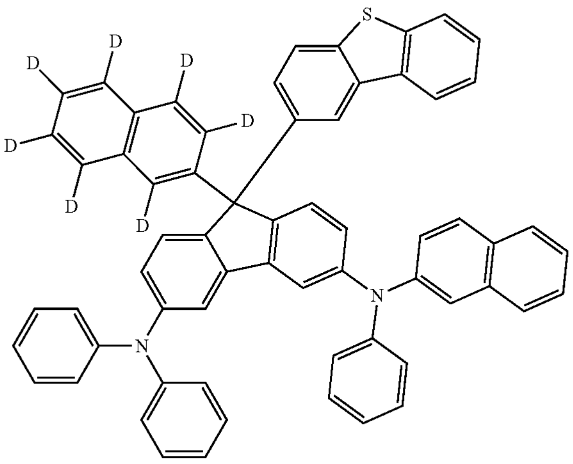
219
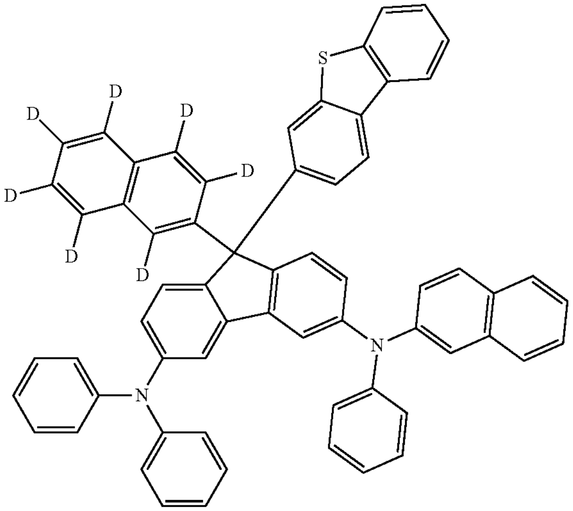

-continued
220
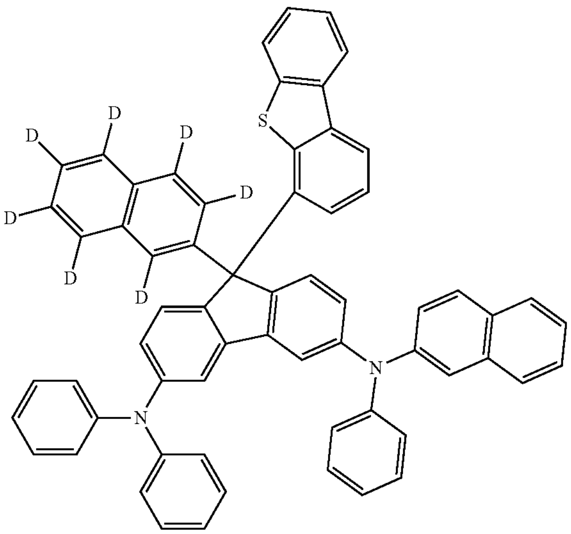
221
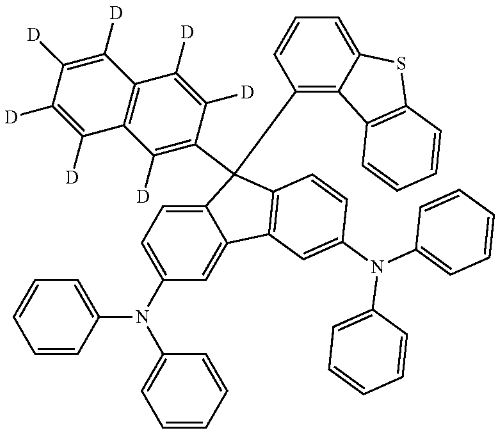
222
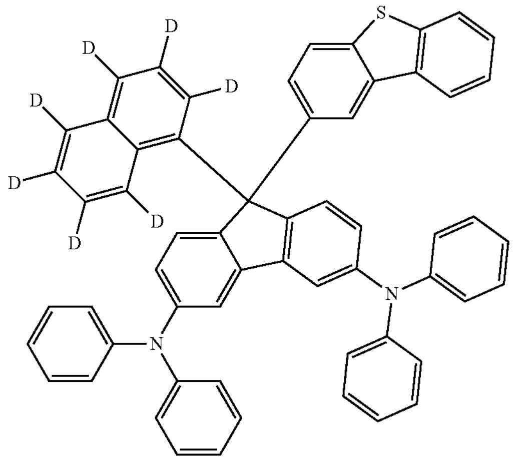
-continued
223
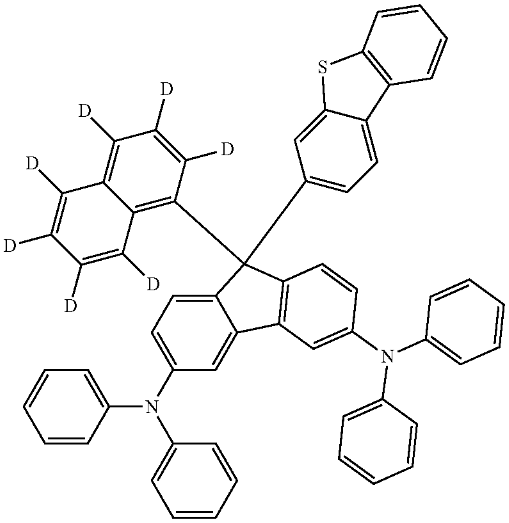
224
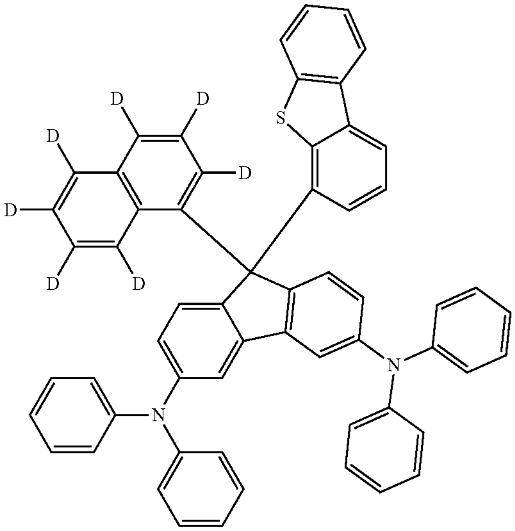
225
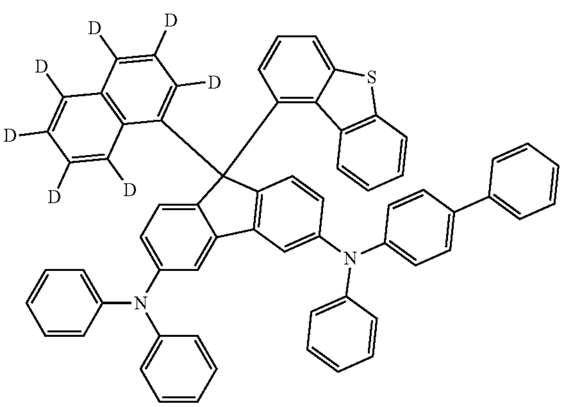

-continued
226
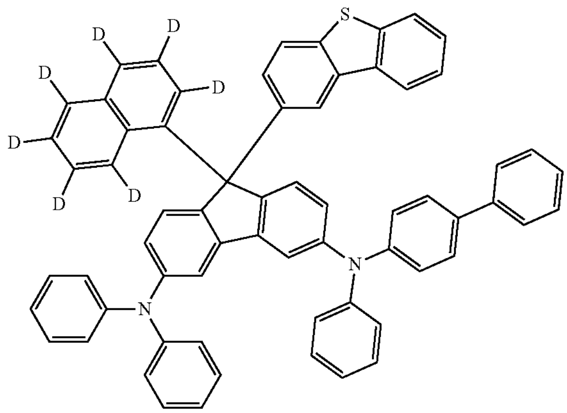
227
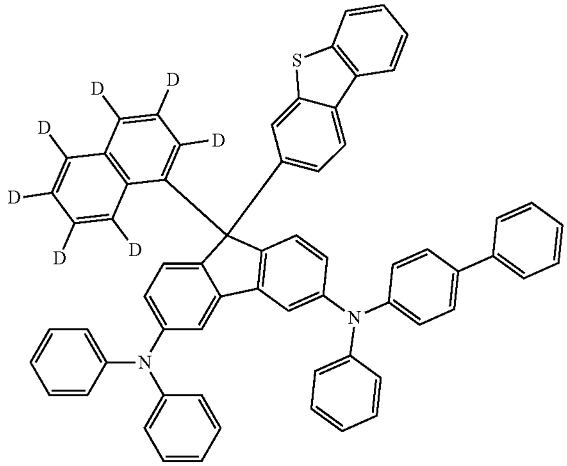
228
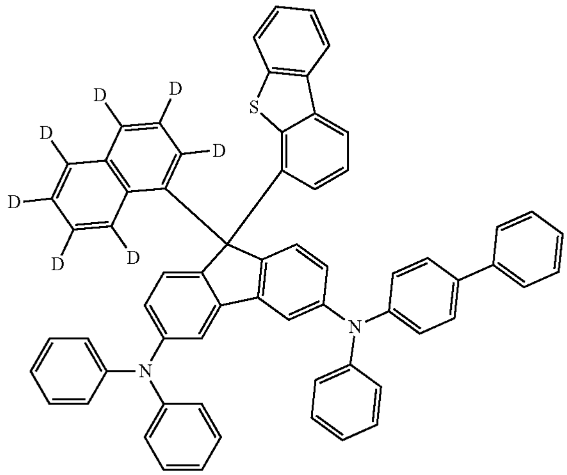
-continued
229
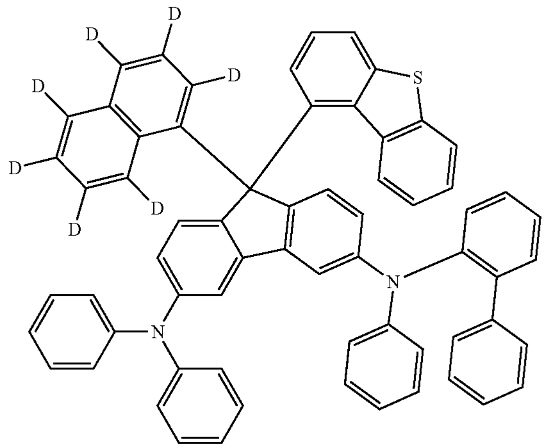
230
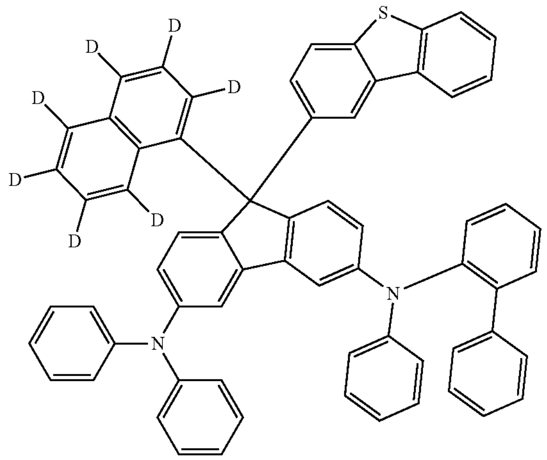
231
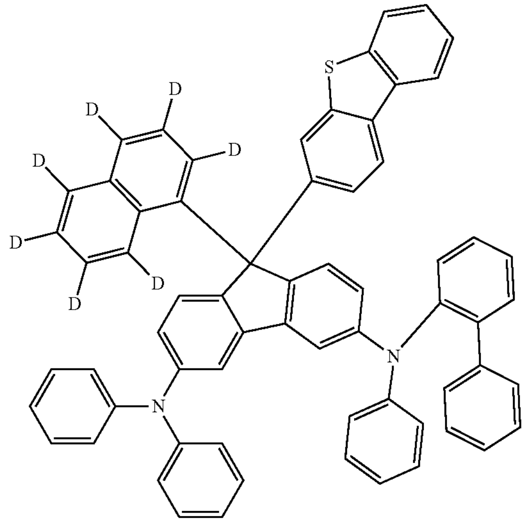

-continued
232
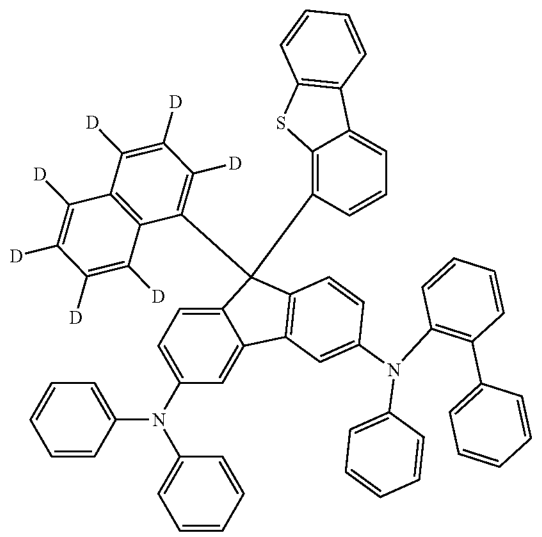
233
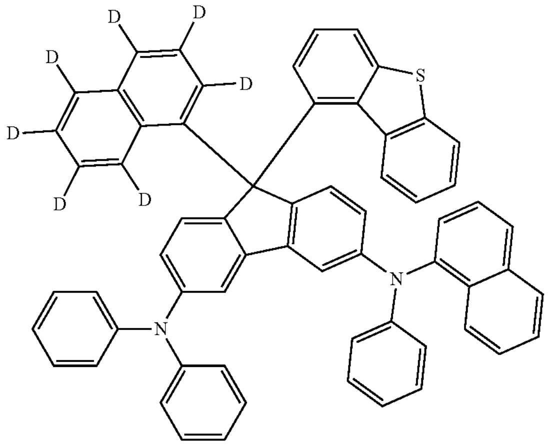
234
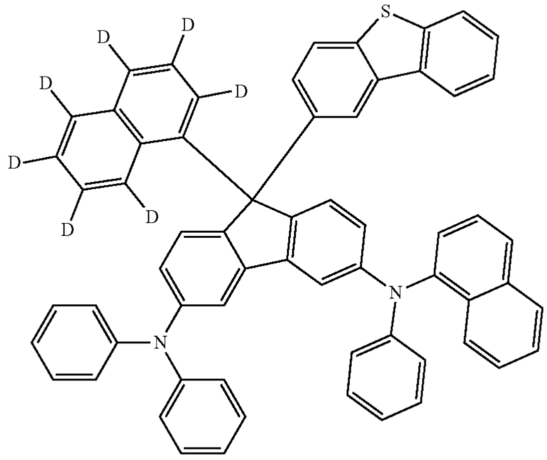
-continued
235
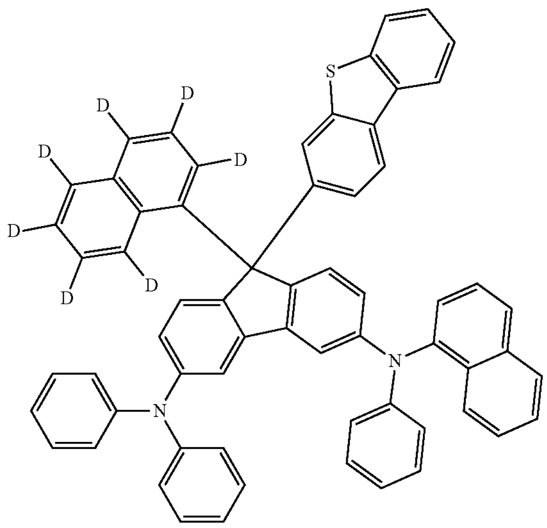
236
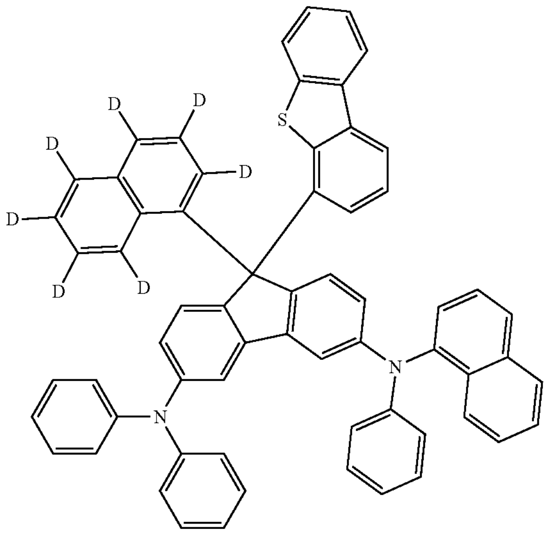
237
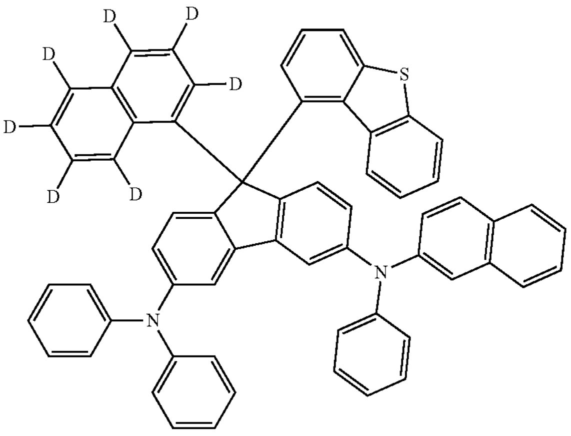

-continued
238
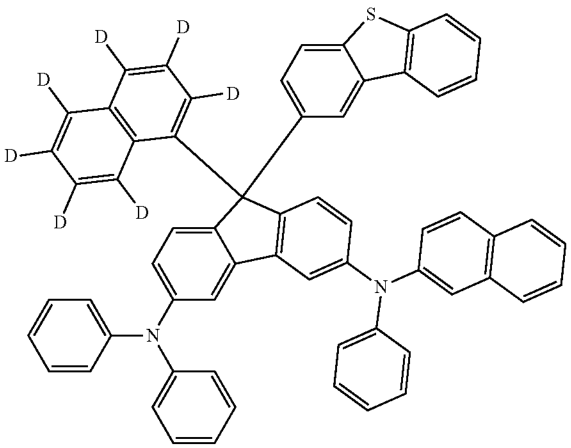
239
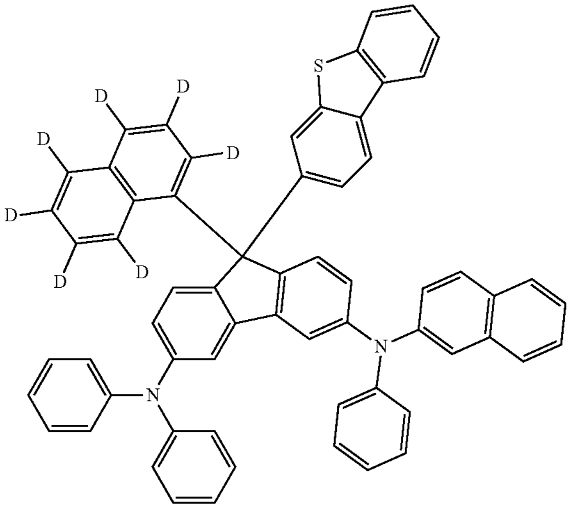
240
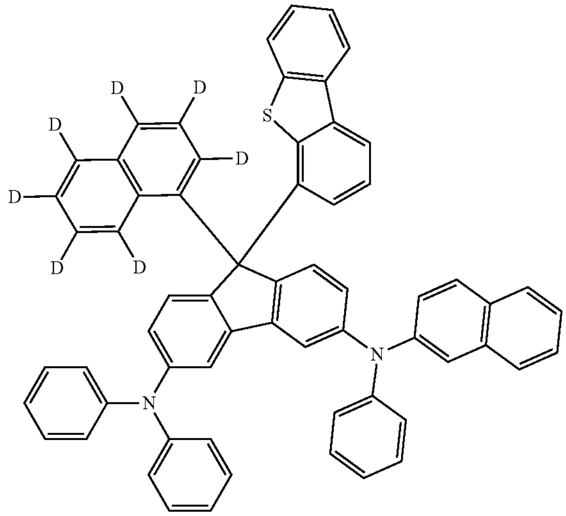
241
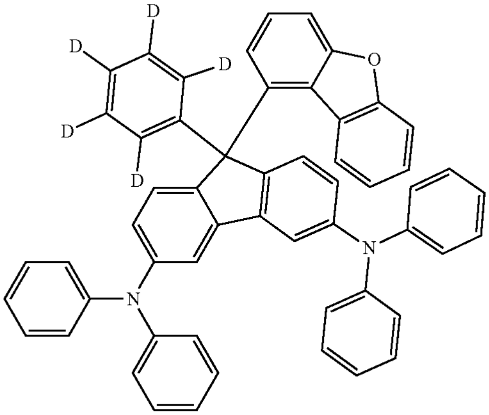
242
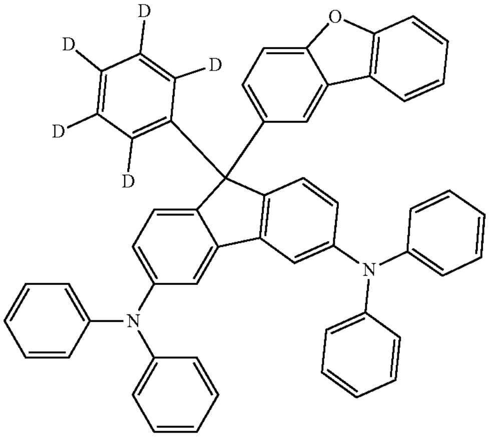
243
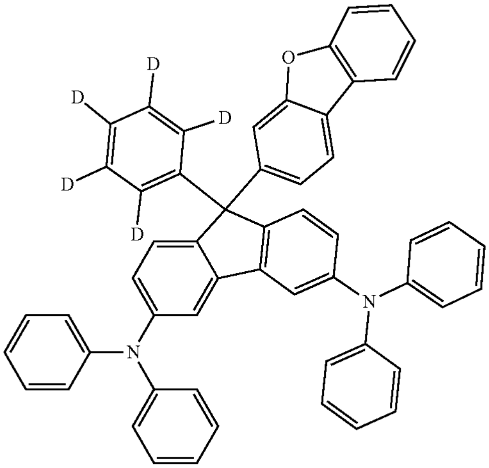

-continued
244
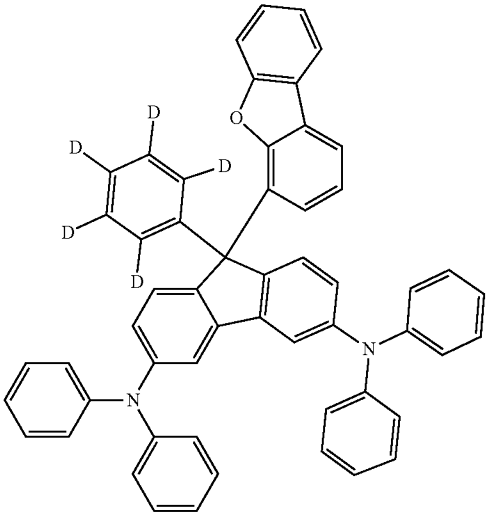
245
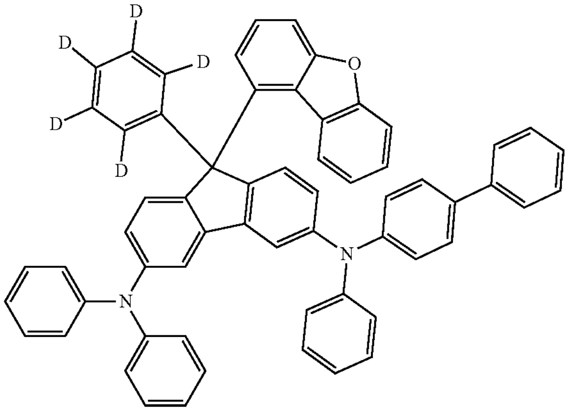
246
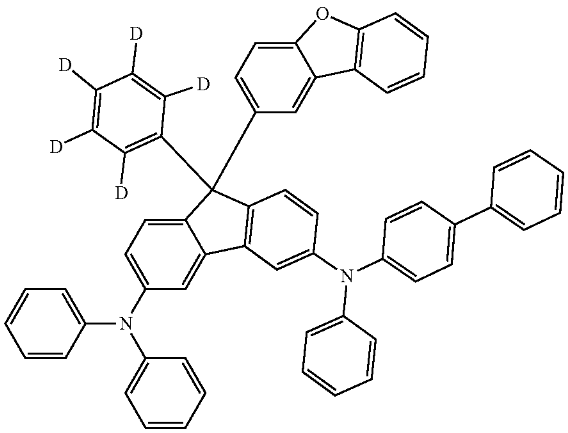
-continued
247
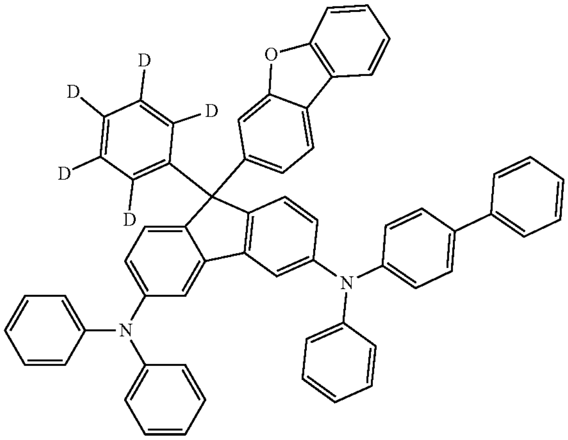
248
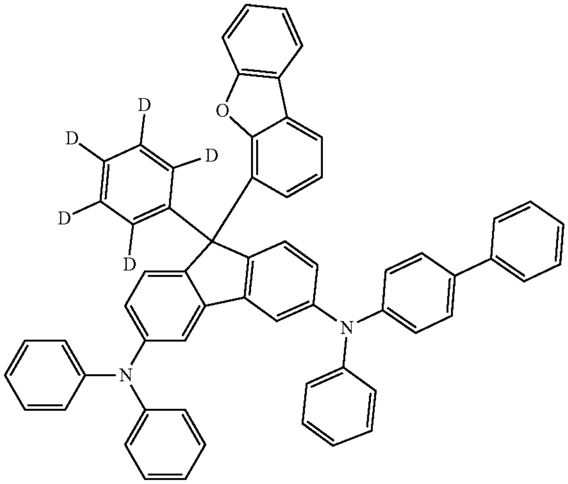
249
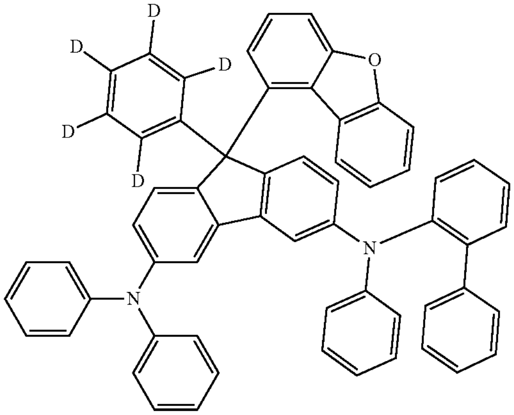

-continued
250
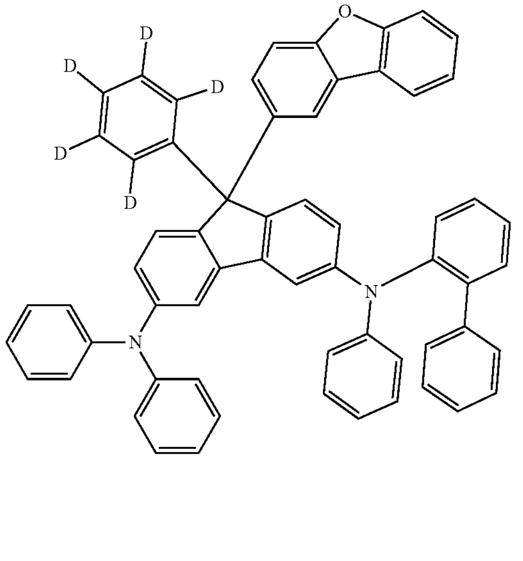
251
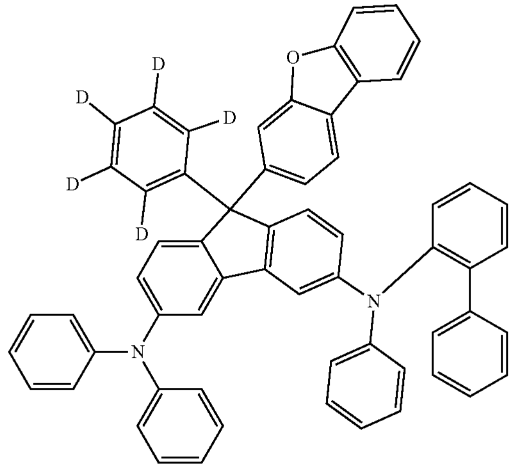
252
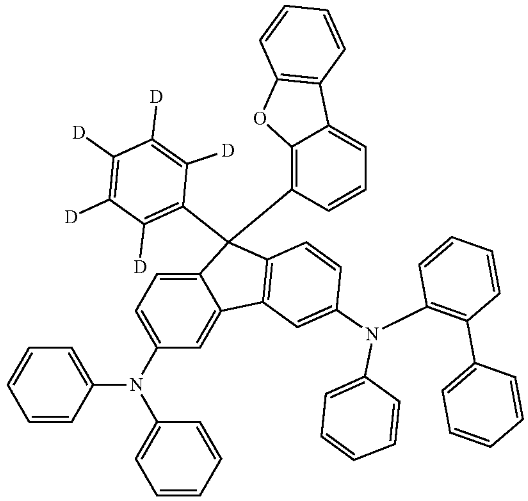
-continued
253
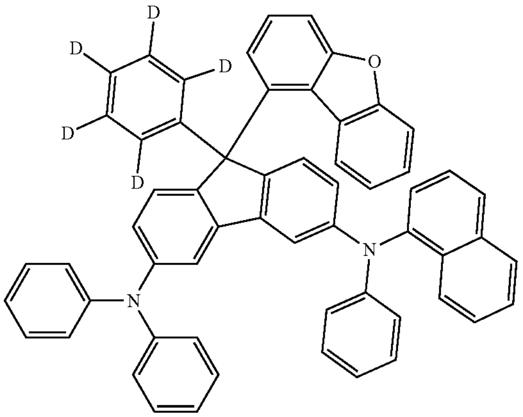
254
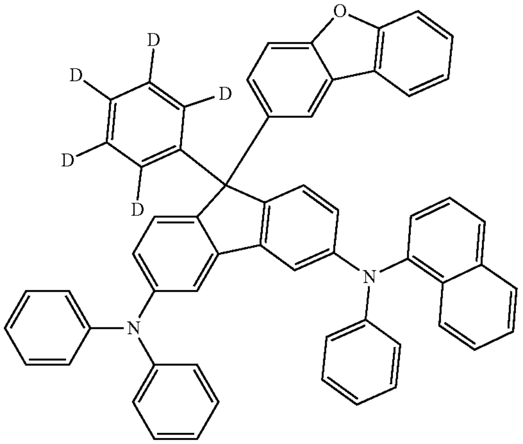
255
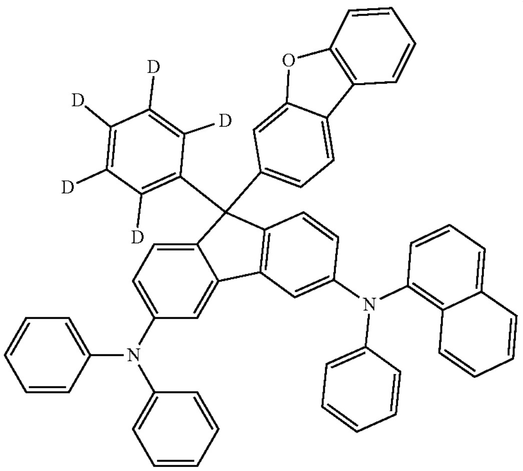

-continued
256
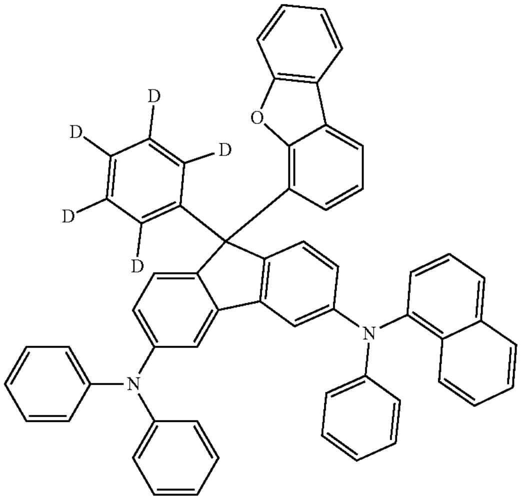
257
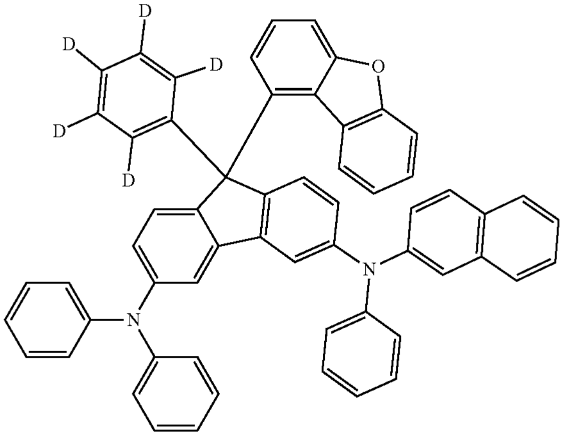
258
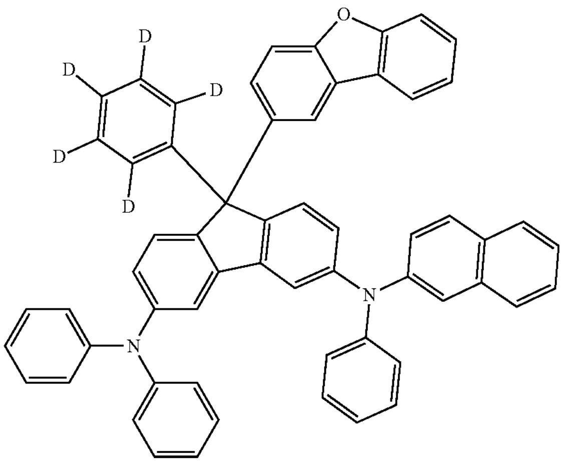
-continued
259
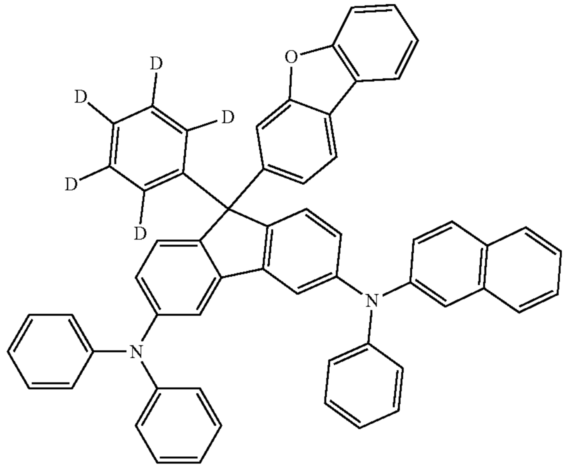
260
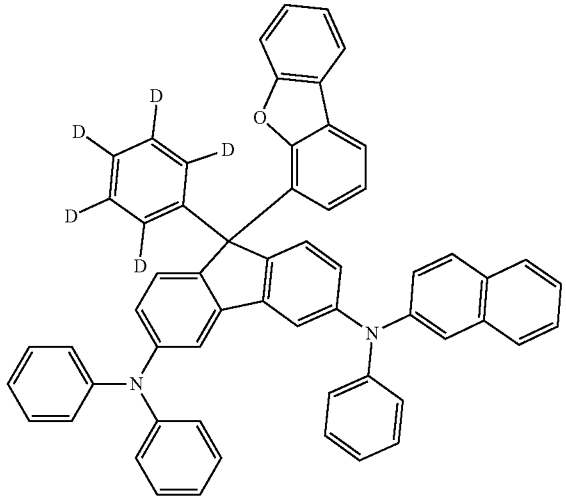
261
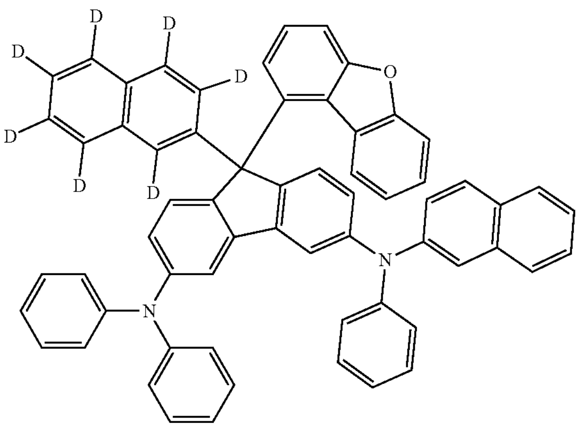

-continued
262
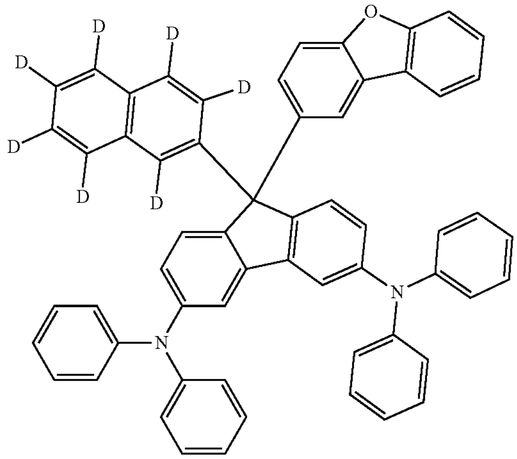
263
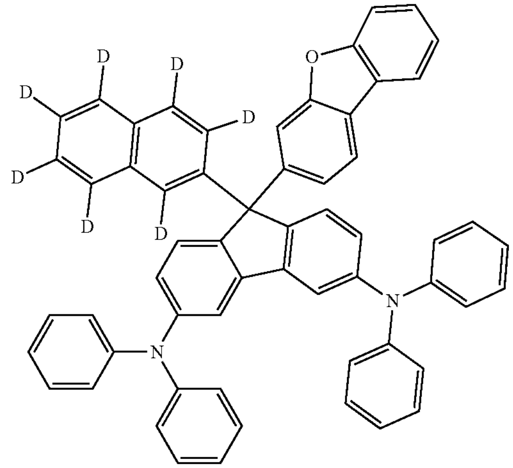
264
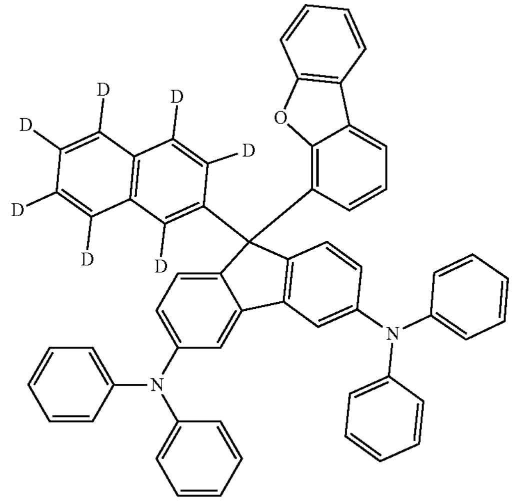
-continued
265
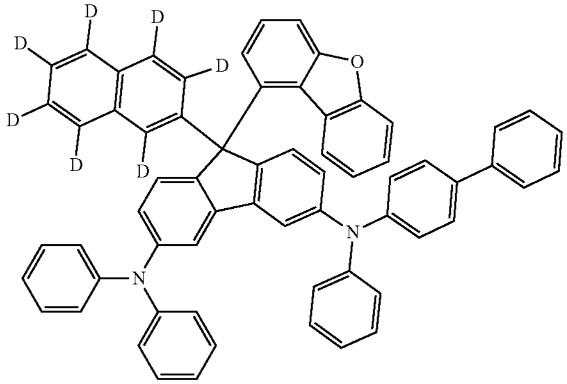
266
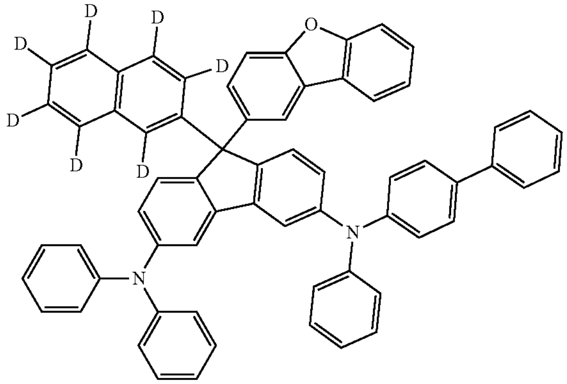
267
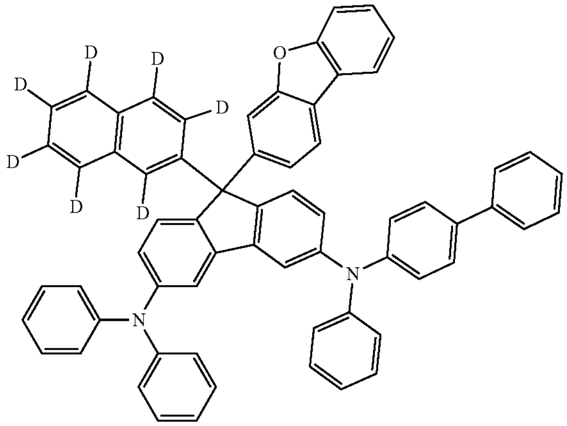

-continued
268
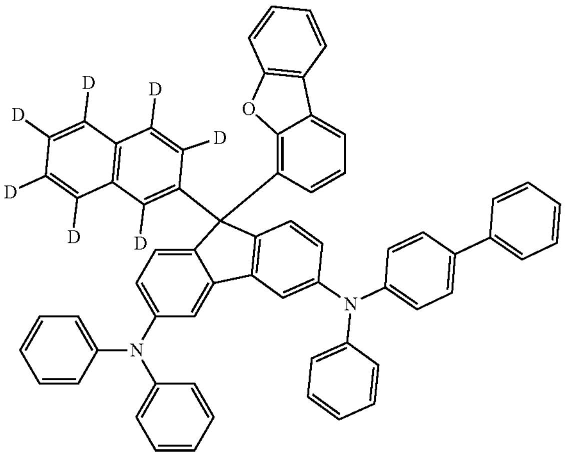
269
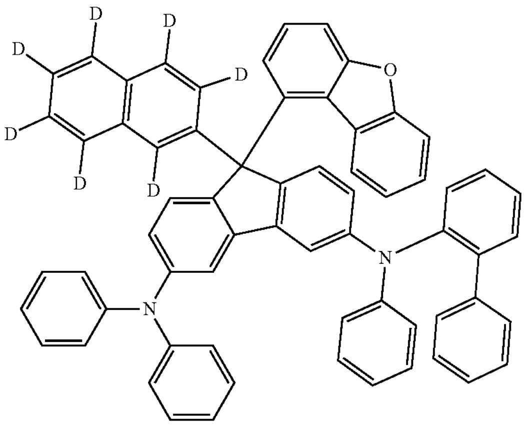
270
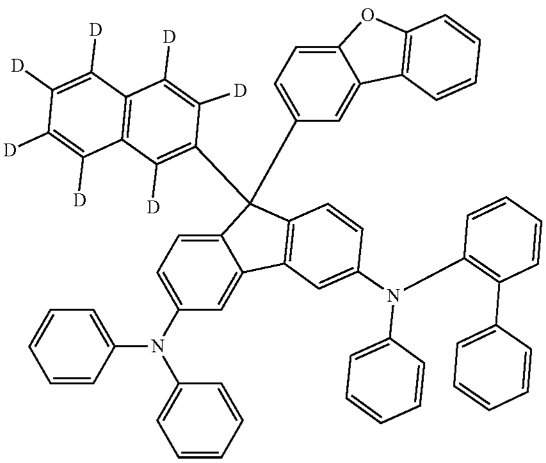
-continued
271
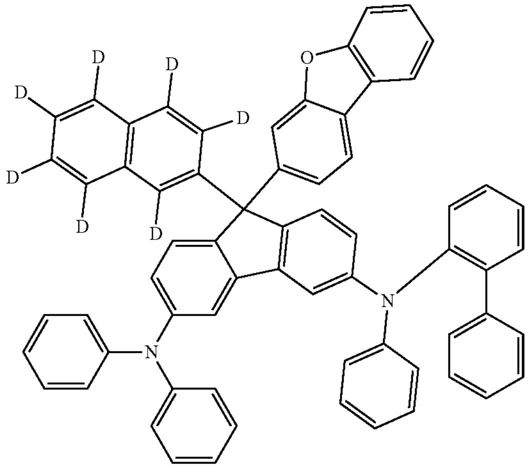
272
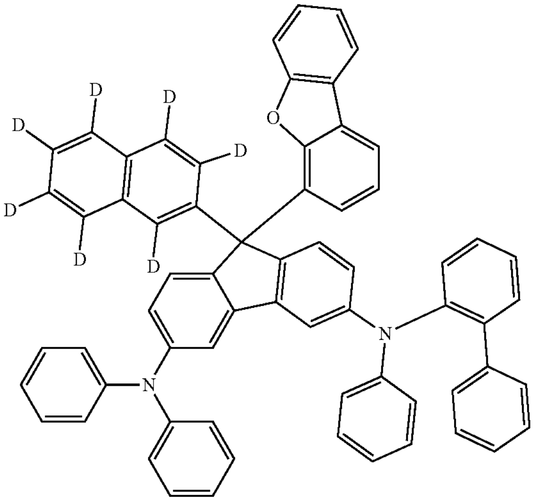
273
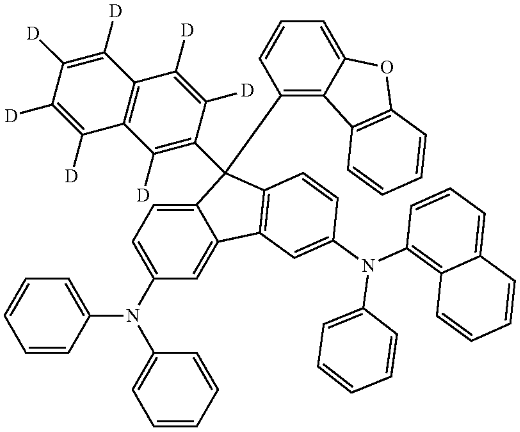

-continued
274
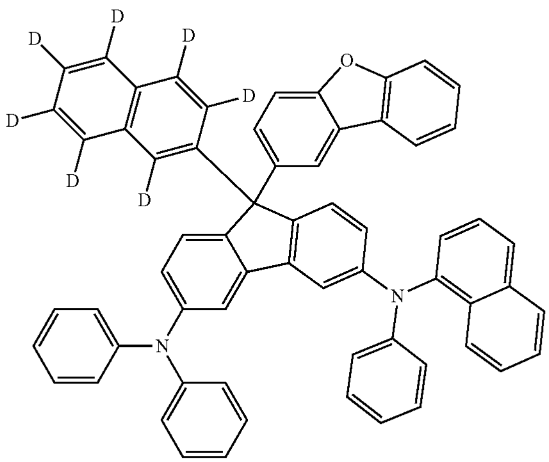
275
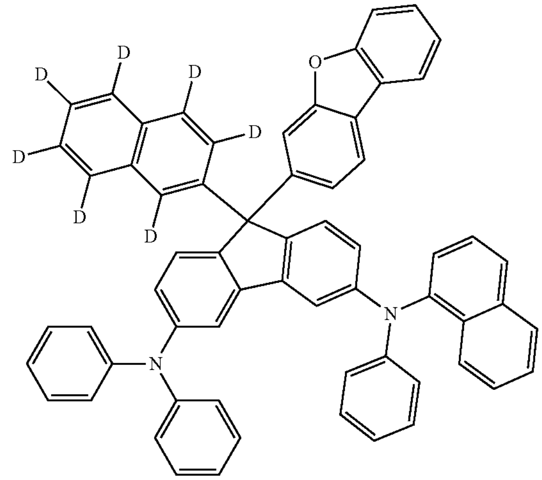
276
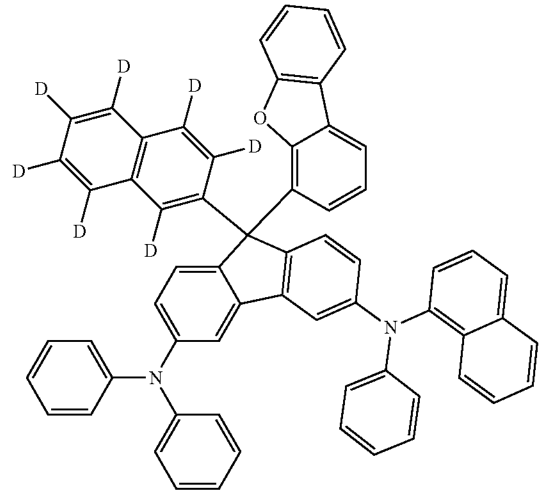
-continued
277
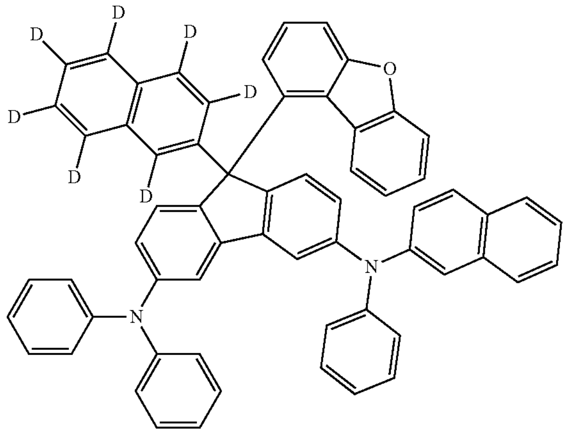
278
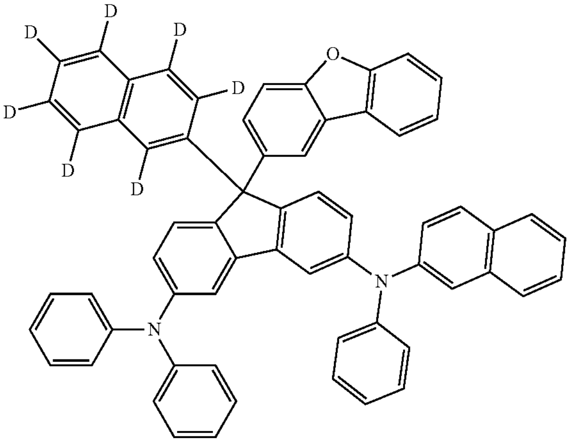
279
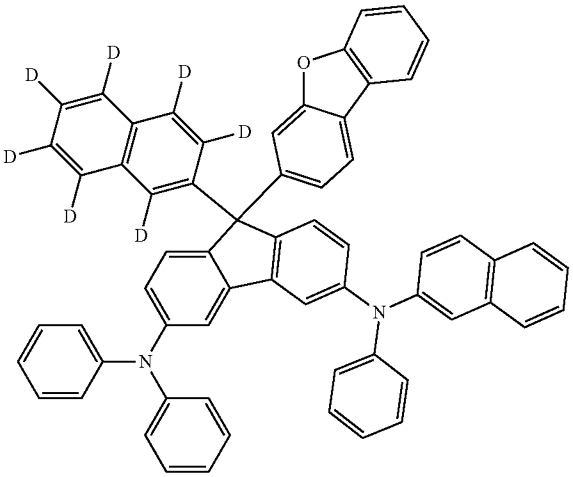

-continued
280
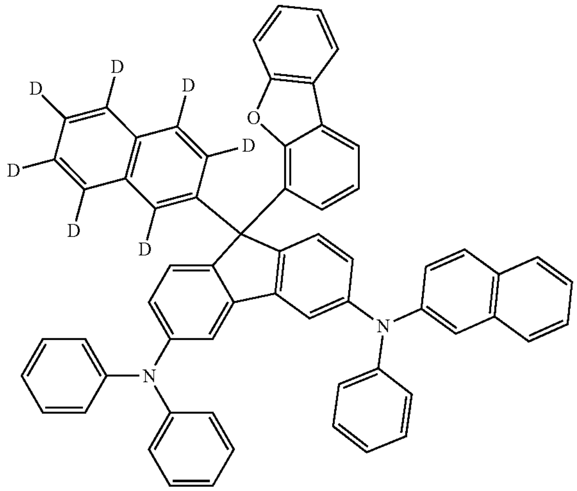
281
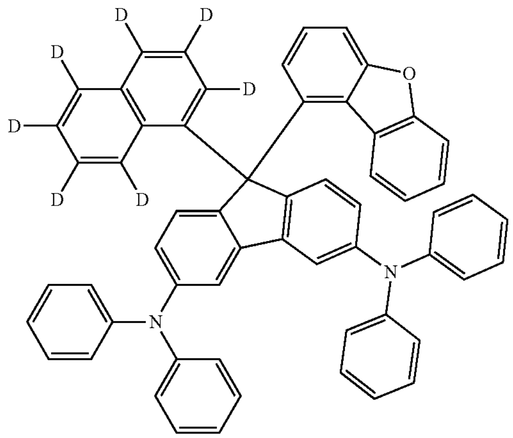
282
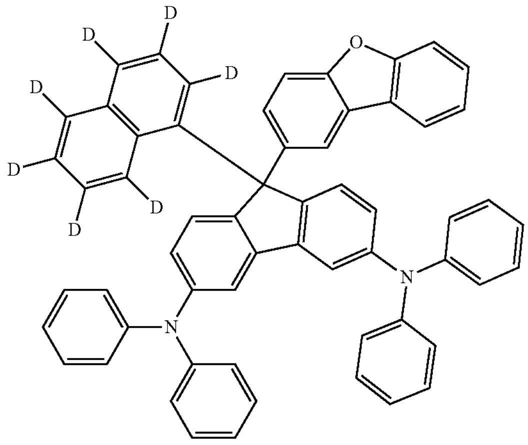
-continued
283
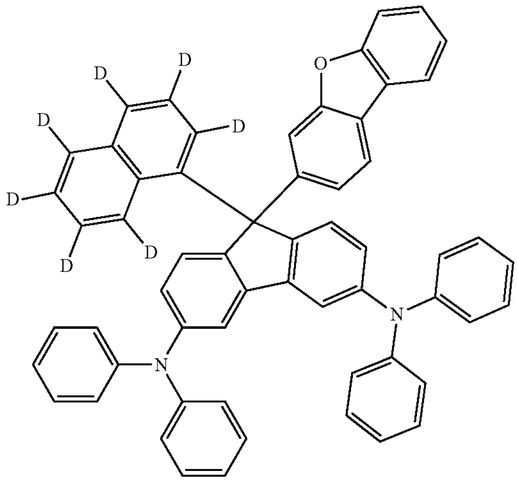
284
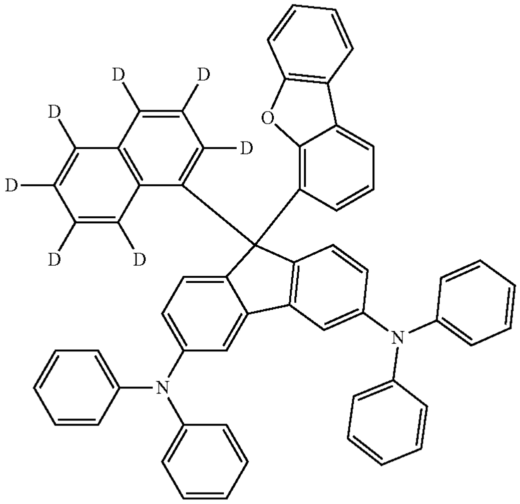
285
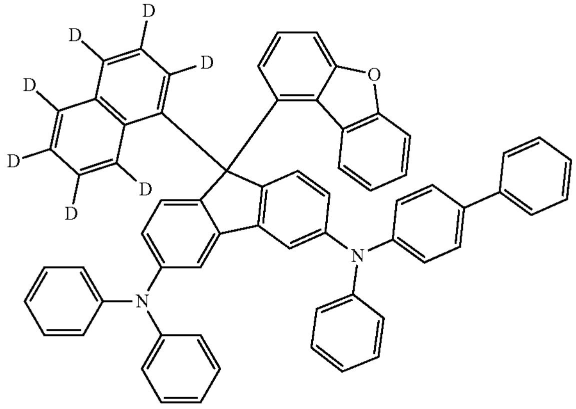

-continued
286
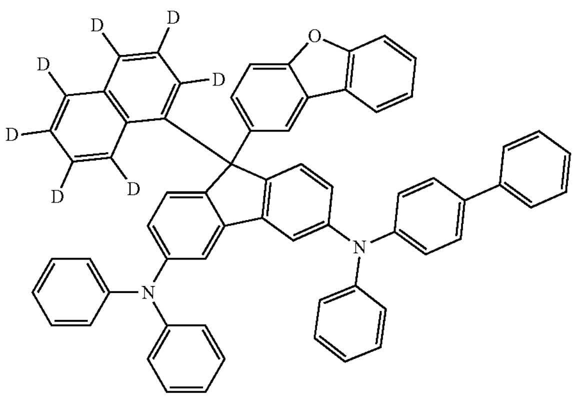
287
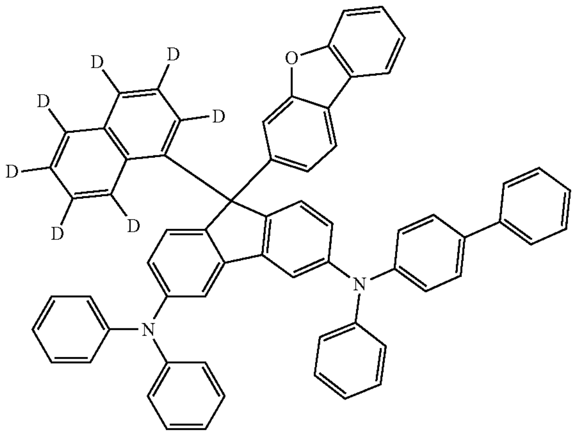
288
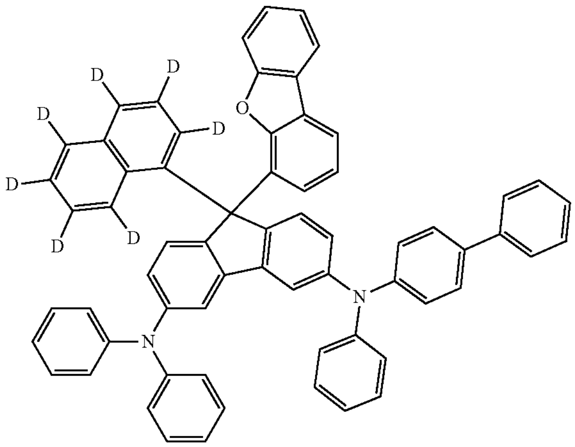
-continued
289
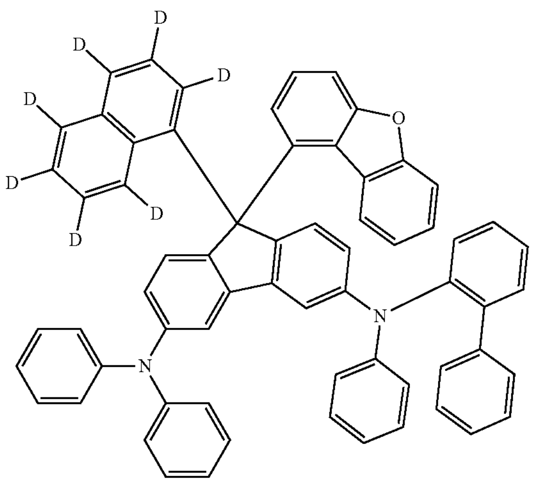
290
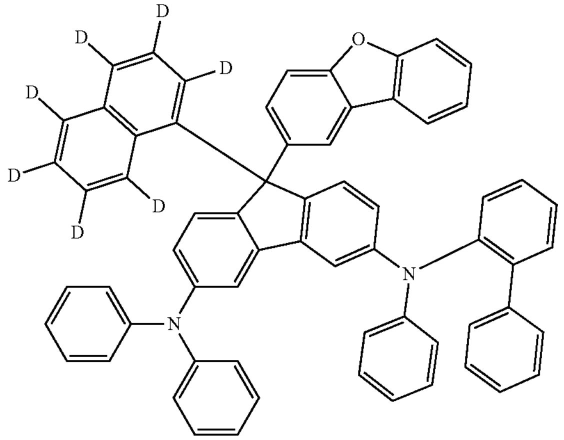
291
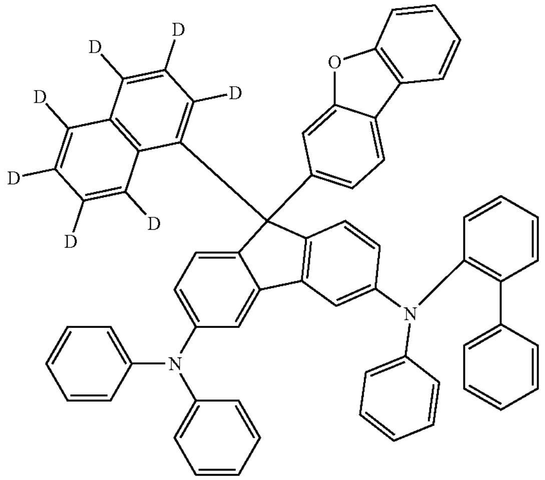

-continued
292
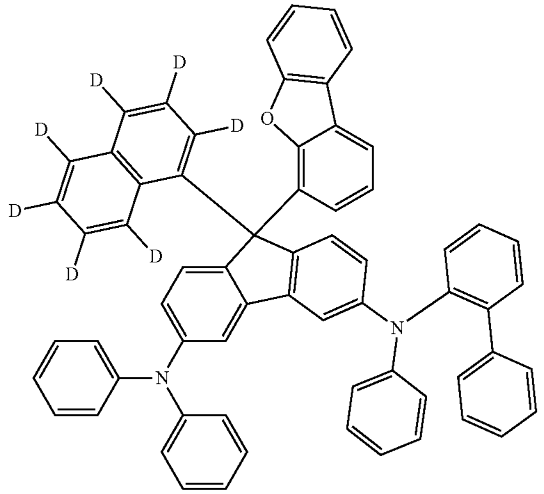
293
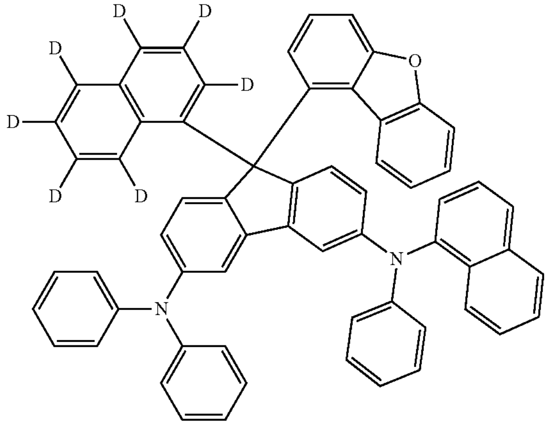
294
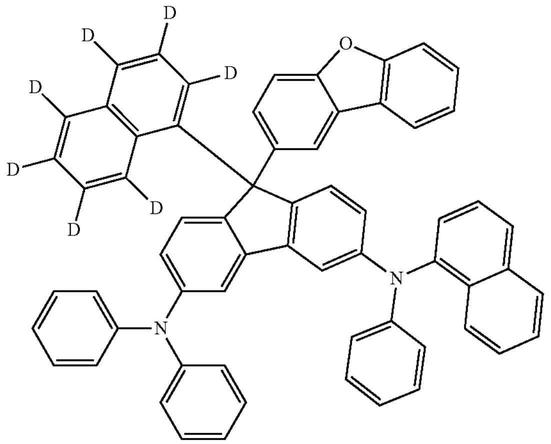
-continued
295
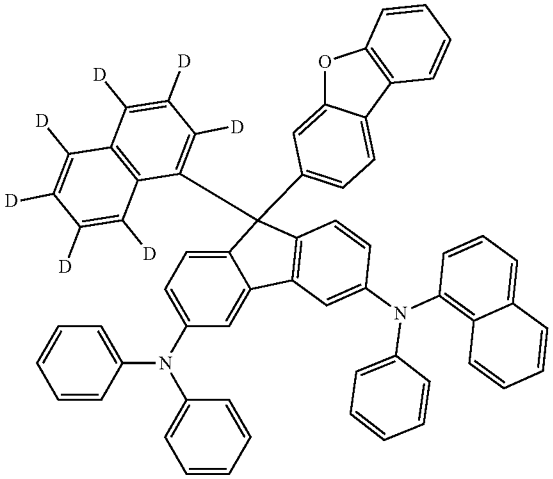
296
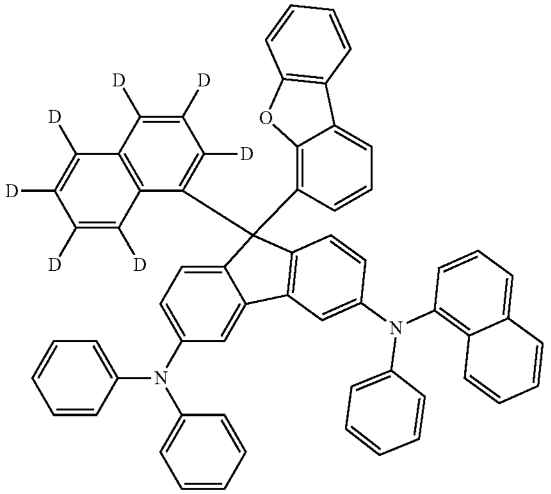
297
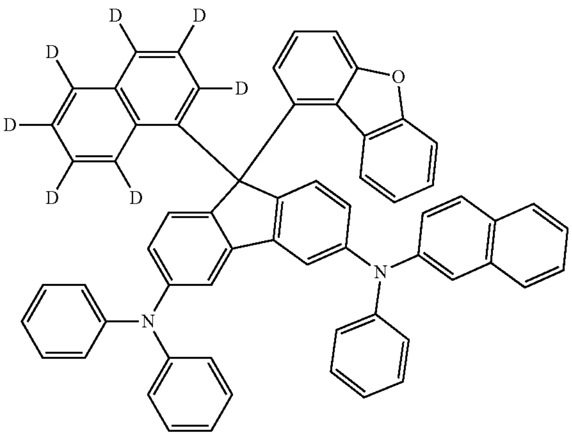

-continued
298
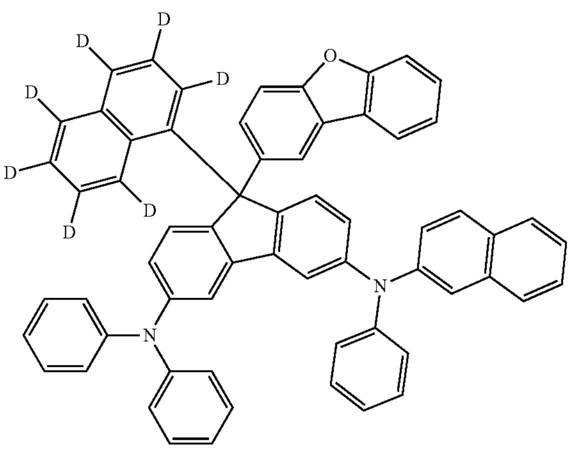
301
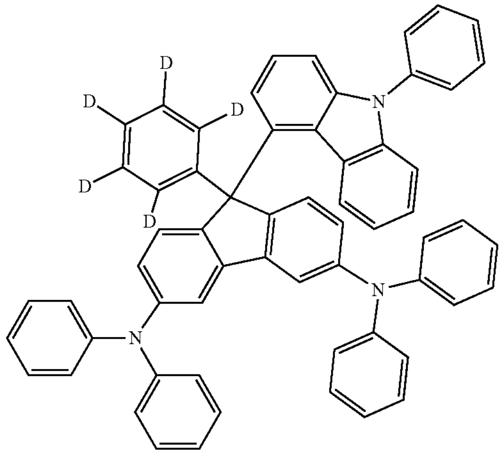
299
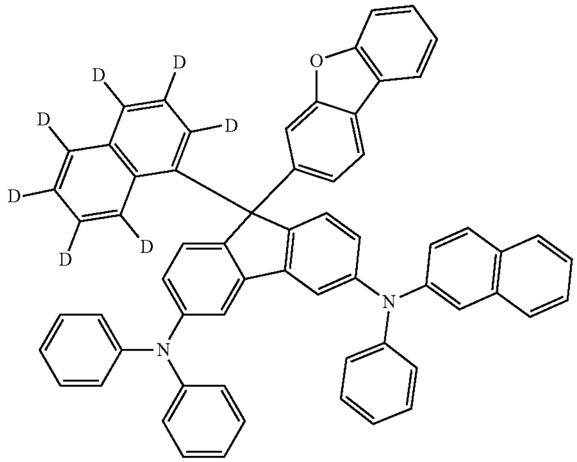
302
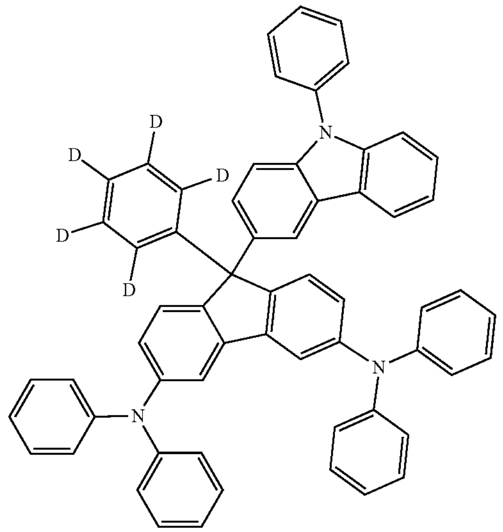
300
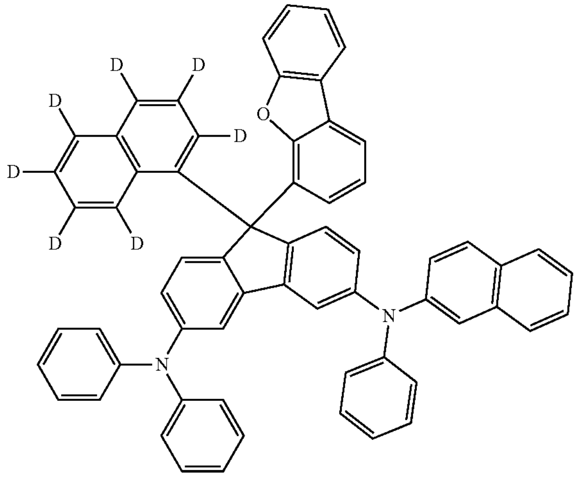
303
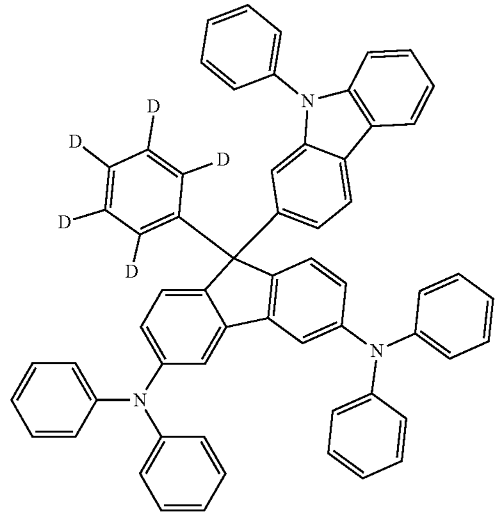

304
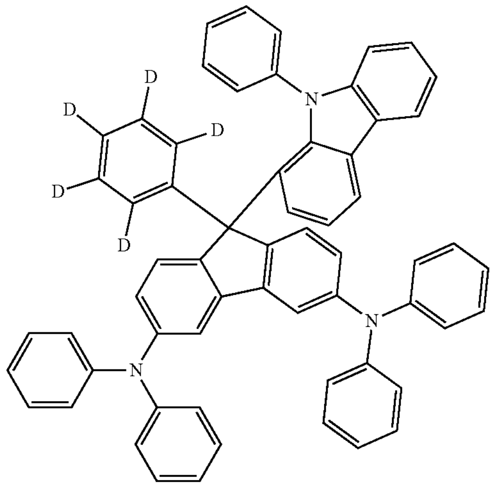
305
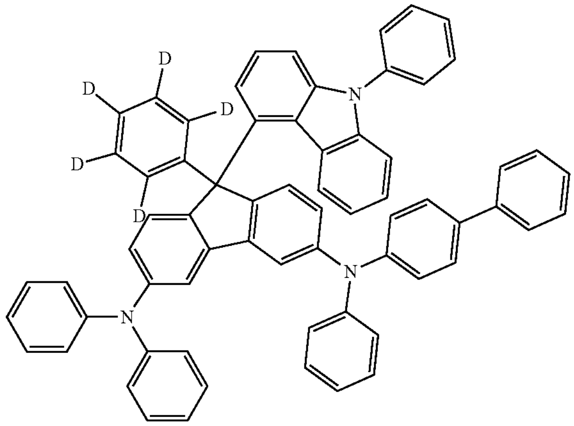
306
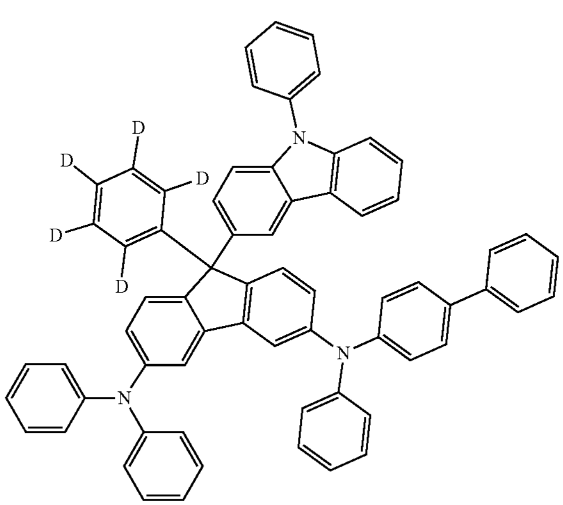
307
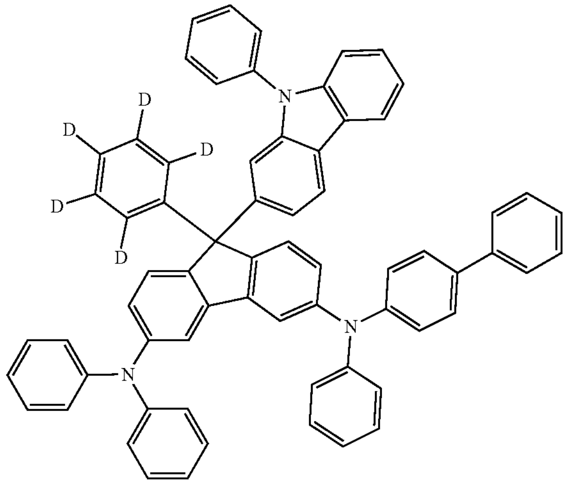
308
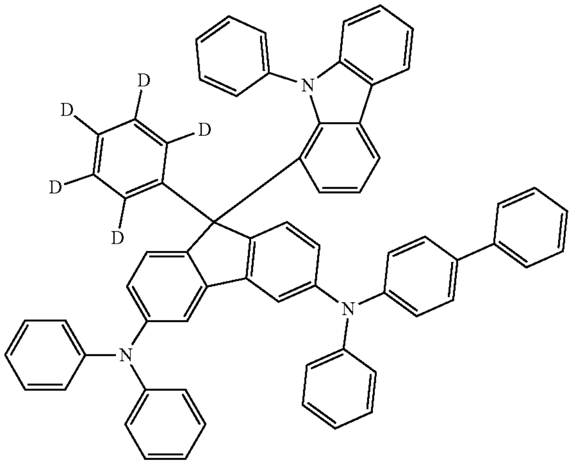
309
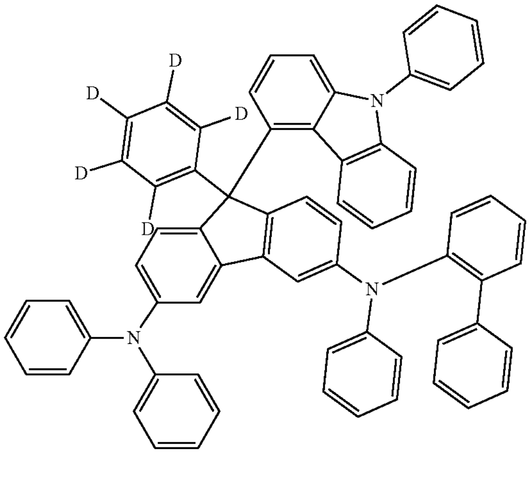

-continued
310
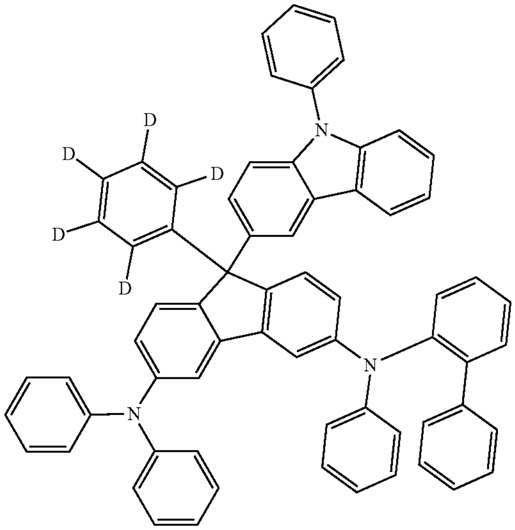
311
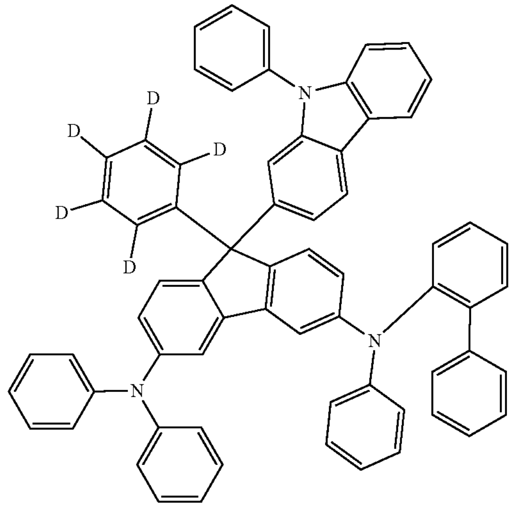
312
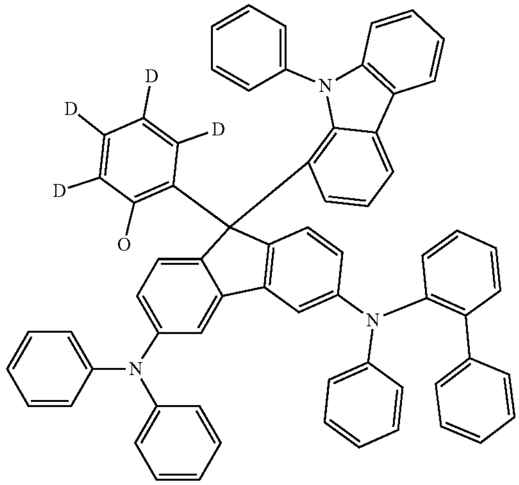
-continued
313
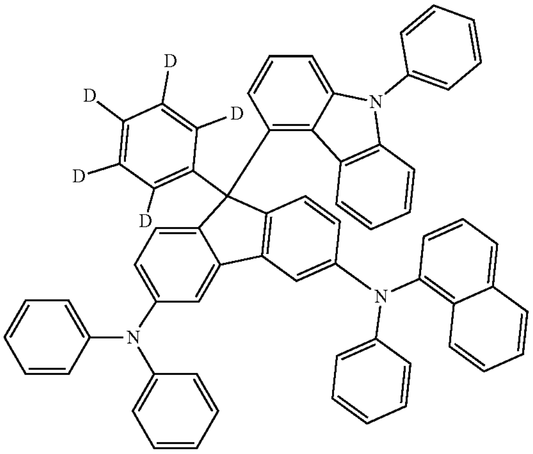
314
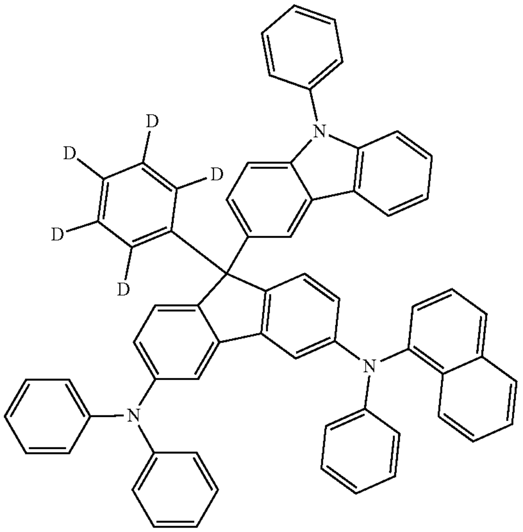
315
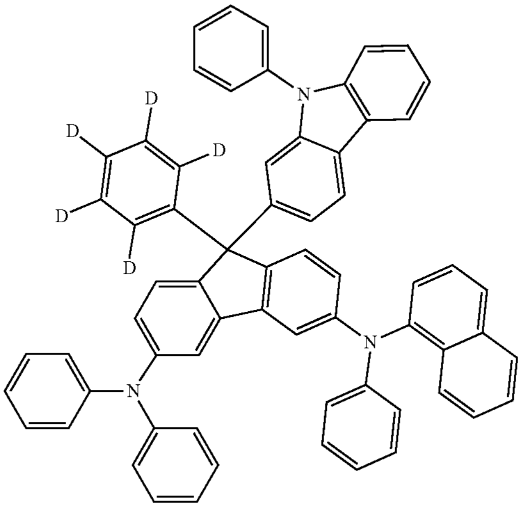

-continued
316
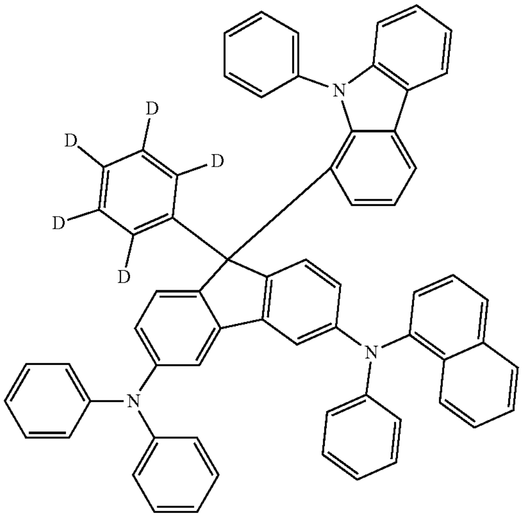
317
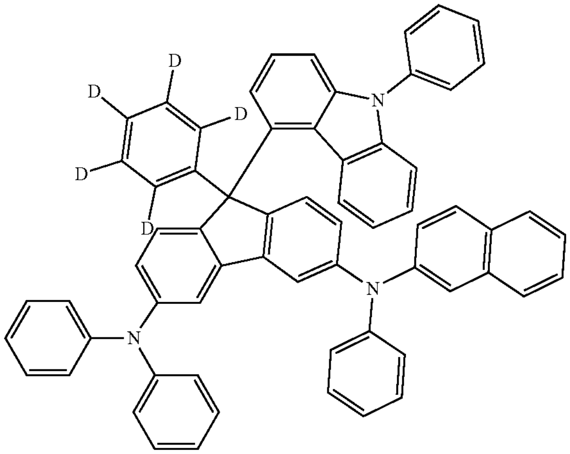
318
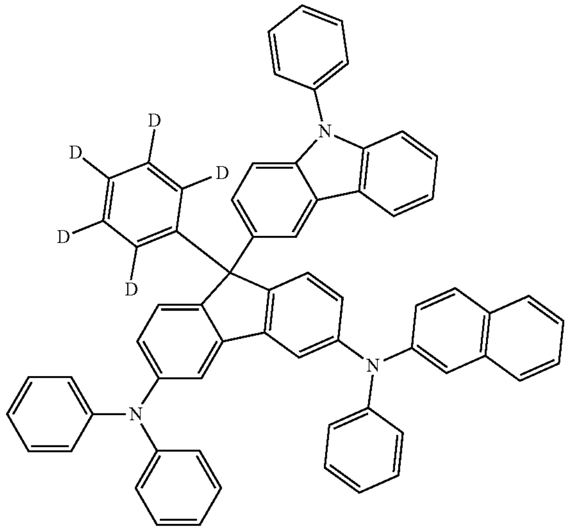
-continued
319
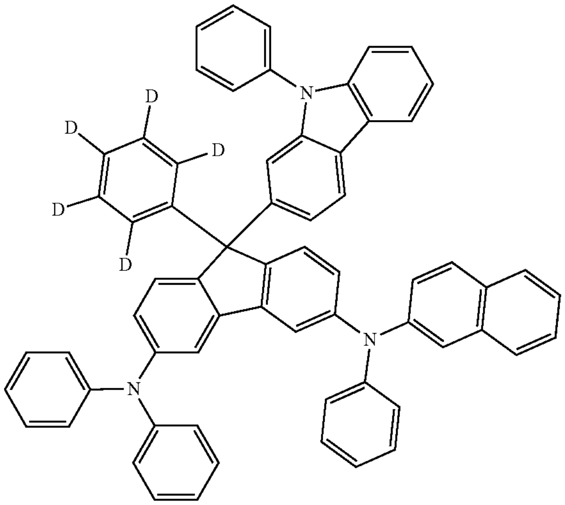
320
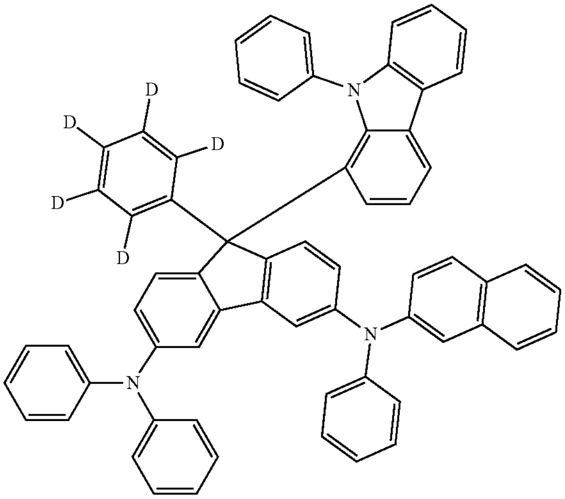
321
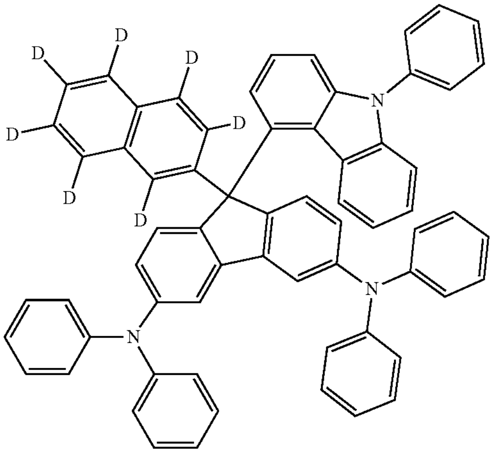

-continued
322
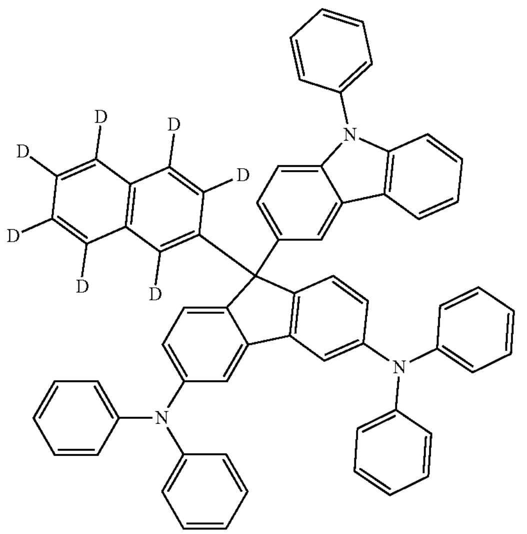
323
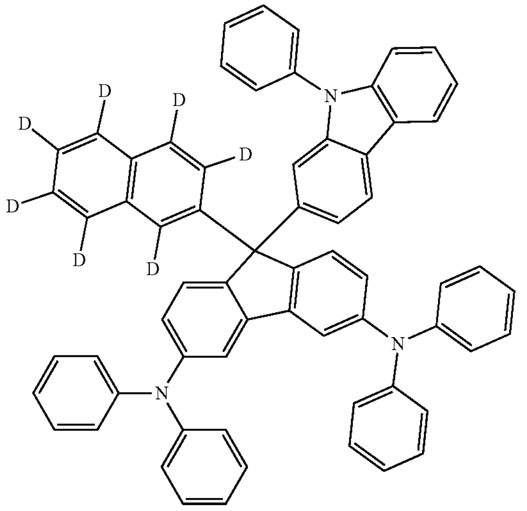
324
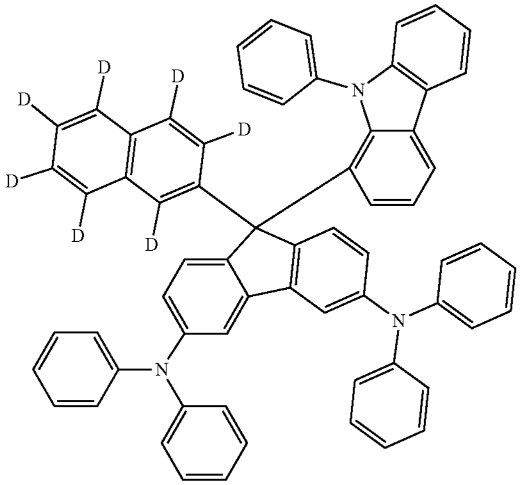
-continued
325
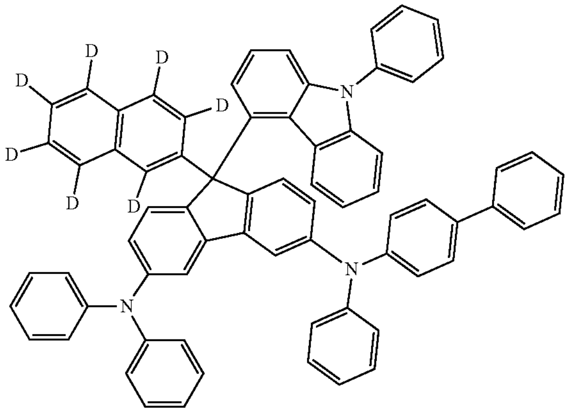
326
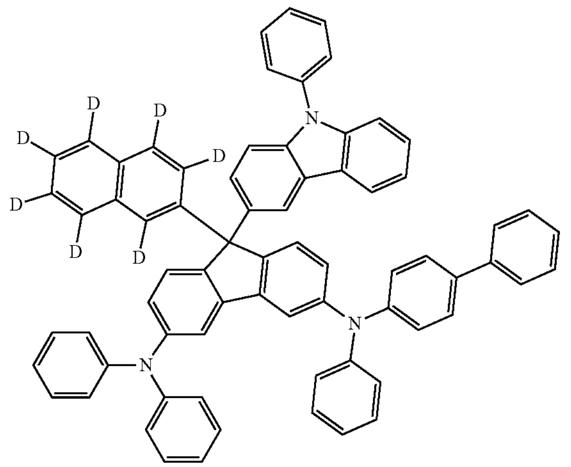
327
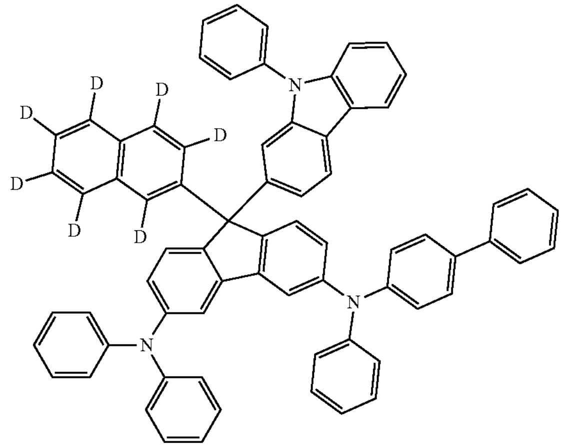

-continued
328
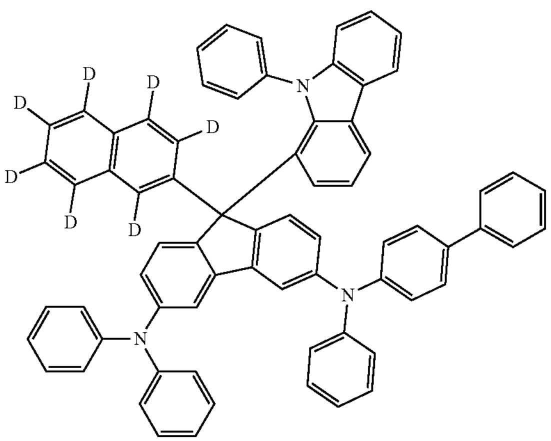
329
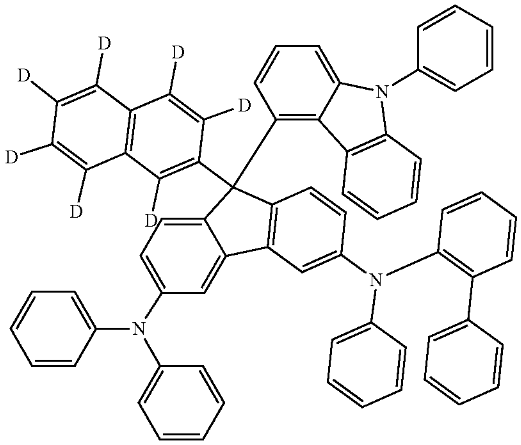
330
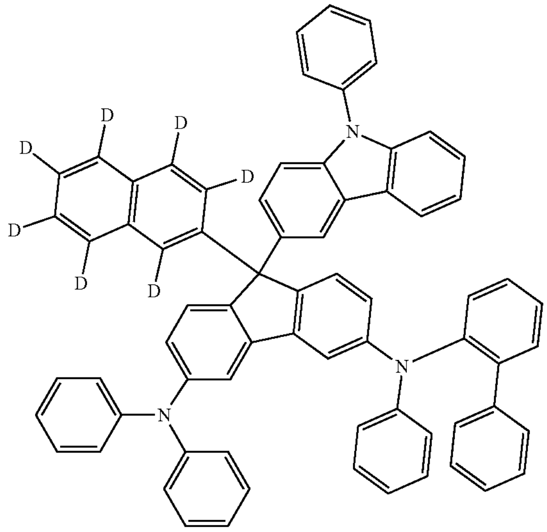
-continued
331
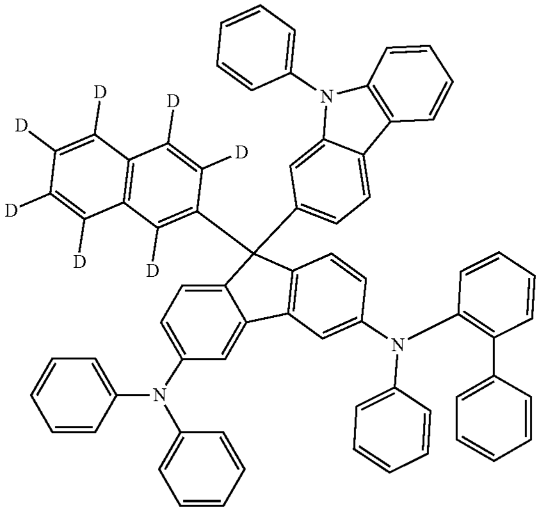
332
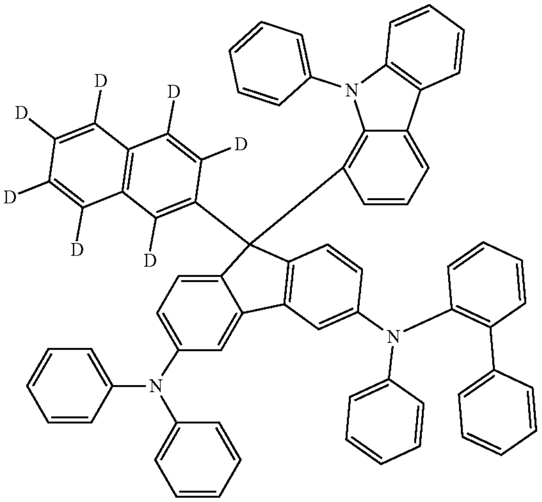
333
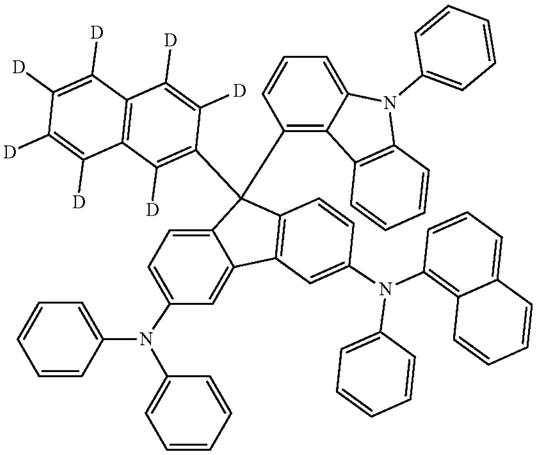

-continued
334
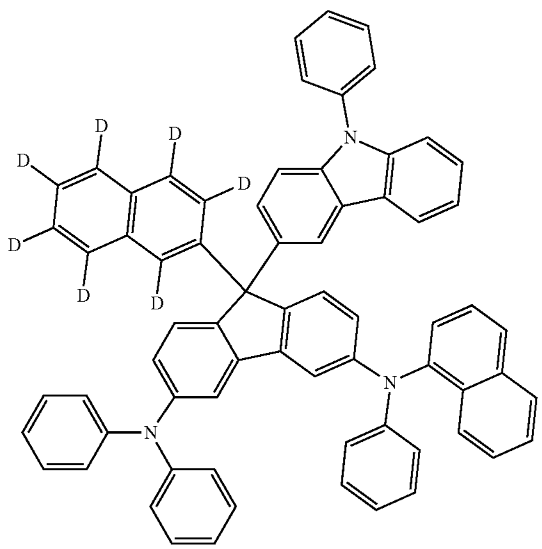
335
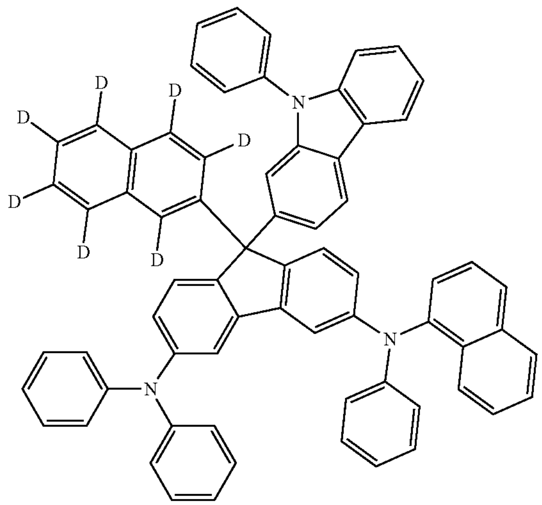
336
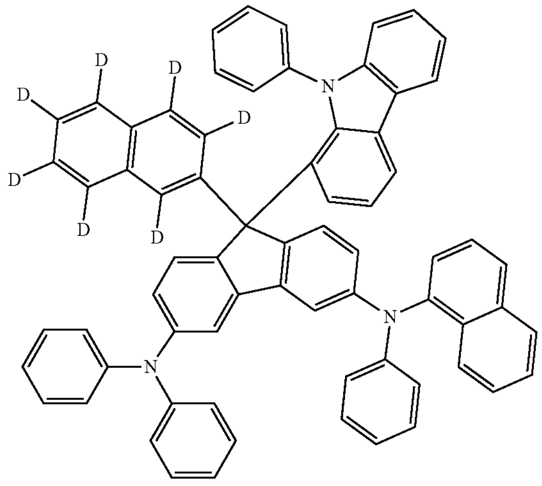
-continued
337
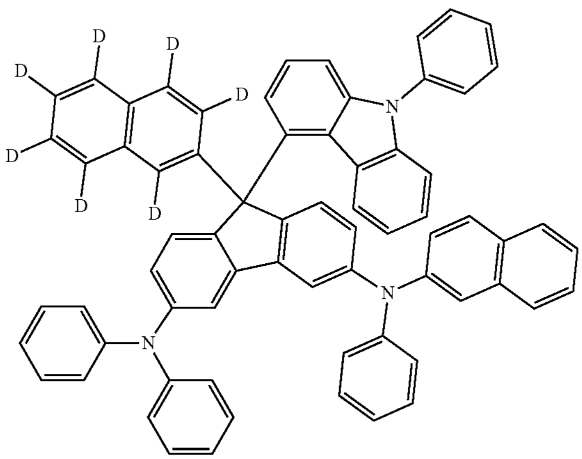
338
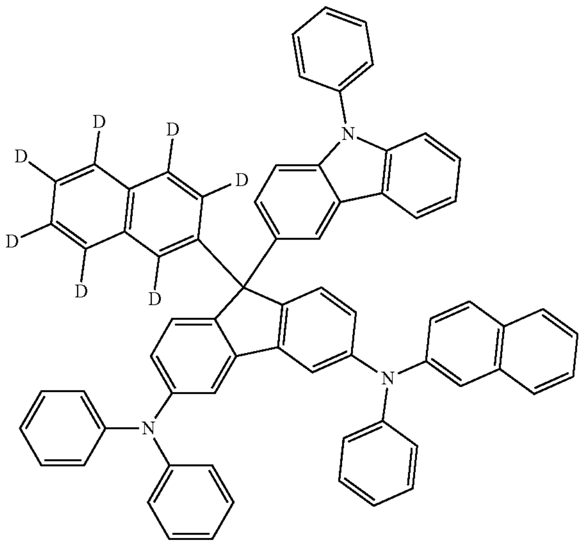
339
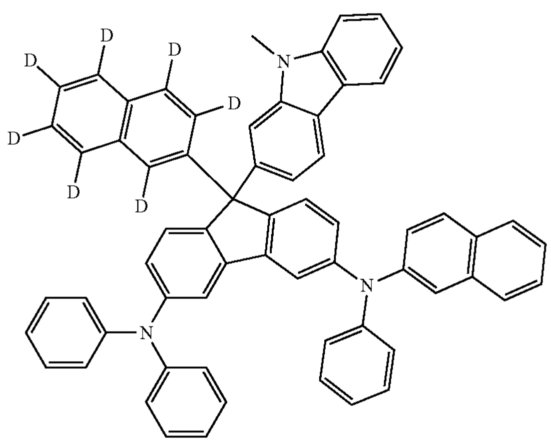

340
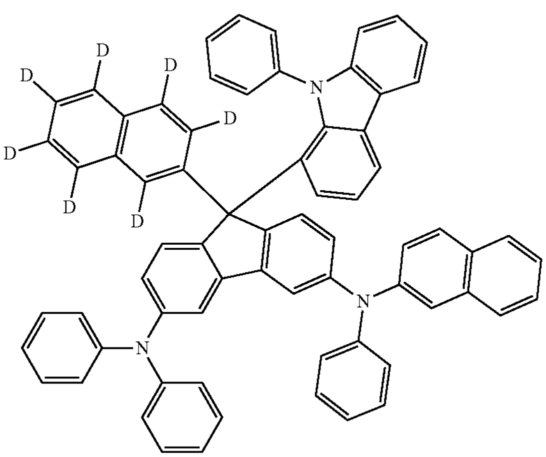
341
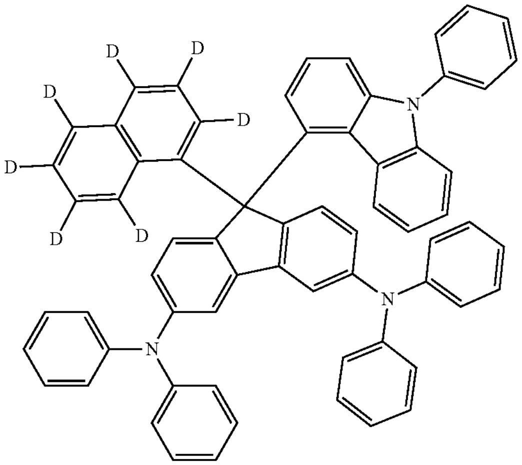
342
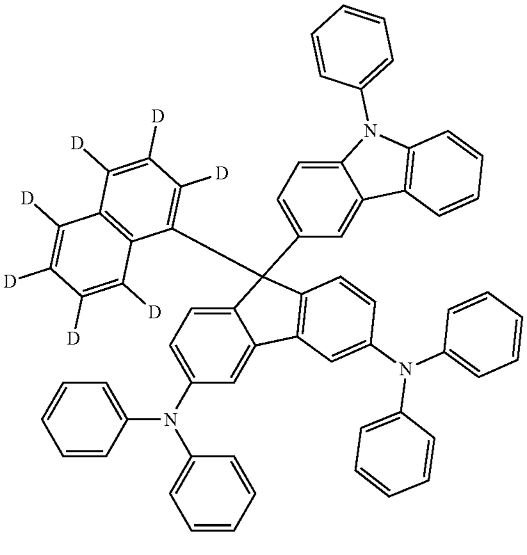
343
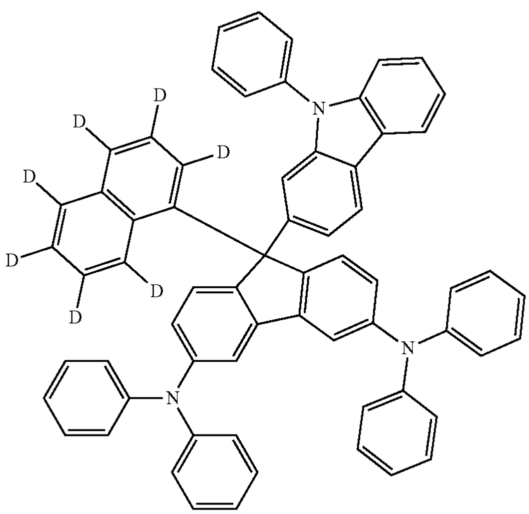
344
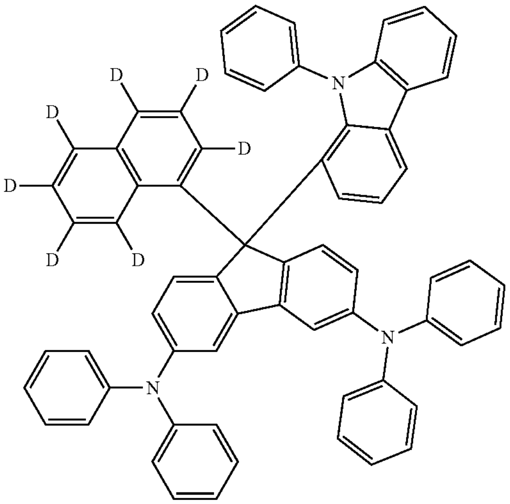
345
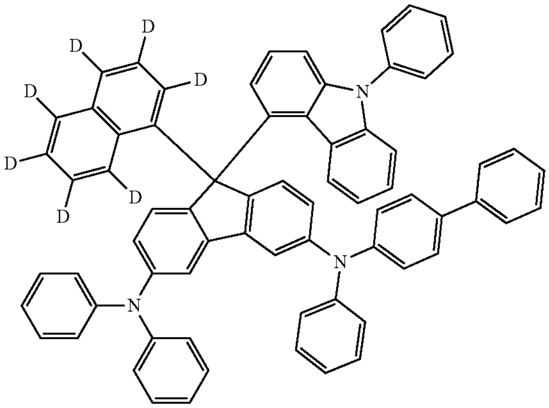

-continued
346
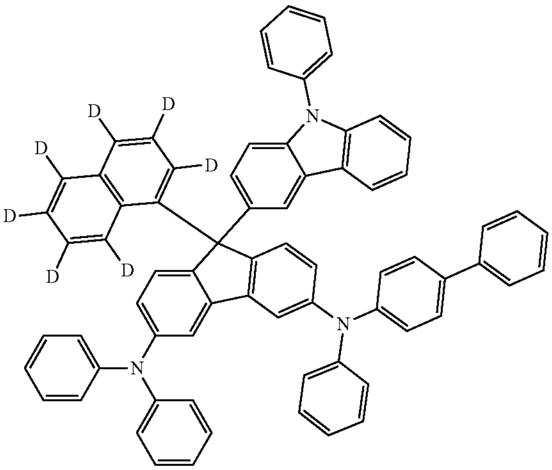
347
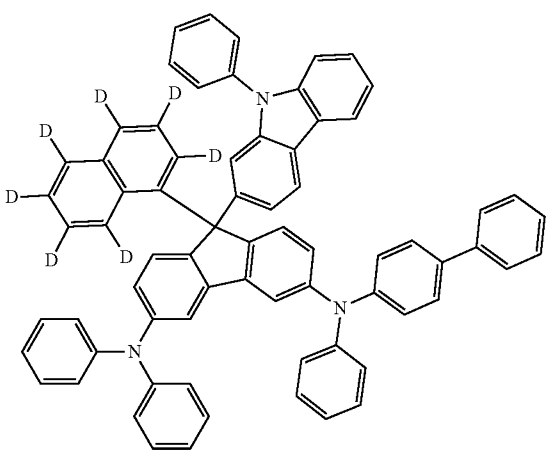
348
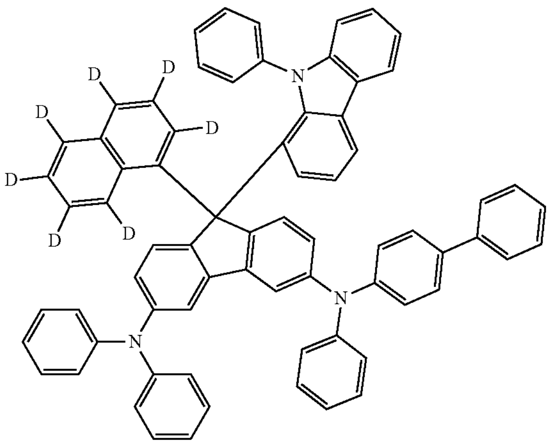
-continued
349
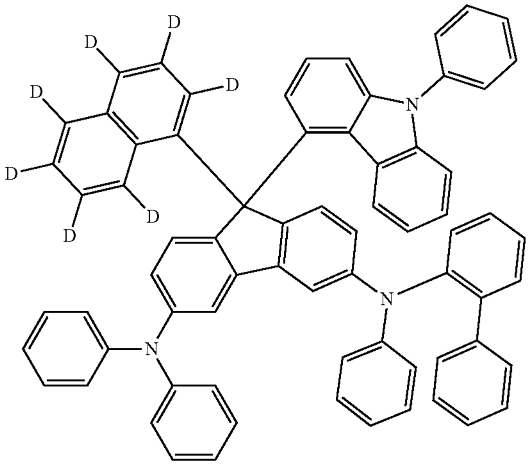
350
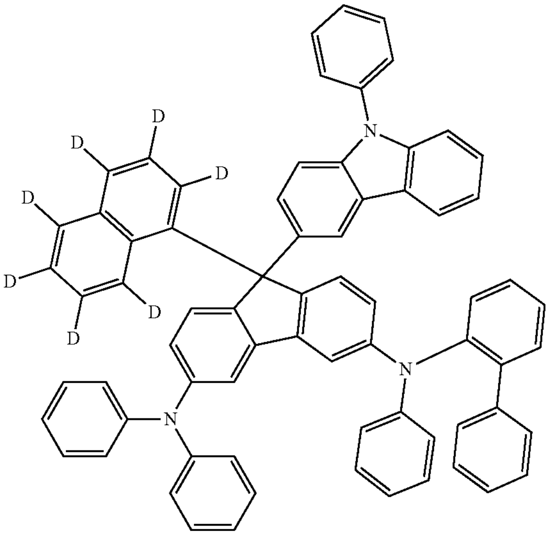
351
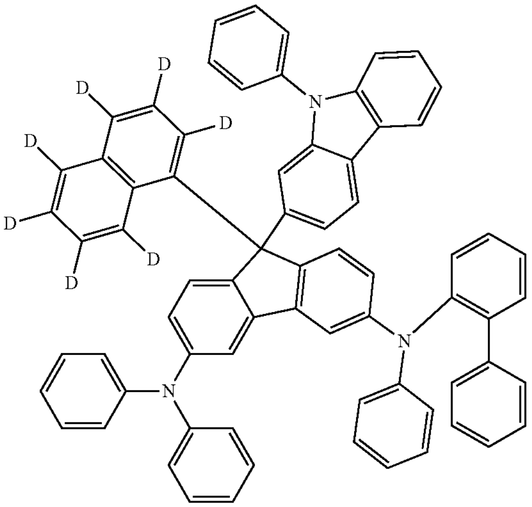

-continued
352
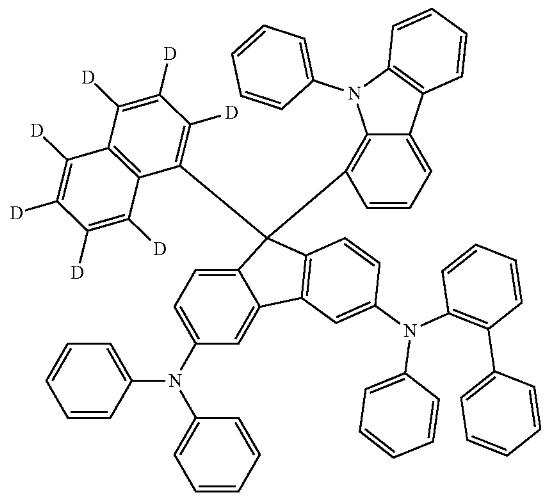
353
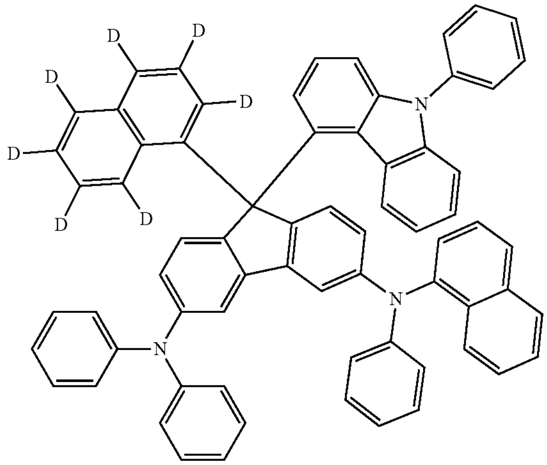
354
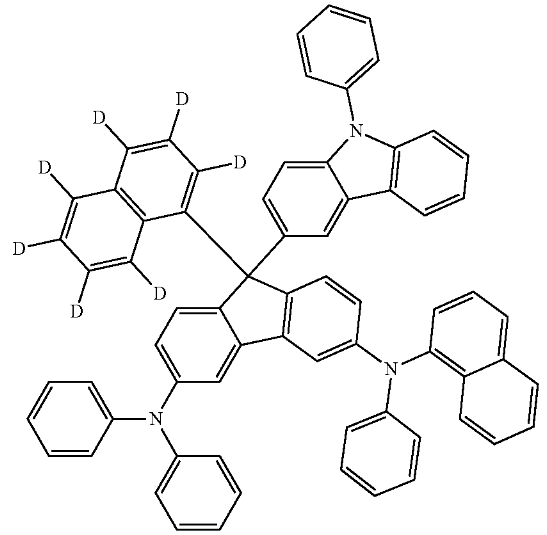
-continued
355
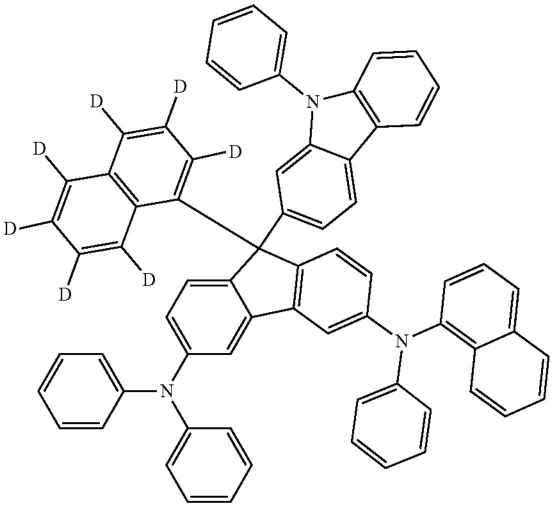
356
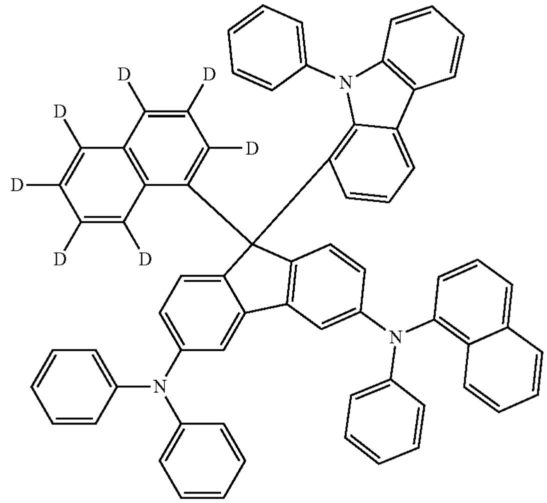

-continued
357
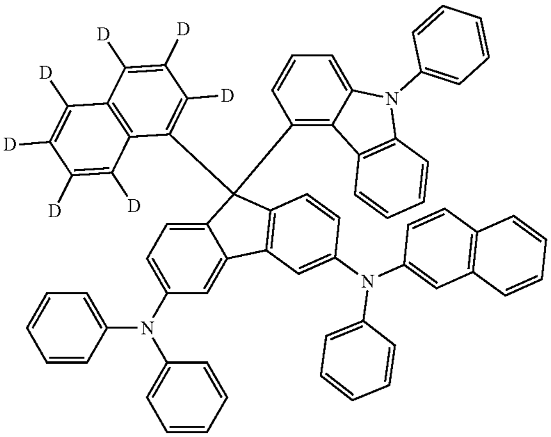
358
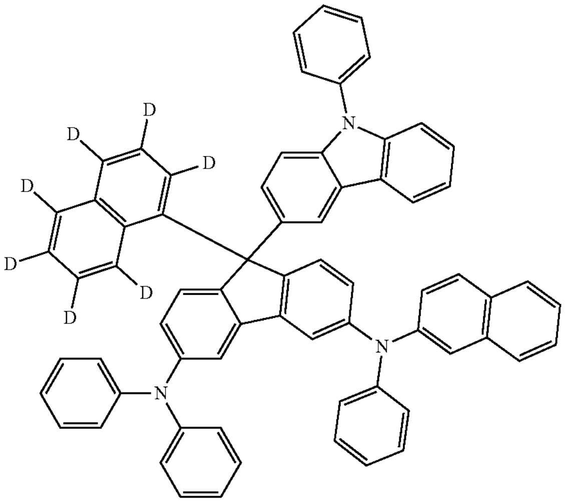
-continued
359
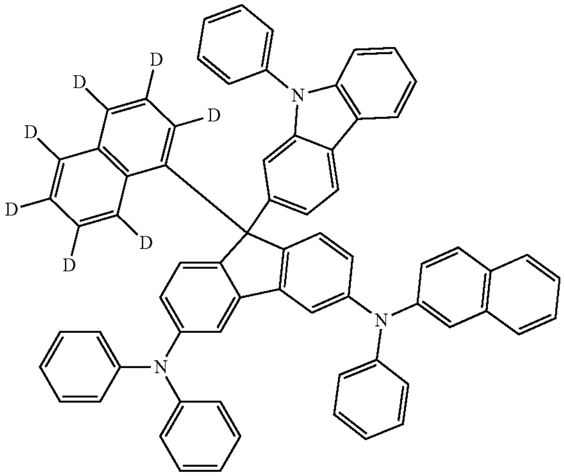
360
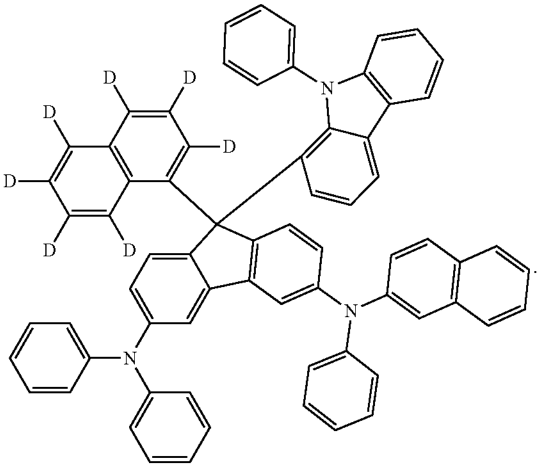
.
* * * * *